(12) United States Patent
Hagihara et al.

(10) Patent No.: US 7,294,625 B2
(45) Date of Patent: Nov. 13, 2007

(54) PYRAZOLE COMPOUNDS

(75) Inventors: Masahiko Hagihara, Ube (JP); Nobuhiko Shibakawa, Ube (JP); Masamichi Nishihara, Ube (JP); Toshiyuki Shirai, Ube (JP); Motohisa Shimizu, Ube (JP); Tohru Hasegawa, Ube (JP); Yasunori Tokunaga, Ube (JP); Naoto Suzuki, Ube (JP); Yukinori Wada, Ube (JP)

(73) Assignee: Ube Industries, Ltd., Yamaguchi (JP)

( * ) Notice: Subject to any disclaimer, the term of this patent is extended or adjusted under 35 U.S.C. 154(b) by 322 days.

(21) Appl. No.: 10/528,994

(22) PCT Filed: Sep. 25, 2003

(86) PCT No.: PCT/JP03/12254

§ 371 (c)(1), (2), (4) Date: Mar. 24, 2005

(87) PCT Pub. No.: WO2004/029043

PCT Pub. Date: Apr. 8, 2004

(65) Prior Publication Data

US 2006/0063934 A1  Mar. 23, 2006

(30) Foreign Application Priority Data

Sep. 25, 2002  (JP) .............................. 2002-279385

(51) Int. Cl.
*C07D 487/04* (2006.01)
*C07D 401/14* (2006.01)
*C07D 403/14* (2006.01)
*A61K 31/501* (2006.01)
*A61K 31/5025* (2006.01)

(52) U.S. Cl. ............ 514/248; 514/252.02; 514/252.03; 544/236; 544/238

(58) Field of Classification Search ................ 544/236, 544/238; 514/248, 252.02, 252.03
See application file for complete search history.

(56) References Cited

U.S. PATENT DOCUMENTS 6,511,997 B1 * 1/2003 Minami et al. ............. 514/341

FOREIGN PATENT DOCUMENTS

| WO | WO-95/31451 A1 | 11/1995 |
| WO | WO-98/52937 A2 | 11/1998 |
| WO | WO-98/52941 A1 | 11/1998 |

(Continued)

*Primary Examiner*—Kahsay Habte
(74) *Attorney, Agent, or Firm*—Birch, Stewart, Kolasch & Birch, LLP

(57) ABSTRACT

The present invention relates to pyrazole compounds represented by the formula (I):

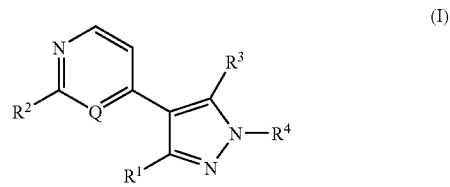

wherein $R^1$ represents phenyl which may be substituted, $R^2$ represents H, halogen, alkyl, alkoxy, alkylthio, alkylsulfinyl, alkylsulfonyl or substituted amino, Q represents CH or N, $R^3$ represents H, alkyl or amino, $R^4$ represents the formula (II) to (V):

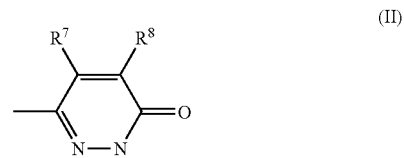

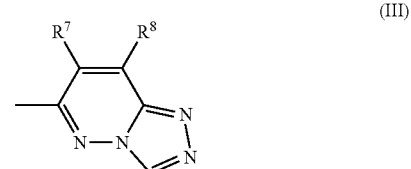

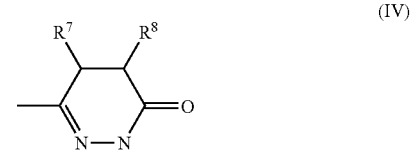

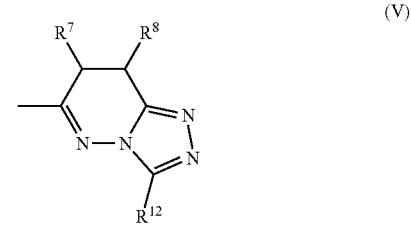

wherein $R^7$ represents H or alkyl, $R^8$ represents H, alkyl or substituted amino, $R^9$ represents H or alkyl, $R^{12}$ represents H, alkyl, halogeno alkyl or substituted amino, or pharmaceutically acceptable salts thereof, and a medical composition containing the same as effective ingredient.

35 Claims, No Drawings

FOREIGN PATENT DOCUMENTS

| | | |
|---|---|---|
| WO | WO-98/56377 A1 | 12/1998 |
| WO | WO-99/57101 A1 | 11/1999 |
| WO | WO-00/31063 A1 | 6/2000 |
| WO | WO-00/39116 A1 | 7/2000 |
| WO | WO-01/021591 A1 | 3/2001 |
| WO | WO-02/057265 A1 | 7/2002 |

* cited by examiner

PYRAZOLE COMPOUNDS

TECHNICAL FIELD

The present invention relates to novel pyrazole compounds having a p38MAP kinase inhibitory activity and an excellent inhibitory activity against the production of cytokines based thereon. More specifically, it relates to novel pyrazole compounds having an inhibitory activity against the production of inflammatory cytokines such as tumor necrosis factor (TNF-α) and interleukin (IL-1, IL-6, IL-8, etc.), etc., and being useful as an antipyretic, analgesic and anti-inflammatory agent, and as a treatment agent for autoimmune diseases such as chronic rheumatism, bone diseases such as osteoporosis, and other diseases to which the above-mentioned cytokines pertain.

BACKGROUND ART

Conventional non-steroid type anti-inflammatory drug (NSAID) causes digestive tract disorder such as gastric ulcer, etc. from its function and mechanism, so that they have a problem in continuous use for a long period of time. Also, a disease modified type anti-rheumatoid drug (DMARD) which is used for chronic rheumatism as the etiotropic purpose has not yet been shown its clear medical effect stably as of today. On the other hand, an antibody theraphy of TNF-α which is a kind of inflammatory cytokines and considered to induce various events after occurrence of inflammation shows remarkable effects on chronic rheumatism, and exemplifies that inhibition of production of cytokines is preferred as a mechanism for an anti-rheumatoid drug, etc. Moreover, with regard to cytokines such as IL-1, IL-6, IL-8, etc., various functions as inflammatory mediators have been clarified. p38MAP kinase which has been cloned as a homolog of MAP kinase pertains to inhibition of production of these inflammatory cytokines and to a signal transduction pathway coupled with a receptor, and thus, a novel inflammatory cytokine-inhibiting agent due to p38MAP kinase inhibition is now expected to be a treating agent as an antipyretic, analgesic and anti-inflammatory agent with a different function and mechanism from the conventional ones, and for diseases including autoimmune disease such as chronic rheumatism, bone diseases such as osteoporosis, and other diseases to which these cytokines pertain.

There are conventional pyrazole compounds having a function of inhibiting production of these inflammatory cytokines (for example, WO 98/52940A publication, WO 00/31063A publication, WO 95/31451A publication, WO 02/57265A publication and WO 00/39116A publication), but it has been desired to develop a compound having more excellent in medical effects, pharmacokinetic profile and safety.

An object of the present invention is to provide a series of the pyrazole compounds or pharmaceutically acceptable salts thereof showing more potent medical effect, excellent pharmacokinetic profile and high safety in the research of low molecular compounds having a function of inhibiting production of inflammatory cytokines due to the above-mentioned p38MAP kinase inhibition.

DISCLOSURE OF THE INVENTION

The present inventors have studied intensively on a pyrazole compound, and as a result, they have found that in a series of the pyrazole compounds in which the 3-position of the pyrazole ring is substituted by a phenyl group, and, the 4-position is substituted by a pyridyl or pyrimidyl group, a series of the pyrazole compounds wherein they have a specific substituent at the 1-position of said pyrazole ring, i.e., that having a 1,6-dihydro-6-oxopyridazin-3-yl group, a [1,2,4]triazolo[4,3-b]pyridazin-6-yl group, a 1,4,5,6-tetrahydro-6-oxopyridazin-3-yl group or a 7,8-dihydro-[1,2,4]triazolo[4,3-b]pyridazin-6-yl group, have an excellent production inhibitory activity of inflammatory cytokine due to p38MAP kinase inhibition and excellent in vivo action and high safety, whereby they have accomplished the present invention.

That is, the present invention relates to a pyrazole compound represented by the formula (I):

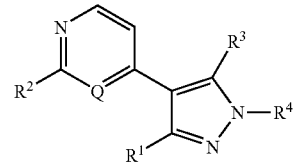

wherein $R^1$ represents a phenyl group which may be substituted by a group(s) selected from the group consisting of a halogen atom, a $C_1$-$C_6$ alkyl group, a halogeno $C_1$-$C_6$ alkyl group, a $C_1$-$C_6$ alkoxy group, a halogeno $C_1$-$C_6$ alkoxy group and a $C_1$-$C_6$ alkylthio group, $R^2$ represents a hydrogen atom, a halogen atom, a $C_1$-$C_6$ alkyl group, a $C_1$-$C_6$ alkoxy group, a $C_1$-$C_6$ alkylthio group, a $C_1$-$C_6$ alkylsulfinyl group, a $C_1$-$C_6$ alkylsulfonyl group or a group: —$NR^5R^6$ wherein $R^5$ and $R^6$ may be the same or different from each other, and each represents a hydrogen atom, a $C_1$-$C_6$ alkyl group, a halogeno $C_1$-$C_6$ alkyl group, a $C_3$-$C_7$ cycloalkyl group, a $C_1$-$C_6$ alkyl-carbonyl group, a $C_3$-$C_7$ cycloalkyl-carbonyl group, a formyl group, a $C_1$-$C_6$ alkoxy-carbonyl group or a $C_1$-$C_6$ alkylsulfonyl group, or a $C_7$-$C_{12}$ aralkyl group or a benzoyl group each of which may be substituted by a group(s) selected from the group consisting of a halogen atom, a $C_1$-$C_6$ alkyl group, a halogeno $C_1$-$C_6$ alkyl group, a $C_1$-$C_6$ alkoxy group and a halogeno $C_1$-$C_6$ alkoxy group, Q represents CH or a nitrogen atom, $R^3$ represents a hydrogen atom, a $C_1$-$C_6$ alkyl group or an amino group, $R^4$ represents the formula (II):

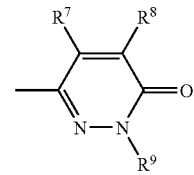

the formula (III):

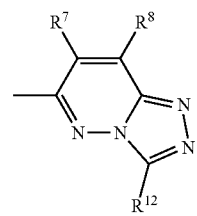

the formula (IV):

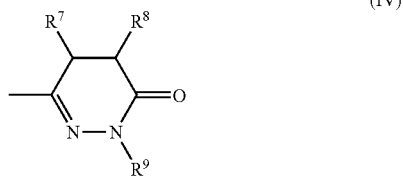

or the formula (V):

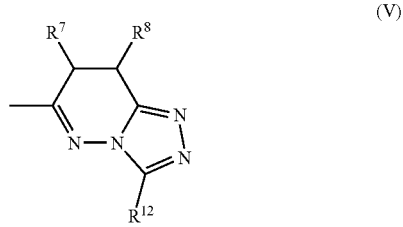

wherein $R^7$ represents a hydrogen atom or a $C_1$-$C_6$ alkyl group, $R^8$ represents a hydrogen atom, a $C_1$-$C_6$ alkyl group or a group: —$NR^{10}R^{11}$ wherein $R^{10}$ and $R^{11}$ may be the same or different from each other, and each represents a hydrogen atom, a $C_1$-$C_6$ alkyl group, a $C_1$-$C_6$ alkyl-carbonyl group, a formyl group, a $C_1$-$C_6$ alkoxy-carbonyl group or a $C_1$-$C_6$ alkylsulfonyl group, $R^9$ represents a hydrogen atom or a $C_1$-$C_6$ alkyl group,
$R^{12}$ represents a hydrogen atom, a $C_1$-$C_6$ alkyl group, a halogeno $C_1$-$C_6$ alkyl group or a group: —$NR^{10}R^{11}$ wherein $R^{10}$ and $R^{11}$ may be the same or different from each other, and each represents a hydrogen atom, a $C_1$-$C_6$ alkyl group, a $C_1$-$C_6$ alkyl-carbonyl group, a formyl group, a $C_1$-$C_6$ alkoxy-carbonyl group or a $C_1$-$C_6$ alkylsulfonyl group, or a pharmaceutically acceptable salt thereof.

The present invention also relates to a pharmaceutical composition containing the above-mentioned pyrazole compound or a pharmaceutically acceptable salt thereof as an effective ingredient.

The present invention further relates to a p38MAP kinase inhibiting agent containing the above-mentioned pyrazole compound or a pharmaceutically acceptable salt thereof as an effective ingredient.

The present invention further relates to a rheumatoid treating agent containing the above-mentioned pyrazole compound or a pharmaceutically acceptable salt thereof as an effective ingredient.

BEST MODE FOR CARRYING OUT THE INVENTION

The substituent(s) a "halogen atom" as a substituent(s) for the phenyl group, a "halogeno portion" of the halogeno $C_1$-$C_6$ alkyl group, and a "halogeno portion" of the halogeno $C_1$-$C_6$ alkoxy group represented by $R^1$; a "halogen atom" represented by $R^2$; a "halogen atom" of the halogeno $C_1$-$C_6$ alkyl group represented by $R^5$ and $R^6$ in $R^2$, a "halogen atom", a "halogeno portion" of the halogeno $C_1$-$C_6$ alkyl group, and a "halogeno portion" of the halogeno $C_1$-$C_6$ alkoxy group as a substituent(s) for the $C_7$-$C_{12}$ aralkyl group and the benzoyl group; and a "halogeno portion" of the halogeno $C_1$-$C_6$ alkyl group represented by $R^{12}$, each means a "halogen atom" having the same meanings, and such a halogen atom may be mentioned, for example, a fluorine atom, chlorine atom, bromine atom or iodine atom, preferably a fluorine atom, chlorine atom or bromine atom, more preferably a fluorine atom or chlorine atom.

The substituent(s) the "$C_1$-$C_6$ alkyl group" as a substituent(s) for the phenyl group, a "$C_1$-$C_6$ alkyl group portion" of the halogeno $C_1$-$C_6$ alkyl group, and a "$C_1$-$C_6$ alkyl group portion" of the $C_1$-$C_6$ alkylthio group represented by $R^1$; the "$C_1$-$C_6$ alkyl group", a "$C_1$-$C_6$ alkyl group portion" of the $C_1$-$C_6$ alkylthio group, a "$C_1$-$C_6$ alkyl group portion" of the $C_1$-$C_6$ alkylsulfinyl group, and a "$C_1$-$C_6$ alkyl group portion" of the $C_1$-$C_6$ alkylsulfonyl group represented by $R^2$; the "$C_1$-$C_6$ alkyl group", a "$C_1$-$C_6$ alkyl group portion" of the halogeno $C_1$-$C_6$ alkyl group, a "$C_1$-$C_6$ alkyl group portion" of the $C_1$-$C_6$ alkyl-carbonyl group, and a "$C_1$-$C_6$ alkyl group portion" of the $C_1$-$C_6$ alkylsulfonyl group represented by $R^5$ and $R^6$ in $R^2$, a "$C_1$-$C_6$ alkyl group", and a "$C_1$-$C_6$ alkyl group portion" of the halogeno $C_1$-$C_6$ alkyl group as a substituent(s) for the $C_7$-$C_{12}$ aralkyl group and the benzoyl group; the "$C_1$-$C_6$ alkyl group" represented by $R^3$; the "$C_1$-$C_6$ alkyl group" represented by $R^7$; the "$C_1$-$C_6$ alkyl group" represented by $R^8$; the "$C_1$-$C_6$ alkyl group", a "$C_1$-$C_6$ alkyl group portion" of the $C_1$-$C_6$ alkyl-carbonyl group, and a "$C_1$-$C_6$ alkyl group portion" of the $C_1$-$C_6$ alkylsulfonyl group represented by $R^{10}$ and $R^{11}$ in $R^8$ and $R^{12}$; the "$C_1$-$C_6$ alkyl group" represented by $R^9$; the "$C_1$-$C_6$ alkyl group", and a "$C_1$-$C_6$ alkyl group portion" of the halogeno $C_1$-$C_6$ alkyl group represented by $R^{12}$, each means a "$C_1$-$C_6$ alkyl group" having the same meanings, and such a $C_1$-$C_6$ alkyl group may be mentioned, for example, a straight or branched $C_1$-$C_6$ alkyl group such as a methyl group, ethyl group, propyl group, isopropyl group, butyl group, isobutyl group, s-butyl group, t-butyl group, pentyl group, isopentyl group, neopentyl group, 1-ethylpropyl group, 1-methylbutyl group, 2-methylbutyl group, hexyl group, 1-methylpentyl group, 2-methylpentyl group, 3-methylpentyl group, 4-methylpentyl group, 1-ethylbutyl group or 2-ethylbutyl group, preferably a $C_1$-$C_4$ alkyl group, more preferably a methyl group, ethyl group or isopropyl group, particularly preferably a methyl group or ethyl group.

The "halogeno $C_1$-$C_6$ alkyl group" as a substituent(s) for the phenyl group represented by $R^1$; the "halogeno $C_1$-$C_6$ alkyl group" represented by $R^5$ and $R^6$ in $R^2$, the "halogeno $C_1$-$C_6$ alkyl group" as a substituent(s) for the $C_7$-$C_{12}$ aralkyl group and the benzoyl group; and the "halogeno $C_1$-$C_6$ alkyl group" represented by $R^{12}$, each means a "halogeno $C_1$-$C_6$ alkyl group" having the same meanings, and such a "halogeno $C_1$-$C_6$ alkyl group" may be mentioned, for example, the "$C_1$-$C_6$ alkyl group" to which 1 or 2 or more of the above-mentioned halogen atom(s) is/are substituted, and may include a fluoromethyl group, chloromethyl group, bromo-methyl group, iodomethyl group, difluoromethyl group, dichloromethyl group, dibromomethyl group, diiodomethyl group, trifluoromethyl group, trichloromethyl group, 1-fluoroethyl group, 2-fluoroethyl group, 2-chloroethyl group, 2-bromoethyl group, 2,2-difluoroethyl group, 2,2,2-trifluoroethyl group, pentafluoroethyl group, 2,2-dichloroethyl group, 2,2,2-trichloroethyl group, 1-fluoropropyl group, 2-fluoropropyl group, 3-fluoropropyl group, 3,3,3-trifluoropropyl group, perfluoropropyl group, 2-fluoro-1-methylethyl group, 2,2-difluoro-1-methylethyl group, 2,2,2-trifluoro-1-methylethyl group, 1-fluoro-1-methylethyl group, 4-fluorobutyl group, perfluorobutyl group, 5-fluoropentyl group, perfluoropentyl group, 6-fluorohexyl group or perfluorohexyl group, preferably a fluoro $C_1$-$C_4$ alkyl group, more preferably a difluoromethyl group, trifluoromethyl group, 2-fluoroethyl group or 2,2,2-trifluoroethyl group, particularly preferably a difluoromethyl group, trifluoromethyl group or 2,2,2-trifluoroethyl group.

The "$C_1$-$C_6$ alkoxy group" and a "$C_1$-$C_6$ alkoxy group portion" of the halogeno $C_1$-$C_6$ alkoxy group as a substituent(s) for the phenyl group represented by $R^1$; the "$C_1$-$C_6$ alkoxy group" represented by $R^2$; a "$C_1$-$C_6$ alkoxy portion" of the $C_1$-$C_6$ alkoxy-carbonyl group represented by $R^5$ and $R^6$ in $R^2$, the "$C_1$-$C_6$ alkoxy group", and a "$C_1$-$C_6$ alkoxy group portion" of the halogeno $C_1$-$C_6$ alkoxy group as a substituent(s) for the $C_7$-$C_{12}$ aralkyl group and the benzoyl group; and a "$C_1$-$C_6$ alkoxy portion" of the $C_1$-$C_6$ alkoxycarbonyl group represented by $R^{10}$ and $R^{11}$ in $R^8$ and $R^{12}$, each means a "$C_1$-$C_6$ alkoxy group" having the same meanings, and such a "$C_1$-$C_6$ alkoxy group" may be mentioned, for example, a straight or branched $C_1$-$C_6$ alkoxy group such as a methoxy group, ethoxy group, propoxy group, isopropoxy group, butoxy group, isobutoxy group, s-butoxy group, t-butoxy group, pentyloxy group, isopentyloxy group, neopentyloxy group, 1-ethylpropoxy group, 1-methylbutoxy group, 2-methylbutoxy group, hexyloxy group, 1-methylpentyloxy group, 2-methylpentyloxy group, 3-methylpentyloxy group, 4-methylpentyloxy group, 1-ethylbutoxy group or 2-ethylbutoxy group, preferably a $C_1$-$C_4$ alkoxy group, more preferably a methoxy group, ethoxy group or isopropoxy group, particularly preferably a methoxy group.

The "halogeno $C_1$-$C_6$ alkoxy group" as a substituent(s) for the phenyl group represented by $R^1$; and the "halogeno $C_1$-$C_6$ alkoxy group" as a substituent(s) for the $C_7$-$C_{12}$ aralkyl group and the benzoyl group represented by $R^5$ and $R^6$ in $R^2$, each means a "halogeno $C_1$-$C_6$ alkoxy group" having the same meanings, and such a "halogeno $C_1$-$C_6$ alkoxy group" may be mentioned, for example, the above-mentioned "$C_1$-$C_6$ alkoxy group" to which 1 or 2 or more of the above-mentioned halogen atom(s) is/are substituted, and may include a fluoromethoxy group, chloromethoxy group, bromomethoxy group, iodomethoxy group, difluoromethoxy group, dichloromethoxy group, dibromomethoxy group, diiodomethoxy group, trifluoromethoxy group, trichloromethoxy group, 1-fluoroethoxy group, 2-fluoroethoxy group, 2,2-difluoroethoxy group, 2,2,2-trifluoroethoxy group, perfluoroethoxy group, 2-chloroethoxy group, 3-fluoropropoxy group, 3,3,3-trifluoropropoxy group, perfluoropropoxy group, 4-fluorobutoxy group, perfluorobutoxy group, 5-fluoropentyloxy group or 6-fluorohexyloxy group, preferably a fluoro $C_1$-$C_4$ alkoxy group, more preferably a fluoromethoxy group, difluoromethoxy group or trifluoromethoxy group, particularly preferably a difluoromethoxy group.

The "$C_1$-$C_6$ alkylthio group" as a substituent(s) for the phenyl group represented by $R^1$; and the "$C_1$-$C_6$ alkylthio group" represented by $R^2$, each means a "$C_1$-$C_6$ alkylthio group" having the same meanings, and such a "$C_1$-$C_6$ alkylthio group" may be mentioned, for example, a straight or branched $C_1$-$C_6$ alkylthio group such as a methylthio group, ethylthio group, propylthio group, isopropylthio group, butylthio group, isobutylthio group, s-butylthio group, t-butylthio group, pentylthio group, isopentylthio group, neopentylthio group, 1-ethylpropylthio group, 1-methylbutylthio group, 2-methylbutylthio group, hexylthio group, 1-methylpentylthio group, 2-methylpentylthio group, 3-methylpentylthio group, 4-methylpentylthio group, 1-ethylbutylthio group or 2-ethylbutylthio group, preferably a $C_1$-$C_4$ alkylthio group, more preferably a methylthio group, ethylthio group or isopropylthio group, particularly preferably a methylthio group.

As a substituent(s) for the phenyl group represented by $R^1$, there may be preferably mentioned a halogen atom, $C_1$-$C_4$ alkyl group, fluoro $C_1$-$C_4$ alkyl group, $C_1$-$C_4$ alkoxy group, fluoro $C_1$-$C_4$ alkoxy group or $C_1$-$C_4$ alkylthio group, more preferably a fluorine atom, chlorine atom, bromine atom, methyl group, ethyl group, isopropyl group, difluoromethyl group, trifluoromethyl group, 2-fluoroethyl group, 2,2,2-trifluoroethyl group, methoxy group, ethoxy group, isopropoxy group, fluoromethoxy group, difluoromethoxy group, trifluoromethoxy group or methylthio group, further more preferably a fluorine atom, chlorine atom, methyl group, difluoromethyl group, trifluoromethyl group, methoxy group, fluoromethoxy group, difluoromethoxy group or trifluoromethoxy group, particularly preferably a fluorine atom, chlorine atom, trifluoromethyl group or difluoromethoxy group.

In the formula (I), a number of the substituent(s) on the phenyl group represented by $R^1$ is, for example, 1 to 5, preferably 1 to 3, particularly preferably 1 to 2.

$R^1$ is specifically mentioned, preferably a phenyl group, 2-fluorophenyl group, 3-fluorophenyl group, 4-fluorophenyl group, 3,4-difluorophenyl group, 2,4-difluorophenyl group, 3,5-difluorophenyl group, 2,5-difluorophenyl group, 2,3-difluorophenyl group, 2,6-difluorophenyl group, 2,3,4-trifluorophenyl group, 3,4,5-trifluorophenyl group, 2,3,5-trifluorophenyl group, 2,4,5-trifluorophenyl group, 2,4,6-trifluorophenyl group, 2-chlorophenyl group, 3-chlorophenyl group, 4-chlorophenyl group, 3,4-dichlorophenyl group, 2,4-dichlorophenyl group, 3,5-dichlorophenyl group, 2,5-dichlorophenyl group, 2,3,4-trichlorophenyl group, 3,4,5-trichlorophenyl group, 2,3,5-trichlorophenyl group, 2,4,5-trichlorophenyl group, 2-bromophenyl group, 3-bromophenyl group, 4-bromophenyl group, 3,4-dibromophenyl group, 2,4-dibromophenyl group, 3,5-dibromophenyl group, 2-chloro-3-fluorophenyl group, 3-chloro-2-fluorophenyl group, 2-chloro-4-fluorophenyl group, 4-chloro-2-fluorophenyl group, 3-chloro-4-fluorophenyl group, 4-chloro-3-fluorophenyl group, 3-chloro-5-fluorophenyl group, 4-bromo-3-fluorophenyl group, 3-bromo-4-fluorophenyl group, 3-fluoro-4-iodophenyl group, 3-bromo-4-chlorophenyl group, 4-bromo-3-chlorophenyl group, 2-difluoromethylphenyl group, 3-difluoromethylphenyl group, 4-difluoromethylphenyl group, 2-trifluoromethylphenyl group, 3-trifluoromethylphenyl group, 4-trifluoromethylphenyl group, 4-fluoro-3-trifluoromethylphenyl group, 3-fluoro-4-trifluoromethylphenyl group, 5-fluoro-3-trifluoromethylphenyl group, 2-fluoro-3-trifluoromethylphenyl group, 4-chloro-3-trifluoromethylphenyl group, 4-fluoro-3-difluoromethylphenyl group, 2-methylphenyl group, 3-methylphenyl group, 4-methylphenyl group, 2-methoxyphenyl group, 3-methoxyphenyl group, 4-methoxyphenyl group, 2-difluoromethoxyphenyl group, 3-difluoromethoxyphenyl group, 4-difluoromethoxyphenyl group, 2-methylthiophenyl group, 3-methylthiophenyl group, 4-methylthiophenyl group, 4-fluoro-3-methylphenyl group, 3-fluoro-4-methylphenyl group, 4-fluoro-3-methoxyphenyl group or 3-fluoro-4-methoxyphenyl group, more preferably a phenyl group, 2-fluorophenyl group, 3-fluorophenyl group, 4-fluorophenyl group, 3-chlorophenyl group, 4-chlorophenyl group, 3,4-difluorophenyl group, 2,4-difluorophenyl group, 3,4-dichlorophenyl group, 3-chloro-4-fluorophenyl group, 4-chloro-3-fluorophenyl group or 3-trifluoromethylphenyl group, particularly preferably a phenyl group, 2-fluorophenyl group, 3-fluorophenyl group, 4-fluorophenyl group, 3-chlorophenyl group, 4-chlorophenyl group, 3,4-difluorophenyl group, 3,4-dichlorophenyl group or 3-trifluoromethylphenyl group.

As the "$C_1$-$C_6$ alkylsulfinyl group" represented by $R^2$, there may be mentioned a straight or branched $C_1$-$C_6$ alkylsulfinyl group, for example, a methylsulfinyl group, ethylsulfinyl group, propylsulfinyl group, isopropylsulfinyl group, butylsulfinyl group, isobutylsulfinyl group, s-butylsulfinyl group, t-butylsulfinyl group, pentylsulfinyl group, isopentylsulfinyl group, neopentylsulfinyl group, 1-ethylpropylsulfinyl group, 1-methylbutylsulfinyl group, 2-methylbutylsulfinyl group, hexylsulfinyl group, 1-methylpentylsulfinyl group, 2-methylpentylsulfinyl group, 3-methylpentylsulfinyl group, 4-methylpentylsulfinyl group, 1-ethylbutylsulfinyl group or 2-ethylbutylsulfinyl group, preferably a $C_1$-$C_4$ alkylsulfinyl group, more preferably a methylsulfinyl group, ethylsulfinyl group or isopropylsulfinyl group, particularly preferably a methylsulfinyl group.

The "$C_1$-$C_6$ alkylsulfonyl group" represented by $R^2$; the "$C_1$-$C_6$ alkylsulfonyl group" represented by $R^5$ and $R^6$ in $R^2$; and the "$C_1$-$C_6$ alkylsulfonyl group" represented by $R^{10}$ and $R^{11}$ in $R^8$ and $R^{12}$ represents a "$C_1$-$C_6$ alkylsulfonyl group" each having the same meanings, and such a "$C_1$-$C_6$ alkylsulfonyl group" may be mentioned a straight or branched $C_1$-$C_6$ alkylsulfonyl group, for example, a methylsulfonyl group, ethylsulfonyl group, propylsulfonyl group, isopropylsulfonyl group, butylsulfonyl group, isobutylsulfonyl group, s-butylsulfonyl group, t-butylsulfonyl group, pentylsulfonyl group, isopentylsulfonyl group, neopentylsulfonyl group, 1-ethylpropylsulfonyl group, 1-methylbutylsulfonyl group, 2-methylbutylsulfonyl group, hexylsulfonyl group, 1-methylpentylsulfonyl group, 2-methylpentylsulfonyl group, 3-methylpentylsulfonyl group, 4-methylpentylsulfonyl group, 1-ethylbutylsulfonyl group or 2-ethylbutylsulfonyl group, preferably a $C_1$-$C_4$ alkylsulfonyl group, more preferably a methylsulfonyl group, ethylsulfonyl group or isopropylsulfonyl group, particularly preferably a methylsulfonyl group.

In $R^2$, as the "$C_3$-$C_7$ cycloalkyl group" represented by $R^5$ and $R^6$, there may be mentioned, for example, a cyclopropyl group, cyclobutyl group, cyclopentyl group, cyclohexyl group or cycloheptyl group, preferably a cyclopropyl group, cyclopentyl group or cyclohexyl group, more preferably a cyclopropyl group or cyclopentyl group, particularly preferably a cyclopropyl group.

In $R^2$, the "$C_1$-$C_6$ alkyl-carbonyl group" represented by $R^5$ and $R^6$; and the "$C_1$-$C_6$ alkyl-carbonyl group" represented by $R^{10}$ and $R^{11}$ in $R^8$ and $R^{12}$ represent a "$C_1$-$C_6$ alkyl-carbonyl group" each having the same meanings, and such a "$C_1$-$C_6$ alkyl-carbonyl group" may be mentioned, for example, a straight or branched $C_1$-$C_6$ alkyl-carbonyl group, etc., such as an acetyl group, propionyl group, butyryl group, isobutyryl group, valeryl group, isovaleryl group, pivaloyl group, hexanoyl group or heptanoyl group, preferably a $C_1$-$C_4$ alkyl-carbonyl group, more preferably an acetyl group or propionyl group, particularly preferably an acetyl group.

In $R^2$, as the "$C_3$-$C_7$ cycloalkyl-carbonyl group" represented by $R^5$ and $R^6$, there may be mentioned a $C_3$-$C_7$ cycloalkyl-carbonyl group in which the cycloalkyl portion is the above-mentioned "$C_3$-$C_7$ cycloalkyl group", for example, a cyclopropylcarbonyl group, cyclobutylcarbonyl group, cyclopentylcarbonyl group, cyclohexylcarbonyl group or cycloheptylcarbonyl group, preferably a cyclopropylcarbonyl group, cyclobutylcarbonyl group, cyclopentylcarbonyl group or cyclohexylcarbonyl group, more preferably a cyclopropylcarbonyl group, cyclopentylcarbonyl group or cyclohexylcarbonyl group, particularly preferably a cyclopropylcarbonyl group or cyclopentylcarbonyl group.

In $R^2$, the "$C_1$-$C_6$ alkoxy-carbonyl group" represented by $R^5$ and $R^6$; and the "$C_1$-$C_6$ alkoxy-carbonyl group" represented by $R^{10}$ and $R^{11}$ in $R^8$ and $R^{12}$ each represents the "$C_1$-$C_6$ alkoxy-carbonyl group" having the same meanings, and such a "$C_1$-$C_6$ alkoxy-carbonyl group" may include a $C_1$-$C_6$ alkoxy-carbonyl group in which the alkoxy portion is the above-mentioned "$C_1$-$C_6$ alkoxy group", for example, a methoxycarbonyl group, ethoxycarbonyl group, propoxycarbonyl group, isopropoxycarbonyl group, butoxycarbonyl group, isobutoxycarbonyl group, s-butoxycarbonyl group, t-butoxycarbonyl group, pentyloxycarbonyl group, isopentyloxycarbonyl group, neopentyloxycarbonyl group, 1-ethylpropoxycarbonyl group, 1-methylbutoxycarbonyl group, 2-methylbutoxycarbonyl group or hexyloxycarbonyl, preferably a $C_1$-$C_4$ alkoxy-carbonyl group, more preferably a methoxycarbonyl group, ethoxycarbonyl group or t-butoxycarbonyl group, particularly preferably a methoxycarbonyl group.

In $R^2$, as the "$C_7$-$C_{12}$ aralkyl group" of "the $C_7$-$C_{12}$ aralkyl group which may be substituted by a group(s) selected from the group consisting of a halogen atom, $C_1$-$C_6$ alkyl group, halogeno $C_1$-$C_6$ alkyl group, $C_1$-$C_6$ alkoxy group and halogeno $C_1$-$C_6$ alkoxy group" represented by $R^5$ and $R^6$, there may be mentioned groups in which the aryl group portion is a phenyl group or naphthyl group, and the alkylene portion is a straight or branched $C_7$-$C_{12}$ aralkyl group, for example, a benzyl group, 1-phenethyl group, 2-phenethyl group, 1-phenylpropyl group, 2-phenylpropyl group, 3-phenylpropyl group, 1-methyl-2-phenylethyl group, 1-methyl-1-phenylethyl group, 1-phenylbutyl group, 2-phenylbutyl group, 3-phenylbutyl group, 4-phenylbutyl group, 1,1-dimethyl-2-phenylethyl group, 1-methyl-2-phenylpropyl group, 1-phenylpentyl group, 2-phenylpentyl group, 3-phenylpentyl group, 4-phenylpentyl group, 5-phenylpentyl group, 1-phenylhexyl group, 2-phenylhexyl group, 3-phenylhexyl group, 4-phenylhexyl group, 5-phenylhexyl group, 6-phenylhexyl group, α-naphthylmethyl group, β-naphthylmethyl group, 1-(α-naphthyl)ethyl group, 2-(α-naphthyl)ethyl group, 1-(β-naphthyl)ethyl group or 2-(β-naphthyl)ethyl group, preferably a benzyl group, 1-phenethyl group, 2-phenethyl group or 1-methyl-2-phenylethyl group, more preferably a benzyl group, 1-phenethyl group or 2-phenethyl group, particularly preferably a benzyl group or 1-phenethyl group.

In $R^2$, the halogen atom, $C_1$-$C_6$ alkyl group, halogeno $C_1$-$C_6$ alkyl group, $C_1$-$C_6$ alkoxy group and halogeno $C_1$-$C_6$ alkoxy group which are a substituent on an aryl group of the $C_7$-$C_{12}$ aralkyl group and the benzoyl group represented by $R^5$ and $R^6$, there may be preferably mentioned a halogen atom, $C_1$-$C_4$ alkyl group, fluoro $C_1$-$C_4$ alkyl group, $C_1$-$C_4$ alkoxy group or fluoro $C_1$-$C_4$ alkoxy group, more preferably a fluorine atom, chlorine atom, methyl group, ethyl group, trifluoromethyl group, methoxy group, ethoxy group or difluoromethoxy group, further more preferably a fluorine atom, methyl group, trifluoromethyl group, methoxy group or difluoromethoxy group, particularly preferably a fluorine atom or methoxy group.

As the "group: —$NR^5R^6$" represented by $R^2$, there may be preferably mentioned an amino group, $C_1$-$C_4$ alkylamino group, di($C_1$-$C_4$ alkyl)amino group, fluoro $C_1$-$C_4$ alkylamino group, $C_3$-$C_6$ cycloalkylamino group, $C_1$-$C_4$ alkyl-carbonylamino group, $C_3$-$C_6$ cycloalkyl-carbonylamino group, N-($C_3$-$C_6$ cycloalkyl-carbonyl)-N-($C_1$-$C_4$ alkyl)amino group, formylamino group, $C_1$-$C_4$ alkoxy-carbonylamino group, $C_1$-$C_4$ alkylsulfonylamino group, or a benzylamino group, 1-phenethylamino group or benzoylamino group the phenyl group portion thereof may be substituted by a group(s) selected from the group consisting of a halogen atom, $C_1$-$C_4$ alkyl group, fluoro $C_1$-$C_4$ alkyl group, $C_1$-$C_4$ alkoxy group and fluoro $C_1$-$C_4$ alkoxy group, more preferably an amino group, methylamino group, dimethylamino group, ethylamino group, diethylamino group, propylamino group, isopropylamino group, trifluoromethylamino group, 2,2,2-trifluoroethylamino group, cyclopropylamino group, cyclohexylamino group, acetylamino group, propionylamino group, cyclopropylcarbonylamino group, cyclopentylcarbonylamino group, N-cyclopropylcarbonyl-N-methylamino group, formylamino group, methoxycarbonylamino group, ethoxycarbonylamino group, t-butoxycarbonylamino group, methylsulfonylamino group, ethylsulfonylamino group, or a benzylamino group, 1-phenethylamino group or benzoylamino group the phenyl group portion thereof may be substituted by a group(s) selected from the group consisting of a fluorine atom, methyl group, trifluoromethyl group, methoxy group and difluoromethoxy group, further more preferably an amino group, methylamino group, dimethylamino group, ethylamino group, isopropylamino group, 2,2,2-trifluoroethylamino group, cyclopropylamino group, acetylamino group, cyclopropylcarbonylamino group, cyclopentylcarbonylamino group, N-cyclopropylcarbonyl-N-methylamino group, methoxycarbonylamino group, methylsulfonylamino group, benzylamino group, 4-fluorobenzylamino group, 4-methoxybenzylamino group, 1-phenethylamino group, 1-(4-fluorophenyl)ethylamino group or benzoylamino group, particularly preferably an amino group, methylamino group, ethylamino group, isopropylamino group, 2,2,2-trifluoroethylamino group, acetylamino group, cyclopropylcarbonylamino group, cyclopentylcarbonylamino group, methoxycarbonylamino group, 4-methoxybenzylamino group, 1-phenethylamino group or benzoylamino group.

As $R^2$, there may be preferably mentioned a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group, amino group, $C_1$-$C_4$ alkylamino group, di($C_1$-$C_4$ alkyl)amino group, fluoro $C_1$-$C_4$ alkylamino group, $C_3$-$C_6$ cycloalkylamino group, $C_1$-$C_4$ alkyl-carbonylamino group, $C_3$-$C_6$ cycloalkyl-carbonylamino group, N-($C_3$-$C_6$ cycloalkyl-carbonyl)-N-($C_1$-$C_4$ alkyl)amino group, formylamino group, $C_1$-$C_4$ alkoxy-carbonylamino group, $C_1$-$C_4$ alkylsulfonylamino group, or a benzylamino group, 1-phenethylamino group or benzoylamino group the phenyl group portion thereof may be substituted by a group(s) selected from the group consisting of a halogen atom, $C_1$-$C_4$ alkyl group, fluoro $C_1$-$C_4$ alkyl group, $C_1$-$C_4$ alkoxy group and fluoro $C_1$-$C_4$ alkoxy group, more preferably a hydrogen atom, fluorine atom, chlorine atom, methyl group, methoxy group, methylthio group, methylsulfinyl group, methylsulfonyl group, amino group, methylamino group, dimethylamino group, ethylamino group, diethylamino group, propylamino group, isopropylamino group, trifluoromethylamino group, 2,2,2-trifluoroethylamino group, cyclopropylamino group, cyclohexylamino group, acetylamino group, propionylamino group, cyclopropylcarbonylamino group, cyclopentylcarbonylamino group, N-cyclopropylcarbonyl-N-methylamino group, formylamino group, methoxycarbonylamino group, ethoxycarbonylamino group, t-butoxycarbonylamino group, methylsulfonylamino group, ethylsulfonylamino group, or a benzylamino group, 1-phenethylamino group or benzoylamino group the phenyl group portion thereof may be substituted by a group consisting of a fluorine atom, methyl group, trifluoromethyl group, methoxy group and difluoromethoxy group, further more preferably a hydrogen atom, fluorine atom, methyl group, methoxy group, methylthio group, methylsulfinyl group, methylsulfonyl group, amino group, methylamino group, dimethylamino group, ethylamino group, isopropylamino group, 2,2,2-trifluoroethylamino group, cyclopropylamino group, acetylamino group, cyclopropylcarbonylamino group, cyclopentylcarbonylamino group, N-cyclopropylcarbonyl-N-methylamino group, methoxycarbonylamino group, methylsulfonylamino group, 4-methoxybenzylamino group, 1-phenethylamino group or benzoylamino group, particularly preferably a hydrogen atom, methoxy group, amino group, methylamino group, ethylamino group, isopropylamino group, 2,2,2-trifluoroethylamino group, acetylamino group, cyclopropylcarbonylamino group, cyclopentylcarbonylamino group, methoxycarbonylamino group, methylsulfonylamino group, 4-methoxybenzylamino group, 1-phenethylamino group or benzoylamino group.

Q represents CH or a nitrogen atom.

$R_3$ is preferably a hydrogen atom, $C_1$-$C_4$ alkyl group or amino group, more preferably a hydrogen atom, methyl group or amino group, particularly preferably a hydrogen atom.

$R_7$ is preferably a hydrogen atom or $C_1$-$C_4$ alkyl group, more preferably a hydrogen atom, methyl group or ethyl group, particularly preferably a hydrogen atom or methyl group.

As the "group: —$NR^{10}R^{11}$" represented by $R^8$ and $R^{12}$, there may be preferably mentioned an amino group, $C_1$-$C_4$ alkylamino group, di($C_1$-$C_4$ alkyl)amino group, $C_1$-$C_4$ alkyl-carbonylamino group, formylamino group, $C_1$-$C_4$ alkoxy-carbonylamino group or $C_1$-$C_4$ alkylsulfonylamino group, more preferably an amino group, methylamino group, dimethylamino group, ethylamino group, diethylamino group, isopropylamino group, acetylamino group, formylamino group, methoxy-carbonylamino group, ethoxycarbonylamino group, methylsulfonyl-amino group or ethylsulfonylamino group, particularly preferably an amino group, methylamino group, dimethylamino group, acetylamino group, formylamino group, methoxy-carbonylamino group or methylsulfonylamino group.

As $R^8$, there may be preferably mentioned a hydrogen atom, $C_1$-$C_4$ alkyl group, amino group, $C_1$-$C_4$ alkylamino group, di($C_1$-$C_4$ alkyl)amino group, $C_1$-$C_4$ alkyl-carbonylamino group, formylamino group, $C_1$-$C_4$ alkoxy-carbonylamino group or $C_1$-$C_4$ alkylsulfonylamino group, more preferably a hydrogen atom, methyl group, ethyl group, amino group, methylamino group, dimethylamino group, ethylamino group, diethylamino group, isopropylamino group, acetylamino group, formylamino group, methoxycarbonylamino group, ethoxycarbonylamino group, methylsulfonylamino group or ethylsulfonylamino group, further more preferably a hydrogen atom, methyl group, amino group, methylamino group, dimethylamino group, acetylamino group, formylamino group, methoxycarbonylamino group or methylsulfonylamino group, particularly preferably a hydrogen atom, methyl group or amino group.

$R^9$ is preferably a hydrogen atom or $C_1$-$C_4$ alkyl group, more preferably a hydrogen atom, methyl group or ethyl group, particularly preferably a hydrogen atom or methyl group.

$R^{12}$ is preferably a hydrogen atom, $C_1$-$C_4$ alkyl group, fluoro $C_1$-$C_4$ alkyl group, amino group, $C_1$-$C_4$ alkylamino group, di($C_1$-$C_4$ alkyl)amino group, $C_1$-$C_4$ alkyl-carbonylamino group, formylamino group, $C_1$-$C_4$ alkoxy-carbonylamino group or $C_1$-$C_4$ alkylsulfonylamino group, more preferably a hydrogen atom, methyl group, ethyl group, trifluoromethyl group, 2,2,2-trifluoroethyl group, amino group, methylamino group, dimethylamino group, ethylamino group, diethylamino group, isopropylamino group, acetylamino group, formylamino group, methoxycarbonylamino group, ethoxycarbonylamino group, methylsulfonylamino group or ethylsulfonylamino group, further more preferably a hydrogen atom, methyl group, trifluoromethyl group, amino group, methylamino group, dimethylamino group, acetylamino group, formylamino group, methoxycarbonylamino group or methylsulfonylamino group, particularly preferably a hydrogen atom, methyl group, trifluoromethyl group, amino group or acetylamino group.

$R^4$ is preferably a 1,6-dihydro-6-oxopyridazin-3-yl group, 1,6-dihydro-4-methyl-6-oxopyridazin-3-yl group, 4-ethyl-1,6-dihydro-6-oxopyridazin-3-yl group, 1,6-dihydro-5-methyl-6-oxopyridazin-3-yl group, 5-ethyl-1,6-dihydro-6-oxopyridazin-3-yl group, 5-amino-1,6-dihydro-6-oxopyridazin-3-yl group, 1,6-dihydro-5-methylamino-6-oxopyridazin-3-yl group, 5-dimethylamino-1,6-dihydro-6-oxopyridazin-3-yl group, 5-ethylamino-1,6-dihydro-6-oxopyridazin-3-yl group, 5-diethylamino-1,6-dihydro-6-oxopyridazin-3-yl group, 1,6-dihydro-5-isopropylamino-6-oxopyridazin-3-yl group, 5-formylamino-1,6-dihydro-6-oxopyridazin-3-yl group, 5-acetylamino-1,6-dihydro-6-oxopyridazin-3-yl group, 1,6-dihydro-5-methoxycarbonylamino-6-oxopyridazin-3-yl group, 5-ethoxycarbonylamino-1,6-dihydro-6-oxopyridazin-3-yl group, 1,6-dihydro-5-methylsulfonylamino-6-oxopyridazin-3-yl group, 5-ethylsulfonylamino-1,6-dihydro-6-oxopyridazin-3-yl group, 1,6-dihydro-1-methyl-6-oxopyridazin-3-yl group, 1-ethyl-1,6-dihydro-6-oxopyridazin-3-yl group, 1,6-dihydro-1,4-dimethyl-6-oxopyridazin-3-yl group, 1,6-dihydro-1,5-dimethyl-6-oxopyridazin-3-yl group, 1,6-dihydro-4,5-dimethyl-6-oxopyridazin-3-yl group, 5-amino-1,6-dihydro-4-methyl-6-oxopyridazin-3-yl group, 5-amino-1,6-dihydro-1-methyl-6-oxopyridazin-3-yl group, 1,6-dihydro-1-methyl-5-methylamino-6-oxopyridazin-3-yl group, 5-dimethylamino-1,6-dihydro-1-methyl-6-oxopyridazin-3-yl group, 5-acetylamino-1,6-dihydro-1-methyl-6-oxopyridazin-3-yl group, 1,6-dihydro-5-methoxycarbonylamino-1-methyl-6-oxopyridazin-3-yl group, 1,6-dihydro-1-methyl-5-methylsulfonylamino-6-oxopyridazin-3-yl group, 1,6-dihydro-1,4,5-trimethyl-6-oxopyridazin-3-yl group, 5-amino-1,6-dihydro-1,4-dimethyl-6-oxopyridazin-3-yl group, [1,2,4]triazolo[4,3-b]pyridazin-6-yl group, 3-methyl-[1,2,4]triazolo[4,3-b]pyridazin-6-yl group, 3-ethyl-[1,2,4]triazolo[4,3-b]pyridazin-6-yl group, 3-trifluoromethyl-[1,2,4]triazolo[4,3-b]pyridazin-6-yl group, 3-(2,2,2-trifluoroethyl)-[1,2,4]triazolo[4,3-b]-pyridazin-6-yl group, 3-amino-[1,2,4]triazolo[4,3-b]-pyridazin-6-yl group, 3-methylamino-[1,2,4]triazolo[4,3-b]-pyridazin-6-yl group, 3-dimethylamino-[1,2,4]triazolo[4,3-b]pyridazin-6-yl group, 3-ethylamino-[1,2,4]triazolo[4,3-b]pyridazin-6-yl group, 3-formylamino-[1,2,4]triazolo[4,3-b]pyridazin-6-yl group, 3-acetylamino-[1,2,4]triazolo[4,3-b]pyridazin-6-yl group, 3-methoxycarbonylamino-[1,2,4]triazolo[4,3-b]pyridazin-6-yl group, 3-ethoxycarbonylamino-[1,2,4]triazolo[4,3-b]pyridazin-6-yl group, 3-methylsulfonylamino-[1,2,4]triazolo[4,3-b]pyridazin-6-yl group, 3-ethylsulfonylamino-[1,2,4]triazolo[4,3-b]pyridazin-6-yl group, 7-methyl-[1,2,4]triazolo[4,3-b]pyridazin-6-yl group, 7-ethyl-[1,2,4]triazolo[4,3-b]pyridazin-6-yl group, 8-methyl-[1,2,4]triazolo[4,3-b]pyridazin-6-yl group, 8-ethyl-[1,2,4]triazolo[4,3-b]pyridazin-6-yl group, 8-amino-[1,2,4]triazolo[4,3-b]pyridazin-6-yl group, 8-methylamino-[1,2,4]triazolo[4,3-b]pyridazin-6-yl group, 8-dimethylamino-[1,2,4]triazolo[4,3-b]pyridazin-6-yl group, 8-ethylamino-[1,2,4]triazolo[4,3-b]pyridazin-6-yl group, 8-formylamino-[1,2,4]triazolo[4,3-b]pyridazin-6-yl group, 8-acetylamino-[1,2,4]triazolo[4,3-b]pyridazin-6-yl group, 8-methoxycarbonylamino-[1,2,4]triazolo[4,3-b]pyridazin-6-yl group, 8-ethoxycarbonylamino-[1,2,4]triazolo[4,3-b]pyridazin-6-yl group, 8-methylsulfonylamino-[1,2,4]triazolo[4,3-b]pyridazin-6-yl group, 8-ethylsulfonylamino-[1,2,4]triazolo[4,3-b]pyridazin-6-yl group, 3,8-dimethyl-[1,2,4]triazolo[4,3-b]pyridazin-6-yl group, 7,8-dimethyl-[1,2,4]triazolo[4,3-b]pyridazin-6-yl group, 3-amino-8-methyl-[1,2,4]-triazolo[4,3-b]pyridazin-6-yl group, 8-amino-3-methyl-[1,2,4]triazolo[4,3-b]pyridazin-6-yl group, 3,8-diamino-[1,2,4]triazolo[4,3-b]pyridazin-6-yl group, 1,4,5,6-tetrahydro-6-oxopyridazin-3-yl group, 1,4,5,6-tetrahydro-4-methyl-6-oxopyridazin-3-yl group, 4-ethyl-1,4,5,6-tetrahydro-6-oxopyridazin-3-yl group, 1,4,5,6-tetrahydro-5-methyl-6-oxopyridazin-3-yl group, 5-ethyl-1,4,5,6-tetrahydro-6-oxopyridazin-3-yl group, 5-amino-1,4,5,6-tetrahydro-6-oxopyridazin-3-yl group, 1,4,5,6-tetrahydro-5-methylamino-6-oxopyridazin-3-yl group, 5-dimethylamino-1,4,5,6-tetrahydro-6-oxopyridazin-3-yl group, 5-ethylamino-1,4,5,6-tetrahydro-6-oxopyridazin-3-yl group, 5-diethylamino-1,4,5,6-tetrahydro-6-oxopyridazin-3-yl group, 1,4,5,6-tetrahydro-5-isopropylamino-6-oxopyridazin-3-yl group, 5-formylamino-1,4,5,6-tetrahydro-6-oxopyridazin-3-yl group, 5-acetylamino-1,4,5,6-tetrahydro-6-oxopyridazin-3-yl group, 1,4,5,6-tetrahydro-5-methoxycarbonylamino-6-oxopyridazin-3-yl group, 5-ethoxycarbonylamino-1,4,5,6-tetrahydro-6-oxopyridazin-3-yl group, 1,4,5,6-tetrahydro-5-methylsulfonylamino-6-oxopyridazin-3-yl group, 5-ethylsulfonylamino-1,4,5,6-tetrahydro-6-oxopyridazin-3-yl group, 1,4,5,6-tetrahydro-1-methyl-6-oxopyridazin-3-yl group, 1-ethyl-1,4,5,6-tetrahydro-6-oxopyridazin-3-yl group, 1,4,5,6-tetrahydro-1,4-dimethyl-6-oxopyridazin-3-yl group, 1,4,5,6-tetrahydro-1,5-dimethyl-6-oxopyridazin-3-yl group, 1,4,5,6-tetrahydro-4,5-dimethyl-6-oxopyridazin-3-yl group, 5-amino-1,4,5,6-tetrahydro-1-methyl-6-oxopyridazin-3-yl group, 7,8-dihydro-[1,2,4]triazolo[4,3-b]pyridazin-6-yl group, 7,8-dihydro-3-methyl-[1,2,4]triazolo[4,3-b]pyridazin-6-yl group, 7,8-dihydro-3-trifluoromethyl-[1,2,4]triazolo[4,3-b]pyridazin-6-yl group, 7,8-dihydro-3-(2,2,2-trifluoroethyl)-[1,2,4]triazolo[4,3-b]pyridazin-6-yl group, 3-amino-7,8-dihydro-[1,2,4]triazolo[4,3-b]pyridazin-6-yl group, 7,8-dihydro-3-methylamino-[1,2,4]triazolo[4,3-b]pyridazin-6-yl group, 3-dimethylamino-7,8-dihydro-[1,2,4]-triazolo[4,3-b]pyridazin-6-yl group, 3-acetylamino-7,8-dihydro-[1,2,4]triazolo[4,3-b]pyridazin-6-yl group, 7,8-dihydro-3-methoxycarbonylamino-[1,2,4]triazolo[4,3-b]-pyridazin-6-yl group, 7,8-dihydro-3-methylsulfonylamino-[1,2,4]triazolo[4,3-b]pyridazin-6-yl group, 7,8-dihydro-7-methyl-[1,2,4]triazolo[4,3-b]pyridazin-6-yl group, 7,8-dihydro-8-methyl-[1,2,4]triazolo[4,3-b]pyridazin-6-yl group, 8-amino-7,8-dihydro-[1,2,4]triazolo[4,3-b]pyridazin-6-yl group, 7,8-dihydro-8-methylamino-[1,2,4]triazolo[4,3-b]pyridazin-6-yl group, 8-dimethylamino-7,8-dihydro-[1,2,4]triazolo[4,3-b]pyridazin-6-yl group, 8-acetylamino-7,8-dihydro-[1,2,4]triazolo[4,3-b]pyridazin-6-yl group, 7,8-dihydro-8-methoxycarbonylamino-[1,2,4]triazolo[4,3-b]pyridazin-6-yl group, 7,8-dihydro-8-methylsulfonylamino-[1,2,4]triazolo[4,3-b]pyridazin-6-yl group, 7,8-dihydro-3,8-dimethyl-[1,2,4]triazolo[4,3-b]pyridazin-6-yl group, 7,8-dihydro-7,8-dimethyl-[1,2,4]triazolo[4,3-b]pyridazin-6-yl group, 3-amino-7,8-dihydro-8-methyl-[1,2,4]triazolo[4,3-b]pyridazin-6-yl group or 8-amino-7,8-dihydro-3-methyl-[1,2,4]triazolo[4,3-b]pyridazin-6-yl group, more preferably a 1,6-dihydro-6-oxopyridazin-3-yl group, 1,6-dihydro-4-methyl-6-oxopyridazin-3-yl group, 1,6-dihydro-5-methyl-6-oxopyridazin-3-yl group, 5-amino-1,6-dihydro-6-oxopyridazin-3-yl group, 1,6-dihydro-5-methyl-amino-6-oxopyridazin-3-yl group, 5-dimethylamino-1,6-dihydro-6-oxopyridazin-3-yl group, 5-acetylamino-1,6-dihydro-6-oxopyridazin-3-yl group, 1,6-dihydro-5-methoxy-carbonylamino-6-oxopyridazin-3-yl group, 1,6-dihydro-5-methylsulfonylamino-6-oxopyridazin-3-yl group, 1,6-dihydro-1-methyl-6-oxopyridazin-3-yl group, 1-ethyl-1,6-dihydro-6-oxopyridazin-3-yl group, 1,6-dihydro-1,5-dimethyl-6-oxo-pyridazin-3-yl group, 5-amino-1,6-dihydro-1-methyl-6-oxo-pyridazin-3-yl group, [1,2,4]triazolo[4,3-b]pyridazin-6-yl group, 3-methyl-[1,2,4]triazolo[4,3-b]pyridazin-6-yl group, 3-trifluoromethyl-[1,2,4]triazolo[4,3-b]pyridazin-6-yl group, 3-(2,2,2-trifluoroethyl)-[1,2,4]triazolo[4,3-b]-pyridazin-6-yl group, 3-amino-[1,2,4]triazolo[4,3-b]pyridazin-6-yl group, 3-methylamino-[1,2,4]triazolo[4,3-b]pyridazin-6-yl group, 3-dimethylamino-[1,2,4]triazolo[4,3-b]-pyridazin-6-yl group, 3-acetylamino-[1,2,4]triazolo[4,3-b]-pyridazin-6-yl group, 3-methoxycarbonylamino-[1,2,4]triazolo[4,3-b]pyridazin-6-yl group, 3-methylsulfonylamino-[1,2,4]triazolo[4,3-b]pyridazin-6-yl group, 7-methyl-[1,2,4]triazolo[4,3-b]pyridazin-6-yl group, 8-methyl-[1,2,4]triazolo[4,3-b]pyridazin-6-yl group, 8-amino-[1,2,4]triazolo[4,3-b]pyridazin-6-yl group, 8-methylamino-[1,2,4]triazolo[4,3-b]pyridazin-6-yl group, 8-dimethylamino-[1,2,4]triazolo[4,3-b]pyridazin-6-yl group, 8-acetylamino-[1,2,4]triazolo[4,3-b]pyridazin-6-yl group, 8-methoxycarbonylamino-[1,2,4]triazolo[4,3-b]pyridazin-6-yl group, 8-methylsulfonylamino-[1,2,4]triazolo[4,3-b]pyridazin-6-yl group, 3,8-dimethyl-[1,2,4]triazolo[4,3-b]pyridazin-6-yl group, 7,8-dimethyl-[1,2,4]triazolo[4,3-b]pyridazin-6-yl group, 3-amino-8-methyl-[1,2,4]triazolo[4,3-b]-pyridazin-6-yl group, 8-amino-3-methyl-[1,2,4]triazolo[4,3-b]pyridazin-6-yl group, 1,4,5,6-tetrahydro-6-oxopyridazin-3-yl group, 1,4,5,6-tetrahydro-4-methyl-6-oxopyridazin-3-yl group, 1,4,5,6-tetrahydro-5-methyl-6-oxopyridazin-3-yl group, 5-amino-1,4,5,6-tetrahydro-6-oxopyridazin-3-yl group, 1,4,5,6-tetrahydro-5-methylamino-6-oxopyridazin-3-yl group, 5-acetylamino-1,4,5,6-tetrahydro-6-oxopyridazin-3-yl group, 1,4,5,6-tetrahydro-5-methoxycarbonylamino-6-oxopyridazin-3-yl group, 1,4,5,6-tetrahydro-5-methylsulfonyl-amino-6-oxopyridazin-3-yl group, 1,4,5,6-tetrahydro-1-methyl-6-oxopyridazin-3-yl group, 1,4,5,6-tetrahydro-1,4-dimethyl-6-oxopyridazin-3-yl group, 1,4,5,6-tetrahydro-1,5-dimethyl-6-oxopyridazin-3-yl group, 5-amino-1,4,5,6-tetrahydro-1-methyl-6-oxopyridazin-3-yl group, 7,8-dihydro-[1,2,4]triazolo[4,3-b]pyridazin-6-yl group, 7,8-dihydro-3-methyl-[1,2,4]triazolo[4,3-b]pyridazin-6-yl group, 7,8-dihydro-3-trifluoromethyl-[1,2,4]triazolo[4,3-b]pyridazin-6-yl group, 3-amino-7,8-dihydro-[1,2,4]triazolo[4,3-b]-pyridazin-6-yl group, 7,8-dihydro-3-methylamino-[1,2,4]triazolo[4,3-b]pyridazin-6-yl group, 3-acetylamino-7,8-dihydro-[1,2,4]triazolo[4,3-b]pyridazin-6-yl group, 7,8-dihydro-3-methoxycarbonylamino-[1,2,4]triazolo[4,3-b]-pyridazin-6-yl group, 7,8-dihydro-3-methylsulfonylamino-[1,2,4]triazolo[4,3-b]pyridazin-6-yl group, 7,8-dihydro-7-methyl-[1,2,4]triazolo[4,3-b]pyridazin-6-yl group, 7,8-dihydro-8-methyl-[1,2,4]triazolo[4,3-b]pyridazin-6-yl group or 8-amino-7,8-dihydro-[1,2,4]triazolo[4,3-b]pyridazin-6-yl group, further more preferably a 1,6-dihydro-6-oxopyridazin-3-yl group, 1,6-dihydro-4-methyl-6-oxopyridazin-3-yl group, 1,6-dihydro-5-methyl-6-oxopyridazin-3-yl group, 5-amino-1,6-dihydro-6-oxopyridazin-3-yl group, 5-acetylamino-1,6-dihydro-6-oxopyridazin-3-yl group, 1,6-dihydro-5-methoxycarbonylamino-6-oxopyridazin-3-yl group, 1,6-dihydro-5-methylsulfonylamino-6-oxopyridazin-3-yl group, 1,6-dihydro-1-methyl-6-oxopyridazin-3-yl group, 5-amino-1,6-dihydro-1-methyl-6-oxopyridazin-3-yl group, [1,2,4]triazolo[4,3-b]-pyridazin-6-yl group, 3-methyl-[1,2,4]triazolo[4,3-b]-pyridazin-6-yl group, 3-trifluoromethyl-[1,2,4]triazolo-[4,3-b]pyridazin-6-yl group, 3-amino-[1,2,4]triazolo[4,3-b]pyridazin-6-yl group, 3-methylamino-[1,2,4]triazolo[4,3-b]pyridazin-6-yl group, 3-acetylamino-[1,2,4]triazolo[4,3-b]pyridazin-6-yl group, 3-methoxycarbonylamino-[1,2,4]triazolo[4,3-b]pyridazin-6-yl group, 3-methylsulfonylamino-[1,2,4]triazolo[4,3-b]pyridazin-6-yl group, 7-methyl-[1,2,4]triazolo[4,3-b]pyridazin-6-yl group, 8-methyl-[1,2,4]triazolo[4,3-b]pyridazin-6-yl group, 8-amino-[1,2,4]triazolo[4,3-b]pyridazin-6-yl group, 1,4,5,6-tetrahydro-6-oxopyridazin-3-yl group, 1,4,5,6-tetrahydro-4-methyl-6-oxopyridazin-3-yl group, 1,4,5,6-tetrahydro-5-methyl-6-oxopyridazin-3-yl group, 5-amino-1,4,5,6-tetrahydro-6-oxopyridazin-3-yl group, 1,4,5,6-tetrahydro-1-methyl-6-oxopyridazin-3-yl group, 1,4,5,6-tetrahydro-1,5-dimethyl-6-oxopyridazin-3-yl group, 7,8-dihydro-[1,2,4]triazolo[4,3-b]pyridazin-6-yl group, 7,8-dihydro-3-methyl-[1,2,4]triazolo[4,3-b]pyridazin-6-yl group, 7,8-dihydro-3-trifluoromethyl-[1,2,4]triazolo[4,3-b]pyridazin-6-yl group, 3-amino-7,8-dihydro-[1,2,4]triazolo[4,3-b]pyridazin-6-yl group, 7,8-dihydro-7-methyl-[1,2,4]triazolo[4,3-b]pyridazin-6-yl group or 7,8-dihydro-8-methyl-[1,2,4]triazolo[4,3-b]pyridazin-6-yl group, particularly preferably a 1,6-dihydro-6-oxopyridazin-3-yl group, 1,6-dihydro-4-methyl-6-oxopyridazin-3-yl group, 1,6-dihydro-5-methyl-6-oxopyridazin-3-yl group, 5-amino-1,6-dihydro-6-oxopyridazin-3-yl group, 1,6-dihydro-1-methyl-6-oxopyridazin-3-yl group, [1,2,4]triazolo[4,3-b]-pyridazin-6-yl group, 3-methyl-[1,2,4]triazolo[4,3-b]-pyridazin-6-yl group, 3-trifluoromethyl-[1,2,4]triazolo-[4,3-b]pyridazin-6-yl group, 3-amino-[1,2,4]triazolo[4,3-b]pyridazin-6-yl group, 3-acetylamino-[1,2,4]triazolo[4,3-b]pyridazin-6-yl group, 1,4,5,6-tetrahydro-6-oxopyridazin-3-yl group, 1,4,5,6-tetrahydro-4-methyl-6-oxopyridazin-3-yl group, 1,4,5,6-tetrahydro-5-methyl-6-oxopyridazin-3-yl group, 1,4,5,6-tetrahydro-1-methyl-6-oxopyridazin-3-yl group, 7,8-dihydro-[1,2,4]triazolo[4,3-b]pyridazin-6-yl group or 7,8-dihydro-3-methyl-[1,2,4]triazolo[4,3-b]-pyridazin-6-yl group.

In the compounds represented by the formula (I), there are cases in which they have an asymmetric center(s) in the molecule, and in such a case, there exists an optical isomer (R-isomer, S-isomer), and the present invention also includes such isomers.

In the compounds represented by the formula (I) of the present invention, there may be preferably mentioned, (1) a compound wherein $R^1$ represents a phenyl group which may be substituted by 1 to 3 group(s) selected from the group consisting of a halogen atom, $C_1$-$C_4$ alkyl group, halogen $C_1$-$C_4$ alkyl group, $C_1$-$C_4$ alkoxy group, halogen $C_1$-$C_4$ alkoxy group and $C_1$-$C_4$ alkylthio group, (2) a compound wherein $R^1$ represents a phenyl group which may be substituted by 1 to 2 group(s) selected from the group consisting of a halogen atom, $C_1$-$C_4$ alkyl group, fluoro $C_1$-$C_4$ alkyl group, $C_1$-$C_4$ alkoxy group, fluoro $C_1$-$C_4$ alkoxy group and $C_1$-$C_4$ alkylthio group, (3) a compound wherein $R^1$ represents a phenyl group which may be substituted by 1 to 2 group(s) selected from the group consisting of a fluorine atom, chlorine atom, bromine atom, methyl group, ethyl group, isopropyl group, difluoromethyl group, trifluoromethyl group, 2-fluoroethyl group, 2,2,2-trifluoroethyl group, methoxy group, ethoxy group, isopropoxy group, fluoromethoxy group, difluoromethoxy group, trifluoromethoxy group and methylthio group, (4) a compound wherein $R^1$ represents a phenyl group which may be substituted by 1 to 2 group(s) selected from the group consisting of a fluorine atom, chlorine atom, methyl group, difluoromethyl group, trifluoromethyl group, methoxy group, fluoromethoxy group, difluoromethoxy group and trifluoromethoxy group, (5) a compound wherein $R^1$ represents a phenyl group, 2-fluorophenyl group, 3-fluorophenyl group, 4-fluorophenyl group, 3-chlorophenyl group, 4-chlorophenyl group, 3,4-difluorophenyl group, 2,4-difluorophenyl group, 3,4-dichlorophenyl group, 3-chloro-4-fluorophenyl group, 4-chloro-3-fluorophenyl group or 3-trifluoromethylphenyl group, (6) a compound wherein $R^2$ represents a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group or group: —$NR^5R^6$ (wherein $R^5$ and $R^6$ may be the same or different from each other, and each represents a hydrogen atom, $C_1$-$C_4$ alkyl group, halogen $C_1$-$C_4$ alkyl group, $C_3$-$C_6$ cycloalkyl group, $C_1$-$C_4$ alkylcarbonyl group, $C_3$-$C_6$ cycloalkyl-carbonyl group, formyl group, $C_1$-$C_4$ alkoxycarbonyl group or $C_1$-$C_4$ alkylsulfonyl group, or a $C_7$-$C_{12}$ aralkyl group or benzoyl group which may be substituted by the group(s) selected from the group consisting of a halogen atom, $C_1$-$C_4$ alkyl group, halogen $C_1$-$C_4$ alkyl group, $C_1$-$C_4$ alkoxy group and halogen $C_1$-$C_4$ alkoxy group.), (7) a compound wherein $R^2$ represents a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group, amino group, $C_1$-$C_4$ alkylamino group, di($C_1$-$C_4$ alkyl)amino group, fluoro $C_1$-$C_4$ alkylamino group, $C_3$-$C_6$ cycloalkylamino group, $C_1$-$C_4$ alkylcarbonylamino group, $C_3$-$C_6$ cycloalkyl-carbonylamino group, N—($C_3$-$C_6$ cycloalkylcarbonyl)—N—($C_1$-$C_4$ alkyl)amino group, formylamino group, $C_1$-$C_4$ alkoxycarbonylamino group, $C_1$-$C_4$ alkylsulfonylamino group, or a benzylamino group, 1-phenethylamino group or benzoylamino group the phenyl group portion thereof may be substituted by the group(s) selected from the group consisting of a halogen atom, $C_1$-$C_4$ alkyl group, fluoro $C_1$-$C_4$ alkyl group, $C_1$-$C_4$ alkoxy group and fluoro $C_1$-$C_4$ alkoxy group, (8) a compound wherein $R^2$ represents a hydrogen atom, fluorine atom, chlorine atom, methyl group, methoxy group, methylthio group, methylsulfinyl group, methylsulfonyl group, amino group, methylamino group, dimethylamino group, ethylamino group, diethylamino group, propylamino group, isopropylamino group, trifluoromethylamino group, 2,2,2-trifluoroethylamino group, cyclopropylamino group, cyclohexylamino group, acetylamino group, propionylamino group, cyclopropylcarbonylamino group, cyclopentylcarbonylamino group, N-cyclopropylcarbonyl-N-methylamino group, formylamino group, methoxycarbonylamino group, ethoxycarbonylamino group, t-butoxycarbonylamino group, methylsulfonylamino group, ethylsulfonylamino group, or a benzylamino group, 1-phenethylamino group or benzoylamino group the phenyl group portion thereof may be substituted by a group(s) selected from the group consisting of a fluorine atom, methyl group, trifluoromethyl group, methoxy group and difluoromethoxy group, (9) a compound wherein $R^2$ represents a hydrogen atom, fluorine atom, methyl group, methoxy group, methylthio group, methylsulfinyl group, methylsulfonyl group, amino group, methylamino group, dimethylamino group, ethylamino group, isopropylamino group, 2,2,2-trifluoroethylamino group, acetylamino group, cyclopropylcarbonylamino group, cyclopentylcarbonylamino group, N-cyclopropylcarbonyl-N-methylamino group, methoxycarbonylamino group, methylsulfonylamino group, 4-methoxybenzylamino group, 1-phenethylamino group or benzoylamino group,

(10) a compound wherein $R^2$ represents a hydrogen atom, methoxy group, amino group, methylamino group, ethylamino group, isopropylamino group, 2,2,2-trifluoroethylamino group, acetylamino group, cyclopropylcarbonylamino group, cyclopentylcarbonylamino group, methoxycarbonylamino group, methylsulfonylamino group, 4-methoxybenzylamino group, 1-phenethylamino group or benzoylamino group,

(11) a compound wherein $R^3$ represents a hydrogen atom, $C_1$-$C_4$ alkyl group or amino group,

(12) a compound wherein $R^3$ represents a hydrogen atom, methyl group or amino group,

(13) a compound wherein $R^3$ represents a hydrogen atom,

(14) a compound wherein $R^7$ in $R^4$ represents a hydrogen atom or $C_1$-$C_4$ alkyl group, $R^8$ represents a hydrogen atom, $C_1$-$C_4$ alkyl group, amino group, $C_1$-$C_4$ alkylamino group, di($C_1$-$C_4$ alkyl)amino group, $C_1$-$C_4$ alkyl-carbonylamino group, formylamino group, $C_1$-$C_4$ alkoxy-carbonylamino group or $C_1$-$C_4$ alkylsulfonylamino group, $R^9$ represents a hydrogen atom or $C_1$-$C_4$ alkyl group, $R^{12}$ represents a hydrogen atom, $C_1$-$C_4$ alkyl group, fluoro $C_1$-$C_4$ alkyl group, amino group, $C_1$-$C_4$ alkylamino group, di($C_1$-$C_4$ alkyl)amino group, $C_1$-$C_4$ alkylcarbonylamino group, formylamino group, $C_1$-$C_4$ alkoxycarbonylamino group or $C_1$-$C_4$ alkylsulfonylamino group (provided that $R^9$ and $R^{12}$ are not present at the same time),

(15) a compound wherein $R^7$ in $R^4$ represents a hydrogen atom, methyl group or ethyl group, $R^8$ represents a hydrogen atom, methyl group, ethyl group, amino group, methylamino group, dimethylamino group, ethylamino group, diethylamino group, isopropylamino group, acetylamino group, formylamino group, methoxycarbonylamino group, ethoxycarbonylamino group, methylsulfonylamino group or ethylsulfonylamino group, $R^9$ represents a hydrogen atom, methyl group or ethyl group, $R^{12}$ represents a hydrogen atom, methyl group, ethyl group, trifluoromethyl group, 2,2,2-trifluoroethyl group, amino group, methylamino group, dimethylamino group, ethylamino group, diethylamino group, isopropylamino group, acetylamino group, formylamino group, methoxycarbonylamino group, ethoxycarbonylamino group, methylsulfonylamino group or ethylsulfonylamino group (provided that $R^9$ and $R^{12}$ are not present at the same time),

(16) a compound wherein $R^7$ in $R^4$ represents a hydrogen atom or methyl group, $R^8$ represents a hydrogen atom, methyl group, amino group, methylamino group, dimethylamino group, acetylamino group, formylamino group, methoxycarbonylamino group or methylsulfonylamino group, $R^9$ represents a hydrogen atom or methyl group, $R^{12}$ represents a hydrogen atom, methyl group, trifluoromethyl group, amino group, methylamino group, dimethylamino group, acetylamino group, formylamino group, methoxycarbonylamino group or methylsulfonylamino group (provided that $R^9$ and $R^{12}$ are not present at the same time),

(17) a compound wherein $R^4$ represented by the formula (II) represents a 1,6-dihydro-6-oxopyridazin-3-yl group, 1,6-dihydro-4-methyl-6-oxopyridazin-3-yl group, 1,6-dihydro-5-methyl-6-oxopyridazin-3-yl group, 5-amino-1,6-dihydro-6-oxopyridazin-3-yl group, 1,6-dihydro-5-methylamino-6-oxopyridazin-3-yl group, 5-dimethylamino-1,6-dihydro-6-oxopyridazin-3-yl group, 5-acetylamino-1,6-dihydro-6-oxopyridazin-3-yl group, 1,6-dihydro-5-methoxycarbonylamino-6-oxopyridazin-3-yl group, 1,6-dihydro-5-methylsulfonylamino-6-oxopyridazin-3-yl group, 1,6-dihydro-1-methyl-6-oxopyridazin-3-yl group, 1-ethyl-1,6-dihydro-6-oxopyridazin-3-yl group, 1,6-dihydro-1,5-dimethyl-6-oxopyridazin-3-yl group or 5-amino-1,6-dihydro-1-methyl-6-oxopyridazin-3-yl group,

(18) a compound wherein $R^4$ represented by the formula (II) represents a 1,6-dihydro-6-oxopyridazin-3-yl group, 1,6-dihydro-4-methyl-6-oxopyridazin-3-yl group, 1,6-dihydro-5-methyl-6-oxopyridazin-3-yl group, 5-amino-1,6-dihydro-6-oxopyridazin-3-yl group, 5-acetylamino-1,6-dihydro-6-oxopyridazin-3-yl group, 1,6-dihydro-5-methoxycarbonylamino-6-oxopyridazin-3-yl group, 1,6-dihydro-5-methylsulfonylamino-6-oxopyridazin-3-yl group, 1,6-dihydro-1-methyl-6-oxopyridazin-3-yl group or 5-amino-1,6-dihydro-1-methyl-6-oxopyridazin-3-yl group,

(19) a compound wherein $R^4$ represented by the formula (II) represents a 1,6-dihydro-6-oxopyridazin-3-yl group, 1,6-dihydro-4-methyl-6-oxopyridazin-3-yl group, 1,6-dihydro-5-methyl-6-oxopyridazin-3-yl group, 5-amino-1,6-dihydro-6-oxopyridazin-3-yl group or 1,6-dihydro-1-methyl-6-oxo-pyridazin-3-yl group,

(20) a compound wherein $R^4$ represented by the formula (III) represents a [1,2,4]triazolo[4,3-b]pyridazin-6-yl group, 3-methyl-[1,2,4]triazolo[4,3-b]pyridazin-6-yl group, 3-trifluoromethyl-[1,2,4]triazolo[4,3-b]pyridazin-6-yl group, 3-(2,2,2-trifluoroethyl-[1,2,4]triazolo[4,3-b]pyridazin-6-yl group, 3-amino-[1,2,4]triazolo[4,3-b]pyridazin-6-yl group, 3-methylamino-[1,2,4]triazolo[4,3-b]pyridazin-6-yl group, 3-dimethylamino-[1,2,4]triazolo[4,3-b]pyridazin-6-yl group, 3-acetylamino-[1,2,4]triazolo[4,3-b]pyridazin-6-yl group, 3-methoxycarbonylamino-[1,2,4]triazolo[4,3-b]pyridazin-6-yl group, 3-methylsulfonylamino-[1,2,4]triazolo[4,3-b]pyridazin-6-yl group, 7-methyl-[1,2,4]triazolo[4,3-b]pyridazin-6-yl group, 8-methyl-[1,2,4]triazolo[4,3-b]pyridazin-6-yl group, 8-amino-[1,2,4]triazolo[4,3-b]pyridazin-6-yl group, 8-methylamino-[1,2,4]triazolo[4,3-b]pyridazin-6-yl group, 8-dimethylamino-[1,2,4]triazolo[4,3-b]pyridazin-6-yl group, 8-acetylamino-[1,2,4]triazolo[4,3-b]pyridazin-6-yl group, 8-methoxycarbonylamino-[1,2,4]triazolo[4,3-b]pyridazin-6-yl group, 8-methylsulfonylamino-[1,2,4]triazolo[4,3-b]pyridazin-6-yl group, 3,8-dimethyl-[1,2,4]triazolo[4,3-b]pyridazin-6-yl group, 7,8-dimethyl-[1,2,4]triazolo[4,3-b]pyridazin-6-yl group, 3-amino-8-methyl-[1,2,4]triazolo[4,3-b]pyridazin-6-yl group or 8-amino-3-methyl-[1,2,4]triazolo[4,3-b]pyridazin-6-yl group,

(21) a compound wherein $R^4$ represented by the formula (III) represents a [1,2,4]triazolo[4,3-b]pyridazin-6-yl group, 3-methyl-[1,2,4]triazolo[4,3-b]pyridazin-6-yl group, 3-trifluoromethyl-[1,2,4]triazolo[4,3-b]pyridazin-6-yl group, 3-amino-[1,2,4]triazolo[4,3-b]pyridazin-6-yl group, 3-methylamino-[1,2,4]triazolo[4,3-b]pyridazin-6-yl group, 3-acetylamino-[1,2,4]triazolo[4,3-b]pyridazin-6-yl group, 3-methoxycarbonylamino-[1,2,4]triazolo[4,3-b]pyridazin-6-yl group, 3-methylsulfonylamino-[1,2,4]triazolo[4,3-b]pyridazin-6-yl group, 7-methyl-[1,2,4]triazolo[4,3-b]pyridazin-6-yl group, 8-methyl-[1,2,4]triazolo[4,3-b]pyridazin-6-yl group or 8-amino-[1,2,4]triazolo[4,3-b]pyridazin-6-yl group,

(22) a compound wherein $R^4$ represented by the formula (III) represents a [1,2,4]triazolo[4,3-b]pyridazin-6-yl group, 3-methyl-[1,2,4]triazolo[4,3-b]pyridazin-6-yl group, 3-trifluoromethyl-[1,2,4]triazolo[4,3-b]pyridazin-6-yl group, 3-amino-[1,2,4]triazolo[4,3-b]pyridazin-6-yl group or 3-acetylamino-[1,2,4]triazolo[4,3-b]pyridazin-6-yl group,

(23) a compound wherein $R^4$ represented by the formula (IV) represents a 1,4,5,6-tetrahydro-6-oxopyridazin-3-yl group, 1,4,5,6-tetrahydro-4-methyl-6-oxopyridazin-3-yl group, 1,4,5,6-tetrahydro-5-methyl-6-oxopyridazin-3-yl group, 5-amino-1,4,5,6-tetrahydro-6-oxopyridazin-3-yl group, 1,4,5,6-tetrahydro-5-methylamino-6-oxopyridazin-3-yl group, 5-acetylamino-1,4,5,6-tetrahydro-6-oxopyridazin-3-yl group, 1,4,5,6-tetrahydro-5-methoxycarbonylamino-6-oxopyridazin-3-yl group, 1,4,5,6-tetrahydro-5-methylsulfonylamino-6-oxopyridazin-3-yl group, 1,4,5,6-tetrahydro-1-methyl-6-oxopyridazin-3-yl group, 1,4,5,6-tetrahydro-1,4-dimethyl-6-oxopyridazin-3-yl group, 1,4,5,6-tetrahydro-1,5-dimethyl-6-oxopyridazin-3-yl group or 5-amino-1,4,5,6-tetrahydro-1-methyl-6-oxopyridazin-3-yl group,

(24) a compound wherein $R^4$ represented by the formula (IV) represents a 1,4,5,6-tetrahydro-6-oxopyridazin-3-yl group, 1,4,5,6-tetrahydro-4-methyl-6-oxopyridazin-3-yl group, 1,4,5,6-tetrahydro-5-methyl-6-oxopyridazin-3-yl group, 5-amino-1,4,5,6-tetrahydro-6-oxopyridazin-3-yl group, 1,4,5,6-tetrahydro-1-methyl-6-oxopyridazin-3-yl group or 1,4,5,6-tetrahydro-1,5-dimethyl-6-oxopyridazin-3-yl group,

(25) a compound wherein $R^4$ represented by the formula (IV) represents a 1,4,5,6-tetrahydro-6-oxopyridazin-3-yl group, 1,4,5,6-tetrahydro-4-methyl-6-oxopyridazin-3-yl group, 1,4,5,6-tetrahydro-5-methyl-6-oxopyridazin-3-yl group or 1,4,5,6-tetrahydro-1-methyl-6-oxopyridazin-3-yl group,

(26) a compound wherein $R^4$ represented by the formula (V) represents a 7,8-dihydro-[1,2,4]triazolo[4,3-b]pyridazin-6-yl group, 7,8-dihydro-3-methyl-[1,2,4]triazolo[4,3-b]pyridazin-6-yl group, 7,8-dihydro-3-trifluoromethyl-[1,2,4]triazolo[4,3-b]pyridazin-6-yl group, 3-amino-7,8-dihydro-[1,2,4]triazolo[4,3-b]pyridazin-6-yl group, 7,8-dihydro-3-methylamino-[1,2,4]triazolo[4,3-b]pyridazin-6-yl group, 3-acetylamino-7,8-dihydro-[1,2,4]triazolo[4,3-b]pyridazin-6-yl group, 7,8-dihydro-3-methoxycarbonylamino-[1,2,4]triazolo[4,3-b]pyridazin-6-yl group, 7,8-dihydro-3-methylsulfonylamino-[1,2,4]triazolo[4,3-b]pyridazin-6-yl group, 7,8-dihydro-7-methyl-[1,2,4]triazolo[4,3-b]pyridazin-6-yl group, 7,8-dihydro-8-methyl-[1,2,4]triazolo[4,3-b]pyridazin-6-yl group or 8-amino-7,8-dihydro-[1,2,4]triazolo[4,3-b]pyridazin-6-yl group,

(27) a compound wherein $R^4$ represented by the formula (V) represents a 7,8-dihydro-[1,2,4]triazolo[4,3-b]pyridazin-6-yl group, 7,8-dihydro-3-methyl-[1,2,4]triazolo[4,3-b]pyridazin-6-yl group, 7,8-dihydro-3-trifluoromethyl-[1,2,4]triazolo[4,3-b]pyridazin-6-yl group, 3-amino-7,8-dihydro-[1,2,4]triazolo[4,3-b]pyridazin-6-yl group, 7,8-dihydro-7-methyl-[1,2,4]triazolo[4,3-b]pyridazin-6-yl group or 7,8-dihydro-8-methyl-[1,2,4]triazolo[4,3-b]pyridazin-6-yl group,

(28) a compound wherein $R^4$ represented by the formula (V) represents a 7,8-dihydro-[1,2,4]triazolo[4,3-b]pyridazin-6-yl group or 7,8-dihydro-3-methyl-[1,2,4]triazolo[4,3-b]-pyridazin-6-yl group.

Also, in the groups of the above-mentioned (1)-(5), (6)-(10), (11)-(13) and (14)-(16), the larger number represents more preferred compound, and a compound(s) optionally selected $R^1$ from the groups (1)-(5), $R^2$ from the groups (6)-(10), $R^3$ from the groups (11)-(13), $R^4$ from the groups (14)-(16), (17)-(19), (20)-(22), (23)-(25) or (26)-(28), and these are optionally combined is/are also preferred compound(s). For example, the following compounds may be mentioned.

(29) a compound represented by the formula (I):

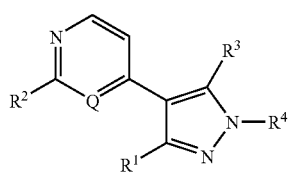

(I)

[wherein $R^1$ represents a phenyl group which may be substituted by the group(s) selected from the group consisting of a halogen atom, $C_1$-$C_6$ alkyl group, halogeno $C_1$-$C_6$ alkyl group, $C_1$-$C_6$ alkoxy group, halogeno $C_1$-$C_6$ alkoxy group and $C_1$-$C6$ alkylthio group, $R^2$ represents a hydrogen atom, halogen atom, $C_1$-$C_6$ alkyl group, $C_1$-$C_6$ alkoxy group, $C_1$-$C_6$ alkylthio group, $C_1$-$C_6$ alkylsulfinyl group, $C_1$-$C_6$ alkylsulfonyl group or group: —$NR^5R^6$ (wherein $R^5$ and $R_6$ may be the same or different from each other, and each represents a hydrogen atom, $C_1$-$C_6$ alkyl group, halogeno $C_1$-$C_6$ alkyl group, $C_3$-$C_7$ cycloalkyl group, $C_1$-$C_6$ alkyl-carbonyl group, $C_3$-$C_7$ cycloalkyl-carbonyl group, formyl group, $C_1$-$C_6$ alkoxy-carbonyl group or $C_1$-$C_6$ alkylsulfonyl group, or a $C_7$-$C_{12}$ aralkyl group or benzoyl group each of which may be substituted by the group(s) selected from the group consisting of a halogen atom, $C_1$-$C_6$ alkyl group, halogeno $C_1$-$C_6$ alkyl group, $C_1$-$C_6$ alkoxy group and halogeno $C_1$-$C_6$ alkoxy group.), Q represents CH or a nitrogen atom, $R^3$ represents a hydrogen atom, $C_1$-$C_6$ alkyl group or amino group, $R^4$ represents the formula (II):

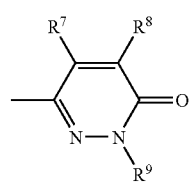

(II)

[wherein $R^7$ represents a hydrogen atom or $C_1$-$C_6$ alkyl group, $R^8$ represents a hydrogen atom, $C_1$-$C_6$ alkyl group or group: —$NR^{10}R^{11}$ (wherein $R^{10}$ and $R^{11}$ may be the same or different from each other, and each represents a hydrogen atom, $C_1$-$C_6$ alkyl group, $C_1$-$C_6$ alkyl-carbonyl group, formyl group, $C_1$-$C_6$ alkoxy-carbonyl group or $C_1$-$C_6$ alkylsulfonyl group.), $R^9$ represents a hydrogen atom or $C_1$-$C_6$ alkyl group.].],

(30) a compound wherein $R^1$ represents a phenyl group which may be substituted by 1 to 3 group(s) selected from the group consisting of a halogen atom, $C_1$-$C_4$ alkyl group, halogeno $C_1$-$C_4$ alkyl group, $C_1$-$C_4$ alkoxy group, halogeno $C_1$-$C_4$ alkoxy group and $C_1$-$C_4$ alkylthio group, $R^2$ represents a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group or group: —$NR^5R^6$ (wherein $R^5$ and $R^6$ may be the same or different from each other, and each represents a hydrogen atom, $C_1$-$C_4$ alkyl group, halogeno $C_1$-$C_4$ alkyl group, $C_3$-$C_6$ cycloalkyl group, $C_1$-$C_4$ alkyl-carbonyl group, $C_3$-$C_6$ cycloalkyl-carbonyl group, formyl group, $C_1$-$C_4$ alkoxy-carbonyl group or $C_1$-$C_4$ alkylsulfonyl group, or a $C_7$-$C_{12}$ aralkyl group or benzoyl group each of which may be substituted by the group(s) selected from the group consisting of a halogen atom, $C_1$-$C_4$ alkyl group, halogeno $C_1$-$C_4$ alkyl group, $C_1$-$C_4$ alkoxy group and halogeno $C_1$-$C_4$ alkoxy group.), $R^3$ represents a hydrogen atom, $C_1$-$C_4$ alkyl group or amino group, $R^4$ represents the formula (II) (wherein $R^7$ represents a hydrogen atom or $C_1$-$C_4$ alkyl group, $R^8$ represents a hydrogen atom, $C_1$-$C_4$ alkyl group, amino group, $C_1$-$C_4$ alkylamino group, di($C_1$-$C_4$ alkyl)amino group, $C_1$-$C_4$ alkyl-carbonylamino group, formylamino group, $C_1$-$C_4$ alkoxy-carbonylamino group or $C_1$-$C_4$ alkylsulfonylamino group, and $R^9$ represents a hydrogen atom or $C_1$-$C_4$ alkyl group.),

(31) a compound wherein $R^1$ represents a phenyl group which may be substituted by 1 to 2 group(s) selected from the group consisting of a halogen atom, $C_1$-$C_4$ alkyl group, fluoro $C_1$-$C_4$ alkyl group, $C_1$-$C_4$ alkoxy group, fluoro $C_1$-$C_4$ alkoxy group and $C_1$-$C_4$ alkylthio group, $R^2$ represents a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group, amino group, $C_1$-$C_4$ alkylamino group, di($C_1$-$C_4$ alkyl)amino group, fluoro $C_1$-$C_4$ alkylamino group, $C_3$-$C_6$ cycloalkylamino group, $C_1$-$C_4$ alkyl-carbonylamino group, $C_3$-$C_6$ cycloalkyl-carbonylamino group, N-($C_3$-$C_6$ cycloalkyl-carbonyl)-N-($C_1$-$C_4$ alkyl)-amino group, formylamino group, $C_1$-$C_4$ alkoxy-carbonylamino group, $C_1$-$C_4$ alkylsulfonylamino group, or a benzylamino group, 1-phenethylamino group or benzoylamino group the phenyl group portion thereof may be substituted by a group(s) selected from the group consisting of a halogen atom, $C_1$-$C_4$ alkyl group, fluoro $C_1$-$C_4$ alkyl group, $C_1$-$C_4$ alkoxy group and fluoro $C_1$-$C_4$ alkoxy group, $R^3$ represents a hydrogen atom, methyl group or amino group, $R^4$ represents the formula (II) (wherein $R^7$ represents a hydrogen atom, methyl group or ethyl group, $R^8$ represents a hydrogen atom, methyl group, ethyl group, amino group, methylamino group, dimethylamino group, ethylamino group, diethylamino group, isopropylamino group, acetylamino group, formylamino group, methoxycarbonylamino group, ethoxycarbonylamino group, methylsulfonylamino group or ethylsulfonylamino group, and $R^9$ represents a hydrogen atom, methyl group or ethyl group.),

(32) a compound wherein $R^1$ represents a phenyl group which may be substituted by 1 to 2 group(s) selected from the group consisting of a fluorine atom, chlorine atom, bromine atom, methyl group, ethyl group, isopropyl group, difluoromethyl group, trifluoromethyl group, 2-fluoroethyl group, 2,2,2-trifluoroethyl group, methoxy group, ethoxy group, isopropoxy group, fluoromethoxy group, difluoromethoxy group, trifluoromethoxy group and methylthio group, R² represents a hydrogen atom, fluorine atom, chlorine atom, methyl group, methoxy group, methylthio group, methylsulfinyl group, methylsulfonyl group, amino group, methylamino group, dimethylamino group, ethylamino group, diethylamino group, propylamino group, isopropylamino group, trifluoromethylamino group, 2,2,2-trifluoroethylamino group, cyclopropylamino group, cyclohexylamino group, acetylamino group, propionylamino group, cyclopropylcarbonylamino group, cyclopentylcarbonylamino group, N-cyclopropylcarbonyl-N-methylamino group, formylamino group, methoxycarbonylamino group, ethoxycarbonylamino group, t-butoxycarbonylamino group, methylsulfonylamino group, ethylsulfonylamino group, or a benzylamino group, 1-phenethylamino group or benzoylamino group the phenyl group portion thereof may be substituted by a group(s) selected from the group consisting of a fluorine atom, methyl group, trifluoromethyl group, methoxy group and difluoromethoxy group, R³ represents a hydrogen atom, methyl group or amino group, R⁴ represents the formula (II) (wherein R⁷ represents a hydrogen atom or methyl group, R⁸ represents a hydrogen atom, a methyl group, amino group, methylamino group, dimethylamino group, acetylamino group, formylamino group, methoxycarbonylamino group or methylsulfonylamino group, R⁹ represents a hydrogen atom or methyl group.),

(33) a compound wherein R¹ represents a phenyl group which may be substituted by 1 or 2 group(s) selected from the group consisting of a fluorine atom, chlorine atom, methyl group, difluoromethyl group, trifluoromethyl group, methoxy group, fluoromethoxy group, difluoromethoxy group and trifluoromethoxy group, R² represents a hydrogen atom, fluorine atom, methyl group, methoxy group, methylthio group, methylsulfinyl group, methylsulfonyl group, amino group, methylamino group, dimethylamino group, ethylamino group, isopropylamino group, 2,2,2-trifluoroethylamino group, cyclopropylamino group, acetylamino group, cyclopropylcarbonylamino group, cyclopentylcarbonylamino group, N-cyclopropylcarbonyl-N-methylamino group, methoxycarbonylamino group, methylsulfonylamino group, 4-methoxybenzylamino group, 1-phenethylamino group or benzoylamino group, R³ represents a hydrogen atom, methyl group or amino group, R⁴ represents a 1,6-dihydro-6-oxopyridazin-3-yl group, 1,6-dihydro-4-methyl-6-oxopyridazin-3-yl group, 1,6-dihydro-5-methyl-6-oxopyridazin-3-yl group, 5-amino-1,6-dihydro-6-oxopyridazin-3-yl group, 1,6-dihydro-5-methylamino-6-oxopyridazin-3-yl group, 5-dimethylamino-1,6-dihydro-6-oxopyridazin-3-yl group, 5-acetylamino-1,6-dihydro-6-oxopyridazin-3-yl group, 1,6-dihydro-5-methoxycarbonylamino-6-oxopyridazin-3-yl group, 1,6-dihydro-5-methylsulfonylamino-6-oxopyridazin-3-yl group, 1,6-dihydro-1-methyl-6-oxopyridazin-3-yl group, 1-ethyl-1,6-dihydro-6-oxopyridazin-3-yl group, 1,6-dihydro-1,5-dimethyl-6-oxo-pyridazin-3-yl group or 5-amino-1, 6-dihydro-1-methyl-6-oxopyridazin-3-yl group,

(34) a compound wherein R¹ represents a phenyl group, 2-fluorophenyl group, 3-fluorophenyl group, 4-fluorophenyl group, 3-chlorophenyl group, 4-chlorophenyl group, 3,4-difluorophenyl group, 2,4-difluorophenyl group, 3,4-dichlorophenyl group, 3-chloro-4-fluorophenyl group, 4-chloro-3-fluorophenyl group or 3-trifluoromethylphenyl group, R² represents a hydrogen atom, methoxy group, amino group, methylamino group, ethylamino group, isopropylamino group, 2,2,2-trifluoroethylamino group, acetylamino group, cyclopropylcarbonylamino group, cyclopentylcarbonylamino group, methoxycarbonylamino group, methylsulfonylamino group, 4-methoxybenzylamino group, 1-phenethylamino group or benzoylamino group, R³ represents a hydrogen atom, methyl group or amino group, R⁴ represents a 1,6-dihydro-6-oxopyridazin-3-yl group, 1,6-dihydro-4-methyl-6-oxopyridazin-3-yl group, 1,6-dihydro-5-methyl-6-oxopyridazin-3-yl group, 5-amino-1,6-dihydro-6-oxopyridazin-3-yl group, 5-acetylamino-1,6-dihydro-6-oxopyridazin-3-yl group, 1,6-dihydro-5-methoxycarbonylamino-6-oxopyridazin-3-yl group, 1,6-dihydro-5-methylsulfonylamino-6-oxopyridazin-3-yl group, 1,6-dihydro-1-methyl-6-oxopyridazin-3-yl group or 5-amino-1,6-dihydro-1-methyl-6-oxopyridazin-3-yl group,

(35) a compound wherein R¹ represents a phenyl group, 2-fluorophenyl group, 3-fluorophenyl group, 4-fluorophenyl group, 3-chlorophenyl group, 4-chlorophenyl group, 3,4-difluorophenyl group, 2,4-difluorophenyl group, 3,4-dichlorophenyl group, 3-chloro-4-fluorophenyl group, 4-chloro-3-fluorophenyl group or 3-trifluoromethylphenyl group, R² represents a hydrogen atom, methoxy group, amino group, methylamino group, ethylamino group, isopropylamino group, 2,2,2-trifluoroethylamino group, acetylamino group, cyclopropylcarbonylamino group, cyclopentylcarbonylamino group, methoxycarbonylamino group, methylsulfonylamino group, 4-methoxybenzylamino group, 1-phenethylamino group or benzoylamino group, R³ represents a hydrogen atom, R⁴ represents a 1,6-dihydro-6-oxopyridazin-3-yl group, 1,6-dihydro-4-methyl-6-oxopyridazin-3-yl group, 1,6-dihydro-5-methyl-6-oxopyridazin-3-yl group, 5-amino-1,6-dihydro-6-oxopyridazin-3-yl group or 1,6-dihydro-1-methyl-6-oxopyridazin-3-yl group,

(36) a compound wherein 4-(2-aminopyridin-4-yl)-1-(1,6-dihydro-6-oxopyridazin-3-yl)-3-phenyl-1H-pyrazole, 3-(4-fluorophenyl)-1-(1,6-dihydro-6-oxopyridazin-3-yl)-4-(pyridin-4-yl)-1H-pyrazole, 1-(5-amino-1,6-dihydro-6-oxopyridazin-3-yl)-3-(4-fluorophenyl)-4-(pyridin-4-yl)-1H-pyrazole, 4-(2-aminopyridin-4-yl)-3-(4-fluorophenyl)-1-(1,6-dihydro-6-oxopyridazin-3-yl)-1H-pyrazole, 3-(4-fluorophenyl)-1-(1,6-dihydro-6-oxopyridazin-3-yl)-4-(2-methylaminopyridin-4-yl)-1H-pyrazole, 4-(2-ethylaminopyridin-4-yl)-3-(4-fluorophenyl)-1-(1,6-dihydro-6-oxopyridazin-3-yl)-1H-pyrazole, 3-(4-fluorophenyl)-1-(1,6-dihydro-6-oxopyridazin-3-yl)-4-[2-(2,2,2-trifluoroethyl)aminopyridin-4-yl]-1H-pyrazole, 4-(2-acetylaminopyridin-4-yl)-3-(4-fluorophenyl)-1-(1,6-dihydro-6-oxopyridazin-3-yl)-1H-pyrazole, 3-(4-fluorophenyl)-1-(1,6-dihydro-6-oxopyridazin-3-yl)-4-(2-methoxycarbonylaminopyridin-4-yl)-1H-pyrazole, 4-(2-aminopyridin-4-yl)-3-(4-fluorophenyl)-1-(1,6-dihydro-4-methyl-6-oxopyridazin-3-yl)-1H-pyrazole, 4-(2-aminopyridin-4-yl)-3-(4-fluorophenyl)-1-(1,6-dihydro-5-methyl-6-oxopyridazin-3-yl)-1H-pyrazole, 1-(5-amino-1,6-dihydro-6-oxopyridazin-3-yl)-4-(2-amino-pyridin-4-yl)-3-(4-fluorophenyl)-1H-pyrazole, 4-(2-aminopyridin-4-yl)-3-(4-fluorophenyl)-1-(1,6-dihydro-1-methyl-6-oxopyridazin-3-yl)-1H-pyrazole, 4-(2-aminopyrimidin-4-yl)-3-(4-fluorophenyl)-1-(1,6-dihydro-6-oxopyridazin-3-yl)-1H-pyrazole, 4-(2-aminopyridin-4-yl)-3-(3-fluorophenyl)-1-(1,6-dihydro-6-oxopyridazin-3-yl)-1H- pyrazole, 4-(2-aminopyridin-4-yl)-3-(4-chlorophenyl)-1-(1,6-dihydro-6-oxopyridazin-3-yl)-1H-pyrazole, 4-(2-aminopyridin-4-yl)-3-(3-chlorophenyl)-1-(1,6-dihydro-6-oxopyridazin-3-yl)-1H-pyrazole, 4-(2-aminopyridin-4-yl)-3-(3,4-difluorophenyl)-1-(1,6-dihydro-6-oxopyridazin-3-yl)-1H-pyrazole, 4-(2-aminopyridin-4-yl)-3-(3,4-dichlorophenyl)-1-(1,6-dihydro-6-oxopyridazin-3-yl)-1H-pyrazole, 4-(2-aminopyridin-4-yl)-1-(1,6-dihydro-6-oxopyridazin-3-yl)-3-(3-trifluoromethylphenyl)-1H-pyrazole, 4-(2-aminopyridin-4-yl)-3-(2-fluorophenyl)-1-(1,6-dihydro-6-oxopyridazin-3-yl)-1H-pyrazole, 3-(2-fluorophenyl)-1-(1,6-dihydro-6-oxopyridazin-3-yl)-4-[2-(2,2,2-trifluoroethyl)aminopyridin-4-yl]-1H-pyrazole, 4-(2-acetylaminopyridin-4-yl)-3-(2-fluorophenyl)-1-(1,6-dihydro-6-oxopyridazin-3-yl)-1H-pyrazole, 4-(2-aminopyrimidin-4-yl)-3-(2-fluorophenyl)-1-(1,6-dihydro-6-oxopyridazin-3-yl)-1H-pyrazole, 4-(2-aminopyridin-4-yl)-3-(2,4-difluorophenyl)-1-(1,6-dihydro-6-oxopyridazin-3-yl)-1H-pyrazole, 4-(2-cyclopropylcarbonylaminopyridin-4-yl)-3-(4-fluorophenyl)-1-(1,6-dihydro-6-oxopyridazin-3-yl)-1H-pyrazole, 4-(2-cyclopropylcarbonylaminopyridin-4-yl)-3-(2-fluorophenyl)-1-(1,6-dihydro-6-oxopyridazin-3-yl)-1H-pyrazole, or 3-(4-fluorophenyl)-1-(1,6-dihydro-6-oxopyridazin-3-yl)-4-[2-(4-methoxybenzylamino)pyrimidin-4-yl]-1H-pyrazole, (37) a compound wherein the formula (I):

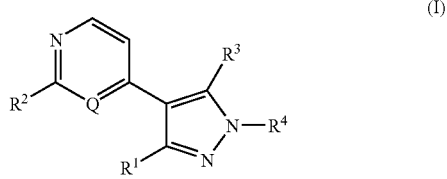

(I)

[wherein $R^1$ represents a phenyl group which may be substituted by the group(s) selected from the group consisting of a halogen atom, $C_1$-$C_6$ alkyl group, halogeno $C_1$-$C_6$ alkyl group, $C_1$-$C_6$ alkoxy group, halogeno $C_1$-$C_6$ alkoxy group and $C_1$-$C_6$ alkylthio group, $R^2$ represents a hydrogen atom, halogen atom, $C_1$-$C_6$ alkyl group, $C_1$-$C_6$ alkoxy group, $C_1$-$C_6$ alkylthio group, $C_1$-$C_6$ alkylsulfinyl group, $C_1$-$C_6$ alkylsulfonyl group or group: —$NR^5R^6$ (wherein $R^5$ and $R^6$ may be the same or different from each other, and each represents a hydrogen atom, $C_1$-$C_6$ alkyl group, halogeno $C_1$-$C_6$ alkyl group, $C_3$-$C_7$ cycloalkyl group, $C_1$-$C_6$ alkyl-carbonyl group, $C_3$-$C_7$ cycloalkyl-carbonyl group, formyl group, $C_1$-$C_6$ alkoxy-carbonyl group or $C_1$-$C_6$ alkylsulfonyl group, or a $C_7$-$C_{12}$ aralkyl group or benzoyl group each of which may be substituted by the group(s) selected from the group consisting of a halogen atom, $C_1$-$C_6$ alkyl group, halogeno $C_1$-$C_6$ alkyl group, $C_1$-$C_6$ alkoxy group and halogeno $C_1$-$C_6$ alkoxy group.), Q represents CH or a nitrogen atom, $R^3$ represents a hydrogen atom, $C_1$-$C_6$ alkyl group or amino group, $R^4$ represents the formula (III):

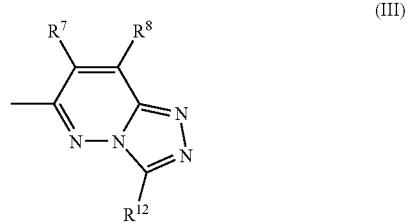

(III)

[wherein $R^7$ represents a hydrogen atom or $C_1$-$C_6$ alkyl group, $R^8$ represents a hydrogen atom, $C_1$-$C_6$ alkyl group or group: —$NR^{10}R^{11}$ (wherein $R^{10}$ and $R^{11}$ may be the same or different from each other, and each represents a hydrogen atom, $C_1$-$C_6$ alkyl group, $C_1$-$C_6$ alkyl-carbonyl group, formyl group, $C_1$-$C_6$ alkoxy-carbonyl group or $C_1$-$C_6$ alkylsulfonyl group.), $R^{12}$ represents a hydrogen atom, $C_1$-$C_6$ alkyl group, halogeno $C_1$-$C_6$ alkyl group or group: —$NR^{10}R^{11}$ (wherein $R^{10}$ and $R^{11}$ may be the same or different from each other, and each represents a hydrogen atom, $C_1$-$C_6$ alkyl group, $C_1$-$C_6$ alkyl-carbonyl group, formyl group, $C_1$-$C_6$ alkoxy-carbonyl group or $C_1$-$C_6$ alkylsulfonyl group.).],

(38) a compound wherein $R^1$ represents a phenyl group which may be substituted by 1 or 3 group(s) selected from the group consisting of a halogen atom, $C_1$-$C_4$ alkyl group, halogeno $C_1$-$C_4$ alkyl group, $C_1$-$C_4$ alkoxy group, halogeno $C_1$-$C_4$ alkoxy group and $C_1$-$C_4$ alkylthio group, $R^2$ represents a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group or group: —$NR^5R^6$ (wherein $R^5$ and $R^6$ may be the same or different from each other, and each represents a hydrogen atom, $C_1$-$C_4$ alkyl group, halogeno $C_1$-$C_4$ alkyl group, $C_3$-$C_6$ cycloalkyl group, $C_1$-$C_4$ alkyl-carbonyl group, $C_3$-$C_6$ cycloalkyl-carbonyl group, formyl group, $C_1$-$C_4$ alkoxy-carbonyl group or $C_1$-$C_4$ alkylsulfonyl group, or a $C_7$-$C_{12}$ aralkyl group or benzoyl group each of which may be substituted by a group(s) selected from the group consisting of a halogen atom, $C_1$-$C_4$ alkyl group, halogeno $C_1$-$C_4$ alkyl group, $C_1$-$C_4$ alkoxy group and halogeno $C_1$-$C_4$ alkoxy group.), $R^3$ represents a hydrogen atom, $C_1$-$C_4$ alkyl group or amino group, $R^4$ represents the formula (III) (wherein $R^7$ represents a hydrogen atom or $C_1$-$C_4$ alkyl group, $R^8$ represents a hydrogen atom, $C_1$-$C_4$ alkyl group, amino group, $C_1$-$C_4$ alkylamino group, di($C_1$-$C_4$ alkyl)amino group, $C_1$-$C_4$ alkyl-carbonylamino group, formylamino group, $C_1$-$C_4$ alkoxycarbonylamino group or $C_1$-$C_4$ alkylsulfonylamino group, $R^{12}$ represents a hydrogen atom, $C_1$-$C_4$ alkyl group, fluoro $C_1$-$C_4$ alkyl group, amino group, $C_1$-$C_4$ alkylamino group, di($C_1$-$C_4$ alkyl)amino group, $C_1$-$C_4$ alkyl-carbonylamino group, formylamino group, $C_1$-$C_4$ alkoxy-carbonylamino group or $C_1$-$C_4$ alkylsulfonylamino group.),

(39) a compound wherein $R^1$ represents a phenyl group which may be substituted by 1 or 2 group(s) selected from the group consisting of a halogen atom, $C_1$-$C_4$ alkyl group, fluoro $C_1$-$C_4$ alkyl group, $C_1$-$C_4$ alkoxy group, fluoro $C_1$-$C_4$ alkoxy group and $C_1$-$C_4$ alkylthio group, $R^2$ represents a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group, amino group, $C_1$-$C_4$ alkylamino group, di($C_1$-$C_4$ alkyl)amino group, fluoro $C_1$-$C_4$ alkylamino group, $C_3$-$C_6$ cycloalkylamino group, $C_1$-$C_4$ alkyl-carbonylamino group, $C_3$-$C_6$ cycloalkyl-carbonylamino group, N-($C_3$-C6 cycloalkyl-carbonyl)-N-($C_1$-$C_4$ alkyl)amino group, formylamino group, $C_1$-$C_4$ alkoxy-carbonylamino group, $C_1$-$C_4$ alkylsulfonylamino group, or a benzylamino group, 1-phenethylamino group or benzoylamino group the phenyl group portion thereof may be substituted by a group(s) selected from the group consisting of a halogen atom, $C_1$-$C_4$ alkyl group, fluoro $C_1$-$C_4$ alkyl group, $C_1$-$C_4$ alkoxy group and fluoro $C_1$-$C_4$ alkoxy group, $R^3$ represents a hydrogen atom, methyl group or amino group, R$^4$ represents the formula (III) (wherein
R$^7$ represents a hydrogen atom, methyl group or ethyl group, R$^8$ represents a hydrogen atom, methyl group, ethyl group, amino group, methylamino group, dimethylamino group, ethylamino group, diethylamino group, isopropylamino group, acetylamino group, formylamino group, methoxycarbonylamino group, ethoxycarbonylamino group, methylsulfonylamino group or ethylsulfonylamino group, R$^{12}$ represents a hydrogen atom, methyl group, ethyl group, trifluoromethyl group, 2,2,2-trifluoroethyl group, amino group, methylamino group, dimethylamino group, ethylamino group, diethylamino group, isopropylamino group, acetylamino group, formylamino group, methoxycarbonylamino group, ethoxycarbonylamino group, methylsulfonylamino group or ethylsulfonylamino group.),

(40) a compound wherein R$^1$ represents a phenyl group which may be substituted by 1 to 2 group(s) selected from the group consisting of a fluorine atom, chlorine atom, bromine atom, methyl group, ethyl group, isopropyl group, difluoromethyl group, trifluoromethyl group, 2-fluoroethyl group, 2,2,2-trifluoroethyl group, methoxy group, ethoxy group, isopropoxy group, fluoromethoxy group, difluoromethoxy group, trifluoromethoxy group and methylthio group, R$^2$ represents a hydrogen atom, fluorine atom, chlorine atom, methyl group, methoxy group, methylthio group, methylsulfinyl group, methylsulfonyl group, amino group, methylamino group, dimethylamino group, ethylamino group, diethylamino group, propylamino group, isopropylamino group, trifluoromethylamino group, 2,2,2-trifluoroethylamino group, cyclopropylamino group, cyclohexylamino group, acetylamino group, propionylamino group, cyclopropylcarbonylamino group, cyclopentylcarbonylamino group, N-cyclopropylcarbonyl-N-methylamino group, formylamino group, methoxycarbonylamino group, ethoxycarbonylamino group, t-butoxycarbonylamino group, methylsulfonylamino group, ethylsulfonylamino group, or a benzylamino group, 1-phenethylamino group or benzoylamino group the phenyl group portion thereof may be substituted by a group(s) selected from the group consisting of a fluorine atom, methyl group, trifluoromethyl group, methoxy group and difluoromethoxy group, R$^3$ represents a hydrogen atom, methyl group or amino group, R$^4$ represents the formula (III) (wherein
R$^7$ represents a hydrogen atom or methyl group, R$^8$ represents a hydrogen atom, methyl group, amino group, methylamino group, dimethylamino group, acetylamino group, formylamino group, methoxycarbonylamino group or methylsulfonylamino group, R$^{12}$ represents a hydrogen atom, a methyl group, a trifluoromethyl group, amino group, methylamino group, dimethylamino group, acetylamino group, formylamino group, methoxycarbonylamino group or methylsulfonylamino group.),

(41) a compound wherein R$^1$ represents a phenyl group which may be substituted by 1 or 2 group(s) selected from the group consisting of a fluorine atom, chlorine atom, methyl group, difluoromethyl group, trifluoromethyl group, methoxy group, fluoromethoxy group, difluoromethoxy group and trifluoromethoxy group, R$^2$ represents a hydrogen atom, fluorine atom, methyl group, methoxy group, methylthio group, methylsulfinyl group, methylsulfonyl group, amino group, methylamino group, dimethylamino group, ethylamino group, isopropylamino group, 2,2,2-trifluoroethylamino group, cyclopropylamino group, acetylamino group, cyclopropylcarbonylamino group, cyclopentylcarbonylamino group, N-cyclopropylcarbonyl-N-methylamino group, methoxycarbonylamino group, methylsulfonylamino group, 4-methoxybenzylamino group, 1-phenethylamino group or benzoylamino group, R$^3$ represents a hydrogen atom, methyl group or amino group, R$^4$ represents a [1,2,4]triazolo[4,3-b]pyridazin-6-yl group, 3-methyl-[1,2,4]triazolo[4,3-b]pyridazin-6-yl group, 3-trifluoromethyl-[1,2,4]triazolo[4,3-b]pyridazin-6-yl group, 3-(2,2,2-trifluoroethyl-[1,2,4]triazolo[4,3-b]pyridazin-6-yl group, 3-amino-[1,2,4]triazolo[4,3-b]pyridazin-6-yl group, 3-methylamino-[1,2,4]triazolo[4,3-b]pyridazin-6-yl group, 3-dimethylamino-[1,2,4]triazolo[4,3-b]pyridazin-6-yl group, 3-acetylamino-[1,2,4]triazolo[4,3-b]pyridazin-6-yl group, 3-methoxycarbonylamino-[1,2,4]triazolo[4,3-b]-pyridazin-6-yl group, 3-methylsulfonylamino-[1,2,4]triazolo[4,3-b]pyridazin-6-yl group, 7-methyl-[1,2,4]triazolo[4,3-b]pyridazin-6-yl group, 8-methyl-[1,2,4]triazolo-[4,3-b]pyridazin-6-yl group, 8-amino-[1,2,4]triazolo[4,3-b]pyridazin-6-yl group, 8-methylamino-[1,2,4]triazolo[4,3-b]pyridazin-6-yl group, 8-dimethylamino-[1,2,4]triazolo-[4,3-b]pyridazin-6-yl group, 8-acetylamino-[1,2,4]triazolo-[4,3-b]pyridazin-6-yl group, 8-methoxycarbonylamino-[1,2,4]triazolo[4,3-b]pyridazin-6-yl group, 8-methylsulfonylamino-[1,2,4]triazolo[4,3-b]pyridazin-6-yl group, 3,8-dimethyl-[1,2,4]triazolo[4,3-b]pyridazin-6-yl group, 7,8-dimethyl-[1,2,4]triazolo[4,3-b]pyridazin-6-yl group, 3-amino-8-methyl-[1,2,4]triazolo[4,3-b]pyridazin-6-yl group or 8-amino-3-methyl-[1,2,4]triazolo[4,3-b]pyridazin-6-yl group,

(42) a compound wherein R$^1$ represents a phenyl group, 2-fluorophenyl group, 3-fluorophenyl group, 4-fluorophenyl group, 3-chlorophenyl group, 4-chlorophenyl group, 3,4-difluorophenyl group, 2,4-difluorophenyl group, 3,4-dichlorophenyl group, 3-chloro-4-fluorophenyl group, 4-chloro-3-fluorophenyl group or 3-trifluoromethylphenyl group, R$^2$ represents a hydrogen atom, methoxy group, amino group, methylamino group, ethylamino group, isopropylamino group, 2,2,2-trifluoroethylamino group, acetylamino group, cyclopropylcarbonylamino group, cyclopentylcarbonylamino group, methoxycarbonylamino group, methylsulfonylamino group, 4-methoxybenzylamino group, 1-phenethylamino group or benzoylamino group, R$^3$ represents a hydrogen atom, methyl group or amino group, R$^4$ represents a [1,2,4]triazolo[4,3-b]pyridazin-6-yl group, 3-methyl-[1,2,4]triazolo[4,3-b]pyridazin-6-yl group, 3-trifluoromethyl-[1,2,4]triazolo[4,3-b]pyridazin-6-yl group, 3-amino-[1,2,4]triazolo[4,3-b]pyridazin-6-yl group, 3-methylamino-[1,2,4]triazolo[4,3-b]pyridazin-6-yl group, 3-acetylamino-[1,2,4]triazolo[4,3-b]pyridazin-6-yl group, 3-methoxycarbonylamino-[1,2,4]triazolo[4,3-b]pyridazin-6-yl group, 3-methylsulfonylamino-[1,2,4]triazolo[4,3-b]pyridazin-6-yl group, 7-methyl-[1,2,4]triazolo[4,3-b]pyridazin-6-yl group, 8-methyl-[1,2,4]triazolo[4,3-b]pyridazin-6-yl group or 8-amino-[1,2,4]triazolo[4,3-b]pyridazin-6-yl group,

(43) a compound wherein R$^1$ represents a phenyl group, 2-fluorophenyl group, 3-fluorophenyl group, 4-fluorophenyl group, 3-chlorophenyl group, 4-chlorophenyl group, 3,4-difluorophenyl group, 2,4-difluorophenyl group, 3,4-dichlorophenyl group, 3-chloro-4-fluorophenyl group, 4-chloro-3-fluorophenyl group or 3-trifluoromethylphenyl group, R$^2$ represents a hydrogen atom, methoxy group, amino group, methylamino group, ethylamino group, isopropylamino group, 2,2,2-trifluoroethylamino group, acetylamino group, cyclopropylcarbonylamino group, cyclopentylcarbonylamino group, methoxycarbonylamino group, methylsulfonylamino group, 4-methoxybenzylamino group, 1-phenethylamino group or benzoylamino group, R³ represents a hydrogen atom, R⁴ represents a [1,2,4]triazolo[4,3-b]pyridazin-6-yl group, 3-methyl-[1,2,4]triazolo[4,3-b]pyridazin-6-yl group, 3-trifluoromethyl-[1,2,4]triazolo[4,3-b]pyridazin-6-yl group, 3-amino-[1,2,4]triazolo[4,3-b]pyridazin-6-yl group or 3-acetylamino-[1,2,4]triazolo[4,3-b]pyridazin-6-yl group,

(44) a compound wherein 4-(2-aminopyridin-4-yl)-3-phenyl-1-([1,2,4]triazolo[4,3-b]pyridazin-6-yl)-1H-pyrazole, 3-(4-fluorophenyl)-4-(pyridin-4-yl)-1-([1,2,4]triazolo[4,3-b]pyridazin-6-yl)-1H-pyrazole, 3-(4-fluorophenyl)-4-(2-methoxypyridin-4-yl)-1-([1,2,4]-triazolo[4,3-b]pyridazin-6-yl)-1H-pyrazole, 4-(2-aminopyridin-4-yl)-3-(4-fluorophenyl)-1-([1,2,4]-triazolo[4,3-b]pyridazin-6-yl)-1H-pyrazole, 3-(4-fluorophenyl)-4-(2-methylaminopyridin-4-yl)-1-([1,2,4]triazolo[4,3-b]pyridazin-6-yl)-1H-pyrazole, 4-(2-ethylaminopyridin-4-yl)-3-(4-fluorophenyl)-1-([1,2,4]triazolo[4,3-b]pyridazin-6-yl)-1H-pyrazole, 3-(4-fluorophenyl)-4-(2-isopropylaminopyridin-4-yl)-1-([1,2,4]triazolo[4,3-b]pyridazin-6-yl)-1H-pyrazole, 3-(4-fluorophenyl)-1-([1,2,4]triazolo[4,3-b]pyridazin-6-yl)-4-[2-(2,2,2-trifluoroethyl)aminopyridin-4-yl]-1H-pyrazole, 4-(2-acetylaminopyridin-4-yl)-3-(4-fluorophenyl)-1-([1,2,4]triazolo[4,3-b]pyridazin-6-yl)-1H-pyrazole, 3-(4-fluorophenyl)-4-(2-methoxycarbonylaminopyridin-4-yl)-1-([1,2,4]triazolo[4,3-b]pyridazin-6-yl)-1H-pyrazole, 3-(4-fluorophenyl)-4-(2-methylsulfonylaminopyridin-4-yl)-1-([1,2,4]triazolo[4,3-b]pyridazin-6-yl)-1H-pyrazole, 3-(4-fluorophenyl)-4-[2-(1-phenethylamino)pyridin-4-yl]-1-([1,2,4]triazolo[4,3-b]pyridazin-6-yl)-1H-pyrazole, 4-(2-benzoylaminopyridin-4-yl)-3-(4-fluorophenyl)-1-([1,2,4]triazolo[4,3-b]pyridazin-6-yl)-1H-pyrazole, 4-(2-aminopyridin-4-yl)-3-(4-fluorophenyl)-1-(3-methyl-[1,2,4]triazolo[4,3-b]pyridazin-6-yl)-1H-pyrazole, 4-(2-aminopyridin-4-yl)-3-(4-fluorophenyl)-1-(3-trifluoromethyl-[1,2,4]triazolo[4,3-b]pyridazin-6-yl)-1H-pyrazole, 4-(2-aminopyridin-4-yl)-1-(3-amino-[1,2,4]triazolo[4,3-b]pyridazin-6-yl)-3-(4-fluorophenyl)-1H-pyrazole, 1-(3-acetylamino-[1,2,4]triazolo[4,3-b]pyridazin-6-yl)-4-(2-aminopyridin-4-yl)-3-(4-fluorophenyl)-1H-pyrazole, 4-(2-aminopyrimidin-4-yl)-3-(4-fluorophenyl)-1-([1,2,4]-triazolo[4,3-b]pyridazin-6-yl)-1H-pyrazole, 3-(3-fluorophenyl)-4-(pyridin-4-yl)-1-([1,2,4]triazolo[4,3-b]pyridazin-6-yl)-1H-pyrazole, 4-(2-aminopyridin-4-yl)-3-(3-fluorophenyl)-1-([1,2,4]triazolo[4,3-b]pyridazin-6-yl)-1H-pyrazole, 4-(2-aminopyridin-4-yl)-3-(4-chlorophenyl)-1-([1,2,4]triazolo[4,3-b]pyridazin-6-yl)-1H-pyrazole, 4-(2-aminopyridin-4-yl)-3-(3-chlorophenyl)-1-([1,2,4]triazolo[4,3-b]pyridazin-6-yl)-1H-pyrazole, 3-(3,4-difluorophenyl)-4-(pyridin-4-yl)-1-([1,2,4]triazolo[4,3-b]pyridazin-6-yl)-1H-pyrazole, 4-(2-aminopyridin-4-yl)-3-(3,4-difluorophenyl)-1-([1,2,4]-triazolo[4,3-b]pyridazin-6-yl)-1H-pyrazole, 4-(2-aminopyridin-4-yl)-3-(3,4-dichlorophenyl)-1-([1,2,4]-triazolo[4,3-b]pyridazin-6-yl)-1H-pyrazole, 4-(2-aminopyridin-4-yl)-3-(3-chloro-4-fluorophenyl)-1-([1,2,4]triazolo[4,3-b]pyridazin-6-yl)-1H-pyrazole, 4-(2-aminopyridin-4-yl)-3-(4-chloro-3-fluorophenyl)-1-([1,2,4]triazolo[4,3-b]pyridazin-6-yl)-1H-pyrazole, 4-(2-aminopyridin-4-yl)-1-([1,2,4]triazolo[4,3-b]pyridazin-6-yl)-3-(3-trifluoromethylphenyl)-1H-pyrazole, 4-(2-aminopyridin-4-yl)-3-(2-fluorophenyl)-1-([1,2,4]triazolo[4,3-b]pyridazin-6-yl)-1H-pyrazole, 4-(2-aminopyrimidin-4-yl)-3-(2-fluorophenyl)-1-([1,2,4]triazolo[4,3-b]pyridazin-6-yl)-1H-pyrazole, 4-(2-aminopyridin-4-yl)-3-(2,4-difluorophenyl)-1-([1,2,4]-triazolo[4,3-b]pyridazin-6-yl)-1H-pyrazole, 4-(2-cyclopropylcarbonylaminopyridin-4-yl)-3-(4-fluorophenyl)-1-([1,2,4]triazolo[4,3-b]pyridazin-6-yl)-1H-pyrazole, 4-(2-cyclopentylcarbonylaminopyridin-4-yl)-3-(4-fluorophenyl)-1-([1,2,4]triazolo[4,3-b]pyridazin-6-yl)-1H-pyrazole or 3-(4-fluorophenyl)-4-[2-(4-methoxybenzyl)aminopyrimidin-4-yl]-1-([1,2,4]triazolo[4,3-b]pyridazin-6-yl)-1H-pyrazole,

(45) a compound represented by the formula (I):

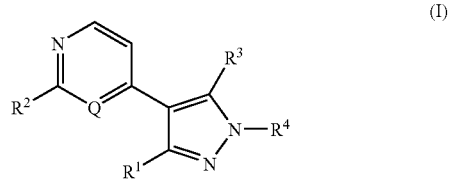

(I)

[wherein R¹ represents a phenyl group which may be substituted by a group(s) selected from the group consisting of a halogen atom, $C_1$-$C_6$ alkyl group, halogeno $C_1$-$C_6$ alkyl group, $C_1$-$C_6$ alkoxy group, halogeno $C_1$-$C_6$ alkoxy group and $C_1$-$C_6$ alkylthio group, R² represents a hydrogen atom, halogen atom, $C_1$-$C_6$ alkyl group, $C_1$-$C_6$ alkoxy group, $C_1$-$C_6$ alkylthio group, $C_1$-$C_6$ alkylsulfinyl group, $C_1$-$C_6$ alkylsulfonyl group or group: —NR⁵R⁶ (wherein R⁵ and R⁶ may be the same or different from each other, and each represents a hydrogen atom, $C_1$-$C_6$ alkyl group, halogeno $C_1$-$C_6$ alkyl group, $C_3$-$C_7$ cycloalkyl group, $C_1$-$C_6$ alkylcarbonyl group, $C_3$-$C_7$ cycloalkyl-carbonyl group, formyl group, $C_1$-$C_6$ alkoxy-carbonyl group or $C_1$-$C_6$ alkylsulfonyl group, or a $C_7$-$C_{12}$ aralkyl group or benzoyl group each of which may be substituted by a group(s) selected from the group consisting of a halogen atom, $C_1$-$C_6$ alkyl group, halogeno $C_1$-$C_6$ alkyl group, $C_1$-$C_6$ alkoxy group and halogeno $C_1$-$C_6$ alkoxy group.), Q represents CH or a nitrogen atom, R³ represents a hydrogen atom, $C_1$-$C_6$ alkyl group or amino group, R⁴ represents the formula (IV):

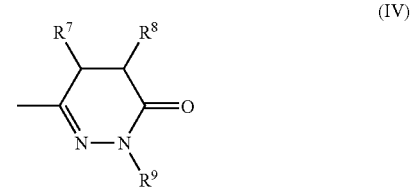

(IV)

[wherein R⁷ represents a hydrogen atom or $C_1$-$C_6$ alkyl group, R⁸ represents a hydrogen atom, $C_1$-$C_6$ alkyl group or group: —NR¹⁰R¹¹ (wherein R¹⁰ and R¹¹ may be the same or different from each other, and each represents a hydrogen atom, $C_1$-$C_6$ alkyl group, $C_1$-$C_6$ alkyl-carbonyl group, formyl group, $C_1$-$C_6$ alkoxy-carbonyl group or $C_1$-$C_6$ alkylsulfonyl group.), R⁹ represents a hydrogen atom or $C_1$-$C_6$ alkyl group.].],

(46) a compound wherein R¹ represents a phenyl group which may be substituted by 1 to 3 group(s) selected from the group consisting of a halogen atom, $C_1$-$C_4$ alkyl group, halogeno $C_1$-$C_4$ alkyl group, $C_1$-$C_4$ alkoxy group, halogeno $C_1$-$C_4$ alkoxy group and $C_1$-$C_4$ alkylthio group, R² represents a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group or group: —NR$^5$R$^6$ (wherein R$^5$ and R$^6$ may be the same or different from each other, and each represents a hydrogen atom, $C_1$-$C_4$ alkyl group, halogeno $C_1$-$C_4$ alkyl group, $C_3$-$C_6$ cycloalkyl group, $C_1$-$C_4$ alkyl-carbonyl group, $C_3$-$C_6$ cycloalkyl-carbonyl group, formyl group, $C_1$-$C_4$ alkoxycarbonyl group or $C_1$-$C_4$ alkylsulfonyl group, or a $C_7$-$C_{12}$ aralkyl group or benzoyl group each of which may be substituted by a group(s) selected from the group consisting of a halogen atom, $C_1$-$C_4$ alkyl group, halogeno $C_1$-$C_4$ alkyl group, $C_1$-$C_4$ alkoxy group and halogeno $C_1$-$C_4$ alkoxy group.), R$^3$ represents a hydrogen atom, $C_1$-$C_4$ alkyl group or amino group, R$^4$ represents the formula (IV) (wherein R$^7$ represents a hydrogen atom or $C_1$-$C_4$ alkyl group, R$^8$ represents a hydrogen atom, $C_1$-$C_4$ alkyl group, amino group, $C_1$-$C_4$ alkylamino group, di($C_1$-$C_4$ alkyl)amino group, $C_1$-$C_4$ alkyl-carbonylamino group, formylamino group, $C_1$-$C_4$ alkoxy-carbonylamino group or $C_1$-$C_4$ alkylsulfonylamino group, R$^9$ represents a hydrogen atom or $C_1$-$C_4$ alkyl group.),

(47) a compound wherein R$^1$ represents a phenyl group which may be substituted by 1 to 2 group(s) selected from the group consisting of a halogen atom, $C_1$-$C_4$ alkyl group, fluoro $C_1$-$C_4$ alkyl group, $C_1$-$C_4$ alkoxy group, fluoro $C_1$-$C_4$ alkoxy group and $C_1$-$C_4$ alkylthio group, R$^2$ represents a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group, amino group, $C_1$-$C_4$ alkylamino group, di($C_1$-$C_4$ alkyl)amino group, fluoro $C_1$-$C_4$ alkylamino group, $C_3$-$C_6$ cycloalkylamino group, $C_1$-$C_4$ alkyl-carbonylamino group, $C_3$-$C_6$ cycloalkyl-carbonylamino group, N-($C_3$-$C_6$ cycloalkyl-carbonyl)-N-($C_1$-$C_4$ alkyl)-amino group, formylamino group, $C_1$-$C_4$ alkoxy-carbonylamino group, $C_1$-$C_4$ alkylsulfonylamino group, or a benzylamino group, 1-phenethylamino group or benzoylamino group the phenyl group portion thereof may be substituted by a group(s) selected from the group consisting of a halogen atom, $C_1$-$C_4$ alkyl group, fluoro $C_1$-$C_4$ alkyl group, $C_1$-$C_4$ alkoxy group and fluoro $C_1$-$C_4$ alkoxy group, R$^3$ represents a hydrogen atom, methyl group or amino group, R$^4$ represents the formula (IV) (wherein R$^7$ represents a hydrogen atom, methyl group or ethyl group, R$^8$ represents a hydrogen atom, methyl group, ethyl group, amino group, methylamino group, dimethylamino group, ethylamino group, diethylamino group, isopropylamino group, acetylamino group, formylamino group, methoxycarbonylamino group, ethoxycarbonylamino group, methylsulfonylamino group or ethylsulfonylamino group, R$^9$ represents a hydrogen atom, methyl group or ethyl group.),

(48) a compound wherein R$^1$ represents a phenyl group which may be substituted by 1 to 2 group(s) selected from the group consisting of a fluorine atom, chlorine atom, bromine atom, methyl group, ethyl group, isopropyl group, difluoromethyl group, trifluoromethyl group, 2-fluoroethyl group, 2,2,2-trifluoroethyl group, methoxy group, ethoxy group, isopropoxy group, fluoromethoxy group, difluoromethoxy group, trifluoromethoxy group and methylthio group, R$^2$ represents a hydrogen atom, fluorine atom, chlorine atom, methyl group, methoxy group, methylthio group, methylsulfinyl group, methylsulfonyl group, amino group, methylamino group, dimethylamino group, ethylamino group, diethylamino group, propylamino group, isopropylamino group, trifluoromethylamino group, 2,2,2-trifluoromethylamino group, cyclopropylamino group, cyclohexylamino group, acetylamino group, propionylamino group, cyclopropylcarbonylamino group, cyclopentylcarbonylamino group, N-cyclopropylcarbonyl-N-methylamino group, formylamino group, methoxycarbonylamino group, ethoxycarbonylamino group, t-butoxycarbonylamino group, methylsulfonylamino group, ethylsulfonylamino group, or a benzylamino group, 1-phenethylamino group or benzoylamino group the phenyl group portion thereof may be substituted by a group(s) selected from the group consisting of a fluorine atom, a methyl group, a trifluoromethyl group, methoxy group and difluoromethoxy group, R$^3$ represents a hydrogen atom, methyl group or amino group, R$^4$ represents the formula (IV) (wherein R$^7$ represents a hydrogen atom or methyl group, R$^8$ represents a hydrogen atom, methyl group, amino group, methylamino group, dimethylamino group, acetylamino group, formylamino group, methoxycarbonylamino group or methylsulfonylamino group, R$^9$ represents a hydrogen atom or methyl group.),

(49) a compound wherein R$^1$ represents a phenyl group which may be substituted by 1 to 2 group(s) selected from the group consisting of a fluorine atom, a chlorine atom, a methyl group, a difluoromethyl group, a trifluoromethyl group, methoxy group, fluoromethoxy group, difluoromethoxy group and trifluoromethoxy group, R$^2$ represents a hydrogen atom, fluorine atom, methyl group, methoxy group, methylthio group, methylsulfinyl group, methylsulfonyl group, amino group, methylamino group, dimethylamino group, ethylamino group, isopropylamino group, 2,2,2-trifluoromethylamino group, cyclopropylamino group, acetylamino group, cyclopropylcarbonylamino group, cyclopentylcarbonylamino group, N-cyclopropylcarbonyl-N-methylamino group, methoxycarbonylamino group, methylsulfonylamino group, 4-methoxybenzylamino group, 1-phenethylamino group or benzoylamino group, R$^3$ represents a hydrogen atom, methyl group or amino group, R$^4$ represents a 1,4,5,6-tetrahydro-6-oxopyridazin-3-yl group, 1,4,5,6-tetrahydro-4-methyl-6-oxopyridazin-3-yl group, 1,4,5,6-tetrahydro-5-methyl-6-oxopyridazin-3-yl group, 5-amino-1,4,5,6-tetrahydro-6-oxopyridazin-3-yl group, 1,4,5,6-tetrahydro-5-methylamino-6-oxopyridazin-3-yl group, 5-acetylamino-1,4,5,6-tetrahydro-6-oxopyridazin-3-yl group, 1,4,5,6-tetrahydro-5-methoxycarbonylamino-6-oxopyridazin-3-yl group, 1,4,5,6-tetrahydro-5-methylsulfonylamino-6-oxopyridazin-3-yl group, 1,4,5,6-tetrahydro-1-methyl-6-oxopyridazin-3-yl group, 1,4,5,6-tetrahydro-1,4-dimethyl-6-oxopyridazin-3-yl group, 1,4,5,6-tetrahydro-1,5-dimethyl-6-oxopyridazin-3-yl group or 5-amino-1,4,5,6-tetrahydro-1-methyl-6-oxopyridazin-3-yl group,

(50) a compound wherein R$^1$ represents a phenyl group, 2-fluorophenyl group, 3-fluorophenyl group, 4-fluorophenyl group, 3-chlorophenyl group, 4-chlorophenyl group, 3,4-difluorophenyl group, 2,4-difluorophenyl group, 3,4-dichlorophenyl group, 3-chloro-4-fluorophenyl group, 4-chloro-3-fluorophenyl group or 3-trifluoromethylphenyl group, R$^2$ represents a hydrogen atom, methoxy group, amino group, methylamino group, ethylamino group, isopropylamino group, 2,2,2-trifluoromethylamino group, acetylamino group, cyclopropylcarbonylamino group, cyclopentylcarbonylamino group, methoxycarbonylamino group, methylsulfonylamino group, 4-methoxybenzylamino group, 1-phenethylamino group or benzoylamino group, R³ represents a hydrogen atom, methyl group or amino group, R⁴ represents a 1,4,5,6-tetrahydro-6-oxopyridazin-3-yl group, 1,4,5,6-tetrahydro-4-methyl-6-oxopyridazin-3-yl group, 1,4,5,6-tetrahydro-5-methyl-6-oxopyridazin-3-yl group, 5-amino-1,4,5,6-tetrahydro-6-oxopyridazin-3-yl group, 1,4,5,6-tetrahydro-1-methyl-6-oxopyridazin-3-yl group or 1,4,5,6-tetrahydro-1,5-dimethyl-6-oxopyridazin-3-yl group,

(51) a compound wherein R¹ represents a phenyl group, 2-fluorophenyl group, 3-fluorophenyl group, 4-fluorophenyl group, 3-chlorophenyl group, 4-chlorophenyl group, 3,4-difluorophenyl group, 2,4-difluorophenyl group, 3,4-dichlorophenyl group, 3-chloro-4-fluorophenyl group, 4-chloro-3-fluorophenyl group or 3-trifluoromethylphenyl group, R² represents a hydrogen atom, methoxy group, amino group, methylamino group, ethylamino group, isopropylamino group, 2,2,2-trifluoromethylamino group, acetylamino group, cyclopropylcarbonylamino group, cyclopentylcarbonylamino group, methoxycarbonylamino group, methylsulfonylamino group, 4-methoxybenzylamino group, 1-phenethylamino group or benzoylamino group, R³ represents a hydrogen atom, R⁴ represents a 1,4,5,6-tetrahydro-6-oxopyridazin-3-yl group, 1,4,5,6-tetrahydro-4-methyl-6-oxopyridazin-3-yl group, 1,4,5,6-tetrahydro-5-methyl-6-oxopyridazin-3-yl group or 1,4,5,6-tetrahydro-1-methyl-6-oxopyridazin-3-yl group,

(52) a compound wherein 4-(2-aminopyridin-4-yl)-1-(1,4,5,6-tetrahydro-6-oxopyridazin-3-yl)-3-phenyl-1H-pyrazole, 3-(4-fluorophenyl)-1(1,4,5,6-tetrahydro-6-oxopyridazin-3-yl)-4-(pyridin-4-yl)-1H-pyrazole, 4-(2-aminopyridin-4-yl)-3-(4-fluorophenyl)-1-(1,4,5,6-tetrahydro-6-oxopyridazin-3-yl)-1H-pyrazole, 3-(4-fluorophenyl)-1-(1,4,5,6-tetrahydro-6-oxopyridazin-3-yl)-4-[2-(2,2,2-trifluoroethyl)aminopyridin-4-yl]-1H-pyrazole, 4-(2-acetylaminopyridin-4-yl)-3-(4-fluorophenyl)-1-(1,4,5,6-tetrahydro-6-oxopyridazin-3-yl)-1H-pyrazole, 4-(2-aminopyridin-4-yl)-3-(4-fluorophenyl)-1-(1,4,5,6-tetrahydro-4-methyl-6-oxopyridazin-3-yl)-1H-pyrazole, 4-(2-aminopyridin-4-yl)-3-(4-fluorophenyl)-1-(1,4,5,6-tetrahydro-5-methyl-6-oxopyridazin-3-yl)-1H-pyrazole, 4-(2-aminopyridin-4-yl)-3-(4-fluorophenyl)-1-(1,4,5,6-tetrahydro-1-methyl-6-oxopyridazin-3-yl)-1H-pyrazole, 4-(2-aminopyrimidin-4-yl)-3-(4-fluorophenyl)-1-(1,4,5,6-tetrahydro-6-oxopyridazin-3-yl)-1H-pyrazole, 4-(2-aminopyridin-4-yl)-3-(3-fluorophenyl)-1-(1,4,5,6-tetrahydro-6-oxopyridazin-3-yl)-1H-pyrazole, 4-(2-aminopyridin-4-yl)-3-(4-chlorophenyl)-1-(1,4,5,6-tetrahydro-6-oxopyridazin-3-yl)-1H-pyrazole, 4-(2-aminopyridin-4-yl)-3-(3-chlorophenyl)-1-(1,4,5,6-tetrahydro-6-oxopyridazin-3-yl)-1H-pyrazole, 4-(2-aminopyridin-4-yl)-3-(3,4-difluorophenyl)-1-(1,4,5,6-tetrahydro-6-oxopyridazin-3-yl)-1H-pyrazole, 4-(2-aminopyridin-4-yl)-3-(3,4-dichlorophenyl)-1-(1,4,5,6-tetrahydro-6-oxopyridazin-3-yl)-1H-pyrazole, 4-(2-aminopyridin-4-yl)-3-(3-chloro-4-fluorophenyl)-1-(1,4,5,6-tetrahydro-6-oxopyridazin-3-yl)-1H-pyrazole, 4-(2-aminopyridin-4-yl)-3-(4-chloro-3-fluorophenyl)-1-(1,4,5,6-tetrahydro-6-oxopyridazin-3-yl)-1H-pyrazole, 4-(2-aminopyridin-4-yl)-1-(1,4,5,6-tetrahydro-6-oxopyridazin-3-yl) -3-(3-trifluoromethylphenyl)-1H-pyrazole, 4-(2-aminopyridin-4-yl)-3-(2-fluorophenyl)-1-(1,4,5,6-tetrahydro-6-oxopyridazin-3-yl)-1H-pyrazole, 3-(2-fluorophenyl)-1-(1,4,5,6-tetrahydro-6-oxopyridazin-3-yl)-4-[2-(2,2,2-trifluoroethyl)aminopyridin-4-yl]-1H-pyrazole, 4-(2-acetylaminopyridin-4-yl)-3-(2-fluorophenyl)-1-(1,4,5,6-tetrahydro-6-oxopyridazin-3-yl)-1H-pyrazole, 4-(2-aminopyrimidin-4-yl)-3-(2-fluorophenyl)-1-(1,4,5,6-tetrahydro-6-oxopyridazin-3-yl)-1H-pyrazole, 4-(2-aminopyridin-4-yl)-3-(2,4-difluorophenyl)-1-(1,4,5,6-tetrahydro-6-oxopyridazin-3-yl)-1H-pyrazole, 4-(2-cyclopropylcarbonylaminopyridin-4-yl)-(1,4,5,6-tetrahydro-6-oxopyridazin-3-yl)-3-phenyl-1-1H-pyrazole, 4-(2-cyclopropylcarbonylaminopyridin-4-yl)-3-(4-fluoro-phenyl)-1-(1,4,5,6-tetrahydro-6-oxopyridazin-3-yl)-1H-pyrazole or 4-(2-cyclopropylcarbonylaminopyridin-4-yl)-3-(2-fluorophenyl)-1-(1,4,5,6-tetrahydro-6-oxopyridazin-3-yl)-1H-pyrazole,

(53) a compound represented by the formula (I)

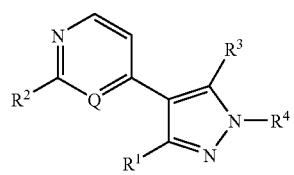

(I)

[wherein R¹ represents a phenyl group which may be substituted by a group(s) selected from the group consisting of a halogen atom, $C_1$-$C_6$ alkyl group, halogeno $C_1$-$C_6$ alkyl group, $C_1$-$C_6$ alkoxy group, halogeno $C_1$-$C_6$ alkoxy group and $C_1$-$C_6$ alkylthio group, R² represents a hydrogen atom, halogen atom, $C_1$-$C_6$ alkyl group, $C_1$-$C_6$ alkoxy group, $C_1$-$C_6$ alkylthio group, $C_1$-$C_6$ alkylsulfinyl group, $C_1$-$C_6$ alkylsulfonyl group or group: —NR⁵R⁶ (wherein R⁵ and R⁶ may be the same or different from each other, and each represents a hydrogen atom, $C_1$-$C_6$ alkyl group, halogeno $C_1$-$C_6$ alkyl group, $C_3$-$C_7$ cycloalkyl group, $C_1$-$C_6$ alkyl-carbonyl group, $C_3$-$C_7$ cycloalkyl-carbonyl group, formyl group, $C_1$-$C_6$ alkoxycarbonyl group or $C_1$-$C_6$ alkylsulfonyl group, or a $C_7$-$C_{12}$ aralkyl group or benzoyl group each of which may be substituted by a group(s) selected from the group consisting of a halogen atom, $C_1$-$C_6$ alkyl group, halogeno $C_1$-$C_6$ alkyl group, $C_1$-$C_6$ alkoxy group and halogeno $C_1$-$C_6$ alkoxy group.), Q represents CH or a nitrogen atom, R³ represents a hydrogen atom, $C_1$-$C_6$ alkyl group or amino group, R⁴ represents the formula (V):

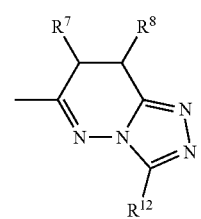

(V)

[wherein R⁷ represents a hydrogen atom or $C_1$-$C_6$ alkyl group, R⁸ represents a hydrogen atom, $C_1$-$C_6$ alkyl group or group: —NR¹⁰R¹¹ (wherein R¹⁰ and R¹¹ may be the same or different from each other, and each represents a hydrogen atom, $C_1$-$C_6$ alkyl group, $C_1$-$C_6$ alkyl-carbonyl group, formyl group, $C_1$-$C_6$ alkoxy-carbonyl group or $C_1$-$C_6$ alkyl-sulfonyl group.), R¹² represents a hydrogen atom, $C_1$-$C_6$ alkyl group, halogeno $C_1$-$C_6$ alkyl group or group: —NR¹⁰R¹¹ (wherein R¹⁰ and R¹¹ may be the same or different from each other, and each represents a hydrogen atom, $C_1$-$C_6$ alkyl group, $C_1$-$C_6$ alkyl-carbonyl group, formyl group, $C_1$-$C_6$ alkoxy-carbonyl group or $C_1$-$C_6$ alkylsulfonyl group.).].],

(54) a compound wherein $R^1$ represents a phenyl group which may be substituted by 1 to 3 group(s) selected from the group consisting of a halogen atom, $C_1$-$C_4$ alkyl group, halogeno $C_1$-$C_4$ alkyl group, $C_1$-$C_4$ alkoxy group, halogeno $C_1$-$C_4$ alkoxy group and $C_1$-$C_4$ alkylthio group, $R^2$ represents a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group or group: —$NR^5R^6$ (wherein $R^5$ and $R^6$ may be the same or different from each other, and each represents a hydrogen atom, $C_1$-$C_4$ alkyl group, halogeno $C_1$-$C_4$ alkyl group, $C^3$-$C^6$ cycloalkyl group, $C_1$-$C_4$ alkyl-carbonyl group, $C^3$-$C^6$ cycloalkyl-carbonyl group, formyl group, $C_1$-$C_4$ alkoxy-carbonyl group or $C_1$-$C_4$ alkylsulfonyl group, or a $C_7$-$C_{12}$ aralkyl group or benzoyl group each of which may be substituted by a group(s) selected from the group consisting of a halogen atom, $C_1$-$C_4$ alkyl group, halogeno $C_1$-$C_4$ alkyl group, $C_1$-$C_4$ alkoxy group and halogeno $C_1$-$C_4$ alkoxy group.), $R^3$ represents a hydrogen atom, $C_1$-$C_4$ alkyl group or amino group, $R^4$ represents the formula (V) (wherein $R^7$ represents a hydrogen atom or $C_1$-$C_4$ alkyl group, $R^8$ represents a hydrogen atom, $C_1$-$C_4$ alkyl group, amino group, $C_1$-$C_4$ alkylamino group, di($C_1$-$C_4$ alkyl)amino group, $C_1$-$C_4$ alkyl-carbonylamino group, formylamino group, $C_1$-$C_4$ alkoxy-carbonylamino group or $C_1$-$C_4$ alkylsulfonylamino group, $R^{12}$ represents a hydrogen atom, $C_1$-$C_4$ alkyl group, fluoro $C_1$-$C_4$ alkyl group, amino group, $C_1$-$C_4$ alkylamino group, di($C_1$-$C_4$ alkyl)amino group, $C_1$-$C_4$ alkyl-carbonylamino group, formylamino group, $C_1$-$C_4$ alkoxy-carbonylamino group or $C_1$-$C_4$ alkylsulfonylamino group.),

(55) a compound wherein $R^1$ represents a phenyl group which may be substituted by 1 to 2 group(s) selected from the group consisting of a halogen atom, $C_1$-$C_4$ alkyl group, fluoro $C_1$-$C_4$ alkyl group, $C_1$-$C_4$ alkoxy group, fluoro $C_1$-$C_4$ alkoxy group and $C_1$-$C_4$ alkylthio group, $R^2$ represents a hydrogen atom, halogen atom, $C_1$-$C_4$ alkyl group, $C_1$-$C_4$ alkoxy group, $C_1$-$C_4$ alkylthio group, $C_1$-$C_4$ alkylsulfinyl group, $C_1$-$C_4$ alkylsulfonyl group, amino group, $C_1$-$C_4$ alkylamino group, di($C_1$-$C_4$ alkyl)amino group, fluoro $C_1$-$C_4$ alkylamino group, $C_3$-$C_6$ cycloalkylamino group, $C_1$-$C_4$ alkyl-carbonylamino group, $C_3$-$C_6$ cycloalkyl-carbonylamino group, N-($C_3$-$C_6$ cycloalkyl-carbonyl)-N-($C_1$-$C_4$ alkyl)-amino group, formylamino group, $C_1$-$C_4$ alkoxy-carbonylamino group, $C_1$-$C_4$ alkylsulfonylamino group, or a benzylamino group, 1-phenethylamino group or benzoylamino group the phenyl group portion thereof may be substituted by a group selected from the group consisting of a halogen atom, $C_1$-$C_4$ alkyl group, fluoro $C_1$-$C_4$ alkyl group, $C_1$-$C_4$ alkoxy group and fluoro $C_1$-$C_4$ alkoxy group, $R^3$ represents a hydrogen atom, methyl group or amino group, $R^4$ represents the formula (V) (wherein $R^7$ represents a hydrogen atom, methyl group or ethyl group, $R^8$ represents a hydrogen atom, methyl group, ethyl group, amino group, methylamino group, dimethylamino group, ethylamino group, diethylamino group, isopropylamino group, acetylamino group, formylamino group, methoxycarbonylamino group, ethoxycarbonylamino group, methylsulfonylamino group or ethylsulfonylamino group, $R^{12}$ represents a hydrogen atom, methyl group, ethyl group, trifluoromethyl group, 2,2,2-trifluoroethyl group, amino group, methylamino group, dimethylamino group, ethylamino group, diethylamino group, isopropylamino group, acetylamino group, formylamino group, methoxycarbonylamino group, ethoxycarbonylamino group, methylsulfonylamino group or ethylsulfonylamino group.),

(56) a compound wherein $R^1$ represents a phenyl group which may be substituted by 1 to 2 group(s) selected from the group consisting of a fluorine atom, chlorine atom, bromine atom, methyl group, ethyl group, isopropyl group, difluoromethyl group, trifluoromethyl group, 2-fluoroethyl group, 2,2,2-trifluoroethyl group, methoxy group, ethoxy group, isopropoxy group, fluoromethoxy group, difluoromethoxy group, trifluoromethoxy group and methylthio group, $R^2$ represents a hydrogen atom, fluorine atom, chlorine atom, methyl group, methoxy group, methylthio group, methylsulfinyl group, methylsulfonyl group, amino group, methylamino group, dimethylamino group, ethylamino group, diethylamino group, propylamino group, isopropylamino group, trifluoromethylamino group, 2,2,2-trifluoromethylamino group, cyclopropylamino group, cyclohexylamino group, acetylamino group, propionylamino group, cyclopropylcarbonylamino group, cyclopentylcarbonylamino group, N-cyclopropylcarbonyl-N-methylamino group, formylamino group, methoxycarbonylamino group, ethoxycarbonylamino group, t-butoxycarbonylamino group, methylsulfonylamino group, ethylsulfonylamino group, or a benzylamino group, 1-phenethylamino group or benzoylamino group the phenyl group portion thereof may be substituted by a group(s) selected from the group consisting of a fluorine atom, methyl group, trifluoromethyl group, methoxy group and difluoromethoxy group, $R^3$ represents a hydrogen atom, methyl group or amino group, $R^4$ represents the formula (V) (wherein $R^7$ represents a hydrogen atom or methyl group, $R^8$ represents a hydrogen atom, methyl group, amino group, methylamino group, dimethylamino group, acetylamino group, formylamino group, methoxycarbonylamino group or methylsulfonylamino group, $R^{12}$ represents a hydrogen atom, methyl group, trifluoromethyl group, amino group, methylamino group, dimethylamino group, acetylamino group, formylamino group, methoxycarbonylamino group or methylsulfonylamino group.),

(57) a compound wherein $R^1$ represents a phenyl group which may be substituted by 1 to 2 group(s) selected from the group consisting of a fluorine atom, chlorine atom, methyl group, difluoromethyl group, trifluoromethyl group, methoxy group, fluoromethoxy group, difluoromethoxy group and trifluoromethoxy group, $R^2$ represents a hydrogen atom, fluorine atom, methyl group, methoxy group, methylthio group, methylsulfinyl group, methylsulfonyl group, amino group, methylamino group, dimethylamino group, ethylamino group, isopropylamino group, 2,2,2-trifluoromethylamino group, cyclopropylamino group, acetylamino group, cyclopropylcarbonylamino group, cyclopentylcarbonylamino group, N-cyclopropylcarbonyl-N-methylamino group, methoxycarbonylamino group, methylsulfonylamino group, 4-methoxybenzylamino group, 1-phenethylamino group or benzoylamino group, $R^3$ represents a hydrogen atom, methyl group or amino group, $R^4$ represents a 7,8-dihydro-[1,2,4]triazolo[4,3-b]-pyridazin-6-yl group, 7,8-dihydro-3-methyl-[1,2,4]triazolo[4,3-b]pyridazin-6-yl group, 7,8-dihydro-3-trifluoromethyl-[1, 2,4]triazolo[4,3-b]pyridazin-6-yl group, 3-amino-7,8-dihydro-[1,2,4]triazolo[4,3-b]pyridazin-6-yl group, 7,8-dihydro-3-methylamino-[1,2,4]triazolo[4,3-b]pyridazin-6-yl group, 3-acetylamino-7,8-dihydro-[1,2,4]triazolo[4,3-b]pyridazin-6-yl group, 7,8-dihydro-3-methoxycarbonylamino-[1,2,4]triazolo[4,3-b]pyridazin-6-yl group, 7,8-dihydro-3-methylsulfonylamino-[1,2,4]triazolo[4,3-b]pyridazin-6-yl group, 7,8-dihydro-7-methyl-[1,2,4]triazolo[4,3-b]pyridazin-6-yl group, 7,8-dihydro-8-methyl-[1,2,4]triazolo[4,3-b]pyridazin-6-yl group or 8-amino-7,8-dihydro-[1,2,4]triazolo[4,3-b]pyridazin-6-yl group,

(58) a compound wherein $R^1$ represents a phenyl group, 2-fluorophenyl group, 3-fluorophenyl group, 4-fluorophenyl group, 3-chlorophenyl group, 4-chlorophenyl group, 3,4-difluorophenyl group, 2,4-difluorophenyl group, 3,4-dichlorophenyl group, 3-chloro-4-fluorophenyl group, 4-chloro-3-fluorophenyl group or 3-trifluoromethylphenyl group, $R^2$ represents a hydrogen atom, methoxy group, amino group, methylamino group, ethylamino group, isopropylamino group, 2,2,2-trifluoromethylamino group, acetylamino group, cyclopropylcarbonylamino group, cyclopentylcarbonylamino group, methoxycarbonylamino group, methylsulfonylamino group, 4-methoxybenzylamino group, 1-phenethylamino group or benzoylamino group, $R^3$ represents a hydrogen atom, methyl group or amino group, $R^4$ represents a 7,8-dihydro-[1,2,4]triazolo[4,3-b]-pyridazin-6-yl group, 7,8-dihydro-3-methyl-[1,2,4]triazolo-[4,3-b]pyridazin-6-yl group, 7,8-dihydro-3-trifluoromethyl-[1,2,4]triazolo[4,3-b]pyridazin-6-yl group, 3-amino-7,8-dihydro-[1,2,4]triazolo[4,3-b]pyridazin-6-yl group, 7,8-dihydro-7-methyl-[1,2,4]triazolo[4,3-b]pyridazin-6-yl group or 7,8-dihydro-8-methyl-[1,2,4]triazolo[4,3-b]pyridazin-6-yl group,

(59) a compound wherein $R^1$ represents a phenyl group, 2-fluorophenyl group, 3-fluorophenyl group, 4-fluorophenyl group, 3-chlorophenyl group, 4-chlorophenyl group, 3,4-difluorophenyl group, 2,4-difluorophenyl group, 3,4-dichlorophenyl group, 3-chloro-4-fluorophenyl group, 4-chloro-3-fluorophenyl group or 3-trifluoromethylphenyl group, $R^2$ represents a hydrogen atom, methoxy group, amino group, methylamino group, ethylamino group, isopropylamino group, 2,2,2-trifluoromethylamino group, acetylamino group, cyclopropylcarbonylamino group, cyclopentylcarbonylamino group, methoxycarbonylamino group, methylsulfonylamino group, 4-methoxybenzylamino group, 1-phenethylamino group or benzoylamino group, $R^3$ represents a hydrogen atom, $R^4$ represents a 7,8-dihydro-[1,2,4]triazolo[4,3-b]-pyridazin-6-yl group or 7,8-dihydro-3-methyl-[1,2,4]triazolo[4,3-b]pyridazin-6-yl group,

(60) a compound wherein 4-(2-aminopyridin-4-yl)-1-(7,8-dihydro-[1,2,4]triazolo[4,3-b]pyridazin-6-yl)-3-phenyl-1H-pyrazole, 3-(4-fluorophenyl)-1-(7,8-dihydro-[1,2,4]triazolo[4,3-b]-pyridazin-6-yl) -4-(pyridin-4-yl)-1H-pyrazole, 4-(2-aminopyridin-4-yl)-3-(4-fluorophenyl)-1-(7,8-dihydro-[1,2,4]triazolo[4,3-b]pyridazin-6-yl)-1H-pyrazole, 3-(4-fluorophenyl)-1-(7,8-dihydro-[1,2,4]triazolo[4,3-b]-pyridazin-6-yl) -4-[2-(2,2,2-trifluoroethyl)aminopyridin-4-yl]-1H-pyrazole, 4-(2-acetylaminopyridin-4-yl)-3-(4-fluorophenyl)-1-(7,8-dihydro-[1,2,4]triazolo[4,3-b]pyridazin-6-yl)-1H-pyrazole, 4-(2-cyclopropylcarbonylaminopyridin-4-yl)-3-(4-fluorophenyl)-1-(7,8-dihydro-[1,2,4]triazolo[4,3-b]pyridazin-6-yl)-1H-pyrazole, 4-(2-aminopyrimidin-4-yl)-3-(4-fluorophenyl)-1-(7,8-dihydro-[1,2,4]triazolo[4,3-b]pyridazin-6-yl)-1H-pyrazole, 4-(2-aminopyridin-4-yl)-3-(3-fluorophenyl)-1-(7,8-dihydro-[1,2,4]triazolo[4,3-b]pyridazin-6-yl)-1H-pyrazole, 4-(2-aminopyridin-4-yl)-3-(2-fluorophenyl)-1-(7,8-dihydro-[1,2,4]triazolo[4,3-b]pyridazin-6-yl)-1H-pyrazole, 3-(2-fluorophenyl)-1-(7,8-dihydro-[1,2,4]triazolo[4,3-b]-pyridazin-6-yl) -4-[2-(2,2,2-trifluoroethyl)aminopyridin-4-yl]-1-H-pyrazole, 4-(2-acetylaminopyridin-4-yl)-3-(2-fluorophenyl)-1-(7,8-dihydro-[1,2,4]triazolo[4,3-b]pyridazin-6-yl)-1H-pyrazole, 4-(2-cyclopropylcarbonylaminopyridin-4-yl)-3-(2-fluorophenyl)-1-(7,8-dihydro-[1,2,4]triazolo[4,3-b]pyridazin-6-yl)-1-H-pyrazole, 4-(2-aminopyridin-4-yl)-3-(4-chlorophenyl)-1-(7,8-dihydro-[1,2,4]triazolo[4,3-b]pyridazin-6-yl)-1H-pyrazole, 4-(2-aminopyridin-4-yl)-3-(3-chlorophenyl)-1-(7,8-dihydro-[1,2,4]triazolo[4,3-b]pyridazin-6-yl)-1H-pyrazole, 4-(2-aminopyridin-4-yl)-3-(3,4-difluorophenyl)-1-(7,8-dihydro-[1,2,4]triazolo[4,3-b]pyridazin-6-yl)-1H-pyrazole, 3-(3,4-difluorophenyl)-1-(7,8-dihydro-[1,2,4]triazolo[4,3-b]pyridazin-6-yl)-4-[2-(2,2,2-trifluoroethyl)aminopyridin-4-yl-1]-H-pyrazole, 4-(2-acetylaminopyridin-4-yl)-3-(3,4-difluorophenyl)-1-(7,8-dihydro-[1,2,4]triazolo[4,3-b]pyridazin-6-yl)-1H-pyrazole, 4-(2-cyclopropylcarbonylaminopyridin-4-yl)-3-(3,4-difluorophenyl)-1-(7,8-dihydro-[1,2,4]triazolo[4,3-b]pyridazin-6-yl)-1-H-pyrazole, 4-(2-aminopyridin-4-yl)-3-(3,4-dichlorophenyl)-1-(7,8-dihydro-[1,2,4]triazolo[4,3-b]pyridazin-6-yl)-1H-pyrazole or 4-(2-aminopyridin-4-yl)-1-(7,8-dihydro-[1,2,4]triazolo[4,3-b]pyridazin-6-yl)-3-(3-trifluoromethylphenyl)-1H-pyrazole.

In the present invention, preferred compounds having the formula (I) may be specifically exemplified by the compounds shown in Table 1 to Table 4.

TABLE 1

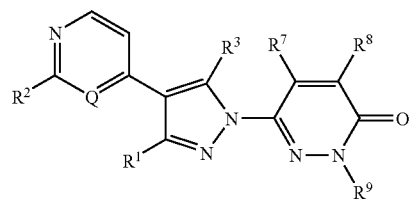

| Compound No | $R^1$ | $R^2$ | $R^3$ | $R^7$ | $R^8$ | $R^9$ | Q |
|---|---|---|---|---|---|---|---|
| 1-1 | Ph | H | H | H | H | H | CH |
| 1-2 | Ph | $NH_2$ | H | H | H | H | CH |

TABLE 1-continued

| Compound No | R¹ | R² | R³ | R⁷ | R⁸ | R⁹ | Q |
|---|---|---|---|---|---|---|---|
| 1-3 | Ph | NHMe | H | H | H | H | CH |
| 1-4 | Ph | NMe₂ | H | H | H | H | CH |
| 1-5 | Ph | NHEt | H | H | H | H | CH |
| 1-6 | Ph | NHCH₂CF₃ | H | H | H | H | CH |
| 1-7 | Ph | NHPrⁱ | H | H | H | H | CH |
| 1-8 | Ph | NHCOMe | H | H | H | H | CH |
| 1-9 | Ph | NHCOOMe | H | H | H | H | CH |
| 1-10 | Ph | NHSO₂Me | H | H | H | H | CH |
| 1-11 | Ph | NH(4-F-Bn) | H | H | H | H | CH |
| 1-12 | Ph | NH(α-Me-Bn) | H | H | H | H | CH |
| 1-13 | Ph | NHCOPh | H | H | H | H | CH |
| 1-14 | Ph | NH₂ | Me | H | H | H | CH |
| 1-15 | Ph | NH₂ | NH₂ | H | H | H | CH |
| 1-16 | Ph | NH₂ | H | Me | H | H | CH |
| 1-17 | Ph | NH₂ | H | H | Me | H | CH |
| 1-18 | Ph | NH₂ | H | H | NH₂ | H | CH |
| 1-19 | Ph | NH₂ | H | H | NHMe | H | CH |
| 1-20 | Ph | NH₂ | H | H | NMe₂ | H | CH |
| 1-21 | Ph | NH₂ | H | H | NHCOMe | H | CH |
| 1-22 | Ph | NH₂ | H | H | NHCOOMe | H | CH |
| 1-23 | Ph | NH₂ | H | H | NHSO₂Me | H | CH |
| 1-24 | Ph | NH₂ | H | H | H | Me | CH |
| 1-25 | Ph | NH₂ | H | H | NH₂ | Me | CH |
| 1-26 | Ph | H | H | H | H | H | N |
| 1-27 | Ph | NH₂ | H | H | H | H | N |
| 1-28 | Ph | NHMe | H | H | H | H | N |
| 1-29 | Ph | NMe₂ | H | H | H | H | N |
| 1-30 | Ph | NHEt | H | H | H | H | N |
| 1-31 | Ph | NHPrⁱ | H | H | H | H | N |
| 1-32 | Ph | NHCH₂CF₃ | H | H | H | H | N |
| 1-33 | Ph | NHPrⁱ | H | H | H | H | N |
| 1-34 | Ph | NHCOMe | H | H | H | H | N |
| 1-35 | Ph | NHCOOMe | H | H | H | H | N |
| 1-36 | Ph | NHSO₂Me | H | H | H | H | N |
| 1-37 | Ph | NH(4-F-Bn) | H | H | H | H | N |
| 1-38 | Ph | NH(α-Me-Bn) | H | H | H | H | N |
| 1-39 | Ph | NHCOPh | H | H | H | H | N |
| 1-40 | Ph | NH₂ | H | H | Me | H | N |
| 1-41 | Ph | NH₂ | H | H | NH₂ | H | N |
| 1-42 | 4-F-Ph | H | H | H | H | H | CH |
| 1-43 | 4-F-Ph | H | Me | H | H | H | CH |
| 1-44 | 4-F-Ph | H | Et | H | H | H | CH |
| 1-45 | 4-F-Ph | H | NH₂ | H | H | H | CH |
| 1-46 | 4-F-Ph | H | H | Me | H | H | CH |
| 1-47 | 4-F-Ph | H | H | Et | H | H | CH |
| 1-48 | 4-F-Ph | H | H | H | Me | H | CH |
| 1-49 | 4-F-Ph | H | H | H | Et | H | CH |
| 1-50 | 4-F-Ph | H | H | H | NH₂ | H | CH |
| 1-51 | 4-F-Ph | H | H | H | NHMe | H | CH |
| 1-52 | 4-F-Ph | H | H | H | NHEt | H | CH |
| 1-53 | 4-F-Ph | H | H | H | NMe₂ | H | CH |
| 1-54 | 4-F-Ph | H | H | H | NEt₂ | H | CH |
| 1-55 | 4-F-Ph | H | H | H | NHCHO | H | CH |
| 1-56 | 4-F-Ph | H | H | H | NHCOMe | H | CH |
| 1-57 | 4-F-Ph | H | H | H | NHCOEt | H | CH |
| 1-58 | 4-F-Ph | H | H | H | NHCOOMe | H | CH |
| 1-59 | 4-F-Ph | H | H | H | NHCOOEt | H | CH |
| 1-60 | 4-F-Ph | H | H | H | NHSO₂Me | H | CH |
| 1-61 | 4-F-Ph | H | H | H | NHSO₂Et | H | CH |
| 1-62 | 4-F-Ph | H | H | H | H | Me | CH |
| 1-63 | 4-F-Ph | H | H | H | H | Et | CH |
| 1-64 | 4-F-Ph | F | H | H | H | H | CH |
| 1-65 | 4-F-Ph | Cl | H | H | H | H | CH |
| 1-66 | 4-F-Ph | Me | H | H | H | H | CH |
| 1-67 | 4-F-Ph | Et | H | H | H | H | CH |

TABLE 1-continued

| Compound No | R¹ | R² | R³ | R⁷ | R⁸ | R⁹ | Q |
|---|---|---|---|---|---|---|---|
| 1-68 | 4-F-Ph | OMe | H | H | H | H | CH |
| 1-69 | 4-F-Ph | OEt | H | H | H | H | CH |
| 1-70 | 4-F-Ph | SMe | H | H | H | H | CH |
| 1-71 | 4-F-Ph | SOMe | H | H | H | H | CH |
| 1-72 | 4-F-Ph | SO₂Me | H | H | H | H | CH |
| 1-73 | 4-F-Ph | NH₂ | H | H | H | H | CH |
| 1-74 | 4-F-Ph | NHMe | H | H | H | H | CH |
| 1-75 | 4-F-Ph | NMe₂ | H | H | H | H | CH |
| 1-76 | 4-F-Ph | NHEt | H | H | H | H | CH |
| 1-77 | 4-F-Ph | NHPrⁱ | H | H | H | H | CH |
| 1-78 | 4-F-Ph | NHCH₂CF₃ | H | H | H | H | CH |
| 1-79 | 4-F-Ph | NHPrᶜ | H | H | H | H | CH |
| 1-80 | 4-F-Ph | NHCHO | H | H | H | H | CH |
| 1-81 | 4-F-Ph | NHCOMe | H | H | H | H | CH |
| 1-82 | 4-F-Ph | NHCOEt | H | H | H | H | CH |
| 1-83 | 4-F-Ph | NHCOPr | H | H | H | H | CH |
| 1-84 | 4-F-Ph | NHCOOMe | H | H | H | H | CH |
| 1-85 | 4-F-Ph | NHCOOEt | H | H | H | H | CH |
| 1-86 | 4-F-Ph | NHSO₂Me | H | H | H | H | CH |
| 1-87 | 4-F-Ph | NHSO₂Et | H | H | H | H | CH |
| 1-88 | 4-F-Ph | NHBn | H | H | H | H | CH |
| 1-89 | 4-F-Ph | NH(4-F-Bn) | H | H | H | H | CH |
| 1-90 | 4-F-Ph | NH(α-Me-Bn) | H | H | H | H | CH |
| 1-91 | 4-F-Ph | NHCOPh | H | H | H | H | CH |
| 1-92 | 4-F-Ph | NH₂ | Me | H | H | H | CH |
| 1-93 | 4-F-Ph | NH₂ | NH₂ | H | H | H | CH |
| 1-94 | 4-F-Ph | NH₂ | H | Me | H | H | CH |
| 1-95 | 4-F-Ph | NH₂ | H | H | Me | H | CH |
| 1-96 | 4-F-Ph | NH₂ | H | Me | Me | H | CH |
| 1-97 | 4-F-Ph | NH₂ | H | H | NH₂ | H | CH |
| 1-98 | 4-F-Ph | NH₂ | H | H | NHMe | H | CH |
| 1-99 | 4-F-Ph | NH₂ | H | H | NHEt | H | CH |
| 1-100 | 4-F-Ph | NH₂ | H | H | NMe₂ | H | CH |
| 1-101 | 4-F-Ph | NH₂ | H | H | NHCOMe | H | CH |
| 1-102 | 4-F-Ph | NH₂ | H | H | NHCOOMe | H | CH |
| 1-103 | 4-F-Ph | NH₂ | H | H | NHSO₂Me | H | CH |
| 1-104 | 4-F-Ph | NH₂ | H | H | H | Me | CH |
| 1-105 | 4-F-Ph | NH₂ | H | H | Me | Me | CH |
| 1-106 | 4-F-Ph | NH₂ | H | H | NH₂ | Me | CH |
| 1-107 | 4-F-Ph | H | H | H | H | H | N |
| 1-108 | 4-F-Ph | H | Me | H | H | H | N |
| 1-109 | 4-F-Ph | H | NH₂ | H | H | H | N |
| 1-110 | 4-F-Ph | H | H | Me | H | H | N |
| 1-111 | 4-F-Ph | H | H | H | Me | H | N |
| 1-112 | 4-F-Ph | H | H | H | NH₂ | H | N |
| 1-113 | 4-F-Ph | H | H | H | NHMe | H | N |
| 1-114 | 4-F-Ph | H | H | H | NMe₂ | H | N |
| 1-115 | 4-F-Ph | H | H | H | NHCOMe | H | N |
| 1-116 | 4-F-Ph | H | H | H | NHCOOMe | H | N |
| 1-117 | 4-F-Ph | H | H | H | NHSO₂Me | H | N |
| 1-118 | 4-F-Ph | H | H | H | H | Me | N |
| 1-119 | 4-F-Ph | NH₂ | H | H | H | H | N |
| 1-120 | 4-F-Ph | NHMe | H | H | H | H | N |
| 1-121 | 4-F-Ph | NMe₂ | H | H | H | H | N |
| 1-122 | 4-F-Ph | NHEt | H | H | H | H | N |
| 1-123 | 4-F-Ph | NHPrⁱ | H | H | H | H | N |
| 1-124 | 4-F-Ph | NHCH₂CF₃ | H | H | H | H | N |
| 1-125 | 4-F-Ph | NHPrᶜ | H | H | H | H | N |
| 1-126 | 4-F-Ph | NHCOMe | H | H | H | H | N |
| 1-127 | 4-F-Ph | NHCOOMe | H | H | H | H | N |
| 1-128 | 4-F-Ph | NHSO₂Me | H | H | H | H | N |
| 1-129 | 4-F-Ph | NH(4-F-Bn) | H | H | H | H | N |
| 1-130 | 4-F-Ph | NH(α-Me-Bn) | H | H | H | H | N |
| 1-131 | 4-F-Ph | NHCOPh | H | H | H | H | N |
| 1-132 | 4-F-Ph | NH₂ | Me | H | H | H | N |

TABLE 1-continued

| Compound No | R¹ | R² | R³ | R⁷ | R⁸ | R⁹ | Q |
|---|---|---|---|---|---|---|---|
| 1-133 | 4-F-Ph | NH₂ | H | Me | H | H | N |
| 1-134 | 4-F-Ph | NH₂ | H | H | Me | H | N |
| 1-135 | 4-F-Ph | NH₂ | H | H | NH₂ | H | N |
| 1-136 | 4-F-Ph | NH₂ | H | H | H | Me | N |
| 1-137 | 3-F-Ph | H | H | H | H | H | CH |
| 1-138 | 3-F-Ph | H | Me | H | H | H | CH |
| 1-139 | 3-F-Ph | H | NH₂ | H | H | H | CH |
| 1-140 | 3-F-Ph | H | H | Me | H | H | CH |
| 1-141 | 3-F-Ph | H | H | H | Me | H | CH |
| 1-142 | 3-F-Ph | H | H | H | NH₂ | H | CH |
| 1-143 | 3-F-Ph | H | H | H | NHMe | H | CH |
| 1-144 | 3-F-Ph | H | H | H | NMe₂ | H | CH |
| 1-145 | 3-F-Ph | H | H | H | NHCOMe | H | CH |
| 1-146 | 3-F-Ph | H | H | H | NHCOOMe | H | CH |
| 1-147 | 3-F-Ph | H | H | H | NHSO₂Me | H | CH |
| 1-148 | 3-F-Ph | H | H | H | H | Me | CH |
| 1-149 | 3-F-Ph | F | H | H | H | H | CH |
| 1-150 | 3-F-Ph | Cl | H | H | H | H | CH |
| 1-151 | 3-F-Ph | Me | H | H | H | H | CH |
| 1-152 | 3-F-Ph | OMe | H | H | H | H | CH |
| 1-153 | 3-F-Ph | SMe | H | H | H | H | CH |
| 1-154 | 3-F-Ph | SOMe | H | H | H | H | CH |
| 1-155 | 3-F-Ph | SO₂Me | H | H | H | H | CH |
| 1-156 | 3-F-Ph | NH₂ | H | H | H | H | CH |
| 1-157 | 3-F-Ph | NHMe | H | H | H | H | CH |
| 1-158 | 3-F-Ph | NMe₂ | H | H | H | H | CH |
| 1-159 | 3-F-Ph | NHEt | H | H | H | H | CH |
| 1-160 | 3-F-Ph | NHPrⁱ | H | H | H | H | CH |
| 1-161 | 3-F-Ph | NHCH₂CF₃ | H | H | H | H | CH |
| 1-162 | 3-F-Ph | NHPrᶜ | H | H | H | H | CH |
| 1-163 | 3-F-Ph | NHCOMe | H | H | H | H | CH |
| 1-164 | 3-F-Ph | NHCOOMe | H | H | H | H | CH |
| 1-165 | 3-F-Ph | NHSO₂Me | H | H | H | H | CH |
| 1-166 | 3-F-Ph | NH(4-F-Bn) | H | H | H | H | CH |
| 1-167 | 3-F-Ph | NH(α-Me-Bn) | H | H | H | H | CH |
| 1-168 | 3-FPh | NHCOPh | H | H | H | H | CH |
| 1-169 | 3-F-Ph | NH₂ | Me | H | H | H | CH |
| 1-170 | 3-F-Ph | NH₂ | NH₂ | H | H | H | CH |
| 1-171 | 3-F-Ph | NH₂ | H | Me | H | H | CH |
| 1-172 | 3-F-Ph | NH₂ | H | H | Me | H | CH |
| 1-173 | 3-F-Ph | NH₂ | H | Me | Me | H | CH |
| 1-174 | 3-F-Ph | NH₂ | H | H | NH₂ | H | CH |
| 1-175 | 3-F-Ph | NH₂ | H | H | NHMe | H | CH |
| 1-176 | 3-F-Ph | NH₂ | H | H | NMe₂ | H | CH |
| 1-177 | 3-F-Ph | NH₂ | H | H | NHCOMe | H | CH |
| 1-178 | 3-F-Ph | NH₂ | H | H | NHCOOMe | H | CH |
| 1-179 | 3-F-Ph | NH₂ | H | H | NHSO₂Me | H | CH |
| 1-180 | 3-F-Ph | NH₂ | H | H | H | Me | CH |
| 1-181 | 3-FPh | NH₂ | H | H | Me | Me | CH |
| 1-182 | 3-F-Ph | NH₂ | H | H | NH₂ | Me | CH |
| 1-183 | 3-F-Ph | H | H | H | H | H | N |
| 1-184 | 3-F-Ph | H | NH₂ | H | H | H | N |
| 1-185 | 3-F-Ph | H | H | H | Me | H | N |
| 1-186 | 3-F-Ph | H | H | H | NH₂ | H | N |
| 1-187 | 3-F-Ph | H | H | H | NHMe | H | N |
| 1-188 | 3-F-Ph | H | H | H | H | Me | N |
| 1-189 | 3-F-Ph | NH₂ | H | H | H | H | N |
| 1-190 | 3-F-Ph | NHMe | H | H | H | H | N |
| 1-191 | 3-F-Ph | NMe₂ | H | H | H | H | N |
| 1-192 | 3-F-Ph | NHEt | H | H | H | H | N |
| 1-193 | 3-F-Ph | NHPrⁱ | H | H | H | H | N |
| 1-194 | 3-F-Ph | NHCH₂CF₃ | H | H | H | H | N |
| 1-195 | 3-F-Ph | NHPrᶜ | H | H | H | H | N |
| 1-196 | 3-F-Ph | NHCOMe | H | H | H | H | N |
| 1-197 | 3-F-Ph | NHCOOMe | H | H | H | H | N |

TABLE 1-continued

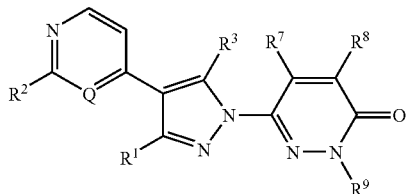

| Compound No | $R^1$ | $R^2$ | $R^3$ | $R^7$ | $R^8$ | $R^9$ | Q |
|---|---|---|---|---|---|---|---|
| 1-198 | 3-F-Ph | NHSO$_2$Me | H | H | H | H | N |
| 1-199 | 3-F-Ph | NH(4-F-Bn) | H | H | H | H | N |
| 1-200 | 3-F-Ph | NH(α-Me-Bn) | H | H | H | H | N |
| 1-201 | 3-F-Ph | NHCOPh | H | H | H | H | N |
| 1-202 | 3-F-Ph | NH$_2$ | Me | H | H | H | N |
| 1-203 | 3-F-Ph | NH$_2$ | H | Me | H | H | N |
| 1-204 | 3-F-Ph | NH$_2$ | H | H | Me | H | N |
| 1-205 | 3-F-Ph | NH$_2$ | H | H | NH$_2$ | H | N |
| 1-206 | 3-F-Ph | NH$_2$ | H | H | H | Me | N |
| 1-207 | 4-Cl-Ph | H | H | H | H | H | CH |
| 1-208 | 4-Cl-Ph | H | Me | H | H | H | CH |
| 1-209 | 4-Cl-Ph | H | Et | H | H | H | CH |
| 1-210 | 4-Cl-Ph | H | NH$_2$ | H | H | H | CH |
| 1-211 | 4-Cl-Ph | H | H | Me | H | H | CH |
| 1-212 | 4-Cl-Ph | H | H | H | Me | H | CH |
| 1-213 | 4-Cl-Ph | H | H | H | Et | H | CH |
| 1-214 | 4-Cl-Ph | H | H | H | NH$_2$ | H | CH |
| 1-215 | 4-Cl-Ph | H | H | H | NHMe | H | CH |
| 1-216 | 4-Cl-Ph | H | H | H | NHEt | H | CH |
| 1-217 | 4-Cl-Ph | H | H | H | NMe$_2$ | H | CH |
| 1-218 | 4-Cl-Ph | H | H | H | NEt$_2$ | H | CH |
| 1-219 | 4-Cl-Ph | H | H | H | NHCHO | H | CH |
| 1-220 | 4-Cl-Ph | H | H | H | NHCOMe | H | CH |
| 1-221 | 4-Cl-Ph | H | H | H | NHCOEt | H | CH |
| 1-222 | 4-Cl-Ph | H | H | H | NHCOOMe | H | CH |
| 1-223 | 4-Cl-Ph | H | H | H | NHCOOEt | H | CH |
| 1-224 | 4-Cl-Ph | H | H | H | NHSO$_2$Me | H | CH |
| 1-225 | 4-Cl-Ph | H | H | H | NHSO$_2$Et | H | CH |
| 1-226 | 4-Cl-Ph | H | H | H | H | Me | CH |
| 1-227 | 4-Cl-Ph | H | H | H | H | Et | CH |
| 1-228 | 4-Cl-Ph | F | H | H | H | H | CH |
| 1-229 | 4-Cl-Ph | Cl | H | H | H | H | CH |
| 1-230 | 4-Cl-Ph | Me | H | H | H | H | CH |
| 1-231 | 4-Cl-Ph | Et | H | H | H | H | CH |
| 1-232 | 4-Cl-Ph | OMe | H | H | H | H | CH |
| 1-233 | 4-Cl-Ph | OEt | H | H | H | H | CH |
| 1-234 | 4-Cl-Ph | SMe | H | H | H | H | CH |
| 1-235 | 4-Cl-Ph | SOMe | H | H | H | H | CH |
| 1-236 | 4-Cl-Ph | SO$_2$Me | H | H | H | H | CH |
| 1-237 | 4-Cl-Ph | NH$_2$ | H | H | H | H | CH |
| 1-238 | 4-Cl-Ph | NHMe | H | H | H | H | CH |
| 1-239 | 4-Cl-Ph | NMe$_2$ | H | H | H | H | CH |
| 1-240 | 4-Cl-Ph | NHEt | H | H | H | H | CH |
| 1-241 | 4-Cl-Ph | NHPr$^i$ | H | H | H | H | CH |
| 1-242 | 4-Cl-Ph | NHCH$_2$CF$_3$ | H | H | H | H | CH |
| 1-243 | 4-Cl-Ph | NHPr$^c$ | H | H | H | H | CH |
| 1-244 | 4-Cl-Ph | NHCHO | H | H | H | H | CH |
| 1-245 | 4-Cl-Ph | NHCOMe | H | H | H | H | CH |
| 1-246 | 4-Cl-Ph | NHCOEt | H | H | H | H | CH |
| 1-247 | 4-Cl-Ph | NHCOPr | H | H | H | H | CH |
| 1-248 | 4-Cl-Ph | NHCOOMe | H | H | H | H | CH |
| 1-249 | 4-Cl-Ph | NHCOOEt | H | H | H | H | CH |
| 1-250 | 4-Cl-Ph | NHSO$_2$Me | H | H | H | H | CH |
| 1-251 | 4-Cl-Ph | NHSO$_2$Et | H | H | H | H | CH |
| 1-252 | 4-Cl-Ph | NHBn | H | H | H | H | CH |
| 1-253 | 4-Cl-Ph | NH(4-F-Bn) | H | H | H | H | CH |
| 1-254 | 4-Cl-Ph | NH(α-Me-Bn) | H | H | H | H | CH |
| 1-255 | 4-Cl-Ph | NHCOPh | H | H | H | H | CH |
| 1-256 | 4-Cl-Ph | NH$_2$ | Me | H | H | H | CH |
| 1-257 | 4-Cl-Ph | NH$_2$ | NH$_2$ | H | H | H | CH |
| 1-258 | 4-Cl-Ph | NH$_2$ | H | Me | H | H | CH |
| 1-259 | 4-Cl-Ph | NH$_2$ | H | H | Me | H | CH |
| 1-260 | 4-Cl-Ph | NH$_2$ | H | Me | Me | H | CH |
| 1-261 | 4-Cl-Ph | NH$_2$ | H | H | NH$_2$ | H | CH |
| 1-262 | 4-Cl-Ph | NH$_2$ | H | H | NHMe | H | CH |

TABLE 1-continued

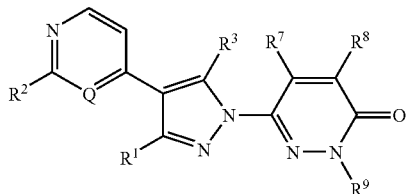

| Compound No | R¹ | R² | R³ | R⁷ | R⁸ | R⁹ | Q |
|---|---|---|---|---|---|---|---|
| 1-263 | 4-Cl-Ph | NH₂ | H | H | NHEt | H | CH |
| 1-264 | 4-Cl-Ph | NH₂ | H | H | NMe₂ | H | CH |
| 1-265 | 4-Cl-Ph | NH₂ | H | H | NHCOMe | H | CH |
| 1-266 | 4-Cl-Ph | NH₂ | H | H | NHCOOMe | H | CH |
| 1-267 | 4-Cl-Ph | NH₂ | H | H | NHSO₂Me | H | CH |
| 1-268 | 4-Cl-Ph | NH₂ | H | H | H | Me | CH |
| 1-269 | 4-Cl-Ph | NH₂ | H | H | Me | Me | CH |
| 1-270 | 4-Cl-Ph | NH₂ | H | H | NH₂ | Me | CH |
| 1-271 | 4-Cl-Ph | H | H | H | H | H | N |
| 1-272 | 4-Cl-Ph | H | Me | H | H | H | N |
| 1-273 | 4-Cl-Ph | H | NH₂ | H | H | H | N |
| 1-274 | 4-Cl-Ph | H | H | Me | H | H | N |
| 1-275 | 4-Cl-Ph | H | H | H | Me | H | N |
| 1-276 | 4-Cl-Ph | H | H | H | NH₂ | H | N |
| 1-277 | 4-Cl-Ph | H | H | H | NHMe | H | N |
| 1-278 | 4-Cl-Ph | H | H | H | NMe₂ | H | N |
| 1-279 | 4-Cl-Ph | H | H | H | NHCOMe | H | N |
| 1-280 | 4-Cl-Ph | H | H | H | NHCOOMe | H | N |
| 1-281 | 4-Cl-Ph | H | H | H | NHSO₂Me | H | N |
| 1-282 | 4-Cl-Ph | H | H | H | H | Me | N |
| 1-283 | 4-Cl-Ph | NH₂ | H | H | H | H | N |
| 1-284 | 4-Cl-Ph | NHMe | H | H | H | H | N |
| 1-285 | 4-Cl-Ph | NMe₂ | H | H | H | H | N |
| 1-286 | 4-Cl-Ph | NHEt | H | H | H | H | N |
| 1-287 | 4-Cl-Ph | NHPrⁱ | H | H | H | H | N |
| 1-288 | 4-Cl-Ph | NHCH₂CF₃ | H | H | H | H | N |
| 1-289 | 4-Cl-Ph | NHPrᶜ | H | H | H | H | N |
| 1-290 | 4-Cl-Ph | NHCOMe | H | H | H | H | N |
| 1-291 | 4-Cl-Ph | NHCOOMe | H | H | H | H | N |
| 1-292 | 4-Cl-Ph | NHSO₂Me | H | H | H | H | N |
| 1-293 | 4-Cl-Ph | NH(4-F-Bn) | H | H | H | H | N |
| 1-294 | 4-Cl-Ph | NH(α-Me-Bn) | H | H | H | H | N |
| 1-295 | 4-Cl-Ph | NHCOPh | H | H | H | H | N |
| 1-296 | 4-Cl-Ph | NH₂ | Me | H | H | H | N |
| 1-297 | 4-Cl-Ph | NH₂ | H | Me | H | H | N |
| 1-298 | 4-Cl-Ph | NH₂ | H | H | Me | H | N |
| 1-299 | 4-Cl-Ph | NH₂ | H | H | NH₂ | H | N |
| 1-300 | 4-Cl-Ph | NH₂ | H | H | H | Me | N |
| 1-301 | 3-Cl-Ph | H | H | H | H | H | CH |
| 1-302 | 3-Cl-Ph | H | Me | H | H | H | CH |
| 1-303 | 3-Cl-Ph | H | NH₂ | H | H | H | CH |
| 1-304 | 3-Cl-Ph | H | H | Me | H | H | CH |
| 1-305 | 3-Cl-Ph | H | H | H | Me | H | CH |
| 1-306 | 3-Cl-Ph | H | H | H | NH₂ | H | CH |
| 1-307 | 3-Cl-Ph | H | H | H | NHMe | H | CH |
| 1-308 | 3-Cl-Ph | H | H | H | NMe₂ | H | CH |
| 1-309 | 3-Cl-Ph | H | H | H | NHCOMe | H | CH |
| 1-310 | 3-Cl-Ph | H | H | H | NHCOOMe | H | CH |
| 1-311 | 3-Cl-Ph | H | H | H | NHSO₂Me | H | CH |
| 1-312 | 3-Cl-Ph | H | H | H | H | Me | CH |
| 1-313 | 3-Cl-Ph | F | H | H | H | H | CH |
| 1-314 | 3-Cl-Ph | Cl | H | H | H | H | CH |
| 1-315 | 3-Cl-Ph | Me | H | H | H | H | CH |
| 1-316 | 3-Cl-Ph | OMe | H | H | H | H | CH |
| 1-317 | 3-Cl-Ph | SMe | H | H | H | H | CH |
| 1-318 | 3-Cl-Ph | SOMe | H | H | H | H | CH |
| 1-319 | 3-Cl-Ph | SO₂Me | H | H | H | H | CH |
| 1-320 | 3-Cl-Ph | NH₂ | H | H | H | H | CH |
| 1-321 | 3-Cl-Ph | NHMe | H | H | H | H | CH |
| 1-322 | 3-Cl-Ph | NMe₂ | H | H | H | H | CH |
| 1-323 | 3-Cl-Ph | NHEt | H | H | H | H | CH |
| 1-324 | 3-Cl-Ph | NHPrⁱ | H | H | H | H | CH |
| 1-325 | 3-Cl-Ph | NHCH₂CF₃ | H | H | H | H | CH |
| 1-326 | 3-Cl-Ph | NHPrᶜ | H | H | H | H | CH |
| 1-327 | 3-Cl-Ph | NHCOMe | H | H | H | H | CH |

TABLE 1-continued

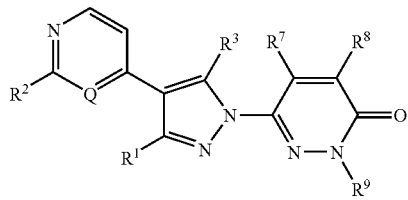

| Compound No | $R^1$ | $R^2$ | $R^3$ | $R^7$ | $R^8$ | $R^9$ | Q |
|---|---|---|---|---|---|---|---|
| 1-328 | 3-Cl-Ph | NHCOOMe | H | H | H | H | CH |
| 1-329 | 3-Cl-Ph | NHSO$_2$Me | H | H | H | H | CH |
| 1-330 | 3-Cl-Ph | NH(4-F-Bn) | H | H | H | H | CH |
| 1-331 | 3-Cl-Ph | NH(α-Me-Bn) | H | H | H | H | CH |
| 1-332 | 3-Cl-Ph | NHCOPh | H | H | H | H | CH |
| 1-333 | 3-Cl-Ph | NH$_2$ | Me | H | H | H | CH |
| 1-334 | 3-Cl-Ph | NH$_2$ | NH$_2$ | H | H | H | CH |
| 1-335 | 3-Cl-Ph | NH$_2$ | H | Me | H | H | CH |
| 1-336 | 3-Cl-Ph | NH$_2$ | H | H | Me | H | CH |
| 1-337 | 3-Cl-Ph | NH$_2$ | H | Me | Me | H | CH |
| 1-338 | 3-Cl-Ph | NH$_2$ | H | H | NH$_2$ | H | CH |
| 1-339 | 3-Cl-Ph | NH$_2$ | H | H | NHMe | H | CH |
| 1-340 | 3-Cl-Ph | NH$_2$ | H | H | NMe$_2$ | H | CH |
| 1-341 | 3-Cl-Ph | NH$_2$ | H | H | NHCOMe | H | CH |
| 1-342 | 3-Cl-Ph | NH$_2$ | H | H | NHCOOMe | H | CH |
| 1-343 | 3-Cl-Ph | NH$_2$ | H | H | NHSO$_2$Me | H | CH |
| 1-344 | 3-Cl-Ph | NH$_2$ | H | H | H | Me | CH |
| 1-345 | 3-Cl-Ph | NH$_2$ | H | H | Me | Me | CH |
| 1-346 | 3-Cl-Ph | NH$_2$ | H | H | NH$_2$ | Me | CH |
| 1-347 | 3-Cl-Ph | H | H | H | H | H | N |
| 1-348 | 3-Cl-Ph | H | NH$_2$ | H | H | H | N |
| 1-349 | 3-Cl-Ph | H | H | H | Me | H | N |
| 1-350 | 3-Cl-Ph | H | H | H | NH$_2$ | H | N |
| 1-351 | 3-Cl-Ph | H | H | H | NHMe | H | N |
| 1-352 | 3-Cl-Ph | H | H | H | H | Me | N |
| 1-353 | 3-Cl-Ph | NH$_2$ | H | H | H | H | N |
| 1-354 | 3-Cl-Ph | NHMe | H | H | H | H | N |
| 1-355 | 3-Cl-Ph | NMe$_2$ | H | H | H | H | N |
| 1-356 | 3-Cl-Ph | NHEt | H | H | H | H | N |
| 1-357 | 3-Cl-Ph | NHPr$^i$ | H | H | H | H | N |
| 1-358 | 3-Cl-Ph | NHCH$_2$CF$_3$ | H | H | H | H | N |
| 1-359 | 3-Cl-Ph | NHPr$^c$ | H | H | H | H | N |
| 1-360 | 3-Cl-Ph | NHCOMe | H | H | H | H | N |
| 1-361 | 3-Cl-Ph | NHCOOMe | H | H | H | H | N |
| 1-362 | 3-Cl-Ph | NHSO$_2$Me | H | H | H | H | N |
| 1-363 | 3-Cl-Ph | NH(4-F-Bn) | H | H | H | H | N |
| 1-364 | 3-Cl-Ph | NH(α-Me-Bn) | H | H | H | H | N |
| 1-365 | 3-Cl-Ph | NHCOPh | H | H | H | H | N |
| 1-366 | 3-Cl-Ph | NH$_2$ | Me | H | H | H | N |
| 1-367 | 3-Cl-Ph | NH$_2$ | H | Me | H | H | N |
| 1-368 | 3-Cl-Ph | NH$_2$ | H | H | Me | H | N |
| 1-369 | 3-Cl-Ph | NH$_2$ | H | H | NH$_2$ | H | N |
| 1-370 | 3-Cl-Ph | NH$_2$ | H | H | H | Me | N |
| 1-371 | 3,4-diF-Ph | H | H | H | H | H | CH |
| 1-372 | 3,4-diF-Ph | H | Me | H | H | H | CH |
| 1-373 | 3,4-diF-Ph | H | Et | H | H | H | CH |
| 1-374 | 3,4-diF-Ph | H | NH$_2$ | H | H | H | CH |
| 1-375 | 3,4-diF-Ph | H | H | Me | H | H | CH |
| 1-376 | 3,4-diF-Ph | H | H | H | Me | H | CH |
| 1-377 | 3,4-diF-Ph | H | H | H | Et | H | CH |
| 1-378 | 3,4-diF-Ph | H | H | H | NH$_2$ | H | CH |
| 1-379 | 3,4-diF-Ph | H | H | H | NHMe | H | CH |
| 1-380 | 3,4-diF-Ph | H | H | H | NHEt | H | CH |
| 1-381 | 3,4-diF-Ph | H | H | H | NMe$_2$ | H | CH |
| 1-382 | 3,4-diF-Ph | H | H | H | NEt$_2$ | H | CH |
| 1-383 | 3,4-diF-Ph | H | H | H | NHCHO | H | CH |
| 1-384 | 3,4-diF-Ph | H | H | H | NHCOMe | H | CH |
| 1-385 | 3,4-diF-Ph | H | H | H | NHCOEt | H | CH |
| 1-386 | 3,4-diF-Ph | H | H | H | NHCOOMe | H | CH |
| 1-387 | 3,4-diF-Ph | H | H | H | NHCOOEt | H | CH |
| 1-388 | 3,4-diF-Ph | H | H | H | NHSO$_2$Me | H | CH |
| 1-389 | 3,4-diF-Ph | H | H | H | NHSO$_2$Et | H | CH |
| 1-390 | 3,4-diF-Ph | H | H | H | H | Me | CH |
| 1-391 | 3,4-diF-Ph | H | H | H | H | Et | CH |
| 1-392 | 3,4-diF-Ph | F | H | H | H | H | CH |

TABLE 1-continued

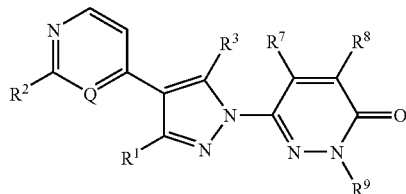

| Compound No | $R^1$ | $R^2$ | $R^3$ | $R^7$ | $R^8$ | $R^9$ | Q |
|---|---|---|---|---|---|---|---|
| 1-393 | 3,4-diF-Ph | Cl | H | H | H | H | CH |
| 1-394 | 3,4-diF-Ph | Me | H | H | H | H | CH |
| 1-395 | 3,4-diF-Ph | Et | H | H | H | H | CH |
| 1-396 | 3,4-diF-Ph | OMe | H | H | H | H | CH |
| 1-397 | 3,4-diF-Ph | OEt | H | H | H | H | CH |
| 1-398 | 3,4-diF-Ph | SMe | H | H | H | H | CH |
| 1-399 | 3,4-diF-Ph | SOMe | H | H | H | H | CH |
| 1-400 | 3,4-diF-Ph | $SO_2Me$ | H | H | H | H | CH |
| 1-401 | 3,4-diF-Ph | $NH_2$ | H | H | H | H | CH |
| 1-402 | 3,4-diF-Ph | NHMe | H | H | H | H | CH |
| 1-403 | 3,4-diF-Ph | $NMe_2$ | H | H | H | H | CH |
| 1-404 | 3,4-diF-Ph | NHEt | H | H | H | H | CH |
| 1-405 | 3,4-diF-Ph | $NHPr^i$ | H | H | H | H | CH |
| 1-406 | 3,4-diF-Ph | $NHCH_2CF_3$ | H | H | H | H | CH |
| 1-407 | 3,4-diF-Ph | $NHPr^c$ | H | H | H | H | CH |
| 1-408 | 3,4-diF-Ph | NHCHO | H | H | H | H | CH |
| 1-409 | 3,4-diF-Ph | NHCOMe | H | H | H | H | CH |
| 1-410 | 3,4-diF-Ph | NHCOEt | H | H | H | H | CH |
| 1-411 | 3,4-diF-Ph | NHCOPr | H | H | H | H | CH |
| 1-412 | 3,4-diF-Ph | NHCOOMe | H | H | H | H | CH |
| 1-413 | 3,4-diF-Ph | NHCOOEt | H | H | H | H | CH |
| 1-414 | 3,4-diF-Ph | $NHSO_2Me$ | H | H | H | H | CH |
| 1-415 | 3,4-diF-Ph | $NHSO_2Et$ | H | H | H | H | CH |
| 1-416 | 3,4-diF-Ph | NHBn | H | H | H | H | CH |
| 1-417 | 3,4-diF-Ph | NH(4-F-Bn) | H | H | H | H | CH |
| 1-418 | 3,4-diF-Ph | NH(α-Me-Bn) | H | H | H | H | CH |
| 1-419 | 3,4-diF-Ph | NHCOPh | H | H | H | H | CH |
| 1-420 | 3,4-diF-Ph | $NH_2$ | Me | H | H | H | CH |
| 1-421 | 3,4-diF-Ph | $NH_2$ | $NH_2$ | H | H | H | CH |
| 1-422 | 3,4-diF-Ph | $NH_2$ | H | Me | H | H | CH |
| 1-423 | 3,4-diF-Ph | $NH_2$ | H | H | Me | H | CH |
| 1-424 | 3,4-diF-Ph | $NH_2$ | H | Me | Me | H | CH |
| 1-425 | 3,4-diF-Ph | $NH_2$ | H | H | $NH_2$ | H | CH |
| 1-426 | 3,4-diF-Ph | $NH_2$ | H | H | NHMe | H | CH |
| 1-427 | 3,4-diF-Ph | $NH_2$ | H | H | NHet | H | CH |
| 1-428 | 3,4-diF-Ph | $NH_2$ | H | H | $NMe_2$ | H | CH |
| 1-429 | 3,4-diF-Ph | $NH_2$ | H | H | NHCOMe | H | CH |
| 1-430 | 3,4-diF-Ph | $NH_2$ | H | H | NHCOOMe | H | CH |
| 1-431 | 3,4-diF-Ph | $NH_2$ | H | H | $NHSO_2Me$ | H | CH |
| 1-432 | 3,4-diF-Ph | $NH_2$ | H | H | H | Me | CH |
| 1-433 | 3,4-diF-Ph | $NH_2$ | H | H | Me | Me | CH |
| 1-434 | 3,4-diF-Ph | $NH_2$ | H | H | $NH_2$ | Me | CH |
| 1-435 | 3,4-diF-Ph | H | H | H | H | H | N |
| 1-436 | 3,4-diF-Ph | H | Me | H | H | H | N |
| 1-437 | 3,4-diF-Ph | H | $NH_2$ | H | H | H | N |
| 1-438 | 3,4-diF-Ph | H | H | Me | H | H | N |
| 1-439 | 3,4-diF-Ph | H | H | H | Me | H | N |
| 1-440 | 3,4-diF-Ph | H | H | H | $NH_2$ | H | N |
| 1-441 | 3,4-diF-Ph | H | H | H | NHMe | H | N |
| 1-442 | 3,4-diF-Ph | H | H | H | $NMe_2$ | H | N |
| 1-443 | 3,4-diF-Ph | H | H | H | NHCOMe | H | N |
| 1-444 | 3,4-diF-Ph | H | H | H | NHCOOMe | H | N |
| 1-445 | 3,4-diF-Ph | H | H | H | $NHSO_2Me$ | H | N |
| 1-446 | 3,4-diF-Ph | H | H | H | H | Me | N |
| 1-447 | 3,4-diF-Ph | $NH_2$ | H | H | H | H | N |
| 1-448 | 3,4-diF-Ph | NHMe | H | H | H | H | N |
| 1-449 | 3,4-diF-Ph | $NMe_2$ | H | H | H | H | N |
| 1-450 | 3,4-diF-Ph | NHEt | H | H | H | H | N |
| 1-451 | 3,4-diF-Ph | $NHPr^i$ | H | H | H | H | N |
| 1-452 | 3,4-diF-Ph | $NHCH_2CF_3$ | H | H | H | H | N |
| 1-453 | 3,4-diF-Ph | $NHPr^c$ | H | H | H | H | N |
| 1-454 | 3,4-diF-Ph | NHCOMe | H | H | H | H | N |
| 1-455 | 3,4-diF-Ph | NHCOOMe | H | H | H | H | N |
| 1-456 | 3,4-diF-Ph | $NHSO_2Me$ | H | H | H | H | N |
| 1-457 | 3,4-diF-Ph | NH(4-F-Bn) | H | H | H | H | N |

TABLE 1-continued

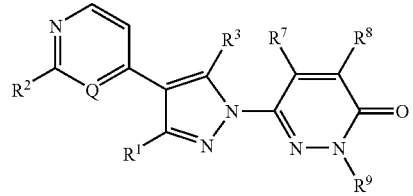

| Compound No | R¹ | R² | R³ | R⁷ | R⁸ | R⁹ | Q |
|---|---|---|---|---|---|---|---|
| 1-458 | 3,4-diF-Ph | NH(α-Me-Bn) | H | H | H | H | N |
| 1-459 | 3,4-diF-Ph | NHCOPh | H | H | H | H | N |
| 1-460 | 3,4-diF-Ph | NH₂ | Me | H | H | H | N |
| 1-461 | 3,4-diF-Ph | NH₂ | H | Me | H | H | N |
| 1-462 | 3,4-diF-Ph | NH₂ | H | H | Me | H | N |
| 1-463 | 3,4-diF-Ph | NH₂ | H | H | NH₂ | H | N |
| 1-464 | 3,4-diF-Ph | NH₂ | H | H | H | Me | N |
| 1-465 | 3,4-diCl-Ph | H | H | H | H | H | CH |
| 1-466 | 3,4-diCl-Ph | H | Me | H | H | H | CH |
| 1-467 | 3,4-diCl-Ph | H | NH₂ | H | H | H | CH |
| 1-468 | 3,4-diCl-Ph | H | H | Me | H | H | CH |
| 1-469 | 3,4-diCl-Ph | H | H | H | Me | H | CH |
| 1-470 | 3,4-diCl-Ph | H | H | H | NH₂ | H | CH |
| 1-471 | 3,4-diCl-Ph | H | H | H | NHMe | H | CH |
| 1-472 | 3,4-diCl-Ph | H | H | H | NMe₂ | H | CH |
| 1-473 | 3,4-diCl-Ph | H | H | H | NHCOMe | H | CH |
| 1-474 | 3,4-diCl-Ph | H | H | H | NHCOOMe | H | CH |
| 1-475 | 3,4-diCl-Ph | H | H | H | NHSO₂Me | H | CH |
| 1-476 | 3,4-diCl-Ph | H | H | H | H | Me | CH |
| 1-477 | 3,4-diCl-Ph | F | H | H | H | H | CH |
| 1-478 | 3,4-diCl-Ph | Cl | H | H | H | H | CH |
| 1-479 | 3,4-diCl-Ph | Me | H | H | H | H | CH |
| 1-480 | 3,4-diCl-Ph | OMe | H | H | H | H | CH |
| 1-481 | 3,4-diCl-Ph | SMe | H | H | H | H | CH |
| 1-482 | 3,4-diCl-Ph | SOMe | H | H | H | H | CH |
| 1-483 | 3,4-diCl-Ph | SO₂Me | H | H | H | H | CH |
| 1-484 | 3,4-diCl-Ph | NH₂ | H | H | H | H | CH |
| 1-485 | 3,4-diCl-Ph | NHMe | H | H | H | H | CH |
| 1-486 | 3,4-diCl-Ph | NMe₂ | H | H | H | H | CH |
| 1-487 | 3,4-diCl-Ph | NHEt | H | H | H | H | CH |
| 1-488 | 3,4-diCl-Ph | NHPrⁱ | H | H | H | H | CH |
| 1-489 | 3,4-diCl-Ph | NHCH₂CF₃ | H | H | H | H | CH |
| 1-490 | 3,4-diCl-Ph | NHPrᶜ | H | H | H | H | CH |
| 1-491 | 3,4-diCl-Ph | NHCOMe | H | H | H | H | CH |
| 1-492 | 3,4-diCl-Ph | NHCOOMe | H | H | H | H | CH |
| 1-493 | 3,4-diCl-Ph | NHSO₂Me | H | H | H | H | CH |
| 1-494 | 3,4-diCl-Ph | NH(4-F-Bn) | H | H | H | H | CH |
| 1-495 | 3,4-diCl-Ph | NH(α-Me-Bn) | H | H | H | H | CH |
| 1-496 | 3,4-diCl-Ph | NHCOPh | H | H | H | H | CH |
| 1-497 | 3,4-diCl-Ph | NH₂ | Me | H | H | H | CH |
| 1-498 | 3,4-diCl-Ph | NH₂ | NH₂ | H | H | H | CH |
| 1-499 | 3,4-diCl-Ph | NH₂ | H | Me | H | H | CH |
| 1-500 | 3,4-diCl-Ph | NH₂ | H | H | Me | H | CH |
| 1-501 | 3,4-diCl-Ph | NH₂ | H | Me | Me | H | CH |
| 1-502 | 3,4-diCl-Ph | NH₂ | H | H | NH₂ | H | CH |
| 1-503 | 3,4-diCl-Ph | NH₂ | H | H | NHMe | H | CH |
| 1-504 | 3,4-diCl-Ph | NH₂ | H | H | NMe₂ | H | CH |
| 1-505 | 3,4-diCl-Ph | NH₂ | H | H | NHCOMe | H | CH |
| 1-506 | 3,4-diCl-Ph | NH₂ | H | H | NHCOOMe | H | CH |
| 1-507 | 3,4-diCl-Ph | NH₂ | H | H | NHSO₂Me | H | CH |
| 1-508 | 3,4-diCl-Ph | NH₂ | H | H | H | Me | CH |
| 1-509 | 3,4-diCl-Ph | NH₂ | H | H | Me | Me | CH |
| 1-510 | 3,4-diCl-Ph | NH₂ | H | H | NH₂ | Me | CH |
| 1-511 | 3,4-diCl-Ph | H | H | H | H | H | N |
| 1-512 | 3,4-diCl-Ph | H | NH₂ | H | H | H | N |
| 1-513 | 3,4-diCl-Ph | H | H | H | Me | H | N |
| 1-514 | 3,4-diCl-Ph | H | H | H | NH₂ | H | N |
| 1-515 | 3,4-diCl-Ph | H | H | H | NHMe | H | N |
| 1-516 | 3,4-diCl-Ph | H | H | H | H | Me | N |
| 1-517 | 3,4-diCl-Ph | NH₂ | H | H | H | H | N |
| 1-518 | 3,4-diCl-Ph | NHMe | H | H | H | H | N |
| 1-519 | 3,4-diCl-Ph | NMe₂ | H | H | H | H | N |
| 1-520 | 3,4-diCl-Ph | NHEt | H | H | H | H | N |
| 1-521 | 3,4-diCl-Ph | NHPrⁱ | H | H | H | H | N |
| 1-522 | 3,4-diCl-Ph | NHCH₂CF₃ | H | H | H | H | N |

TABLE 1-continued

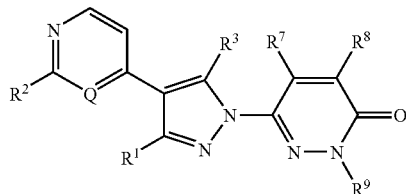

| Compound No | R¹ | R² | R³ | R⁷ | R⁸ | R⁹ | Q |
|---|---|---|---|---|---|---|---|
| 1-523 | 3,4-diCl-Ph | NHPr$^c$ | H | H | H | H | N |
| 1-524 | 3,4-diCl-Ph | NHCOMe | H | H | H | H | N |
| 1-525 | 3,4-diCl-Ph | NHCOOMe | H | H | H | H | N |
| 1-526 | 3,4-diCl-Ph | NHSO₂Me | H | H | H | H | N |
| 1-527 | 3,4-diCl-Ph | NH(4-F-Bn) | H | H | H | H | N |
| 1-528 | 3,4-diCl-Ph | NH(α-Me-Bn) | H | H | H | H | N |
| 1-529 | 3,4-diCl-Ph | NHCOPh | H | H | H | H | N |
| 1-530 | 3,4-diCl-Ph | NH₂ | Me | H | H | H | N |
| 1-531 | 3,4-diCl-Ph | NH₂ | H | Me | H | H | N |
| 1-532 | 3,4-diCl-Ph | NH₂ | H | H | Me | H | N |
| 1-533 | 3,4-diCl-Ph | NH₂ | H | H | NH₂ | H | N |
| 1-534 | 3,4-diCl-Ph | NH₂ | H | H | H | Me | N |
| 1-535 | 3-Cl-4-F-Ph | H | H | H | H | H | CH |
| 1-536 | 3-Cl-4-F-Ph | NH₂ | H | H | H | H | CH |
| 1-537 | 3-Cl-4-F-Ph | NHMe | H | H | H | H | CH |
| 1-538 | 3-Cl-4-F-Ph | NMe₂ | H | H | H | H | CH |
| 1-539 | 3-Cl-4-F-Ph | NHEt | H | H | H | H | CH |
| 1-540 | 3-Cl-4-F-Ph | NHCH₂CF₃ | H | H | H | H | CH |
| 1-541 | 3-Cl-4-F-Ph | NHPr$^c$ | H | H | H | H | CH |
| 1-542 | 3-Cl-4-F-Ph | NHCOMe | H | H | H | H | CH |
| 1-543 | 3-Cl-4-F-Ph | NHCOOMe | H | H | H | H | CH |
| 1-544 | 3-Cl-4-F-Ph | NHSO₂Me | H | H | H | H | CH |
| 1-545 | 3-Cl-4-F-Ph | NH(4-F-Bn) | H | H | H | H | CH |
| 1-546 | 3-Cl-4-F-Ph | NH(α-Me-Bn) | H | H | H | H | CH |
| 1-547 | 3-Cl-4-F-Ph | NHCOPh | H | H | H | H | CH |
| 1-548 | 3-Cl-4-F-Ph | NH₂ | Me | H | H | H | CH |
| 1-549 | 3-Cl-4-F-Ph | NH₂ | NH₂ | H | H | H | CH |
| 1-550 | 3-Cl-4-F-Ph | NH₂ | H | Me | H | H | CH |
| 1-551 | 3-Cl-4-F-Ph | NH₂ | H | H | Me | H | CH |
| 1-552 | 3-Cl-4-F-Ph | NH₂ | H | H | NH₂ | H | CH |
| 1-553 | 3-Cl-4-F-Ph | NH₂ | H | H | NHMe | H | CH |
| 1-554 | 3-Cl-4-F-Ph | NH₂ | H | H | NMe₂ | H | CH |
| 1-555 | 3-Cl-4-F-Ph | NH₂ | H | H | NHCOMe | H | CH |
| 1-556 | 3-Cl-4-F-Ph | NH₂ | H | H | NHCOOMe | H | CH |
| 1-557 | 3-Cl-4-F-Ph | NH₂ | H | H | NHSO₂Me | H | CH |
| 1-558 | 3-Cl-4-F-Ph | NH₂ | H | H | H | Me | CH |
| 1-559 | 3-Cl-4-F-Ph | NH₂ | H | H | NH₂ | Me | CH |
| 1-560 | 3-Cl-4-F-Ph | H | H | H | H | H | N |
| 1-561 | 3-Cl-4-F-Ph | NH₂ | H | H | H | H | N |
| 1-562 | 3-Cl-4-F-Ph | NHMe | H | H | H | H | N |
| 1-563 | 3-Cl-4-F-Ph | NMe₂ | H | H | H | H | N |
| 1-564 | 3-Cl-4-F-Ph | NHEt | H | H | H | H | N |
| 1-565 | 3-Cl-4-F-Ph | NHPr$^i$ | H | H | H | H | N |
| 1-566 | 3-Cl-4-F-Ph | NHCH₂CF₃ | H | H | H | H | N |
| 1-567 | 3-Cl-4-F-Ph | NHPr$^c$ | H | H | H | H | N |
| 1-568 | 3-Cl-4-F-Ph | NHCOMe | H | H | H | H | N |
| 1-569 | 3-Cl-4-F-Ph | NHCOMe | H | H | H | H | N |
| 1-570 | 3-Cl-4-F-Ph | NHSO₂Me | H | H | H | H | N |
| 1-571 | 3-Cl-4-F-Ph | NH(4-F-Bn) | H | H | H | H | N |
| 1-572 | 3-Cl-4-F-Ph | NH(α-Me-Bn) | H | H | H | H | N |
| 1-573 | 3-Cl-4-F-Ph | NHCOPh | H | H | H | H | N |
| 1-574 | 3-Cl-4-F-Ph | NH₂ | H | H | Me | H | N |
| 1-575 | 3-Cl-4-F-Ph | NH₂ | H | H | NH₂ | H | N |
| 1-576 | 4-Cl-3-F-Ph | H | H | H | H | H | CH |
| 1-577 | 4-Cl-3-F-Ph | NH₂ | H | H | H | H | CH |
| 1-578 | 4-Cl-3-F-Ph | NHMe | H | H | H | H | CH |
| 1-579 | 4-Cl-3-F-Ph | NMe₂ | H | H | H | H | CH |
| 1-580 | 4-Cl-3-F-Ph | NHEt | H | H | H | H | CH |
| 1-581 | 4-Cl-3-F-Ph | NHCH₂CF₃ | H | H | H | H | CH |
| 1-582 | 4-Cl-3-F-Ph | NHPr$^c$ | H | H | H | H | CH |
| 1-583 | 4-Cl-3-F-Ph | NHCOMe | H | H | H | H | CH |
| 1-584 | 4-Cl-3-F-Ph | NHCOOMe | H | H | H | H | CH |
| 1-585 | 4-Cl-3-F-Ph | NHSO₂Me | H | H | H | H | CH |
| 1-586 | 4-Cl-3-F-Ph | NH(4-F-Bn) | H | H | H | H | CH |
| 1-587 | 4-Cl-3-F-Ph | NH(α-Me-Bn) | H | H | H | H | CH |

TABLE 1-continued

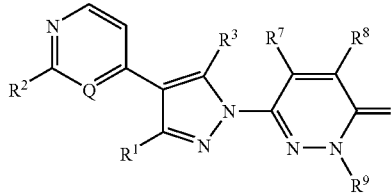

| Compound No | R¹ | R² | R³ | R⁷ | R⁸ | R⁹ | Q |
|---|---|---|---|---|---|---|---|
| 1-588 | 4-Cl-3-F-Ph | NHCOPh | H | H | H | H | CH |
| 1-589 | 4-Cl-3-F-Ph | NH₂ | Me | H | H | H | CH |
| 1-590 | 4-Cl-3-F-Ph | NH₂ | NH₂ | H | H | H | CH |
| 1-591 | 4-Cl-3-F-Ph | NH₂ | H | Me | H | H | CH |
| 1-592 | 4-Cl-3-F-Ph | NH₂ | H | H | Me | H | CH |
| 1-593 | 4-Cl-3-F-Ph | NH₂ | H | H | NH₂ | H | CH |
| 1-594 | 4-Cl-3-F-Ph | NH₂ | H | H | NHMe | H | CH |
| 1-595 | 4-Cl-3-F-Ph | NH₂ | H | H | NMe₂ | H | CH |
| 1-596 | 4-Cl-3-F-Ph | NH₂ | H | H | NHCOMe | H | CH |
| 1-597 | 4-Cl-3-F-Ph | NH₂ | H | H | NHCOOMe | H | CH |
| 1-598 | 4-Cl-3-F-Ph | NH₂ | H | H | NHSO₂Me | H | CH |
| 1-599 | 4-Cl-3-F-Ph | NH₂ | H | H | H | Me | CH |
| 1-600 | 4-Cl-3-F-Ph | NH₂ | H | H | NH₂ | Me | CH |
| 1-601 | 4-Cl-3-F-Ph | H | H | H | H | H | N |
| 1-602 | 4-Cl-3-F-Ph | NH₂ | H | H | H | H | N |
| 1-603 | 4-Cl-3-F-Ph | NHMe | H | H | H | H | N |
| 1-604 | 4-Cl-3-F-Ph | NMe₂ | H | H | H | H | N |
| 1-605 | 4-Cl-3-F-Ph | NHEt | H | H | H | H | N |
| 1-606 | 4-Cl-3-F-Ph | NHPrⁱ | H | H | H | H | N |
| 1-607 | 4-Cl-3-F-Ph | NHCH₂CF₃ | H | H | H | H | N |
| 1-608 | 4-Cl-3-F-Ph | NHPrᶜ | H | H | H | H | N |
| 1-609 | 4-Cl-3-F-Ph | NHCOMe | H | H | H | H | N |
| 1-610 | 4-Cl-3-F-Ph | NHCOOMe | H | H | H | H | N |
| 1-611 | 4-Cl-3-F-Ph | NHSO₂Me | H | H | H | H | N |
| 1-612 | 4-Cl-3-F-Ph | NH(4-F-Bn) | H | H | H | H | N |
| 1-613 | 4-Cl-3-F-Ph | NH(α-Me-Bn) | H | H | H | H | N |
| 1-614 | 4-Cl-3-F-Ph | NHCOPh | H | H | H | H | N |
| 1-615 | 4-Cl-3-F-Ph | NH₂ | H | H | Me | H | N |
| 1-616 | 4-Cl-3-F-Ph | NH₂ | H | H | NH₂ | H | N |
| 1-617 | 3-CF₃-Ph | H | H | H | H | H | CH |
| 1-618 | 3-CF₃-Ph | NH₂ | H | H | H | H | CH |
| 1-619 | 3-CF₃-Ph | NHMe | H | H | H | H | CH |
| 1-620 | 3-CF₃-Ph | NMe₂ | H | H | H | H | CH |
| 1-621 | 3-CF₃-Ph | NHEt | H | H | H | H | CH |
| 1-622 | 3-CF₃-Ph | NH₂CF₃ | H | H | H | H | CH |
| 1-623 | 3-CF₃-Ph | NHPrᶜ | H | H | H | H | CH |
| 1-624 | 3-CF₃-Ph | NHCOMe | H | H | H | H | CH |
| 1-625 | 3-CF₃-Ph | NHCOOMe | H | H | H | H | CH |
| 1-626 | 3-CF₃-Ph | NHSO₂Me | H | H | H | H | CH |
| 1-627 | 3-CF₃-Ph | NH(4-F-Bn) | H | H | H | H | CH |
| 1-628 | 3-CF₃-Ph | NH(α-Me-Bn) | H | H | H | H | CH |
| 1-629 | 3-CF₃-Ph | NHCOPh | H | H | H | H | CH |
| 1-630 | 3-CF₃-Ph | NH₂ | Me | H | H | H | CH |
| 1-631 | 3-CF₃-Ph | NH₂ | NH₂ | H | H | H | CH |
| 1-632 | 3-CF₃-Ph | NH₂ | H | Me | H | H | CH |
| 1-633 | 3-CF₃-Ph | NH₂ | H | H | Me | H | CH |
| 1-634 | 3-CF₃-Ph | NH₂ | H | H | NH₂ | H | CH |
| 1-635 | 3-CF₃-Ph | NH₂ | H | H | NHMe | H | CH |
| 1-636 | 3-CF₃-Ph | NH₂ | H | H | NMe₂ | H | CH |
| 1-637 | 3-CF₃-Ph | NH₂ | H | H | NHCOMe | H | CH |
| 1-638 | 3-CF₃-Ph | NH₂ | H | H | NHCOOMe | H | CH |
| 1-639 | 3-CF₃-Ph | NH₂ | H | H | NHSO₂Me | H | CH |
| 1-640 | 3-CF₃-Ph | NH₂ | H | H | H | Me | CH |
| 1-641 | 3-CF₃-Ph | NH₂ | H | H | NH₂ | Me | CH |
| 1-642 | 3-CF₃-Ph | H | H | H | H | H | N |
| 1-643 | 3-CF₃-Ph | NH₂ | H | H | H | H | N |
| 1-644 | 3-CF₃-Ph | NHMe | H | H | H | H | N |
| 1-645 | 3-CF₃-Ph | NMe₂ | H | H | H | H | N |
| 1-646 | 3-CF₃-Ph | NHEt | H | H | H | H | N |
| 1-647 | 3-CF₃-Ph | NHPrⁱ | H | H | H | H | N |
| 1-648 | 3-CF₃-Ph | NHCH₂CF₃ | H | H | H | H | N |
| 1-649 | 3-CF₃-Ph | NHPrᶜ | H | H | H | H | N |
| 1-650 | 3-CF₃-Ph | NHCOMe | H | H | H | H | N |
| 1-651 | 3-CF₃-Ph | NHCOOMe | H | H | H | H | N |
| 1-652 | 3-CF₃-Ph | NHSO₂Me | H | H | H | H | N |

TABLE 1-continued

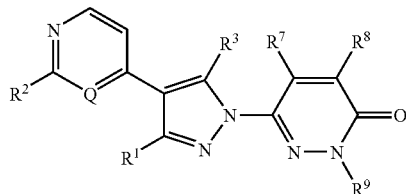

| Compound No | R¹ | R² | R³ | R⁷ | R⁸ | R⁹ | Q |
|---|---|---|---|---|---|---|---|
| 1-653 | 3-CF₃-Ph | NH(4-F-Bn) | H | H | H | H | N |
| 1-654 | 3-CF₃-Ph | NH(α-Me-Bn) | H | H | H | H | N |
| 1-655 | 3-CF₃-Ph | NHCOPh | H | H | H | H | N |
| 1-656 | 3-CF₃-Ph | NH₂ | H | H | Me | H | N |
| 1-657 | 3-CF₃-Ph | NH₂ | H | H | NH₂ | H | N |
| 1-658 | 2-F-Ph | H | H | H | H | H | CH |
| 1-659 | 2-F-Ph | H | Me | H | H | H | CH |
| 1-660 | 2-F-Ph | H | NH₂ | H | H | H | CH |
| 1-661 | 2-F-Ph | H | H | Me | H | H | CH |
| 1-662 | 2-F-Ph | H | H | H | Me | H | CH |
| 1-663 | 2-F-Ph | H | H | H | NH₂ | H | CH |
| 1-664 | 2-F-Ph | H | H | H | NHMe | H | CH |
| 1-665 | 2-F-Ph | H | H | H | NMe₂ | H | CH |
| 1-666 | 2-F-Ph | H | H | H | NHCOMe | H | CH |
| 1-667 | 2-F-Ph | H | H | H | NHCOOMe | H | CH |
| 1-668 | 2-F-Ph | H | H | H | NHSO₂Me | H | CH |
| 1-669 | 2-F-Ph | H | H | H | H | Me | CH |
| 1-670 | 2-F-Ph | F | H | H | H | H | CH |
| 1-671 | 2-F-Ph | Cl | H | H | H | H | CH |
| 1-672 | 2-F-Ph | Me | H | H | H | H | CH |
| 1-673 | 2-F-Ph | OMe | H | H | H | H | CH |
| 1-674 | 2-F-Ph | SMe | H | H | H | H | CH |
| 1-675 | 2-F-Ph | SOMe | H | H | H | H | CH |
| 1-676 | 2-F-Ph | SO₂Me | H | H | H | H | CH |
| 1-677 | 2-F-Ph | NH₂ | H | H | H | H | CH |
| 1-678 | 2-F-Ph | NHMe | H | H | H | H | CH |
| 1-679 | 2-F-Ph | NMe₂ | H | H | H | H | CH |
| 1-680 | 2-F-Ph | NHEt | H | H | H | H | CH |
| 1-681 | 2-F-Ph | NHPrⁱ | H | H | H | H | CH |
| 1-682 | 2-F-Ph | NHCH₂CF₃ | H | H | H | H | CH |
| 1-683 | 2-F-Ph | NHPrᶜ | H | H | H | H | CH |
| 1-684 | 2-F-Ph | NHCOMe | H | H | H | H | CH |
| 1-685 | 2-F-Ph | NHCOOMe | H | H | H | H | CH |
| 1-686 | 2-F-Ph | NHSO₂Me | H | H | H | H | CH |
| 1-687 | 2-F-Ph | NH(4-F-Bn) | H | H | H | H | CH |
| 1-688 | 2-F-Ph | NH(α-Me-Bn) | H | H | H | H | CH |
| 1-689 | 3-FPh | NHCOPh | H | H | H | H | CH |
| 1-690 | 2-F-Ph | NH₂ | Me | H | H | H | CH |
| 1-691 | 2-F-Ph | NH₂ | NH₂ | H | H | H | CH |
| 1-692 | 2-F-Ph | NH₂ | H | Me | H | H | CH |
| 1-693 | 2-F-Ph | NH₂ | H | H | Me | H | CH |
| 1-694 | 2-F-Ph | NH₂ | H | Me | Me | H | CH |
| 1-695 | 2-F-Ph | NH₂ | H | Me | NH₂ | H | CH |
| 1-696 | 2-F-Ph | NH₂ | H | H | NHMe | H | CH |
| 1-697 | 2-F-Ph | NH₂ | H | H | NMe₂ | H | CH |
| 1-698 | 2-F-Ph | NH₂ | H | H | NHCOMe | H | CH |
| 1-699 | 2-F-Ph | NH₂ | H | H | NHCOOMe | H | CH |
| 1-700 | 2-F-Ph | NH₂ | H | H | NHSO₂Me | H | CH |
| 1-701 | 2-F-Ph | NH₂ | H | H | H | Me | CH |
| 1-702 | 2-FPh | NH₂ | H | H | Me | Me | CH |
| 1-703 | 2-F-Ph | NH₂ | H | H | NH₂ | Me | CH |
| 1-704 | 2-F-Ph | H | H | H | H | H | N |
| 1-705 | 2-F-Ph | H | NH₂ | H | H | H | N |
| 1-706 | 2-F-Ph | H | H | H | Me | H | N |
| 1-707 | 2-F-Ph | H | H | H | NH₂ | H | N |
| 1-708 | 2-F-Ph | H | H | H | NHMe | H | N |
| 1-709 | 2-F-Ph | H | H | H | H | Me | N |
| 1-710 | 2-F-Ph | NH₂ | H | H | H | H | N |
| 1-711 | 2-F-Ph | NHMe | H | H | H | H | N |
| 1-712 | 2-F-Ph | NMe₂ | H | H | H | H | N |
| 1-713 | 2-F-Ph | NHEt | H | H | H | H | N |
| 1-714 | 2-F-Ph | NHPrⁱ | H | H | H | H | N |
| 1-715 | 2-F-Ph | NHCH₂CF₃ | H | H | H | H | N |
| 1-716 | 2-F-Ph | NHPrᶜ | H | H | H | H | N |
| 1-717 | 2-F-Ph | NHCOMe | H | H | H | H | N |

TABLE 1-continued

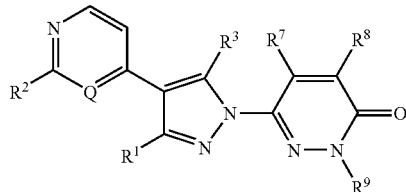

| Compound No | R¹ | R² | R³ | R⁷ | R⁸ | R⁹ | Q |
|---|---|---|---|---|---|---|---|
| 1-718 | 2-F-Ph | NHCOOMe | H | H | H | H | N |
| 1-719 | 2-F-Ph | NHSO₂Me | H | H | H | H | N |
| 1-720 | 2-F-Ph | NH(4-F-Bn) | H | H | H | H | N |
| 1-721 | 2-F-Ph | NH(α-Me-Bn) | H | H | H | H | N |
| 1-722 | 2-F-Ph | NHCOPh | H | H | H | H | N |
| 1-723 | 2-F-Ph | NH₂ | Me | H | H | H | N |
| 1-724 | 2-F-Ph | NH₂ | H | Me | H | H | N |
| 1-725 | 2-F-Ph | NH₂ | H | H | Me | H | N |
| 1-726 | 2-F-Ph | NH₂ | H | H | NH₂ | H | N |
| 1-727 | 2-F-Ph | NH₂ | H | H | H | Me | N |
| 1-728 | 2,4-diF-Ph | H | H | H | H | H | CH |
| 1-729 | 2,4-diF-Ph | NH₂ | H | H | H | H | CH |
| 1-730 | 2,4-diF-Ph | NHMe | H | H | H | H | CH |
| 1-731 | 2,4-diF-Ph | NMe₂ | H | H | H | H | CH |
| 1-732 | 2,4-diF-Ph | NHEt | H | H | H | H | CH |
| 1-733 | 2,4-diF-Ph | NHCH₂CF₃ | H | H | H | H | CH |
| 1-734 | 2,4-diF-Ph | NHPrⁱ | H | H | H | H | CH |
| 1-735 | 2,4-diF-Ph | NHCOMe | H | H | H | H | CH |
| 1-736 | 2,4-diF-Ph | NHCOOMe | H | H | H | H | CH |
| 1-737 | 2,4-diF-Ph | NHSO₂Me | H | H | H | H | CH |
| 1-738 | 2,4-diF-Ph | NH(4-F-Bn) | H | H | H | H | CH |
| 1-739 | 2,4-diF-Ph | NH(α-Me-Bn) | H | H | H | H | CH |
| 1-740 | 2,4-diF-Ph | NHCOPh | H | H | H | H | CH |
| 1-741 | 2,4-diF-Ph | NH₂ | Me | H | H | H | CH |
| 1-742 | 2,4-diF-Ph | NH₂ | NH₂ | H | H | H | CH |
| 1-743 | 2,4-diF-Ph | NH₂ | H | Me | H | H | CH |
| 1-744 | 2,4-diF-Ph | NH₂ | H | H | Me | H | CH |
| 1-745 | 2,4-diF-Ph | NH₂ | H | H | NH₂ | H | CH |
| 1-746 | 2,4-diF-Ph | NH₂ | H | H | NHMe | H | CH |
| 1-747 | 2,4-diF-Ph | NH₂ | H | H | NMe₂ | H | CH |
| 1-748 | 2,4-diF-Ph | NH₂ | H | H | NHCOMe | H | CH |
| 1-749 | 2,4-diF-Ph | NH₂ | H | H | NHCOOMe | H | CH |
| 1-750 | 2,4-diF-Ph | NH₂ | H | H | NHSO₂Me | H | CH |
| 1-751 | 2,4-diF-Ph | NH₂ | H | H | H | Me | CH |
| 1-752 | 2,4-diF-Ph | NH₂ | H | H | NH₂ | Me | CH |
| 1-753 | 2,4-diF-Ph | H | H | H | H | H | N |
| 1-754 | 2,4-diF-Ph | NH₂ | H | H | H | H | N |
| 1-755 | 2,4-diF-Ph | NHMe | H | H | H | H | N |
| 1-756 | 2,4-diF-Ph | NMe₂ | H | H | H | H | N |
| 1-757 | 2,4-diF-Ph | NHEt | H | H | H | H | N |
| 1-758 | 2,4-diF-Ph | NHPrⁱ | H | H | H | H | N |
| 1-759 | 2,4-diF-Ph | NHCH₂CF₃ | H | H | H | H | N |
| 1-760 | 2,4-diF-Ph | NHPrᶜ | H | H | H | H | N |
| 1-761 | 2,4-diF-Ph | NHCOMe | H | H | H | H | N |
| 1-762 | 2,4-diF-Ph | NHCOOMe | H | H | H | H | N |
| 1-763 | 2,4-diF-Ph | NHSO₂Me | H | H | H | H | N |
| 1-764 | 2,4-diF-Ph | NH(4-F-Bn) | H | H | H | H | N |
| 1-765 | 2,4-diF-Ph | NH(α-Me-Bn) | H | H | H | H | N |
| 1-766 | 2,4-diF-Ph | NHCOPh | H | H | H | H | N |
| 1-767 | 2,4-diF-Ph | NH₂ | H | H | Me | H | N |
| 1-768 | 2,4-diF-Ph | NH₂ | H | H | NH₂ | H | N |
| 1-769 | Ph | NHCOPrᶜ | H | H | H | H | CH |
| 1-770 | Ph | N(Me)COPrᶜ | H | H | H | H | CH |
| 1-771 | Ph | NHCOPrᶜ | H | H | H | H | N |
| 1-772 | Ph | NHCOPnᶜ | H | H | H | H | CH |
| 1-773 | Ph | NHCOPnᶜ | H | H | H | H | N |
| 1-774 | 4-F-Ph | NHCOPrᶜ | H | H | H | H | CH |
| 1-775 | 4-F-Ph | N(Me)COPrᶜ | H | H | H | H | CH |
| 1-776 | 4-F-Ph | NHCOPrᶜ | H | H | H | H | N |
| 1-777 | 4-F-Ph | N(Me)COPrᶜ | H | H | H | H | N |
| 1-778 | 4-F-Ph | NHCOPnᶜ | H | H | H | H | CH |
| 1-779 | 4-F-Ph | N(Me)COPnᶜ | H | H | H | H | CH |
| 1-780 | 4-F-Ph | NHCOPnᶜ | H | H | H | H | N |
| 1-781 | 4-F-Ph | NHCOHxᶜ | H | H | H | H | CH |
| 1-782 | 4-F-Ph | NHCOHxᶜ | H | H | H | H | N |

TABLE 1-continued

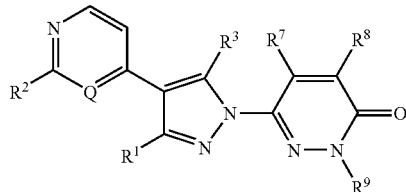

| Compound No | $R^1$ | $R^2$ | $R^3$ | $R^7$ | $R^8$ | $R^9$ | Q |
|---|---|---|---|---|---|---|---|
| 1-783 | 3-F-Ph | NHCOPr$^c$ | H | H | H | H | CH |
| 1-784 | 3-F-Ph | N(Me)COPr$^c$ | H | H | H | H | CH |
| 1-785 | 3-F-Ph | NHCOPr$^c$ | H | H | H | H | N |
| 1-786 | 3-F-Ph | NHCOPn$^c$ | H | H | H | H | CH |
| 1-787 | 3-F-Ph | NHCOPn$^c$ | H | H | H | H | N |
| 1-788 | 4-Cl-Ph | NHCOPr$^c$ | H | H | H | H | CH |
| 1-789 | 4-Cl-Ph | N(Me)COPr$^c$ | H | H | H | H | CH |
| 1-790 | 4-Cl-Ph | NHCOPr$^c$ | H | H | H | H | N |
| 1-791 | 4-Cl-Ph | NHCOPn$^c$ | H | H | H | H | CH |
| 1-792 | 4-Cl-Ph | NHCOPn$^c$ | H | H | H | H | N |
| 1-793 | 3-Cl-Ph | NHCOPr$^c$ | H | H | H | H | CH |
| 1-794 | 3-Cl-Ph | N(Me)COPr$^c$ | H | H | H | H | CH |
| 1-795 | 3-Cl-Ph | NHCOPr$^c$ | H | H | H | H | N |
| 1-796 | 3-Cl-Ph | NHCOPn$^c$ | H | H | H | H | CH |
| 1-797 | 3-Cl-Ph | NHCOPn$^c$ | H | H | H | H | N |
| 1-798 | 3,4-diF-Ph | NHCOPr$^c$ | H | H | H | H | CH |
| 1-799 | 3,4-diF-Ph | N(Me)COPr$^c$ | H | H | H | H | CH |
| 1-800 | 3,4-diF-Ph | NHCOPr$^c$ | H | H | H | H | N |
| 1-801 | 3,4-diF-Ph | NHCOPn$^c$ | H | H | H | H | CH |
| 1-802 | 3,4-diF-Ph | NHCOPn$^c$ | H | H | H | H | N |
| 1-803 | 3,4-diCl-Ph | NHCOPr$^c$ | H | H | H | H | CH |
| 1-804 | 3,4-diCl-Ph | N(Me)COPr$^c$ | H | H | H | H | CH |
| 1-805 | 3,4-diCl-Ph | NHCOPr$^c$ | H | H | H | H | N |
| 1-806 | 3,4-diCl-Ph | NHCOPn$^c$ | H | H | H | H | CH |
| 1-807 | 3,4-diCl-Ph | NHCOPn$^c$ | H | H | H | H | N |
| 1-808 | 3-Cl-4-F-Ph | NHCOPr$^c$ | H | H | H | H | CH |
| 1-809 | 3-Cl-4-F-Ph | N(Me)COPr$^c$ | H | H | H | H | CH |
| 1-810 | 3-Cl-4-F-Ph | NHCOPr$^c$ | H | H | H | H | N |
| 1-811 | 3-Cl-4-F-Ph | NHCOPn$^c$ | H | H | H | H | CH |
| 1-812 | 3-Cl-4-F-Ph | NHCOPn$^c$ | H | H | H | H | N |
| 1-813 | 4-Cl-3-F-Ph | NHCOPr$^c$ | H | H | H | H | CH |
| 1-814 | 4-Cl-3-F-Ph | N(Me)COPr$^c$ | H | H | H | H | CH |
| 1-815 | 4-Cl-3-F-Ph | NHCOPr$^c$ | H | H | H | H | N |
| 1-816 | 4-Cl-3-F-Ph | NHCOPn$^c$ | H | H | H | H | CH |
| 1-817 | 4-Cl-3-F-Ph | NHCOPn$^c$ | H | H | H | H | N |
| 1-818 | 3-CF$_3$-Ph | NHCOPr$^c$ | H | H | H | H | CH |
| 1-819 | 3-CF$_3$-Ph | N(Me)COPr$^c$ | H | H | H | H | CH |
| 1-820 | 3-CF$_3$-Ph | NHCOPr$^c$ | H | H | H | H | N |
| 1-821 | 3-CF$_3$-Ph | NHCOPn$^c$ | H | H | H | H | CH |
| 1-822 | 3-CF$_3$-Ph | NHCOPn$^c$ | H | H | H | H | N |
| 1-823 | 2-F-Ph | NHCOPr$^c$ | H | H | H | H | CH |
| 1-824 | 2-F-Ph | N(Me)COPr$^c$ | H | H | H | H | CH |
| 1-825 | 2-F-Ph | NHCOPr$^c$ | H | H | H | H | N |
| 1-826 | 2-F-Ph | NHCOPn$^c$ | H | H | H | H | CH |
| 1-827 | 2-F-Ph | NHCOPn$^c$ | H | H | H | H | N |
| 1-828 | 2,4-diF-Ph | NHCOPr$^c$ | H | H | H | H | CH |
| 1-829 | 2,4-diF-Ph | N(Me)COPr$^c$ | H | H | H | H | CH |
| 1-830 | 2,4-diF-Ph | NHCOPr$^c$ | H | H | H | H | N |
| 1-831 | 2,4-diF-Ph | NHCOPn$^c$ | H | H | H | H | CH |
| 1-832 | 2,4-diF-Ph | NHCOPn$^c$ | H | H | H | H | N |
| 1-833 | Ph | SMe | H | H | H | H | N |
| 1-834 | Ph | SOMe | H | H | H | H | N |
| 1-835 | Ph | SO$_2$Me | H | H | H | H | N |
| 1-836 | Ph | NH(4-OMe-Bn) | H | H | H | H | N |
| 1-837 | 4-F-Ph | SMe | H | H | H | H | N |
| 1-838 | 4-F-Ph | SOMe | H | H | H | H | N |
| 1-839 | 4-F-Ph | SO$_2$Me | H | H | H | H | N |
| 1-840 | 4-F-Ph | NH(4-OMe-Bn) | H | H | H | H | N |
| 1-841 | 3-F-Ph | SMe | H | H | H | H | N |
| 1-842 | 3-F-Ph | SOMe | H | H | H | H | N |
| 1-843 | 3-F-Ph | SO$_2$Me | H | H | H | H | N |
| 1-844 | 3-F-Ph | NH(4-OMe-Bn) | H | H | H | H | N |
| 1-845 | 4-Cl-Ph | SMe | H | H | H | H | N |
| 1-846 | 4-Cl-Ph | SOMe | H | H | H | H | N |
| 1-847 | 4-Cl-Ph | SO$_2$Me | H | H | H | H | N |

TABLE 1-continued

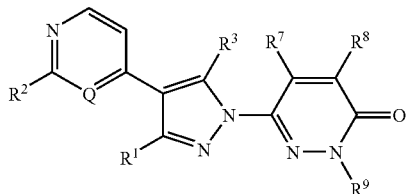

| Compound No | R¹ | R² | R³ | R⁷ | R⁸ | R⁹ | Q |
|---|---|---|---|---|---|---|---|
| 1-848 | 4-Cl-Ph | NH(4-OMe-Bn) | H | H | H | H | N |
| 1-849 | 3-Cl-Ph | SMe | H | H | H | H | N |
| 1-850 | 3-Cl-Ph | SOMe | H | H | H | H | N |
| 1-851 | 3-Cl-Ph | SO₂Me | H | H | H | H | N |
| 1-852 | 3-Cl-Ph | NH(4-OMe-Bn) | H | H | H | H | N |
| 1-853 | 3,4-diF-Ph | SMe | H | H | H | H | N |
| 1-854 | 3,4-diF-Ph | SOMe | H | H | H | H | N |
| 1-855 | 3,4-diF-Ph | SO₂Me | H | H | H | H | N |
| 1-856 | 3,4-diF-Ph | NH(4-OMe-Bn) | H | H | H | H | N |
| 1-857 | 3,4-diCl-Ph | SMe | H | H | H | H | N |
| 1-858 | 3,4-diCl-Ph | SOMe | H | H | H | H | N |
| 1-859 | 3,4-diCl-Ph | SO₂Me | H | H | H | H | N |
| 1-860 | 3,4-diCl-Ph | NH(4-OMe-Bn) | H | H | H | H | N |
| 1-861 | 3-Cl-4-F-Ph | SMe | H | H | H | H | N |
| 1-862 | 3-Cl-4-F-Ph | SOMe | H | H | H | H | N |
| 1-863 | 3-Cl-4-F-Ph | SO₂Me | H | H | H | H | N |
| 1-864 | 3-Cl-4-F-Ph | NH(4-OMe-Bn) | H | H | H | H | N |
| 1-865 | 4-Cl-3-F-Ph | SMe | H | H | H | H | N |
| 1-866 | 4-Cl-3-F-Ph | SOMe | H | H | H | H | N |
| 1-867 | 4-Cl-3-F-Ph | SO₂Me | H | H | H | H | N |
| 1-868 | 4-Cl-3-F-Ph | NH(4-OMe-Bn) | H | H | H | H | N |
| 1-869 | 3-CF₃-Ph | SMe | H | H | H | H | N |
| 1-870 | 3-CF₃-Ph | SOMe | H | H | H | H | N |
| 1-871 | 3-CF₃-Ph | SO₂Me | H | H | H | H | N |
| 1-872 | 3-CF₃-Ph | NH(4-OMe-Bn) | H | H | H | H | N |
| 1-873 | 2-F-Ph | SMe | H | H | H | H | N |
| 1-874 | 2-F-Ph | SOMe | H | H | H | H | N |
| 1-875 | 2-F-Ph | SO₂Me | H | H | H | H | N |
| 1-876 | 2-F-Ph | NH(4-OMe-Bn) | H | H | H | H | N |
| 1-877 | 2,4-diF-Ph | SMe | H | H | H | H | N |
| 1-878 | 2,4-diF-Ph | SOMe | H | H | H | H | N |
| 1-879 | 2,4-diF-Ph | SO₂Me | H | H | H | H | N |
| 1-880 | 2,4-diF-Ph | NH(4-OMe-Bn) | H | H | H | H | N |

TABLE 2

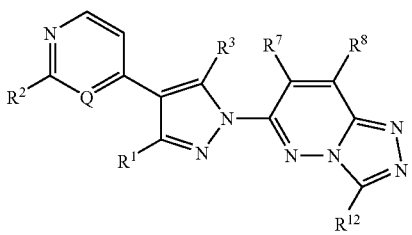

| Compound No | R¹ | R² | R³ | R⁷ | R⁸ | R⁹ | Q |
|---|---|---|---|---|---|---|---|
| 2-1 | Ph | H | H | H | H | H | CH |
| 2-2 | Ph | Me | H | H | H | H | CH |
| 2-3 | Ph | OMe | H | H | H | H | CH |
| 2-4 | Ph | SMe | H | H | H | H | CH |
| 2-5 | Ph | NH₂ | H | H | H | H | CH |
| 2-6 | Ph | NHMe | H | H | H | H | CH |
| 2-7 | Ph | NMe₂ | H | H | H | H | CH |
| 2-8 | Ph | NHEt | H | H | H | H | CH |
| 2-9 | Ph | NHPrⁱ | H | H | H | H | CH |
| 2-10 | Ph | NHCH₂CF₃ | H | H | H | H | CH |
| 2-11 | Ph | NHPrᶜ | H | H | H | H | CH |
| 2-12 | Ph | NHCOMe | H | H | H | H | CH |

TABLE 2-continued

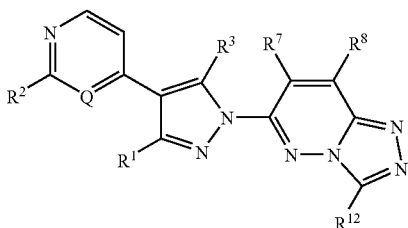

| Compound No | R¹ | R² | R³ | R⁷ | R⁸ | R⁹ | Q |
|---|---|---|---|---|---|---|---|
| 2-13 | Ph | NHCOOMe | H | H | H | H | CH |
| 2-14 | Ph | NHSO₂Me | H | H | H | H | CH |
| 2-15 | Ph | NH(α-Me-Bn) | H | H | H | H | CH |
| 2-16 | Ph | NHCOPh | H | H | H | H | CH |
| 2-17 | Ph | NH₂ | Me | H | H | H | CH |
| 2-18 | Ph | NH₂ | NH₂ | H | H | H | CH |
| 2-19 | Ph | NH₂ | H | Me | H | H | CH |
| 2-20 | Ph | NH₂ | H | H | Me | H | CH |
| 2-21 | Ph | NH₂ | H | Me | Me | H | CH |
| 2-22 | Ph | NH₂ | H | H | NH₂ | H | CH |
| 2-23 | Ph | NH₂ | H | H | NHMe | H | CH |
| 2-24 | Ph | NH₂ | H | H | NMe₂ | H | CH |
| 2-25 | Ph | NH₂ | H | H | H | Me | CH |
| 2-26 | Ph | NH₂ | H | H | H | CF₃ | CH |
| 2-27 | Ph | NH₂ | H | H | H | CH₂CF₃ | CH |
| 2-28 | Ph | NH₂ | H | H | H | NH₂ | CH |
| 2-29 | Ph | NH₂ | H | H | H | NHMe | CH |
| 2-30 | Ph | NH₂ | H | H | H | NMe₂ | CH |
| 2-31 | Ph | NH₂ | H | H | H | NHCOMe | CH |
| 2-32 | Ph | NH₂ | H | H | H | NHCOOMe | CH |
| 2-33 | Ph | NH₂ | H | H | H | NHSO₂Me | CH |
| 2-34 | Ph | NH₂ | H | H | Me | Me | CH |
| 2-35 | Ph | NH₂ | H | H | Me | NH₂ | CH |
| 2-36 | Ph | NH₂ | H | H | NH₂ | Me | CH |
| 2-37 | Ph | H | H | H | H | H | N |
| 2-38 | Ph | NH₂ | H | H | H | H | N |
| 2-39 | Ph | NHMe | H | H | H | H | N |
| 2-40 | Ph | NMe₂ | H | H | H | H | N |
| 2-41 | Ph | NHEt | H | H | H | H | N |
| 2-42 | Ph | NEt₂ | H | H | H | H | N |
| 2-43 | Ph | NHPrⁱ | H | H | H | H | N |
| 2-44 | Ph | NHCH₂CF₃ | H | H | H | H | N |
| 2-45 | Ph | NHPrᶜ | H | H | H | H | N |
| 2-46 | Ph | NHCOMe | H | H | H | H | N |
| 2-47 | Ph | NHCOOMe | H | H | H | H | N |
| 2-48 | Ph | NHSO₂Me | H | H | H | H | N |
| 2-49 | Ph | NH(4-F-Bn) | H | H | H | H | N |
| 2-50 | Ph | NH(α-Me-Bn) | H | H | H | H | N |
| 2-51 | Ph | NHCOPh | H | H | H | H | N |
| 2-52 | Ph | NH₂ | H | H | Me | H | N |
| 2-53 | Ph | NH₂ | H | H | NH₂ | H | N |
| 2-54 | Ph | NH₂ | H | H | NHMe | H | N |
| 2-55 | Ph | NH₂ | H | H | NMe₂ | H | N |
| 2-56 | Ph | NH₂ | H | H | H | Me | N |
| 2-57 | Ph | NH₂ | H | H | H | NH₂ | N |
| 2-58 | Ph | NH₂ | H | H | H | NHMe | N |
| 2-59 | Ph | NH₂ | H | H | H | NMe₂ | N |
| 2-60 | 4-F-Ph | H | H | H | H | H | CH |
| 2-61 | 4-F-Ph | H | Me | H | H | H | CH |
| 2-62 | 4-F-Ph | H | NH₂ | H | H | H | CH |
| 2-63 | 4-F-Ph | H | H | Me | H | H | CH |
| 2-64 | 4-F-Ph | H | H | H | Me | H | CH |
| 2-65 | 4-F-Ph | H | H | H | NH₂ | H | CH |
| 2-66 | 4-F-Ph | H | H | H | NHMe | H | CH |
| 2-67 | 4-F-Ph | H | H | H | NMe₂ | H | CH |
| 2-68 | 4-F-Ph | H | H | H | NHCOMe | H | CH |
| 2-69 | 4-F-Ph | H | H | H | NHSOOMe | H | CH |
| 2-70 | 4-F-Ph | H | H | H | NHSO₂Me | H | CH |
| 2-71 | 4-F-Ph | H | H | H | H | Me | CH |
| 2-72 | 4-F-Ph | H | H | H | H | CF₃ | CH |
| 2-73 | 4-F-Ph | H | H | H | H | NH₂ | CH |
| 2-74 | 4-F-Ph | H | H | H | H | NHMe | CH |
| 2-75 | 4-F-Ph | H | H | H | H | NMe₂ | CH |
| 2-76 | 4-F-Ph | H | H | H | H | NHCOMe | CH |

TABLE 2-continued

| Compound No | R¹ | R² | R³ | R⁷ | R⁸ | R⁹ | Q |
|---|---|---|---|---|---|---|---|
| 2-77 | 4-F-Ph | H | H | H | H | NHCOOMe | CH |
| 2-78 | 4-F-Ph | H | H | H | H | NHSO₂Me | CH |
| 2-79 | 4-F-Ph | H | H | H | Me | Me | CH |
| 2-80 | 4-F-Ph | H | H | H | Me | NH₂ | CH |
| 2-81 | 4-F-Ph | H | H | H | NH₂ | Me | CH |
| 2-82 | 4-F-Ph | F | H | H | H | H | CH |
| 2-83 | 4-F-Ph | Cl | H | H | H | H | CH |
| 2-84 | 4-F-Ph | Me | H | H | H | H | CH |
| 2-85 | 4-F-Ph | Et | H | H | H | H | CH |
| 2-86 | 4-F-Ph | OMe | H | H | H | H | CH |
| 2-87 | 4-F-Ph | OEt | H | H | H | H | CH |
| 2-88 | 4-F-Ph | SMe | H | H | H | H | CH |
| 2-89 | 4-F-Ph | SEt | H | H | H | H | CH |
| 2-90 | 4-F-Ph | SOMe | H | H | H | H | CH |
| 2-91 | 4-F-Ph | SOEt | H | H | H | H | CH |
| 2-92 | 4-F-Ph | SO₂Me | H | H | H | H | CH |
| 2-93 | 4-F-Ph | SO₂Et | H | H | H | H | CH |
| 2-94 | 4-F-Ph | NH₂ | H | H | H | H | CH |
| 2-95 | 4-F-Ph | NHMe | H | H | H | H | CH |
| 2-96 | 4-F-Ph | NMe₂ | H | H | H | H | CH |
| 2-97 | 4-F-Ph | NHEt | H | H | H | H | CH |
| 2-98 | 4-F-Ph | NEt₂ | H | H | H | H | CH |
| 2-99 | 4-F-Ph | NHPr | H | H | H | H | CH |
| 2-100 | 4-F-Ph | NHPrⁱ | H | H | H | H | CH |
| 2-101 | 4-F-Ph | NHCH₂CF₃ | H | H | H | H | CH |
| 2-102 | 4-F-Ph | NHPrᶜ | H | H | H | H | CH |
| 2-103 | 4-F-Ph | NHHxᶜ | H | H | H | H | CH |
| 2-104 | 4-F-Ph | NHCHO | H | H | H | H | CH |
| 2-105 | 4-F-Ph | NHCOMe | H | H | H | H | CH |
| 2-106 | 4-F-Ph | NHCOEt | H | H | H | H | CH |
| 2-107 | 4-F-Ph | NHCOPr | H | H | H | H | CH |
| 2-108 | 4-F-Ph | NHCOOMe | H | H | H | H | CH |
| 2-109 | 4-F-Ph | NHCOOEt | H | H | H | H | CH |
| 2-110 | 4-F-Ph | NHCOOPr | H | H | H | H | CH |
| 2-111 | 4-F-Ph | NHSO₂Me | H | H | H | H | CH |
| 2-112 | 4-F-Ph | NHSO₂Et | H | H | H | H | CH |
| 2-113 | 4-F-Ph | NHSO₂Pr | H | H | H | H | CH |
| 2-114 | 4-F-Ph | NHBn | H | H | H | H | CH |
| 2-115 | 4-F-Ph | NH(4-F-Bn) | H | H | H | H | CH |
| 2-116 | 4-F-Ph | NH(α-Me-Bn) | H | H | H | H | CH |
| 2-117 | 4-F-Ph | NHCOPh | H | H | H | H | CH |
| 2-118 | 4-F-Ph | NH₂ | Me | H | H | H | CH |
| 2-119 | 4-F-Ph | NH₂ | NH₂ | H | H | H | CH |
| 2-120 | 4-F-Ph | NH₂ | H | Me | H | H | CH |
| 2-121 | 4-F-Ph | NH₂ | H | H | Me | H | CH |
| 2-122 | 4-F-Ph | NH₂ | H | Me | Me | H | CH |
| 2-123 | 4-F-Ph | NH₂ | H | H | NH₂ | H | CH |
| 2-124 | 4-F-Ph | NH₂ | H | H | NHMe | H | CH |
| 2-125 | 4-F-Ph | NH₂ | H | H | NMe₂ | H | CH |
| 2-126 | 4-F-Ph | NH₂ | H | H | NHCOMe | H | CH |
| 2-127 | 4-F-Ph | NH₂ | H | H | NHCOOMe | H | CH |
| 2-128 | 4-F-Ph | NH₂ | H | H | NHSO₂Me | H | CH |
| 2-129 | 4-F-Ph | NH₂ | H | H | H | Me | CH |
| 2-130 | 4-F-Ph | NH₂ | H | H | H | CF₃ | CH |
| 2-131 | 4-F-Ph | NH₂ | H | H | H | CH₂CF₃ | CH |
| 2-132 | 4-F-Ph | NH₂ | H | H | H | NH₂ | CH |
| 2-133 | 4-F-Ph | NH₂ | H | H | H | NHMe | CH |
| 2-134 | 4-F-Ph | NH₂ | H | H | H | NMe₂ | CH |
| 2-135 | 4-F-Ph | NH₂ | H | H | H | NHCOMe | CH |
| 2-136 | 4-F-Ph | NH₂ | H | H | H | NHCOOMe | CH |
| 2-137 | 4-F-Ph | NH₂ | H | H | H | NHSO₂Me | CH |
| 2-138 | 4-F-Ph | NH₂ | H | H | Me | Me | CH |
| 2-139 | 4-F-Ph | NH₂ | H | H | Me | NH₂ | CH |
| 2-140 | 4-F-Ph | NH₂ | H | H | NH₂ | Me | CH |

TABLE 2-continued

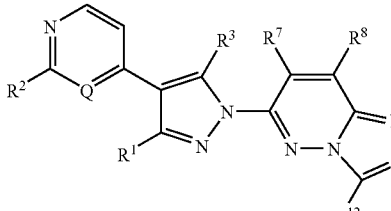

| Compound No | $R^1$ | $R^2$ | $R^3$ | $R^7$ | $R^8$ | $R^9$ | Q |
|---|---|---|---|---|---|---|---|
| 2-141 | 4-F-Ph | NHMe | H | H | Me | H | CH |
| 2-142 | 4-F-Ph | NHMe | H | H | $NH_2$ | H | CH |
| 2-143 | 4-F-Ph | NHMe | H | H | H | Me | CH |
| 2-144 | 4-F-Ph | NHMe | H | H | H | $NH_2$ | CH |
| 2-145 | 4-F-Ph | H | H | H | H | H | N |
| 2-146 | 4-F-Ph | H | $NH_2$ | H | H | H | N |
| 2-147 | 4-F-Ph | H | H | H | Me | H | N |
| 2-148 | 4-F-Ph | H | H | H | $NH_2$ | H | N |
| 2-149 | 4-F-Ph | H | H | H | NHMe | H | N |
| 2-150 | 4-F-Ph | H | H | H | $NMe_2$ | H | N |
| 2-151 | 4-F-Ph | $NH_2$ | H | H | H | H | N |
| 2-152 | 4-F-Ph | NHMe | H | H | H | H | N |
| 2-153 | 4-F-Ph | $NMe_2$ | H | H | H | H | N |
| 2-154 | 4-F-Ph | NHEt | H | H | H | H | N |
| 2-155 | 4-F-Ph | $NEt_2$ | H | H | H | H | N |
| 2-156 | 4-F-Ph | NHPr | H | H | H | H | N |
| 2-157 | 4-F-Ph | NHPr$^i$ | H | H | H | H | N |
| 2-158 | 4-F-Ph | $NHCH_2CF_3$ | H | H | H | H | N |
| 2-159 | 4-F-Ph | NHPr$^c$ | H | H | H | H | N |
| 2-160 | 4-F-Ph | NHCOMe | H | H | H | H | N |
| 2-161 | 4-F-Ph | NHCOEt | H | H | H | H | N |
| 2-162 | 4-F-Ph | NHCOOMe | H | H | H | H | N |
| 2-163 | 4-F-Ph | NHCOOEt | H | H | H | H | N |
| 2-164 | 4-F-Ph | $NHSO_2Me$ | H | H | H | H | N |
| 2-165 | 4-F-Ph | $NHSO_2Et$ | H | H | H | H | N |
| 2-166 | 4-F-Ph | NH(4-F-Bn) | H | H | H | H | N |
| 2-167 | 4-F-Ph | NH(α-Me-Bn) | H | H | H | H | N |
| 2-168 | 4-F-Ph | NHCOPh | H | H | H | H | N |
| 2-169 | 4-F-Ph | $NH_2$ | H | H | Me | H | N |
| 2-170 | 4-F-Ph | $NH_2$ | H | H | $NH_2$ | H | N |
| 2-171 | 4-F-Ph | $NH_2$ | H | H | NHMe | H | N |
| 2-172 | 4-F-Ph | $NH_2$ | H | H | $NMe_2$ | H | N |
| 2-173 | 4-F-Ph | $NH_2$ | H | H | H | Me | N |
| 2-174 | 4-F-Ph | $NH_2$ | H | H | H | $NH_2$ | N |
| 2-175 | 4-F-Ph | $NH_2$ | H | H | H | NHMe | N |
| 2-176 | 4-F-Ph | $NH_2$ | H | H | H | $NMe_2$ | N |
| 2-177 | 3-F-Ph | H | H | H | H | H | CH |
| 2-178 | 3-F-Ph | H | $NH_2$ | H | H | H | CH |
| 2-179 | 3-F-Ph | H | H | H | Me | H | CH |
| 2-180 | 3-F-Ph | H | H | H | $NH_2$ | H | CH |
| 2-181 | 3-F-Ph | H | H | H | NHMe | H | CH |
| 2-182 | 3-F-Ph | H | H | H | $NMe_2$ | H | CH |
| 2-183 | 3-F-Ph | H | H | H | H | Me | CH |
| 2-184 | 3-F-Ph | H | H | H | H | $CF_3$ | CH |
| 2-185 | 3-F-Ph | H | H | H | H | $NH_2$ | CH |
| 2-186 | 3-F-Ph | H | H | H | H | NHMe | CH |
| 2-187 | 3-F-Ph | H | H | H | H | $NMe_2$ | CH |
| 2-188 | 3-F-Ph | H | H | H | H | NHCOMe | CH |
| 2-189 | 3-F-Ph | H | H | H | H | NHCOOMe | CH |
| 2-190 | 3-F-Ph | H | H | H | H | $NHSO_2Me$ | CH |
| 2-191 | 3-F-Ph | F | H | H | H | H | CH |
| 2-192 | 3-F-Ph | Cl | H | H | H | H | CH |
| 2-193 | 3-F-Ph | Me | H | H | H | H | CH |
| 2-194 | 3-F-Ph | OMe | H | H | H | H | CH |
| 2-195 | 3-F-Ph | SMe | H | H | H | H | CH |
| 2-196 | 3-F-Ph | $NH_2$ | H | H | H | H | CH |
| 2-197 | 3-F-Ph | NHMe | H | H | H | H | CH |
| 2-198 | 3-F-Ph | $NMe_2$ | H | H | H | H | CH |
| 2-199 | 3-F-Ph | NHEt | H | H | H | H | CH |
| 2-200 | 3-F-Ph | $NEt_2$ | H | H | H | H | CH |
| 2-201 | 3-F-Ph | NHPr$^i$ | H | H | H | H | CH |
| 2-202 | 3-F-Ph | $NHCH_2CF_3$ | H | H | H | H | CH |
| 2-203 | 3-F-Ph | NHPr$^c$ | H | H | H | H | CH |
| 2-204 | 3-F-Ph | NHCHO | H | H | H | H | CH |

TABLE 2-continued

| Compound No | R¹ | R² | R³ | R⁷ | R⁸ | R⁹ | Q |
|---|---|---|---|---|---|---|---|
| 2-205 | 3-F-Ph | NHCOMe | H | H | H | H | CH |
| 2-206 | 3-F-Ph | NHCOEt | H | H | H | H | CH |
| 2-207 | 3-F-Ph | NHCOOMe | H | H | H | H | CH |
| 2-208 | 3-F-Ph | NHCOOEt | H | H | H | H | CH |
| 2-209 | 3-F-Ph | NHSO₂Me | H | H | H | H | CH |
| 2-210 | 3-F-Ph | NHSO₂Et | H | H | H | H | CH |
| 2-211 | 3-F-Ph | NH(4-F-Bn) | H | H | H | H | CH |
| 2-212 | 3-F-Ph | NH(α-Me-Bn) | H | H | H | H | CH |
| 2-213 | 3-F-Ph | NHCOPh | H | H | H | H | CH |
| 2-214 | 3-F-Ph | NH₂ | Me | H | H | H | CH |
| 2-215 | 3-F-Ph | NH₂ | NH₂ | H | H | H | CH |
| 2-216 | 3-F-Ph | NH₂ | H | Me | H | H | CH |
| 2-217 | 3-F-Ph | NH₂ | H | H | Me | H | CH |
| 2-218 | 3-F-Ph | NH₂ | H | Me | Me | H | CH |
| 2-219 | 3-F-Ph | NH₂ | H | H | NH₂ | H | CH |
| 2-220 | 3-F-Ph | NH₂ | H | H | NHMe | H | CH |
| 2-221 | 3-F-Ph | NH₂ | H | H | NMe₂ | H | CH |
| 2-222 | 3-F-Ph | NH₂ | H | H | NHCOMe | H | CH |
| 2-223 | 3-F-Ph | NH₂ | H | H | NHCOOMe | H | CH |
| 2-224 | 3-F-Ph | NH₂ | H | H | NHSO₂Me | H | CH |
| 2-225 | 3-F-Ph | NH₂ | H | H | H | Me | CH |
| 2-226 | 3-F-Ph | NH₂ | H | H | H | CF₃ | CH |
| 2-227 | 3-F-Ph | NH₂ | H | H | H | CH₂CF₃ | CH |
| 2-228 | 3-F-Ph | NH₂ | H | H | H | NH₂ | CH |
| 2-229 | 3-F-Ph | NH₂ | H | H | H | NHMe | CH |
| 2-230 | 3-F-Ph | NH₂ | H | H | H | NMe₂ | CH |
| 2-231 | 3-F-Ph | NH₂ | H | H | H | NHCOMe | CH |
| 2-232 | 3-F-Ph | NH₂ | H | H | H | NHCOOMe | CH |
| 2-233 | 3-F-Ph | NH₂ | H | H | H | NHSO₂Me | CH |
| 2-234 | 3-F-Ph | NH₂ | H | H | Me | Me | CH |
| 2-235 | 3-F-Ph | NH₂ | H | H | Me | NH₂ | CH |
| 2-236 | 3-F-Ph | NH₂ | H | H | NH₂ | Me | CH |
| 2-237 | 3-F-Ph | H | H | H | H | H | N |
| 2-238 | 3-F-Ph | H | NH₂ | H | H | H | N |
| 2-239 | 3-F-Ph | H | H | H | Me | H | N |
| 2-240 | 3-F-Ph | H | H | H | NH₂ | H | N |
| 2-241 | 3-F-Ph | H | H | H | NHMe | H | N |
| 2-242 | 3-F-Ph | H | H | H | NMe₂ | H | N |
| 2-243 | 3-F-Ph | NH₂ | H | H | H | H | N |
| 2-244 | 3-F-Ph | NHMe | H | H | H | H | N |
| 2-245 | 3-F-Ph | NMe₂ | H | H | H | H | N |
| 2-246 | 3-F-Ph | NHEt | H | H | H | H | N |
| 2-247 | 3-F-Ph | NHPrⁱ | H | H | H | H | N |
| 2-248 | 3-F-Ph | NHCH₂CF₃ | H | H | H | H | N |
| 2-249 | 3-F-Ph | NHPrᶜ | H | H | H | H | N |
| 2-250 | 3-F-Ph | NHCOMe | H | H | H | H | N |
| 2-251 | 3-F-Ph | NHCOEt | H | H | H | H | N |
| 2-252 | 3-F-Ph | NHCOOMe | H | H | H | H | N |
| 2-253 | 3-F-Ph | NHSO₂Me | H | H | H | H | N |
| 2-254 | 3-F-Ph | NH(α-Me-Bn) | H | H | H | H | N |
| 2-255 | 3-F-Ph | NHCOPh | H | H | H | H | N |
| 2-256 | 3-F-Ph | NH₂ | H | H | Me | H | N |
| 2-257 | 3-F-Ph | NH₂ | H | H | NH₂ | H | N |
| 2-258 | 3-F-Ph | NH₂ | H | H | NHMe | H | N |
| 2-259 | 3-F-Ph | H | H | N | Me₂ | H | N |
| 2-260 | 3-F-Ph | NH₂ | H | H | H | Me | N |
| 2-261 | 3-F-Ph | NH₂ | H | H | H | NH₂ | N |
| 2-262 | 3-F-Ph | NH₂ | H | H | H | NHMe | N |
| 2-263 | 3-F-Ph | NH₂ | H | H | H | NMe₂ | N |
| 2-264 | 4-Cl-Ph | H | H | H | H | H | CH |
| 2-265 | 4-Cl-Ph | H | NH₂ | H | H | H | CH |
| 2-266 | 4-Cl-Ph | H | H | H | Me | H | CH |
| 2-267 | 4-Cl-Ph | H | H | H | NH₂ | H | CH |
| 2-268 | 4-Cl-Ph | H | H | H | NHMe | H | CH |

TABLE 2-continued

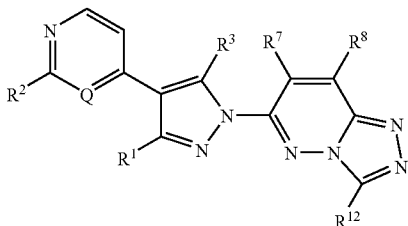

| Compound No | $R^1$ | $R^2$ | $R^3$ | $R^7$ | $R^8$ | $R^9$ | Q |
|---|---|---|---|---|---|---|---|
| 2-269 | 4-Cl-Ph | H | H | H | $NMe_2$ | H | CH |
| 2-270 | 4-Cl-Ph | H | H | H | NHCOMe | H | CH |
| 2-271 | 4-Cl-Ph | H | H | H | NHCOOMe | H | CH |
| 2-272 | 4-Cl-Ph | H | H | H | $NHSO_2Me$ | H | CH |
| 2-273 | 4-Cl-Ph | H | H | H | H | Me | CH |
| 2-274 | 4-Cl-Ph | H | H | H | H | $CF_3$ | CH |
| 2-275 | 4-Cl-Ph | H | H | H | H | $NH_2$ | CH |
| 2-276 | 4-Cl-Ph | H | H | H | H | NHMe | CH |
| 2-277 | 4-Cl-Ph | H | H | H | H | $NMe_2$ | CH |
| 2-278 | 4-Cl-Ph | H | H | H | H | NHCOMe | CH |
| 2-279 | 4-Cl-Ph | H | H | H | H | NHCOOMe | CH |
| 2-280 | 4-Cl-Ph | H | H | H | H | $NHSO_2Me$ | CH |
| 2-281 | 4-Cl-Ph | F | H | H | H | H | CH |
| 2-282 | 4-Cl-Ph | Cl | H | H | H | H | CH |
| 2-283 | 4-Cl-Ph | Me | H | H | H | H | CH |
| 2-284 | 4-Cl-Ph | OMe | H | H | H | H | CH |
| 2-285 | 4-Cl-Ph | OEt | H | H | H | H | CH |
| 2-286 | 4-Cl-Ph | SMe | H | H | H | H | CH |
| 2-287 | 4-Cl-Ph | $NH_2$ | H | H | H | H | CH |
| 2-288 | 4-Cl-Ph | NHMe | H | H | H | H | CH |
| 2-289 | 4-Cl-Ph | $NMe_2$ | H | H | H | H | CH |
| 2-290 | 4-Cl-Ph | NHEt | H | H | H | H | CH |
| 2-291 | 4-Cl-Ph | $NEt_2$ | H | H | H | H | CH |
| 2-292 | 4-Cl-Ph | NHPr | H | H | H | H | CH |
| 2-293 | 4-Cl-Ph | $NHPr^i$ | H | H | H | H | CH |
| 2-294 | 4-Cl-Ph | $NHCH_2CF_3$ | H | H | H | H | CH |
| 2-295 | 4-Cl-Ph | $NHPr^c$ | H | H | H | H | CH |
| 2-296 | 4-Cl-Ph | $NHHx^c$ | H | H | H | H | CH |
| 2-297 | 4-Cl-Ph | NHCHO | H | H | H | H | CH |
| 2-298 | 4-Cl-Ph | NHCOMe | H | H | H | H | CH |
| 2-299 | 4-Cl-Ph | NHCOEt | H | H | H | H | CH |
| 2-300 | 4-Cl-Ph | NHCOPr | H | H | H | H | CH |
| 2-301 | 4-Cl-Ph | NHCOOMe | H | H | H | H | CH |
| 2-302 | 4-Cl-Ph | NHCOOEt | H | H | H | H | CH |
| 2-303 | 4-Cl-Ph | NHCOOPr | H | H | H | H | CH |
| 2-304 | 4-Cl-Ph | $NHSO_2Me$ | H | H | H | H | CH |
| 2-305 | 4-Cl-Ph | $NHSO_2Et$ | H | H | H | H | CH |
| 2-306 | 4-Cl-Ph | NHBn | H | H | H | H | CH |
| 2-307 | 4-Cl-Ph | NH(4-F-Bn) | H | H | H | H | CH |
| 2-308 | 4-Cl-Ph | NH(α-Me-Bn) | H | H | H | H | CH |
| 2-309 | 4-Cl-Ph | NHCOPh | H | H | H | H | CH |
| 2-310 | 4-Cl-Ph | $NH_2$ | Me | H | H | H | CH |
| 2-311 | 4-Cl-Ph | $NH_2$ | $NH_2$ | H | H | H | CH |
| 2-312 | 4-Cl-Ph | $NH_2$ | H | Me | H | H | CH |
| 2-313 | 4-Cl-Ph | $NH_2$ | H | H | Me | H | CH |
| 2-314 | 4-Cl-Ph | $NH_2$ | H | Me | Me | H | CH |
| 2-315 | 4-Cl-Ph | $NH_2$ | H | H | $NH_2$ | H | CH |
| 2-316 | 4-Cl-Ph | $NH_2$ | H | H | NHMe | H | CH |
| 2-317 | 4-Cl-Ph | $NH_2$ | H | H | $NMe_2$ | H | CH |
| 2-318 | 4-Cl-Ph | $NH_2$ | H | H | NHCOMe | H | CH |
| 2-319 | 4-Cl-Ph | $NH_2$ | H | H | NHCOOMe | H | CH |
| 2-320 | 4-Cl-Ph | $NH_2$ | H | H | $NHSO_2Me$ | H | CH |
| 2-321 | 4-Cl-Ph | $NH_2$ | H | H | H | Me | CH |
| 2-322 | 4-Cl-Ph | $NH_2$ | H | H | H | $CF_3$ | CH |
| 2-323 | 4-Cl-Ph | $NH_2$ | H | H | H | $CH_2CF_3$ | CH |
| 2-324 | 4-Cl-Ph | $NH_2$ | H | H | H | $NH_2$ | CH |
| 2-325 | 4-Cl-Ph | $NH_2$ | H | H | H | NHMe | CH |
| 2-326 | 4-Cl-Ph | $NH_2$ | H | H | H | $NMe_2$ | CH |
| 2-327 | 4-Cl-Ph | $NH_2$ | H | H | H | NHCOMe | CH |
| 2-328 | 4-Cl-Ph | $NH_2$ | H | H | H | NHCOOMe | CH |
| 2-329 | 4-Cl-Ph | $NH_2$ | H | H | H | $NHSO_2Me$ | CH |
| 2-330 | 4-Cl-Ph | $NH_2$ | H | H | Me | Me | CH |
| 2-331 | 4-Cl-Ph | $NH_2$ | H | H | Me | $NH_2$ | CH |
| 2-332 | 4-Cl-Ph | $NH_2$ | H | H | $NH_2$ | Me | CH |

TABLE 2-continued

| Compound No | R¹ | R² | R³ | R⁷ | R⁸ | R⁹ | Q |
|---|---|---|---|---|---|---|---|
| 2-333 | 4-Cl-Ph | NHMe | H | H | Me | H | CH |
| 2-334 | 4-Cl-Ph | NHMe | H | H | NH₂ | H | CH |
| 2-335 | 4-Cl-Ph | NHMe | H | H | H | Me | CH |
| 2-336 | 4-Cl-Ph | NHMe | H | H | H | NH₂ | CH |
| 2-337 | 4-Cl-Ph | H | H | H | H | H | N |
| 2-338 | 4-Cl-Ph | H | NH₂ | H | H | H | N |
| 2-339 | 4-Cl-Ph | H | H | H | Me | H | N |
| 2-340 | 4-Cl-Ph | H | H | H | NH₂ | H | N |
| 2-341 | 4-Cl-Ph | H | H | H | NHMe | H | N |
| 2-342 | 4-Cl-Ph | H | H | H | NMe₂ | H | N |
| 2-343 | 4-Cl-Ph | NH₂ | H | H | H | H | N |
| 2-344 | 4-Cl-Ph | NHMe | H | H | H | H | N |
| 2-345 | 4-Cl-Ph | NMe₂ | H | H | H | H | N |
| 2-346 | 4-Cl-Ph | NHEt | H | H | H | H | N |
| 2-347 | 4-Cl-Ph | NEt₂ | H | H | H | H | N |
| 2-348 | 4-Cl-Ph | NHPrⁱ | H | H | H | H | N |
| 2-349 | 4-Cl-Ph | NHCH₂CF₃ | H | H | H | H | N |
| 2-350 | 4-Cl-Ph | NHPrᶜ | H | H | H | H | N |
| 2-351 | 4-Cl-Ph | NHCOMe | H | H | H | H | N |
| 2-352 | 4-Cl-Ph | NHCOEt | H | H | H | H | N |
| 2-353 | 4-Cl-Ph | NHCOOMe | H | H | H | H | N |
| 2-354 | 4-Cl-Ph | NHSO₂Me | H | H | H | H | N |
| 2-355 | 4-Cl-Ph | NH(4-F-Bn) | H | H | H | H | N |
| 2-356 | 4-Cl-Ph | NH(α-Me-Bn) | H | H | H | H | N |
| 2-357 | 4-Cl-Ph | NHCOPh | H | H | H | H | N |
| 2-358 | 4-Cl-Ph | NH₂ | H | H | Me | H | N |
| 2-359 | 4-Cl-Ph | NH₂ | H | H | NH₂ | H | N |
| 2-360 | 4-Cl-Ph | NH₂ | H | H | NHMe | H | N |
| 2-361 | 4-Cl-Ph | NH₂ | H | H | NMe₂ | H | N |
| 2-362 | 4-Cl-Ph | NH₂ | H | H | H | Me | N |
| 2-363 | 4-Cl-Ph | NH₂ | H | H | H | NH₂ | N |
| 2-364 | 4-Cl-Ph | NH₂ | H | H | H | NHMe | N |
| 2-365 | 4-Cl-Ph | NH₂ | H | H | H | NMe₂ | N |
| 2-366 | 3-Cl-Ph | H | H | H | H | H | CH |
| 2-367 | 3-Cl-Ph | H | NH₂ | H | H | H | CH |
| 2-368 | 3-Cl-Ph | H | H | H | Me | H | CH |
| 2-369 | 3-Cl-Ph | H | H | H | NH₂ | H | CH |
| 2-370 | 3-Cl-Ph | H | H | H | NHMe | H | CH |
| 2-371 | 3-Cl-Ph | H | H | H | NMe₂ | H | CH |
| 2-372 | 3-Cl-Ph | H | H | H | H | Me | CH |
| 2-373 | 3-Cl-Ph | H | H | H | H | CF₃ | CH |
| 2-374 | 3-Cl-Ph | H | H | H | H | NH₂ | CH |
| 2-375 | 3-Cl-Ph | H | H | H | H | NHMe | CH |
| 2-376 | 3-Cl-Ph | H | H | H | H | NMe₂ | CH |
| 2-377 | 3-Cl-Ph | H | H | H | H | NHCOMe | CH |
| 2-378 | 3-Cl-Ph | H | H | H | H | NHCOOMe | CH |
| 2-379 | 3-Cl-Ph | H | H | H | H | NHSO₂Me | CH |
| 2-380 | 3-Cl-Ph | F | H | H | H | H | CH |
| 2-381 | 3-Cl-Ph | Cl | H | H | H | H | CH |
| 2-382 | 3-Cl-Ph | Me | H | H | H | H | CH |
| 2-383 | 3-Cl-Ph | OMe | H | H | H | H | CH |
| 2-384 | 3-Cl-Ph | SMe | H | H | H | H | CH |
| 2-385 | 3-Cl-Ph | NH₂ | H | H | H | H | CH |
| 2-386 | 3-Cl-Ph | NHMe | H | H | H | H | CH |
| 2-387 | 3-Cl-Ph | NMe₂ | H | H | H | H | CH |
| 2-388 | 3-Cl-Ph | NHEt | H | H | H | H | CH |
| 2-389 | 3-Cl-Ph | NEt₂ | H | H | H | H | CH |
| 2-390 | 3-Cl-Ph | NHPrⁱ | H | H | H | H | CH |
| 2-391 | 3-Cl-Ph | NHCH₂CF₃ | H | H | H | H | CH |
| 2-392 | 3-Cl-Ph | NHPrᶜ | H | H | H | H | CH |
| 2-393 | 3-Cl-Ph | NHCHO | H | H | H | H | CH |
| 2-394 | 3-Cl-Ph | NHCOMe | H | H | H | H | CH |
| 2-395 | 3-Cl-Ph | NHCOEt | H | H | H | H | CH |
| 2-396 | 3-Cl-Ph | NHCOOMe | H | H | H | H | CH |

TABLE 2-continued

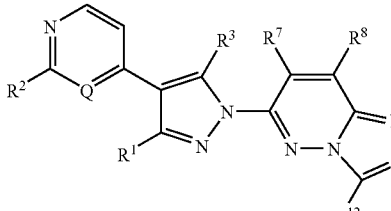

| Compound No | $R^1$ | $R^2$ | $R^3$ | $R^7$ | $R^8$ | $R^9$ | Q |
|---|---|---|---|---|---|---|---|
| 2-397 | 3-Cl-Ph | NHCOOEt | H | H | H | H | CH |
| 2-398 | 3-Cl-Ph | NHSO$_2$Me | H | H | H | H | CH |
| 2-399 | 3-Cl-Ph | NHSO$_2$Et | H | H | H | H | CH |
| 2-400 | 3-Cl-Ph | NH(4-F-Bn) | H | H | H | H | CH |
| 2-401 | 3-Cl-Ph | NH(α-Me-Bn) | H | H | H | H | CH |
| 2-402 | 3-Cl-Ph | NHCOPh | H | H | H | H | CH |
| 2-403 | 3-Cl-Ph | NH$_2$ | Me | H | H | H | CH |
| 2-404 | 3-Cl-Ph | NH$_2$ | NH$_2$ | H | H | H | CH |
| 2-405 | 3-Cl-Ph | NH$_2$ | H | Me | H | H | CH |
| 2-406 | 3-Cl-Ph | NH$_2$ | H | H | Me | H | CH |
| 2-407 | 3-Cl-Ph | NH$_2$ | H | Me | Me | H | CH |
| 2-408 | 3-Cl-Ph | NH$_2$ | H | H | NH$_2$ | H | CH |
| 2-409 | 3-Cl-Ph | NH$_2$ | H | H | NHMe | H | CH |
| 2-410 | 3-Cl-Ph | NH$_2$ | H | H | NMe$_2$ | H | CH |
| 2-411 | 3-Cl-Ph | NH$_2$ | H | H | NHCOMe | H | CH |
| 2-412 | 3-Cl-Ph | NH$_2$ | H | H | NHCOOMe | H | CH |
| 2-413 | 3-Cl-Ph | NH$_2$ | H | H | NHSO$_2$Me | H | CH |
| 2-414 | 3-Cl-Ph | NH$_2$ | H | H | H | Me | CH |
| 2-415 | 3-Cl-Ph | NH$_2$ | H | H | H | CF$_3$ | CH |
| 2-416 | 3-Cl-Ph | NH$_2$ | H | H | H | CH$_2$CF$_3$ | CH |
| 2-417 | 3-Cl-Ph | NH$_2$ | H | H | H | NH$_2$ | CH |
| 2-418 | 3-Cl-Ph | NH$_2$ | H | H | H | NHMe | CH |
| 2-419 | 3-Cl-Ph | NH$_2$ | H | H | H | NMe$_2$ | CH |
| 2-420 | 3-Cl-Ph | NH$_2$ | H | H | H | NHCOMe | CH |
| 2-421 | 3-Cl-Ph | NH$_2$ | H | H | H | NHCOOMe | CH |
| 2-422 | 3-Cl-Ph | NH$_2$ | H | H | H | NHSO$_2$Me | CH |
| 2-423 | 3-Cl-Ph | NH$_2$ | H | H | Me | Me | CH |
| 2-424 | 3-Cl-Ph | NH$_2$ | H | H | Me | NH$_2$ | CH |
| 2-425 | 3-Cl-Ph | NH$_2$ | H | H | NH$_2$ | Me | CH |
| 2-426 | 3-Cl-Ph | H | H | H | H | H | N |
| 2-427 | 3-Cl-Ph | H | NH$_2$ | H | H | H | N |
| 2-428 | 3-Cl-Ph | H | H | H | Me | H | N |
| 2-429 | 3-Cl-Ph | H | H | H | NH$_2$ | H | N |
| 2-430 | 3-Cl-Ph | H | H | H | NHMe | H | N |
| 2-431 | 3-Cl-Ph | H | H | H | NMe$_2$ | H | N |
| 2-432 | 3-Cl-Ph | NH$_2$ | H | H | H | H | N |
| 2-433 | 3-Cl-Ph | NHMe | H | H | H | H | N |
| 2-434 | 3-Cl-Ph | NMe$_2$ | H | H | H | H | N |
| 2-435 | 3-Cl-Ph | NHEt | H | H | H | H | N |
| 2-436 | 3-Cl-Ph | NHPr$^i$ | H | H | H | H | N |
| 2-437 | 3-Cl-Ph | NHCH$_2$CF$_3$ | H | H | H | H | N |
| 2-438 | 3-Cl-Ph | NHPr$^c$ | H | H | H | H | N |
| 2-439 | 3-Cl-Ph | NHCOMe | H | H | H | H | N |
| 2-440 | 3-Cl-Ph | NHCOEt | H | H | H | H | N |
| 2-441 | 3-Cl-Ph | NHCOOMe | H | H | H | H | N |
| 2-442 | 3-Cl-Ph | NHSO$_2$Me | H | H | H | H | N |
| 2-443 | 3-Cl-Ph | NH(α-Me-Bn) | H | H | H | H | N |
| 2-444 | 3-Cl-Ph | NHCOPh | H | H | H | H | N |
| 2-445 | 3-Cl-Ph | NH$_2$ | H | H | Me | H | N |
| 2-446 | 3-Cl-Ph | NH$_2$ | H | H | NH$_2$ | H | N |
| 2-447 | 3-Cl-Ph | NH$_2$ | H | H | NHMe | H | N |
| 2-448 | 3-Cl-Ph | NH$_2$ | H | H | NMe$_2$ | H | N |
| 2-449 | 3-Cl-Ph | NH$_2$ | H | H | H | Me | N |
| 2-450 | 3-Cl-Ph | NH$_2$ | H | H | H | NH$_2$ | N |
| 2-451 | 3-Cl-Ph | NH$_2$ | H | H | H | NHMe | N |
| 2-452 | 3-Cl-Ph | NH$_2$ | H | H | H | NMe$_2$ | N |
| 2-453 | 3,4-diF-Ph | H | H | H | H | H | CH |
| 2-454 | 3,4-diF-Ph | H | NH$_2$ | H | H | H | CH |
| 2-455 | 3,4-diF-Ph | H | H | H | Me | H | CH |
| 2-456 | 3,4-diF-Ph | H | H | H | NH$_2$ | H | CH |
| 2-457 | 3,4-diF-Ph | H | H | H | NHMe | H | CH |
| 2-458 | 3,4-diF-Ph | H | H | H | NMe$_2$ | H | CH |
| 2-459 | 3,4-diF-Ph | H | H | H | NHCOMe | H | CH |
| 2-460 | 3,4-diF-Ph | H | H | H | NHCOOMe | H | CH |

TABLE 2-continued

| Compound No | R¹ | R² | R³ | R⁷ | R⁸ | R⁹ | Q |
|---|---|---|---|---|---|---|---|
| 2-461 | 3,4-diF-Ph | H | H | H | NHSO₂Me | H | CH |
| 2-462 | 3,4-diF-Ph | H | H | H | H | Me | CH |
| 2-463 | 3,4-diF-Ph | H | H | H | H | CF₃ | CH |
| 2-464 | 3,4-diF-Ph | H | H | H | H | NH₂ | CH |
| 2-465 | 3,4-diF-Ph | H | H | H | H | NHMe | CH |
| 2-466 | 3,4-diF-Ph | H | H | H | H | NMe₂ | CH |
| 2-467 | 3,4-diF-Ph | H | H | H | H | NHCOMe | CH |
| 2-468 | 3,4-diF-Ph | H | H | H | H | NHCOOMe | CH |
| 2-469 | 3,4-diF-Ph | H | H | H | H | NHSO₂Me | CH |
| 2-470 | 3,4-diF-Ph | F | H | H | H | H | CH |
| 2-471 | 3,4-diF-Ph | Cl | H | H | H | H | CH |
| 2-472 | 3,4-diF-Ph | Me | H | H | H | H | CH |
| 2-473 | 3,4-diF-Ph | OMe | H | H | H | H | CH |
| 2-474 | 3,4-diF-Ph | OEt | H | H | H | H | CH |
| 2-475 | 3,4-diF-Ph | SMe | H | H | H | H | CH |
| 2-476 | 3,4-diF-Ph | NH₂ | H | H | H | H | CH |
| 2-477 | 3,4-diF-Ph | NHMe | H | H | H | H | CH |
| 2-478 | 3,4-diF-Ph | NMe₂ | H | H | H | H | CH |
| 2-479 | 3,4-diF-Ph | NHEt | H | H | H | H | CH |
| 2-480 | 3,4-diF-Ph | NEt₂ | H | H | H | H | CH |
| 2-481 | 3,4-diF-Ph | NHPr | H | H | H | H | CH |
| 2-482 | 3,4-diF-Ph | NHPrⁱ | H | H | H | H | CH |
| 2-483 | 3,4-diF-Ph | NHCH₂CF₃ | H | H | H | H | CH |
| 2-484 | 3,4-diF-Ph | NHPrᶜ | H | H | H | H | CH |
| 2-485 | 3,4-diF-Ph | NHHxᶜ | H | H | H | H | CH |
| 2-486 | 3,4-diF-Ph | NHCHO | H | H | H | H | CH |
| 2-487 | 3,4-diF-Ph | NHCOMe | H | H | H | H | CH |
| 2-488 | 3,4-diF-Ph | NHCOEt | H | H | H | H | CH |
| 2-489 | 3,4-diF-Ph | NHCOPr | H | H | H | H | CH |
| 2-490 | 3,4-diF-Ph | NHCOOMe | H | H | H | H | CH |
| 2-491 | 3,4-diF-Ph | NHCOOEt | H | H | H | H | CH |
| 2-492 | 3,4-diF-Ph | NHCOOPr | H | H | H | H | CH |
| 2-493 | 3,4-diF-Ph | NHSO₂Me | H | H | H | H | CH |
| 2-494 | 3,4-diF-Ph | NHSO₂Et | H | H | H | H | CH |
| 2-495 | 3,4-diF-Ph | NHBn | H | H | H | H | CH |
| 2-496 | 3,4-diF-Ph | NH(4-F-Bn) | H | H | H | H | CH |
| 2-497 | 3,4-diF-Ph | NH(α-Me-Bn) | H | H | H | H | CH |
| 2-498 | 3,4-diF-Ph | NHCOPh | H | H | H | H | CH |
| 2-499 | 3,4-diF-Ph | NH₂ | Me | H | H | H | CH |
| 2-500 | 3,4-diF-Ph | NH₂ | NH₂ | H | H | H | CH |
| 2-501 | 3,4-diF-Ph | NH₂ | H | Me | H | H | CH |
| 2-502 | 3,4-diF-Ph | NH₂ | H | H | Me | H | CH |
| 2-503 | 3,4-diF-Ph | NH₂ | H | Me | Me | H | CH |
| 2-504 | 3,4-diF-Ph | NH₂ | H | H | NH₂ | H | CH |
| 2-505 | 3,4-diF-Ph | NH₂ | H | H | NHMe | H | CH |
| 2-506 | 3,4-diF-Ph | NH₂ | H | H | NMe₂ | H | CH |
| 2-507 | 3,4-diF-Ph | NH₂ | H | H | NHCOMe | H | CH |
| 2-508 | 3,4-diF-Ph | NH₂ | H | H | NHCOOMe | H | CH |
| 2-509 | 3,4-diF-Ph | NH₂ | H | H | NHSO₂Me | H | CH |
| 2-510 | 3,4-diF-Ph | NH₂ | H | H | H | Me | CH |
| 2-511 | 3,4-diF-Ph | NH₂ | H | H | H | CF₃ | CH |
| 2-512 | 3,4-diF-Ph | NH₂ | H | H | H | CH₂CF₃ | CH |
| 2-513 | 3,4-diF-Ph | NH₂ | H | H | H | NH₂ | CH |
| 2-514 | 3,4-diF-Ph | NH₂ | H | H | H | NHMe | CH |
| 2-515 | 3,4-diF-Ph | NH₂ | H | H | H | NMe₂ | CH |
| 2-516 | 3,4-diF-Ph | NH₂ | H | H | H | NHCOMe | CH |
| 2-517 | 3,4-diF-Ph | NH₂ | H | H | H | NHCOOMe | CH |
| 2-518 | 3,4-diF-Ph | NH₂ | H | H | H | NHSO₂Me | CH |
| 2-519 | 3,4-diF-Ph | NH₂ | H | H | Me | Me | CH |
| 2-520 | 3,4-diF-Ph | NH₂ | H | H | Me | NH₂ | CH |
| 2-521 | 3,4-diF-Ph | NH₂ | H | H | NH₂ | Me | CH |
| 2-522 | 3,4-diF-Ph | NHMe | H | H | Me | H | CH |
| 2-523 | 3,4-diF-Ph | NHMe | H | H | NH₂ | H | CH |
| 2-524 | 3,4-diF-Ph | NHMe | H | H | H | Me | CH |

TABLE 2-continued

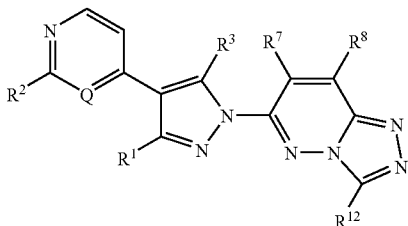

| Compound No | R¹ | R² | R³ | R⁷ | R⁸ | R⁹ | Q |
|---|---|---|---|---|---|---|---|
| 2-525 | 3,4-diF-Ph | NHMe | H | H | H | NH₂ | CH |
| 2-526 | 3,4-diF-Ph | H | H | H | H | H | N |
| 2-527 | 3,4-diF-Ph | H | NH₂ | H | H | H | N |
| 2-528 | 3,4-diF-Ph | H | H | H | Me | H | N |
| 2-529 | 3,4-diF-Ph | H | H | H | NH₂ | H | N |
| 2-530 | 3,4-diF-Ph | H | H | H | NHMe | H | N |
| 2-531 | 3,4-diF-Ph | H | H | H | NMe₂ | H | N |
| 2-532 | 3,4-diF-Ph | NH₂ | H | H | H | H | N |
| 2-533 | 3,4-diF-Ph | NHMe | H | H | H | H | N |
| 2-534 | 3,4-diF-Ph | NMe₂ | H | H | H | H | N |
| 2-535 | 3,4-diF-Ph | NHEt | H | H | H | H | N |
| 2-536 | 3,4-diF-Ph | NEt₂ | H | H | H | H | N |
| 2-537 | 3,4-diF-Ph | NHPrⁱ | H | H | H | H | N |
| 2-538 | 3,4-diF-Ph | NHCH₂CF₃ | H | H | H | H | N |
| 2-539 | 3,4-diF-Ph | NHPrᶜ | H | H | H | H | N |
| 2-540 | 3,4-diF-Ph | NHCOMe | H | H | H | H | N |
| 2-541 | 3,4-diF-Ph | NHCOEt | H | H | H | H | N |
| 2-542 | 3,4-diF-Ph | NHCOOMe | H | H | H | H | N |
| 2-543 | 3,4-diF-Ph | NHSO₂Me | H | H | H | H | N |
| 2-544 | 3,4-diF-Ph | NH(4-F-Bn) | H | H | H | H | N |
| 2-545 | 3,4-diF-Ph | NH(α-Me-Bn) | H | H | H | H | N |
| 2-546 | 3,4-diF-Ph | NHCOPh | H | H | H | H | N |
| 2-547 | 3,4-diF-Ph | NH₂ | H | H | Me | H | N |
| 2-548 | 3,4-diF-Ph | NH₂ | H | H | NH₂ | H | N |
| 2-549 | 3,4-diF-Ph | NH₂ | H | H | NHMe | H | N |
| 2-550 | 3,4-diF-Ph | NH₂ | H | H | NMe₂ | H | N |
| 2-551 | 3,4-diF-Ph | NH₂ | H | H | H | Me | N |
| 2-552 | 3,4-diF-Ph | NH₂ | H | H | H | NH₂ | N |
| 2-553 | 3,4-diF-Ph | NH₂ | H | H | H | NHMe | N |
| 2-554 | 3,4-diF-Ph | NH₂ | H | H | H | NMe₂ | N |
| 2-555 | 3,4-diCl-Ph | H | H | H | H | H | CH |
| 2-556 | 3,4-diCl-Ph | H | NH₂ | H | H | H | CH |
| 2-557 | 3,4-diCl-Ph | H | H | H | Me | H | CH |
| 2-558 | 3,4-diCl-Ph | H | H | H | NH₂ | H | CH |
| 2-559 | 3,4-diCl-Ph | H | H | H | NHMe | H | CH |
| 2-560 | 3,4-diCl-Ph | H | H | H | NMe₂ | H | CH |
| 2-561 | 3,4-diCl-Ph | H | H | H | H | Me | CH |
| 2-562 | 3,4-diCl-Ph | H | H | H | H | CF₃ | CH |
| 2-563 | 3,4-diCl-Ph | H | H | H | H | NH₂ | CH |
| 2-564 | 3,4-diCl-Ph | H | H | H | H | NHMe | CH |
| 2-565 | 3,4-diCl-Ph | H | H | H | H | NMe₂ | CH |
| 2-566 | 3,4-diCl-Ph | H | H | H | H | NHCOMe | CH |
| 2-567 | 3,4-diCl-Ph | H | H | H | H | NHCOOMe | CH |
| 2-568 | 3,4-diCl-Ph | H | H | H | H | NHSO₂Me | CH |
| 2-569 | 3,4-diCl-Ph | F | H | H | H | H | CH |
| 2-570 | 3,4-diCl-Ph | Cl | H | H | H | H | CH |
| 2-571 | 3,4-diCl-Ph | Me | H | H | H | H | CH |
| 2-572 | 3,4-diCl-Ph | OMe | H | H | H | H | CH |
| 2-573 | 3,4-diCl-Ph | SMe | H | H | H | H | CH |
| 2-574 | 3,4-diCl-Ph | NH₂ | H | H | H | H | CH |
| 2-575 | 3,4-diCl-Ph | NHMe | H | H | H | H | CH |
| 2-576 | 3,4-diCl-Ph | NMe₂ | H | H | H | H | CH |
| 2-577 | 3,4-diCl-Ph | NHEt | H | H | H | H | CH |
| 2-578 | 3,4-diCl-Ph | NEt₂ | H | H | H | H | CH |
| 2-579 | 3,4-diCl-Ph | NHPrⁱ | H | H | H | H | CH |
| 2-580 | 3,4-diCl-Ph | NHCH₂CF₃ | H | H | H | H | CH |
| 2-581 | 3,4-diCl-Ph | NHPrᶜ | H | H | H | H | CH |
| 2-582 | 3,4-diCl-Ph | NHCHO | H | H | H | H | CH |
| 2-583 | 3,4-diCl-Ph | NHCOEt | H | H | H | H | CH |
| 2-585 | 3,4-diCl-Ph | NHCOOMe | H | H | H | H | CH |
| 2-586 | 3,4-diCl-Ph | NHCOOEt | H | H | H | H | CH |
| 2-587 | 3,4-diCl-Ph | NHSO₂Me | H | H | H | H | CH |
| 2-588 | 3,4-diCl-Ph | NHSO₂Et | H | H | H | H | CH |
| 2-589 | 3,4-diCl-Ph | NH(4-F-Bn) | H | H | H | H | CH |

TABLE 2-continued

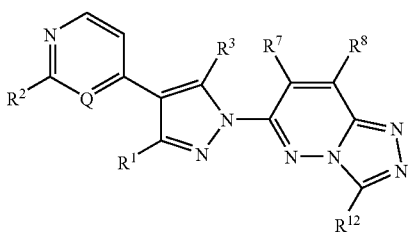

| Compound No | $R^1$ | $R^2$ | $R^3$ | $R^7$ | $R^8$ | $R^9$ | Q |
|---|---|---|---|---|---|---|---|
| 2-590 | 3,4-diCl-Ph | NH(α-Me-Bn) | H | H | H | H | CH |
| 2-591 | 3,4-diCl-Ph | NHCOPh | H | H | H | H | CH |
| 2-592 | 3,4-diCl-Ph | $NH_2$ | Me | H | H | H | CH |
| 2-593 | 3,4-diCl-Ph | $NH_2$ | $NH_2$ | H | H | H | CH |
| 2-594 | 3,4-diCl-Ph | $NH_2$ | H | Me | H | H | CH |
| 2-595 | 3,4-diCl-Ph | $NH_2$ | H | H | Me | H | CH |
| 2-596 | 3,4-diCl-Ph | $NH_2$ | H | Me | Me | H | CH |
| 2-597 | 3,4-diCl-Ph | $NH_2$ | H | H | $NH_2$ | H | CH |
| 2-598 | 3,4-diCl-Ph | $NH_2$ | H | H | NHMe | H | CH |
| 2-599 | 3,4-diCl-Ph | $NH_2$ | H | H | $NMe_2$ | H | CH |
| 2-600 | 3,4-diCl-Ph | $NH_2$ | H | H | NHCOMe | H | CH |
| 2-601 | 3,4-diCl-Ph | $NH_2$ | H | H | NHCOOMe | H | CH |
| 2-602 | 3,4-diCl-Ph | $NH_2$ | H | H | $NHSO_2Me$ | H | CH |
| 2-603 | 3,4-diCl-Ph | $NH_2$ | H | H | H | Me | CH |
| 2-604 | 3,4-diCl-Ph | $NH_2$ | H | H | H | $CF_3$ | CH |
| 2-605 | 3,4-diCl-Ph | $NH_2$ | H | H | H | $CH_2CF_3$ | CH |
| 2-606 | 3,4-diCl-Ph | $NH_2$ | H | H | H | $NH_2$ | CH |
| 2-607 | 3,4-diCl-Ph | $NH_2$ | H | H | H | NHMe | CH |
| 2-608 | 3,4-diCl-Ph | $NH_2$ | H | H | H | $NMe_2$ | CH |
| 2-609 | 3,4-diCl-Ph | $NH_2$ | H | H | H | NHCOMe | CH |
| 2-610 | 3,4-diCl-Ph | $NH_2$ | H | H | H | NHCOOMe | CH |
| 2-611 | 3,4-diCl-Ph | $NH_2$ | H | H | H | $NHSO_2Me$ | CH |
| 2-612 | 3,4-diCl-Ph | $NH_2$ | H | H | Me | Me | CH |
| 2-613 | 3,4-diCl-Ph | $NH_2$ | H | H | Me | $NH_2$ | CH |
| 2-614 | 3,4-diCl-Ph | $NH_2$ | H | H | $NH_2$ | Me | CH |
| 2-615 | 3,4-diCl-Ph | H | H | H | H | H | N |
| 2-616 | 3,4-diCl-Ph | H | $NH_2$ | H | H | H | N |
| 2-617 | 3,4-diCl-Ph | H | H | H | Me | H | N |
| 2-618 | 3,4-diCl-Ph | H | H | H | $NH_2$ | H | N |
| 2-619 | 3,4-diCl-Ph | H | H | H | NHMe | H | N |
| 2-620 | 3,4-diCl-Ph | H | H | H | $NMe_2$ | H | N |
| 2-621 | 3,4-diCl-Ph | $NH_2$ | H | H | H | H | N |
| 2-622 | 3,4-diCl-Ph | NHMe | H | H | H | H | N |
| 2-623 | 3,4-diCl-Ph | $NMe_2$ | H | H | H | H | N |
| 2-624 | 3,4-diCl-Ph | NHEt | H | H | H | H | N |
| 2-625 | 3,4-diCl-Ph | $NHPr^i$ | H | H | H | H | N |
| 2-626 | 3,4-diCl-Ph | $NHCH_2CF_3$ | H | H | H | H | N |
| 2-627 | 3,4-diCl-Ph | $NHPr^c$ | H | H | H | H | N |
| 2-628 | 3,4-diCl-Ph | NHCOMe | H | H | H | H | N |
| 2-629 | 3,4-diCl-Ph | NHCOEt | H | H | H | H | N |
| 2-630 | 3,4-diCl-Ph | NHCOOMe | H | H | H | H | N |
| 2-631 | 3,4-diCl-Ph | $NHSO_2Me$ | H | H | H | H | N |
| 2-632 | 3,4-diCl-Ph | NH(α-Me-Bn) | H | H | H | H | N |
| 2-633 | 3,4-diCl-Ph | NHCOPh | H | H | H | H | N |
| 2-634 | 3,4-diCl-Ph | $NH_2$ | H | H | Me | H | N |
| 2-635 | 3,4-diCl-Ph | $NH_2$ | H | H | $NH_2$ | H | N |
| 2-636 | 3,4-diCl-Ph | $NH_2$ | H | H | NHMe | H | N |
| 2-637 | 3,4-diCl-Ph | $NH_2$ | H | H | $NMe_2$ | H | N |
| 2-638 | 3,4-diCl-Ph | $NH_2$ | H | H | H | Me | N |
| 2-639 | 3,4-diCl-Ph | $NH_2$ | H | H | H | $NH_2$ | N |
| 2-640 | 3,4-diCl-Ph | $NH_2$ | H | H | H | NHMe | N |
| 2-641 | 3,4-diCl-Ph | $NH_2$ | H | H | H | $NMe_2$ | N |
| 2-642 | 3-Cl-4-F-Ph | H | H | H | H | H | CH |
| 2-643 | 3-Cl-4-F-Ph | Me | H | H | H | H | CH |
| 2-644 | 3-Cl-4-F-Ph | OMe | H | H | H | H | CH |
| 2-645 | 3-Cl-4-F-Ph | SMe | H | H | H | H | CH |
| 2-646 | 3-Cl-4-F-Ph | $NH_2$ | H | H | H | H | CH |
| 2-647 | 3-Cl-4-F-Ph | NHMe | H | H | H | H | CH |
| 2-648 | 3-Cl-4-F-Ph | $NMe_2$ | H | H | H | H | CH |
| 2-649 | 3-Cl-4-F-Ph | NHEt | H | H | H | H | CH |
| 2-650 | 3-Cl-4-F-Ph | $NHPr^i$ | H | H | H | H | CH |
| 2-651 | 3-Cl-4-F-Ph | $NHCH_2CF_3$ | H | H | H | H | CH |
| 2-652 | 3-Cl-4-F-Ph | $NHPr^c$ | H | H | H | H | CH |
| 2-653 | 3-Cl-4-F-Ph | NHCOMe | H | H | H | H | CH |

TABLE 2-continued

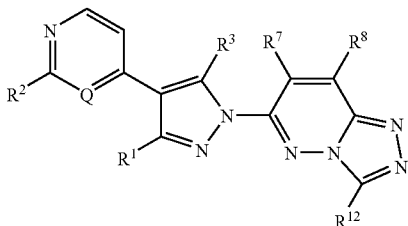

| Compound No | R¹ | R² | R³ | R⁷ | R⁸ | R⁹ | Q |
|---|---|---|---|---|---|---|---|
| 2-654 | 3-Cl-4-F-Ph | NHCOOMe | H | H | H | H | CH |
| 2-655 | 3-Cl-4-F-Ph | NHSO₂Me | H | H | H | H | CH |
| 2-656 | 3-Cl-4-F-Ph | NH(α-Me-Bn) | H | H | H | H | CH |
| 2-657 | 3-Cl-4-F-Ph | NHCOPh | H | H | H | H | CH |
| 2-658 | 3-Cl-4-F-Ph | NH₂ | Me | H | H | H | CH |
| 2-659 | 3-Cl-4-F-Ph | NH₂ | NH₂ | H | H | H | CH |
| 2-660 | 3-Cl-4-F-Ph | NH₂ | H | Me | H | H | CH |
| 2-661 | 3-Cl-4-F-Ph | NH₂ | H | H | Me | H | CH |
| 2-662 | 3-Cl-4-F-Ph | NH₂ | H | Me | Me | H | CH |
| 2-663 | 3-Cl-4-F-Ph | NH₂ | H | H | NH₂ | H | CH |
| 2-664 | 3-Cl-4-F-Ph | NH₂ | H | H | NHMe | H | CH |
| 2-665 | 3-Cl-4-F-Ph | NH₂ | H | H | NMe₂ | H | CH |
| 2-666 | 3-Cl-4-F-Ph | NH₂ | H | H | H | Me | CH |
| 2-667 | 3-Cl-4-F-Ph | NH₂ | H | H | H | CF₃ | CH |
| 2-668 | 3-Cl-4-F-Ph | NH₂ | H | H | H | CH₂CF₃ | CH |
| 2-669 | 3-Cl-4-F-Ph | NH₂ | H | H | H | NH₂ | CH |
| 2-670 | 3-Cl-4-F-Ph | NH₂ | H | H | H | NHMe | CH |
| 2-671 | 3-Cl-4-F-Ph | NH₂ | H | H | H | NMe₂ | CH |
| 2-672 | 3-Cl-4-F-Ph | NH₂ | H | H | H | NHCOMe | CH |
| 2-673 | 3-Cl-4-F-Ph | NH₂ | H | H | H | NHCOOMe | CH |
| 2-674 | 3-Cl-4-F-Ph | NH₂ | H | H | H | NHSO₂Me | CH |
| 2-675 | 3-Cl-4-F-Ph | NH₂ | H | H | Me | Me | CH |
| 2-676 | 3-Cl-4-F-Ph | NH₂ | H | H | Me | NH₂ | CH |
| 2-677 | 3-Cl-4-F-Ph | NH₂ | H | H | NH₂ | Me | CH |
| 2-678 | 3-Cl-4-F-Ph | H | H | H | H | H | N |
| 2-679 | 3-Cl-4-F-Ph | NH₂ | H | H | H | H | N |
| 2-680 | 3-Cl-4-F-Ph | NHMe | H | H | H | H | N |
| 2-681 | 3-Cl-4-F-Ph | NMe₂ | H | H | H | H | N |
| 2-682 | 3-Cl-4-F-Ph | NHEt | H | H | H | H | N |
| 2-683 | 3-Cl-4-F-Ph | NEt₂ | H | H | H | H | N |
| 2-684 | 3-Cl-4-F-Ph | NHPrⁱ | H | H | H | H | N |
| 2-685 | 3-Cl-4-F-Ph | NHCH₂CF₃ | H | H | H | H | N |
| 2-686 | 3-Cl-4-F-Ph | NHPrᶜ | H | H | H | H | N |
| 2-687 | 3-Cl-4-F-Ph | NHCOMe | H | H | H | H | N |
| 2-688 | 3-Cl-4-F-Ph | NHCOOMe | H | H | H | H | N |
| 2-689 | 3-Cl-4-F-Ph | NHSO₂Me | H | H | H | H | N |
| 2-690 | 3-Cl-4-F-Ph | NH(4-F-Bn) | H | H | H | H | N |
| 2-691 | 3-Cl-4-F-Ph | NH(α-Me-Bn) | H | H | H | H | N |
| 2-692 | 3-Cl-4-F-Ph | NHCOPh | H | H | H | H | N |
| 2-693 | 3-Cl-4-F-Ph | NH₂ | H | H | Me | H | N |
| 2-694 | 3-Cl-4-F-Ph | NH₂ | H | H | NH₂ | H | N |
| 2-695 | 3-Cl-4-F-Ph | NH₂ | H | H | NHMe | H | N |
| 2-696 | 3-Cl-4-F-Ph | NH₂ | H | H | NMe₂ | H | N |
| 2-697 | 3-Cl-4-F-Ph | NH₂ | H | H | H | Me | N |
| 2-698 | 3-Cl-4-F-Ph | NH₂ | H | H | H | NH₂ | N |
| 2-699 | 3-Cl-4-F-Ph | NH₂ | H | H | H | NHMe | N |
| 2-700 | 3-Cl-4-F-Ph | NH₂ | H | H | H | NMe₂ | N |
| 2-701 | 4-Cl-3-F-Ph | H | H | H | H | H | CH |
| 2-702 | 4-Cl-3-F-Ph | Me | H | H | H | H | CH |
| 2-703 | 4-Cl-3-F-Ph | OMe | H | H | H | H | CH |
| 2-704 | 4-Cl-3-F-Ph | SMe | H | H | H | H | CH |
| 2-705 | 4-Cl-3-F-Ph | NH₂ | H | H | H | H | CH |
| 2-706 | 4-Cl-3-F-Ph | NHMe | H | H | H | H | CH |
| 2-707 | 4-Cl-3-F-Ph | NMe₂ | H | H | H | H | CH |
| 2-708 | 4-Cl-3-F-Ph | NHEt | H | H | H | H | CH |
| 2-709 | 4-Cl-3-F-Ph | NHPrⁱ | H | H | H | H | CH |
| 2-710 | 4-Cl-3-F-Ph | NHCH₂CF₃ | H | H | H | H | CH |
| 2-711 | 4-Cl-3-F-Ph | NHPrᶜ | H | H | H | H | CH |
| 2-712 | 4-Cl-3-F-Ph | NHCOMe | H | H | H | H | CH |
| 2-713 | 4-Cl-3-F-Ph | NHCOOMe | H | H | H | H | CH |
| 2-714 | 4-Cl-3-F-Ph | NHSO₂Me | H | H | H | H | CH |
| 2-715 | 4-Cl-3-F-Ph | NH(α-Me-Bn) | H | H | H | H | CH |
| 2-716 | 4-Cl-3-F-Ph | NHCOPh | H | H | H | H | CH |
| 2-717 | 4-Cl-3-F-Ph | NH₂ | Me | H | H | H | CH |

TABLE 2-continued

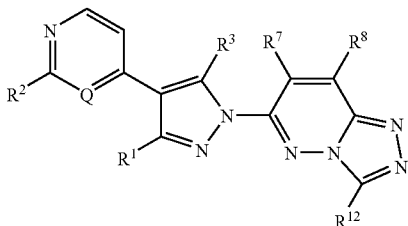

| Compound No | R¹ | R² | R³ | R⁷ | R⁸ | R⁹ | Q |
|---|---|---|---|---|---|---|---|
| 2-718 | 4-Cl-3-F-Ph | NH₂ | NH₂ | H | H | H | CH |
| 2-719 | 4-Cl-3-F-Ph | NH₂ | H | Me | H | H | CH |
| 2-720 | 4-Cl-3-F-Ph | NH₂ | H | H | Me | H | CH |
| 2-721 | 4-Cl-3-F-Ph | NH₂ | H | Me | Me | H | CH |
| 2-722 | 4-Cl-3-F-Ph | NH₂ | H | H | NH₂ | H | CH |
| 2-723 | 4-Cl-3-F-Ph | NH₂ | H | H | NHMe | H | CH |
| 2-724 | 4-Cl-3-F-Ph | NH₂ | H | H | NMe₂ | H | CH |
| 2-725 | 4-Cl-3-F-Ph | NH₂ | H | H | H | Me | CH |
| 2-726 | 4-Cl-3-F-Ph | NH₂ | H | H | H | CF₃ | CH |
| 2-727 | 4-Cl-3-F-Ph | NH₂ | H | H | H | CH₂CF₃ | CH |
| 2-728 | 4-Cl-3-F-Ph | NH₂ | H | H | H | NH₂ | CH |
| 2-729 | 4-Cl-3-F-Ph | NH₂ | H | H | H | NHMe | CH |
| 2-730 | 4-Cl-3-F-Ph | NH₂ | H | H | H | NMe₂ | CH |
| 2-731 | 4-Cl-3-F-Ph | NH₂ | H | H | H | NHCOMe | CH |
| 2-732 | 4-Cl-3-F-Ph | NH₂ | H | H | H | NHCOOMe | CH |
| 2-733 | 4-Cl-3-F-Ph | NH₂ | H | H | H | NHSO₂Me | CH |
| 2-734 | 4-Cl-3-F-Ph | NH₂ | H | H | Me | Me | CH |
| 2-735 | 4-Cl-3-F-Ph | NH₂ | H | H | Me | NH₂ | CH |
| 2-736 | 4-Cl-3-F-Ph | NH₂ | H | H | NH₂ | Me | CH |
| 2-737 | 4-Cl-3-F-Ph | H | H | H | H | H | N |
| 2-738 | 4-Cl-3-F-Ph | NH₂ | H | H | H | H | N |
| 2-739 | 4-Cl-3-F-Ph | NHMe | H | H | H | H | N |
| 2-740 | 4-Cl-3-F-Ph | NMe₂ | H | H | H | H | N |
| 2-741 | 4-Cl-3-F-Ph | NHEt | H | H | H | H | N |
| 2-742 | 4-Cl-3-F-Ph | NEt₂ | H | H | H | H | N |
| 2-743 | 4-Cl-3-F-Ph | NHPrⁱ | H | H | H | H | N |
| 2-744 | 4-Cl-3-F-Ph | NHCH₂CF₃ | H | H | H | H | N |
| 2-745 | 4-Cl-3-F-Ph | NHPrᶜ | H | H | H | H | N |
| 2-746 | 4-Cl-3-F-Ph | NHCOMe | H | H | H | H | N |
| 2-747 | 4-Cl-3-F-Ph | NHCOOMe | H | H | H | H | N |
| 2-748 | 4-Cl-3-F-Ph | NHSO₂Me | H | H | H | H | N |
| 2-749 | 4-Cl-3-F-Ph | NH(4-F-Bn) | H | H | H | H | N |
| 2-750 | 4-Cl-3-F-Ph | NH(α-Me-Bn) | H | H | H | H | N |
| 2-751 | 4-Cl-3-F-Ph | NHCOPh | H | H | H | H | N |
| 2-752 | 4-Cl-3-F-Ph | NH₂ | H | H | Me | H | N |
| 2-753 | 4-Cl-3-F-Ph | NH₂ | H | H | Me | H | N |
| 2-753 | 4-Cl-3-F-Ph | NH₂ | H | H | NH₂ | H | N |
| 2-754 | 4-Cl-3-F-Ph | NH₂ | H | H | NHMe | H | N |
| 2-755 | 4-Cl-3-F-Ph | NH₂ | H | H | NMe₂ | H | N |
| 2-756 | 4-Cl-3-F-Ph | NH₂ | H | H | H | Me | N |
| 2-757 | 4-Cl-3-F-Ph | NH₂ | H | H | H | NH₂ | N |
| 2-758 | 4-Cl-3-F-Ph | NH₂ | H | H | H | NHMe | N |
| 2-759 | 4-Cl-3-F-Ph | NH₂ | H | H | H | NMe₂ | N |
| 2-760 | 3-CF₃-Ph | H | H | H | H | H | CH |
| 2-761 | 3-CF₃-Ph | Me | H | H | H | H | CH |
| 2-762 | 3-CF₃-Ph | OMe | H | H | H | H | CH |
| 2-763 | 3-CF₃-Ph | SMe | H | H | H | H | CH |
| 2-764 | 3-CF₃-Ph | NH₂ | H | H | H | H | CH |
| 2-765 | 3-CF₃-Ph | NHMe | H | H | H | H | CH |
| 2-766 | 3-CF₃-Ph | NMe₂ | H | H | H | H | CH |
| 2-767 | 3-CF₃-Ph | NHEt | H | H | H | H | CH |
| 2-768 | 3-CF₃-Ph | NHPrⁱ | H | H | H | H | CH |
| 2-769 | 3-CF₃-Ph | NHCH₂CF₃ | H | H | H | H | CH |
| 2-770 | 3-CF₃-Ph | NHPrᶜ | H | H | H | H | CH |
| 2-771 | 3-CF₃-Ph | NHCOMe | H | H | H | H | CH |
| 2-772 | 3-CF₃-Ph | NHCOOMe | H | H | H | H | CH |
| 2-773 | 3-CF₃-Ph | NHSO₂Me | H | H | H | H | CH |
| 2-774 | 3-CF₃-Ph | NH(α-Me-Bn) | H | H | H | H | CH |
| 2-775 | 3-CF₃-Ph | NHCOPh | H | H | H | H | CH |
| 2-776 | 3-CF₃-Ph | NH₂ | Me | H | H | H | CH |
| 2-777 | 3-CF₃-Ph | NH₂ | NH₂ | H | H | H | CH |
| 2-778 | 3-CF₃-Ph | NH₂ | H | Me | H | H | CH |
| 2-779 | 3-CF₃-Ph | NH₂ | H | H | Me | H | CH |
| 2-780 | 3-CF₃-Ph | NH₂ | H | Me | Me | H | CH |

TABLE 2-continued

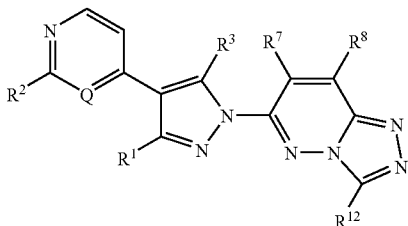

| Compound No | $R^1$ | $R^2$ | $R^3$ | $R^7$ | $R^8$ | $R^9$ | Q |
| --- | --- | --- | --- | --- | --- | --- | --- |
| 2-781 | 3-CF$_3$-Ph | NH$_2$ | H | H | NH$_2$ | H | CH |
| 2-782 | 3-CF$_3$-Ph | NH$_2$ | H | H | NHMe | H | CH |
| 2-783 | 3-CF$_3$-Ph | NH$_2$ | H | H | NMe$_2$ | H | CH |
| 2-784 | 3-CF$_3$-Ph | NH$_2$ | H | H | H | Me | CH |
| 2-785 | 3-CF$_3$-Ph | NH$_2$ | H | H | H | CF$_3$ | CH |
| 2-786 | 3-CF$_3$-Ph | NH$_2$ | H | H | H | CH$_2$CF$_3$ | CH |
| 2-787 | 3-CF$_3$-Ph | NH$_2$ | H | H | H | NH$_2$ | CH |
| 2-788 | 3-CF$_3$-Ph | NH$_2$ | H | H | H | NHMe | CH |
| 2-789 | 3-CF$_3$-Ph | NH$_2$ | H | H | H | NMe$_2$ | CH |
| 2-790 | 3-CF$_3$-Ph | NH$_2$ | H | H | H | NHCOMe | CH |
| 2-791 | 3-CF$_3$-Ph | NH$_2$ | H | H | H | NHCOOMe | CH |
| 2-792 | 3-CF$_3$-Ph | NH$_2$ | H | H | H | NHSO$_2$Me | CH |
| 2-793 | 3-CF$_3$-Ph | NH$_2$ | H | H | Me | Me | CH |
| 2-794 | 3-CF$_3$-Ph | NH$_2$ | H | H | Me | NH$_2$ | CH |
| 2-795 | 3-CF$_3$-Ph | NH$_2$ | H | H | NH$_2$ | Me | CH |
| 2-796 | 3-CF$_3$-Ph | H | H | H | H | H | N |
| 2-797 | 3-CF$_3$-Ph | NH$_2$ | H | H | H | H | N |
| 2-798 | 3-CF$_3$-Ph | NHMe | H | H | H | H | N |
| 2-799 | 3-CF$_3$-Ph | NMe$_2$ | H | H | H | H | N |
| 2-800 | 3-CF$_3$-Ph | NHEt | H | H | H | H | N |
| 2-801 | 3-CF$_3$-Ph | NEt$_2$ | H | H | H | H | N |
| 2-802 | 3-CF$_3$-Ph | NHPr$^i$ | H | H | H | H | N |
| 2-803 | 3-CF$_3$-Ph | NHCH$_2$CF$_3$ | H | H | H | H | N |
| 2-804 | 3-CF$_3$-Ph | NHPr$^c$ | H | H | H | H | N |
| 2-805 | 3-CF$_3$-Ph | NHCOMe | H | H | H | H | N |
| 2-806 | 3-CF$_3$-Ph | NHCOOMe | H | H | H | H | N |
| 2-807 | 3-CF$_3$-Ph | NHSO$_2$Me | H | H | H | H | N |
| 2-808 | 3-CF$_3$-Ph | NH(4-F-Bn) | H | H | H | H | N |
| 2-809 | 3-CF$_3$-Ph | NH(α-Me-Bn) | H | H | H | H | N |
| 2-810 | 3-CF$_3$-Ph | NHCOPh | H | H | H | H | N |
| 2-811 | 3-CF$_3$-Ph | NH$_2$ | H | H | Me | H | N |
| 2-812 | 3-CF$_3$-Ph | NH$_2$ | H | H | NH$_2$ | H | N |
| 2-813 | 3-CF$_3$-Ph | NH$_2$ | H | H | NHMe | H | N |
| 2-814 | 3-CF$_3$-Ph | NH$_2$ | H | H | NMe$_2$ | H | N |
| 2-815 | 3-CF$_3$-Ph | NH$_2$ | H | H | H | Me | N |
| 2-816 | 3-CF$_3$-Ph | NH$_2$ | H | H | H | NH$_2$ | N |
| 2-817 | 3-CF$_3$-Ph | NH$_2$ | H | H | H | NHMe | N |
| 2-818 | 3-CF$_3$-Ph | NH$_2$ | H | H | H | NMe$_2$ | N |
| 2-819 | 2-F-Ph | H | H | H | H | H | CH |
| 2-820 | 2-F-Ph | H | NH$_2$ | H | H | H | CH |
| 2-821 | 2-F-Ph | H | H | H | Me | H | CH |
| 2-822 | 2-F-Ph | H | H | H | NH$_2$ | H | CH |
| 2-823 | 2-F-Ph | H | H | H | NHMe | H | CH |
| 2-824 | 2-F-Ph | H | H | H | NMe$_2$ | H | CH |
| 2-825 | 2-F-Ph | H | H | H | H | Me | CH |
| 2-826 | 2-F-Ph | H | H | H | H | CF$_3$ | CH |
| 2-827 | 2-F-Ph | H | H | H | H | NH$_2$ | CH |
| 2-828 | 2-F-Ph | H | H | H | H | NHMe | CH |
| 2-829 | 2-F-Ph | H | H | H | H | NMe$_2$ | CH |
| 2-830 | 2-F-Ph | H | H | H | H | NHCOMe | CH |
| 2-831 | 2-F-Ph | H | H | H | H | NHCOOMe | CH |
| 2-832 | 2-F-Ph | H | H | H | H | NHSO$_2$Me | CH |
| 2-833 | 2-F-Ph | F | H | H | H | H | CH |
| 2-834 | 2-F-Ph | Cl | H | H | H | H | CH |
| 2-835 | 2-F-Ph | Me | H | H | H | H | CH |
| 2-836 | 2-F-Ph | OMe | H | H | H | H | CH |
| 2-837 | 2-F-Ph | SMe | H | H | H | H | CH |
| 2-838 | 2-F-Ph | NH$_2$ | H | H | H | H | CH |
| 2-839 | 2-F-Ph | NHMe | H | H | H | H | CH |
| 2-840 | 2-F-Ph | NMe$_2$ | H | H | H | H | CH |
| 2-841 | 2-F-Ph | NHEt | H | H | H | H | CH |
| 2-842 | 2-F-Ph | NEt$_2$ | H | H | H | H | CH |
| 2-843 | 2-F-Ph | NHPr$^i$ | H | H | H | H | CH |
| 2-844 | 2-F-Ph | NHCH$_2$CF$_3$ | H | H | H | H | CH |

TABLE 2-continued

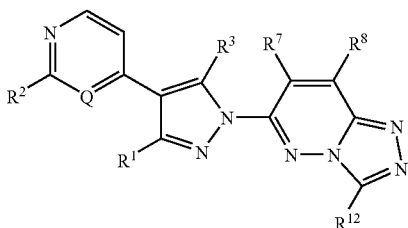

| Compound No | R¹ | R² | R³ | R⁷ | R⁸ | R⁹ | Q |
|---|---|---|---|---|---|---|---|
| 2-845 | 2-F-Ph | NHPr$^c$ | H | H | H | H | CH |
| 2-846 | 2-F-Ph | NHCHO | H | H | H | H | CH |
| 2-847 | 2-F-Ph | NHCOMe | H | H | H | H | CH |
| 2-848 | 2-F-Ph | NHCOEt | H | H | H | H | CH |
| 2-849 | 2-F-Ph | NHCOOMe | H | H | H | H | CH |
| 2-850 | 2-F-Ph | NHCOOEt | H | H | H | H | CH |
| 2-851 | 2-F-Ph | NHSO$_2$Me | H | H | H | H | CH |
| 2-852 | 2-F-Ph | NHSO$_2$Et | H | H | H | H | CH |
| 2-853 | 2-F-Ph | NH(4-F-Bn) | H | H | H | H | CH |
| 2-854 | 2-F-Ph | NH(α-Me-Bn) | H | H | H | H | CH |
| 2-855 | 2-F-Ph | NHCOPh | H | H | H | H | CH |
| 2-856 | 2-F-Ph | NH$_2$ | Me | H | H | H | CH |
| 2-857 | 2-F-Ph | NH$_2$ | NH$_2$ | H | H | H | CH |
| 2-858 | 2-F-Ph | NH$_2$ | H | Me | H | H | CH |
| 2-859 | 2-F-Ph | NH$_2$ | H | H | Me | H | CH |
| 2-860 | 2-F-Ph | NH$_2$ | H | Me | Me | H | CH |
| 2-861 | 2-F-Ph | NH$_2$ | H | H | NH$_2$ | H | CH |
| 2-862 | 2-F-Ph | NH$_2$ | H | H | NHMe | H | CH |
| 2-863 | 2-F-Ph | NH$_2$ | H | H | NMe$_2$ | H | CH |
| 2-864 | 2-F-Ph | NH$_2$ | H | H | NHCOMe | H | CH |
| 2-865 | 2-F-Ph | NH$_2$ | H | H | NHCOOMe | H | CH |
| 2-866 | 2-F-Ph | NH$_2$ | H | H | NHSO$_2$Me | H | CH |
| 2-867 | 2-F-Ph | NH$_2$ | H | H | H | Me | CH |
| 2-868 | 2-F-Ph | NH$_2$ | H | H | H | CF$_3$ | CH |
| 2-869 | 2-F-Ph | NH$_2$ | H | H | H | CH$_2$CF$_3$ | CH |
| 2-870 | 2-F-Ph | NH$_2$ | H | H | H | NH$_2$ | CH |
| 2-871 | 2-F-Ph | NH$_2$ | H | H | H | NHMe | CH |
| 2-872 | 2-F-Ph | NH$_2$ | H | H | H | NMe$_2$ | CH |
| 2-873 | 2-F-Ph | NH$_2$ | H | H | H | NHCOMe | CH |
| 2-874 | 2-F-Ph | NH$_2$ | H | H | H | NHCOOMe | CH |
| 2-875 | 2-F-Ph | NH$_2$ | H | H | H | NHSO$_2$Me | CH |
| 2-876 | 2-F-Ph | NH$_2$ | H | H | Me | Me | CH |
| 2-877 | 2-F-Ph | NH$_2$ | H | H | Me | NH$_2$ | CH |
| 2-878 | 2-F-Ph | NH$_2$ | H | H | NH$_2$ | Me | CH |
| 2-879 | 2-F-Ph | H | H | H | H | H | N |
| 2-880 | 2-F-Ph | H | NH$_2$ | H | H | H | N |
| 2-881 | 2-F-Ph | H | H | H | Me | H | N |
| 2-882 | 2-F-Ph | H | H | H | NH$_2$ | H | N |
| 2-883 | 2-F-Ph | H | H | H | NHMe | H | N |
| 2-884 | 2-F-Ph | H | H | H | NMe$_2$ | H | N |
| 2-885 | 2-F-Ph | NH$_2$ | H | H | H | H | N |
| 2-886 | 2-F-Ph | NHMe | H | H | H | H | N |
| 2-887 | 2-F-Ph | NMe$_2$ | H | H | H | H | N |
| 2-888 | 2-F-Ph | NHEt | H | H | H | H | N |
| 2-889 | 2-F-Ph | NHPr$^i$ | H | H | H | H | N |
| 2-890 | 2-F-Ph | NHCH$_2$CF$_3$ | H | H | H | H | N |
| 2-891 | 2-F-Ph | NHPr$^c$ | H | H | H | H | N |
| 2-892 | 2-F-Ph | NHCOMe | H | H | H | H | N |
| 2-893 | 2-F-Ph | NHCOEt | H | H | H | H | N |
| 2-894 | 2-F-Ph | NHCOOMe | H | H | H | H | N |
| 2-895 | 2-F-Ph | NHSO$_2$Me | H | H | H | H | N |
| 2-896 | 2-F-Ph | NH(α-Me-Bn) | H | H | H | H | N |
| 2-897 | 2-F-Ph | NHCOPh | H | H | H | H | N |
| 2-898 | 2-F-Ph | NH$_2$ | H | H | Me | H | N |
| 2-899 | 2-F-Ph | NH$_2$ | H | H | NH$_2$ | H | N |
| 2-900 | 2-F-Ph | NH$_2$ | H | H | NHMe | H | N |
| 2-901 | 2-F-Ph | NH$_2$ | H | H | NMe$_2$ | H | N |
| 2-902 | 2-F-Ph | NH$_2$ | H | H | H | Me | N |
| 2-903 | 2-F-Ph | NH$_2$ | H | H | H | NH$_2$ | N |
| 2-904 | 2-F-Ph | NH$_2$ | H | H | H | NHMe | N |
| 2-905 | 2-F-Ph | NH$_2$ | H | H | H | NMe$_2$ | N |
| 2-906 | 2,4-diF-Ph | H | H | H | H | H | CH |
| 2-907 | 2,4-diF-Ph | Me | H | H | H | H | CH |
| 2-908 | 2,4-diF-Ph | OMe | H | H | H | H | CH |

TABLE 2-continued

| Compound No | R¹ | R² | R³ | R⁷ | R⁸ | R⁹ | Q |
|---|---|---|---|---|---|---|---|
| 2-909 | 2,4-diF-Ph | SMe | H | H | H | H | CH |
| 2-910 | 2,4-diF-Ph | NH₂ | H | H | H | H | CH |
| 2-911 | 2,4-diF-Ph | NHMe | H | H | H | H | CH |
| 2-912 | 2,4-diF-Ph | NMe₂ | H | H | H | H | CH |
| 2-913 | 2,4-diF-Ph | NHEt | H | H | H | H | CH |
| 2-914 | 2,4-diF-Ph | NHPrⁱ | H | H | H | H | CH |
| 2-915 | 2,4-diF-Ph | NHCH₂CF₃ | H | H | H | H | CH |
| 2-916 | 2,4-diF-Ph | NHPrᶜ | H | H | H | H | CH |
| 2-917 | 2,4-diF-Ph | NHCOMe | H | H | H | H | CH |
| 2-918 | 2,4-diF-Ph | NHCOOMe | H | H | H | H | CH |
| 2-919 | 2,4-diF-Ph | NHSO₂Me | H | H | H | H | CH |
| 2-920 | 2,4-diF-Ph | NH(α-Me-Bn) | H | H | H | H | CH |
| 2-921 | 2,4-diF-Ph | NHCOPh | H | H | H | H | CH |
| 2-922 | 2,4-diF-Ph | NH₂ | Me | H | H | H | CH |
| 2-923 | 2,4-diF-Ph | NH₂ | NH₂ | H | H | H | CH |
| 2-924 | 2,4-diF-Ph | NH₂ | H | Me | H | H | CH |
| 2-925 | 2,4-diF-Ph | NH₂ | H | H | Me | H | CH |
| 2-926 | 2,4-diF-Ph | NH₂ | H | Me | Me | H | CH |
| 2-927 | 2,4-diF-Ph | NH₂ | H | H | NH₂ | H | CH |
| 2-928 | 2,4-diF-Ph | NH₂ | H | H | NHMe | H | CH |
| 2-929 | 2,4-diF-Ph | NH₂ | H | H | NMe₂ | H | CH |
| 2-930 | 2,4-diF-Ph | NH₂ | H | H | H | Me | CH |
| 2-931 | 2,4-diF-Ph | NH₂ | H | H | H | CF₃ | CH |
| 2-932 | 2,4-diF-Ph | NH₂ | H | H | H | CH₂CF₃ | CH |
| 2-933 | 2,4-diF-Ph | NH₂ | H | H | H | NH₂ | CH |
| 2-934 | 2,4-diF-Ph | NH₂ | H | H | H | NHMe | CH |
| 2-935 | 2,4-diF-Ph | NH₂ | H | H | H | NMe₂ | CH |
| 2-936 | 2,4-diF-Ph | NH₂ | H | H | H | NHCOMe | CH |
| 2-937 | 2,4-diF-Ph | NH₂ | H | H | H | NHCOOMe | CH |
| 2-938 | 2,4-diF-Ph | NH₂ | H | H | H | NHSO₂Me | CH |
| 2-939 | 2,4-diF-Ph | NH₂ | H | H | Me | Me | CH |
| 2-940 | 2,4-diF-Ph | NH₂ | H | H | Me | NH₂ | CH |
| 2-941 | 2,4-diF-Ph | NH₂ | H | H | NH₂ | Me | CH |
| 2-942 | 2,4-diF-Ph | H | H | H | H | H | N |
| 2-943 | 2,4-diF-Ph | NH₂ | H | H | H | H | N |
| 2-944 | 2,4-diF-Ph | NHMe | H | H | H | H | N |
| 2-945 | 2,4-diF-Ph | NMe₂ | H | H | H | H | N |
| 2-946 | 2,4-diF-Ph | NHEt | H | H | H | H | N |
| 2-947 | 2,4-diF-Ph | NEt₂ | H | H | H | H | N |
| 2-948 | 2,4-diF-Ph | NHPrⁱ | H | H | H | H | N |
| 2-949 | 2,4-diF-Ph | NHCH₂CF₃ | H | H | H | H | N |
| 2-950 | 2,4-diF-Ph | NHPrᶜ | H | H | H | H | N |
| 2-951 | 2,4-diF-Ph | NHCOMe | H | H | H | H | N |
| 2-952 | 2,4-diF-Ph | NHCOOMe | H | H | H | H | N |
| 2-953 | 2,4-diF-Ph | NHSO₂Me | H | H | H | H | N |
| 2-954 | 2,4-diF-Ph | NH(4-F-Bn) | H | H | H | H | N |
| 2-955 | 2,4-diF-Ph | NH(α-Me-Bn) | H | H | H | H | N |
| 2-956 | 2,4-diF-Ph | NHCOPh | H | H | H | H | N |
| 2-957 | 2,4-diF-Ph | NH₂ | H | H | Me | H | N |
| 2-958 | 2,4-diF-Ph | NH₂ | H | H | NH₂ | H | N |
| 2-959 | 2,4-diF-Ph | NH₂ | H | H | NHMe | H | N |
| 2-960 | 2,4-diF-Ph | NH | H | H | NMe₂ | H | N |
| 2-961 | 2,4-diF-Ph | NH₂ | H | H | H | Me | N |
| 2-962 | 2,4-diF-Ph | NH₂ | H | H | H | NH₂ | N |
| 2-963 | 2,4-diF-Ph | NH₂ | H | H | H | NHMe | N |
| 2-964 | 2,4-diF-Ph | NH₂ | H | H | H | NMe₂ | N |
| 2-965 | Ph | NHCOPrᶜ | H | H | H | H | CH |
| 2-966 | Ph | N(Me)COPrᶜ | H | H | H | H | CH |
| 2-967 | Ph | NHCOPrᶜ | H | H | H | H | N |
| 2-968 | Ph | NHCOPnᶜ | H | H | H | H | CH |
| 2-969 | Ph | NHCOPnᶜ | H | H | H | H | N |
| 2-970 | 4-F-Ph | NHCOPrᶜ | H | H | H | H | CH |
| 2-971 | 4-F-Ph | N(Me)COPrᶜ | H | H | H | H | CH |
| 2-972 | 4-F-Ph | NHCOPrᶜ | H | H | H | H | N |

TABLE 2-continued

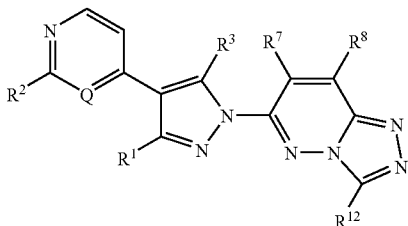

| Compound No | R¹ | R² | R³ | R⁷ | R⁸ | R⁹ | Q |
|---|---|---|---|---|---|---|---|
| 2-973 | 4-F-Ph | N(Me)COPr$^c$ | H | H | H | H | N |
| 2-974 | 4-F-Ph | NHCOPn$^c$ | H | H | H | H | CH |
| 2-975 | 4-F-Ph | N(Me)COPn$^c$ | H | H | H | H | CH |
| 2-976 | 4-F-Ph | NHCOPn$^c$ | H | H | H | H | N |
| 2-977 | 4-F-Ph | NHCOHx$^c$ | H | H | H | H | CH |
| 2-978 | 4-F-Ph | NHCOHx$^c$ | H | H | H | H | N |
| 2-979 | 3-F-Ph | NHCOPr$^c$ | H | H | H | H | CH |
| 2-980 | 3-F-Ph | N(Me)COPr$^c$ | H | H | H | H | CH |
| 2-981 | 3-F-Ph | NHCOPr$^c$ | H | H | H | H | N |
| 2-982 | 3-F-Ph | NHCOPn$^c$ | H | H | H | H | CH |
| 2-983 | 3-F-Ph | NHCOPn$^c$ | H | H | H | H | N |
| 2-984 | 4-Cl-Ph | NHCOPr$^c$ | H | H | H | H | CH |
| 2-985 | 4-Cl-Ph | N(Me)COPr$^c$ | H | H | H | H | CH |
| 2-986 | 4-Cl-Ph | NHCOPr$^c$ | H | H | H | H | N |
| 2-987 | 4-Cl-Ph | NHCOPn$^c$ | H | H | H | H | CH |
| 2-988 | 4-Cl-Ph | NHCOPn$^c$ | H | H | H | H | N |
| 2-989 | 3-Cl-Ph | NHCOPr$^c$ | H | H | H | H | CH |
| 2-990 | 3-Cl-Ph | N(Me)COPr$^c$ | H | H | H | H | CH |
| 2-991 | 3-Cl-Ph | NHCOPr$^c$ | H | H | H | H | N |
| 2-992 | 3-Cl-Ph | NHCOPn$^c$ | H | H | H | H | CH |
| 2-993 | 3-Cl-Ph | NHCOPn$^c$ | H | H | H | H | N |
| 2-994 | 3,4-diF-Ph | NHCOPr$^c$ | H | H | H | H | CH |
| 2-995 | 3,4-diF-Ph | N(Me)COPr$^c$ | H | H | H | H | CH |
| 2-996 | 3,4-diF-Ph | NHCOPr$^c$ | H | H | H | H | N |
| 2-997 | 3,4-diF-Ph | NHCOPn$^c$ | H | H | H | H | CH |
| 2-998 | 3,4-diF-Ph | NHCOPn$^c$ | H | H | H | H | N |
| 2-999 | 3,4-diCl-Ph | NHCOPr$^c$ | H | H | H | H | CH |
| 2-1000 | 3,4-diCl-Ph | N(Me)COPr$^c$ | H | H | H | H | CH |
| 2-1001 | 3,4-diCl-Ph | NHCOPr$^c$ | H | H | H | H | N |
| 2-1002 | 3,4-diCl-Ph | NHCOPn$^c$ | H | H | H | H | CH |
| 2-1003 | 3,4-diCl-Ph | NHCOPn$^c$ | H | H | H | H | N |
| 2-1004 | 3-Cl-4-F-Ph | NHCOPr$^c$ | H | H | H | H | CH |
| 2-1005 | 3-Cl-4-F-Ph | N(Me)COPr$^c$ | H | H | H | H | CH |
| 2-1006 | 3-Cl-4-F-Ph | NHCOPr$^c$ | H | H | H | H | N |
| 2-1007 | 3-Cl-4-F-Ph | NHCOPn$^c$ | H | H | H | H | CH |
| 2-1008 | 3-Cl-4-F-Ph | NHCOPn$^c$ | H | H | H | H | N |
| 2-1009 | 4-Cl-3-F-Ph | NHCOPr$^c$ | H | H | H | H | CH |
| 2-1010 | 4-Cl-3-F-Ph | N(Me)COPr$^c$ | H | H | H | H | CH |
| 2-1011 | 4-Cl-3-F-Ph | NHCOPr$^c$ | H | H | H | H | N |
| 2-1012 | 4-Cl-3-F-Ph | NHCOPn$^c$ | H | H | H | H | CH |
| 2-1013 | 4-Cl-3-F-Ph | NHCOPn$^c$ | H | H | H | H | N |
| 2-1014 | 3-CF$_3$-Ph | NHCOPr$^c$ | H | H | H | H | CH |
| 2-1015 | 3-CF$_3$-Ph | NHCOPr$^c$ | H | H | H | H | N |
| 2-1017 | 3-CF$_3$-Ph | NHCOPn$^c$ | H | H | H | H | CH |
| 2-1018 | 3-CF$_3$-Ph | NHCOPn$^c$ | H | H | H | H | N |
| 2-1019 | 2-F-Ph | NHCOPr$^c$ | H | H | H | H | CH |
| 2-1020 | 2-F-Ph | N(Me)COPr$^c$ | H | H | H | H | CH |
| 2-1021 | 2-F-Ph | NHCOPr$^c$ | H | H | H | H | N |
| 2-1022 | 2-F-Ph | NHCOPn$^c$ | H | H | H | H | CH |
| 2-1023 | 2-F-Ph | NHCOPn$^c$ | H | H | H | H | N |
| 2-1024 | 2,4-diF-Ph | NHCOPr$^c$ | H | H | H | H | CH |
| 2-1025 | 2,4-diF-Ph | N(Me)COPr$^c$ | H | H | H | H | CH |
| 2-1026 | 2,4-diF-Ph | NHCOPr$^c$ | H | H | H | H | N |
| 2-1027 | 2,4-diF-Ph | NHCOPn$^c$ | H | H | H | H | CH |
| 2-1028 | 2,4-diF-Ph | NHCOPn$^c$ | H | H | H | H | N |
| 2-1029 | Ph | SMe | H | H | H | H | N |
| 2-1030 | Ph | SOMe | H | H | H | H | N |
| 2-1031 | Ph | SO$_2$Me | H | H | H | H | N |
| 2-1032 | Ph | NH(4-OMe-Bn) | H | H | H | H | N |
| 2-1033 | 4-F-Ph | SMe | H | H | H | H | N |
| 2-1034 | 4-F-Ph | SOMe | H | H | H | H | N |
| 2-1035 | 4-F-Ph | SO$_2$Me | H | H | H | H | N |
| 2-1036 | 4-F-Ph | NH(4-OMe-Bn) | H | H | H | H | N |
| 2-1037 | 3-F-Ph | SMe | H | H | H | H | N |

TABLE 2-continued

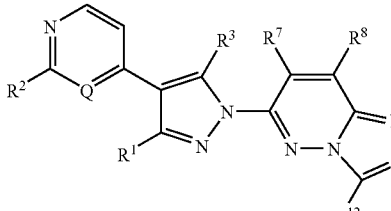

| Compound No | R$^1$ | R$^2$ | R$^3$ | R$^7$ | R$^8$ | R$^9$ | Q |
|---|---|---|---|---|---|---|---|
| 2-1038 | 3-F-Ph | SOMe | H | H | H | H | N |
| 2-1039 | 3-F-Ph | SO$_2$Me | H | H | H | H | N |
| 2-1040 | 3-F-Ph | NH(4-OMe-Bn) | H | H | H | H | N |
| 2-1041 | 4-Cl-Ph | SMe | H | H | H | H | N |
| 2-1042 | 4-Cl-Ph | SOMe | H | H | H | H | N |
| 2-1043 | 4-Cl-Ph | SO$_2$Me | H | H | H | H | N |
| 2-1044 | 4-Cl-Ph | NH(4-OMe-Bn) | H | H | H | H | N |
| 2-1045 | 3-Cl-Ph | SMe | H | H | H | H | N |
| 2-1046 | 3-Cl-Ph | SOMe | H | H | H | H | N |
| 2-1047 | 3-Cl-Ph | SO$_2$Me | H | H | H | H | N |
| 2-1048 | 3-Cl-Ph | NH(4-OMe-Bn) | H | H | H | H | N |
| 2-1049 | 3,4-diF-Ph | SMe | H | H | H | H | N |
| 2-1050 | 3,4-diF-Ph | SOMe | H | H | H | H | N |
| 2-1051 | 3,4-diF-Ph | SO$_2$Me | H | H | H | H | N |
| 2-1052 | 3,4-diF-Ph | NH(4-OMe-Bn) | H | H | H | H | N |
| 2-1053 | 3,4-diCl-Ph | SMe | H | H | H | H | N |
| 2-1054 | 3,4-diCl-Ph | SOMe | H | H | H | H | N |
| 2-1055 | 3,4-diCl-Ph | SO$_2$Me | H | H | H | H | N |
| 2-1056 | 3,4-diCl-Ph | NH(4-OMe-Bn) | H | H | H | H | N |
| 2-1057 | 3-Cl-4-F-Ph | SMe | H | H | H | H | N |
| 2-1058 | 3-Cl-4-F-Ph | SOMe | H | H | H | H | N |
| 2-1059 | 3-Cl-4-F-Ph | SO$_2$Me | H | H | H | H | N |
| 2-1060 | 3-Cl-4-F-Ph | NH(4-OMe-Bn) | H | H | H | H | N |
| 2-1061 | 4-Cl-3-F-Ph | SMe | H | H | H | H | N |
| 2-1062 | 4-Cl-3-F-Ph | SOMe | H | H | H | H | N |
| 2-1063 | 4-Cl-3-F-Ph | SO$_2$Me | H | H | H | H | N |
| 2-1064 | 4-Cl-3-F-Ph | NH(4-OMe-Bn) | H | H | H | H | N |
| 2-1065 | 3-CF$_3$-Ph | SMe | H | H | H | H | N |
| 2-1066 | 3-CF$_3$-Ph | SOMe | H | H | H | H | N |
| 2-1067 | 3-CF$_3$-Ph | SO$_2$Me | H | H | H | H | N |
| 2-1068 | 3-CF$_3$-Ph | NH(4-OMe-Bn) | H | H | H | H | N |
| 2-1069 | 2-F-Ph | SMe | H | H | H | H | N |
| 2-1070 | 2-F-Ph | SOMe | H | H | H | H | N |
| 2-1071 | 2-F-Ph | SO$_2$Me | H | H | H | H | N |
| 2-1072 | 2-F-Ph | NH(4-OMe-Bn) | H | H | H | H | N |
| 2-1073 | 2,4-diF-Ph | SMe | H | H | H | H | N |
| 2-1074 | 2,4-diF-Ph | SOMe | H | H | H | H | N |
| 2-1075 | 2,4-diF-Ph | SO$_2$Me | H | H | H | H | N |
| 2-1076 | 2,4-diF-Ph | NH(4-OMe-Bn) | H | H | H | H | N |

TABLE 3

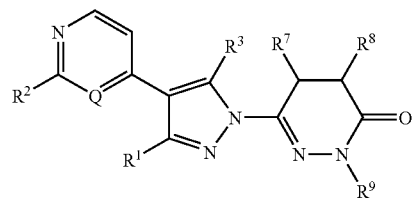

| Compound No | R$^1$ | R$^2$ | R$^3$ | R$^7$ | R$^8$ | R$^9$ | Q |
|---|---|---|---|---|---|---|---|
| 3-1 | Ph | H | H | H | H | H | CH |
| 3-2 | Ph | NH$_2$ | H | H | H | H | CH |
| 3-3 | Ph | NHMe | H | H | H | H | CH |
| 3-4 | Ph | NMe$_2$ | H | H | H | H | CH |
| 3-5 | Ph | NHEt | H | H | H | H | CH |
| 3-6 | Ph | NHCH$_2$CF$_3$ | H | H | H | H | CH |

TABLE 3-continued

| Compound No | R¹ | R² | R³ | R⁷ | R⁸ | R⁹ | Q |
|---|---|---|---|---|---|---|---|
| 3-7 | Ph | NHPr$^c$ | H | H | H | H | CH |
| 3-8 | Ph | NHCOMe | H | H | H | H | CH |
| 3-9 | Ph | NHCOOMe | H | H | H | H | CH |
| 3-10 | Ph | NHSO$_2$Me | H | H | H | H | CH |
| 3-11 | Ph | NH(4-F-Bn) | H | H | H | H | CH |
| 3-12 | Ph | NH(α-Me-Bn) | H | H | H | H | CH |
| 3-13 | Ph | NHCOPh | H | H | H | H | CH |
| 3-14 | Ph | NH$_2$ | Me | H | H | H | CH |
| 3-15 | Ph | NH$_2$ | NH$_2$ | H | H | H | CH |
| 3-16 | Ph | NH$_2$ | H | Me | H | H | CH |
| 3-17 | Ph | NH$_2$ | H | H | Me | H | CH |
| 3-18 | Ph | NH$_2$ | H | H | NH$_2$ | H | CH |
| 3-19 | Ph | NH$_2$ | H | H | NHMe | H | CH |
| 3-20 | Ph | NH$_2$ | H | H | NMe$_2$ | H | CH |
| 3-21 | Ph | NH$_2$ | H | H | NHCOMe | H | CH |
| 3-22 | Ph | NH$_2$ | H | H | NHCOOMe | H | CH |
| 3-23 | Ph | NH$_2$ | H | H | NHSO$_2$Me | H | CH |
| 3-24 | Ph | NH$_2$ | H | H | H | Me | CH |
| 3-25 | Ph | NH$_2$ | H | H | NH$_2$ | Me | CH |
| 3-26 | Ph | H | H | H | H | H | N |
| 3-27 | Ph | NH$_2$ | H | H | H | H | N |
| 3-28 | Ph | NHMe | H | H | H | H | N |
| 3-29 | Ph | NHEt | H | H | H | H | N |
| 3-30 | Ph | NHPr$^i$ | H | H | H | H | N |
| 3-31 | Ph | NHCH$_2$CF$_3$ | H | H | H | H | N |
| 3-32 | Ph | NHCOMe | H | H | H | H | N |
| 3-33 | Ph | NHCOOMe | H | H | H | H | N |
| 3-34 | Ph | NHSO$_2$Me | H | H | H | H | N |
| 3-35 | Ph | NH(α-Me-Bn) | H | H | H | H | N |
| 3-36 | Ph | NHCOPh | H | H | H | H | N |
| 3-37 | Ph | NH$_2$ | H | H | H | Me | N |
| 3-38 | 4-F-Ph | H | H | H | H | H | CH |
| 3-39 | 4-F-Ph | H | Me | H | H | H | CH |
| 3-40 | 4-F-Ph | H | Et | H | H | H | CH |
| 3-41 | 4-F-Ph | H | NH$_2$ | H | H | H | CH |
| 3-42 | 4-F-Ph | H | H | Me | H | H | CH |
| 3-43 | 4-F-Ph | H | H | Et | H | H | CH |
| 3-44 | 4-F-Ph | H | H | H | Me | H | CH |
| 3-45 | 4-F-Ph | H | H | H | Et | H | CH |
| 3-46 | 4-F-Ph | H | H | H | NH$_2$ | H | CH |
| 3-47 | 4-F-Ph | H | H | H | NHMe | H | CH |
| 3-48 | 4-F-Ph | H | H | H | NHEt | H | CH |
| 3-49 | 4-F-Ph | H | H | H | NMe$_2$ | H | CH |
| 3-50 | 4-F-Ph | H | H | H | NEt$_2$ | H | CH |
| 3-51 | 4-F-Ph | H | H | H | NHCHO | H | CH |
| 3-52 | 4-F-Ph | H | H | H | NHCOMe | H | CH |
| 3-53 | 4-F-Ph | H | H | H | NHCOEt | H | CH |
| 3-54 | 4-F-Ph | H | H | H | NHCOOMe | H | CH |
| 3-55 | 4-F-Ph | H | H | H | NHCOOEt | H | CH |
| 3-56 | 4-F-Ph | H | H | H | NHSO$_2$Me | H | CH |
| 3-57 | 4-F-Ph | H | H | H | NHSO$_2$Et | H | CH |
| 3-58 | 4-F-Ph | H | H | H | H | Me | CH |
| 3-59 | 4-F-Ph | H | H | H | H | Et | CH |
| 3-60 | 4-F-Ph | F | H | H | H | H | CH |
| 3-61 | 4-F-Ph | Cl | H | H | H | H | CH |
| 3-62 | 4-F-Ph | Me | H | H | H | H | CH |
| 3-63 | 4-F-Ph | Et | H | H | H | H | CH |
| 3-64 | 4-F-Ph | OMe | H | H | H | H | CH |
| 3-65 | 4-F-Ph | OEt | H | H | H | H | CH |
| 3-66 | 4-F-Ph | SMe | H | H | H | H | CH |
| 3-67 | 4-F-Ph | SOMe | H | H | H | H | CH |
| 3-68 | 4-F-Ph | SO$_2$Me | H | H | H | H | CH |
| 3-69 | 4-F-Ph | NH$_2$ | H | H | H | H | CH |
| 3-70 | 4-F-Ph | NHMe | H | H | H | H | CH |
| 3-71 | 4-F-Ph | NMe$_2$ | H | H | H | H | CH |

TABLE 3-continued

| Compound No | R¹ | R² | R³ | R⁷ | R⁸ | R⁹ | Q |
|---|---|---|---|---|---|---|---|
| 3-72 | 4-F-Ph | NHEt | H | H | H | H | CH |
| 3-73 | 4-F-Ph | NHPrⁱ | H | H | H | H | CH |
| 3-74 | 4-F-Ph | NHCH₂CF₃ | H | H | H | H | CH |
| 3-75 | 4-F-Ph | NHPrᶜ | H | H | H | H | CH |
| 3-76 | 4-F-Ph | NHCHO | H | H | H | H | CH |
| 3-77 | 4-F-Ph | NHCOMe | H | H | H | H | CH |
| 3-78 | 4-F-Ph | NHCOEt | H | H | H | H | CH |
| 3-79 | 4-F-Ph | NHCOPr | H | H | H | H | CH |
| 3-80 | 4-F-Ph | NHCOOMe | H | H | H | H | CH |
| 3-81 | 4-F-Ph | NHCOOEt | H | H | H | H | CH |
| 3-82 | 4-F-Ph | NHSO₂Me | H | H | H | H | CH |
| 3-83 | 4-F-Ph | NHSO₂Et | H | H | H | H | CH |
| 3-84 | 4-F-Ph | NHBn | H | H | H | H | CH |
| 3-85 | 4-F-Ph | NH(4-F-Bn) | H | H | H | H | CH |
| 3-86 | 4-F-Ph | NH(α-Me-Bn) | H | H | H | H | CH |
| 3-87 | 4-F-Ph | NHCOPh | H | H | H | H | CH |
| 3-88 | 4-F-Ph | NH₂ | Me | H | H | H | CH |
| 3-89 | 4-F-Ph | NH₂ | NH₂ | H | H | H | CH |
| 3-90 | 4-F-Ph | NH₂ | H | Me | H | H | CH |
| 3-91 | 4-F-Ph | NH₂ | H | H | Me | H | CH |
| 3-92 | 4-F-Ph | NH₂ | H | Me | Me | H | CH |
| 3-93 | 4-F-Ph | NH₂ | H | H | NH₂ | H | CH |
| 3-94 | 4-F-Ph | NH₂ | H | H | NHMe | H | CH |
| 3-95 | 4-F-Ph | NH₂ | H | H | NHEt | H | CH |
| 3-96 | 4-F-Ph | NH₂ | H | H | NMe2 | H | CH |
| 3-97 | 4-F-Ph | NH₂ | H | H | NHCOMe | H | CH |
| 3-98 | 4-F-Ph | NH₂ | H | H | NHCOOMe | H | CH |
| 3-99 | 4-F-Ph | NH₂ | H | H | NHSO₂Me | H | CH |
| 3-100 | 4-F-Ph | NH₂ | H | H | H | Me | CH |
| 3-101 | 4-F-Ph | NH₂ | H | H | Me | Me | CH |
| 3-102 | 4-F-Ph | NH₂ | H | H | NH₂ | Me | CH |
| 3-103 | 4-F-Ph | H | H | H | H | H | N |
| 3-104 | 4-F-Ph | H | Me | H | H | H | N |
| 3-105 | 4-F-Ph | H | NH₂ | H | H | H | N |
| 3-106 | 4-F-Ph | H | H | Me | H | H | N |
| 3-107 | 4-F-Ph | H | H | H | Me | H | N |
| 3-108 | 4-F-Ph | H | H | H | NH₂ | H | N |
| 3-109 | 4-F-Ph | H | H | H | NHMe | H | N |
| 3-110 | 4-F-Ph | H | H | H | NMe₂ | H | N |
| 3-111 | 4-F-Ph | H | H | H | NHCOMe | H | N |
| 3-112 | 4-F-Ph | H | H | H | NHCOOMe | H | N |
| 3-113 | 4-F-Ph | H | H | H | NHSO₂Me | H | N |
| 3-114 | 4-F-Ph | H | H | H | H | Me | N |
| 3-115 | 4-F-Ph | NH₂ | H | H | H | H | N |
| 3-116 | 4-F-Ph | NHMe | H | H | H | H | N |
| 3-117 | 4-F-Ph | NMe₂ | H | H | H | H | N |
| 3-118 | 4-F-Ph | NHEt | H | H | H | H | N |
| 3-119 | 4-F-Ph | NHPrⁱ | H | H | H | H | N |
| 3-120 | 4-F-Ph | NHCH₂CF₃ | H | H | H | H | N |
| 3-121 | 4-F-Ph | NHPrᶜ | H | H | H | H | N |
| 3-122 | 4-F-Ph | NHCOMe | H | H | H | H | N |
| 3-123 | 4-F-Ph | NHCOOMe | H | H | H | H | N |
| 3-124 | 4-F-Ph | NHSO₂Me | H | H | H | H | N |
| 3-125 | 4-F-Ph | NH(4-F-Bn) | H | H | H | H | N |
| 3-126 | 4-F-Ph | NH(α-Me-Bn) | H | H | H | H | N |
| 3-127 | 4-F-Ph | NHCOPh | H | H | H | H | N |
| 3-128 | 4-F-Ph | NH₂ | Me | H | H | H | N |
| 3-129 | 4-F-Ph | NH₂ | H | Me | H | H | N |
| 3-130 | 4-F-Ph | NH₂ | H | H | Me | H | N |
| 3-131 | 4-F-Ph | NH₂ | H | H | NH₂ | H | N |
| 3-132 | 4-F-Ph | NH₂ | H | H | H | Me | N |
| 3-133 | 3-F-Ph | H | H | H | H | H | CH |
| 3-134 | 3-F-Ph | H | Me | H | H | H | CH |
| 3-135 | 3-F-Ph | H | NH₂ | H | H | H | CH |
| 3-136 | 3-F-Ph | H | H | Me | H | H | CH |

TABLE 3-continued

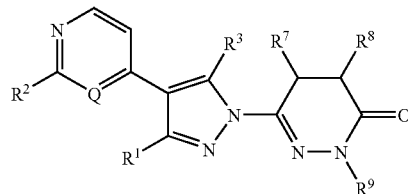

| Compound No | $R^1$ | $R^2$ | $R^3$ | $R^7$ | $R^8$ | $R^9$ | Q |
|---|---|---|---|---|---|---|---|
| 3-137 | 3-F-Ph | H | H | H | Me | H | CH |
| 3-138 | 3-F-Ph | H | H | H | $NH_2$ | H | CH |
| 3-139 | 3-F-Ph | H | H | H | NHMe | H | CH |
| 3-140 | 3-F-Ph | H | H | H | NHCOMe | H | CH |
| 3-141 | 3-F-Ph | H | H | H | NHCOOMe | H | CH |
| 3-142 | 3-F-Ph | H | H | H | $NHSO_2Me$ | H | CH |
| 3-143 | 3-F-Ph | H | H | H | H | Me | CH |
| 3-144 | 3-F-Ph | Me | H | H | H | H | CH |
| 3-145 | 3-F-Ph | OMe | H | H | H | H | CH |
| 3-146 | 3-F-Ph | SMe | H | H | H | H | CH |
| 3-147 | 3-F-Ph | SOMe | H | H | H | H | CH |
| 3-148 | 3-F-Ph | $SO_2Me$ | H | H | H | H | CH |
| 3-149 | 3-F-Ph | $NH_2$ | H | H | H | H | CH |
| 3-150 | 3-F-Ph | NHMe | H | H | H | H | CH |
| 3-151 | 3-F-Ph | $NMe_2$ | H | H | H | H | CH |
| 3-152 | 3-F-Ph | NHEt | H | H | H | H | CH |
| 3-153 | 3-F-Ph | $NHPr^i$ | H | H | H | H | CH |
| 3-154 | 3-F-Ph | $NHCH_2CF_3$ | H | H | H | H | CH |
| 3-155 | 3-F-Ph | $NHPr^c$ | H | H | H | H | CH |
| 3-156 | 3-F-Ph | NHCOMe | H | H | H | H | CH |
| 3-157 | 3-F-Ph | NHCOOMe | H | H | H | H | CH |
| 3-158 | 3-F-Ph | $NHSO_2Me$ | H | H | H | H | CH |
| 3-159 | 3-F-Ph | NH(4-F-Bn) | H | H | H | H | CH |
| 3-160 | 3-F-Ph | NH (α-Me-Bn) | H | H | H | H | CH |
| 3-161 | 3-F-Ph | NHCOPh | H | H | H | H | CH |
| 3-162 | 3-F-Ph | $NH_2$ | Me | H | H | H | CH |
| 3-163 | 3-F-Ph | $NH_2$ | $NH_2$ | H | H | H | CH |
| 3-164 | 3-F-Ph | $NH_2$ | H | Me | H | H | CH |
| 3-165 | 3-F-Ph | $NH_2$ | H | H | Me | H | CH |
| 3-166 | 3-F-Ph | $NH_2$ | H | Me | Me | H | CH |
| 3-167 | 3-F-Ph | $NH_2$ | H | H | $NH_2$ | H | CH |
| 3-168 | 3-F-Ph | $NH_2$ | H | H | NHMe | H | CH |
| 3-169 | 3-F-Ph | $NH_2$ | H | H | $NMe_2$ | H | CH |
| 3-170 | 3-F-Ph | $NH_2$ | H | H | NHCOMe | H | CH |
| 3-171 | 3-F-Ph | $NH_2$ | H | H | NHCOOMe | H | CH |
| 3-172 | 3-F-Ph | $NH_2$ | H | H | $NHSO_2Me$ | H | CH |
| 3-173 | 3-F-Ph | $NH_2$ | H | H | H | Me | CH |
| 3-174 | 3-F-Ph | $NH_2$ | H | H | Me | Me | CH |
| 3-175 | 3-F-Ph | $NH_2$ | H | H | $NH_2$ | Me | CH |
| 3-176 | 3-F-Ph | H | H | H | H | H | N |
| 3-177 | 3-F-Ph | H | $NH_2$ | H | H | H | N |
| 3-178 | 3-F-Ph | H | H | H | Me | H | N |
| 3-179 | 3-F-Ph | H | H | H | $NH_2$ | H | N |
| 3-180 | 3-F-Ph | H | H | H | H | Me | N |
| 3-181 | 3-F-Ph | $NH_2$ | H | H | H | H | N |
| 3-182 | 3-F-Ph | NHMe | H | H | H | H | N |
| 3-183 | 3-F-Ph | NHEt | H | H | H | H | N |
| 3-184 | 3-F-Ph | $NHPr^i$ | H | H | H | H | N |
| 3-185 | 3-F-Ph | $NHCH_2CF_3$ | H | H | H | H | N |
| 3-186 | 3-F-Ph | NHCOMe | H | H | H | H | N |
| 3-187 | 3-F-Ph | NHCOOMe | H | H | H | H | N |
| 3-188 | 3-F-Ph | $NHSO_2Me$ | H | H | H | H | N |
| 3-189 | 3-F-Ph | NH(α-Me-Bn) | H | H | H | H | N |
| 3-190 | 3-F-Ph | NHCOPh | H | H | H | H | N |
| 3-191 | 3-F-Ph | $NH_2$ | H | H | Me | H | N |
| 3-192 | 3-F-Ph | $NH_2$ | H | H | H | Me | N |
| 3-193 | 4-Cl-Ph | H | H | H | H | H | CH |
| 3-194 | 4-Cl-Ph | H | Me | H | H | H | CH |
| 3-195 | 4-Cl-Ph | H | $NH_2$ | H | H | H | CH |
| 3-196 | 4-Cl-Ph | H | H | Me | H | H | CH |
| 3-197 | 4-Cl-Ph | H | H | H | Me | H | CH |
| 3-198 | 4-Cl-Ph | H | H | H | $NH_2$ | H | CH |
| 3-199 | 4-Cl-Ph | H | H | H | NHMe | H | CH |
| 3-200 | 4-Cl-Ph | H | H | H | $NMe_2$ | H | CH |
| 3-201 | 4-Cl-Ph | H | H | H | NHCOMe | H | CH |

TABLE 3-continued

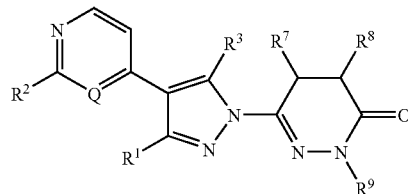

| Compound No | R¹ | R² | R³ | R⁷ | R⁸ | R⁹ | Q |
|---|---|---|---|---|---|---|---|
| 3-202 | 4-Cl-Ph | H | H | H | NHCOOMe | H | CH |
| 3-203 | 4-Cl-Ph | H | H | H | NHSO₂Me | H | CH |
| 3-204 | 4-Cl-Ph | H | H | H | H | Me | CH |
| 3-205 | 4-Cl-Ph | F | H | H | H | H | CH |
| 3-206 | 4-Cl-Ph | Cl | H | H | H | H | CH |
| 3-207 | 4-Cl-Ph | Me | H | H | H | H | CH |
| 3-208 | 4-Cl-Ph | OMe | H | H | H | H | CH |
| 3-209 | 4-Cl-Ph | SMe | H | H | H | H | CH |
| 3-210 | 4-Cl-Ph | SOMe | H | H | H | H | CH |
| 3-211 | 4-Cl-Ph | SO₂Me | H | H | H | H | CH |
| 3-212 | 4-Cl-Ph | NH₂ | H | H | H | H | CH |
| 3-213 | 4-Cl-Ph | NHMe | H | H | H | H | CH |
| 3-214 | 4-Cl-Ph | NMe₂ | H | H | H | H | CH |
| 3-215 | 4-Cl-Ph | NHEt | H | H | H | H | CH |
| 3-216 | 4-Cl-Ph | NHPrⁱ | H | H | H | H | CH |
| 3-217 | 4-Cl-Ph | NHCH₂CF₃ | H | H | H | H | CH |
| 3-218 | 4-Cl-Ph | NHPrᶜ | H | H | H | H | CH |
| 3-219 | 4-Cl-Ph | NHCHO | H | H | H | H | CH |
| 3-220 | 4-Cl-Ph | NHCOMe | H | H | H | H | CH |
| 3-221 | 4-Cl-Ph | NHCOOMe | H | H | H | H | CH |
| 3-222 | 4-Cl-Ph | NHSO₂Me | H | H | H | H | CH |
| 3-223 | 4-Cl-Ph | NH(4-F-Bn) | H | H | H | H | CH |
| 3-224 | 4-Cl-Ph | NH(α-Me-Bn) | H | H | H | H | CH |
| 3-225 | 4-Cl-Ph | NHCOPh | H | H | H | H | CH |
| 3-226 | 4-Cl-Ph | NH₂ | Me | H | H | H | CH |
| 3-227 | 4-Cl-Ph | NH₂ | NH₂ | H | H | H | CH |
| 3-228 | 4-Cl-Ph | NH₂ | H | Me | H | H | CH |
| 3-229 | 4-Cl-Ph | NH₂ | H | H | Me | H | CH |
| 3-230 | 4-Cl-Ph | NH₂ | H | Me | Me | H | CH |
| 3-231 | 4-Cl-Ph | NH₂ | H | H | NH₂ | H | CH |
| 3-232 | 4-Cl-Ph | NH₂ | H | H | NHMe | H | CH |
| 3-233 | 4-Cl-Ph | NH₂ | H | H | NMe₂ | H | CH |
| 3-234 | 4-Cl-Ph | NH₂ | H | H | NHCOMe | H | CH |
| 3-235 | 4-Cl-Ph | NH₂ | H | H | NHCOOMe | H | CH |
| 3-236 | 4-Cl-Ph | NH₂ | H | H | NHSO₂Me | H | CH |
| 3-237 | 4-Cl-Ph | NH₂ | H | H | H | Me | CH |
| 3-238 | 4-Cl-Ph | NH₂ | H | H | Me | Me | CH |
| 3-239 | 4-Cl-Ph | NH₂ | H | H | NH₂ | Me | CH |
| 3-240 | 4-Cl-Ph | H | H | H | H | H | N |
| 3-241 | 4-Cl-Ph | H | NH₂ | H | H | H | N |
| 3-242 | 4-Cl-Ph | H | H | H | Me | H | N |
| 3-243 | 4-Cl-Ph | H | H | H | NH₂ | H | N |
| 3-244 | 4-Cl-Ph | H | H | H | NHMe | H | N |
| 3-245 | 4-Cl-Ph | H | H | H | H | Me | N |
| 3-246 | 4-Cl-Ph | NH₂ | H | H | H | H | N |
| 3-247 | 4-Cl-Ph | NHMe | H | H | H | H | N |
| 3-248 | 4-Cl-Ph | NMe₂ | H | H | H | H | N |
| 3-249 | 4-Cl-Ph | NHEt | H | H | H | H | N |
| 3-250 | 4-Cl-Ph | NHPrⁱ | H | H | H | H | N |
| 3-251 | 4-Cl-Ph | NHCH₂CF₃ | H | H | H | H | N |
| 3-252 | 4-Cl-Ph | NHPrᶜ | H | H | H | H | N |
| 3-253 | 4-Cl-Ph | NHCOMe | H | H | H | H | N |
| 3-254 | 4-Cl-Ph | NHCOOMe | H | H | H | H | N |
| 3-255 | 4-Cl-Ph | NHSO₂Me | H | H | H | H | N |
| 3-256 | 4-Cl-Ph | NH(4-F-Bn) | H | H | H | H | N |
| 3-257 | 4-Cl-Ph | NH(α-Me-Bn) | H | H | H | H | N |
| 3-258 | 4-Cl-Ph | NHCOPh | H | H | H | H | N |
| 3-259 | 4-Cl-Ph | NH₂ | Me | H | H | H | N |
| 3-260 | 4-Cl-Ph | NH₂ | H | Me | H | H | N |
| 3-261 | 4-Cl-Ph | NH₂ | H | H | Me | H | N |
| 3-262 | 4-Cl-Ph | NH₂ | H | H | NH₂ | H | N |
| 3-263 | 4-Cl-Ph | NH₂ | H | H | H | Me | N |
| 3-264 | 3-Cl-Ph | H | H | H | H | H | CH |
| 3-265 | 3-Cl-Ph | H | Me | H | H | H | CH |
| 3-266 | 3-Cl-Ph | H | NH₂ | H | H | H | CH |

TABLE 3-continued

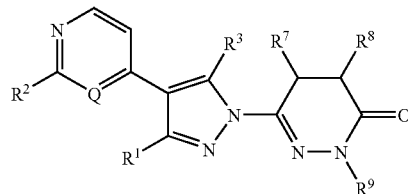

| Compound No | R¹ | R² | R³ | R⁷ | R⁸ | R⁹ | Q |
|---|---|---|---|---|---|---|---|
| 3-267 | 3-Cl-Ph | H | H | Me | H | H | CH |
| 3-268 | 3-Cl-Ph | H | H | H | Me | H | CH |
| 3-269 | 3-Cl-Ph | H | H | H | NH$_2$ | H | CH |
| 3-270 | 3-Cl-Ph | H | H | H | NHMe | H | CH |
| 3-271 | 3-Cl-Ph | H | H | H | NHCOMe | H | CH |
| 3-272 | 3-Cl-Ph | H | H | H | NHCOOMe | H | CH |
| 3-273 | 3-Cl-Ph | H | H | H | NHSO$_2$Me | H | CH |
| 3-274 | 3-Cl-Ph | H | H | H | H | Me | CH |
| 3-275 | 3-Cl-Ph | Me | H | H | H | H | CH |
| 3-276 | 3-Cl-Ph | OMe | H | H | H | H | CH |
| 3-277 | 3-Cl-Ph | SMe | H | H | H | H | CH |
| 3-278 | 3-Cl-Ph | SOMe | H | H | H | H | CH |
| 3-279 | 3-Cl-Ph | SO$_2$Me | H | H | H | H | CH |
| 3-280 | 3-Cl-Ph | NH$_2$ | H | H | H | H | CH |
| 3-281 | 3-Cl-Ph | NHMe | H | H | H | H | CH |
| 3-282 | 3-Cl-Ph | NMe$_2$ | H | H | H | H | CH |
| 3-283 | 3-Cl-Ph | NHEt | H | H | H | H | CH |
| 3-284 | 3-Cl-Ph | NHPr$^i$ | H | H | H | H | CH |
| 3-285 | 3-Cl-Ph | NHCH$_2$CF$_3$ | H | H | H | H | CH |
| 3-286 | 3-Cl-Ph | NHPr$^c$ | H | H | H | H | CH |
| 3-287 | 3-Cl-Ph | NHCOMe | H | H | H | H | CH |
| 3-288 | 3-Cl-Ph | NHCOOMe | H | H | H | H | CH |
| 3-289 | 3-Cl-Ph | NHSO$_2$Me | H | H | H | H | CH |
| 3-290 | 3-Cl-Ph | NH(4-F-Bn) | H | H | H | H | CH |
| 3-291 | 3-Cl-Ph | NH(α-Me-Bn) | H | H | H | H | CH |
| 3-292 | 3-Cl-Ph | NHCOPh | H | H | H | H | CH |
| 3-293 | 3-Cl-Ph | NH$_2$ | Me | H | H | H | CH |
| 3-294 | 3-Cl-Ph | NH$_2$ | NH$_2$ | H | H | H | CH |
| 3-295 | 3-Cl-Ph | NH$_2$ | H | Me | H | H | CH |
| 3-296 | 3-Cl-Ph | NH$_2$ | H | H | Me | H | CH |
| 3-297 | 3-Cl-Ph | NH$_2$ | H | Me | Me | H | CH |
| 3-298 | 3-Cl-Ph | NH$_2$ | H | H | NH$_2$ | H | CH |
| 3-299 | 3-Cl-Ph | NH$_2$ | H | H | NHMe | H | CH |
| 3-300 | 3-Cl-Ph | NH$_2$ | H | H | NMe$_2$ | H | CH |
| 3-301 | 3-Cl-Ph | NH$_2$ | H | H | NHCOMe | H | CH |
| 3-302 | 3-Cl-Ph | NH$_2$ | H | H | NHCOOMe | H | CH |
| 3-303 | 3-Cl-Ph | NH$_2$ | H | H | NHSO$_2$Me | H | CH |
| 3-304 | 3-Cl-Ph | NH$_2$ | H | H | H | Me | CH |
| 3-305 | 3-Cl-Ph | NH$_2$ | H | H | Me | Me | CH |
| 3-306 | 3-Cl-Ph | NH$_2$ | H | H | NH$_2$ | Me | CH |
| 3-307 | 3-Cl-Ph | H | H | H | H | H | N |
| 3-308 | 3-Cl-Ph | H | NH$_2$ | H | H | H | N |
| 3-309 | 3-Cl-Ph | H | H | H | Me | H | N |
| 3-310 | 3-Cl-Ph | H | H | H | NH$_2$ | H | N |
| 3-311 | 3-Cl-Ph | H | H | H | H | Me | N |
| 3-312 | 3-Cl-Ph | NH$_2$ | H | H | H | H | N |
| 3-313 | 3-Cl-Ph | NHMe | H | H | H | H | N |
| 3-314 | 3-Cl-Ph | NHEt | H | H | H | H | N |
| 3-315 | 3-Cl-Ph | NHPr$^i$ | H | H | H | H | N |
| 3-316 | 3-Cl-Ph | NHCH$_2$CF$_3$ | H | H | H | H | N |
| 3-317 | 3-Cl-Ph | NHCOMe | H | H | H | H | N |
| 3-318 | 3-Cl-Ph | NHCOOMe | H | H | H | H | N |
| 3-319 | 3-Cl-Ph | NHSO$_2$Me | H | H | H | H | N |
| 3-320 | 3-Cl-Ph | NH(α-Me-Bn) | H | H | H | H | N |
| 3-321 | 3-Cl-Ph | NHCOPh | H | H | H | H | N |
| 3-322 | 3-Cl-Ph | NH$_2$ | H | H | Me | H | N |
| 3-323 | 3-Cl-Ph | NH$_2$ | H | H | H | Me | N |
| 3-324 | 3,4-diF-Ph | H | H | H | H | H | CH |
| 3-325 | 3,4-diF-Ph | H | Me | H | H | H | CH |
| 3-326 | 3,4-diF-Ph | H | NH$_2$ | H | H | H | CH |
| 3-327 | 3,4-diF-Ph | H | H | Me | H | H | CH |
| 3-328 | 3,4-diF-Ph | H | H | H | Me | H | CH |
| 3-329 | 3,4-diF-Ph | H | H | H | NH$_2$ | H | CH |
| 3-330 | 3,4-diF-Ph | H | H | H | NHMe | H | CH |
| 3-331 | 3,4-diF-Ph | H | H | H | NMe$_2$ | H | CH |

TABLE 3-continued

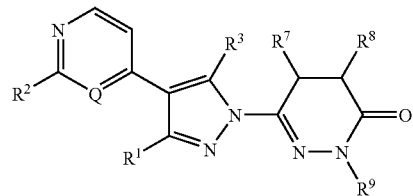

| Compound No | R¹ | R² | R³ | R⁷ | R⁸ | R⁹ | Q |
|---|---|---|---|---|---|---|---|
| 3-332 | 3,4-diF-Ph | H | H | H | NHCOMe | H | CH |
| 3-333 | 3,4-diF-Ph | H | H | H | NHCOOMe | H | CH |
| 3-334 | 3,4-diF-Ph | H | H | H | NHSO$_2$Me | H | CH |
| 3-335 | 3,4-diF-Ph | H | H | H | H | Me | CH |
| 3-336 | 3,4-diF-Ph | F | H | H | H | H | CH |
| 3-337 | 3,4-diF-Ph | Cl | H | H | H | H | CH |
| 3-338 | 3,4-diF-Ph | Me | H | H | H | H | CH |
| 3-339 | 3,4-diF-Ph | OMe | H | H | H | H | CH |
| 3-340 | 3,4-diF-Ph | SMe | H | H | H | H | CH |
| 3-341 | 3,4-diF-Ph | SOMe | H | H | H | H | CH |
| 3-342 | 3,4-diF-Ph | SO$_2$Me | H | H | H | H | CH |
| 3-343 | 3,4-diF-Ph | NH$_2$ | H | H | H | H | CH |
| 3-344 | 3,4-diF-Ph | NHMe | H | H | H | H | CH |
| 3-345 | 3,4-diF-Ph | NMe$_2$ | H | H | H | H | CH |
| 3-346 | 3,4-diF-Ph | NHEt | H | H | H | H | CH |
| 3-347 | 3,4-diF-Ph | NHPr$^i$ | H | H | H | H | CH |
| 3-348 | 3,4-diF-Ph | NHCH$_2$CF$_3$ | H | H | H | H | CH |
| 3-349 | 3,4-diF-Ph | NHPr$^c$ | H | H | H | H | CH |
| 3-350 | 3,4-diF-Ph | NHCHO | H | H | H | H | CH |
| 3-351 | 3,4-diF-Ph | NHCOMe | H | H | H | H | CH |
| 3-352 | 3,4-diF-Ph | NHCOOMe | H | H | H | H | CH |
| 3-353 | 3,4-diF-Ph | NHSO$_2$Me | H | H | H | H | CH |
| 3-354 | 3,4-diF-Ph | NH(4-F-Bn) | H | H | H | H | CH |
| 3-355 | 3,4-diF-Ph | NH(α-Me-Bn) | H | H | H | H | CH |
| 3-356 | 3,4-diF-Ph | NHCOPh | H | H | H | H | CH |
| 3-357 | 3,4-diF-Ph | NH$_2$ | Me | H | H | H | CH |
| 3-358 | 3,4-diF-Ph | NH$_2$ | NH$_2$ | H | H | H | CH |
| 3-359 | 3,4-diF-Ph | NH$_2$ | H | Me | H | H | CH |
| 3-360 | 3,4-diF-Ph | NH$_2$ | H | H | Me | H | CH |
| 3-361 | 3,4-diF-Ph | NH$_2$ | H | Me | Me | H | CH |
| 3-362 | 3,4-diF-Ph | NH$_2$ | H | H | NH$_2$ | H | CH |
| 3-363 | 3,4-diF-Ph | NH$_2$ | H | H | NHMe | H | CH |
| 3-364 | 3,4-diF-Ph | NH$_2$ | H | H | NMe$_2$ | H | CH |
| 3-365 | 3,4-diF-Ph | NH$_2$ | H | H | NHCOMe | H | CH |
| 3-366 | 3,4-diF-Ph | NH$_2$ | H | H | NHCOOMe | H | CH |
| 3-367 | 3,4-diF-Ph | NH$_2$ | H | H | NHSO$_2$Me | H | CH |
| 3-368 | 3,4-diF-Ph | NH$_2$ | H | H | H | Me | CH |
| 3-369 | 3,4-diF-Ph | NH$_2$ | H | H | Me | Me | CH |
| 3-370 | 3,4-diF-Ph | NH$_2$ | H | H | NH$_2$ | Me | CH |
| 3-371 | 3,4-diF-Ph | H | H | H | H | H | N |
| 3-372 | 3,4-diF-Ph | H | NH$_2$ | H | H | H | N |
| 3-373 | 3,4-diF-Ph | H | H | H | Me | H | N |
| 3-374 | 3,4-diF-Ph | H | H | H | NH$_2$ | H | N |
| 3-375 | 3,4-diF-Ph | H | H | H | NHMe | H | N |
| 3-376 | 3,4-diF-Ph | H | H | H | H | Me | N |
| 3-377 | 3,4-diF-Ph | NH$_2$ | H | H | H | H | N |
| 3-378 | 3,4-diF-Ph | NHMe | H | H | H | H | N |
| 3-379 | 3,4-diF-Ph | NMe$_2$ | H | H | H | H | N |
| 3-380 | 3,4-diF-Ph | NHEt | H | H | H | H | N |
| 3-381 | 3,4-diF-Ph | NHPr$^i$ | H | H | H | H | N |
| 3-382 | 3,4-diF-Ph | NHCH$_2$CF$_3$ | H | H | H | H | N |
| 3-383 | 3,4-diF-Ph | NHPr$^c$ | H | H | H | H | N |
| 3-384 | 3,4-diF-Ph | NHCOMe | H | H | H | H | N |
| 3-385 | 3,4-diF-Ph | NHCOOMe | H | H | H | H | N |
| 3-386 | 3,4-diF-Ph | NHSO$_2$Me | H | H | H | H | N |
| 3-387 | 3,4-diF-Ph | NH(4-F-Bn) | H | H | H | H | N |
| 3-388 | 3,4-diF-Ph | NH(α-Me-Bn) | H | H | H | H | N |
| 3-389 | 3,4-diF-Ph | NHCOPh | H | H | H | H | N |
| 3-390 | 3,4-diF-Ph | NH$_2$ | Me | H | H | H | N |
| 3-391 | 3,4-diF-Ph | NH$_2$ | H | Me | H | H | N |
| 3-392 | 3,4-diF-Ph | NH$_2$ | H | H | Me | H | N |
| 3-393 | 3,4-diF-Ph | NH$_2$ | H | H | NH$_2$ | H | N |
| 3-394 | 3,4-diF-Ph | NH$_2$ | H | H | H | Me | N |
| 3-395 | 3,4-diCl-Ph | H | H | H | H | H | CH |
| 3-396 | 3,4-diCl-Ph | H | Me | H | H | H | CH |

TABLE 3-continued

| Compound No | R¹ | R² | R³ | R⁷ | R⁸ | R⁹ | Q |
|---|---|---|---|---|---|---|---|
| 3-397 | 3,4-diCl-Ph | H | $NH_2$ | H | H | H | CH |
| 3-398 | 3,4-diCl-Ph | H | H | Me | H | H | CH |
| 3-399 | 3,4-diCl-Ph | H | H | H | Me | H | CH |
| 3-400 | 3,4-diCl-Ph | H | H | H | $NH_2$ | H | CH |
| 3-401 | 3,4-diCl-Ph | H | H | H | NHMe | H | CH |
| 3-402 | 3,4-diCl-Ph | H | H | H | NHCOMe | H | CH |
| 3-403 | 3,4-diCl-Ph | H | H | H | NHCOOMe | H | CH |
| 3-404 | 3,4-diCl-Ph | H | H | H | $NHSO_2Me$ | H | CH |
| 3-405 | 3,4-diCl-Ph | H | H | H | H | Me | CH |
| 3-406 | 3,4-diCl-Ph | Me | H | H | H | H | CH |
| 3-407 | 3,4-diCl-Ph | OMe | H | H | H | H | CH |
| 3-408 | 3,4-diCl-Ph | SMe | H | H | H | H | CH |
| 3-409 | 3,4-diCl-Ph | SOMe | H | H | H | H | CH |
| 3-410 | 3,4-diCl-Ph | $SO_2Me$ | H | H | H | H | CH |
| 3-411 | 3,4-diCl-Ph | $NH_2$ | H | H | H | H | CH |
| 3-412 | 3,4-diCl-Ph | NHMe | H | H | H | H | CH |
| 3-413 | 3,4-diCl-Ph | $NMe_2$ | H | H | H | H | CH |
| 3-414 | 3,4-diCl-Ph | NHEt | H | H | H | H | CH |
| 3-415 | 3,4-diCl-Ph | NHPr^i | H | H | H | H | CH |
| 3-416 | 3,4-diCl-Ph | $NHCH_2CF_3$ | H | H | H | H | CH |
| 3-417 | 3,4-diCl-Ph | NHPr^c | H | H | H | H | CH |
| 3-418 | 3,4-diCl-Ph | NHCOMe | H | H | H | H | CH |
| 3-419 | 3,4-diCl-Ph | NHCOOMe | H | H | H | H | CH |
| 3-420 | 3,4-diCl-Ph | $NHSO_2Me$ | H | H | H | H | CH |
| 3-421 | 3,4-diCl-Ph | NH(4-F-Bn) | H | H | H | H | CH |
| 3-422 | 3,4-diCl-Ph | NH(α-Me-Bn) | H | H | H | H | CH |
| 3-423 | 3,4-diCl-Ph | NHCOPh | H | H | H | H | CH |
| 3-424 | 3,4-diCl-Ph | $NH_2$ | Me | H | H | H | CH |
| 3-425 | 3,4-diCl-Ph | $NH_2$ | $NH_2$ | H | H | H | CH |
| 3-426 | 3,4-diCl-Ph | $NH_2$ | H | Me | H | H | CH |
| 3-427 | 3,4-diCl-Ph | $NH_2$ | H | H | Me | H | CH |
| 3-428 | 3,4-diCl-Ph | $NH_2$ | H | Me | Me | H | CH |
| 3-429 | 3,4-diCl-Ph | $NH_2$ | H | H | $NH_2$ | H | CH |
| 3-430 | 3,4-diCl-Ph | $NH_2$ | H | H | NHMe | H | CH |
| 3-431 | 3,4-diCl-Ph | $NH_2$ | H | H | $NMe_2$ | H | CH |
| 3-432 | 3,4-diCl-Ph | $NH_2$ | H | H | NHCOMe | H | CH |
| 3-433 | 3,4-diCl-Ph | $NH_2$ | H | H | NHCOOMe | H | CH |
| 3-434 | 3,4-diCl-Ph | $NH_2$ | H | H | $NHSO_2Me$ | H | CH |
| 3-435 | 3,4-diCl-Ph | $NH_2$ | H | H | H | Me | CH |
| 3-436 | 3,4-diCl-Ph | $NH_2$ | H | H | Me | Me | CH |
| 3-437 | 3,4-diCl-Ph | $NH_2$ | H | H | $NH_2$ | Me | CH |
| 3-438 | 3,4-diCl-Ph | H | H | H | H | H | N |
| 3-439 | 3,4-diCl-Ph | H | $NH_2$ | H | H | H | N |
| 3-440 | 3,4-diCl-Ph | H | H | H | Me | H | N |
| 3-441 | 3,4-diCl-Ph | H | H | H | $NH_2$ | H | N |
| 3-442 | 3,4-diCl-Ph | H | H | H | H | Me | N |
| 3-443 | 3,4-diCl-Ph | $NH_2$ | H | H | H | H | N |
| 3-444 | 3,4-diCl-Ph | NHMe | H | H | H | H | N |
| 3-445 | 3,4-diCl-Ph | NHEt | H | H | H | H | N |
| 3-446 | 3,4-diCl-Ph | NHPr^i | H | H | H | H | N |
| 3-447 | 3,4-diCl-Ph | $NHCH_2CF_3$ | H | H | H | H | N |
| 3-448 | 3,4-diCl-Ph | NHCOMe | H | H | H | H | N |
| 3-449 | 3,4-diCl-Ph | NHCOOMe | H | H | H | H | N |
| 3-450 | 3,4-diCl-Ph | $NHSO_2Me$ | H | H | H | H | N |
| 3-451 | 3,4-diCl-Ph | NH(α-Me-Bn) | H | H | H | H | N |
| 3-452 | 3,4-diCl-Ph | NHCOPh | H | H | H | H | N |
| 3-453 | 3,4-diCl-Ph | $NH_2$ | H | H | Me | H | N |
| 3-454 | 3,4-diCl-Ph | $NH_2$ | H | H | H | Me | N |
| 3-455 | 3-Cl-4-F-Ph | H | H | H | H | H | CH |
| 3-456 | 3-Cl-4-F-Ph | $NH_2$ | H | H | H | H | CH |
| 3-457 | 3-Cl-4-F-Ph | NHMe | H | H | H | H | CH |
| 3-458 | 3-Cl-4-F-Ph | $NMe_2$ | H | H | H | H | CH |
| 3-459 | 3-Cl-4-F-Ph | NHEt | H | H | H | H | CH |
| 3-460 | 3-Cl-4-F-Ph | $NHCH_2CF_3$ | H | H | H | H | CH |
| 3-461 | 3-Cl-4-F-Ph | NHPr^c | H | H | H | H | CH |

TABLE 3-continued

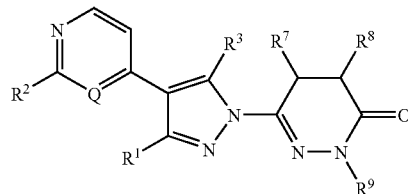

| Compound No | R$^1$ | R$^2$ | R$^3$ | R$^7$ | R$^8$ | R$^9$ | Q |
|---|---|---|---|---|---|---|---|
| 3-462 | 3-Cl-4-F-Ph | NHCOMe | H | H | H | H | CH |
| 3-463 | 3-Cl-4-F-Ph | NHCOOMe | H | H | H | H | CH |
| 3-464 | 3-Cl-4-F-Ph | NHSO$_2$Me | H | H | H | H | CH |
| 3-465 | 3-Cl-4-F-Ph | NH(4-F-Bn) | H | H | H | H | CH |
| 3-466 | 3-Cl-4-F-Ph | NH(α-Me-Bn) | H | H | H | H | CH |
| 3-467 | 3-Cl-4-F-Ph | NHCOPh | H | H | H | H | CH |
| 3-468 | 3-Cl-4-F-Ph | NH$_2$ | Me | H | H | H | CH |
| 3-469 | 3-Cl-4-F-Ph | NH$_2$ | NH$_2$ | H | H | H | CH |
| 3-470 | 3-Cl-4-F-Ph | NH$_2$ | H | Me | H | H | CH |
| 3-471 | 3-Cl-4-F-Ph | NH$_2$ | H | H | Me | H | CH |
| 3-472 | 3-Cl-4-F-Ph | NH$_2$ | H | H | NH$_2$ | H | CH |
| 3-473 | 3-Cl-4-F-Ph | NH$_2$ | H | H | NHMe | H | CH |
| 3-474 | 3-Cl-4-F-Ph | NH$_2$ | H | H | NMe$_2$ | H | CH |
| 3-475 | 3-Cl-4-F-Ph | NH$_2$ | H | H | NHCOMe | H | CH |
| 3-476 | 3-Cl-4-F-Ph | NH$_2$ | H | H | NHCOOMe | H | CH |
| 3-477 | 3-Cl-4-F-Ph | NH$_2$ | H | H | NHSO$_2$Me | H | CH |
| 3-478 | 3-Cl-4-F-Ph | NH$_2$ | H | H | H | Me | CH |
| 3-479 | 3-Cl-4-F-Ph | NH$_2$ | H | H | NH$_2$ | Me | CH |
| 3-480 | 3-Cl-4-F-Ph | H | H | H | H | H | N |
| 3-481 | 3-Cl-4-F-Ph | NH$_2$ | H | H | H | H | N |
| 3-482 | 3-Cl-4-F-Ph | NHMe | H | H | H | H | N |
| 3-483 | 3-Cl-4-F-Ph | NMe$_2$ | H | H | H | H | N |
| 3-484 | 3-Cl-4-F-Ph | NHEt | H | H | H | H | N |
| 3-485 | 3-Cl-4-F-Ph | NHPr$^i$ | H | H | H | H | N |
| 3-486 | 3-Cl-4-F-Ph | NHCH$_2$CF$_3$ | H | H | H | H | N |
| 3-487 | 3-Cl-4-F-Ph | NHPr$^c$ | H | H | H | H | N |
| 3-488 | 3-Cl-4-F-Ph | NHCOMe | H | H | H | H | N |
| 3-489 | 3-Cl-4-F-Ph | NHCOOMe | H | H | H | H | N |
| 3-490 | 3-Cl-4-F-Ph | NHSO$_2$Me | H | H | H | H | N |
| 3-491 | 3-Cl-4-F-Ph | NH(4-F-Bn) | H | H | H | H | N |
| 3-492 | 3-Cl-4-F-Ph | NH(α-Me-Bn) | H | H | H | H | N |
| 3-493 | 3-Cl-4-F-Ph | NHCOPh | H | H | H | H | N |
| 3-494 | 3-Cl-4-F-Ph | NH$_2$ | H | H | Me | H | N |
| 3-495 | 3-Cl-4-F-Ph | NH$_2$ | H | H | NH$_2$ | H | N |
| 3-496 | 4-Cl-3-F-Ph | H | H | H | H | H | CH |
| 3-497 | 4-Cl-3-F-Ph | NH$_2$ | H | H | H | H | CH |
| 3-498 | 4-Cl-3-F-Ph | NHMe | H | H | H | H | CH |
| 3-499 | 4-Cl-3-F-Ph | NMe$_2$ | H | H | H | H | CH |
| 3-500 | 4-Cl-3-F-Ph | NHEt | H | H | H | H | CH |
| 3-501 | 4-Cl-3-F-Ph | NHCH$_2$CF$_3$ | H | H | H | H | CH |
| 3-502 | 4-Cl-3-F-Ph | NHPr$^c$ | H | H | H | H | CH |
| 3-503 | 4-Cl-3-F-Ph | NHCOMe | H | H | H | H | CH |
| 3-504 | 4-Cl-3-F-Ph | NHCOOMe | H | H | H | H | CH |
| 3-505 | 4-Cl-3-F-Ph | NHSO$_2$Me | H | H | H | H | CH |
| 3-506 | 4-Cl-3-F-Ph | NH(4-F-Bn) | H | H | H | H | CH |
| 3-507 | 4-Cl-3-F-Ph | NH(α-Me-Bn) | H | H | H | H | CH |
| 3-508 | 4-Cl-3-F-Ph | NHCOPh | H | H | H | H | CH |
| 3-509 | 4-Cl-3-F-Ph | NH$_2$ | Me | H | H | H | CH |
| 3-510 | 4-Cl-3-F-Ph | NH$_2$ | NH$_2$ | H | H | H | CH |
| 3-511 | 4-Cl-3-F-Ph | NH$_2$ | H | Me | H | H | CH |
| 3-512 | 4-Cl-3-F-Ph | NH$_2$ | H | H | Me | H | CH |
| 3-513 | 4-Cl-3-F-Ph | NH$_2$ | H | H | NH$_2$ | H | CH |
| 3-514 | 4-Cl-3-F-Ph | NH$_2$ | H | H | NHMe | H | CH |
| 3-515 | 4-Cl-3-F-Ph | NH$_2$ | H | H | NMe$_2$ | H | CH |
| 3-516 | 4-Cl-3-F-Ph | NH$_2$ | H | H | NHCOMe | H | CH |
| 3-517 | 4-Cl-3-F-Ph | NH$_2$ | H | H | NHCOOMe | H | CH |
| 3-518 | 4-Cl-3-F-Ph | NH$_2$ | H | H | NHSO$_2$Me | H | CH |
| 3-519 | 4-Cl-3-F-Ph | NH$_2$ | H | H | H | Me | CH |
| 3-520 | 4-Cl-3-F-Ph | NH$_2$ | H | H | NH$_2$ | Me | CH |
| 3-521 | 4-Cl-3-F-Ph | H | H | H | H | H | N |
| 3-522 | 4-Cl-3-F-Ph | NH$_2$ | H | H | H | H | N |
| 3-523 | 4-Cl-3-F-Ph | NHMe | H | H | H | H | N |
| 3-524 | 4-Cl-3-F-Ph | NMe$_2$ | H | H | H | H | N |
| 3-525 | 4-Cl-3-F-Ph | NHEt | H | H | H | H | N |
| 3-526 | 4-Cl-3-F-Ph | NHPr$^i$ | H | H | H | H | N |

TABLE 3-continued

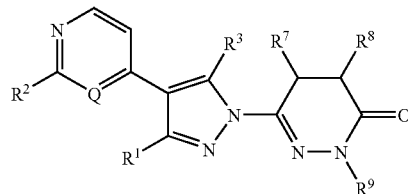

| Compound No | R¹ | R² | R³ | R⁷ | R⁸ | R⁹ | Q |
|---|---|---|---|---|---|---|---|
| 3-527 | 4-Cl-3-F-Ph | NHCH₂CF₃ | H | H | H | H | N |
| 3-528 | 4-Cl-3-F-Ph | NHPrᶜ | H | H | H | H | N |
| 3-529 | 4-Cl-3-F-Ph | NHCOMe | H | H | H | H | N |
| 3-530 | 4-Cl-3-F-Ph | NHCOOMe | H | H | H | H | N |
| 3-531 | 4-Cl-3-F-Ph | NHSO₂Me | H | H | H | H | N |
| 3-532 | 4-Cl-3-F-Ph | NH(4-F-Bn) | H | H | H | H | N |
| 3-533 | 4-Cl-3-F-Ph | NH(α-Me-Bn) | H | H | H | H | N |
| 3-534 | 4-Cl-3-F-Ph | NHCOPh | H | H | H | H | N |
| 3-535 | 4-Cl-3-F-Ph | NH₂ | H | H | Me | H | N |
| 3-536 | 4-Cl-3-F-Ph | NH₂ | H | H | NH₂ | H | N |
| 3-537 | 3-CF₃-Ph | H | H | H | H | H | CH |
| 3-538 | 3-CF₃-Ph | NH₂ | H | H | H | H | CH |
| 3-539 | 3-CF₃-Ph | NHMe | H | H | H | H | CH |
| 3-540 | 3-CF₃-Ph | NMe₂ | H | H | H | H | CH |
| 3-541 | 3-CF₃-Ph | NHEt | H | H | H | H | CH |
| 3-542 | 3-CF₃-Ph | NHCH₂CF₃ | H | H | H | H | CH |
| 3-543 | 3-CF₃-Ph | NHPrᶜ | H | H | H | H | CH |
| 3-544 | 3-CF₃-Ph | NHCOMe | H | H | H | H | CH |
| 3-545 | 3-CF₃-Ph | NHCOOMe | H | H | H | H | CH |
| 3-546 | 3-CF₃-Ph | NHSO₂Me | H | H | H | H | CH |
| 3-547 | 3-CF₃-Ph | NH(4-F-Bn) | H | H | H | H | CH |
| 3-548 | 3-CF₃-Ph | NH(α-Me-Bn) | H | H | H | H | CH |
| 3-549 | 3-CF₃-Ph | NHCOPh | H | H | H | H | CH |
| 3-550 | 3-CF₃-Ph | NH₂ | Me | H | H | H | CH |
| 3-551 | 3-CF₃-Ph | NH₂ | NH₂ | H | H | H | CH |
| 3-552 | 3-CF₃-Ph | NH₂ | H | Me | H | H | CH |
| 3-553 | 3-CF₃-Ph | NH₂ | H | H | Me | H | CH |
| 3-554 | 3-CF₃-Ph | NH₂ | H | H | NH₂ | H | CH |
| 3-555 | 3-CF₃-Ph | NH₂ | H | H | NHMe | H | CH |
| 3-556 | 3-CF₃-Ph | NH₂ | H | H | NMe₂ | H | CH |
| 3-557 | 3-CF₃-Ph | NH₂ | H | H | NHCOMe | H | CH |
| 3-558 | 3-CF₃-Ph | NH₂ | H | H | NHCOOMe | H | CH |
| 3-559 | 3-CF₃-Ph | NH₂ | H | H | NHSO₂Me | H | CH |
| 3-560 | 3-CF₃-Ph | NH₂ | H | H | H | Me | CH |
| 3-561 | 3-CF₃-Ph | NH₂ | H | H | NH₂ | Me | CH |
| 3-562 | 3-CF₃-Ph | H | H | H | H | H | N |
| 3-563 | 3-CF₃-Ph | NH₂ | H | H | H | H | N |
| 3-564 | 3-CF₃-Ph | NHMe | H | H | H | H | N |
| 3-565 | 3-CF₃-Ph | NMe₂ | H | H | H | H | N |
| 3-566 | 3-CF₃-Ph | NHEt | H | H | H | H | N |
| 3-567 | 3-CF₃-Ph | NHPrⁱ | H | H | H | H | N |
| 3-568 | 3-CF₃-Ph | NHCH₂CF₃ | H | H | H | H | N |
| 3-569 | 3-CF₃-Ph | NHPrᶜ | H | H | H | H | N |
| 3-570 | 3-CF₃-Ph | NHCOMe | H | H | H | H | N |
| 3-571 | 3-CF₃-Ph | NHCOOMe | H | H | H | H | N |
| 3-572 | 3-CF₃-Ph | NHSO₂Me | H | H | H | H | N |
| 3-573 | 3-CF₃-Ph | NH(4-F-Bn) | H | H | H | H | N |
| 3-574 | 3-CF₃-Ph | NH(α-Me-Bn) | H | H | H | H | N |
| 3-575 | 3-CF₃-Ph | NHCOPh | H | H | H | H | N |
| 3-576 | 3-CF₃-Ph | NH₂ | H | H | Me | H | N |
| 3-577 | 3-CF₃-Ph | NH₂ | H | H | NH₂ | H | N |
| 3-578 | 2-F-Ph | H | H | H | H | H | CH |
| 3-579 | 2-F-Ph | H | Me | H | H | H | CH |
| 3-580 | 2-F-Ph | H | NH₂ | H | H | H | CH |
| 3-581 | 2-F-Ph | H | H | Me | H | H | CH |
| 3-582 | 2-F-Ph | H | H | H | Me | H | CH |
| 3-583 | 2-F-Ph | H | H | H | NH₂ | H | CH |
| 3-584 | 2-F-Ph | H | H | H | NHMe | H | CH |
| 3-585 | 2-F-Ph | H | H | H | NMe₂ | H | CH |
| 3-586 | 2-F-Ph | H | H | H | NHCOMe | H | CH |
| 3-587 | 2-F-Ph | H | H | H | NHCOOMe | H | CH |
| 3-588 | 2-F-Ph | H | H | H | NHSO₂Me | H | CH |
| 3-589 | 2-F-Ph | H | H | H | H | Me | CH |
| 3-590 | 2-F-Ph | F | H | H | H | H | CH |
| 3-591 | 2-F-Ph | Cl | H | H | H | H | CH |

TABLE 3-continued

| Compound No | R¹ | R² | R³ | R⁷ | R⁸ | R⁹ | Q |
|---|---|---|---|---|---|---|---|
| 3-592 | 2-F-Ph | Me | H | H | H | H | CH |
| 3-593 | 2-F-Ph | OMe | H | H | H | H | CH |
| 3-594 | 2-F-Ph | SMe | H | H | H | H | CH |
| 3-595 | 2-F-Ph | SOMe | H | H | H | H | CH |
| 3-596 | 2-F-Ph | SO₂Me | H | H | H | H | CH |
| 3-597 | 2-F-Ph | NH₂ | H | H | H | H | CH |
| 3-598 | 2-F-Ph | NHMe | H | H | H | H | CH |
| 3-599 | 2-F-Ph | NMe₂ | H | H | H | H | CH |
| 3-600 | 2-F-Ph | NHEt | H | H | H | H | CH |
| 3-601 | 2-F-Ph | NHPrⁱ | H | H | H | H | CH |
| 3-602 | 2-F-Ph | NHCH₂CF₃ | H | H | H | H | CH |
| 3-603 | 2-F-Ph | NHPrᶜ | H | H | H | H | CH |
| 3-604 | 2-F-Ph | NHCHO | H | H | H | H | CH |
| 3-605 | 2-F-Ph | NHCOMe | H | H | H | H | CH |
| 3-606 | 2-F-Ph | NHCOOMe | H | H | H | H | CH |
| 3-607 | 2-F-Ph | NHSO₂Me | H | H | H | H | CH |
| 3-608 | 2-F-Ph | NH(4-F-Bn) | H | H | H | H | CH |
| 3-609 | 2-F-Ph | NH(α-Me-Bn) | H | H | H | H | CH |
| 3-610 | 2-F-Ph | NHCOPh | H | H | H | H | CH |
| 3-611 | 2-F-Ph | NH₂ | Me | H | H | H | CH |
| 3-612 | 2-F-Ph | NH₂ | NH₂ | H | H | H | CH |
| 3-613 | 2-F-Ph | NH₂ | H | Me | H | H | CH |
| 3-614 | 2-F-Ph | NH₂ | H | H | Me | H | CH |
| 3-615 | 2-F-Ph | NH₂ | H | Me | Me | H | CH |
| 3-616 | 2-F-Ph | NH₂ | H | H | NH₂ | H | CH |
| 3-617 | 2-F-Ph | NH₂ | H | H | NHMe | H | CH |
| 3-618 | 2-F-Ph | NH₂ | H | H | NMe₂ | H | CH |
| 3-619 | 2-F-Ph | NH₂ | H | H | NHCOMe | H | CH |
| 3-620 | 2-F-Ph | NH₂ | H | H | NHCOOMe | H | CH |
| 3-621 | 2-F-Ph | NH₂ | H | H | NHSO₂Me | H | CH |
| 3-622 | 2-F-Ph | NH₂ | H | H | H | Me | CH |
| 3-623 | 2-FPh | NH₂ | H | H | Me | Me | CH |
| 3-624 | 2-F-Ph | NH₂ | H | H | NH₂ | Me | CH |
| 3-625 | 2-F-Ph | H | H | H | H | H | N |
| 3-626 | 2-F-Ph | H | NH₂ | H | H | H | N |
| 3-627 | 2-F-Ph | H | H | H | Me | H | N |
| 3-628 | 2-F-Ph | H | H | H | NH₂ | H | N |
| 3-629 | 2-F-Ph | H | H | H | NHMe | H | N |
| 3-630 | 2-F-Ph | H | H | H | H | Me | N |
| 3-631 | 2-F-Ph | NH₂ | H | H | H | H | N |
| 3-632 | 2-F-Ph | NHMe | H | H | H | H | N |
| 3-633 | 2-F-Ph | NMe₂ | H | H | H | H | N |
| 3-634 | 2-F-Ph | NHEt | H | H | H | H | N |
| 3-635 | 2-F-Ph | NHPrⁱ | H | H | H | H | N |
| 3-636 | 2-F-Ph | NHCH₂CF₃ | H | H | H | H | N |
| 3-637 | 2-F-Ph | NHPrᶜ | H | H | H | H | N |
| 3-638 | 2-F-Ph | NHCOMe | H | H | H | H | N |
| 3-639 | 2-F-Ph | NHCOOMe | H | H | H | H | N |
| 3-640 | 2-F-Ph | NHSO₂Me | H | H | H | H | N |
| 3-641 | 2-F-Ph | NH(4-F-Bn) | H | H | H | H | N |
| 3-642 | 2-F-Ph | NH(α-Me-Bn) | H | H | H | H | N |
| 3-643 | 2-F-Ph | NHCOPh | H | H | H | H | N |
| 3-644 | 2-F-Ph | NH₂ | Me | H | H | H | N |
| 3-645 | 2-F-Ph | NH₂ | H | Me | H | H | N |
| 3-646 | 2-F-Ph | NH₂ | H | H | Me | H | N |
| 3-647 | 2-F-Ph | NH₂ | H | H | NH₂ | H | N |
| 3-648 | 2-F-Ph | NH₂ | H | H | H | Me | N |
| 3-649 | 2,4-diF-Ph | H | H | H | H | H | CH |
| 3-650 | 2,4-diF-Ph | NH₂ | H | H | H | H | CH |
| 3-651 | 2,4-diF-Ph | NHMe | H | H | H | H | CH |
| 3-652 | 2,4-diF-Ph | NMe₂ | H | H | H | H | CH |
| 3-653 | 2,4-diF-Ph | NHEt | H | H | H | H | CH |
| 3-654 | 2,4-diF-Ph | NHCH₂CF₃ | H | H | H | H | CH |
| 3-655 | 2,4-diF-Ph | NHPrᶜ | H | H | H | H | CH |
| 3-656 | 2,4-diF-Ph | NHCOMe | H | H | H | H | CH |

TABLE 3-continued

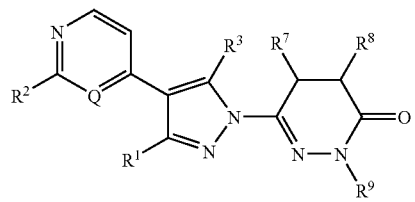

| Compound No | R¹ | R² | R³ | R⁷ | R⁸ | R⁹ | Q |
|---|---|---|---|---|---|---|---|
| 3-657 | 2,4-diF-Ph | NHCOOMe | H | H | H | H | CH |
| 3-658 | 2,4-diF-Ph | NHSO₂Me | H | H | H | H | CH |
| 3-659 | 2,4-diF-Ph | NH(4-F-Bn) | H | H | H | H | CH |
| 3-660 | 2,4-diF-Ph | NH(α-Me-Bn) | H | H | H | H | CH |
| 3-661 | 2,4-diF-Ph | NHCOPh | H | H | H | H | CH |
| 3-662 | 2,4-diF-Ph | NH₂ | Me | H | H | H | CF |
| 3-663 | 2,4-diF-Ph | NH₂ | NH₂ | H | H | H | CH |
| 3-664 | 2,4-diF-Ph | NH₂ | H | Me | H | H | CH |
| 3-665 | 2,4-diF-Ph | NH₂ | H | H | Me | H | CH |
| 3-666 | 2,4-diF-Ph | NH₂ | H | H | NH₂ | H | CH |
| 3-667 | 2,4-diF-Ph | NH₂ | H | H | NHMe | H | CH |
| 3-668 | 2,4-diF-Ph | NH₂ | H | H | NMe₂ | H | CH |
| 3-669 | 2,4-diF-Ph | NH₂ | H | H | NHCOMe | H | CH |
| 3-670 | 2,4-diF-Ph | NH₂ | H | H | NHCOOMe | H | CH |
| 3-671 | 2,4-diF-Ph | NH₂ | H | H | NHSO₂Me | H | CH |
| 3-672 | 2,4-diF-Ph | NH₂ | H | H | H | Me | CH |
| 3-673 | 2,4-diF-Ph | NH₂ | H | H | NH₂ | Me | CH |
| 3-674 | 2,4-diF-Ph | H | H | H | H | H | N |
| 3-675 | 2,4-diF-Ph | NH₂ | H | H | H | H | N |
| 3-676 | 2,4-diF-Ph | NHMe | H | H | H | H | N |
| 3-677 | 2,4-diF-Ph | NMe₂ | H | H | H | H | N |
| 3-678 | 2,4-diF-Ph | NHEt | H | H | H | H | N |
| 3-679 | 2,4-diF-Ph | NHPrⁱ | H | H | H | H | N |
| 3-680 | 2,4-diF-Ph | NHCH₂CF₃ | H | H | H | H | N |
| 3-681 | 2,4-diF-Ph | NHPrᶜ | H | H | H | H | N |
| 3-682 | 2,4-diF-Ph | NHCOMe | H | H | H | H | N |
| 3-683 | 2,4-diF-Ph | NHCOOMe | H | H | H | H | N |
| 3-684 | 2,4-diF-Ph | NHSO₂Me | H | H | H | H | N |
| 3-685 | 2,4-diF-Ph | NH(4-F-Bn) | H | H | H | H | N |
| 3-686 | 2,4-diF-Ph | NH(α-Me-Bn) | H | H | H | H | N |
| 3-687 | 2,4-diF-Ph | NHCOPh | H | H | H | H | N |
| 3-688 | 2,4-diF-Ph | NH₂ | H | H | Me | H | N |
| 3-689 | 2,4-diF-Ph | NH₂ | H | H | NH₂ | H | N |
| 3-690 | Ph | NHCOPrᶜ | H | H | H | H | CH |
| 3-691 | Ph | NHCOPrᶜ | H | H | H | H | N |
| 3-692 | Ph | NHCOPnᶜ | H | H | H | H | CH |
| 3-693 | Ph | NHCOPnᶜ | H | H | H | H | N |
| 3-694 | 4-F-Ph | NHCOPrᶜ | H | H | H | H | CH |
| 3-695 | 4-F-Ph | N(Me)COPrᶜ | H | H | H | H | CH |
| 3-696 | 4-F-Ph | NHCOPrᶜ | H | H | H | H | N |
| 3-697 | 4-F-Ph | N(Me)COPrᶜ | H | H | H | H | N |
| 3-698 | 4-F-Ph | NHCOPnᶜ | H | H | H | H | CH |
| 3-699 | 4-F-Ph | N(Me)COPnᶜ | H | H | H | H | CH |
| 3-700 | 4-F-Ph | NHCOPnᶜ | H | H | H | H | N |
| 3-701 | 4-F-Ph | NHCOHxᶜ | H | H | H | H | CH |
| 3-702 | 4-F-Ph | NHCOHxᶜ | H | H | H | H | N |
| 3-703 | 3-F-Ph | NHCOPrᶜ | H | H | H | H | CH |
| 3-704 | 3-F-Ph | NHCOPrᶜ | H | H | H | H | N |
| 3-705 | 3-F-Ph | NHCOPnᶜ | H | H | H | H | CH |
| 3-706 | 3-F-Ph | NHCOPnᶜ | H | H | H | H | N |
| 3-707 | 4-Cl-Ph | NHCOPrᶜ | H | H | H | H | CH |
| 3-708 | 4-Cl-Ph | N(Me)COPrᶜ | H | H | H | H | CH |
| 3-709 | 4-Cl-Ph | NHCOPrᶜ | H | H | H | H | N |
| 3-710 | 4-Cl-Ph | NHCOPnᶜ | H | H | H | H | CH |
| 3-711 | 4-Cl-Ph | NHCOPnᶜ | H | H | H | H | N |
| 3-712 | 3-Cl-Ph | NHCOPrᶜ | H | H | H | H | CH |
| 3-713 | 3-Cl-Ph | NHCOPrᶜ | H | H | H | H | N |
| 3-714 | 3,4-diF-Ph | NHCOPrᶜ | H | H | H | H | CH |
| 3-715 | 3,4-diF-Ph | N(Me)COPrᶜ | H | H | H | H | CH |
| 3-716 | 3,4-diF-Ph | NHCOPrᶜ | H | H | H | H | N |
| 3-717 | 3,4-diF-Ph | NHCOPnᶜ | H | H | H | H | CH |
| 3-718 | 3,4-diF-Ph | NHCOPnᶜ | H | H | H | H | N |
| 3-719 | 3,4-diCl-Ph | NHCOPrᶜ | H | H | H | H | CH |
| 3-720 | 3,4-diCl-Ph | NHCOPrᶜ | H | H | H | H | N |
| 3-721 | 3,4-diCl-Ph | NHCOPnᶜ | H | H | H | H | CH |

TABLE 3-continued

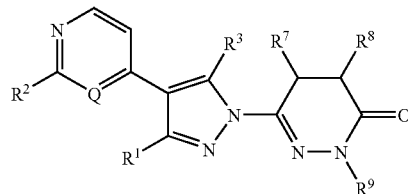

| Compound No | R¹ | R² | R³ | R⁷ | R⁸ | R⁹ | Q |
|---|---|---|---|---|---|---|---|
| 3-722 | 3,4-diCl-Ph | NHCOPn$^c$ | H | H | H | H | N |
| 3-723 | 3-Cl-4-F-Ph | NHCOPr$^c$ | H | H | H | H | CH |
| 3-724 | 3-Cl-4-F-Ph | NHCOPr$^c$ | H | H | H | H | N |
| 3-725 | 4-Cl-3-F-Ph | NHCOPr$^c$ | H | H | H | H | CH |
| 3-726 | 4-Cl-3-F-Ph | NHCOPr$^c$ | H | H | H | H | N |
| 3-727 | 3-CF$_3$-Ph | NHCOPr$^c$ | H | H | H | H | CH |
| 3-728 | 3-CF$_3$-Ph | NHCOPr$^c$ | H | H | H | H | N |
| 3-729 | 3-CF$_3$-Ph | NHCOPn$^c$ | H | H | H | H | CH |
| 3-730 | 3-CF$_3$-Ph | NHCOPn$^c$ | H | H | H | H | N |
| 3-731 | 2-F-Ph | NHCOPr$^c$ | H | H | H | H | CH |
| 3-732 | 2-F-Ph | N(Me)COPr$^c$ | H | H | H | H | CH |
| 3-733 | 2-F-Ph | NHCOPr$^c$ | H | H | H | H | N |
| 3-734 | 2-F-Ph | NHCOPn$^c$ | H | H | H | H | CH |
| 3-735 | 2-F-Ph | NHCOPn$^c$ | H | H | H | H | N |
| 3-736 | 2,4-diF-Ph | NHCOPr$^c$ | H | H | H | H | CH |
| 3-737 | 2,4-diF-Ph | NHCOPr$^c$ | H | H | H | H | N |
| 3-738 | 2,4-diF-Ph | NHCOPn$^c$ | H | H | H | H | CH |
| 3-739 | 2,4-diF-Ph | NHCOPn$^c$ | H | H | H | H | N |

TABLE 4

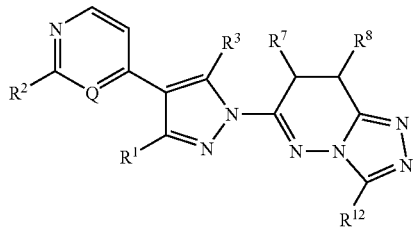

| Compound No | R¹ | R² | R³ | R⁷ | R⁸ | R⁹ | Q |
|---|---|---|---|---|---|---|---|
| 4-1 | Ph | H | H | H | H | H | CH |
| 4-2 | Ph | NH$_2$ | H | H | H | H | CH |
| 4-3 | Ph | NHMe | H | H | H | H | CH |
| 4-4 | Ph | NMe$_2$ | H | H | H | H | CH |
| 4-5 | Ph | NHEt | H | H | H | H | CH |
| 4-6 | Ph | NHPr$^i$ | H | H | H | H | CH |
| 4-7 | Ph | NHCH$_2$CF$_3$ | H | H | H | H | CH |
| 4-8 | Ph | NHPr$^c$ | H | H | H | H | CH |
| 4-9 | Ph | NHCOMe | H | H | H | H | CH |
| 4-10 | Ph | NHCOPr$^c$ | H | H | H | H | CH |
| 4-11 | Ph | N(Me)COPr$^c$ | H | H | H | H | CH |
| 4-12 | Ph | NHCOPn$^c$ | H | H | H | H | CH |
| 4-13 | Ph | NHCOOMe | H | H | H | H | CH |
| 4-14 | Ph | NHSO$_2$Me | H | H | H | H | CH |
| 4-15 | Ph | NH(α-Me-Bn) | H | H | H | H | CH |
| 4-16 | Ph | NHCOPh | H | H | H | H | CH |
| 4-17 | Ph | NH$_2$ | Me | H | H | H | CH |
| 4-18 | Ph | NH$_2$ | NH$_2$ | H | H | H | CH |
| 4-19 | Ph | NH$_2$ | H | Me | H | H | CH |
| 4-20 | Ph | NH$_2$ | H | H | Me | H | CH |
| 4-21 | Ph | NH$_2$ | H | Me | Me | H | CH |
| 4-22 | Ph | NH$_2$ | H | H | NH$_2$ | H | CH |
| 4-23 | Ph | NH$_2$ | H | H | H | Me | CH |
| 4-24 | Ph | NH$_2$ | H | H | H | CF$_3$ | CH |
| 4-25 | Ph | NH$_2$ | H | H | H | NH$_2$ | CH |
| 4-26 | Ph | NH$_2$ | H | H | H | NHMe | CH |
| 4-27 | Ph | NH$_2$ | H | H | H | NMe$_2$ | CH |

TABLE 4-continued

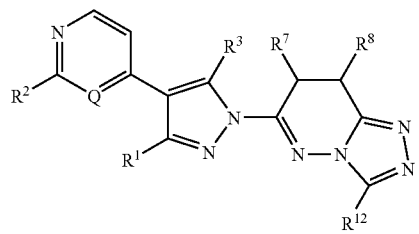

| Compound No | R¹ | R² | R³ | R⁷ | R⁸ | R⁹ | Q |
|---|---|---|---|---|---|---|---|
| 4-28 | Ph | NH₂ | H | H | H | NHCOMe | CH |
| 4-29 | Ph | NH₂ | H | H | H | NHCOOMe | CH |
| 4-30 | Ph | NH₂ | H | H | H | NHSO₂Me | CH |
| 4-31 | Ph | NH₂ | H | H | Me | Me | CH |
| 4-32 | Ph | NH₂ | H | H | Me | NH₂ | CH |
| 4-33 | Ph | NH₂ | H | H | NH₂ | Me | CH |
| 4-34 | Ph | H | H | H | H | H | N |
| 4-35 | Ph | NH₂ | H | H | H | H | N |
| 4-36 | Ph | NHMe | H | H | H | H | N |
| 4-37 | Ph | NMe₂ | H | H | H | H | N |
| 4-38 | Ph | NHEt | H | H | H | H | N |
| 4-39 | Ph | NHPrⁱ | H | H | H | H | N |
| 4-40 | Ph | NHCH₂CF₃ | H | H | H | H | N |
| 4-41 | Ph | NHCOMe | H | H | H | H | N |
| 4-42 | Ph | NHCOOMe | H | H | H | H | N |
| 4-43 | Ph | NHSO₂Me | H | H | H | H | N |
| 4-44 | Ph | NH(α-Me-Bn) | H | H | H | H | N |
| 4-45 | Ph | NH(4-OMe-Bn) | H | H | H | H | N |
| 4-46 | Ph | NHCOPh | H | H | H | H | N |
| 4-47 | Ph | NH₂ | H | H | Me | H | N |
| 4-48 | Ph | NH₂ | H | H | NH₂ | H | N |
| 4-49 | Ph | NH₂ | H | H | H | Me | N |
| 4-50 | Ph | NH₂ | H | H | H | NH₂ | N |
| 4-51 | 4-F-Ph | H | H | H | H | H | CH |
| 4-52 | 4-F-Ph | H | NH₂ | H | H | H | CH |
| 4-53 | 4-F-Ph | H | H | H | Me | H | CH |
| 4-54 | 4-F-Ph | H | H | H | NH₂ | H | CH |
| 4-55 | 4-F-Ph | H | H | H | NHMe | H | CH |
| 4-56 | 4-F-Ph | H | H | H | NMe₂ | H | CH |
| 4-57 | 4-F-Ph | H | H | H | H | Me | CH |
| 4-58 | 4-F-Ph | H | H | H | H | CF₃ | CH |
| 4-59 | 4-F-Ph | H | H | H | H | NH₂ | CH |
| 4-60 | 4-F-Ph | H | H | H | H | NHMe | CH |
| 4-61 | 4-F-Ph | H | H | H | H | NMe₂ | CH |
| 4-62 | 4-F-Ph | H | H | H | H | NHCOMe | CH |
| 4-63 | 4-F-Ph | H | H | H | H | NHCOOMe | CH |
| 4-64 | 4-F-Ph | H | H | H | H | NHSO₂Me | CH |
| 4-65 | 4-F-Ph | F | H | H | H | H | CH |
| 4-66 | 4-F-Ph | Cl | H | H | H | H | CH |
| 4-67 | 4-F-Ph | Me | H | H | H | H | CH |
| 4-68 | 4-F-Ph | OMe | H | H | H | H | CH |
| 4-69 | 4-F-Ph | SMe | H | H | H | H | CH |
| 4-70 | 4-F-Ph | NH₂ | H | H | H | H | CH |
| 4-71 | 4-F-Ph | NHMe | H | H | H | H | CH |
| 4-72 | 4-F-Ph | NMe₂ | H | H | H | H | CH |
| 4-73 | 4-F-Ph | NHEt | H | H | H | H | CH |
| 4-74 | 4-F-Ph | NEt₂ | H | H | H | H | CH |
| 4-75 | 4-F-Ph | NHPrⁱ | H | H | H | H | CH |
| 4-76 | 4-F-Ph | NHCH₂CF₃ | H | H | H | H | CH |
| 4-77 | 4-F-Ph | NHPrᶜ | H | H | H | H | CH |
| 4-78 | 4-F-Ph | NHCHO | H | H | H | H | CH |
| 4-79 | 4-F-Ph | NHCOMe | H | H | H | H | CH |
| 4-80 | 4-F-Ph | NHCOEt | H | H | H | H | CH |
| 4-81 | 4-F-Ph | NHCOPrᶜ | H | H | H | H | CH |
| 4-82 | 4-F-Ph | N(Me)COPrᶜ | H | H | H | H | CH |
| 4-83 | 4-F-Ph | NHCOPnᶜ | H | H | H | H | CH |
| 4-84 | 4-F-Ph | NHCOHxᶜ | H | H | H | H | CH |
| 4-85 | 4-F-Ph | NHCOOMe | H | H | H | H | CH |
| 4-86 | 4-F-Ph | NHCOOEt | H | H | H | H | CH |
| 4-87 | 4-F-Ph | NHSO₂Me | H | H | H | H | CH |
| 4-88 | 4-F-Ph | NHSO₂Et | H | H | H | H | CH |
| 4-89 | 4-F-Ph | NH(4-F-Bn) | H | H | H | H | CH |
| 4-90 | 4-F-Ph | NH(α-Me-Bn) | H | H | H | H | CH |
| 4-91 | 4-F-Ph | NHCOPh | H | H | H | H | CH |

TABLE 4-continued

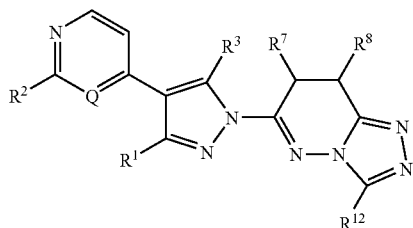

| Compound No | R¹ | R² | R³ | R⁷ | R⁸ | R⁹ | Q |
|---|---|---|---|---|---|---|---|
| 4-92 | 4-F-Ph | NH₂ | Me | H | H | H | CH |
| 4-93 | 4-F-Ph | NH₂ | NH₂ | H | H | H | CH |
| 4-94 | 4-F-Ph | NH₂ | H | Me | H | H | CH |
| 4-95 | 4-F-Ph | NH₂ | H | H | Me | H | CH |
| 4-96 | 4-F-Ph | NH₂ | H | Me | Me | H | CH |
| 4-97 | 4-F-Ph | NH₂ | H | H | NH₂ | H | CH |
| 4-98 | 4-F-Ph | NH₂ | H | H | NHMe | H | CH |
| 4-99 | 4-F-Ph | NH₂ | H | H | NMe₂ | H | CH |
| 4-100 | 4-F-Ph | NH₂ | H | H | NHCOMe | H | CH |
| 4-101 | 4-F-Ph | NH₂ | H | H | NHCOOMe | H | CH |
| 4-102 | 4-F-Ph | NH₂ | H | H | NHSO₂Me | H | CH |
| 4-103 | 4-F-Ph | NH₂ | H | H | H | Me | CH |
| 4-104 | 4-F-Ph | NH₂ | H | H | H | CF₃ | CH |
| 4-105 | 4-F-Ph | NH₂ | H | H | H | CH₂CF₃ | CH |
| 4-106 | 4-F-Ph | NH₂ | H | H | H | NH₂ | CH |
| 4-107 | 4-F-Ph | NH₂ | H | H | H | NHMe | CH |
| 4-108 | 4-F-Ph | NH₂ | H | H | H | NMe₂ | CH |
| 4-109 | 4-F-Ph | NH₂ | H | H | H | NHCOMe | CH |
| 4-110 | 4-F-Ph | NH₂ | H | H | H | NHCOOMe | CH |
| 4-111 | 4-F-Ph | NH₂ | H | H | H | NHSO₂Me | CH |
| 4-112 | 4-F-Ph | NH₂ | H | H | Me | Me | CH |
| 4-113 | 4-F-Ph | NH₂ | H | H | Me | NH₂ | CH |
| 4-114 | 4-F-Ph | NH₂ | H | H | NH₂ | Me | CH |
| 4-115 | 4-F-Ph | H | H | H | H | H | N |
| 4-116 | 4-F-Ph | H | NH₂ | H | H | H | N |
| 4-117 | 4-F-Ph | H | H | H | Me | H | N |
| 4-118 | 4-F-Ph | H | H | H | NH₂ | H | N |
| 4-119 | 4-F-Ph | NH₂ | H | H | H | H | N |
| 4-120 | 4-F-Ph | NHMe | H | H | H | H | N |
| 4-121 | 4-F-Ph | NMe₂ | H | H | H | H | N |
| 4-122 | 4-F-Ph | NHEt | H | H | H | H | N |
| 4-123 | 4-F-Ph | NHPrⁱ | H | H | H | H | N |
| 4-124 | 4-F-Ph | NHCH₂CF₃ | H | H | H | H | N |
| 4-125 | 4-F-Ph | NHPrᶜ | H | H | H | H | N |
| 4-126 | 4-F-Ph | NHCOMe | H | H | H | H | N |
| 4-127 | 4-F-Ph | NHCOPrᶜ | H | H | H | H | N |
| 4-128 | 4-F-Ph | NHCOPnᶜ | H | H | H | H | N |
| 4-129 | 4-F-Ph | NHCOOMe | H | H | H | H | N |
| 4-130 | 4-F-Ph | NHSO₂Me | H | H | H | H | N |
| 4-131 | 4-F-Ph | NH(α-Me-Bn) | H | H | H | H | N |
| 4-132 | 4-F-Ph | NH(4-OMe-Bn) | H | H | H | H | N |
| 4-133 | 4-F-Ph | NHCOPh | H | H | H | H | N |
| 4-134 | 4-F-Ph | NH₂ | H | H | Me | H | N |
| 4-135 | 4-F-Ph | NH₂ | H | H | NH₂ | H | N |
| 4-136 | 4-F-Ph | NH₂ | H | H | H | Me | N |
| 4-137 | 4-F-Ph | NH₂ | H | H | H | NH₂ | N |
| 4-138 | 3-F-Ph | H | H | H | H | H | CH |
| 4-139 | 3-F-Ph | NH₂ | H | H | H | H | CH |
| 4-140 | 3-F-Ph | NHMe | H | H | H | H | CH |
| 4-141 | 3-F-Ph | NMe₂ | H | H | H | H | CH |
| 4-142 | 3-F-Ph | NHEt | H | H | H | H | CH |
| 4-143 | 3-F-Ph | NHPrⁱ | H | H | H | H | CH |
| 4-144 | 3-F-Ph | NHCH₂CF₃ | H | H | H | H | CH |
| 4-145 | 3-F-Ph | NHPrᶜ | H | H | H | H | CH |
| 4-146 | 3-F-Ph | NHCOMe | H | H | H | H | CH |
| 4-147 | 3-F-Ph | NHCOPrᶜ | H | H | H | H | CH |
| 4-148 | 3-F-Ph | N(Me)COPrᶜ | H | H | H | H | CH |
| 4-149 | 3-F-Ph | NHCOPnᶜ | H | H | H | H | CH |
| 4-150 | 3-F-Ph | NHCOOMe | H | H | H | H | CH |
| 4-151 | 3-F-Ph | NHSO₂Me | H | H | H | H | CH |
| 4-152 | 3-F-Ph | NH(α-Me-Bn) | H | H | H | H | CH |
| 4-153 | 3-F-Ph | NHCOPh | H | H | H | H | CH |
| 4-154 | 3-F-Ph | NH₂ | Me | H | H | H | CH |
| 4-155 | 3-F-Ph | NH₂ | NH₂ | H | H | H | CH |

TABLE 4-continued

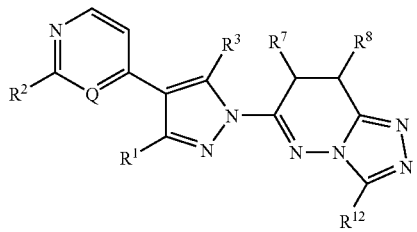

| Compound No | $R^1$ | $R^2$ | $R^3$ | $R^7$ | $R^8$ | $R^9$ | Q |
|---|---|---|---|---|---|---|---|
| 4-156 | 3-F-Ph | $NH_2$ | H | Me | H | H | CH |
| 4-157 | 3-F-Ph | $NH_2$ | H | H | Me | H | CH |
| 4-158 | 3-F-Ph | $NH_2$ | H | Me | Me | H | CH |
| 4-159 | 3-F-Ph | $NH_2$ | H | H | $NH_2$ | H | CH |
| 4-160 | 3-F-Ph | $NH_2$ | H | H | H | Me | CH |
| 4-161 | 3-F-Ph | $NH_2$ | H | H | H | $CF_3$ | CH |
| 4-162 | 3-F-Ph | $NH_2$ | H | H | H | $NH_2$ | CH |
| 4-163 | 3-F-Ph | $NH_2$ | H | H | H | NHMe | CH |
| 4-164 | 3-F-Ph | $NH_2$ | H | H | H | $NMe_2$ | CH |
| 4-165 | 3-F-Ph | $NH_2$ | H | H | H | NHCOMe | CH |
| 4-166 | 3-F-Ph | $NH_2$ | H | H | H | NHCOOMe | CH |
| 4-167 | 3-F-Ph | $NH_2$ | H | H | H | $NHSO_2Me$ | CH |
| 4-168 | 3-F-Ph | $NH_2$ | H | H | Me | Me | CH |
| 4-169 | 3-F-Ph | $NH_2$ | H | H | Me | $NH_2$ | CH |
| 4-170 | 3-F-Ph | $NH_2$ | H | H | $NH_2$ | Me | CH |
| 4-171 | 3-F-Ph | H | H | H | H | H | N |
| 4-172 | 3-F-Ph | $NH_2$ | H | H | H | H | N |
| 4-173 | 3-F-Ph | NHMe | H | H | H | H | N |
| 4-174 | 3-F-Ph | $NMe_2$ | H | H | H | H | N |
| 4-175 | 3-F-Ph | NHEt | H | H | H | H | N |
| 4-176 | 3-F-Ph | NHPr$^i$ | H | H | H | H | N |
| 4-177 | 3-F-Ph | $NHCH_2CF_3$ | H | H | H | H | N |
| 4-178 | 3-F-Ph | NHCOMe | H | H | H | H | N |
| 4-179 | 3-F-Ph | NHCOOMe | H | H | H | H | N |
| 4-180 | 3-F-Ph | $NHSO_2Me$ | H | H | H | H | N |
| 4-181 | 3-F-Ph | NH(α-Me-Bn) | H | H | H | H | N |
| 4-182 | 3-F-Ph | NH(4-OMe-Bn) | H | H | H | H | N |
| 4-183 | 3-F-Ph | NHCOPh | H | H | H | H | N |
| 4-184 | 3-F-Ph | $NH_2$ | H | H | Me | H | N |
| 4-185 | 3-F-Ph | $NH_2$ | H | H | $NH_2$ | H | N |
| 4-186 | 3-F-Ph | $NH_2$ | H | H | H | Me | N |
| 4-187 | 3-F-Ph | $NH_2$ | H | H | H | $NH_2$ | N |
| 4-188 | 2-F-Ph | H | H | H | H | H | CH |
| 4-189 | 2-F-Ph | H | $NH_2$ | H | H | H | CH |
| 4-190 | 2-F-Ph | H | H | H | Me | H | CH |
| 4-191 | 2-F-Ph | H | H | H | $NH_2$ | H | CH |
| 4-192 | 2-F-Ph | H | H | H | H | Me | CH |
| 4-193 | 2-F-Ph | H | H | H | H | $CF_3$ | CH |
| 4-194 | 2-F-Ph | H | H | H | H | $NH_2$ | CH |
| 4-195 | 2-F-Ph | H | H | H | H | NHCOMe | CH |
| 4-196 | 2-F-Ph | H | H | H | H | NHCOOMe | CH |
| 4-197 | 2-F-Ph | H | H | H | H | $NHSO_2Me$ | CH |
| 4-198 | 2-F-Ph | F | H | H | H | H | CH |
| 4-199 | 2-F-Ph | Cl | H | H | H | H | CH |
| 4-200 | 2-F-Ph | Me | H | H | H | H | CH |
| 4-201 | 2-F-Ph | OMe | H | H | H | H | CH |
| 4-202 | 2-F-Ph | SMe | H | H | H | H | CH |
| 4-203 | 2-F-Ph | $NH_2$ | H | H | H | H | CH |
| 4-204 | 2-F-Ph | NHMe | H | H | H | H | CH |
| 4-205 | 2-F-Ph | $NMe_2$ | H | H | H | H | CH |
| 4-206 | 2-F-Ph | NHEt | H | H | H | H | CH |
| 4-207 | 2-F-Ph | $NEt_2$ | H | H | H | H | CH |
| 4-208 | 2-F-Ph | NHPr$^i$ | H | H | H | H | CH |
| 4-209 | 2-F-Ph | $NHCH_2CF_3$ | H | H | H | H | CH |
| 4-210 | 2-F-Ph | NHPr$^c$ | H | H | H | H | CH |
| 4-211 | 2-F-Ph | NHCHO | H | H | H | H | CH |
| 4-212 | 2-F-Ph | NHCOMe | H | H | H | H | CH |
| 4-213 | 2-F-Ph | NHCOEt | H | H | H | H | CH |
| 4-214 | 2-F-Ph | NHCOPr$^c$ | H | H | H | H | CH |
| 4-215 | 2-F-Ph | N(Me)COPr$^c$ | H | H | H | H | CH |
| 4-216 | 2-F-Ph | NHCOPn$^c$ | H | H | H | H | CH |
| 4-217 | 2-F-Ph | NHCOHx$^c$ | H | H | H | H | CH |
| 4-218 | 2-F-Ph | NHCOOMe | H | H | H | H | CH |
| 4-219 | 2-F-Ph | NHCOOEt | H | H | H | H | CH |

TABLE 4-continued

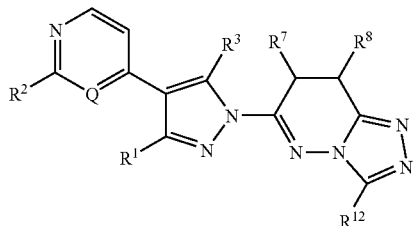

| Compound No | R¹ | R² | R³ | R⁷ | R⁸ | R⁹ | Q |
|---|---|---|---|---|---|---|---|
| 4-220 | 2-F-Ph | NHSO₂Me | H | H | H | H | CH |
| 4-221 | 2-F-Ph | NHSO₂Et | H | H | H | H | CH |
| 4-222 | 2-F-Ph | NH(4-F-Bn) | H | H | H | H | CH |
| 4-223 | 2-F-Ph | NH(α-Me-Bn) | H | H | H | H | CH |
| 4-224 | 2-F-Ph | NHCOPh | H | H | H | H | CH |
| 4-225 | 2-F-Ph | NH₂ | Me | H | H | H | CH |
| 4-226 | 2-F-Ph | NH₂ | NH₂ | H | H | H | CH |
| 4-227 | 2-F-Ph | NH₂ | H | Me | H | H | CH |
| 4-228 | 2-F-Ph | NH₂ | H | H | Me | H | CH |
| 4-229 | 2-F-Ph | NH₂ | H | Me | Me | H | CH |
| 4-230 | 2-F-Ph | NH₂ | H | H | NH₂ | H | CH |
| 4-231 | 2-F-Ph | NH₂ | H | H | NHMe | H | CH |
| 4-232 | 2-F-Ph | NH₂ | H | H | NMe₂ | H | CH |
| 4-233 | 2-F-Ph | NH₂ | H | H | NHCOMe | H | CH |
| 4-234 | 2-F-Ph | NH₂ | H | H | NHCOOMe | H | CH |
| 4-235 | 2-F-Ph | NH₂ | H | H | NHSO₂Me | H | CH |
| 4-236 | 2-F-Ph | NH₂ | H | H | H | Me | CH |
| 4-237 | 2-F-Ph | NH₂ | H | H | H | CF₃ | CH |
| 4-238 | 2-F-Ph | NH₂ | H | H | H | CH₂CF₃ | CH |
| 4-239 | 2-F-Ph | NH₂ | H | H | H | NH₂ | CH |
| 4-240 | 2-F-Ph | NH₂ | H | H | H | NHMe | CH |
| 4-241 | 2-F-Ph | NH₂ | H | H | H | NMe₂ | CH |
| 4-242 | 2-F-Ph | NH₂ | H | H | H | NHCOMe | CH |
| 4-243 | 2-F-Ph | NH₂ | H | H | H | NHCOOMe | CH |
| 4-244 | 2-F-Ph | NH₂ | H | H | H | NHSO₂Me | CH |
| 4-245 | 2-F-Ph | NH₂ | H | H | Me | Me | CH |
| 4-246 | 2-F-Ph | NH₂ | H | H | Me | NH₂ | CH |
| 4-247 | 2-F-Ph | NH₂ | H | H | NH₂ | Me | CH |
| 4-248 | 2-F-Ph | H | H | H | H | H | N |
| 4-249 | 2-F-Ph | H | NH₂ | H | H | H | N |
| 4-250 | 2-F-Ph | H | H | H | Me | H | N |
| 4-251 | 2-F-Ph | H | H | H | NH₂ | H | N |
| 4-252 | 2-F-Ph | NH₂ | H | H | H | H | N |
| 4-253 | 2-F-Ph | NHMe | H | H | H | H | N |
| 4-254 | 2-F-Ph | NMe₂ | H | H | H | H | N |
| 4-255 | 2-F-Ph | NHEt | H | H | H | H | N |
| 4-256 | 2-F-Ph | NHPrⁱ | H | H | H | H | N |
| 4-257 | 2-F-Ph | NHCH₂CF₃ | H | H | H | H | N |
| 4-258 | 2-F-Ph | NHPrᶜ | H | H | H | H | N |
| 4-259 | 2-F-Ph | NHCOMe | H | H | H | H | N |
| 4-260 | 2-F-Ph | NHCOPrᶜ | H | H | H | H | N |
| 4-261 | 2-F-Ph | NHCOPnᶜ | H | H | H | H | N |
| 4-262 | 2-F-Ph | NHCOOMe | H | H | H | H | N |
| 4-263 | 2-F-Ph | NHSO₂Me | H | H | H | H | N |
| 4-264 | 2-F-Ph | NH(α-Me-Bn) | H | H | H | H | N |
| 4-265 | 2-F-Ph | NH(4-OMe-Bn) | H | H | H | H | N |
| 4-266 | 2-F-Ph | NHCOPh | H | H | H | H | N |
| 4-267 | 2-F-Ph | NH₂ | H | H | Me | H | N |
| 4-268 | 2-F-Ph | NH₂ | H | H | NH₂ | H | N |
| 4-269 | 2-F-Ph | NH₂ | H | H | H | Me | N |
| 4-270 | 2-F-Ph | NH₂ | H | H | H | NH₂ | N |
| 4-271 | 4-Cl-Ph | H | H | H | H | H | CH |
| 4-272 | 4-Cl-Ph | H | NH₂ | H | H | H | CH |
| 4-273 | 4-Cl-Ph | H | H | H | Me | H | CH |
| 4-274 | 4-Cl-Ph | H | H | H | NH₂ | H | CH |
| 4-275 | 4-Cl-Ph | H | H | H | H | Me | CH |
| 4-276 | 4-Cl-Ph | H | H | H | H | CF₃ | CH |
| 4-277 | 4-Cl-Ph | H | H | H | H | NH₂ | CH |
| 4-278 | 4-Cl-Ph | Me | H | H | H | H | CH |
| 4-279 | 4-Cl-Ph | OMe | H | H | H | H | CH |
| 4-280 | 4-Cl-Ph | SMe | H | H | H | H | CH |
| 4-281 | 4-Cl-Ph | NH₂ | H | H | H | H | CH |
| 4-282 | 4-Cl-Ph | NHMe | H | H | H | H | CH |
| 4-283 | 4-Cl-Ph | NMe₂ | H | H | H | H | CH |

TABLE 4-continued

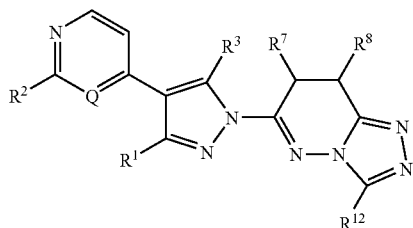

| Compound No | R¹ | R² | R³ | R⁷ | R⁸ | R⁹ | Q |
|---|---|---|---|---|---|---|---|
| 4-284 | 4-Cl-Ph | NHEt | H | H | H | H | CH |
| 4-285 | 4-Cl-Ph | NHPr$^i$ | H | H | H | H | CH |
| 4-286 | 4-Cl-Ph | NHCH$_2$CF$_3$ | H | H | H | H | CH |
| 4-287 | 4-Cl-Ph | NHPr$^c$ | H | H | H | H | CH |
| 4-288 | 4-Cl-Ph | NHCHO | H | H | H | H | CH |
| 4-289 | 4-Cl-Ph | NHCOMe | H | H | H | H | CH |
| 4-290 | 4-Cl-Ph | NHCOEt | H | H | H | H | CH |
| 4-291 | 4-Cl-Ph | NHCOPr$^c$ | H | H | H | H | CH |
| 4-292 | 4-Cl-Ph | N(Me)COPr$^c$ | H | H | H | H | CH |
| 4-293 | 4-Cl-Ph | NHCOPn$^c$ | H | H | H | H | CH |
| 4-294 | 4-Cl-Ph | NHCOHx$^c$ | H | H | H | H | CH |
| 4-295 | 4-Cl-Ph | NHCOOMe | H | H | H | H | CH |
| 4-296 | 4-Cl-Ph | NHCOOEt | H | H | H | H | CH |
| 4-297 | 4-Cl-Ph | NHSO$_2$Me | H | H | H | H | CH |
| 4-298 | 4-Cl-Ph | NHSO$_2$Et | H | H | H | H | CH |
| 4-299 | 4-Cl-Ph | NH(4-F-Bn) | H | H | H | H | CH |
| 4-300 | 4-Cl-Ph | NH(α-Me-Bn) | H | H | H | H | CH |
| 4-301 | 4-Cl-Ph | NHCOPh | H | H | H | H | CH |
| 4-302 | 4-Cl-Ph | NH$_2$ | Me | H | H | H | CH |
| 4-303 | 4-Cl-Ph | NH$_2$ | NH$_2$ | H | H | H | CH |
| 4-304 | 4-Cl-Ph | NH$_2$ | H | Me | H | H | CH |
| 4-305 | 4-Cl-Ph | NH$_2$ | H | H | Me | H | CH |
| 4-306 | 4-Cl-Ph | NH$_2$ | H | Me | Me | H | CH |
| 4-307 | 4-Cl-Ph | NH$_2$ | H | H | NH$_2$ | H | CH |
| 4-308 | 4-Cl-Ph | NH$_2$ | H | H | NHCOMe | H | CH |
| 4-309 | 4-Cl-Ph | NH$_2$ | H | H | NHCOOMe | H | CH |
| 4-310 | 4-Cl-Ph | NH$_2$ | H | H | NHSO$_2$Me | H | CH |
| 4-311 | 4-Cl-Ph | NH$_2$ | H | H | H | Me | CH |
| 4-312 | 4-Cl-Ph | NH$_2$ | H | H | H | CF$_3$ | CH |
| 4-313 | 4-Cl-Ph | NH$_2$ | H | H | H | NH$_2$ | CH |
| 4-314 | 4-Cl-Ph | NH$_2$ | H | H | H | NHMe | CH |
| 4-315 | 4-Cl-Ph | NH$_2$ | H | H | H | NMe$_2$ | CH |
| 4-316 | 4-Cl-Ph | NH$_2$ | H | H | H | NHCOMe | CH |
| 4-317 | 4-Cl-Ph | NH$_2$ | H | H | H | NHCOOMe | CH |
| 4-318 | 4-Cl-Ph | NH$_2$ | H | H | H | NHSO$_2$Me | CH |
| 4-319 | 4-Cl-Ph | NH$_2$ | H | H | Me | Me | CH |
| 4-320 | 4-Cl-Ph | NH$_2$ | H | H | Me | NH$_2$ | CH |
| 4-321 | 4-Cl-Ph | NH$_2$ | H | H | NH$_2$ | Me | CH |
| 4-322 | 4-Cl-Ph | H | H | H | H | H | N |
| 4-323 | 4-Cl-Ph | H | NH$_2$ | H | H | H | N |
| 4-324 | 4-Cl-Ph | H | H | H | Me | H | N |
| 4-325 | 4-Cl-Ph | H | H | H | NH$_2$ | H | N |
| 4-326 | 4-Cl-Ph | NH$_2$ | H | H | H | H | N |
| 4-327 | 4-Cl-Ph | NHMe | H | H | H | H | N |
| 4-328 | 4-Cl-Ph | NMe$_2$ | H | H | H | H | N |
| 4-329 | 4-Cl-Ph | NHEt | H | H | H | H | N |
| 4-330 | 4-Cl-Ph | NHPr$^i$ | H | H | H | H | N |
| 4-331 | 4-Cl-Ph | NHCH$_2$CF$_3$ | H | H | H | H | N |
| 4-332 | 4-Cl-Ph | NHPr$^c$ | H | H | H | H | N |
| 4-333 | 4-Cl-Ph | NHCOMe | H | H | H | H | N |
| 4-334 | 4-Cl-Ph | NHCOPr$^c$ | H | H | H | H | N |
| 4-335 | 4-Cl-Ph | NHCOOMe | H | H | H | H | N |
| 4-336 | 4-Cl-Ph | NHSO$_2$Me | H | H | H | H | N |
| 4-337 | 4-Cl-Ph | NH(α-Me-Bn) | H | H | H | H | N |
| 4-338 | 4-Cl-Ph | NH(4-OMe-Bn) | H | H | H | H | N |
| 4-339 | 4-Cl-Ph | NHCOPh | H | H | H | H | N |
| 4-340 | 4-Cl-Ph | NH$_2$ | H | H | Me | H | N |
| 4-341 | 4-Cl-Ph | NH$_2$ | H | H | NH$_2$ | H | N |
| 4-342 | 4-Cl-Ph | NH$_2$ | H | H | H | Me | N |
| 4-343 | 4-Cl-Ph | NH$_2$ | H | H | H | NH$_2$ | N |
| 4-344 | 3-Cl-Ph | H | H | H | H | H | CH |
| 4-345 | 3-Cl-Ph | NH$_2$ | H | H | H | H | CH |
| 4-346 | 3-Cl-Ph | NHMe | H | H | H | H | CH |
| 4-347 | 3-Cl-Ph | NHEt | H | H | H | H | CH |

TABLE 4-continued

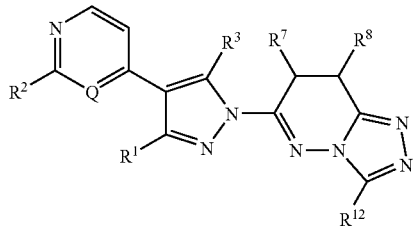

| Compound No | $R^1$ | $R^2$ | $R^3$ | $R^7$ | $R^8$ | $R^9$ | Q |
|---|---|---|---|---|---|---|---|
| 4-348 | 3-Cl-Ph | NHPr$^i$ | H | H | H | H | CH |
| 4-349 | 3-Cl-Ph | NHCH$_2$CF$_3$ | H | H | H | H | CH |
| 4-350 | 3-Cl-Ph | NHPr$^c$ | H | H | H | H | CH |
| 4-351 | 3-Cl-Ph | NHCOMe | H | H | H | H | CH |
| 4-352 | 3-Cl-Ph | NHCOPr$^c$ | H | H | H | H | CH |
| 4-353 | 3-Cl-Ph | NHCOPn$^c$ | H | H | H | H | CH |
| 4-354 | 3-Cl-Ph | NHCOOMe | H | H | H | H | CH |
| 4-355 | 3-Cl-Ph | NHSO$_2$Me | H | H | H | H | CH |
| 4-356 | 3-Cl-Ph | NH(α-Me-Bn) | H | H | H | H | CH |
| 4-357 | 3-Cl-Ph | NHCOPh | H | H | H | H | CH |
| 4-358 | 3-Cl-Ph | NH$_2$ | H | Me | H | H | CH |
| 4-359 | 3-Cl-Ph | NH$_2$ | H | H | Me | H | CH |
| 4-360 | 3-Cl-Ph | NH$_2$ | H | Me | Me | H | CH |
| 4-361 | 3-Cl-Ph | NH$_2$ | H | H | NH$_2$ | H | CH |
| 4-362 | 3-Cl-Ph | NH$_2$ | H | H | H | Me | CH |
| 4-363 | 3-Cl-Ph | NH$_2$ | H | H | H | CF$_3$ | CH |
| 4-364 | 3-Cl-Ph | NH$_2$ | H | H | H | NH$_2$ | CH |
| 4-365 | 3-Cl-Ph | NH$_2$ | H | H | H | NHMe | CH |
| 4-366 | 3-Cl-Ph | NH$_2$ | H | H | H | NMe$_2$ | CH |
| 4-367 | 3-Cl-Ph | NH$_2$ | H | H | H | NHCOMe | CH |
| 4-368 | 3-Cl-Ph | NH$_2$ | H | H | H | NHCOOMe | CH |
| 4-369 | 3-Cl-Ph | NH$_2$ | H | H | H | NHSO$_2$Me | CU |
| 4-370 | 3-Cl-Ph | NH$_2$ | H | H | Me | Me | CH |
| 4-371 | 3-Cl-Ph | NH$_2$ | H | H | Me | NH$_2$ | CH |
| 4-372 | 3-Cl-Ph | NH$_2$ | H | H | NH$_2$ | Me | CU |
| 4-373 | 3-Cl-Ph | H | H | H | H | H | N |
| 4-374 | 3-Cl-Ph | NH$_2$ | H | H | H | H | N |
| 4-375 | 3-Cl-Ph | NHMe | H | H | H | H | N |
| 4-376 | 3-Cl-Ph | NHEt | H | H | H | H | N |
| 4-377 | 3-Cl-Ph | NHPr$^i$ | H | H | H | H | N |
| 4-378 | 3-Cl-Ph | NHCH$_2$CF$_3$ | H | H | H | H | N |
| 4-379 | 3-Cl-Ph | NHCOMe | H | H | H | H | N |
| 4-380 | 3-Cl-Ph | NHCOOMe | H | H | H | H | N |
| 4-381 | 3-Cl-Ph | NHSO$_2$Me | H | H | H | H | N |
| 4-382 | 3-Cl-Ph | NH(α-Me-Bn) | H | H | H | H | N |
| 4-383 | 3-Cl-Ph | NHCOPh | H | H | H | H | N |
| 4-384 | 3-Cl-Ph | NH$_2$ | H | H | Me | H | N |
| 4-385 | 3-Cl-Ph | NH$_2$ | H | H | NH$_2$ | H | N |
| 4-386 | 3-Cl-Ph | NH$_2$ | H | H | H | Me | N |
| 4-387 | 3-Cl-Ph | NH$_2$ | H | H | H | NH$_2$ | N |
| 4-388 | 3,4-diF-Ph | H | H | H | H | H | CH |
| 4-389 | 3,4-diF-Ph | H | NH$_2$ | H | H | H | CH |
| 4-390 | 3,4-diF-Ph | H | H | H | Me | H | CH |
| 4-391 | 3,4-diF-Ph | H | H | H | NH$_2$ | H | CH |
| 4-392 | 3,4-diF-Ph | H | H | H | H | Me | CH |
| 4-393 | 3,4-diF-Ph | H | H | H | H | CF$_3$ | CH |
| 4-394 | 3,4-diF-Ph | H | H | H | H | NH$_2$ | CH |
| 4-395 | 3,4-diF-Ph | Me | H | H | H | H | CH |
| 4-396 | 3,4-diF-Ph | OMe | H | H | H | H | CH |
| 4-397 | 3,4-diF-Ph | SMe | H | H | H | H | CH |
| 4-398 | 3,4-diF-Ph | NH$_2$ | H | H | H | H | CH |
| 4-399 | 3,4-diF-Ph | NHMe | H | H | H | H | CH |
| 4-400 | 3,4-diF-Ph | NMe$_2$ | H | H | H | H | CH |
| 4-401 | 3,4-diF-Ph | NHEt | H | H | H | H | CH |
| 4-402 | 3,4-diF-Ph | NHPr$^i$ | H | H | H | H | CH |
| 4-403 | 3,4-diF-Ph | NHCH$_2$CF$_3$ | H | H | H | H | CH |
| 4-404 | 3,4-diF-Ph | NHPr$^c$ | H | H | H | H | CH |
| 4-405 | 3,4-diF-Ph | NHCHO | H | H | H | H | CH |
| 4-406 | 3,4-diF-Ph | NHCOMe | H | H | H | H | CH |
| 4-407 | 3,4-diF-Ph | NHCOEt | H | H | H | H | CH |
| 4-408 | 3,4-diF-Ph | NHCOPr$^c$ | H | H | H | H | CH |
| 4-409 | 3,4-diF-Ph | N(Me)COPr$^c$ | H | H | H | H | CH |
| 4-410 | 3,4-diF-Ph | NHCOPn$^c$ | H | H | H | H | CH |
| 4-411 | 3,4-diF-Ph | NHCOHx$^c$ | H | H | H | H | CH |

TABLE 4-continued

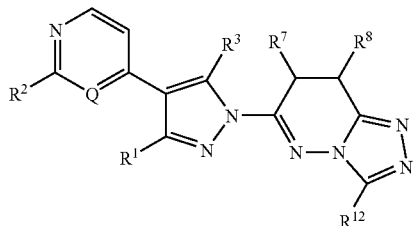

| Compound No | R¹ | R² | R³ | R⁷ | R⁸ | R⁹ | Q |
|---|---|---|---|---|---|---|---|
| 4-412 | 3,4-diF-Ph | NHCOOMe | H | H | H | H | CH |
| 4-413 | 3,4-diF-Ph | NHCOOEt | H | H | H | H | CH |
| 4-414 | 3,4-diF-Ph | NHSO₂Me | H | H | H | H | CH |
| 4-415 | 3,4-diF-Ph | NHSO₂Et | H | H | H | H | CH |
| 4-416 | 3,4-diF-Ph | NH(4-F-Bn) | H | H | H | H | CH |
| 4-417 | 3,4-diF-Ph | NH(α-Me-Bn) | H | H | H | H | CH |
| 4-418 | 3,4-diF-Ph | NHCOPh | H | H | H | H | CH |
| 4-419 | 3,4-diF-Ph | NH₂ | Me | H | H | H | CH |
| 4-420 | 3,4-diF-Ph | NH₂ | NH₂ | H | H | H | CH |
| 4-421 | 3,4-diF-Ph | NH₂ | H | Me | H | H | CH |
| 4-422 | 3,4-diF-Ph | NH₂ | H | H | Me | H | CH |
| 4-423 | 3,4-diF-Ph | NH₂ | H | Me | Me | H | CH |
| 4-424 | 3,4-diF-Ph | NH₂ | H | H | NH₂ | H | CH |
| 4-425 | 3,4-diF-Ph | NH₂ | H | H | NHCOMe | H | CH |
| 4-426 | 3,4-diF-Ph | NH₂ | H | H | NHCOOMe | H | CH |
| 4-427 | 3,4-diF-Ph | NH₂ | H | H | NHSO₂Me | H | CH |
| 4-428 | 3,4-diF-Ph | NH₂ | H | H | H | Me | CH |
| 4-429 | 3,4-diF-Ph | NH₂ | H | H | H | CF₃ | CH |
| 4-430 | 3,4-diF-Ph | NH₂ | H | H | H | NH₂ | CH |
| 4-431 | 3,4-diF-Ph | NH₂ | H | H | H | NHMe | CH |
| 4-432 | 3,4-diF-Ph | NH₂ | H | H | H | NMe₂ | CH |
| 4-433 | 3,4-diF-Ph | NH₂ | H | H | H | NHCOMe | CH |
| 4-434 | 3,4-diF-Ph | NH₂ | H | H | H | NHCOOMe | CH |
| 4-435 | 3,4-diF-Ph | NH₂ | H | H | H | NHSO₂Me | CH |
| 4-436 | 3,4-diF-Ph | NH₂ | H | H | Me | Me | CH |
| 4-437 | 3,4-diF-Ph | NH₂ | H | H | Me | NH₂ | CH |
| 4-438 | 3,4-diF-Ph | NH₂ | H | H | NH₂ | Me | CH |
| 4-439 | 3,4-diF-Ph | H | H | H | H | H | N |
| 4-440 | 3,4-diF-Ph | H | NH₂ | H | H | H | N |
| 4-441 | 3,4-diF-Ph | H | H | H | Me | H | N |
| 4-442 | 3,4-diF-Ph | H | H | H | NH₂ | H | N |
| 4-443 | 3,4-diF-Ph | NH₂ | H | H | H | H | N |
| 4-444 | 3,4-diF-Ph | NHMe | H | H | H | H | N |
| 4-445 | 3,4-diF-Ph | NMe₂ | H | H | H | H | N |
| 4-446 | 3,4-diF-Ph | NHEt | H | H | H | H | N |
| 4-447 | 3,4-diF-Ph | NHPrⁱ | H | H | H | H | N |
| 4-448 | 3,4-diF-Ph | NHCH₂CF₃ | H | H | H | H | N |
| 4-449 | 3,4-diF-Ph | NHPrᶜ | H | H | H | H | N |
| 4-450 | 3,4-diF-Ph | NHCOMe | H | H | H | H | N |
| 4-451 | 3,4-diF-Ph | NHCOPrᶜ | H | H | H | H | N |
| 4-452 | 3,4-diF-Ph | NHCOOMe | H | H | H | H | N |
| 4-453 | 3,4-diF-Ph | NHSO₂Me | H | H | H | H | N |
| 4-454 | 3,4-diF-Ph | NH(α-Me-Bn) | H | H | H | H | N |
| 4-455 | 3,4-diF-Ph | NH(4-OMe-Bn) | H | H | H | H | N |
| 4-456 | 3,4-diF-Ph | NHCOPh | H | H | H | H | N |
| 4-457 | 3,4-diF-Ph | NH₂ | H | H | Me | H | N |
| 4-458 | 3,4-diF-Ph | NH₂ | H | H | NH₂ | H | N |
| 4-459 | 3,4-diF-Ph | NH₂ | H | H | H | Me | N |
| 4-460 | 3,4-diF-Ph | NH₂ | H | H | H | NH₂ | N |
| 4-461 | 3,4-diCl-Ph | H | H | H | H | H | CH |
| 4-462 | 3,4-diCl-Ph | NH₂ | H | H | H | H | CH |
| 4-463 | 3,4-diCl-Ph | NHMe | H | H | H | H | CH |
| 4-464 | 3,4-diCl-Ph | NHEt | H | H | H | H | CH |
| 4-465 | 3,4-diCl-Ph | NHPrⁱ | H | H | H | H | CH |
| 4-466 | 3,4-diCl-Ph | NHCH₂CF₃ | H | H | H | H | CH |
| 4-467 | 3,4-diCl-Ph | NHPrᶜ | H | H | H | H | CH |
| 4-468 | 3,4-diCl-Ph | NHCOMe | H | H | H | H | CH |
| 4-469 | 3,4-diCl-Ph | NHCOPrᶜ | H | H | H | H | CH |
| 4-470 | 3,4-diCl-Ph | NHCOPnᶜ | H | H | H | H | CH |
| 4-471 | 3,4-diCl-Ph | NHCOOMe | H | H | H | H | CH |
| 4-472 | 3,4-diCl-Ph | NHSO₂Me | H | H | H | H | CH |
| 4-473 | 3,4-diCl-Ph | NH(α-Me-Bn) | H | H | H | H | CH |
| 4-474 | 3,4-diCl-Ph | NHCOPh | H | H | H | H | CH |
| 4-475 | 3,4-diCl-Ph | NH₂ | H | Me | H | H | CH |

TABLE 4-continued

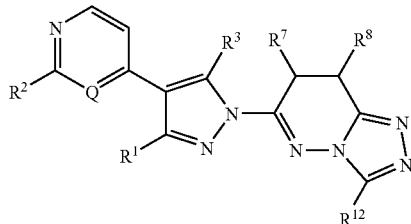

| Compound No | R¹ | R² | R³ | R⁷ | R⁸ | R⁹ | Q |
|---|---|---|---|---|---|---|---|
| 4-476 | 3,4-diCl-Ph | NH₂ | H | H | Me | H | CH |
| 4-477 | 3,4-diCl-Ph | NH₂ | H | Me | Me | H | CH |
| 4-478 | 3,4-diCl-Ph | NH₂ | H | H | NH₂ | H | CH |
| 4-479 | 3,4-diCl-Ph | NH₂ | H | H | H | Me | CH |
| 4-480 | 3,4-diCl-Ph | NH₂ | H | H | H | CF₃ | CH |
| 4-481 | 3,4-diCl-Ph | NH₂ | H | H | H | NH₂ | CH |
| 4-482 | 3,4-diCl-Ph | NH₂ | H | H | H | NHMe | CH |
| 4-483 | 3,4-diCl-Ph | NH2 | H | H | H | NMe₂ | CH |
| 4-484 | 3,4-diCl-Ph | NH₂ | H | H | H | NHCOMe | CH |
| 4-485 | 3,4-diCl-Ph | NH₂ | H | H | H | NHCOOMe | CH |
| 4-486 | 3,4-diCl-Ph | NH₂ | H | H | H | NHSO₂Me | CH |
| 4-487 | 3,4-diCl-Ph | NH₂ | H | H | Me | Me | CH |
| 4-488 | 3,4-diCl-Ph | NH₂ | H | H | Me | NH₂ | CH |
| 4-489 | 3,4-diCl-Ph | NH₂ | H | H | NH2 | Me | CH |
| 4-490 | 3,4-diCl-Ph | H | H | H | H | H | N |
| 4-491 | 3,4-diCl-Ph | NH₂ | H | H | H | H | N |
| 4-492 | 3,4-diCl-Ph | NHMe | H | H | H | H | N |
| 4-493 | 3,4-diCl-Ph | NHEt | H | H | H | H | N |
| 4-494 | 3,4-diCl-Ph | NHPrⁱ | H | H | H | H | N |
| 4-495 | 3,4-diCl-Ph | NHCH₂CF₃ | H | H | H | H | N |
| 4-496 | 3,4-diCl-Ph | NHCOMe | H | H | H | H | N |
| 4-497 | 3,4-diCl-Ph | NHCOOMe | H | H | H | H | N |
| 4-498 | 3,4-diCl-Ph | NHSO₂Me | H | H | H | H | N |
| 4-499 | 3,4-diCl-Ph | NH(α-Me-Bn) | H | H | H | H | N |
| 4-500 | 3,4-diCl-Ph | NHCOPh | H | H | H | H | N |
| 4-501 | 3,4-diCl-Ph | NH₂ | H | H | Me | H | N |
| 4-502 | 3,4-diCl-Ph | NH₂ | H | H | NH₂ | H | N |
| 4-503 | 3,4-diCl-Ph | NH₂ | H | H | H | Me | N |
| 4-504 | 3,4-diCl-Ph | NH₂ | H | H | H | NH₂ | N |
| 4-505 | 2,4-diF-Ph | H | H | H | H | H | CH |
| 4-506 | 2,4-diF-Ph | NH₂ | H | H | H | H | CH |
| 4-507 | 2,4-diF-Ph | NHMe | H | H | H | H | CH |
| 4-508 | 2,4-diF-Ph | NHEt | H | H | H | H | CH |
| 4-509 | 2,4-diF-Ph | NHPrⁱ | H | H | H | H | CH |
| 4-510 | 2,4-diF-Ph | NHCH₂CF₃ | H | H | H | H | CH |
| 4-511 | 2,4-diF-Ph | NHPrᶜ | H | H | H | H | CH |
| 4-512 | 2,4-diF-Ph | NHCOMe | H | H | H | H | CH |
| 4-513 | 2,4-diF-Ph | NHCOPrᶜ | H | H | H | H | CH |
| 4-514 | 2,4-diF-Ph | NHCOPnᶜ | H | H | H | H | CH |
| 4-515 | 2,4-diF-Ph | NHCOOMe | H | H | H | H | CH |
| 4-516 | 2,4-diF-Ph | NHSO₂Me | H | H | H | H | CH |
| 4-517 | 2,4-diF-Ph | NH(α-Me-Bn) | H | H | H | H | CH |
| 4-518 | 2,4-diF-Ph | NHCOPh | H | H | H | H | CH |
| 4-519 | 2,4-diF-Ph | NH₂ | H | Me | H | H | CH |
| 4-520 | 2,4-diF-Ph | NH₂ | H | H | Me | H | CH |
| 4-521 | 2,4-diF-Ph | NH₂ | H | Me | Me | H | CH |
| 4-522 | 2,4-diF-Ph | NH₂ | H | H | NH₂ | H | CH |
| 4-523 | 2,4-diF-Ph | NH₂ | H | H | H | Me | CH |
| 4-524 | 2,4-diF-Ph | NH₂ | H | H | H | CF₃ | CH |
| 4-525 | 2,4-diF-Ph | NH₂ | H | H | H | NH₂ | CH |
| 4-526 | 2,4-diF-Ph | NH₂ | H | H | H | NHMe | CH |
| 4-527 | 2,4-diF-Ph | NH₂ | H | H | H | NMe₂ | CH |
| 4-528 | 2,4-diF-Ph | NH₂ | H | H | H | NHCOMe | CH |
| 4-529 | 2,4-diF-Ph | NH₂ | H | H | H | NHCOOMe | CH |
| 4-530 | 2,4-diF-Ph | NH₂ | H | H | H | NHSO₂Me | CH |
| 4-531 | 2,4-diF-Ph | NH₂ | H | H | Me | Me | CH |
| 4-532 | 2,4-diF-Ph | NH₂ | H | H | Me | NH₂ | CH |
| 4-533 | 2,4-diF-Ph | NH₂ | H | H | NH₂ | Me | CH |
| 4-534 | 2,4-diF-Ph | H | H | H | H | H | N |
| 4-535 | 2,4-diF-Ph | NH₂ | H | H | H | H | N |
| 4-536 | 2,4-diF-Ph | NHMe | H | H | H | H | N |
| 4-537 | 2,4-diF-Ph | NHEt | H | H | H | H | N |
| 4-538 | 2,4-diF-Ph | NHPrⁱ | H | H | H | H | N |
| 4-539 | 2,4-diF-Ph | NHCH₂CF₃ | H | H | H | H | N |

TABLE 4-continued

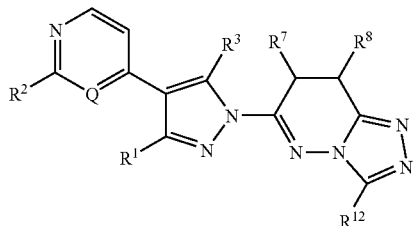

| Compound No | R¹ | R² | R³ | R⁷ | R⁸ | R⁹ | Q |
|---|---|---|---|---|---|---|---|
| 4-540 | 2,4-diF-Ph | NHCOMe | H | H | H | H | N |
| 4-541 | 2,4-diF-Ph | NHCOOMe | H | H | H | H | N |
| 4-542 | 2,4-diF-Ph | NHSO$_2$Me | H | H | H | H | N |
| 4-543 | 2,4-diF-Ph | NH(α-Me-Bn) | H | H | H | H | N |
| 4-544 | 2,4-diF-Ph | NHCOPh | H | H | H | H | N |
| 4-545 | 2,4-diF-Ph | NH$_2$ | H | H | Me | H | N |
| 4-546 | 2,4-diF-Ph | NH$_2$ | H | H | NH$_2$ | H | N |
| 4-547 | 2,4-diF-Ph | NH$_2$ | H | H | H | Me | N |
| 4-548 | 2,4-diF-Ph | NH$_2$ | H | H | H | NH$_2$ | N |
| 4-549 | 3-Cl-4-F-Ph | H | H | H | H | H | CH |
| 4-550 | 3-Cl-4-F-Ph | NH$_2$ | H | H | H | H | CH |
| 4-551 | 3-Cl-4-F-Ph | NHMe | H | H | H | H | CH |
| 4-552 | 3-Cl-4-F-Ph | NHEt | H | H | H | H | CH |
| 4-553 | 3-Cl-4-F-Ph | NHPr$^i$ | H | H | H | H | CH |
| 4-554 | 3-Cl-4-F-Ph | NHCH$_2$CF$_3$ | H | H | H | H | CH |
| 4-555 | 3-Cl-4-F-Ph | NHPr$^c$ | H | H | H | H | CH |
| 4-556 | 3-Cl-4-F-Ph | NHCOMe | H | H | H | H | CH |
| 4-557 | 3-Cl-4-F-Ph | NHCOPr$^c$ | H | H | H | H | CH |
| 4-558 | 3-Cl-4-F-Ph | NHCOPn$^c$ | H | H | H | H | CH |
| 4-559 | 3-Cl-4-F-Ph | NHCOOMe | H | H | H | H | CH |
| 4-560 | 3-Cl-4-F-Ph | NHSO$_2$Me | H | H | H | H | CH |
| 4-561 | 3-Cl-4-F-Ph | NH(α-Me-Bn) | H | H | H | H | CH |
| 4-562 | 3-Cl-4-F-Ph | NHCOPh | H | H | H | H | CH |
| 4-563 | 3-Cl-4-F-Ph | NH$_2$ | H | Me | H | H | CH |
| 4-564 | 3-Cl-4-F-Ph | NH$_2$ | H | H | Me | H | CH |
| 4-565 | 3-Cl-4-F-Ph | NH$_2$ | H | Me | Me | H | CH |
| 4-566 | 3-Cl-4-F-Ph | NH$_2$ | H | H | NH$_2$ | H | CH |
| 4-567 | 3-Cl-4-F-Ph | NH$_2$ | H | H | H | Me | CH |
| 4-568 | 3-Cl-4-F-Ph | NH$_2$ | H | H | H | CF$_3$ | CH |
| 4-569 | 3-Cl-4-F-Ph | NH$_2$ | H | H | H | NH$_2$ | CH |
| 4-570 | 3-Cl-4-F-Ph | NH$_2$ | H | H | H | NHMe | CH |
| 4-571 | 3-Cl-4-F-Ph | NH$_2$ | H | H | H | NMe$_2$ | CH |
| 4-572 | 3-Cl-4-F-Ph | NH$_2$ | H | H | H | NHCOMe | CH |
| 4-573 | 3-Cl-4-F-Ph | NH$_2$ | H | H | H | NHCOOMe | CH |
| 4-574 | 3-Cl-4-F-Ph | NH$_2$ | H | H | H | NHSO$_2$Me | CH |
| 4-575 | 3-Cl-4-F-Ph | NH$_2$ | H | H | Me | Me | CH |
| 4-576 | 3-Cl-4-F-Ph | NH$_2$ | H | H | Me | NH$_2$ | CH |
| 4-577 | 3-Cl-4-F-Ph | NH$_2$ | H | H | NH$_2$ | Me | CH |
| 4-578 | 3-Cl-4-F-Ph | H | H | H | H | H | N |
| 4-579 | 3-Cl-4-F-Ph | NH$_2$ | H | H | H | H | N |
| 4-580 | 3-Cl-4-F-Ph | NHNe | H | H | H | H | N |
| 4-581 | 3-Cl-4-F-Ph | NHEt | H | H | H | H | N |
| 4-582 | 3-Cl-4-F-Ph | NHPr$^i$ | H | H | H | H | N |
| 4-583 | 3-Cl-4-F-Ph | NHCH$_2$CF$_3$ | H | H | H | H | N |
| 4-584 | 3-Cl-4-F-Ph | NHCOMe | H | H | H | H | N |
| 4-585 | 3-Cl-4-F-Ph | NHCOOMe | H | H | H | H | N |
| 4-586 | 3-Cl-4-F-Ph | NHSO$_2$Me | H | H | H | H | N |
| 4-587 | 3-Cl-4-F-Ph | NH(α-Me-Bn) | H | H | H | H | N |
| 4-588 | 3-Cl-4-F-Ph | NHCOPh | H | H | H | H | N |
| 4-589 | 3-Cl-4-F-Ph | NH$_2$ | H | H | Me | H | N |
| 4-590 | 3-Cl-4-F-Ph | NH$_2$ | H | H | NH$_2$ | H | N |
| 4-591 | 3-Cl-4-F-Ph | NH$_2$ | H | H | H | Me | N |
| 4-592 | 3-Cl-4-F-Ph | NH$_2$ | H | H | H | NH$_2$ | N |
| 4-593 | 4-Cl-3-F-Ph | H | H | H | H | H | CH |
| 4-594 | 4-Cl-3-F-Ph | NH$_2$ | H | H | H | H | CH |
| 4-595 | 4-Cl-3-F-Ph | NHMe | H | H | H | H | CH |
| 4-596 | 4-Cl-3-F-Ph | NHEt | H | H | H | H | CH |
| 4-597 | 4-Cl-3-F-Ph | NHPr$^i$ | H | H | H | H | CH |
| 4-598 | 4-Cl-3-F-Ph | NHCH$_2$CF$_3$ | H | H | H | H | CH |
| 4-599 | 4-Cl-3-F-Ph | NHPr$^c$ | H | H | H | H | CH |
| 4-600 | 4-Cl-3-F-Ph | NHCOMe | H | H | H | H | CH |
| 4-601 | 4-Cl-3-F-Ph | NHCOPr$^c$ | H | H | H | H | CH |
| 4-602 | 4-Cl-3-F-Ph | NHCOPn$^c$ | H | H | H | H | CH |
| 4-603 | 4-Cl-3-F-Ph | NHCOOMe | H | H | H | H | CH |

TABLE 4-continued

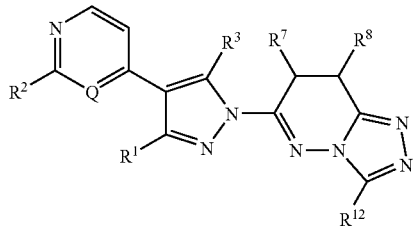

| Compound No | R¹ | R² | R³ | R⁷ | R⁸ | R⁹ | Q |
|---|---|---|---|---|---|---|---|
| 4-604 | 4-Cl-3-F-Ph | NHSO₂Me | H | H | H | H | CH |
| 4-605 | 4-Cl-3-F-Ph | NH(α-Me-Bn) | H | H | H | H | CH |
| 4-606 | 4-Cl-3-F-Ph | NHCOPh | H | H | H | H | CH |
| 4-607 | 4-Cl-3-F-Ph | NH₂ | H | Me | H | H | CH |
| 4-608 | 4-Cl-3-F-Ph | NH₂ | H | H | Me | H | CH |
| 4-609 | 4-Cl-3-F-Ph | NH₂ | H | Me | Me | H | CH |
| 4-610 | 4-Cl-3-F-Ph | NH₂ | H | H | NH₂ | H | CH |
| 4-611 | 4-Cl-3-F-Ph | NH₂ | H | H | H | Me | CH |
| 4-612 | 4-Cl-3-F-Ph | NH₂ | H | H | H | CF₃ | CH |
| 4-613 | 4-Cl-3-F-Ph | NH₂ | H | H | H | NH₂ | CH |
| 4-614 | 4-Cl-3-F-Ph | NH₂ | H | H | H | NHMe | CH |
| 4-615 | 4-Cl-3-F-Ph | NH₂ | H | H | H | NMe₂ | CH |
| 4-616 | 4-Cl-3-F-Ph | NH₂ | H | H | H | NHCOMe | CH |
| 4-617 | 4-Cl-3-F-Ph | NH₂ | H | H | H | NHCOOMe | CH |
| 4-618 | 4-Cl-3-F-Ph | NH₂ | H | H | H | NHSO₂Me | CH |
| 4-619 | 4-Cl-3-F-Ph | NH₂ | H | H | Me | Me | CH |
| 4-620 | 4-Cl-3-F-Ph | NH₂ | H | H | Me | NH₂ | CH |
| 4-621 | 4-Cl-3-F-Ph | NH₂ | H | H | NH₂ | Me | CH |
| 4-622 | 4-Cl-3-F-Ph | H | H | H | H | H | N |
| 4-623 | 4-Cl-3-F-Ph | NH₂ | H | H | H | H | N |
| 4-624 | 4-Cl-3-F-Ph | NHMe | H | H | H | H | N |
| 4-625 | 4-Cl-3-F-Ph | NHEt | H | H | H | H | N |
| 4-626 | 4-Cl-3-F-Ph | NHPrⁱ | H | H | H | H | N |
| 4-627 | 4-Cl-3-F-Ph | NHCH₂CF₃ | H | H | H | H | N |
| 4-628 | 4-Cl-3-F-Ph | NHCOMe | H | H | H | H | N |
| 4-629 | 4-Cl-3-F-Ph | NHCOOMe | H | H | H | H | N |
| 4-630 | 4-Cl-3-F-Ph | NHSO₂Me | H | H | H | H | N |
| 4-631 | 4-Cl-3-F-Ph | NH(α-Me-Bn) | H | H | H | H | N |
| 4-632 | 4-Cl-3-F-Ph | NHCOPh | H | H | H | H | N |
| 4-633 | 4-Cl-3-F-Ph | NH₂ | H | H | Me | H | N |
| 4-634 | 4-Cl-3-F-Ph | NH₂ | H | H | NH₂ | H | N |
| 4-635 | 4-Cl-3-F-Ph | NH₂ | H | H | H | Me | N |
| 4-636 | 4-Cl-3-F-Ph | NH₂ | H | H | H | NH₂ | N |
| 4-637 | 3-CF₃-Ph | H | H | H | H | H | CH |
| 4-638 | 3-CF₃-Ph | NH₂ | H | H | H | H | CH |
| 4-639 | 3-CF₃-Ph | NHMe | H | H | H | H | CH |
| 4-640 | 3-CF₃-Ph | NHEt | H | H | H | H | CH |
| 4-641 | 3-CF₃-Ph | NHPrⁱ | H | H | H | H | CH |
| 4-642 | 3-CF₃-Ph | NHCH₂CF₃ | H | H | H | H | CH |
| 4-643 | 3-CF₃-Ph | NHPrᶜ | H | H | H | H | CH |
| 4-644 | 3-CF₃-Ph | NHCOMe | H | H | H | H | CH |
| 4-645 | 3-CF₃-Ph | NHCOPrᶜ | H | H | H | H | CH |
| 4-646 | 3-CF₃-Ph | NHCOPnᶜ | H | H | H | H | CH |
| 4-647 | 3-CF₃-Ph | NHCOOMe | H | H | H | H | CH |
| 4-648 | 3-CF₃-Ph | NHSO₂Me | H | H | H | H | CH |
| 4-649 | 3-CF₃-Ph | NH(α-Me-Bn) | H | H | H | H | CH |
| 4-650 | 3-CF₃-Ph | NHCOPh | H | H | H | H | CH |
| 4-651 | 3-CF₃-Ph | NH₂ | H | Me | H | H | CH |
| 4-652 | 3-CF₃-Ph | NH₂ | H | H | Me | H | CH |
| 4-653 | 3-CF₃-Ph | NH₂ | H | Me | Me | H | CH |
| 4-654 | 3-CF₃-Ph | NH₂ | H | H | NH₂ | H | CH |
| 4-655 | 3-CF₃-Ph | NH₂ | H | H | H | Me | CH |
| 4-656 | 3-CF₃-Ph | NH₂ | H | H | H | CF₃ | CH |
| 4-657 | 3-CF₃-Ph | NH₂ | H | H | H | NH₂ | CH |
| 4-658 | 3-CF₃-Ph | NH₂ | H | H | H | NHMe | CH |
| 4-659 | 3-CF₃-Ph | NH₂ | H | H | H | NMe₂ | CH |
| 4-660 | 3-CF₃-Ph | NH₂ | H | H | H | NHCOMe | CH |
| 4-661 | 3-CF₃-Ph | NH₂ | H | H | H | NHCOOMe | CH |
| 4-662 | 3-CF₃-Ph | NH₂ | H | H | H | NHSO₂Me | CH |
| 4-663 | 3-CF₃-Ph | NH₂ | H | H | Me | Me | CH |
| 4-664 | 3-CF₃-Ph | NH₂ | H | H | Me | NH₂ | CH |
| 4-665 | 3-CF₃-Ph | NH₂ | H | H | NH₂ | Me | CH |
| 4-666 | 3-CF₃-Ph | H | H | H | H | H | N |
| 4-667 | 3-CF₃-Ph | NH₂ | H | H | H | H | N |

TABLE 4-continued

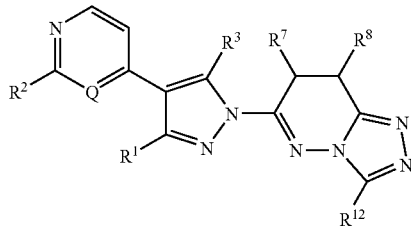

| Compound No | R¹ | R² | R³ | R⁷ | R⁸ | R⁹ | Q |
|---|---|---|---|---|---|---|---|
| 4-668 | 3-CF₃-Ph | NHMe | H | H | H | H | N |
| 4-669 | 3-CF₃-Ph | NHEt | H | H | H | H | N |
| 4-670 | 3-CF₃-Ph | NHPrⁱ | H | H | H | H | N |
| 4-671 | 3-CF₃-Ph | NHCH₂CF₃ | H | H | H | H | N |
| 4-672 | 3-CF₃-Ph | NHCOMe | H | H | H | H | N |
| 4-673 | 3-CF₃-Ph | NHCOOMe | H | H | H | H | N |
| 4-674 | 3-CF₃-Ph | NHSO₂Me | H | H | H | H | N |
| 4-675 | 3-CF₃-Ph | NH(Cl-Me-Bn) | H | H | H | H | N |
| 4-676 | 3-CF₃-Ph | NHCOPh | H | H | H | H | N |
| 4-677 | 3-CF₃-Ph | NH₂ | H | H | Me | H | N |
| 4-678 | 3-CF₃-Ph | NH₂ | H | H | NH₂ | H | N |
| 4-679 | 3-CF₃-Ph | NH₂ | H | H | H | Me | N |
| 4-680 | 3-CF₃-Ph | NH₂ | H | H | H | NH₂ | N |

Abbreviated symbols in the above-mentioned tables represent the following groups.
Me: a methyl group,
Et: an ethyl group,
Pr: a propyl group,
Prⁱ: an isopropyl group,
Prᶜ: a cyclopropyl group,
Pnᶜ: a cyclopentyl group,
Hxᶜ: a cyclohexyl group,
Ph: a phenyl group,
Bn: a benzyl group,
4-F-Bn: a 4-fluorobenzyl group,
4-OMe-Bn: a 4-methoxybenzyl group,
α-Me-Bn: a 1-phenethyl group.

In the above-mentioned tables, more preferred are compounds of Compounds Nos. 1-1, 1-2, 1-3, 1-5, 1-6, 1-8, 1-9, 1-16, 1-17, 1-18, 1-24, 1-26, 1-27, 1-28, 1-32, 1-34, 1-40, 1-41, 1-42, 1-45, 1-46, 1-48, 1-50, 1-51, 1-56, 1-58, 1-60, 1-66, 1-68, 1-70, 1-73, 1-74, 1-75, 1-76, 1-77, 1-78, 1-79, 1-81, 1-84, 1-86, 1-89, 1-90, 1-91, 1-94, 1-95, 1-97, 1-98, 1-100, 1-101, 1-102, 1-103, 1-104, 1-106, 1-107, 1-119, 1-124, 1-126, 1-130, 1-133, 1-134, 1-135, 1-137, 1-156, 1-157, 1-159, 1-160, 1-161, 1-162, 1-163, 1-164, 1-167, 1-171, 1-172, 1-174, 1-175, 1-180, 1-183, 1-189, 1-190, 1-192, 1-193, 1-194, 1-196, 1-203, 1-204, 1-205, 1-207, 1-210, 1-211, 1-212, 1-214, 1-215, 1-220, 1-222, 1-224, 1-230, 1-232, 1-234, 1-237, 1-238, 1-239, 1-240, 1-241, 1-242, 1-243, 1-245, 1-248, 1-250, 1-253, 1-254, 1-255, 1-258, 1-259, 1-261, 1-262, 1-264, 1-265, 1-266, 1-267, 1-268, 1-270, 1-271, 1-283, 1-288, 1-290, 1-297, 1-298, 1-299, 1-301, 1-320, 1-321, 1-323, 1-324, 1-325, 1-326, 1-327, 1-328, 1-331, 1-335, 1-336, 1-338, 1-339, 1-344, 1-347, 1-353, 1-354, 1-356, 1-357, 1-358, 1-360, 1-367, 1-368, 1-369, 1-371, 1-374, 1-378, 1-379, 1-384, 1-386, 1-388, 1-401, 1-402, 1-403, 1-404, 1-405, 1-406, 1-407, 1-409, 1-412, 1-414, 1-418, 1-419, 1-422, 1-423, 1-425, 1-426, 1-428, 1-429, 1-430, 1-431, 1-432, 1-434, 1-435, 1-447, 1-452, 1-454, 1-461, 1-462, 1-463, 1-465, 1-484, 1-485, 1-487, 1-488, 1-489, 1-490, 1-491, 1-492, 1-495, 1-499, 1-500, 1-502, 1-503, 1-508, 1-511, 1-517, 1-518, 1-520, 1-521, 1-522, 1-524, 1-531, 1-532, 1-533, 1-535, 1-536, 1-537, 1-539, 1-540, 1-541, 1-542, 1-543, 1-546, 1-550, 1-551, 1-552, 1-558, 1-560, 1-561, 1-566, 1-568, 1-576, 1-577, 1-578, 1-580, 1-581, 1-582, 1-583, 1-584, 1-587, 1-591, 1-592, 1-593, 1-599, 1-601, 1-602, 1-607, 1-609, 1-617, 1-618, 1-619, 1-621, 1-622, 1-623, 1-624, 1-625, 1-628, 1-632, 1-633, 1-634, 1-640, 1-642, 1-643, 1-648, 1-650, 1-656, 1-657, 1-658, 1-663, 1-672, 1-673, 1-674, 1-677, 1-678, 1-679, 1-680, 1-681, 1-682, 1-683, 1-684, 1-685, 1-686, 1-687, 1-688, 1-689, 1-692, 1-693, 1-695, 1-696, 1-700, 1-701, 1-703, 1-704, 1-710, 1-715, 1-717, 1-721, 1-724, 1-725, 1-726, 1-728, 1-729, 1-730, 1-732, 1-733, 1-734, 1-735, 1-736, 1-739, 1-743, 1-744, 1-745, 1-751, 1-753, 1-754, 1-759, 1-761, 1-769, 1-774, 1-775, 1-776, 1-777, 1-778, 1-779, 1-780, 1-781, 1-782, 1-783, 1-788, 1-789, 1-791, 1-793, 1-798, 1-799, 1-801, 1-803, 1-808, 1-813, 1-818, 1-823, 1-824, 1-825, 1-826, 1-828, 1-836, 1-837, 1-838, 1-839, 1-840, 1-844, 1-845, 1-846, 1-848, 1-852, 1-856, 1-860, 1-872, 1-873, 1-874, 1-875, 1-876, 1-880, 2-1, 2-5, 2-6, 2-8, 2-9, 2-10, 2-11, 2-12, 2-13, 2-14, 2-15, 2-16, 2-22, 2-25, 2-26, 2-28, 2-38, 2-44, 2-46, 2-60, 2-62, 2-64, 2-65, 2-71, 2-72, 2-73, 2-82, 2-83, 2-84, 2-86, 2-88, 2-94, 2-95, 2-96, 2-97, 2-99, 2-100, 2-101, 2-102, 2-104, 2-105, 2-108, 2-111, 2-114, 2-115, 2-116, 2-117, 2-118, 2-120, 2-121, 2-123, 2-126, 2-127, 2-128, 2-129, 2-130, 2-132, 2-133, 2-135, 2-136, 2-137, 2-145, 2-151, 2-152, 2-154, 2-157, 2-158, 2-159, 2-160, 2-162, 2-164, 2-167, 2-168, 2-177, 2-180, 2-185, 2-194, 2-196, 2-197, 2-199, 2-201, 2-202, 2-203, 2-205, 2-207, 2-209, 2-212, 2-213, 2-219, 2-225, 2-226, 2-228, 2-231, 2-232, 2-233, 2-237, 2-243, 2-244, 2-248, 2-250, 2-264, 2-266, 2-267, 2-273, 2-275, 2-281, 2-282, 2-284, 2-287, 2-288, 2-289, 2-290, 2-292, 2-293, 2-294, 2-295, 2-298, 2-301, 2-304, 2-306, 2-307, 2-308, 2-309, 2-315, 2-316, 2-321, 2-322, 2-324, 2-327, 2-328, 2-329, 2-337, 2-343, 2-344, 2-349, 2-351, 2-366, 2-369, 2-374, 2-383, 2-385, 2-386, 2-387, 2-388, 2-390, 2-391, 2-392, 2-394, 2-396, 2-398, 2-401, 2-402, 2-408, 2-414, 2-415, 2-417, 2-420, 2-421, 2-422, 2-426, 2-432, 2-433, 2-437, 2-439, 2-453, 2-455, 2-456, 2-462, 2-464, 2-473, 2-476, 2-477, 2-478, 2-479, 2-482, 2-483, 2-484, 2-487, 2-490, 2-493, 2-497, 2-498, 2-504, 2-510, 2-511, 2-513, 2-514, 2-516, 2-517, 2-518, 2-526, 2-532, 2-533, 2-538, 2-540, 2-555, 2-558, 2-563, 2-572, 2-574, 2-575, 2-577, 2-579, 2-580, 2-581, 2-583, 2-585, 2-587, 2-590, 2-591, 2-597, 2-603, 2-604, 2-606, 2-609, 2-610, 2-611, 2-615, 2-621, 2-622, 2-626, 2-628, 2-642, 2-646, 2-647, 2-648, 2-649, 2-650, 2-651, 2-652, 2-653, 2-654, 2-655, 2-656, 2-657, 2-663, 2-666, 2-669, 2-678, 2-679, 2-680, 2-685, 2-687, 2-701, 2-705, 2-706, 2-707, 2-708, 2-709, 2-710, 2-711, 2-712, 2-713, 2-714, 2-715, 2-716, 2-722, 2-725, 2-728, 2-737, 2-738, 2-739, 2-744, 2-746, 2-760, 2-764, 2-765, 2-766, 2-767, 2-768, 2-769, 2-770, 2-771, 2-772, 2-773, 2-774, 2-775, 2-781, 2-784, 2-787, 2-796, 2-797, 2-798, 2-803, 2-805, 2-819, 2-821, 2-822, 2-825, 2-827, 2-836, 2-838, 2-839, 2-840, 2-841, 2-843, 2-844, 2-845, 2-847, 2-849, 2-851, 2-854, 2-855, 2-861, 2-867, 2-868, 2-870, 2-871, 2-873, 2-874, 2-875, 2-879, 2-885, 2-886, 2-890, 2-892, 2-906, 2-910, 2-911, 2-913, 2-914, 2-915, 2-916, 2-917, 2-918, 2-919, 2-920, 2-921, 2-927, 2-930, 2-931, 2-933, 2-943, 2-949, 2-951, 2-965, 2-970, 2-971, 2-972, 2-973, 2-974, 2-975, 2-976, 2-977, 2-978, 2-979, 2-984, 2-985, 2-987, 2-989, 2-994, 2-995, 2-997, 2-999, 2-1004, 2-1009, 2-1014, 2-1019, 2-1024, 2-1032, 2-1033, 2-1034, 2-1035, 2-1036, 2-1040, 2-1041, 2-1042, 2-1044, 2-1048, 2-1052, 2-1056, 2-1068, 2-1069, 2-1070, 2-1071, 2-1072, 2-1076, 3-1, 3-2, 3-3, 3-5, 3-6, 3-8, 3-9, 3-16, 3-17, 3-18, 3-24, 3-26, 3-27, 3-28, 3-31, 3-32, 3-38, 3-41, 3-42, 3-44, 3-46, 3-47, 3-52, 3-54, 3-56, 3-62, 3-64, 3-66, 3-69, 3-70, 3-71, 3-72, 3-73, 3-74, 3-75, 3-76, 3-77, 3-80, 3-82, 3-85, 3-86, 3-87, 3-90, 3-91, 3-93, 3-94, 3-96, 3-97, 3-98, 3-99, 3-100, 3-101, 3-103, 3-115, 3-120, 3-122, 3-126, 3-129, 3-130, 3-132, 3-133, 3-149, 3-150, 3-152, 3-153, 3-154, 3-155, 3-156, 3-157, 3-160, 3-164, 3-165, 3-167, 3-173, 3-176, 3-181, 3-182, 3-183, 3-184, 3-185, 3-186, 3-191, 3-192, 3-193, 3-195, 3-196, 3-197, 3-198, 3-207, 3-208, 3-209, 3-212, 3-213, 3-214, 3-215, 3-216, 3-217, 3-218, 3-219, 3-220, 3-221, 3-222, 3-223, 3-224, 3-225, 3-228, 3-229, 3-231, 3-234, 3-235, 3-236, 3-237, 3-240, 3-246, 3-251, 3-253, 3-260, 3-261, 3-263, 3-264, 3-280, 3-281, 3-283, 3-284, 3-285, 3-286, 3-287, 3-288, 3-291, 3-295, 3-296, 3-298, 3-304, 3-307, 3-312, 3-313, 3-314, 3-315, 3-316, 3-317, 3-322, 3-323, 3-324, 3-326, 3-327, 3-328, 3-329, 3-338, 3-339, 3-340, 3-343, 3-344, 3-345, 3-346, 3-347, 3-348, 3-349, 3-350, 3-351, 3-352, 3-353, 3-354, 3-355, 3-356, 3-359, 3-360, 3-362, 3-365, 3-366, 3-367, 3-368, 3-371, 3-377, 3-382, 3-384, 3-391, 3-392, 3-394, 3-395, 3-411, 3-412, 3-414, 3-415, 3-416, 3-417, 3-418, 3-419, 3-422, 3-426, 3-427, 3-429, 3-435, 3-438, 3-443, 3-444, 3-445, 3-446, 3-447, 3-448, 3-453, 3-454, 3-455, 3-456, 3-457, 3-459, 3-460, 3-462, 3-463, 3-466, 3-470, 3-471, 3-472, 3-478, 3-480, 3-481, 3-486, 3-488, 3-492, 3-496, 3-497, 3-498, 3-500, 3-501, 3-503, 3-504, 3-507, 3-511, 3-512, 3-513, 3-519, 3-521, 3-522, 3-527, 3-529, 3-533, 3-537, 3-538, 3-539, 3-541, 3-542, 3-544, 3-545, 3-548, 3-552, 3-553, 3-554, 3-560, 3-562, 3-563, 3-568, 3-570, 3-574, 3-578, 3-580, 3-581, 3-582, 3-583, 3-592, 3-593, 3-594, 3-597, 3-598, 3-599, 3-600, 3-601, 3-602, 3-603, 3-604, 3-605, 3-606, 3-607, 3-608, 3-609, 3-610, 3-613, 3-614, 3-616, 3-619, 3-620, 3-621, 3-622, 3-625, 3-631, 3-636, 3-638, 3-642, 3-646, 3-648, 3-649, 3-650, 3-651, 3-653, 3-654, 3-656, 3-657, 3-660, 3-664, 3-665, 3-666, 3-672, 3-674, 3-675, 3-680, 3-682, 3-686, 3-690, 3-694, 3-695, 3-696, 3-697, 3-698, 3-699, 3-700, 3-701, 3-702, 3-703, 3-707, 3-708, 3-710, 3-712, 3-714, 3-715, 3-717, 3-719, 3-723, 3-725, 3-727, 3-731, 3-732, 3-733, 3-734, 3-736, 4-1, 4-2, 4-3, 4-7, 4-9, 4-10, 4-19, 4-20, 4-22, 4-23, 4-24, 4-25, 4-34, 4-35, 4-40, 4-41, 4-51, 4-53, 4-57, 4-70, 4-71, 4-72, 4-73, 4-75, 4-76, 4-77, 4-78, 4-79, 4-81, 4-82, 4-83, 4-85, 4-87, 4-90, 4-91, 4-94, 4-95, 4-97, 4-100, 4-101, 4-102, 4-103, 4-104, 4-106, 4-109, 4-110, 4-111, 4-115, 4-119, 4-124, 4-126, 4-127, 4-132, 4-138, 4-139, 4-140, 4-144, 4-146, 4-147, 4-156, 4-157, 4-159, 4-160, 4-161, 4-162, 4-171, 4-172, 4-177, 4-178, 4-188, 4-203, 4-204, 4-205, 4-206, 4-208, 4-209, 4-210, 4-211, 4-212, 4-214, 4-215, 4-216, 4-218, 4-220, 4-223, 4-224, 4-227, 4-228, 4-230, 4-233, 4-234, 4-235, 4-236, 4-237, 4-239, 4-242, 4-243, 4-244, 4-248, 4-252, 4-257, 4-259, 4-260, 4-271, 4-281, 4-282, 4-283, 4-284, 4-285, 4-286, 4-289, 4-291, 4-295, 4-297, 4-300, 4-301, 4-304, 4-305, 4-307, 4-311, 4-312, 4-313, 4-323, 4-326, 4-331, 4-333, 4-334, 4-344, 4-345, 4-346, 4-349, 4-351, 4-352, 4-358, 4-359, 4-361, 4-362, 4-363, 4-364, 4-373, 4-374, 4-378, 4-379, 4-388, 4-398, 4-399, 4-400, 4-401, 4-402, 4-403, 4-406, 4-408, 4-412, 4-414, 4-417, 4-418, 4-421, 4-422, 4-424, 4-428, 4-429, 4-430, 4-439, 4-443, 4-448, 4-450, 4-451, 4-461, 4-462, 4-463, 4-466, 4-468, 4-469, 4-475, 4-476, 4-478, 4-479, 4-480, 4-481, 4-490, 4-491, 4-495, 4-496, 4-505, 4-506, 4-507, 4-510, 4-512, 4-513, 4-534, 4-535, 4-539, 4-540, 5-549, 5-550, 4-551, 4-554, 4-556, 4-557, 4-578, 4-579, 4-583, 4-584, 4-593, 4-594, 4-595, 4-598, 4-600, 4-601, 4-622, 4-623, 4-627, 4-628, 4-637, 4-638, 4-639, 4-642, 4-644, 4-645, 4-651, 4-652, 4-654, 4-655, 4-656, 4-657, 4-666, 4-667, 4-671 or 4-672, further more preferred are compounds of Compounds Nos. 1-2, 1-3, 1-5, 1-6, 1-8, 1-16, 1-17, 1-18, 1-24, 1-27, 1-42, 1-50, 1-73, 1-74, 1-75, 1-76, 1-77, 1-78, 1-79, 1-81, 1-84, 1-86, 1-90, 1-91, 1-94, 1-95, 1-97, 1-98, 1-100, 1-104, 1-107, 1-119, 1-126, 1-137, 1-156, 1-157, 1-159, 1-161, 1-163, 1-164, 1-171, 1-172, 1-174, 1-180, 1-183, 1-189, 1-196, 1-207, 1-214, 1-237, 1-238, 1-239, 1-240, 1-241, 1-242, 1-243, 1-245, 1-248, 1-250, 1-254, 1-255, 1-258, 1-259, 1-261, 1-262, 1-264, 1-268, 1-271, 1-283, 1-290, 1-301, 1-320, 1-321, 1-323, 1-325, 1-327, 1-328, 1-335, 1-336, 1-338, 1-344, 1-347, 1-353, 1-360, 1-371, 1-378, 1-401, 1-402, 1-403, 1-404, 1-405, 1-406, 1-407, 1-409, 1-412, 1-414, 1-418, 1-419, 1-422, 1-423, 1-425, 1-432, 1-435, 1-447, 1-454, 1-465, 1-484, 1-485, 1-487, 1-489, 1-491, 1-492, 1-499, 1-500, 1-502, 1-508, 1-511, 1-517, 1-524, 1-536, 1-540, 1-542, 1-550, 1-551, 1-552, 1-558, 1-561, 1-577, 1-581, 1-583, 1-591, 1-592, 1-593, 1-599, 1-602, 1-618, 1-619, 1-621, 1-622, 1-624, 1-632, 1-633, 1-634, 1-640, 1-643, 1-658, 1-677, 1-678, 1-679, 1-680, 1-681, 1-682, 1-683, 1-684, 1-685, 1-688, 1-689, 1-692, 1-693, 1-695, 1-696, 1-701, 1-704, 1-710, 1-717, 1-729, 1-733, 1-735, 1-743, 1-744, 1-745, 1-751, 1-754, 1-769, 1-774, 1-775, 1-778, 1-781, 1-783, 1-788, 1-793, 1-798, 1-803, 1-818, 1-823, 1-828, 1-837, 1-838, 1-839, 1-840, 1-848, 1-873, 1-874, 1-875, 1-876, 2-1, 2-5, 2-6, 2-10, 2-12, 2-25, 2-28, 2-38, 2-60, 2-82, 2-83, 2-84, 2-86, 2-94, 2-95, 2-96, 2-97, 2-100, 2-101, 2-102, 2-105, 2-108, 2-111, 2-114, 2-115, 2-116, 2-117, 2-121, 2-123, 2-129, 2-130, 2-132, 2-133, 2-135, 2-136, 2-137, 2-145, 2-151, 2-152, 2-160, 2-177, 2-196, 2-197, 2-199, 2-201, 2-202, 2-205, 2-207, 2-212, 2-213, 2-225, 2-228, 2-243, 2-248, 2-264, 2-281, 2-282, 2-284, 2-287, 2-288, 2-290, 2-293, 2-294, 2-295, 2-298, 2-301, 2-304, 2-308, 2-309, 2-321, 2-322, 2-324, 2-337, 2-343, 2-351, 2-366, 2-385, 2-386, 2-388, 2-390, 2-391, 2-394, 2-396, 2-401, 2-402, 2-414, 2-415, 2-417, 2-432, 2-453, 2-473, 2-476, 2-477, 2-479, 2-482, 2-483, 2-484, 2-487, 2-490, 2-493, 2-497, 2-498, 2-510, 2-511, 2-513, 2-526, 2-532, 2-538, 2-540, 2-555, 2-574, 2-575, 2-577, 2-579, 2-580, 2-583, 2-585, 2-590, 2-591, 2-603, 2-604, 2-606, 2-615, 2-621, 2-642, 2-646, 2-647, 2-649, 2-651, 2-653, 2-654, 2-666, 2-669, 2-679, 2-701, 2-705, 2-706, 2-708, 2-710, 2-712, 2-713, 2-725, 2-728, 2-738, 2-760, 2-764, 2-765, 2-767, 2-769, 2-771, 2-772, 2-784, 2-787, 2-797, 2-819, 2-836, 2-838, 2-839, 2-841, 2-843, 2-844, 2-845, 2-847, 2-849, 2-851, 2-854, 2-855, 2-867, 2-868, 2-870, 2-873, 2-879, 2-885, 2-890, 2-892, 2-906, 2-910, 2-911, 2-915, 2-917, 2-918, 2-930, 2-933, 2-943, 2-965, 2-970, 2-971, 2-974, 2-977, 2-979, 2-984, 2-989, 2-994, 2-999, 2-1019, 2-1033, 2-1034, 2-1035, 2-1036, 2-1044, 2-1069, 2-1070, 2-1071, 2-1072, 3-2, 3-3, 3-5, 3-6, 3-8, 3-16, 3-17, 3-18, 3-24, 3-27, 3-38, 3-46, 3-69, 3-70, 3-71, 3-72, 3-73, 3-74, 3-75, 3-77, 3-80, 3-82, 3-86, 3-87, 3-90, 3-91, 3-93, 3-100, 3-103, 3-115, 3-120, 3-122, 3-133, 3-149, 3-150, 3-152, 3-154, 3-156, 3-157, 3-164, 3-165, 3-167, 3-173, 3-176, 3-181, 3-186, 3-193, 3-212, 3-213, 3-215, 3-216, 3-217, 3-218, 3-220, 3-221, 3-222, 3-224, 3-225, 3-228, 3-229, 3-231, 3-237, 3-240, 3-246, 3-253, 3-264, 3-280, 3-281, 3-283, 3-285, 3-287, 3-288, 3-295, 3-296, 3-298, 3-304, 3-307, 3-312, 3-317, 3-324, 3-343, 3-344, 3-346, 3-347, 3-348, 3-349, 3-351, 3-352, 3-353, 3-355, 3-356, 3-359, 3-360, 3-362, 3-368, 3-371, 3-377, 3-384, 3-395, 3-411, 3-412, 3-414, 3-416, 3-418, 3-419, 3-426, 3-427, 3-429, 3-435, 3-438, 3-443, 3-448, 3-456, 3-459, 3-460, 3-462, 3-470, 3-471, 3-472, 3-478, 3-481, 3-497, 3-500, 3-501, 3-503, 3-511, 3-512, 3-513, 3-519, 3-522, 3-538, 3-541, 3-542, 3-544, 3-552, 3-553, 3-554, 3-560, 3-563, 3-578, 3-597, 3-598, 3-600, 3-601, 3-602, 3-603, 3-605, 3-606, 3-607, 3-609, 3-610, 3-613, 3-614, 3-616, 3-622, 3-625, 3-631, 3-638, 3-650, 3-653, 3-654, 3-656, 3-664, 3-665, 3-666, 3-672, 3-675, 3-690, 3-694, 3-695, 3-698, 3-701, 3-703, 3-707, 3-712, 3-714, 3-719, 3-727, 3-731, 3-732, 4-1, 4-2, 4-7, 4-9, 4-10, 4-20, 4-23, 4-35, 4-51, 4-70, 4-71, 4-73, 4-75, 4-76, 4-79, 4-81, 4-83, 4-85, 4-87, 4-90, 4-91, 4-94, 4-95, 4-97, 4-103, 4-104, 4-106, 4-109, 4-110, 4-111, 4-119, 4-138, 4-139, 4-144, 4-146, 4-147, 4-157, 4-160, 4-172, 4-188, 4-203, 4-204, 4-206, 4-208, 4-209, 4-212, 4-214, 4-218, 4-220, 4-223, 4-224, 4-227, 4-228, 4-230, 4-236, 4-237, 4-239, 4-242, 4-243, 4-244, 4-252, 4-271, 4-281, 4-282, 4-286, 4-289, 4-291, 4-295, 4-297, 4-300, 4-301, 4-305, 4-311, 4-326, 4-345, 4-349, 4-351, 4-352, 4-362, 4-374, 4-388, 4-398, 4-399, 4-403, 4-406, 4-408, 4-412, 4-414, 4-417, 4-418, 4-422, 4-428, 4-443, 4-462, 4-466, 4-468, 4-469, 4-479, 4-491, 4-506, 4-510, 4-512, 4-513, 4-535, 5-550, 4-554, 4-556, 4-557, 4-579, 4-594, 4-598, 4-600, 4-601, 4-623, 4-638, 4-642, 4-644, 4-645, 4-655 or 4-667, particularly preferred are compounds of Compounds Nos. 1-2, 1-16, 1-17, 1-18, 1-42, 1-50, 1-73, 1-74, 1-76, 1-78, 1-81, 1-84, 1-94, 1-95, 1-97, 1-98, 1-100, 1-104, 1-119, 1-156, 1-161, 1-163, 1-171, 1-172, 1-174, 1-180, 1-189, 1-207, 1-237, 1-238, 1-242, 1-245, 1-258, 1-259, 1-261, 1-268, 1-283, 1-320, 1-325, 1-327, 1-335, 1-336, 1-338, 1-344, 1-353, 1-371, 1-401, 1-402, 1-406, 1-409, 1-422, 1-423, 1-425, 1-432, 1-447, 1-484, 1-489, 1-491, 1-499, 1-500, 1-502, 1-508, 1-517, 1-536, 1-540, 1-542, 1-552, 1-577, 1-581, 1-583, 1-593, 1-618, 1-622, 1-624, 1-634, 1-658, 1-677, 1-678, 1-680, 1-682, 1-684, 1-685, 1-692, 1-693, 1-695, 1-701, 1-710, 1-729, 1-733, 1-735, 1-745, 1-774, 1-775, 1-778, 1-788, 1-798, 1-823, 1-837, 1-838, 1-839, 1-840, 1-876, 2-5, 2-12, 2-38, 2-60, 2-82, 2-86, 2-94, 2-95, 2-96, 2-97, 2-100, 2-101, 2-102, 2-105, 2-108, 2-111, 2-115, 2-116, 2-117, 2-121, 2-123, 2-129, 2-130, 2-132, 2-135, 2-151, 2-177, 2-196, 2-197, 2-202, 2-205, 2-243, 2-264, 2-281, 2-287, 2-288, 2-298, 2-301, 2-308, 2-309, 2-343, 2-366, 2-385, 2-391, 2-394, 2-432, 2-453, 2-476, 2-477, 2-483, 2-487, 2-490, 2-497, 2-498, 2-532, 2-555, 2-574, 2-580, 2-583, 2-621, 2-646, 2-651, 2-653, 2-705, 2-710, 2-712, 2-764, 2-769, 2-771, 2-819, 2-838, 2-839, 2-844, 2-847, 2-854, 2-855, 2-885, 2-910, 2-917, 2-970, 2-971, 2-974, 2-984, 2-994, 2-1019, 2-1033, 2-1034, 2-1035, 2-1036, 2-1072, 3-2, 3-6, 3-8, 3-17, 3-27, 3-38, 3-69, 3-70, 3-72, 3-74, 3-77, 3-80, 3-90, 3-91, 3-93, 3-100, 3-115, 3-133, 3-149, 3-154, 3-156, 3-157, 3-173, 3-181, 3-193, 3-212, 3-213, 3-217, 3-220, 3-229, 3-237, 3-240, 3-246, 3-264, 3-280, 3-285, 3-287, 3-288, 3-304, 3-312, 3-324, 3-343, 3-344, 3-348, 3-351, 3-360, 3-368, 3-371, 3-377, 3-395, 3-411, 3-416, 3-418, 3-419, 3-435, 3-443, 3-456, 3-460, 3-462, 3-481, 3-497, 3-501, 3-503, 3-522, 3-538, 3-542, 3-544, 3-563, 3-578, 3-597, 3-598, 3-602, 3-605, 3-613, 3-614, 3-622, 3-625, 3-631, 3-650, 3-654, 3-656, 3-675, 3-690, 3-694, 3-695, 3-698, 3-707, 3-714, 3-731, 4-2, 4-7, 4-9, 4-10, 4-51, 4-70, 4-76, 4-79, 4-81, 4-85, 4-90, 4-95, 4-103, 4-119, 4-139, 4-144, 4-146, 4-147, 4-188, 4-203, 4-209, 4-212, 4-214, 4-218, 4-223, 4-228, 4-236, 4-252, 4-271, 4-281, 4-286, 4-289, 4-291, 4-326, 4-345, 4-351, 4-352, 4-388, 4-398, 4-403, 4-406, 4-408, 4-443, 4-462, 4-466, 4-468, 4-469, 4-506, 4-512, 4-513, 5-550, 4-556, 4-557, 4-594, 4-600, 4-601, 4-638, 4-642, 4-644 or 4-645, most preferred are compounds of Compound No. 1-2: 4-(2-aminopyridin-4-yl)-1-(1,6-dihydro-6-oxopyridazin-3-yl)-3-phenyl-1H-pyrazole, Compound No. 1-42: 3-(4-fluorophenyl)-1-(1,6-dihydro-6-oxopyridazin-3-yl)-4-(pyridin-4-yl)-1H-pyrazole, Compound No. 1-50: 1-(5-amino-1,6-dihydro-6-oxopyridazin-3-yl)-3-(4-fluorophenyl)-4-(pyridin-4-yl)-1H-pyrazole, Compound No. 1-73: 4-(2-aminopyridin-4-yl)-3-(4-fluorophenyl)-1-(1,6-dihydro-6-oxopyridazin-3-yl)-1H-pyrazole, Compound No. 1-74: 3-(4-fluorophenyl)-1-(1,6-dihydro-6-oxopyridazin-3-yl)-4-(2-methylaminopyridin-4-yl)-1H-pyrazole, Compound No. 1-76: 4-(2-ethylaminopyridin-4-yl)-3-(4-fluorophenyl)-1-(1,6-dihydro-6-oxopyridazin-3-yl)-1H-pyrazole, Compound No. 1-78: 3-(4-fluorophenyl)-1-(1,6-dihydro-6-oxopyridazin-3-yl)-4-[2-(2,2,2-trifluoroethyl)aminopyridin-4-yl]-1H-pyrazole, Compound No. 1-81: 4-(2-acetylaminopyridin-4-yl)-3-(4-fluorophenyl)-1-(1,6-dihydro-6-oxopyridazin-3-yl)-1H-pyrazole, Compound No. 1-84: 3-(4-fluorophenyl)-1-(1,6-dihydro-6-oxopyridazin-3-yl)-4-(2-methoxycarbonylaminopyridin-4-yl)-1H-pyrazole, Compound No. 1-94: 4-(2-aminopyridin-4-yl)-3-(4-fluorophenyl)-1-(1,6-dihydro-4-methyl-6-oxopyridazin-3-yl)-1H-pyrazole, Compound No. 1-95: 4-(2-aminopyridin-4-yl)-3-(4-fluorophenyl)-1-(1,6-dihydro-5-methyl-6-oxopyridazin-3-yl)-1H-pyrazole, Compound No. 1-97: 1-(5-amino-1,6-dihydro-6-oxopyridazin-3-yl)-4-(2-aminopyridin-4-yl)-3-(4-fluorophenyl)-1H-pyrazole, Compound No. 1-104: 4-(2-aminopyridin-4-yl)-3-(4-fluorophenyl)-1-(1,6-dihydro-1-methyl-6-oxopyridazin-3-yl)-1H-pyrazole, Compound No. 1-119: 4-(2-aminopyrimidin-4-yl)-3-(4-fluorophenyl)-1-(1,6-dihydro-6-oxopyridazin-3-yl)-1H-pyrazole, Compound No. 1-156: 4-(2-aminopyridin-4-yl)-3-(3-fluorophenyl)-1-(1,6-dihydro-6-oxopyridazin-3-yl)-1H-pyrazole, Compound No. 1-237: 4-(2-aminopyridin-4-yl)-3-(4-chlorophenyl)-1-(1,6-dihydro-6-oxopyridazin-3-yl)-1H-pyrazole, Compound No. 1-320: 4-(2-aminopyridin-4-yl)-3-(3-chlorophenyl)-1-(1,6-dihydro-6-oxopyridazin-3-yl)-1H-pyrazole, Compound No. 1-401: 4-(2-aminopyridin-4-yl)-3-(3,4-difluorophenyl)-1-(1,6-dihydro-6-oxopyridazin-3-yl)-1H-pyrazole, Compound No. 1-484: 4-(2-aminopyridin-4-yl)-3-(3,4-dichlorophenyl)-1-(1,6-dihydro-6-oxopyridazin-3-yl)-1H-pyrazole, Compound No. 1-618: 4-(2-aminopyridin-4-yl)-1-(1,6-dihydro-6-oxopyridazin-3-yl)-3-(3-trifluoromethylphenyl)-1H-pyrazole, Compound No. 1-677: 4-(2-aminopyridin-4-yl)-3-(2-fluorophenyl)-1-(1,6-dihydro-6-oxopyridazin-3-yl)-1H-pyrazole, Compound No. 1-682: 3-(2-fluorophenyl)-1-(1,6-dihydro-6-oxopyridazin-3-yl)-4-[2-(2,2,2-trifluoroethyl)aminopyridin-4-yl]-1H-pyrazole, Compound No. 1-684: 4-(2-acetylaminopyridin-4-yl)-3-(2-fluorophenyl)-1-(1,6-dihydro-6-oxopyridazin-3-yl)-1H-pyrazole, Compound No. 1-710: 4-(2-aminopyrimidin-4-yl)-3-(2-fluorophenyl)-1-(1,6-dihydro-6-oxopyridazin-3-yl)-1H-pyrazole, Compound No. 1-729: 4-(2-aminopyridin-4-yl)-3-(2,4-difluorophenyl)-1-(1,6-dihydro-6-oxopyridazin-3-yl)-1H-pyrazole, Compound No. 1-774: 4-(2-cyclopropylcarbonylaminopyridin-4-yl)-3-(4-fluorophenyl)-1-(1,6-dihydro-6-oxopyridazin-3-yl)-1H-pyrazole, Compound No. 1-823: 4-(2-cyclopropylcarbonylaminopyridin-4-yl)-3-(2-fluorophenyl)-1-(1,6-dihydro-6-oxopyridazin-3-yl)-1H-pyrazole, Compound No. 1-840: 3-(4-fluorophenyl)-1-(1,6-dihydro-6-oxopyridazin-3-yl)-4-[2-(4-methoxybenzylamino)pyrimidin-4-yl]-1H-pyrazole, Compound No. 2-5: 4-(2-aminopyridin-4-yl)-3-phenyl-1-([1,2,4]triazolo[4,3-b]pyridazin-6-yl) -1H-pyrazole, Compound No. 2-60: 3-(4-fluorophenyl)-4-(pyridin-4-yl)-1-([1,2,4]triazolo[4,3-b]pyridazin-6-yl)-1H-pyrazole, Compound No. 2-86: 3-(4-fluorophenyl)-4-(2-methoxypyridin-4-yl)-1-([1,2,4]triazolo[4,3-b]pyridazin-6-yl)-1H-pyrazole, Compound No. 2-94: 4-(2-aminopyridin-4-yl)-3-(4-fluorophenyl)-1-([1,2,4]triazolo[4,3-b]pyridazin-6-yl)-1H-pyrazole, Compound No. 2-95: 3-(4-fluorophenyl)-4-(2-methylaminopyridin-4-yl)-1-([1,2,4]triazolo[4,3-b]pyridazin-6-yl)-1H-pyrazole, Compound No. 2-97: 4-(2-ethylaminopyridin-4-yl)-3-(4-fluorophenyl)-1-([1,2,4]triazolo[4,3-b]pyridazin-6-yl)-1H-pyrazole, Compound No. 2-100: 3-(4-fluorophenyl)-4-(2-isopropylaminopyridin-4-yl)-1-([1,2,4]triazolo[4,3-b]pyridazin-6-yl)-1H-pyrazole, Compound No. 2-101: 3-(4-fluorophenyl)-1-([1,2,4]triazolo-[4,3-b]pyridazin-6-yl)-4-[2-(2,2,2-trifluoroethyl)aminopyridin-4-yl]-1H-pyrazole, Compound No. 2-105: 4-(2-acetylaminopyridin-4-yl)-3-(4-fluorophenyl)-1-([1,2,4]triazolo[4,3-b]pyridazin-6-yl)-1H-pyrazole, Compound No. 2-108: 3-(4-fluorophenyl)-4-(2-methoxycarbonylaminopyridin-4-yl)-1-([1,2,4]triazolo[4,3-b]pyridazin-6-yl)-1H-pyrazole, Compound No. 2-111: 3-(4-fluorophenyl)-4-(2-methylsulfonyl-aminopyridin-4-yl)-1-([1,2,4]triazolo[4,3-b]pyridazin-6-yl)-1H-pyrazole, Compound No. 2-116: 3-(4-fluorophenyl)-4-[2-(1-phenethyl-amino)pyridin-4-yl]-1-([1,2,4]triazolo[4,3-b]pyridazin-6-yl)-1H-pyrazole, Compound No. 2-117: 4-(2-benzoylaminopyridin-4-yl)-3-(4-fluorophenyl)-1-([1,2,4]triazolo[4,3-b]pyridazin-6-yl)-1H-pyrazole, Compound No. 2-129: 4-(2-aminopyridin-4-yl)-3-(4-fluorophenyl)-1-(3-methyl -[1,2,4]triazolo[4,3-b]pyridazin-6-yl)-1H-pyrazole, Compound No. 2-130: 4-(2-aminopyridin-4-yl)-3-(4-fluorophenyl)-1-(3-trifluoromethyl -[1,2,4]triazolo[4,3-b]pyridazin-6-yl)-1H-pyrazole, Compound No. 2-132: 4-(2-aminopyridin-4-yl)-1-(3-amino-[1,2,4]triazolo[4,3-b]pyridazin-6-yl) -3-(4-fluorophenyl)-1H-pyrazole, Compound No. 2-135: 1-(3-acetylamino-[1,2,4]triazolo[4,3-b]pyridazin-6-yl)-4-(2-aminopyridin-4-yl)-3-(4-fluorophenyl)-1H-pyrazole, Compound No. 2-151: 4-(2-aminopyrimidin-4-yl)-3-(4-fluorophenyl)-1-([1,2,4]triazolo[4,3-b]pyridazin-6-yl)-1H-pyrazole, Compound No. 2-177: 3-(3-fluorophenyl)-4-(pyridin-4-yl)-1-([1,2,4]triazolo[4,3-b]pyridazin-6-yl)-1H-pyrazole, Compound No. 2-196: 4-(2-aminopyridin-4-yl)-3-(3-fluorophenyl)-1-([1,2,4]triazolo[4,3-b]pyridazin-6-yl)-1H-pyrazole, Compound No. 2-287: 4-(2-aminopyridin-4-yl)-3-(4-chlorophenyl)-1-([1,2,4]triazolo[4,3-b]pyridazin-6-yl)-1H-pyrazole, Compound No. 2-385: 4-(2-aminopyridin-4-yl)-3-(3-chlorophenyl)-1-([1,2,4]triazolo[4,3-b]pyridazin-6-yl)-1H-pyrazole, Compound No. 2-453: 3-(3,4-difluorophenyl)-4-(pyridin-4-yl)-1-([1,2,4]triazolo[4,3-b]pyridazin-6-yl)-1H-pyrazole, Compound No. 2-476: 4-(2-aminopyridin-4-yl)-3-(3,4-difluorophenyl)-1-([1,2,4]triazolo[4,3-b]pyridazin-6-yl)-1H-pyrazole, Compound No. 2-574: 4-(2-aminopyridin-4-yl)-3-(3,4-dichlorophenyl)-1-([1,2,4]triazolo[4,3-b]pyridazin-6-yl)-1H-pyrazole, Compound No. 2-646: 4-(2-aminopyridin-4-yl)-3-(3-chloro-4-fluorophenyl)-1-([1,2,4]triazolo[4,3-b]pyridazin-6-yl)-1H-pyrazole, Compound No. 2-705: 4-(2-aminopyridin-4-yl)-3-(4-chloro-3-fluorophenyl)-1-([1,2,4]triazolo[4,3-b]pyridazin-6-yl)-1H-pyrazole, Compound No. 2-764: 4-(2-aminopyridin-4-yl)-1-([1,2,4]triazolo[4,3-b]pyridazin-6-yl)-3-(3-trifluoromethylphenyl)-1H-pyrazole, Compound No. 2-838: 4-(2-aminopyridin-4-yl)-3-(2-fluorophenyl)-1-([1,2,4]triazolo[4,3-b]pyridazin-6-yl)-1H-pyrazole, Compound No. 2-885: 4-(2-aminopyrimidin-4-yl)-3-(2-fluorophenyl)-1-([1,2,4]triazolo[4,3-b]pyridazin-6-yl)-1H-pyrazole, Compound No. 2-910: 4-(2-aminopyridin-4-yl)-3-(2,4-difluorophenyl)-1-([1,2,4]triazolo[4,3-b]pyridazin-6-yl)-1H-pyrazole, Compound No. 2-970: 4-(2-cyclopropylcarbonylaminopyridin-4-yl)-3-(4-fluorophenyl)-1-([1,2,4]triazolo[4,3-b]pyridazin-6-yl)-1H-pyrazole, Compound No. 2-974: 4-(2-cyclopentylcarbonylaminopyridin-4-yl)-3-(4-fluorophenyl)-1-([1,2,4]triazolo[4,3-b]pyridazin-6-yl)-1H-pyrazole, Compound No. 2-1036: 3-(4-fluorophenyl)-4-[2-(4-methoxybenzyl)aminopyrimidin-4-yl]-1-([1,2,4]triazolo[4,3-b]-pyridazin-6-yl)-1H-pyrazole, Compound No. 3-2: 4-(2-aminopyridin-4-yl)-1-(1,4,5,6-tetrahydro-6-oxopyridazin-3-yl)-3-phenyl-1H-pyrazole, Compound No. 3-38: 3-(4-fluorophenyl)-1-(1,4,5,6-tetrahydro-6-oxopyridazin-3-yl)-4-(pyridin-4-yl)-1H-pyrazole, Compound No. 3-69: 4-(2-aminopyridin-4-yl)-3-(4-fluorophenyl)-1-(1,4,5,6-tetrahydro-6-oxopyridazin-3-yl)-1H-pyrazole, Compound No. 3-74: 3-(4-fluorophenyl)-1-(1,4,5,6-tetrahydro-6-oxopyridazin-3-yl)-4-[2-(2,2,2-trifluoroethyl)-aminopyridin-4-yl]-1H-pyrazole, Compound No. 3-77: 4-(2-acetylaminopyridin-4-yl)-3-(4-fluorophenyl)-1-(1,4,5,6-tetrahydro-6-oxopyridazin-3-yl)-1H-pyrazole, Compound No. 3-90: 4-(2-aminopyridin-4-yl)-3-(4-fluorophenyl)-1-(1,4,5,6-tetrahydro-4-methyl-6-oxopyridazin-3-yl)-1H-pyrazole, Compound No. 3-91: 4-(2-aminopyridin-4-yl)-3-(4-fluorophenyl)-1-(1,4,5,6-tetrahydro-5-methyl-6-oxopyridazin-3-yl)-1H-pyrazole, Compound No. 3-100: 4-(2-aminopyridin-4-yl)-3-(4-fluorophenyl)-1-(1,4,5,6-tetrahydro-1-methyl-6-oxopyridazin-3-yl)-1H-pyrazole, Compound No. 3-115: 4-(2-aminopyrimidin-4-yl)-3-(4-fluorophenyl)-1-(1,4,5,6-tetrahydro-6-oxopyridazin-3-yl)-1H-pyrazole, Compound No. 3-149: 4-(2-aminopyridin-4-yl)-3-(3-fluorophenyl)-1-(1,4,5,6-tetrahydro-6-oxopyridazin-3-yl)-1H-pyrazole, Compound No. 3-212: 4-(2-aminopyridin-4-yl)-3-(4-chlorophenyl)-1-(1,4,5,6-tetrahydro-6-oxopyridazin-3-yl)-1H-pyrazole, Compound No. 3-280: 4-(2-aminopyridin-4-yl)-3-(3-chlorophenyl)-1-(1,4,5,6-tetrahydro-6-oxopyridazin-3-yl)-1H-pyrazole, Compound No. 3-343: 4-(2-aminopyridin-4-yl)-3-(3,4-difluorophenyl)-1-(1,4,5,6-tetrahydro-6-oxopyridazin-3-yl)-1H-pyrazole, Compound No. 3-411: 4-(2-aminopyridin-4-yl)-3-(3,4-dichlorophenyl)-1-(1,4,5,6-tetrahydro-6-oxopyridazin-3-yl)-1H-pyrazole, Compound No. 3-456: 4-(2-aminopyridin-4-yl)-3-(3-chloro-4-fluorophenyl)-1-(1,4,5,6-tetrahydro-6-oxopyridazin-3-yl)-1H-pyrazole, Compound No. 3-497: 4-(2-aminopyridin-4-yl)-3-(4-chloro-3-fluorophenyl)-1-(1,4,5,6-tetrahydro-6-oxopyridazin-3-yl)-1H-pyrazole, Compound No. 3-538: 4-(2-aminopyridin-4-yl)-1-(1,4,5,6-tetrahydro-6-oxopyridazin-3-yl)-3-(3-trifluoromethylphenyl)-1H-pyrazole, Compound No. 3-597: 4-(2-aminopyridin-4-yl)-3-(2-fluorophenyl)-1-(1,4,5,6-tetrahydro-6-oxopyridazin-3-yl)-1H-pyrazole, Compound No. 3-602: 3-(2-fluorophenyl)-1-(1,4,5,6-tetrahydro-6-oxopyridazin-3-yl)-4-[2-(2,2,2-trifluoroethyl)-aminopyridin-4-yl]-1H-pyrazole, Compound No. 3-605: 4-(2-acetylaminopyridin-4-yl)-3-(2-fluorophenyl)-1-(1,4,5,6-tetrahydro-6-oxopyridazin-3-yl)-1H-pyrazole, Compound No. 3-631: 4-(2-aminopyrimidin-4-yl)-3-(2-fluorophenyl)-1-(1,4,5,6-tetrahydro-6-oxopyridazin-3-yl)-1H-pyrazole, Compound No. 3-650: 4-(2-aminopyridin-4-yl)-3-(2,4-difluorophenyl)-1-(1,4,5,6-tetrahydro-6-oxopyridazin-3-yl)-1H-pyrazole, Compound No. 3-690: 4-(2-cyclopropylcarbonylaminopyridin-4-yl)-(1,4,5,6-tetrahydro-6-oxopyridazin-3-yl)-3-phenyl-1-1H-pyrazole, Compound No. 3-694: 4-(2-cyclopropylcarbonylaminopyridin-4-yl)-3-(4-fluorophenyl)-1-(1,4,5,6-tetrahydro-6-oxopyridazin-3-yl)-1H-pyrazole, Compound No. 3-731: 4-(2-cyclopropylcarbonylaminopyridin-4-yl)-3-(2-fluorophenyl)-1-(1,4,5,6-tetrahydro-6-oxopyridazin-3-yl)-1H-pyrazole, Compound No. 4-2: 4-(2-aminopyridin-4-yl)-1-(7,8-dihydro-[1,2,4]triazolo[4,3-b]pyridazin-6-yl)-3-phenyl-1H-pyrazole, Compound No. 4-51: 3-(4-fluorophenyl)-1-(7,8-dihydro-[1,2,4]triazolo[4,3-b]pyridazin-6-yl)-4-(pyridin-4-yl)-1H-pyrazole, Compound No. 4-70: 4-(2-aminopyridin-4-yl)-3-(4-fluorophenyl)-1-(7,8-dihydro-[1,2,4]triazolo[4,3-b]pyridazin-6-yl)-1H-pyrazole, Compound No. 4-76: 3-(4-fluorophenyl)-1-(7,8-dihydro-[1,2,4]triazolo[4,3-b]pyridazin-6-yl)-4-[2-(2,2,2-trifluoroethyl)aminopyridin-4-yl]-1H-pyrazole, Compound No. 4-79: 4-(2-acetylaminopyridin-4-yl)-3-(4-fluorophenyl)-1-(7,8-dihydro-[1,2,4]triazolo[4,3-b]-pyridazin-6-yl)-1H-pyrazole, Compound No. 4-81: 4-(2-cyclopropylcarbonylaminopyridin-4-yl)-3-(4-fluorophenyl)-1-(7,8-dihydro-[1,2,4]triazolo[4,3-b]pyridazin-6-yl)-1H-pyrazole, Compound No. 4-119: 4-(2-aminopyrimidin-4-yl)-3-(4-fluorophenyl)-1-(7,8-dihydro-[1,2,4]triazolo[4,3-b]pyridazin-6-yl)-1H-pyrazole, Compound No. 4-139: 4-(2-aminopyridin-4-yl)-3-(3-fluorophenyl)-1-(7,8-dihydro-[1,2,4]triazolo[4,3-b]pyridazin-6-yl)-1H-pyrazole, Compound No. 4-203: 4-(2-aminopyridin-4-yl)-3-(2-fluorophenyl)-1-(7,8-dihydro-[1,2,4]triazolo[4,3-b]pyridazin-6-yl)-1H-pyrazole, Compound No. 4-209: 3-(2-fluorophenyl)-1-(7,8-dihydro-[1,2,4]triazolo[4,3-b]pyridazin-6-yl)-4-[2-(2,2,2-trifluoroethyl)aminopyridin-4-yl]-1H-pyrazole, Compound No. 4-212: 4-(2-acetylaminopyridin-4-yl)-3-(2-fluorophenyl)-1-(7,8-dihydro-[1,2,4]triazolo[4,3-b]-pyridazin-6-yl)-1H-pyrazole, Compound No. 4-214: 4-(2-cyclopropylcarbonylaminopyridin-4-yl)-3-(2-fluorophenyl)-1-(7,8-dihydro-[1,2,4]triazolo[4,3-b]pyridazin-6-yl)-1H-pyrazole, Compound No. 4-281: 4-(2-aminopyridin-4-yl)-3-(4-chlorophenyl)-1-(7,8-dihydro-[1,2,4]triazolo[4,3-b]pyridazin-6-yl)-1H-pyrazole, Compound No. 4-345: 4-(2-aminopyridin-4-yl)-3-(3-chlorophenyl)-1-(7,8-dihydro-[1,2,4]triazolo[4,3-b]pyridazin-6-yl)-1H-pyrazole, Compound No. 4-398: 4-(2-aminopyridin-4-yl)-3-(3,4-difluorophenyl)-1-(7,8-dihydro-[1,2,4]triazolo[4,3-b]pyridazin-6-yl)-1H-pyrazole, Compound No. 4-403: 3-(3,4-difluorophenyl)-1-(7,8-dihydro-[1,2,4]triazolo[4,3-b]pyridazin-6-yl)-4-[2-(2,2,2-trifluoroethyl)aminopyridin-4-yl]-1H-pyrazole, Compound No. 4-406: 4-(2-acetylaminopyridin-4-yl)-3-(3,4-difluorophenyl)-1-(7,8-dihydro-[1,2,4]triazolo[4,3-b]-pyridazin-6-yl)-1H-pyrazole, Compound No. 4-408: 4-(2-cyclopropylcarbonylaminopyridin-4-yl)-3-(3,4-difluorophenyl)-1-(7,8-dihydro-[1,2,4]triazolo-[4,3-b]pyridazin-6-yl)-1H-pyrazole, Compound No. 4-462: 4-(2-aminopyridin-4-yl)-3-(3,4-dichlorophenyl)-1-(7,8-dihydro -[1,2,4]triazolo[4,3-b]pyridazin-6-yl)-1H-pyrazole, or Compound No. 4-638: 4-(2-aminopyridin-4-yl)-1-(7,8-dihydro-[1,2,4]triazolo[4,3-b]pyridazin-6-yl)-3-(3-trifluoromethylphenyl)-1H-pyrazole.

The compound having the formula (I) can be prepared, for example, by the method as mentioned below.

[Method 1]

"Method 1" is a general method to prepare a pyrazole compound (Ia) of the present invention wherein $R^3$ represents a hydrogen atom or $C_1$-$C_6$ alkyl group in the formula (I).

diglyme, etc.; amides such as N,N-dimethylformamide, N,N-dimethylacetamide, N-methyl-2-pyrrolidone or hexamethylphosphoryl triamide, etc.; sulfoxides such as dimethylsulfoxide, etc.; or a mixed solvent thereof, preferably ethers, particularly preferably tetrahydrofuran.

As the base to be used, there may be mentioned, for example, amines such as triethylamine, pyridine, 1,8-diazabicyclo [5.4.0]-7-undecene or diisopropylethylamine, etc.; inorganic bases such as sodium hydride, potassium hydride, potassium carbonate, sodium carbonate, sodium hydrogen carbonate, potassium hydroxide or sodium hydroxide, etc.; or organic bases such as methyl lithium, butyl lithium, lithium diisopropylamide, sodium bistrimethylsilylamide,

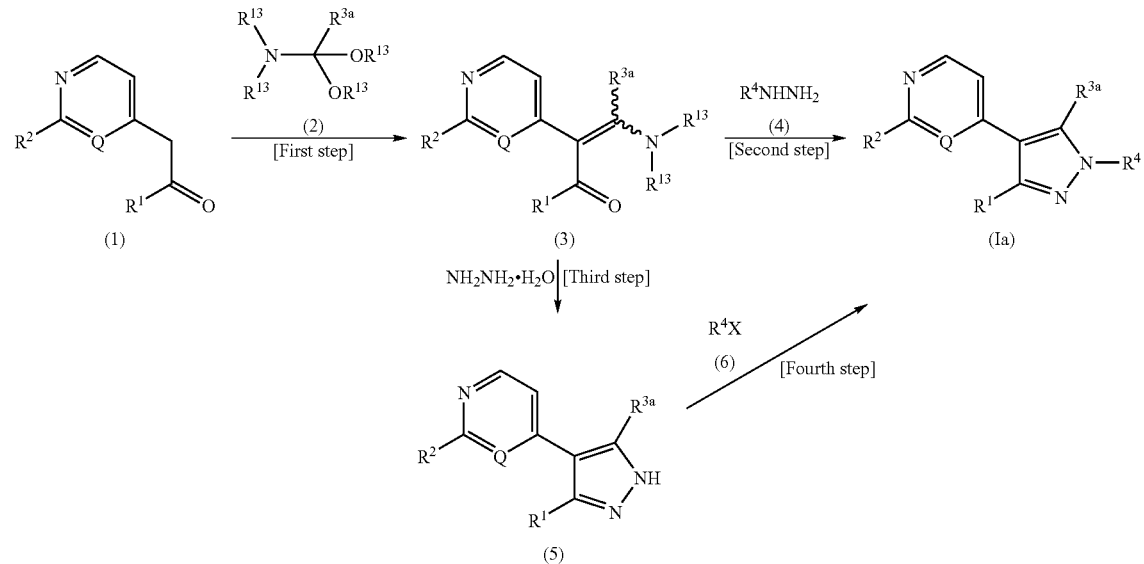

(wherein $R^1$, $R^2$, $R^4$ and Q have the same meanings as defined above, $R^{3a}$ represents a hydrogen atom or $C_1$-$C_6$ alkyl group, $R^{13}$ represents a $C_1$-$C_6$ alkyl group, and X represents a halogen atom.)

The first step is a step to prepare compound (3) by reacting a ketone compound (1) with an acetal compound (2) in an organic solvent. The present step may be carried out in the co-presence of a base or an acid, and may be reacted by using either one of these.

The ketone compound (1) can be prepared by, for example, the method according to those disclosed in WO97/5878 publication.

The acetal compound (2) is a conventionally known compound or can be prepared according to the conventionally known method from a conventionally known compound(s).

An amount of the acetal compound (2) to be used is generally 1 to 10-fold mol based on the amount of the ketone compound (1), and preferably 1 to 3-fold mol.

As the organic solvent to be used, it is not particularly limited so long as it does not inhibit the reaction and it dissolves the starting substances with a certain extent, and there may be mentioned, for example, aromatic hydrocarbons such as benzene, toluene, xylene or mesitylene, etc.; aliphatic hydrocarbons such as pentane, hexane or cyclohexane, etc.; ethers such as tetrahydrofuran, diethyl ether, diisopropyl ether, ethylene glycol dimethyl ether, dioxane or sodium methoxide, sodium ethoxide or potassium t-butoxide, etc., preferably triethylamine.

An amount of the base to be used is generally 0.1 to 5-fold mol based on the amount of the ketone compound (1), and preferably 0.1 to 2-fold mol.

As the acid to be used, there may be mentioned, for example, inorganic acids such as hydrochloric acid, hydrobromic acid, hydriodic acid, sulfuric acid or nitric acid, etc.; or lower aliphatic carboxylic acids such as formic acid, acetic acid, propionic acid or butyric acid, etc., preferably hydrochloric acid or acetic acid.

An amount of the acid to be used is generally 0.1 to 5-fold mol based on the amount of the ketone compound (1), and preferably 0.1 to 2-fold mol.

The reaction temperature may vary depending on the starting compounds, reagents or solvents, etc., and generally 0° C. to 150° C., preferably 0° C. to 100° C.

The reaction time may vary depending on the reaction temperature, and generally 1 hour to 24 hours, preferably 1 hour to 8 hours.

The second step is a step to prepare a pyrazole compound (Ia) of the present invention by condensing compound (3) with a hydrazine compound (4) in an organic solvent.

The hydrazine compound (4) is a conventionally known compound or can be prepared according to the conventionally known method from a conventionally known compound(s).

An amount of the hydrazine compound (4) to be used is generally 1 to 20-fold mol based on the amount of compound (3), and preferably 1 to 10-fold mol.

As the organic solvent to be used, it is not particularly limited so long as it does not inhibit the reaction and it dissolves the starting substances with a certain extent, and the reaction can be carried out, for example, in an alcohol (for example, methanol, ethanol, propanol, butanol or ethylene glycol) or in a mixed solvent of the alcohol and an organic solvent (for example, ethers such as tetrahydrofuran, dioxane or diglyme, etc.; amides such as N,N-dimethylformamide, N,N-dimethylacetamide or N-methyl-2-pyrrolidone, etc.; or sulfoxides such as dimethylsulfoxide, etc. or a mixed solvent thereof, preferably ethers).

The reaction temperature may vary depending on the starting compounds, reagents or solvents, etc., and generally 0° C. to 150° C., preferably 0° C. to 100° C.

The reaction time may vary depending on the reaction temperature, and generally 1 hour to 48 hours, preferably 1 hour to 24 hours.

The third step is a step to prepare a pyrazole compound (5) by subjecting compound (3) to condensation with hydrazine monohydrate in an organic solvent. The present step is carried out according to the above-mentioned "second step" except for using hydrazine monohydrate in place of the hydrazine compound (4).

The fourth step is a step to prepare compound (Ia) of the present invention by reacting the pyrazole compound (5) with a halogen compound (6) using a base in an organic solvent under an inert gas atmosphere.

The halogen compound (6) is a conventionally known compound or can be prepared according to the conventionally known method from a conventionally known compound(s).

The inert gas to be used means a gas inert to the present reaction, and may be mentioned, for example, an argon gas, a nitrogen gas or a helium gas, etc., and used in the state of introducing into a reaction vessel.

As the organic solvent to be used, it is not particularly limited so long as it does not inhibit the reaction and it dissolves the starting substances with a certain extent, and there may be mentioned, for example, ethers such as tetrahydrofuran, diethyl ether, diisopropyl ether, ethylene glycol dimethyl ether, dioxane or diglyme, etc.; amides such as N,N-dimethylformamide, N,N-dimethylacetamide, N-methyl-2-pyrrolidone or hexamethylphosphoryl triamide, etc.; sulfoxides such as dimethylsulfoxide, etc.; or a mixed solvent thereof, preferably ethers, particularly preferably tetrahydrofuran.

As the base to be used, there may be mentioned, for example, amines such as triethylamine, pyridine, 1,8-diazabicyclo [5.4.0]-7-undecene or diisopropylethylamine, etc.; inorganic bases such as sodium hydride, potassium hydride, potassium carbonate, sodium carbonate, sodium hydrogen carbonate, potassium hydroxide or sodium hydroxide, etc.; or organic bases such as methyl lithium, butyl lithium, lithium diisopropylamide, sodium bistrimethylsilylamide, sodium methoxide, sodium ethoxide or potassium t-butoxide, etc., preferably sodium hydride.

An amount of the base to be used is generally 1 to 5-fold mol based on the amount of the pyrazole compound (5), and preferably 1 to 3-fold mol.

An amount of the halogen compound (6) to be used is generally 1 to 5-fold mol based on the amount of the pyrazole compound (5), and preferably 1 to 3-fold mol.

The reaction temperature may vary depending on the starting compounds, reagents or solvents, etc., and generally 0° C. to 150° C., preferably 0° C. to 100° C.

The reaction time may vary depending on the reaction temperature, and generally 1 hour to 24 hours, preferably 1 hour to 12 hours.

[Method 2]

"Method 2" is another method to prepare the pyrazole compound (Ia) of the present invention in which $R^3$ represents a hydrogen atom or $C_1$-$C_6$ alkyl group in the formula (I).

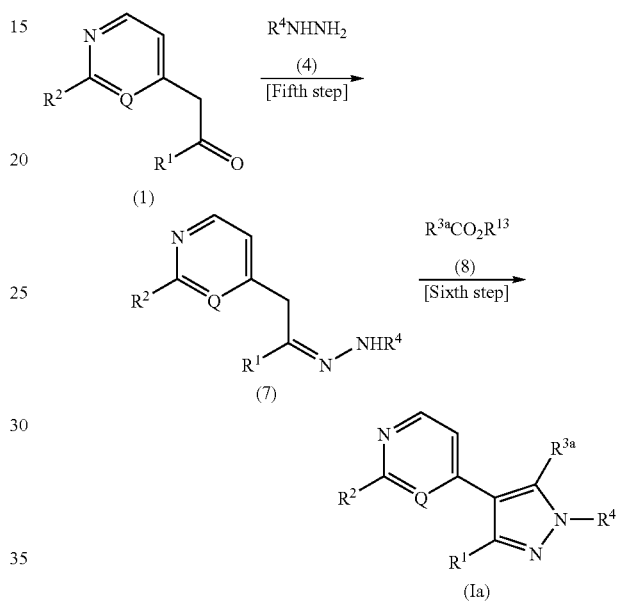

(wherein $R^1$, $R^2$, $R^{3a}$, $R^4$, $R^{13}$ and Q have the same meanings as defined above.)

The fifth step is a step to prepare a hydrazone compound (7) by reacting the ketone compound (1) with the hydrazine compound (4) in an organic solvent. The present step can be carried out according to the conventionally known method as the condensation of the ketone compound and the hydrazine compound.

The sixth step is a step to prepare the pyrazole compound (Ia) of the present invention by reacting the hydrazone compound (7) with an ester compound (8) using a base in an organic solvent. The present step can be carried out according to the method described in, for example, J. Heterocyclic Chem., 24, 555 (1987).

[Method 3]

"Method 3" is a general method to prepare a pyrazole compound (Ib) of the present invention in which $R^3$ represents an amino group in the formula (I).

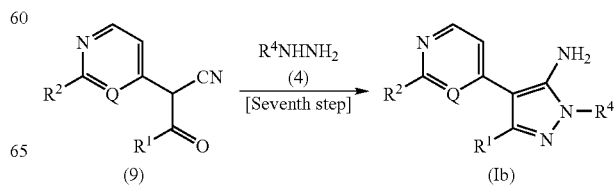

-continued

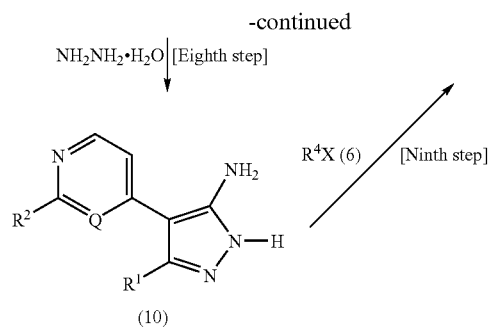

(wherein $R^1$, $R^2$, $R^4$, Q and X have the same meanings as defined above.)

The seventh step is a step to prepare a pyrazole compound (Ib) of the present invention by reacting a ketone compound (9) with the hydrazine compound (4) in an organic solvent.

The ketone compound (9) can be prepared according to the method as described in, for example, WO94/19350.

The present step is carried out according to the above-mentioned "second step" except for using a ketone compound (9) in place of compound (3).

The eighth step is a step to prepare a pyrazole compound (10) by subjecting the ketone compound (9) to condensation with hydrazine monohydrate in an organic solvent. The present step is carried out according to the above-mentioned "third step" except for using a ketone compound (9) in place of the ketone compound (3).

The ninth step is a step to prepare the pyrazole compound (Ib) of the present invention by reacting the pyrazole compound (10) with a halogen compound (6) using a base in an organic solvent under an inert gas atmosphere. The present step is carried out according to the above-mentioned "fourth step" except for using a pyrazole compound (10) in place of the pyrazole compound (5).

[Method 4]

"Method 4" is another method to prepare compound (Id) of the present invention in which $R^2$ represents an amino group and to prepare a pyrazole compound (Ie) of the present invention in which $R^2$ represents a $C_1$-$C_6$ alkyl-carbonylamino group, $C_3$-$C_7$ cycloalkyl-carbonylamino group, $C_1$-$C_6$ alkylsulfonylamino group or $C_1$-$C_6$ alkoxy-carbonylamino group in the formula (I).

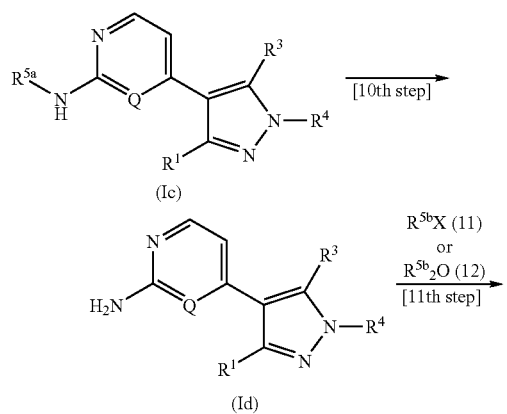

-continued

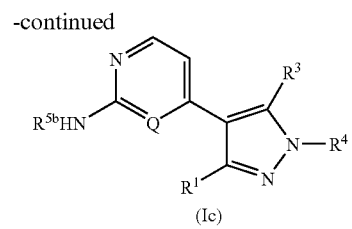

(wherein $R^1$, $R^3$, $R^4$, Q and X have the same meanings as defined above, $R^{5a}$ represents a $C_1$-$C_6$ alkoxy-carbonyl group, $R^{5b}$ represents a $C_1$-$C_6$ alkyl-carbonyl group, $C_3$-$C_7$ cycloalkyl-carbonyl group, $C_1$-$C_6$ alkylsulfonyl group or $C_1$-$C_6$ alkoxy-carbonyl group.)

The tenth step is a step to prepare a pyrazole compound (Id) of the present invention by treating a pyrazole compound (1c) with an acid in an organic solvent.

The pyrazole compound (1c) can be prepared by the above-mentioned "Method 1" to "Method 3".

As the acid to be used, there may be mentioned, for example, inorganic acids such as hydrochloric acid, hydrobromic acid, hydriodic acid, sulfuric acid or nitric acid, etc.; lower aliphatic carboxylic acids such as formic acid, acetic acid, trifluoroacetic acid, propionic acid or butyric acid, etc.; sulfonic acids such as methanesulfonic acid, benzenesulfonic acid, naphthalenesulfonic acid or camphorsulfonic acid, etc.; or a mixed solvent thereof, preferably inorganic acids or lower aliphatic carboxylic acids, particularly preferably hydrochloric acid, sulfuric acid, acetic acid or trifluoroacetic acid.

An amount of the acid to be used is generally 1 to 300-fold mol, preferably 1 to 200-fold mol based on the amount of the pyrazole compound (1c).

The reaction is carried out in the absence of a solvent or in an organic solvent. As the organic solvent to be used, it is not particularly limited so long as it does not inhibit the reaction and it dissolves the starting substances with a certain extent, and there may be mentioned, for example, halogenated hydrocarbons such as dichloromethane, chloroform, dichloroethane or carbon tetrachloride, etc.; alcohols such as methanol, ethanol, propanol, butanol or ethylene glycol, etc.; ethers such as tetrahydrofuran, diethyl ether, diisopropyl ether, ethylene glycol dimethyl ether, dioxane or diglyme, etc.; amides such as N,N-dimethylformamide, N,N-dimethylacetamide or N-methyl-2-pyrrolidone, etc.; sulfoxides such as dimethylsulfoxide, etc.; water or a mixed solvent thereof, preferably alcohols, ethers or water, particularly preferably butanol, dioxane or water.

The reaction temperature may vary depending on the starting compounds, reagents or solvents, etc., and generally 0° C. to 200° C., preferably 50° C. to 150° C.

The reaction time may vary depending on the reaction temperature, and generally 1 hour to 12 hours, preferably 1 hour to 6 hours.

The eleventh step is a step to prepare a pyrazole compound (Ie) of the present invention by reacting the pyrazole compound (Id) with a halogen compound (11) or an acid anhydride (12) using a base under an inert gas atmosphere.

The halogen compound (11) and the acid anhydride (12) are conventionally known compounds or can be prepared according to the conventionally known method from a conventionally known compound(s).

Amounts of the halogen compound (11) and the acid anhydride (12) to be used are generally 1 to 50-fold mol based on the amount of the pyrazole compound (Id), and preferably 1 to 30-fold mol.

The inert gas to be used means a gas inert to the present reaction, and may be mentioned, for example, an argon gas, a nitrogen gas or a helium gas, etc., and used in the state of introducing into a reaction vessel.

The reaction is carried out in the absence of a solvent or in an organic solvent, and as the solvent to be used, it is not particularly limited so long as it does not inhibit the reaction and it dissolves the starting substances with a certain extent, and there may be mentioned, for example, aromatic hydrocarbons such as benzene, toluene, xylene, mesitylene or nitrobenzene, etc.; halogenated hydrocarbons such as dichloromethane, chloroform, dichloroethane or carbon tetrachloride, etc.; aliphatic hydrocarbons such as pentane, hexane or cyclohexane, etc.; or a mixed solvent thereof, preferably halogenated hydrocarbons.

As the base to be used, there may be mentioned, for example, organic amines such as-triethylamine, pyridine, 1,8-diazabicyclo[5.4.0]-7-undecene or diisopropylethylamine, etc., preferably pyridine.

An amount of the base to be used is generally 10 to 500-fold mol based on the amount of the pyrazole compound (Id), and preferably 10 to 300-fold mol.

The reaction temperature may vary depending on the starting compounds, reagents or solvents, etc., and generally 0° C. to 150° C., preferably 0° C. to 100° C.

The reaction time may vary depending on the reaction temperature, and generally 1 hour to 48 hours, preferably 1 hour to 24 hours.

[Method 5]

"Method 5" is another method to prepare a pyrazole compound (If) of the present invention in which $R^2$ represents an amino group which may be substituted by (a $C_7$-$C_{12}$ aralkyl group which may be substituted by a group(s) selected from the group consisting of a $C_1$-$C_6$ alkyl group, $C_3$-$C_7$ cycloalkyl group or halogen atom, $C_1$-$C_6$ alkyl group, halogeno $C_1$-$C_6$ alkyl group, $C_1$-$C_6$ alkoxy group and halogeno $C_1$-$C_6$ alkoxy group), $C_1$-$C_6$ alkoxy group or $C_1$-$C_6$ alkylthio group and to prepare a pyrazole compound (Ig) in which $R^2$ represents a halogen atom in the formula (I).

(wherein $R^1$, $R^3$, $R^4$ $R^{13}$, Q and X have the same meanings as defined above, $R^{5c}$ and $R^{6a}$ may be the same or different from each other, and each represents a hydrogen atom, $C_1$-$C_6$ alkyl group, $C_3$-$C_7$ cycloalkyl group or $C_7$-$C_{12}$ aralkyl group which may be substituted by a group(s) selected from the group consisting of a halogen atom, $C_1$-$C_6$ alkyl group, halogeno $C_1$-$C_6$ alkyl group, $C_1$-$C_6$ alkoxy group and halogeno $C_1$-$C_6$ alkoxy group, $R^{2a}$ represents a group: —$NR^{5c}R^{6a}$, $C_1$-$C_6$ alkoxy group or $C_1$-$C_6$ alkylthio group, $M^+$ represents a cation. As "the cation" in the definition of $M^+$, there may be mentioned, for example, a monovalent metal ion such as a potassium ion, sodium ion, silver ion or copper (I) ion, etc.)

The twelfth step is a step to prepare a pyrazole compound (17) by subjecting a pyrazole compound (13) to nucleophilic substitution reaction with compound (14), compound (15) or compound (16) in an organic solvent.

The pyrazole compound (13) can be prepared by the above-mentioned "third step" or "eighth step".

Compound (14), compound (15) and compound (16) are conventionally known compounds or can be prepared according to the conventionally known method from a conventionally known compound(s).

Amounts of compound (14), compound (15) and compound (16) to be used are generally 1 to 100-fold mol based on the amount of the pyrazole compound (13), and preferably 1 to 50-fold mol.

As the solvent to be used, it is not particularly limited so long as it does not inhibit the reaction and it dissolves the starting substances with a certain extent, and there may be mentioned, for example, alcohols such as methanol, ethanol, propanol or butanol, etc.; ethers such as tetrahydrofuran, diethyl ether, diisopropyl ether, ethylene glycol dimethyl ether, dioxane or diglyme, etc.; amides such as N,N-dimethylformamide, N,N-dimethylacetamide, N-methyl-2-pyrrolidone or hexamethylphosphoryl triamide, etc.; sulfoxides such as dimethylsulfoxide, etc.; or a mixed solvent thereof.

The reaction temperature may vary depending on the starting compounds, reagents or solvents, etc., and generally 50° C. to 250° C., preferably 50° C. to 200° C. at normal pressure or in a sealed tube.

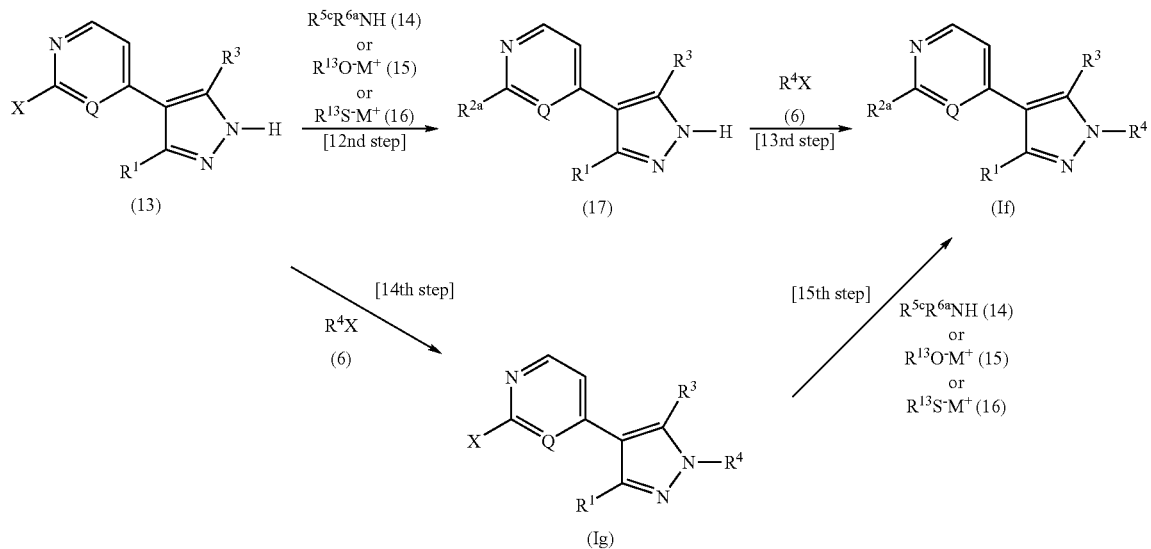

The reaction time may vary depending on the reaction temperature, and generally 1 hour to 48 hours, preferably 1 hour to 24 hours.

In the twelfth step, the reaction of the pyrazole compound (13) and compound (14) may be carried out by using an acid. In this case, when compound (14) is used with a large amount, the organic solvent is not necessarily required.

As the acid to be used, there may be mentioned, for example, inorganic acids such as hydrochloric acid, hydrobromic acid, hydriodic acid, sulfuric acid or nitric acid, etc.; or sulfonic acids such as methanesulfonic acid, benzenesulfonic acid, naphthalenesulfonic acid or camphorsulfonic acid, etc., preferably inorganic acids, particularly preferably hydrochloric acid.

An amount of the acid to be used is generally 0.1 to 100-fold mol based on the amount of the pyrazole compound (13), and preferably 1 to 50-fold mol.

An amount of compound (14) to be used in this case is generally 1 to 100-fold mol based on the amount of the pyrazole compound (13), and preferably 5 to 50-fold mol.

with compound (14), compound (15) or compound (16) in an organic solvent. The present step is carried out according to the above-mentioned "twelfth step" except for using the pyrazole compound (Ig) in place of the pyrazole compound (13).

[Method 6]

"Method 6" is another method to prepare a pyrazole compound (Ih) of the present invention in which $R^2$ represents an amino group di-substituted by a $C_1$-$C_6$ alkoxycarbonyl group and ($C_1$-$C_6$ alkyl group or fluoro $C_1$-$C_6$ alkyl group), a pyrazole compound (Ii) of the present invention in which $R^2$ represents an amino group mono-substituted by a $C_1$-$C_6$ alkyl group or fluoro $C_1$-$C_6$ alkyl group, and a pyrazole compound (Ij) of the present invention in which $R^2$ represents an amino group di-substituted by a ($C_1$-$C_6$ alkyl group or fluoro $C_1$-$C_6$ alkyl group) and ($C_1$-$C_6$ alkyl-carbonyl group, $C_3$-$C_7$ cycloalkyl-carbonyl group, $C_1$-$C_6$ alkyl-sulfonyl group or $C_1$-$C_6$ alkoxy-carbonyl group) in the formula (I).

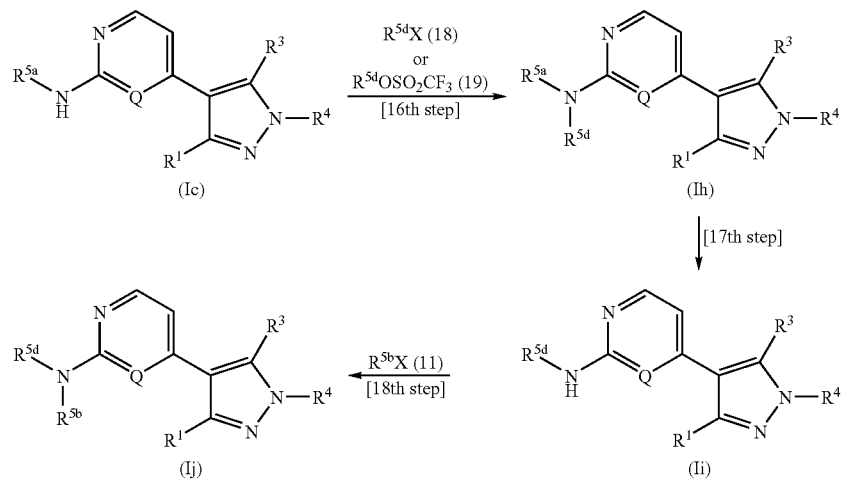

The reaction temperature may vary depending on the starting compounds, reagents or solvents, etc., and generally 50° C. to 200° C., preferably 50° C. to 150° C.

The reaction time may vary depending on the reaction temperature, and generally 1 hour to 24 hours, preferably 1 hour to 12 hours.

The thirteenth step is a step to prepare a pyrazole compound (If) of the present invention by reacting the pyrazole compound (17) with the halogen compound (6) in an organic solvent. The present step is carried out according to the above-mentioned "fourth step" except for using the pyrazole compound (17) in place of the pyrazole compound (5).

The fourteenth step is a step to prepare a pyrazole compound (Ig) of the present invention by reacting the pyrazole compound (13) with the halogen compound (6) in an organic solvent. The present step is carried out according to the above-mentioned "fourth step" except for using the pyrazole compound (13) in place of the pyrazole compound (5).

The fifteenth step is a step to prepare the pyrazole compound (If) of the present invention by subjecting the pyrazole compound (Ig) to nucleophilic substitution reaction (wherein $R^1$, $R^3$, $R^4$, $R^{5a}$, $R^{5b}$, Q and X have the same meanings as defined above, $R^{5d}$ represents a $C_1$-$C_6$ alkyl group or fluoro $C_1$-$C_6$ alkyl group.)

The sixteenth step is a step to prepare a pyrazole compound (Ih) of the present invention by reacting the pyrazole compound (Ic) with a halogen compound (18) or a triflate compound (19) using a base in an organic solvent.

The pyrazole compound (Ic) can be prepared by the above-mentioned "Method 1" or "Method 4".

The halogen compound (18) and the triflate compound (19) are conventionally known compounds or can be prepared according to the conventionally known method from a conventionally known compound(s).

Amounts of the halogen compound (18) and the triflate compound (19) to be used are generally 1 to 40-fold mol based on the amount of the pyrazole compound (Ic), and preferably 1 to 20-fold mol.

As the base to be used, there may be mentioned, for example, amines such as triethylamine, pyridine, 1,8-diazabicyclo[5.4.0]-7-undecene or diisopropylethylamine, etc.; inorganic bases such as sodium hydride, potassium hydride, potassium carbonate, sodium carbonate, sodium hydrogen carbonate, potassium hydroxide or sodium hydroxide, etc.; or organic bases such as methyl lithium, butyl lithium, lithium diisopropylamide, sodium bistrimethylsilylamide, sodium methoxide, sodium ethoxide or potassium t-butoxide, etc., preferably sodium hydride.

An amount of the base to be used is generally 1 to 10-fold mol based on the amount of the pyrazole compound (Ic), and preferably 1 to 5-fold mol.

As the solvent to be used, it is not particularly limited so long as it does not inhibit the reaction and it dissolves the starting substances with a certain extent, and there may be mentioned, for example, ethers such as tetrahydrofuran, diethyl ether, diisopropyl ether, dioxane or diglyme, etc.; amides such as N,N-dimethylformamide, N,N-dimethylacetamide or N-methyl-2-pyrrolidone, etc.; sulfoxides such as dimethylsulfoxide, etc.; or a mixed solvent thereof, preferably amides, particularly preferably N,N-dimethylformamide.

The reaction temperature may vary depending on the starting compounds, reagents or solvents, etc., and generally 0° C. to 200° C., preferably 0° C. to 150° C.

The reaction time may vary depending on the reaction temperature, and generally 1 hour to 24 hours, preferably 1 hour to 8 hours.

The seventeenth step is a step to prepare a pyrazole compound (Ii) of the present invention by reacting the pyrazole compound (Ih) of the present invention using an acid in an organic solvent. The present step is carried out according to the above-mentioned "tenth step" except for using compound (Ih) in place of compound (Ic).

The eighteenth step is a step to prepare a pyrazole compound (Ij) of the present invention by reacting the pyrazole compound (Ii) and the halogen compound (11) using a base under an inert gas atmosphere. The present step is carried out according to the above-mentioned "the eleventh step" except for using compound (Ii) in place of compound (Id).

[Method 7]

"Method 7" is another method to prepare a pyrazole compound (Ik) of the present invention in which $R^4$ is a group represented by the formula (II) and $R^9$ represents a hydrogen atom, and to prepare a pyrazole compound (II) of the present invention in which $R^9$ represents a $C_1$-$C_6$ alkyl group in the formula (I).

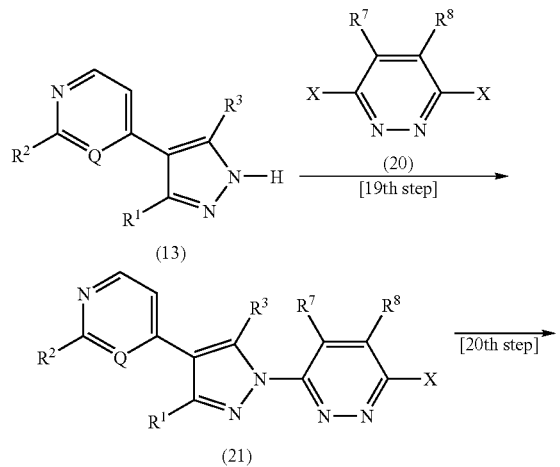

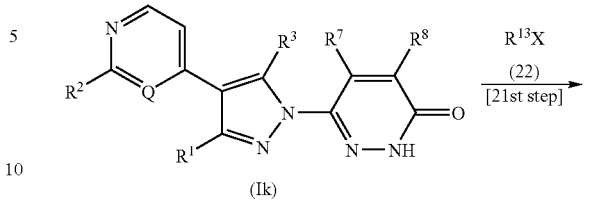

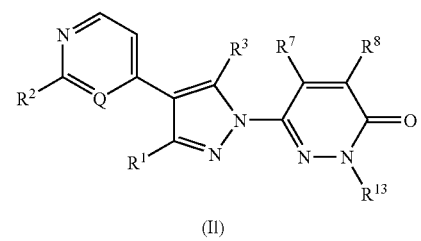

(wherein $R^1$, $R^2$, $R^3$, $R^7$, $R^8$, $R^{13}$, Q and X have the same meanings as defined above.)

The nineteenth step is a step to prepare a pyrazole compound (21) by reacting the pyrazole compound (13) with a halogen compound (20) using a base in an organic solvent. The present step is carried out according to the above-mentioned "fourth step" except for using a halogen compound (20) in place of the halogen compound (6).

The halogen compound (20) is a conventionally known compound or can be prepared according to the conventionally known method from a conventionally known compound(s).

The twentieth step is a step to prepare a pyrazole compound (Ik) of the present invention by subjecting the pyrazole compound (21) to hydrolysis using an acid in water, or a mixed solvent of water and an organic solvent.

As the acid to be used, there may be mentioned, for example, inorganic acids such as hydrochloric acid, hydrobromic acid, hydriodic acid, sulfuric acid or nitric acid, etc.; lower aliphatic carboxylic acids such as formic acid, acetic acid, propionic acid or butyric acid, etc.; sulfonic acids such as methanesulfonic acid, benzenesulfonic acid, naphthalenesulfonic acid or camphorsulfonic acid, etc.; or a mixed solvent thereof, preferably inorganic acids or lower aliphatic carboxylic acids, particularly preferably hydrochloric acid or acetic acid.

An amount of the acid to be used is generally 1 to 200-fold mol based on the amount of the pyrazole compound (21), and preferably 5 to 100-fold mol.

The solvent to be used may be mentioned water, or a mixed solvent of water and an organic solvent (for example, there may be mentioned alcohols such as methanol, ethanol, propanol, butanol or ethylene glycol, etc.; ethers such as tetrahydrofuran, diethyl ether, diisopropyl ether, ethylene glycol dimethyl ether, dioxane or diglyme, etc.; amides such as N,N-dimethylformamide, N,N-dimethylacetamide or N-methyl-2-pyrrolidone, etc.; sulfoxides such as dimethylsulfoxide, etc. or a mixed solvent thereof, preferably ethers) and the reaction is carried out therein.

The reaction temperature may vary depending on the starting compounds, reagents or solvents, etc., and generally 50° C. to 200° C., preferably 50° C. to 150° C.

The reaction time may vary depending on the reaction temperature, and generally 1 hour to 48 hours, preferably 1 hour to 24 hours.

The 21$^{st}$ step is a step to prepare compound (II) of the present invention by reacting compound (Ik) with a halogen compound (22) using a base in an organic solvent under an inert gas atmosphere.

The halogen compound (22) is a conventionally known compound or can be prepared according to the conventionally known method from a conventionally known compound(s).

An amount of the halogen compound (22) to be used is generally 1 to 20-fold mol based on the amount of the pyrazole compound (Ik), and preferably 1 to 10-fold mol.

The inert gas to be used means a gas inert to the present reaction, and may be mentioned, for example, an argon gas, a nitrogen gas or a helium gas, etc., and used in the state of introducing into a reaction vessel.

As the solvent to be used, it is not particularly limited so long as it does not inhibit the reaction and it dissolves the starting substances with a certain extent, and there may be mentioned, for example, ethers such as tetrahydrofuran, diethyl ether, diisopropyl ether, ethylene glycol dimethyl ether, dioxane or diglyme, etc.; amides such as N,N-dimethylformamide, N,N-dimethylacetamide, N-methyl-2-pyrrolidone or hexamethylphosphoryl triamide, etc.; sulfoxides such as dimethylsulfoxide, etc.; or a mixed solvent thereof, preferably aprotic polar solvent, particularly preferably N,N-dimethylformamide.

As the base to be used, there may be mentioned, for example, inorganic bases such as sodium hydride, potassium hydride, lithium carbonate, sodium carbonate, potassium carbonate, cesium carbonate, sodium hydrogen carbonate, potassium hydrogen carbonate, sodium hydroxide or potassium hydroxide, etc.; or organic amines such as triethylamine, 1,8-diazabicyclo[5.4.0]-7-undecene or diisopropylethylamine, etc., preferably inorganic bases, particularly preferably sodium hydride or potassium carbonate.

An amount of the base to be used is generally 1 to 10-fold mol based on the amount of the pyrazole compound (Ik), and preferably 1 to 5-fold mol.

The reaction temperature may vary depending on the starting compounds, reagents or solvents, etc., and generally 0° C. to 150° C., preferably 0° C. to 100° C.

The reaction time may vary depending on the reaction temperature, and generally 1 hour to 48 hours, preferably 1 hour to 24 hours.

[Method 8]

"Method 8" is another method to prepare a pyrazole compound (Im) of the present invention in which R$^4$ is a group represented by the formula (II), and R$^2$ represents an amino group substituted by a C$_1$-C$_6$ alkyl group or fluoro C$_1$-C$_6$ alkyl group in the formula (I).

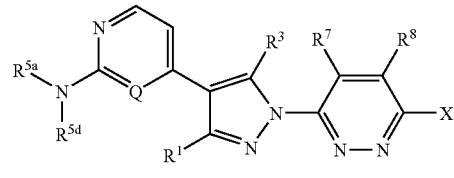

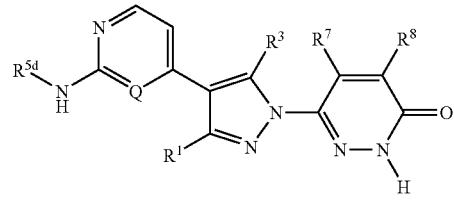

(wherein R$^1$, R$^3$, R$^{5a}$, R$^{5d}$, R$^7$, R$^8$, Q and X have the same meanings as defined above.)

The 22$^{nd}$ step is a step to prepare a pyrazole compound (24) by reacting a pyrazole compound (23) with the halogen compound (18) or the triflate compound (19) using a base in an organic solvent. The present step is carried out according to the above-mentioned "sixteenth step" except for using a pyrazole compound (23) in place of the pyrazole compound (Ic).

The pyrazole compound (23) is a compound in which R$^2$ represents a C$_1$-C$_6$ alkyl-carbonylamino group in the pyrazole compound (21), and can be prepared by the above-mentioned "nineteenth step".

The 23$^{rd}$ step is a step to prepare a pyrazole compound (Im) of the present invention by reacting the pyrazole compound (24) using an acid in an organic solvent.

The present step is carried out by deprotecting the C$_1$-C$_6$ alkoxy-carbonyl group according to the above-mentioned "seventeenth step", and then, subjecting to hydrolysis according to the above-mentioned "twentieth step".

[Method 9]

"Method 9" is another method to prepare a pyrazole compound (Io) of the present invention in which R$^4$ is a group represented by the formula (II), R$^8$ represents an amino group, and R$^9$ represents a hydrogen atom in the formula (I).

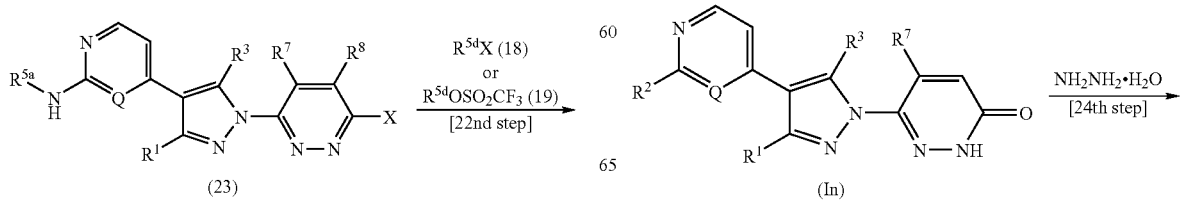

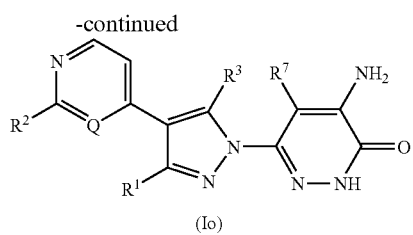

(wherein R¹, R², R³, R⁷ and Q have the same meanings as defined above.)

The 24th step is a step to prepare a pyrazole compound (Io) of the present invention by reacting a pyrazole compound (In) with hydrazine monohydrate in an organic solvent. The present step is carried out according to the method described in, for example, Heterocycles, 29, 1077 (1989).

The pyrazole compound (In) is a compound in which $R^8$ represents a hydrogen atom in the pyrazole compound (Ik) or the pyrazole compound (Im), and can be prepared according to the above-mentioned "twentieth step" or "23rd step". ps [Method 10]

"Method 10" is another method to prepare a pyrazole compound (Ip) of the present invention in which $R^4$ is a group represented by the formula (III), and $R^{12}$ represents a hydrogen atom, $C_1$-$C_6$ alkyl group or halogeno $C_1$-$C_6$ alkyl group, and to prepare a pyrazole compound (Iq) of the present invention in which $R^{12}$ represents an amino group in the formula (I).

The 25th step is a step to prepare a pyrazole compound (Ip) of the present invention by reacting the pyrazole compound (21) with hydrazine monohydrate and compound (25) in an organic solvent.

The pyrazole compound (21) can be prepared by the above-mentioned "nineteenth step".

Compound (25) is a conventionally known compound or can be prepared according to the conventionally known method from a conventionally known compound(s).

As the solvent to be used, it is not particularly limited so long as it does not inhibit the reaction and it dissolves the starting substances with a certain extent, and there may be mentioned, for example, ethers such as diethyl ether, diisopropyl ether, tetrahydrofuran, dioxane, ethylene glycol dimethyl ether or diglyme, etc.; alcohols such as methanol, ethanol, propanol, butanol or ethylene glycol, etc.; sulfoxides such as dimethylsulfoxide, etc.; nitriles such as acetonitrile; esters such as methyl acetate, ethyl acetate, etc.; aromatic hydrocarbons such as benzene, toluene or xylene, etc.; or a mixed solvent thereof, preferably alcohols.

An amount of hydrazine monohydrate to be used is generally 1 to 100-fold mol based on the amount of the pyrazole compound (21), and preferably 10 to 50-fold mol.

An amount of compound (25) to be used is generally 20 to 100-fold mol based on the amount of the pyrazole compound (21), and preferably 40 to 80-fold mol.

The reaction temperature may vary depending on the starting compounds, reagents or solvents, etc., and generally 0° C. to 200° C., preferably 50° C. to 150° C.

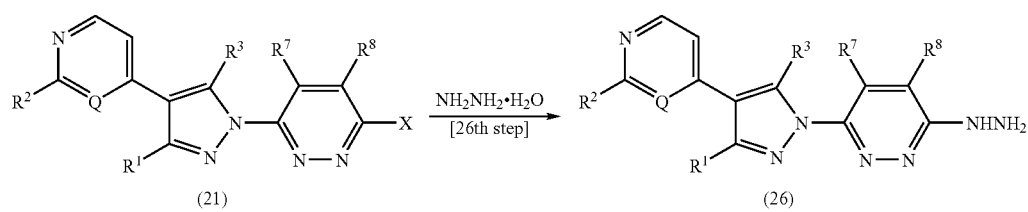

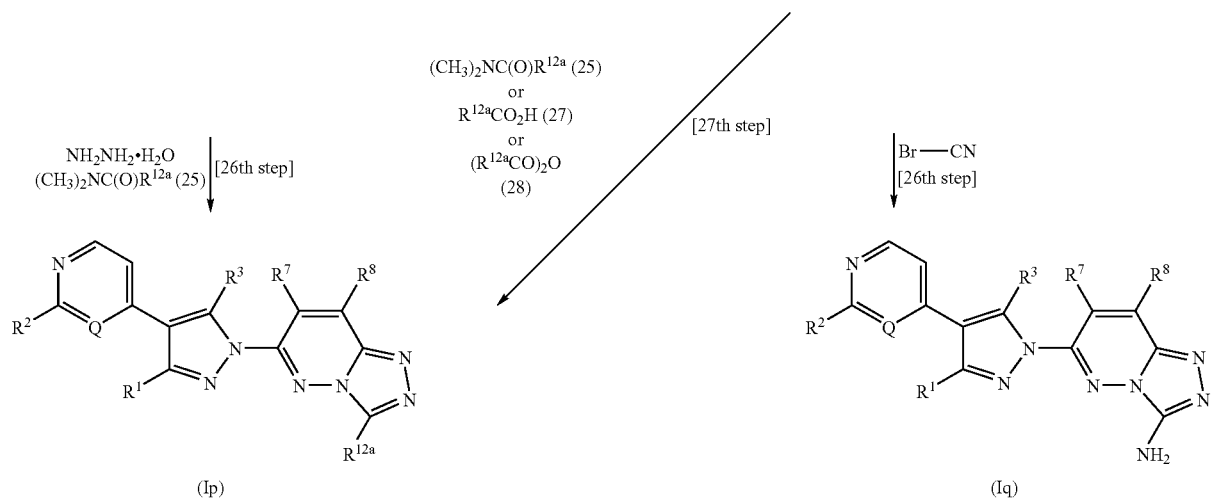

(wherein R₁, R², R³, R⁷, R⁸, Q and X have the same meanings as defined above, $R^{12a}$ represents a hydrogen atom, $C_1$-$C_6$ alkyl group or halogeno $C_1$-$C_6$ alkyl group.)

The reaction time may vary depending on the reaction temperature, and generally 1 hour to 24 hours, preferably 1 hour to 10 hours.

The 26th step is a step to prepare a pyrazole compound (26) by reacting the pyrazole compound (21) with hydrazine monohydrate in an organic solvent.

An amount of hydrazine monohydrate to be used is generally 1 to 50-fold mol based on the amount of the pyrazole compound (21), and preferably 5 to 30-fold mol.

As the solvent to be used, it is not particularly limited so long as it does not inhibit the reaction and it dissolves the starting substances with a certain extent, and there may be mentioned, for example, aromatic hydrocarbons such as benzene, toluene, xylene or mesitylene, etc.; alcohols such as methanol, ethanol, propanol, butanol or ethylene glycol, etc.; ethers such as diethyl ether, diisopropyl ether, tetrahydrofuran, dioxane, ethylene glycol dimethyl ether or diglyme, etc.; or a mixed solvent thereof, preferably alcohols.

The reaction temperature may vary depending on the starting compounds, reagents or solvents, etc., and generally 0° C. to 200° C., preferably 50 to 150° C.

The reaction time may vary depending on the reaction temperature, and generally 1 hour to 24 hours, preferably 1 hour to 10 hours.

The 27th step is a step to prepare a pyrazole compound (Ip) of the present invention by subjecting the pyrazole compound (26) to cyclization reaction with compound (25), compound (27) or compound (28) in an organic solvent.

Compound (27) and compound (28) are conventionally known compounds or can be prepared according to the conventionally known method from a conventionally known compound(s).

The reaction is carried out in the absence of a solvent or in an organic solvent, and as the solvent to be used, it is not particularly limited so long as it does not inhibit the reaction and it dissolves the starting substances with a certain extent, and there may be mentioned, for example, ethers such as diethyl ether, diisopropyl ether, tetrahydrofuran, dioxane, ethylene glycol dimethyl ether or diglyme, etc.; alcohols such as methanol, ethanol, propanol, butanol or ethylene glycol, etc.; sulfoxides such as dimethylsulfoxide, etc.; nitrites such as acetonitrile; esters such as methyl acetate or ethyl acetate, etc.; aromatic hydrocarbons such as benzene, toluene or xylene, etc.; or a mixed solvent thereof, preferably alcohols.

An amount of compound (25), compound (27) or compound (28) to be used is generally 1 to 50-fold mol based on the amount of the pyrazole compound (26), and preferably 10 to 30-fold mol.

The reaction temperature may vary depending on the starting compounds, reagents or solvents, etc., and generally 0° C. to 200° C., preferably 50° C. to 150° C.

The reaction time may vary depending on the reaction temperature, and generally 1 hour to 24 hours, preferably 1 hour to 10 hours.

The 28th step is a step to prepare a pyrazole compound (Iq) of the present invention by subjecting the pyrazole compound (26) to cyclization with cyan bromide in an organic solvent. The present step is carried out according to the method described in, for example, J. Med. Chem., 37, 2153 (1994).

[Method 11]

"Method 11" is another method to prepare a pyrazole compound (Is) of the present invention in which $R^4$ is a group represented by the formula (IV) in the formula (I).

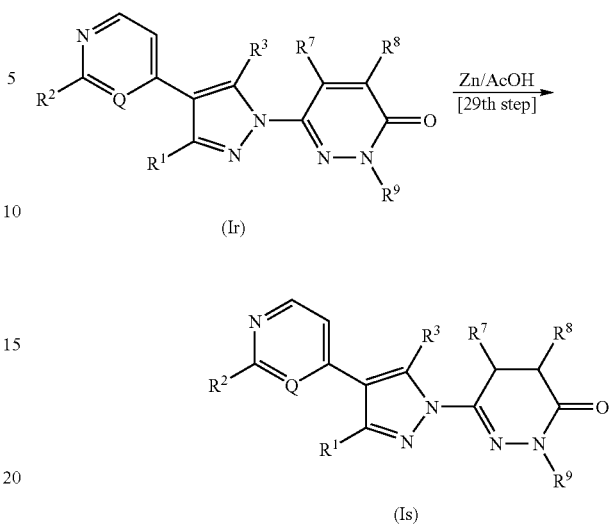

(wherein $R^1$, $R^2$, $R^3$, $R^7$, $R^8$, $R^9$ and Q have the same meanings as defined above.)

The 29th step is a step to prepare a pyrazole compound (Is) by treating a pyrazole compound (Ir) with zinc in acetic acid. The present step is carried out according to the method as disclosed in, for example, J. Chem. Soc. Chem. Commun., 20, 1373(1984).

The pyrazole compound (Ir) can be prepared according to the above-mentioned "Method 7", "Method 8" or "Method 9".

[Method 12]

"Method 12" is another method to prepare a pyrazole compound (Iu) of the present invention in which $R^4$ is a group represented by the formula (IV), and $R^9$ is a $C_1$-$C_6$ alkyl group in the formula (I).

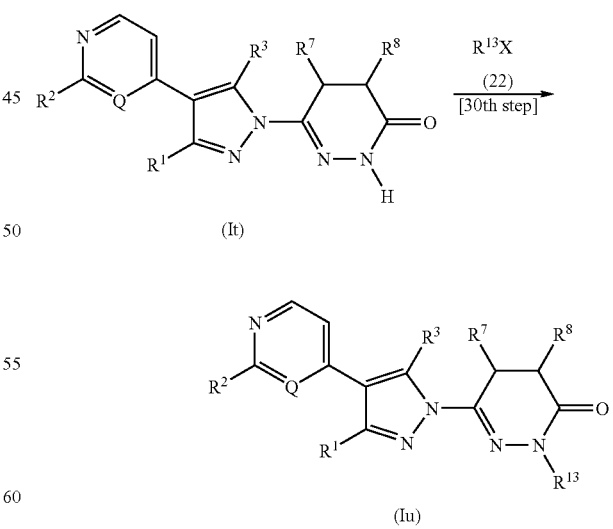

(wherein $R^1$, $R^2$, $R^3$, $R^7$, $R^8$, $R^{13}$, Q and X have the same meanings as defined above.)

The 30th step is a step to prepare a pyrazole compound (Iu) of the present invention by reacting a pyrazole compound (It) with a halogen compound (22) using a base in an organic solvent under an inert gas atmosphere. The present step is carried out according to the above-mentioned "21$^{st}$ step" except for using the pyrazole compound (It) in place of the pyrazole compound (Ik).

The pyrazole compound (It) is a compound in which $R^9$ is a hydrogen atom in the pyrazole compound (Is), and can be prepared by the above-mentioned "Method 11".

[Method 13]

"Method 13" is another method to prepare a pyrazole compound (Iw) of the present invention in which $R^2$ represents a $C_1$-$C_6$ alkylsulfinyl group or $C_1$-$C_6$ alkylsulfonyl group, and a pyrazole compound (Ix) of the present invention in which $R^2$ represents a group: —$NR^5R^6$ or $C_1$-$C_6$ alkoxy group in the formula (I).

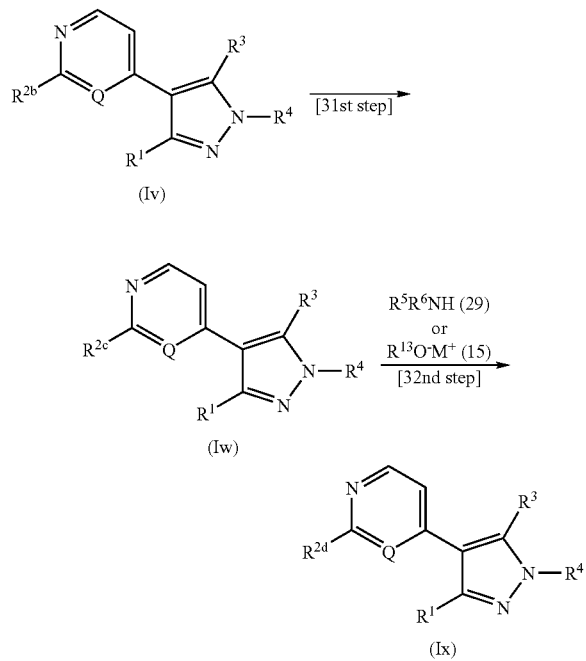

(wherein $R^1$, $R^3$, $R^4$, $R^5$, $R^6$, $R^{13}$, Q and $M^+$ have the same meanings as defined above, $R^{2b}$ represents a $C_1$-$C_6$ alkylthio group, $R^{2c}$ represents a $C_1$-$C_6$ alkylsulfinyl group or $C_1$-$C_6$ alkylsulfonyl group, $R^{2d}$ represents a group: —$NR^5R^6$ or $C_1$-$C_6$ alkoxy group.)

The 31$^{st}$ step is a step to prepare a pyrazole compound (Iw) of the present invention in which $R^2$ represents a $C_1$-$C_6$ alkylsulfinyl group or $C_1$-$C_6$ alkylsulfonyl group by oxidizing a pyrazole compound (Iv) in which $R^2$ represents a $C_1$-$C_6$ alkylthio group using an oxidizing agent in an organic solvent.

The pyrazole compound (Iv) can be prepared according to the above-mentioned "Method 1" or "Method 5".

As the organic solvent to be used, there may be mentioned, for example, aromatic hydrocarbons such as benzene, toluene, xylene or mesitylene, etc.; alcohols such as methanol, ethanol, propanol or butanol, etc.; halogenated hydrocarbons such as dichloromethane, chloroform, carbon tetrachloride or dichloroethane, etc.; lower aliphatic carboxylic acids such as formic acid, acetic acid or propionic acid, etc.; ethers such as diethyl ether, diisopropyl ether, tetrahydrofuran, dioxane, ethylene glycol dimethyl ether or diglyme, etc.; water; or a mixed solvent thereof, preferably alcohols, halogenated hydrocarbons, aliphatic carboxylic acids, water or a mixed solvent thereof, particularly preferably methanol, chloroform, acetic acid, water or a mixed solvent thereof.

As the oxidizing agent to be used, there may be mentioned, for example, peracids such as OXONE (tradename), peracetic acid, perbenzoic acid or m-chloro benzoic acid, etc.; hydrogen peroxide; or alkali metal perhalogenic acids such as sodium metaperchlorate, sodium metaperiodate or potassium metaperiodate, etc., preferably OXONE or peracids, particularly preferably OXONE or m-chloroper-benzoic acid.

An amount of the oxidizing agent to be used is generally 1 to 3-fold mol based on the amount of the pyrazole compound (Iv), and preferably 1 to 2-fold mol.

The reaction temperature may vary depending on the starting compounds, reagents or solvents, and generally –20° C. to 100° C., preferably 0° C. to 50° C.

The reaction time may vary depending on the starting compounds, the reaction temperature, the reagents or the solvents, etc., and generally 10 minutes to 10 hours, preferably 30 minutes to 5 hours.

The 32$^{nd}$ step is a step to prepare a pyrazole compound (Ix) of the present invention by subjecting the pyrazole compound (Iw) to nucleophilic substitution reaction with compound (29) or compound (15) in an inert organic solvent.

The reaction is carried out in the absence of a solvent or in an organic solvent, and as the organic solvent to be used, there may be mentioned, for example, aromatic hydrocarbons such as benzene, toluene, xylene or mesitylene, etc.; alcohols such as methanol, ethanol, propanol, butanol or ethylene glycol, etc.; ethers such as diethyl ether, diisopropyl ether, tetrahydrofuran, dioxane, ethylene glycol dimethyl ether or diglyme, etc.; or a mixed solvent thereof, preferably ethers.

An amount of compound (29) to be used is generally 1 to 100-fold mol based on the amount of compound (Iw), and preferably 5 to 50-fold mol.

An amount of compound (15) to be used is generally 1 to 50-fold mol based on the amount of compound (Iw), and preferably 2 to 10-fold mol.

The reaction temperature may vary depending on the starting compounds, reagents or solvents, and generally 0° C. to 200° C., preferably 50° C. to 150° C.

The reaction time may vary depending on the starting compounds, the reaction temperature, the reagents or the solvents, etc., and generally 10 minutes to 24 hours, preferably 10 minutes to 10 hours.

Incidentally, when $R^{2d}$ represents a group: —$NR^5R^6$, and either on of $R^5$ and $R^6$ is a hydrogen atom, and the other is a 4-methoxybenzyl group in the pyrazole compound (Ix), the 4-methoxybenzyl group can be removed according to the conventionally known method (for example, J. Chem. Soc. Perkin Trans I, 627 (1982)).

[Method 14]

"Method 14" is another method to prepare a pyrazole compound (Iz) of the present invention in which $R^4$ is a group represented by the formula (II) to (IV), and $R^8$ or $R^{12}$ represents a $C_1$-$C_6$ alkyl-carbonylamino group, formylamino group, $C_1$-$C_6$ alkoxy-carbonylamino group or $C_1$-$C_6$ alkylsulfonylamino group in the formula (I).

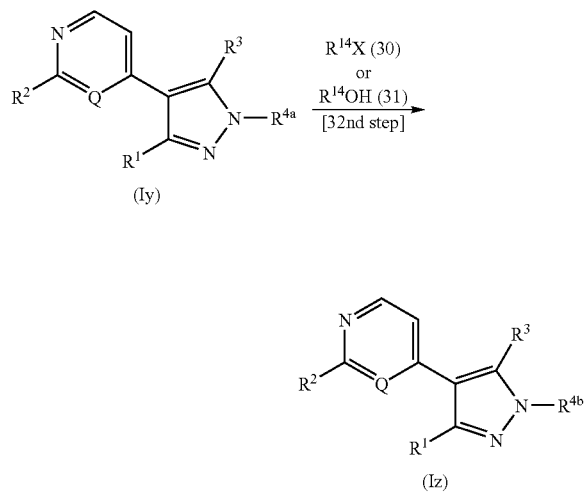

(wherein $R^1$, $R^2$, $R^3$, Q and X have the same meanings as defined above, $R^{14}$ represents a $C_1$-$C_6$ alkyl-carbonyl group, formyl group, $C_1$-$C_6$ alkoxy-carbonyl group or $C_1$-$C_6$ alkyl-sulfonyl group, $R^{4a}$ represents (a 1,6-dihydro-6-oxopyridazin-3-yl group, [1,2,4] triazolo[4,3-b] pyridazin-6-yl group, 1,4,5,6-tetrahydro-6-oxopyridazin-3-yl group or 7,8-dihydro-[1,2,4] triazolo[4,3-b] pyridazin-6-yl group) having an amino group, $R^{4b}$ represents a 1,6-dihydro-6-oxopyridazin-3-yl group, [1,2,4] triazolo[4,3-b] pyridazin-6-yl group, 1,4,5,6-tetrahydro-6-oxopyridazin-3-yl group or 7,8-dihydro-[1,2,4] triazolo[4,3-b] pyridazin-6-yl group each of which has a $C_1$-$C_6$ alkyl-carbonylamino group, formylamino group, $C_1$-$C_6$ alkoxy-carbonylamino group or $C_1$-$C_6$ alkyl-sulfonylamino group. )

The 33$^{rd}$ step is a step to prepare a pyrazole compound (Iz) of the present invention by reacting a pyrazole compound (Iy) with compound (30) or compound (31) in an organic solvent, and when compound (30) is used, it is generally carried out in an organic solvent and in the presence or absence of the base, while when compound (31) is used, the reaction can be carried out by using a condensing agent in an organic solvent.

The pyrazole compound (Iy) is a compound in which $R^8$ is an amino group when $R^4$ is represented by the formula (II) or (IV), or $R^8$ or $R^{12}$ is an amino group when $R^4$ is represented by the formula (III), in compound (I), and can be prepared either of the above-mentioned "Method 1", "Method 9" or "Method 10".

Compound (30) and compound (31) are conventionally known compounds or can be prepared according to the conventionally known method from a conventionally known compound(s).

When it is reacted with compound (30), as the organic solvent to be used, there may be mentioned, for example, ethers such as diethyl ether, diisopropyl ether, tetrahydrofuran, dioxane, ethylene glycol dimethyl ether or diglyme, etc.; aprotic polar solvents such as N,N-dimethylformamide, N,N-dimethylacetamide or dimethylsulfoxide, etc.; aromatic hydrocarbons such as benzene, toluene or xylene, etc.; aliphatic hydrocarbons such as pentane, hexane or heptane, etc.; or a mixed solvent thereof, preferably aprotic polar solvent.

As the base to be used, there may be mentioned, for example, alkali metal alkoxides such as sodium methoxide, sodium ethoxide or potassium t-butoxide, etc.; alkali metal hydroxides such as sodium hydroxide, potassium hydroxide or lithium hydroxide, etc.; alkali metal carbonate such as sodium carbonate or potassium carbonate, etc.; or organic amines such as triethylamine, tributylamine, diisopropyl-ethylamine or 1,8-diazabicyclo[5.4.0]-7-undecene, etc., preferably organic amines or alkali metal carbonates.

An amount of the base to be used is generally 1 to 10-fold mol based on the amount of the pyrazole compound (Iy), and preferably 1 to 5-fold mol.

An amount of compound (30) to be used is generally 1 to 50-fold mol based on the amount of the pyrazole compound (Iy), and preferably 1 to 10-fold mol.

The reaction temperature may vary depending on the starting compounds, reagents or solvents, and generally 0° C. to 200° C., preferably 0° C. to 100° C.

The reaction time may vary depending on the starting compounds, the reaction temperature, the reagents or the solvents, etc., and generally 1 hour to 24 hours, preferably 1 hour to 10 hours.

When it is reacted with compound (31), as the organic solvent to be used, there may be mentioned, for example, ethers such as diethyl ether, diisopropyl ether, tetrahydrofuran, dioxane, ethylene glycol dimethyl ether or diglyme, etc.; aprotic polar solvents such as N,N-dimethylformamide, N,N-dimethylacetamide or dimethylsulfoxide, etc.; aromatic hydrocarbons such as benzene, toluene or xylene, etc.; aliphatic hydrocarbons such as pentane, hexane or heptane, etc.; or a mixed solvent thereof, preferably aprotic polar solvents.

An amount of compound (31) to be used is generally 1 to 5-fold mol based on the amount of the pyrazole compound (Iy), and preferably 1 to 3-fold mol.

As the condensing agent to be used, there may be mentioned, for example, benzotriazol-1-yloxytris(dimethylamino)phosphonium hexafluorophosphate, benzotriazol-1-yloxytripyrrolidinophosphonium hexafluorophosphate, 2-(1H-benzotriazol-1-yl)-1,1,3,3-tetramethyluronium hexafluorophosphate, 2-(1H-benzotriazol-1-yl)-1,1,3,3-tetramethyluronium tetrafluoroborate, bromotripyrrolidinophosphonium hexafluorophosphate, 1-hydroxybenzotriazole, 3-hydroxy-4-oxo-3,4-dihydro-1,2,3-benzotriazine, 1,1'-carbonyldiimid-azole, N,N'-dicyclohexylcarbodiimide, 4-dimethylamino-pyridine, 2-ethoxy-1-ethoxycarbonyl-1,2-dihydroquinoline, 1-ethyl-3-(3'-dimethylaminopropyl)carbodiimide hydrochloride or N-hydroxysuccinimide, etc., and may be mentioned a combination of these condensing agents.

An amount of the condensing agent to be used is generally 1 to 3-fold mol based on the amount of the pyrazole compound (Iy), and preferably 1 to 1.5-fold mol.

The reaction temperature may vary depending on the starting compounds, reagents or solvents, and generally 0° C. to 100° C., preferably 0° C. to 50° C.

The reaction time may vary depending on the starting compounds, the reaction temperature, the reagents or the solvents, etc., and generally 1 hour to 12 hours, preferably 1 hour to 6 hours.

[Method 15]

"Method 15" is another method to prepare a pyrazole compound (Ibb) of the present invention in which $R^4$ is a group represented by the formula (V) in the formula (I).

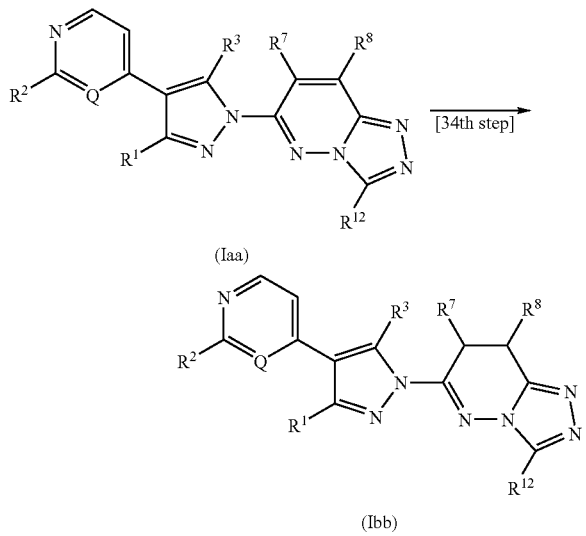

(wherein $R^1$, $R^2$, $R^3$, $R^7$, $R^8$, $R^{12}$ and Q have the same meanings as defined above.)

The 34$^{th}$ step is a step to prepare a pyrazole compound (Ibb) of the present invention by treating a pyrazole compound (Iaa) with a reducing agent.

The present step is carried out according to the above-mentioned "29$^{th}$ step" by using the pyrazole compound (Iaa) in place of using the pyrazole compound (Ir) when it is treated with zinc in acetic acid.

Also, when reduction is carried out by using lithium aluminum hydride or sodium borohydride, it may be carried out according to the method as described in, for example, Pharmazie, 38 (6), 369 (1983).

The pyrazole compound (Iaa) can be prepared according to either of the above-mentioned "Method 1" to "Method 6" and "Method 10".

After completion of the above-mentioned respective reactions, the objective compound may be isolated from the reaction mixture according to the conventional manner. For example, it can be obtained by neutralizing the reaction mixture as needed, removing insoluble materials by filtration, if any one present, adding organic solvents which are not miscible with water such as ethyl acetate, washing with water, separating the organic layer containing the objective compound, drying it over anhydrous magnesium sulfate, etc., and then distillating off the solvent.

The obtained objective compound, if necessary, can be isolated and purified by the conventional methods, for example, by an optional combination of recrystallization, reprecipitation, or a method (for example, adsorption column chromatography method or ion-exchange chromatography method using a carrier such as silica gel, alumina, etc., or normal phase and reverse phase column chromatography method (preferably high performance liquid chromatography.) using silica gel or alkylated silica gel) usually employed for separation and purification of an organic compound by eluting with a suitable eluent.

Compound (I) of the present invention can be easily converted into a pharmaceutically acceptable salt by treating with an acid as mentioned below. As such a salt, there may be mentioned, for example, inorganic acid salts such as hydrochloride, hydrobromide, hydroiodide, nitrate, sulfate or phosphate, etc.; or organic acid salts such as acetate, propionate, butyrate, benzoate, phthalate, oxalate, malonate, succinate, maleate, fumarate, tartarate, citrate, methanesulfonate, ethanesulfonate, trifluoro-methanesulfonate, benzenesulfonate, 2,4-dimethylbenzene-sulfonate, 2,4,6-trimethylbenzenesulfonate, p-toluenesulfonate, 4-ethylbenzenesulfonate, 2-naphthalenesulfonate, glutamate or aspartate, etc., preferably hydrochloride, hydrobromide, sulfate, methanesulfonate or benzenesulfonate.

Moreover, a hydrate of compound (I) or the salt thereof is also included in the present invention.

An acid addition salt of compound (I) of the present invention can be prepared by reacting with an acid in an inert solvent or in the absence of a solvent (preferably in an inert solvent), adding seed crystals depending on necessity, or adding a poor solvent depending on necessity or removing the solvent, and collecting the precipitated crystals by filtration.

An amount of the acid to be used in the reaction may be, in the case of a monovalent acid, for example, 0.1 to 10 equivalents based on the amount of compound (I), preferably 0.3 to 5 equivalents, more preferably 0.5 to 3 equivalents.

An amount of the acid to be used in the reaction may be, in the case of a divalent acid, for example, 0.1 to 5 equivalents based on the amount of compound (I), preferably 0.2 to 3 equivalents, more preferably 0.3 to 1.5 equivalents.

An amount of the acid to be used in the reaction may be, in the case of a trivalent acid, for example, 0.1 to 3 equivalents based on the amount of compound (I), preferably 0.2 to 2 equivalents, more preferably 0.3 to 1 equivalent.

The solvent to be used is not particularly limited so long as it does not inhibit the reaction and it dissolves the starting substances with a certain extent, and there may be mentioned, for example, aliphatic hydrocarbons such as pentane, hexane, heptane or cyclohexane, etc.; aromatic hydrocarbons such as benzene, toluene or xylene, etc.; halogenated hydrocarbons such as methylene chloride, chloroform, dichloroethane, chlorobenzene or dichloro-benzene, etc.; ethers such as diethyl ether, diisopropyl ether, butyl methyl ether, tetrahydrofuran, dioxane, ethylene glycol dimethyl ether or diglyme, etc.; alcohols such as methanol, ethanol, propanol, 2-propanol, butanol, 2-butanol, 2-methyl-1-propanol, 2-methyl-2-propanol or ethylene glycol, etc.; ketones such as acetone, methyl ethyl ketone, methyl isobutyl ketone or cyclohexanone, etc., esters such as methyl acetate, ethyl acetate, propyl acetate or butyl acetate, etc.; nitriles such as acetonitrile, propionitrile, butyronitrile or isobutyronitrile, etc.; amides such as formamide, N,N-dimethylformamide, N,N-dimethylacetamide or N-methyl-2-pyrrolidone, etc.; sulfoxides such as dimethylsulfoxide, etc.; water; or a mixed solvent thereof, preferably alcohols, amides, dimethylsulfoxide or a mixed solvent thereof, further preferably amides, dimethylsulfoxide or a mixed solvent thereof.

The reaction temperature may vary depending on the starting compounds, reagents or solvents, etc., and generally −20° C. to 150° C., preferably 0° C. to 60° C.

The reaction time may vary depending on the reaction temperature, and generally 10 minutes to 24 hours, preferably 30 minutes to 12 hours.

After completion of the reaction, an acid addition salt of compound (I) according to the present invention is isolated from the reaction mixture according to the conventional manner. For example, after completion of the reaction, precipitated crystals are collected by filtration or the solvent is removed whereby an objective compound can be obtained. The obtained objective compound is then, if necessary, purified by the conventionally known method, for example, recrystallization, reprecipitation or column chromatography, etc.

As an administration form of the compounds represented by the formula (I), pharmaceutically acceptable salts thereof or derivatives thereof according to the present invention, there may be mentioned, for example, oral administration by tablets, capsules, granules, powders or syrups, etc., or non-oral administration by injection or suppository, etc. These formulations can be prepared by the conventionally known methods using additives such as an excipient, a lubricant, a binder, a disintegrator, a stabilizer, a corrigent, a diluent, an emulsifying agent, etc.

The excipient may be mentioned, for example, sugar derivatives such as lactose, sucrose, glucose, mannitol, or sorbitol, etc.; starch derivatives such as corn starch, potato starch, α-starch, dextrin, or carboxymethyl starch, etc.; cellulose derivatives such as crystalline cellulose, low-substituted hydroxypropyl cellulose, hydroxypropyl-methyl cellulose, carboxymethyl cellulose, calcium carboxymethyl cellulose, or internally bridged sodium carboxymethyl cellulose, etc.; acacia; dextran; pullulan; silicate derivatives such as light silicic acid anhydride, synthetic aluminum silicate, calcium silicate or magnesium aluminate meta-silicate, etc.; phosphate derivatives such as calcium hydrogen phosphate, etc.; carbonate derivatives such as calcium carbonate, etc.; sulfate derivatives such as calcium sulfate, etc.

The lubricant may be mentioned, for example, talc; stearic acid; metal salts of stearic acid such as calcium stearate or magnesium stearate, etc.; colloidal silica; waxes such as bee gum and spermaceti, etc.; boric acid; glycol; DL-leucine; carboxylic acids such as fumaric acid or adipic acid, etc.; sodium carboxylates such as sodium benzoate, etc.; sulfates such as sodium sulfate, etc.; laurylsulfates such as sodium laurylsulfate or magnesium laurylsulfate, etc.; silicic acids such as silicic acid anhydride or silicic acid hydrate, etc.; one of the starch derivatives described above in relation to the excipient, etc.

The binder may be mentioned, for example, one of the excipients described above; gelatin; polyvinylpyrrolidone; or polyethylene glycol.

The disintegrator may be mentioned, for example, one of the excipients described above; chemically modified starches or cellulose derivatives such as sodium cros-carmellose or sodium carboxymethyl starch, etc.; or bridged polyvinylpyrrolidone, etc.

The stabilizer may be mentioned, for example, para-hydroxybenzoate derivatives such as methylparaben, or propylparaben, etc.; alcohols such as chlorobutanol, benzyl alcohol, or phenylethyl alcohol, etc.; benzalkonium chloride; phenol derivatives such as phenol, or cresol, etc.; thimerosal; acetic anhydride; sorbic acid, etc.

The emulsifying agents may be mentioned, for example, colloidal clay such as bentonite or bee gum; metal hydroxides such as magnesium hydroxide or aluminum hydroxide, etc.; anionic surfactants such as sodium lauryl sulfate or calcium stearate, etc.; cationic surfactant such as benzalkonium chloride, etc.; or nonionic surfactants such as polyoxyethylene alkyl ether, polyoxyethylene sornitan fatty acid ester or sucrose fatty acid ester, etc.

The corrigent may be mentioned, for example, a sweetening, souring, or flavoring agent, which are conventionally used, etc.

The diluent may be mentioned, for example, water, ethanol, propylene glycol, ethoxidized isostearyl alcohol or polyoxyethylene sorbitane fatty acid esters, etc.

The solvent for injection may be mentioned, for example, water, ethanol or glycerin, etc.

The dose for administration of the compounds represented by the formula (I) and pharmaceutically acceptable salts thereof or derivatives thereof of the present invention may vary depending on the condition to be treated, the age of the patient, the administration method, etc. When administered orally, it is administered to an adult in an amount of 0.1 mg (preferably 0.5 mg) a day as a lower limit and 2000 mg (preferably 500 mg) a day as an upper limit. It can be administered in from one to several portions depending on the condition of the patient. When administered intravenously, it is administered to an adult in an amount of 0.01 mg (preferably 0.05 mg) a day as a lower limit and 200 mg (preferably 50 mg) a day as an upper limit. It can be administered in from one to several portions depending on the condition of the patient.

EXAMPLES

In the following, the present invention is explained in more detail by referring to Reference examples, Examples, Test examples and Preparation examples, but the present invention is not limited by these. Incidentally, Rf values in the physical properties in Example are values measured by using thin layer chromatography (available from Merck, TLC plate silica gel 60F$_{254}$ (tradename)), and the description in the brackets represents developing solvents used (volume ratio).

Example 1

3-(4-Fluorophenyl)-1-(1,6-dihydro-6-oxopyridazin-3-yl)-4-(pyridin-4-yl)-1H-pyrazole (Exemplary Compound No. 1-42)

1-1) 3-Dimethylamino-1-(4-fluorophenyl)-2-(pyridin-4-yl)-2-propen-1-one

To 25 ml of a tetrahydrofuran solution containing 15.0 g (69.7 mmol) of 1-(4-fluorophenyl)-2-(pyridin-4-yl)-ethan-1-one (see I. Lantos et al., J. Med. Chem., 27(1), 72 (1984)) was added 25.0 ml (188 mmol) of N,N-dimethylformamide dimethylacetal at room temperature. After the addition, the mixture was stirred for 3 hours.

After completion of the reaction, the residue obtained by concentrating the reaction mixture under reduced pressure was applied to silica gel column chromatography (eluent; ethyl acetate) and the separated fractions containing the objective compound were concentrated under reduced pressure to obtain 10.7 g of the title compound as a yellow powder. (Yield: 57%)

Rf value: 0.70 (chloroform:methanol=9:1).

Mass spectrum (CI, m/z): 271 (M$^+$+1).

$^1$H-NMR spectrum (CDCl$_3$, δ ppm): 2.80 (s, 6H), 6.93-7.02 (m, 2H), 7.06 (dd, J$_1$=4.4 Hz, J$_2$=1.6 Hz, 2H), 7.39-7.47 (m, 3H), 8.49 (dd, J$_1$=4.4 Hz, J$_2$=1.6 Hz, 2H).

1-2) 3-(4-Fluorophenyl)-4-(pyridin-4-yl)-1H-pyrazole

To 40 ml of an ethanol solution containing 5.60 g (20.7 mmol) of 3-dimethylamino-1-(4-fluorophenyl)-2-(pyridin-4-yl)-2-propen-1-one obtained in Example 1-1) was added 2.56 ml (52.8 mmol) of hydrazine monohydrate at room temperature. After the addition, the mixture was stirred for 16 hours.

After completion of the reaction, the reaction mixture was concentrated under reduced pressure, the obtained crude crystals were washed with 60 ml of diisopropyl ether to obtain 4.65 g of the title compound as a pale yellow powder. (Yield: 94%)

Rf value: 0.67 (chloroform:methanol=9:1).

Mass spectrum (CI, m/z): 240 ($M^+$+1).

$^1$H-NMR spectrum (DMSO-d6, δ ppm): 7.23-7.30 (m, 4H), 7.42-7.48 (m, 2H), 8.13 (brs, 1H), 8.45 (dd, $J_1$=4.8 Hz, $J_2$=1.3 Hz, 2H), 13.36 (brs, 1H).

1-3) 1-(6-Chloropyridazin-3-yl)-3-(4-fluorophenyl)-4-(pyridin-4-yl)-1H-pyrazole To 30 ml of a tetrahydrofuran solution containing 0.48 g (12.0 mmol) of sodium hydride (60% dispersed material in mineral oil) was added 2.39 g (10.0 mmol) of 3-(4-fluorophenyl)-4-(pyridin-4-yl)-1H-pyrazole obtained in Example 1-2) under stirring at room temperature and under argon atmosphere. After completion of the addition, the mixture was stirred for 15 minutes, and then, 1.64 g (11.0 mmol) of 3,6-dichloropyridazine was added to the mixture. Moreover, the mixture was stirred for 1 hour, and then, stirred at 50° C. for 45 minutes.

After completion of the reaction, the reaction mixture was poured into 200 ml of ice-water, neutralized with an aqueous saturated ammonium chloride solution, and extracted with 500 ml of a mixed solvent (chloroform: methanol=9:1 (V/V)). The organic layer was washed successively with water, and then, with an aqueous saturated sodium chloride solution, dried over anhydrous magnesium sulfate, and concentrated under reduced pressure. The obtained residue was applied to silica gel column chromatography (eluent; chloroform:ethyl acetate:methanol=30:4:1 (V/V/V)), and the separated factions containing the objective compound were concentrated under reduced pressure.

The obtained crude crystals were washed with 50 ml of a mixed solvent (chloroform:methanol=9:1 (V/V)) to obtain 1.42 g of the title compound as a white powder. (Yield: 40%)

Rf value: 0.36 (chloroform:ethyl acetate:methanol=30:4:1).

Mass spectrum (CI, m/z): 352 ($M^+$+1).

$^1$H-NMR spectrum (DMSO-d$_6$, δ ppm): 7.28-7.36 (m, 2H), 7.38 (dd, $J_1$=4.5 Hz, $J_2$=1.7 Hz, 2H), 7.53-7.60 (m, 2H), 8.15 (d, J=9.3 Hz, 1H), 8.38 (d, J=9.3 Hz, 1H), 8.56 (dd, $J_1$=4.5 Hz, $J_2$=1.7 Hz, 2H), 9.29 (s, 1H).

1-4) 3-(4-Fluorophenyl)-1-(1,6-dihydro-6-oxopyridazin-3-yl)-4-(pyridin-4-yl)-1H-pyrazole To 9 ml of an acetic acid solution containing 352 mg (1.00 mmol) of 1-(6-chloropyridazin-3-yl)-3-(4-fluorophenyl)-4-(pyridin-4-yl)-1H-pyrazole obtained in Example 1-3) was added 3 ml of water, and the mixture was stirred at 110° C. for 4 hours.

After completion of the reaction, the reaction mixture was concentrated under reduced pressure, the obtained residue was applied to silica gel column chromatography (eluent; chloroform:methanol=19:1 (V/V)), the separated fractions containing the objective compound were concentrated under reduced pressure. The obtained crude crystals were washed with 40 ml of a mixed solvent (diisopropyl ether:methanol=19:1 (V/V)) to obtain 249 mg of the title compound as a beige powder. (Yield: 75%)

Rf value: 0.40 (chloroform:methanol=9:1).

Mass spectrum (CI, m/z): 334 ($M^+$+1).

$^1$H-NMR spectrum (DMSO-d$_6$, δ ppm): 7.17 (d, J=10.0 Hz, 1H), 7.30-7.36 (m, 2H), 7.55-7.60 (m, 2H), 7.74 (d, J=6.0 Hz, 2H), 8.14 (d, J=10.0 Hz, 1H), 8.73 (d, J=6.0 Hz, 2H), 9.10 (s, 1H), 13.23 (s, 1H).

Example 2

4-(2-Aminopyridin-4-yl)-3-(4-fluorophenyl)-1-(1,6-dihydro-6-oxopyridazin-3-yl)-1H-pyrazole (Exemplary Compound No. 1-73)

2-1) 2-(2-t-Butoxycarbonylaminopyridin-4-yl)-3-dimethyl-amino-1-(4-fluorophenyl)-2-propen-1-one To 50 ml of a tetrahydrofuran solution containing 10.0 g (30.3 mmol) of 2-(2-t-butoxycarbonylaminopyridin-4-yl)-1-(4-fluorophenyl)ethan-1-one (see WO 0174811 publication) were added 6.04 ml (45.5 mmol) of N,N-dimethylformamide dimethylacetal and 4.64 ml (33.3 mmol) of triethylamine, and the mixture was refluxed for 4 hours.

After completion of the reaction, the reaction mixture was concentrated under reduced pressure, and the obtained crude crystals were washed with 50 ml of a mixed solvent (diisopropyl ether:methanol=19:1 (V/V)) to obtain 10.7 g of the title compound as a pale yellow powder. (Yield: 92%)

Rf value: 0.41 (ethyl acetate:hexane=1:1).

Mass spectrum (CI, m/z): 386 ($M^+$+1).

$^1$H-NMR spectrum (CDCl$_3$, δ ppm): 1.52 (s, 9H), 2.84 (s, 6H), 6.72 (dd, $J_1$=5.2 Hz, $J_2$=1.6 Hz, 1H), 6.91-7.00 (m, 2H), 7.35 (s, 1H), 7.42-7.49 (m, 2H), 7.75 (s, 1H), 7.86 (s, 1H), 8.08 (dd, $J_1$=5.2 Hz, $J_2$=0.7 Hz, 1H).

2-2) 4-(2-t-Butoxycarbonylaminopyridin-4-yl)-3-(4-fluorophenyl)-1H-pyrazole To 54 ml of a mixed solution (tetrahydrofuran/methanol=1:1 (V/V)) containing 1.80 g (4.67 mmol) of 2-(2-t-butoxycarbonylaminopyridin-4-yl)-3-dimethylamino-1-(4-fluorophenyl)-2-propen-1-one obtained in Example 2-1) was added 544 μl (11.2 mmol) of hydrazine monohydrate at room temperature. After the addition, the mixture was stirred for further 2 hours.

After completion of the reaction, the reaction mixture was concentrated under reduced pressure, and the obtained crude crystals were washed with 30 ml of diisopropyl ether to obtain 1.56 g of the title compound as a white powder. (Yield: 95%)

Rf value: 0.31 (ethyl acetate:hexane=1:1).

Mass spectrum (CI, m/z): 355 ($M^+$+1).

$^1$H-NMR spectrum (DMSO-d$_6$, δ ppm): 1.42 (s, 9H), 6.84 (dd, $J_1$=5.2 Hz, $J_2$=1.5 Hz, 1H), 7.21-7.27 (m, 2H), 7.41-7.47 (m, 2H), 7.73 (dd, $J_1$=1.5 Hz, $J_2$=0.7 Hz, 1H), 8.04 (brs, 1H), 8.11 (dd, $J_1$=5.2 Hz, $J_2$=0.7 Hz, 1H), 9.63 (s, 1H), 13.32 (brs, 1H).

2-3) 4-(2-t-Butoxycarbonylaminopyridin-4-yl)-1-(6-chloropyridazin-3-yl)-3-(4-fluorophenyl)-1H-pyrazole The reaction was carried out in the same manner as in Example 1-3) except for using 2.00 g (5.64 mmol) of 4-(2-t-butoxycarbonylaminopyridin-4-yl)-3-(4-fluorophenyl)-1H-pyrazole obtained by the same reaction as in Example 2-2) in place of 3-(4-fluorophenyl)-4-(pyridin-4-yl)-1H-pyrazole, and using 497 mg (12.4 mmol) of sodium hydride (60% dispersed material in mineral oil) to obtain 2.50 g of the title compound as a pale beige powder. (Yield: 95%)

Rf value: 0.26 (ethyl acetate:hexane=1:5).

Mass spectrum (CI, m/z): 467 ($M^+$+1).

$^1$H-NMR spectrum (DMSO-$d_6$, δ ppm): 1.43 (s, 9H), 7.01 (dd, $J_1$=5.1 Hz, $J_2$=1.5 Hz, 1H), 7.23-7.32 (m, 2H), 7.55-7.59 (m, 2H), 7.82 (s, 1H), 8.15 (d, J=9.3 Hz, 1H), 8.21 (d, J=5.1 Hz, 1H), 8.39 (d, J=9.3 Hz, 1H), 9.19 (s, 1H), 9.77 (s, 1H).

2-4) 4-(2-Aminopyridin-4-yl)-3-(4-fluorophenyl)-1-(1,6-dihydro-6-oxopyridazin-3-yl)-1H-pyrazole 30 ml of a 4N hydrochloric acid/dioxane solution (commercially available product) containing 5.50 g (11.8 mmol) of 4-(2-t-butoxycarbonylaminopyridin-4-yl)-1-(6-chloropyridazin-3-yl)-3-(4-fluorophenyl)-1H-pyrazole obtained by the same reaction as in Example 2-3) was stirred at 90° C. for 150 minutes. Then, 15 ml of water and 10 ml of conc. hydrochloric acid were added to the mixture, and the resulting mixture was further stirred at 90° C. for 7 hours.

After completion of the reaction, the reaction mixture was poured into 200 ml of water, neutralized with an aqueous 2N sodium hydroxide solution, and the formed precipitates were collected by filtration. The obtained filtered products were applied to silica gel column chromatography (eluent; chloroform:methanol=14:1 (V/V)), and the separated fractions containing the objective compound were concentrated under reduced pressure. The obtained crude crystals were washed with 10 ml of a mixed solvent (chloroform:methanol=9:1 (V/V)) to obtain 980 mg of the title compound as a white powder. (Yield: 24%)

Rf value: 0.45 (chloroform:methanol=9:1).

Mass spectrum (CI, m/z): 349 ($M^+$+1).

$^1$H-NMR spectrum (DMSO-$d_6$, δ ppm): 5.90 (s, 2H), 6.38 (s, 1H), 6.42 (dd, $J_1$=5.3 Hz, $J_2$=1.6 Hz, 1H), 7.13 (d, J=10.0 Hz, 1H), 7.23-7.31 (m, 2H), 7.52-7.58 (m, 2H), 7.87 (dd, $J_1$=5.3 Hz, $J_2$=0.5 Hz, 1H), 8.13 (d, J=10.0 Hz, 1H), 8.56 (s, 1H), 13.08 (s, 1H).

Example 3

3-(4-Fluorophenyl)-1-(1, 6-dihydro-6-oxopyridazin-3-yl)-4-(2-methylaminopyridin-4-yl)-1H-pyrazole
(Exemplary Compound No. 1-74)

3-1) 4-{2-[(t-butoxycarbonyl)methylamino] pyridin-4-yl}-1-(6-chloropyridazin-3-yl)-3-(4-fluorophenyl)-1H-pyrazole To 100 ml of a N,N-dimethylformamide solution containing 880 mg (1.88 mmol) of 4-(2-t-butoxycarbonyl-aminopyridin-4-yl)-1-(6-chloropyridazin-3-yl)-3-(4-fluorophenyl)-1H-pyrazole obtained by the same reaction as in Example 2-3) was added 226 mg (5.64 mmol) of sodium hydride (60% dispersed material in mineral oil) at 0° C., and a cooling bath was removed and the temperature of the mixture was gradually elevated to room temperature. Then, 1.18 ml (18.8 mmol) of methyl iodide was added to the mixture, and the resulting mixture was stirred at 40° C. for 30 minutes.

After completion of the reaction, the reaction mixture was slowly poured into 700 ml of an aqueous saturated ammonium chloride solution, and the precipitated solid was extracted with 900 ml of chloroform. The organic layer was successively washed with water, and then, with an aqueous saturated sodium chloride solution, dried over anhydrous sodium sulfate, and concentrated under reduced pressure. The obtained residue was applied to silica gel column chromatography (eluent; ethyl acetate:hexane=1:3 (V/V)), and the separated fractions containing the objecttive compound were concentrated under reduced pressure. The obtained crude crystals were washed with 10 ml of diisopropyl ether to obtain 360 mg of the title compound as a white powder. (Yield: 40%)

Rf value: 0.50 (ethyl acetate:hexane=1:1).

Mass spectrum (CI, m/z): 481 ($M^+$+1).

$^1$H-NMR spectrum (DMSO-$d_6$, δ ppm): 1.40 (s, 9H), 3.30 (s, 3H), 7.15 (dd, $J_1$=5.2 Hz, $J_2$=1.5 Hz, 1H), 7.27-7.35 (m, 2H), 7.54-7.61 (m, 2H), 7.68 (dd, $J_1$=1.5 Hz, $J_2$=0.7 Hz, 1H), 8.14 (d, J=9.3 Hz, 1H), 8.35 (dd, $J_1$=5.2 Hz, $J_2$=0.7 Hz, 1H), 8.38 (d, J=9.3 Hz, 1H), 9.24 (s, 1H).

3-2) 3-(4-Fluorophenyl)-1-(1,6-dihydro-6-oxopyridazin-3-yl)-4-(2-methylaminopyridin-4-yl)-1H-pyrazole The reaction was carried out in the same manner as in Example 2-4) except for using 330 mg (0.69 mmol) of 4-{2-[(t-butoxycarbonyl)methylamino]pyridin-4-yl}-1-(6-chloropyridazin-3-yl)-3-(4-fluorophenyl)-1H-pyrazole obtained in Example 3-1) in place of 4-(2-t-butoxycarbonylaminopyridin-4-yl)-1-(6-chloropyridazin-3-yl)-3-(4-fluorophenyl)-1H-pyrazole to obtain 222 mg of the title compound as a pale beige powder. (Yield: 89%)

Rf value: 0.37 (chloroform:methanol=9:1).

Mass spectrum (CI, m/z): 363($M^+$+1).

$^1$H-NMR spectrum (DMSO-$d_6$, δ ppm): 2.78 (d, J=4.4 Hz, 3H), 6.55-6.57 (m, 2H), 7.13-7.33 (m, 4H), 7.53-7.60 (m, 2H), 7.92 (dd, $J_1$=5.6 Hz, $J_2$=0.7 Hz, 1H), 8.13 (d, J=10.0 Hz, 1H), 8.75 (s, 1H), 13.14 (s, 1H).

Example 4

1-(5-Amino-1,6-dihydro-6-oxopyridazin-3-yl)-4-(2-aminopyridin-4-yl)-3-(4-fluorophenyl)-1H-pyrazole
(Exemplary Compound No. 1-97)

To a mixture of 208 mg (0.60 mmol) of 4-(2-aminopyridin -pyridin-4-yl)-3-(4-fluorophenyl)-1-(1,6-dihydro-6-oxopyridazin-3-yl)-1H-pyrazole obtained by the same reaction as in Example 2-4) and 1.16 ml (23.9 mmol) of hydrazine monohydrate was added 3 ml of ethylene glycol, and the mixture was stirred at 150° C. for 1 hour.

After completion of the reaction, the reaction mixture was poured into 50 ml of ice-water, and the formed precipitates were collected by filtration. The obtained filtered products were washed with 20 ml of a mixed solvent (diisopropyl ether:methanol=19:1 (V/V)) to obtain 87.0 mg of the title compound as a pale beige powder. (Yield: 40%)

Rf value: 0.43 (chloroform:methanol=9:1).

Mass spectrum (CI, m/z): 364($M^+$+1).

$^1$H-NMR spectrum (DMSO-$d_6$, δ ppm): 5.88 (s, 2H), 6.37 (s, 1H), 6.41 (dd, $J_1$=5.3 Hz, $J_2$=1.5 Hz, 1H), 6.86 (brs, 2H), 7.00 (s, 1H), 7.24-7.30 (m, 2H), 7.50-7.55 (m, 2H), 7.86 (d, J=5.3 Hz, 1H), 8.46 (s, 1H), 12.60 (s, 1H).

Example 5

3-(4-Fluorophenyl)-4-(pyridin-4-yl)-1-([1,2,4]triazolo[4,3-b]pyridazin-6-yl)-1H-pyrazole (Exemplary Compound No. 2-60)

To 4.2 ml of a tetrahydrofuran solution containing 20.1 mg (0.50 mmol) of sodium hydride (60% dispersed material in mineral oil) was added 100 mg (0.42 mmol) of 3-(4-fluorophenyl)-4-(pyridin-4-yl)-1H-pyrazole obtained in Example 1-2) under stiring at room temperature and under argon atmosphere. After the addition, the mixture was stirred for 10 minutes, and then, 64.6 mg (0.42 mmol) of 6-chloro-[1,2,4]triazolo[4,3-b]pyridazine was added. After the addition, the mixture was stirred for 30 minutes, and then, refluxed for 2 hours.

After completion of the reaction, the reaction mixture was poured into 100 ml of ice-water, neutralized with an aqueous saturated ammonium chloride solution, and extracted with 100 ml of a mixed solvent (chloroform: methanol=9:1 (V/V)). The organic layer was successively washed with water and then with an aqueous saturated sodium chloride solution, dried over anhydrous magnesium sulfate, and concentrated under reduced pressure. The obtained residue was applied to silica gel column chromatography (eluent; chloroform:ethyl acetate:methanol=15:4:1 (V/V/V)), and the separated fractions containing the objective compound were concentrated under reduced pressure. The obtained crude crystals were washed with 10 ml of diethyl ether to obtain 43.3 mg of the title compound as a white powder. (Yield: 26%)

Rf value: 0.37 (chloroform:ethyl acetate:methanol=5:4:1).

Mass spectrum (CI, m/z): 358 ($M^++1$).

$^1$H-NMR spectrum (DMSO-$d_6$, δ ppm): 7.30-7.39 (m, 4H), 7.55-7.60 (m, 2H), 8.13 (d, J=10.0 Hz, 1H), 8.57 (dd, $J_1$=4.5 Hz, $J_2$=1.6 Hz, 2H), 8.60 (d, J=10.0 Hz, 1H), 9.11 (s, 1H), 9.69 (s, 1H).

Example 6

3-(3,4-Difluorophenyl)-4-(pyridin-4-yl)-1-([1,2,4]-triazolo[4,3-b]pyridazin-6-yl)-1H-pyrazole (Exemplary Compound No. 2-453)

6-1) 3-Dimethylamino-1-(3,4-difluorophenyl)-2-(pyridin-4-yl)-2-propen-1-one

The reaction was carried out in the same manner as in Example 1-1) except for using 2.33 g (10.0 mmol) of 1-(3,4-difluorophenyl)-2-(pyridin-4-yl)ethan-1-one (see U.S. Pat. No. 5,837,719 publication) in place of 1-(4-fluorophenyl)-2-(pyridin-4-yl)ethan-1-one to obtain 2.86 g of the title compound as a black oil. (Yield: 99%)

Rf value: 0.50 (chloroform:methanol=9:1).

Mass spectrum (CI, m/z): 289 ($M^++1$).

$^1$H-NMR spectrum (CDCl$_3$, δ ppm): 2.82 (s, 6H), 7.00-7.17 (m, 4H), 7.25-7.32 (m, 1H), 7.41 (s, 1H), 8.50 (dd, $J_1$=4.4 Hz, $J_2$=1.5 Hz, 2H).

6-2) 3-(3,4-Difluorophenyl)-4-(pyridin-4-yl)-1H-pyrazole

The reaction was carried out in the same manner as in Example 1-2) except for using 2.54 g (8.81 mmol) of 3-dimethylamino-1-(3,4-difluorophenyl)-2-(pyridin-4-yl)-2-propen-1-one obtained in Example 6-1) in place of 3-dimethylamino-1-(4-fluorophenyl)-2-(pyridin-4-yl)-2-propen-1-one to obtain 2.05 g of the title compound as a white powder. (Yield: 90%)

Rf value: 0.45 (chloroform:methanol=9:1).

Mass spectrum (CI, m/z): 258 ($M^++1$).

$^1$H-NMR spectrum (DMSO-$d_6$, δ ppm): 7.19-7.27 (m, 3H), 7.43-7.53 (m, 2H), 8.16 (s, 1H), 8.45 (dd, $J_1$=4.5 Hz, $J_2$=1.6 Hz, 2H), 13.20 (brs, 1H).

6-3) 3-(3,4-Difluorophenyl)-4-(pyridin-4-yl)-1-([1,2,4]triazolo[4,3-b]pyridazin-6-yl)-1H-pyrazole The reaction was carried out in the same manner as in Example 5 except for using 566 mg (2.20 mmol) of 3-(3,4-difluorophenyl)-4-(pyridin-4-yl)-1H-pyrazole obtained in Example 6-2) in place of 3-(4-fluorophenyl)-4-(pyridin-4-yl)-1H-pyrazole to obtain 553 mg of the title compound as a white powder. (Yield: 67%)

Rf value: 0.43 (chloroform:ethyl acetate:methanol=5:4:1).

Mass spectrum (CI, m/z): 376 ($M^++1$).

$^1$H-NMR spectrum (DMSO-$d_6$, δ ppm): 7.31-7.34 (m, 1H), 7.40 (dd, $J_1$=4.5 Hz, $J_2$=1.6 Hz, 2H), 7.51-7.69 (m, 2H), 8.15 (d, J=10.0 Hz, 1H), 8.58-8.64 (m, 3H), 9.12 (s, 1H), 9.70 (d, J=0.7 Hz, 1H).

Example 7

3-(3-Fluorophenyl)-4-(pyridin-4-yl)-1-([1,2,4]triazolo[4,3-b]pyridazin-6-yl)-1H-pyrazole (Exemplary Compound No. 2-177)

7-1) 3-Dimethylamino-1-(3-fluorophenyl)-2-(pyridin-4-yl)-2-propen-1-one

The reaction was carried out in the same manner as in Example 1-1) except for using 15.0 g (69.7 mmol) of 1-(3-fluorophenyl)-2-(pyridin-4-yl)ethan-1-one (see WO 0110865 publication) in place of 1-(4-fluorophenyl)-2-(pyridin-4-yl)ethan-1-one to obtain 18.5 g of the title compound as a white powder. (Yield: 98%)

Rf value: 0.45 (chloroform:methanol=9:1).

Mass spectrum (CI, m/z): 271 ($M^++1$).

$^1$H-NMR spectrum (CDCl$_3$, δ ppm): 2.80 (s, 6H), 7.02-7.33 (m, 6H), 7.37 (s, 1H), 8.50 (dd, $J_1$=4.4 Hz, $J_2$=1.7 Hz, 2H).

7-2) 3-(3-Fluorophenyl)-4-(pyridin-4-yl)-1H-pyrazole

The reaction was carried out in the same manner as in Example 1-2) except for using 18.3 g (67.7 mmol) of 3-dimethylamino-1-(3-fluorophenyl)-2-(pyridin-4-yl)-2-propen-1-one obtained in Example 7-1) in place of 3-dimethylamino-1-(4-fluorophenyl)-2-(pyridin-4-yl)-2-propen-1-one to obtain 11.3 g of the title compound as a white powder. (Yield: 70%)

Rf value: 0.40 (chloroform:methanol=9:1).

Mass spectrum (CI, m/z): 240 ($M^++1$).

$^1$H-NMR spectrum (DMSO-$d_6$, δ ppm): 7.20-7.27 (m, 5H), 7.43-7.50 (m, 1H), 8.14 (s, 1H), 8.48 (dd, $J_1$=4.4 Hz, $J_2$=1.7 Hz, 2H), 13.39 (brs, 1H).

7-3) 3-(3-Fluorophenyl)-4-(pyridin-4-yl)-1-([1,2,4]triazolo[4,3-b]pyridazin-6-yl)-1H-pyrazole The reaction was carried out in the same manner as in Example 5 except for using 4.00 g (16.7 mmol) of 3-(3-fluorophenyl)-4-(pyridin-4-yl)-1H-pyrazole obtained in Example 7-2) in place of 3-(4-fluorophenyl)-4-(pyridin-4-yl)-1H-pyrazole to obtain 5.35 g of the title compound as a white powder. (Yield: 90%)

Rf value: 0.31 (chloroform:ethyl acetate:methanol=5:4:1).

Mass spectrum (CI, m/z): 358 ($M^+$+1).

$^1$H-NMR spectrum (DMSO-$d_6$, δ ppm): 7.30-7.40 (m, 5H), 7.48-7.56 (m, 1H), 8.15 (d, J=10.0 Hz, 1H), 8.57-8.63 (m, 3H), 9.11 (s, 1H), 9.70 (d, J=0.7 Hz, 1H).

Example 8

4-(2-Aminopyridin-4-yl)-3-(4-fluorophenyl)-1-([1,2,4]triazolo[4,3-b]pyridazin-6-yl)-1H-pyrazole (Exemplary Compound No. 2-94)

8-1) 4-(2-t-Butoxycarbonylaminopyridin-4-yl)-3-(4-fluorophenyl)-1-([1,2,4]triazolo[4,3-b]pyridazin-6-yl)-1H-pyrazole The reaction was carried out in the same manner as in Example 5 except for using 1.30 g (3.67 mmol) of 4-(2-t-butoxycarbonylaminopyridin-4-yl)-3-(4-fluorophenyl)-1H-pyrazole obtained by the same reaction as in Example 2-2) and 352 mg (8.81 mmol) of sodium hydride (60% dispersed material in mineral oil) in place of 3-(4-fluorophenyl)-4-(pyridin-4-yl)-1H-pyrazole to obtain 1.65 g of the title compound as a beige powder. (Yield: 95%)

Rf value: 0.48 (chloroform:ethyl acetate:methanol=15:4:1).

Mass spectrum (FAB, m/z): 473 ($M^+$+1).

$^1$H-NMR spectrum (DMSO-$d_6$, δ ppm): 1.44 (s, 9H), 6.97 (dd, $J_1$=5.2 Hz, $J_2$=1.6 Hz, 1H), 7.27-7.33 (m, 2H), 7.55-7.61 (m, 2H), 7.85 (s, 1H), 8.13 (d, $J_1$=10.0 Hz, 1H), 8.22 (dd, $J_1$=5.2 Hz, $J_2$=0.5 Hz, 1H), 8.60 (dd, $J_1$=10.0 Hz, $J_2$=0.7Hz, 1H), 9.00 (s, 1H), 9.71 (d, J=0.7 Hz, 1H), 9.81 (s, 1H).

8-2) 4-(2-Aminopyridin-4-yl)-3-(4-fluorophenyl)-1-([1,2,4]-triazolo[4,3-b]pyridazin-6-yl)-1H-pyrazole 3.0 ml of a 4N hydrochloric acid/dioxane solution (commercially available product) containing 200 mg (0.42 mmol) of 4-(2-t-butoxycarbonylaminopyridin-4-yl)-3-(4-fluorophenyl)-1-([1,2,4]triazolo[4,3-b]pyridazin-6-yl)-1H-pyrazole obtained in Example 8-1) was stirred at 90° C. for 2 hours.

After completion of the reaction, the reaction mixture was poured into 100 ml of water, neutralized with 1N aqueous sodium hydroxide solution, and the formed precipitates were collected by filtration. The obtained crude crystals were washed with 5 ml of methanol to obtain 130 mg of the title compound as a pale beige powder. (Yield: 83%)

Rf value: 0.49 (chloroform:methanol=9:1).

Mass spectrum (CI, m/z): 373 ($M^+$+1).

$^1$H-NMR spectrum (DMSO-$d_6$, δ ppm): 5.98 (brs, 2H), 6.42 (s, 1H), 6.46 (dd, $J_1$=5.5 Hz, $J_2$=1.5 Hz, 1H), 7.27-7.35 (m, 2H), 7.57-7.64 (m, 2H), 7.90 (d, J=5.5 Hz, 1H), 8.12 (d, J=10.0 Hz, 1H), 8.59 (dd, $J_1$=10.0 Hz, $J_2$=0.7 Hz, 1H), 8.85 (s, 1H), 9.68 (d, J=0.7 Hz, 1H).

Example 9

4-(2-Acetylaminopyridin-4-yl)-3-(4-fluorophenyl)-1-([1,2,4]triazolo[4,3-b]pyridazin-6-yl)-1H-pyrazole (Exemplary Compound No. 2-105)

To 3 ml of a pyridine solution containing 60.0 mg (0.16 mmol) of 4-(2-aminopyridin-4-yl)-3-(4-fluorophenyl)-1-([1,2,4]triazolo[4,3-b]pyridazin-6-yl)-1H-pyrazole obtained by the same reaction as in Example 8-2) was added 329 mg (3.22 mmol) of acetic anhydride, and the mixture was stirred at 80° C. for 4 hours.

After completion of the reaction, the reaction mixture was concentrated under reduced pressure, and the obtained crude crystals were washed with 2 ml of a mixed solvent (diisopropyl ether:methanol=9:1 (V/V)) to obtain 59.0 mg of the title compound as a pale beige powder. (Yield: 89%)

Rf value: 0.23 (chloroform:ethyl acetate:methanol=15:4:1).

Mass spectrum (CI, m/z): 415 ($M^+$+1).

$^1$H-NMR spectrum (DMSO-$d_6$, δ ppm): 2.07 (s, 3H), 7.05 (dd, $J_1$=5.2 Hz, $J_2$=1.7 Hz, 1H), 7.27-7.33 (m, 2H), 7.55-7.61 (m, 2H), 8.11-8.14 (m, 2H), 8.29 (d, J=5.2 Hz, 1H), 8.60 (d, J=10.0 Hz, 1H), 8.98 (s, 1H), 9.70 (s, 1H), 10.53 (s, 1H).

Example 10

4-(2-Benzoylaminopyridin-4-yl)-3-(4-fluorophenyl)-1-([1,2,4]triazolo[4,3-b]pyridazin-6-yl)-1H-pyrazole (Exemplary Compound No. 2-117)

The reaction was carried out in the same manner as in Example 9 except for using 100 mg (0.27 mmol) of 4-(2-aminopyridin-4-yl)-3-(4-fluorophenyl)-1-([1,2,4]triazolo-[4,3-b])pyridazin-6-yl)-1H-pyrazole obtained by the same reaction as in Example 8-2), and using 170 mg (1.21 mmol) of benzoyl chloride in place of acetic anhydride to obtain 65.1 mg of the title compound as a white powder. (Yield: 51%)

Rf value: 0.41 (chloroform:methanol=9:1).

Mass spectrum (CI, m/z): 477 ($M^+$+1).

$^1$H-NMR spectrum (DMSO-$d_6$, δ ppm): 7.11 (dd, $J_1$=4.8 Hz, $J_2$=1.5 Hz, 1H), 7.29-7.35 (m, 2H), 7.49-7.66 (m, 5H), 8.01 (d, J=7.1 Hz, 2H), 8.14 (d, J=9.7 Hz, 1H), 8.30 (s, 1H), 8.38 (d, J=4.8 Hz, 1H), 8.61 (d, J=9.7 Hz, 1H), 9.04 (s, 1H), 9.71 (s, 1H), 10.85 (s, 1H).

Example 11

3-(4-Fluorophenyl)-4-(2-methoxycarbonylaminopyridin-4-yl)-1-([1,2,4]triazolo[4,3-b]pyridazin-6-yl)-1H-pyrazole (Exemplary Compound No. 2-108)

The reaction was carried out in the same manner as in Example 9 except for using 420 mg (1.13 mmol) of 4-(2-aminopyridin-4-yl)-3-(4-fluorophenyl)-1-([1,2,4]triazolo-[4,3-b])pyridazin-6-yl)-1H-pyrazole obtained by the same reaction as in Example 8-2), and using 0.87 ml (11.3 mmol) of methyl chloroformate in place of acetic anhydride to obtain 283 mg of the title compound as a pale beige powder. (Yield: 58%)

Rf value: 0.66 (chloroform:methanol=9:1).

Mass spectrum (CI, m/z): 431 ($M^+$+1).

$^1$H-NMR spectrum (DMSO-$d_6$, δ ppm): 3.64 (s, 3H), 7.01 (dd, $J_1$=5.1 Hz, $J_2$=1.5 Hz, 1H), 7.27-7.35 (m, 2H), 7.56-7.63 (m, 2H), 7.88 (dd, $J_1$=1.5 Hz, $J_2$=0.8 Hz, 1H), 8.13 (d, J=9.9 Hz, 1H), 8.25 (dd, J₁=5.1 Hz, J₂=0.8 Hz, 1H), 8.60 (dd, J₁=9.9 Hz, J₂=0.8 Hz, 1H), 8.98 (s, 1H), 9.70 (d, J=0.8 Hz, 1H), 10.24 (s, 1H).

Example 12

3-(4-Fluorophenyl)-4-(2-methylsulfonylaminopyridin-4-yl)-1-([1,2,4]triazolo[4,3-b]pyridazin-6-yl)-1H-pyrazole (Exemplary Compound No. 2-111)

The reaction was carried out in the same manner as in Example 9 except for using 300 mg (0.81 mmol) of 4-(2-aminopyridin-4-yl)-3-(4-fluorophenyl)-1-([1,2,4]triazolo-[4,3-b])pyridazin-6-yl)-1H-pyrazole obtained by the same reaction as in Example 8-2), and using 0.37 ml (4.84 mmol) of methanesulfonyl chloride in place of acetic anhydride to obtain 50.7 mg of the title compound as a pale beige powder. (Yield: 14%)

Rf value: 0.37 (chloroform:methanol=9:1).

Mass spectrum (CI, m/z): 451 (M⁺+1).

$^1$H-NMR spectrum (DMSO-d₆, δ ppm): 3.22 (s, 3H), 6.95 (s, 1H), 7.01 (d, J=5.5 Hz, 1H), 7.30-7.36 (m, 2H), 7.57-7.62 (m, 2H), 8.12 (d, J=10.0 Hz, 1H), 8.21 (d, J=5.5 Hz, 1H), 8.59 (d, J=0.7 Hz, 1H), 9.05 (s, 1H), 9.70 (s, 1H), 10.94 (s, 1H).

Example 13

3-(4-Fluorophenyl)-4-(2-methylaminopyridin-4-yl)-1-([1,2,4]triazolo[4,3-b]pyridazin-6-yl)-1H-pyrazole (Exemplary Compound No. 2-95)

13-1) 4-{2-[(t-Butoxycarbonyl)methylamino]pyridin-4-yl}-3-(4-fluorophenyl)-1-([1,2,4]triazolo[4,3-b]pyridazin-6-yl)-1H-pyrazole The reaction was carried out in the same manner as in Example 3-1) except for using 6.00 g (12.7 mmol) of 4-(2-t-butoxycarbonylaminopyridin-4-yl)-3-(4-fluorophenyl)-1-([1,2,4]triazolo[4,3-b]pyridazin-6-yl)-1H-pyrazole obtained by the same reaction as in Example 8-1) in place of 4-(2-t-butoxycarbonylaminopyridin-4-yl)-1-(6-chloropyridazin-3-yl)-3-(4-fluorophenyl)-1H-pyrazole to obtain 4.33 g of the title compound as a brown powder. (Yield: 70%)

Rf value: 0.57 (chloroform:methanol=9:1).

Mass spectrum (CI, m/z): 487 (M⁺+1).

$^1$H-NMR spectrum (DMSO-d₆, δ ppm): 1.41 (s, 9H), 3.30 (s, 3H), 7.14 (dd, J₁=5.2 Hz, J₂=1.6 Hz, 1H), 7.29-7.35 (m, 2H), 7.56-7.61 (m, 2H), 7.70 (s, 1H), 8.13 (d, J=9.9 Hz, 1H), 8.35-8.37 (m, 1H), 8.60 (dd, J₁=9.9 Hz, J₂=0.6 Hz, 1H), 9.06 (s, 1H), 9.70 (d, J=0.6 Hz, 1H).

13-2) 3-(4-Fluorophenyl)-4-(2-methylaminopyridin-4-yl)-1-([1,2,4]triazolo[4,3-b]pyridazin-6-yl)-1H-pyrazole The reaction was carried out in the same manner as in Example 8-2) except for using 4.00 g (8.22 mmol) of 4-{2-[(t-butoxycarbonyl)methylamino]pyridin-4-yl}-3-(4-fluorophenyl)-1-([1,2,4]triazolo[4,3-b]pyridazin-6-yl)-1H-pyrazole obtained by the same reaction as in Example 13-1) in place of 4-(2-t-butoxycarbonylaminopyridin-4-yl)-3-(4-fluorophenyl)-1-([1,2,4]triazolo[4,3-b]pyridazin-6-yl)-1H-pyrazole to obtain 1.52 g of the title compound as a pale beige powder. (Yield: 48%)

Rf value: 0.43 (chloroform:methanol=9:1).

Mass spectrum (CI, m/z): 387 (M⁺+1).

$^1$H-NMR spectrum (DMSO-d₆, δ ppm): 2.73 (d, J=4.9 Hz, 3H), 6.40 (s, 1H), 6.44-6.50 (m, 2H), 7.27-7.34 (m, 2H), 7.57-7.63 (m, 2H), 7.97 (dd, J₁=5.1 Hz, J₂=0.5 Hz, 1H), 8.12 (d, J=10.0 Hz, 1H), 8.59 (dd, J₁=10.0 Hz, J₂=0.7 Hz, 1H), 8.89 (s, 1H), 9.67 (d, J=0.7 Hz, 1H).

Example 14

4-(2-Ethylaminopyridin-4-yl)-3-(4-fluorophenyl)-1-([1,2,4]triazolo[4,3-b]pyridazin-6-yl)-1H-pyrazole (Exemplary Compound No. 2-97)

14-1) 4-{2-[(t-Butoxycarbonyl)ethylamino]pyridin-4-yl}-3-(4-fluorophenyl)-1-([1,2,4]triazolo[4,3-b] pyridazin-6-yl)-1H-pyrazole The reaction was carried out in the same manner as in Example 3-1) except for using 747 mg (1.58 mmol) of 4-(2-t-butoxycarbonylaminopyridin-4-yl)-3-(4-fluorophenyl)-1-([1,2,4]triazolo[4,3-b]pyridazin-6-yl)-1H-pyrazole obtained by the same reaction as in Example 8-1) in place of 4-(2-t-butoxycarbonylaminopyridin-4-yl)-1-(6-chloropyridazin-3-yl)-3-(4-fluorophenyl)-1H-pyrazole, and using 0.38 ml (4.74 mmol) of ethyl iodide in place of methyl iodide to obtain 668 mg of the title compound as a pale beige powder. (Yield: 84%)

Rf value: 0.49 (ethyl acetate).

Mass spectrum (CI, m/z): 501 (M⁺+1).

$^1$H-NMR spectrum (DMSO-d₆, δ ppm): 1.15 (t, J=6.9 Hz, 3H), 1.40 (s, 9H), 3.86 (q, J=6.9 Hz, 2H), 7.16 (dd, J₁=5.1 Hz, J₂=1.5 Hz, 1H), 7.28-7.34 (m, 2H), 7.55-7.61 (m, 3H), 8.12 (d, J=10.0 Hz, 1H), 8.37 (dd, J₁=5.1 Hz, J₂=0.7 Hz, 1H), 8.60 (dd, J₁=10.0 Hz, J₂=0.9 Hz, 1H), 9.08 (s, 1H), 9.70 (d, J=0.9 Hz, 1H).

14-2) 4-(2-Ethylaminopyridin-4-yl)-3-(4-fluorophenyl)-1-([1,2,4]triazolo[4,3-b]pyridazin-6-yl)-1H-pyrazole The reaction was carried out in the same manner as in Example 8-2) except for using 659 mg (1.32 mmol) of 4-{2-[(t-butoxycarbonyl)ethylamino]pyridin-4-yl}-3-(4-fluorophenyl)-1-([1,2,4]triazolo[4,3-b]pyridazin-6-yl)-1H-pyrazole obtained in Example 14-1) in place of 4-(2-t-butoxycarbonylaminopyridin-4-yl)-3-(4-fluorophenyl)-1-([1,2,4]triazolo[4,3-b]pyridazin-6-yl)-1H-pyrazole to obtain 413 mg of the title compound as a beige powder. (Yield: 78%)

Rf value: 0.14 (ethyl acetate).

Mass spectrum (CI, m/z): 401 (M⁺+1).

$^1$H-NMR spectrum (DMSO-d₆, δ ppm): 1.10 (t, J=7.1 Hz, 3H), 3.20 (qd, J₁=7.1 Hz, J₂=5.5 Hz, 2H), 6.39 (s, 1H), 6.44 (dd, J₁=5.1 Hz, J₂=1.5 Hz, 1H), 6.50 (t, J=5.5 Hz, 1H), 7.27-7.35 (m, 2H), 7.57-7.64 (m, 2H), 7.95-7.97 (m, 1H), 8.11 (d, J=9.9 Hz, 1H), 8.59 (dd, J₁=9.9 Hz, J₂=0.7 Hz, 1H), 8.87 (s, 1H), 9.68 (d, J=0.7 Hz, 1H).

Example 15

3-(4-Fluorophenyl)-4-(2-isopropylaminopyridin-4-yl)-1-([1,2,4]triazolo[4,3-b]pyridazin-6-yl)-1H-pyrazole (Exemplary Compound No. 2-100)

The reaction was carried out in the same manner as in Example 3-1) except for using 800 mg (1.69 mmol) of 4-(2-t-butoxycarbonylaminopyridin-4-yl)-3-(4-fluorophenyl)-1-([1,2,4]triazolo[4,3-b]pyridazin-6-yl)-1H-pyrazole obtained by the same reaction as in Example 8-1) in place of 4-(2-t-butoxycarbonylaminopyridin-4-yl)-1-(6-chloropyridazin-3-yl)-3-(4-fluorophenyl)-1H-pyrazole, and 1.68 ml (16.9 mmol) of isopropyl iodide in place of methyl iodide to obtain 362 mg of crude crystals of 4-{2-[(t-butoxycarbonyl)isopropylamino]pyridin-4-yl}-3-(4-fluorophenyl)-1-([1,2,4]triazolo-[4,3-b]pyridazin-6-yl)-1H-pyrazole.

The obtained crude crystals were applied to stirring without purification in 3.5 ml of a 4N hydrochloric acid/dioxane solution (commercially available product), at 90° C. for 1 hour.

After completion of the reaction, the reaction mixture was poured into 100 ml of water, neutralized with 1N aqueous sodium hydroxide solution, and extracted with 100 ml of a mixed solvent (chloroform: methanol=9:1 (V/V)).

The organic layer was washed with an aqueous saturated sodium chloride solution, dried over anhydrous sodium sulfate, and then, concentrated under reduced pressure. The obtained residue was applied to silica gel column chromatography (eluent; chloroform: methanol=30:1 (V/V)), and the separated fractions containing the objective compound were concentrated under reduced pressure. The obtained crude crystals were washed with 20 ml of diisopropyl ether to obtain 20.0 mg of the title compound as a pale yellow powder. (Yield: 3%)

Rf value: 0.48 (chloroform:methanol=19:1).

Mass spectrum (CI, m/z): 415 ($M^+$+1).

$^1$H-NMR spectrum (DMSO-$d_6$, δ ppm): 1.11 (d, J=6.6 Hz, 6H), 3.88-3.95 (m, 1H), 6.35-6.43 (m, 3H), 7.29-7.35 (m, 2H), 7.59-7.64 (m, 2H), 7.95 (d, J=5.1 Hz, 1H), 8.12 (d, J=10.0 Hz, 1H), 8.59 (d, J=10.0 Hz, 1H), 8.87 (s, 1H), 9.68 (s, 1H).

Example 16

3-(4-Fluorophenyl)-1-([1,2,4]triazolo[4,3-b]pyridazin-6-yl)-4-[2-(2,2,2-trifluoroethyl)aminopyridin-4-yl]-1H-pyrazole (Exemplary Compound No. 2-101)

16-1) 4-{2-[(t-Butoxycarbonyl)(2,2,2-trifluoroethyl)amino]-pyridin-4-yl}-3-(4-fluorophenyl)-1-([1,2,4]triazolo[4,3-b]-pyridazin-6-yl)-1H-pyrazole The reaction was carried out in the same manner as in Example 3-1) except for using 300 mg (0.64 mmol) of 4-(2-t-butoxycarbonylaminopyridin-4-yl)-3-(4-fluorophenyl)-1-([1,2,4]triazolo[4,3-b]pyridazin-6-yl)-1H-pyrazole obtained by the same reaction as in Example 8-1) in place of 4-(2-t-butoxycarbonylaminopyridin-4-yl)-1-(6-chloropyridazin-3-yl)-3-(4-fluorophenyl)-1H-pyrazole, and using 0.27 ml (1.91 mmol) of 2,2,2-trifluoroethyl triflate in place of methyl iodide to obtain 290 mg of the title compound as a pale beige powder. (Yield: 82%)

Rf value: 0.46 (ethyl acetate).

Mass spectrum (FAB, m/z): 555 ($M^+$+1).

$^1$H-NMR spectrum (DMSO-$d_6$, δ ppm): 1.40 (s, 9H), 4.78 (q, J=9.1 Hz, 2H), 7.28-7.32 (m, 3H), 7.55-7.59 (m, 3H), 8.13 (d, J=9.8 Hz, 1H), 8.40 (d, J=5.9 Hz, 1H), 8.60 (dd, $J_1$=9.8 Hz, $J_2$=1.0 Hz, 1H), 9.15 (s, 1H), 9.69 (s, 1H)

16-2) 3-(4-Fluorophenyl)-1-([1,2,4]triazolo[4,3-b]pyridazin-6-yl)-4-[2-(2,2,2-trifluoroethyl)aminopyridin-4-yl]-1H-pyrazole.

The reaction was carried out in the same manner as in Example 8-2) except for using 280 mg (0.51 mmol) of 4-{2-[(t-butoxycarbonyl)(2,2,2-trifluoroethyl)amino]pyridin-4-yl}-3-(4-fluorophenyl)-1-([1,2,4]triazolo[4,3-b]pyridazin-6-yl)-1H-pyrazole obtained by the same reaction as in Example 16-1) in place of 4-(2-t-butoxycarbonylaminopyridin-4-yl)-3-(4-fluorophenyl)-1-([1,2,4]triazolo[4,3-b]pyridazin-6-yl)-1H-pyrazole to obtain 120 mg of the title compound as a beige powder. (Yield: 52%)

Rf value: 0.49 (chloroform:methanol=9:1).

Mass spectrum (CI, m/z): 455 ($M^+$+1).

$^1$H-NMR spectrum (DMSO-$d_6$, δ ppm): 4.15 (qd, $J_1$=9.8 Hz, $J_2$=6.8 Hz, 2H), 6.60-6.61 (m, 2H), 7.18 (t, J=6.8 Hz, 1H), 7.30-7.34 (m, 2H), 7.58-7.62 (m, 2H), 8.02 (d, J=5.9 Hz, 1H), 8.12 (d, J=9.5 Hz, 1H), 8.59 (d, J=9.5 Hz, 1H), 8.93 (s, 1H), 9.68 (s, 1H).

Example 17

3-(4-Fluorophenyl)-4-(2-fluoropyridin-4-yl)-1-([1,2,4]triazolo[4,3-b]pyridazin-6-yl)-1H-pyrazole (Exemplary Compound No. 2-82)

17-1) 3-Dimethylamino-1-(4-fluorophenyl)-2-(2-fluoropyridin-4-yl)-2-propen-1-one The reaction was carried out in the same manner as in Example 1-1) except for using 3.80 g (16.3 mmol) of 1-(4-fluorophenyl)-2-(2-fluoropyridin-4-yl)ethan-1-one (see WO 0063204 publication) in place of 1-(4-fluorophenyl)-2-(pyridin-4-yl)ethan-1-one to obtain 4.46 g of the title compound as a yellow oil. (Yield: 95%)

Rf value: 0.55 (chloroform:ethyl acetate:methanol=15:4:1).

Mass spectrum (CI, m/z): 289 ($M^+$+1).

$^1$H-NMR spectrum (CDCl$_3$, δ ppm): 2.83 (s, 6H), 6.70 (s, 1H), 6.94-7.05 (m, 3H), 7.38 (s, 1H), 7.42-7.48 (m, 2H), 8.10 (d, J=5.1 Hz, 1H).

17-2) 3-(4-Fluorophenyl)-4-(2-fluoropyridin-4-yl)-1H-pyrazole

The reaction was carried out in the same manner as in Example 1-2) except for using 4.17 g (14.5 mmol) of 3-dimethylamino-1-(4-fluorophenyl)-2-(2-fluoropyridin-4-yl)-2-propen-1-one obtained in Example 17-1) in place of 3-dimethylamino-1-(4-fluorophenyl)-2-(pyridin-4-yl)-2-propen-1-one to obtain 3.28 g of the title compound as a white powder. (Yield: 88%)

Rf value: 0.67 (chloroform:methanol=9:1).

Mass spectrum (CI, m/z): 258 ($M^+$+1).

$^1$H-NMR spectrum (CDCl$_3$, δ ppm): 6.82-6.83 (m, 1H), 7.04-7.17 (m, 3H), 7.39-7.46 (m, 2H), 7.85 (s, 1H), 8.12 (d, J=5.4 Hz, 1H), 10.49 (s, 1H).

17-3) 3-(4-Fluorophenyl)-4-(2-fluoropyridin-4-yl)-1-([1,2,4]triazolo[4,3-b]pyridazin-6-yl)-1H-pyrazole The reaction was carried out in the same manner as in Example 5 except for using 50.0 mg (0.19 mmol) of 3-(4-fluorophenyl)-4-(2-fluoropyridin-4-yl)-1H-pyrazole obtained in Example 17-2) in place of 3-(4-fluorophenyl)-4-(pyridin-4-yl)-1H-pyrazole to obtain 43.2 mg of the title compound as a white powder. (Yield: 59%)

Rf value: 0.32 (chloroform:ethyl acetate:methanol=15:4:1).

Mass spectrum (CI, m/z): 376 ($M^+$+1).

$^1$H-NMR spectrum (DMSO-$d_6$, δ ppm): 7.24-7.39 (m, 4H), 7.58-7.63 (m, 2H), 8.12 (d, J=9.9 Hz, 1H), 8.22 (d, J=5.4 Hz, 1H), 8.62 (dd, $J_1$=9.9 Hz, $J_2$=0.9 Hz, 1H), 9.23 (s, 1H), 9.69 (d, J=0.9 Hz, 1H).

Example 18

3-(4-Fluorophenyl)-4-[2-(1-phenethylamino)pyridin-4-yl]-1-([1,2,4]triazolo[4,3-b]pyridazin-6-yl)-1H-pyrazole (Exemplary Compound No. 2-116)

18-1) 3-(4-Fluorophenyl)-4-[2-(1-phenethylamino)pyridin-4-yl]-1H-pyrazole

To 100 mg (0.39 mmol) of 3-(4-fluorophenyl)-4-(2-fluoropyridin-4-yl)-1H-pyrazole obtained in Example 17-2) were added 1.5 ml (1.41 g, 11.6 mmol) of 1-phenethylamine and 0.16 ml of conc. hydrochloric acid, and the mixture was stirred at 150° C. for 7 hours.

After completion of the reaction, the reaction mixture was poured into 20 ml of an aqueous saturated ammonium chloride solution, and extracted twice with each 30 ml of ethyl acetate. The organic layer was successively washed with water and then with an aqueous saturated sodium chloride solution, dried over anhydrous magnesium sulfate, and then, concentrated under reduced pressure. The obtained crude crystals were washed with 10 ml of a mixed solvent (diethyl ether:hexane=1:4 (V/V)) to obtain 85.3 mg of the title compound as pale a beige powder. (Yield: 61%)

Rf value: 0.38 (chloroform:ethyl acetate:methanol=15:4:1).

Mass spectrum (CI, m/z): 359 ($M^+$+1).

$^1$H-NMR spectrum (CDCl$_3$+DMSO-d$_6$, δ ppm): 1.48 (d, J=6.8 Hz, 3H), 4.67-4.76 (m, 1H), 5.79 (d, J=6.8 Hz, 1H), 6.24 (s, 1H), 6.41 (dd, J$_1$=5.2 Hz, J$_2$=1.5 Hz, 1H), 7.00-7.06 (m, 2H), 7.15-7.28 (m, 5H), 7.41-7.46 (m, 2H), 7.60 (s, 1H), 7.89 (d, J=5.2 Hz, 1H), 12.89 (brs, 1H).

18-2) 3-(4-Fluorophenyl)-4-[2-(1-phenethylamino)pyridin-4-yl]-1-([1,2,4]triazolo[4,3-b]pyridazin-6-yl)-1H-pyrazole The reaction was carried out in the same manner as in Example 5 except for using 80.0 mg (0.22 mmol) of 3-(4-fluorophenyl)-4-[2-(1-phenethylamino)pyridin-4-yl]-1H-pyrazole obtained in Example 18-1) in place of 3-(4-fluorophenyl)-4-(pyridin-4-yl)-1H-pyrazole to obtain 58.0 mg of the title compound as a pale yellowish white powder. (Yield: 55%)

Rf value: 0.39 (ethyl acetate:methanol=9:1).

Mass spectrum (CI, m/z): 477 ($M^+$+1).

$^1$H-NMR spectrum (DMSO-d$_6$, δ ppm): 1.40 (d, J=6.8 Hz, 3H), 4.90-4.98 (m, 1H), 6.44-6.46 (m, 2H), 7.04 (d, J=7.8 Hz, 1H), 7.14-7.20 (m, 1H), 7.25-7.33 (m, 6H), 7.55-7.60 (m, 2H), 7.91 (d, J=5.9 Hz, 1H), 8.10 (d, J=10.0 Hz, 1H), 8.59 (dd, J$_1$=10.0 Hz, J$_2$=0.7 Hz, 1H), 8.83 (s, 1H), 9.68 (d, J=0.7 Hz, 1H).

Example 19

3-(4-Fluorophenyl)-4-(2-methoxypyridin-4-yl)-1-([1,2,4]triazolo[4,3-b]pyridazin-6-yl)-1H-pyrazole (Exemplary Compound No. 2-86)

19-1) 3-(4-fluorophenyl)-4-(2-methoxypyridin-4-yl)-1H-pyrazole

To 15 ml of a methanol solution containing 300 mg (1.16 mmol) of 3-(4-fluorophenyl)-4-(2-fluoropyridin-4-yl)-1H-pyrazole obtained in Example 17-2) was added 1.11 g (20.6 mmol) of sodium methoxide powder, and the mixture was stirred in a sealed tube at 160° C. for 4 hours.

After completion of the reaction, the reaction mixture was neutralized with a 2N hydrochloric acid, and extracted with 100 ml of chloroform. The organic layer was successively washed with water and then with an aqueous saturated sodium chloride solution, dried over anhydrous magnesium sulfate, and then, concentrated under reduced pressure. The obtained residue was applied to silica gel column chromatography (eluent; chloroform:ethyl acetate:methanol=15:4:1 (V/V/V)), and the separated fractions containing the objective compound were concentrated under reduced pressure. The obtained crude crystals were washed with 22 ml of a mixed solvent (hexane:diisopropyl ether=10:1 (V/V)) to obtain 226 mg of the title compound as a white powder. (Yield: 72%)

Rf value: 0.48 (chloroform:ethyl acetate:methanol=15:4:1).

Mass spectrum (CI, m/z): 270 ($M^+$+1).

$^1$H-NMR spectrum (DMSO-d$_6$, δ ppm): 3.81 (s, 3H), 6.65 (dd, J$_1$=1.5 Hz, J$_2$=0.7 Hz, 1H), 6.83 (dd, J$_1$=5.4 Hz, J$_2$=1.5 Hz, 1H), 7.24-7.30 (m, 2H), 7.42-7.48 (m, 2H), 8.04 (dd, J$_1$=5.4 Hz, J$_2$=0.7 Hz, 1H), 8.10 (brs, 1H), 13.32 (brs, 1H).

19-2) 3-(4-Fluorophenyl)-4-(2-methoxypyridin-4-yl)-1-([1,2,4]triazolo[4,3-b]pyridazin-6-yl)-1H-pyrazole The reaction was carried out in the same manner as in Example 5 except for using 120 mg (0.45 mmol) of 3-(4-fluorophenyl)-4-(2-methoxypyridin-4-yl)-1H-pyrazole obtained in Example 19-1) in place of 3-(4-fluorophenyl)-4-(pyridin-4-yl)-1H-pyrazole to obtain 90.0 mg of the title compound as a pale gray powder. (Yield: 52%)

Rf value: 0.31 (chloroform:ethyl acetate:methanol=15:4:1).

Mass spectrum (CI, m/z): 388 ($M^+$+1).

$^1$H-NMR spectrum (DMSO-d$_6$, δ ppm): 3.85 (s, 3H), 6.80 (s, 1H), 6.96 (dd, J$_1$=5.4 Hz, J$_2$=1.5 Hz, 1H), 7.29-7.37 (m, 2H), 7.55-7.61 (m, 2H), 8.12 (d, J=10.1 Hz, 1H), 8.15 (d, J=5.4 Hz, 1H), 8.60 (d, J=10.1 Hz, 1H), 9.09 (s, 1H), 9.68 (s, 1H).

Example 20

4-(2-Aminopyridin-4-yl)-1-(1,6-dihydro-6-oxopyridazin-3-yl)-3-phenyl-1H-pyrazole (Exemplary Compound No. 1-2)

20-1) 2-(2-t-Butoxycarbonylaminopyridin-4-yl)-3-dimethyl-amino-1-phenyl-2-propen-1-one The reaction was carried out in the same manner as in Example 2-1) except for using 21.9 g (70.0 mmol) of 2-(2-t-butoxycarbonylaminopyridin-4-yl)-1-phenylethan-1-one (see Nathan C. Ihle et al., J. Org. Chem. 61 (14), 4810 (1996)) in place of 2-(2-t-butoxycarbonylaminopyridin-4-yl)-1-(4-fluorophenyl)ethan-1-one to obtain 23.8 g of the title compound as a pale yellow powder. (Yield: 93%)

Rf value: 0.12 (ethyl acetate:hexane=1:1).

Mass spectrum (CI, m/z): 368 ($M^+$+1).

$^1$H-NMR spectrum (CDCl$_3$, δ ppm): 1.46 (s, 9H), 2.75 (brs, 6H), 6.76-6.77 (m, 1H), 7.23 (s, 1H), 7.35-7.46 (m, 5H), 7.57 (s, 1H), 8.09-8.11 (m, 1H), 9.66 (s, 1H).

20-2) 4-(2-t-Butoxycarbonylaminopyridin-4-yl)-3-phenyl-1H-pyrazole

The reaction was carried out in the same manner as in Example 2-2) except for using 18.4 g (50.0 mmol) of 2-(2-t-butoxycarbonylaminopyridin-4-yl)-3-dimethylamino-1-phenyl-2-propen-1-one obtained in Example 20-1) in place of 2-(2-t-butoxycarbonylaminopyridin-4-yl)-3-dimethylamino-1-(4-fluorophenyl)-2-propen-1-one to obtain 14.5 g of the title compound as a white powder. (Yield: 86%)

Rf value: 0.31 (ethyl acetate:hexane=1:1).

Mass spectrum (CI, m/z): 337 ($M^+$+1).

$^1$H-NMR spectrum (DMSO-$d_6$, δ ppm): 1.43 (s, 9H), 6.81 (dd, $J_1$=5.2 Hz, $J_2$=1.6 Hz, 1H), 7.35-7.44 (m, 5H), 7.78 (d, J=0.7 Hz, 1H), 8.00 (brs, 1H), 8.10 (d, J=5.2 Hz, 1H), 9.66 (s, 1H), 13.32 (brs, 1H).

20-3) 4-(2-t-Butoxycarbonylaminopyridin-4-yl)-1-(6-chloropyridazin-3-yl)-3-phenyl-1H-pyrazole The reaction was carried out in the same manner as in Example 1-3) except for using 9.00 g (26.8 mmol) of 4-(2-t-butoxycarbonylaminopyridin-4-yl)-3-phenyl-1H-pyrazole obtained in Example 20-2) in place of 3-(4-fluorophenyl)-4-(pyridin-4-yl)-1H-pyrazole, and using 2.35 g (58.8 mmol) of sodium hydride (60% dispersed material in mineral oil) to obtain 7.01 g of the title compound as a white powder. (Yield: 58%)

Rf value: 0.43 (chloroform:ethyl acetate=30:1).

Mass spectrum (CI, m/z): 449 ($M^+$+1).

$^1$H-NMR spectrum (DMSO-$d_6$, δ ppm): 1.43 (s, 9H), 6.95 (dd, $J_1$=5.3 Hz, $J_2$=1.7 Hz, 1H), 7.44-7.56 (m, 5H), 7.87 (s, 1H), 8.15 (d, J=9.3 Hz, 1H), 8.20 (d, J=5.3 Hz, 1H), 8.39 (d, J=9.3 Hz, 1H), 9.16 (s, 1H), 9.77 (s, 1H).

20-4) 4-(2-Aminopyridin-4-yl)-1-(1,6-dihydro-6-oxopyridazin-3-yl)-3-phenyl-1H-pyrazole The reaction was carried out in the same manner as in Example 1-4) except for using 4.00 g (8.91 mmol) of 4-(2-t-butoxycarbonylaminopyridin-4-yl)-1-(6-chloropyridazin-3-yl)-3-phenyl-1H-pyrazole obtained in Example 20-3) in place of 1-(6-chloropyridazin-3-yl)-3-(4-fluorophenyl)-4-(pyridin-4-yl)-1H-pyrazole to obtain 2.82 g of the title compound as a white powder. (Yield: 96%)

Rf value: 0.32 (chloroform:methanol=9:1).

Mass spectrum (CI, m/z): 331 ($M^+$+1).

$^1$H-NMR spectrum (DMSO-$d_6$, δ ppm): 5.89 (brs, 2H), 6.40-6.42 (m, 2H), 7.14 (d, J=10.0 Hz, 1H), 7.39-7.54 (m, 5H), 7.86 (d, J=5.9 Hz, 1H), 8.13 (d, J=10.0 Hz, 1H), 8.55 (s, 1H), 13.09 (brs, 1H).

Example 21

1-(5-Amino-1,6-dihydro-6-oxopyridazin-3-yl)-3-(4-fluorophenyl)-4-(pyridin-4-yl)-1H-pyrazole (Exemplary Compound No. 1-50)

The reaction was carried out in the same manner as in Example 4 except for using 213 mg (0.64 mmol) of 3-(4-fluorophenyl)-1-(1,6-dihydro-6-oxopyridazin-3-yl)-4-(pyridin-4-yl)-1H-pyrazole obtained in Example 1-4) in place of 4-(2-aminopyridin-4-yl)-3-(4-fluorophenyl)-1-(1,6-dihydro-6-oxopyridazin-3-yl)-1H-pyrazole to obtain 90.3 mg of the title compound as a white powder. (Yield: 40%)

Rf value: 0.25 (chloroform:methanol=9:1).

Mass spectrum (CI, m/z): 349 ($M^+$+1).

$^1$H-NMR spectrum (DMSO-$d_6$, δ ppm): 6.88 (brs, 2H), 7.00 (s, 1H), 7.26-7.29 (m, 2H), 7.32 (dd, $J_1$=4.4 Hz, $J_2$=1.7 Hz, 2H), 7.45-7.52 (m, 2H), 8.51 (dd, $J_1$=4.4 Hz, $J_2$=1.7 Hz, 2H), 8.71 (s, 1H), 12.63 (s, 1H)

Example 22

4-(2-Aminopyridin-4-yl)-3-(3-fluorophenyl)-1-(1,6-dihydro-6-oxopyridazin-3-yl)-1H-pyrazole (Exemplary Compound No. 1-156)

22-1) 2-(2-t-Butoxycarbonylaminopyridin-4-yl)-3-dimethyl-amino-1-(3-fluorophenyl)-2-propen-1-one The reaction was carried out in the same manner as in Example 2-1) except for using 16.5 g (50.0 mmol) of 2-(2-t-butoxycarbonylaminopyridin-4-yl)-1-(3-fluorophenyl)ethan-1-one (see WO 0174811 publication) in place of 2-(2-t-butoxy-carbonylaminopyridin-4-yl)-1(4-fluorophenyl)ethan-1-one to obtain 18.0 g of the title compound as a pale yellow powder. (Yield: 93%)

Rf value: 0.12 (ethyl acetate:hexane=1:2).

Mass spectrum (CI, m/z): 386 ($M^+$+1).

$^1$H-NMR spectrum (CDCl$_3$, δ ppm): 1.52 (s, 9H), 2.84 (brs, 6H), 6.76 (dd, $J_1$=5.1 Hz, $J_2$=1.5 Hz, 1H), 7.01-7.08 (m, 1H), 7.15-7.30 (m, 3H), 7.33 (s, 1H), 7.78 (s, 1H), 8.14 (dd, $J_1$=5.1 Hz, $J_2$=0.7 Hz, 1H), 8.43 (s, 1H)

22-2) 4-(2-t-Butoxycarbonylaminopyridin-4-yl)-3-(3-fluorophenyl)-1H-pyrazole

The reaction was carried out in the same manner as in Example 2-2) except for using 13.5 g (35.0 mmol) of 2-(2-t-butoxycarbonylaminopyridin-4-yl)-3-dimethylamino-1-(3-fluorophenyl)-2-propen-1-one obtained in Example 22-1) in place of 2-(2-t-butoxycarbonylaminopyridin-4-yl)-3-dimethylamino-1-(4-fluorophenyl)-2-propen-1-one to obtain 12.4 g of the title compound as a yellowish white powder. (Yield: quantitative)

Rf value: 0.31 (ethyl acetate:hexane=1:1).

Mass spectrum (CI, m/z): 355 ($M^+$+1).

$^1$H-NMR spectrum (DMSO-$d_6$, δ ppm): 1.43 (s, 9H), 6.86 (dd, $J_1$=5.2 Hz, $J_2$=1.5 Hz, 1H), 7.18-7.26 (m, 3H), 7.40-7.48 (m, 1H), 7.77 (dd, $J_1$=1.5 Hz, $J_2$=0.8 Hz, 1H), 8.07 (s, 1H), 8.13 (dd, $J_1$=5.2 Hz, $J_2$=0.8 Hz, 1H), 9.68 (s, 1H), 13.40 (brs, 1H).

22-3) 4-(2-t-Butoxycarbonylaminopyridin-4-yl)-1-(6-chloropyridazin-3-yl)-3-(3-fluorophenyl)-1H-pyrazole The reaction was carried out in the same manner as in Example 1-3) except for using 4.00 g (11.3 mmol) of 4-(2-t-butoxycarbonylaminopyridin-4-yl)-3-(3-fluorophenyl)-1H-pyrazole obtained in Example 22-2) in place of 3-(4-fluorophenyl)-4-(pyridin-4-yl)-1H-pyrazole, and using 993 mg (24.8 mmol) of sodium hydride (60% dispersed material in mineral oil) to obtain 4.13 g of the title compound as a white powder. (Yield: 78%)

Rf value: 0.38 (ethyl acetate:hexane=1:2).

Mass spectrum (CI, m/z): 467 ($M^+$+1).

$^1$H-NMR spectrum (DMSO-$d_6$, δ ppm): 1.43 (s, 9H), 7.03 (dd, $J_1$=5.3 Hz, $J_2$=1.6 Hz, 1H), 7.26-7.41 (m, 3H), 7.46-7.53 (m, 1H), 7.86 (dd, $J_1$=1.6 Hz, $J_2$=0.9 Hz, 1H), 8.16 (d, J=9.3 Hz, 1H), 8.23 (dd, $J_1$=5.3 Hz, $J_2$=0.9 Hz, 1H), 8.42 (d, J=9.3 Hz, 1H), 9.20 (s, 1H), 9.82 (s, 1H).

22-4) 4-(2-Aminopyridin-4-yl)-3-(3-fluorophenyl)-1-(1,6-dihydro-6-oxopyridazin-3-yl)-1H-pyrazole The reaction was carried out in the same manner as in Example 1-4) except for using 3.00 g (6.43 mmol) of 4-(2-t-butoxycarbonylaminopyridin-4-yl)-1-(6-chloropyridazin-3-yl)-3-(3-fluorophenyl)-1H-pyrazole obtained in Example 22-3) in place of 1-(6-chloropyridazin-3-yl)-3-(4-fluorophenyl)-4-(pyridin-4-yl)-1H-pyrazole to obtain 875 mg of the title compound as a white powder. (Yield: 39%)
Rf value: 0.31 (chloroform:methanol=9:1).
Mass spectrum (CI, m/z): 349 (M$^+$+1).
$^1$H-NMR spectrum (DMSO-d$_6$, δ ppm): 5.94 (s, 2H), 6.40-6.45 (m, 2H), 7.14 (d, J=10.0 Hz, 1H), 7.22-7.35 (m, 3H), 7.44-7.51 (m, 1H), 7.89 (dd, J$_1$=5.1 Hz, J$_2$=0.7 Hz, 1H), 8.15 (d, J=10.0 Hz, 1H), 8.57 (s, 1H), 13.09 (brs, 1H).

Example 23

4-(2-Aminopyridin-4-yl)-3-(4-chlorophenyl)-1-(1,6-dihydro-6-oxopyridazin-3-yl)-1H-pyrazole (Exemplary Compound No. 1-237)

23-1) 2-(2-t-Butoxycarbonylaminopyridin-4-yl)-1-(4-chlorophenyl)-3-dimethylamino-2-propen-1-one The reaction was carried out in the same manner as in Example 2-1) except for using 11.4 g (33.0 mmol) of 2-(2-t-butoxycarbonylaminopyridin-4-yl)-1-(4-chlorophenyl)ethan-1-one (see WO 0174811 publication) in place of 2-(2-t-butoxy-carbonylaminopyridin-4-yl)-1-(4-fluorophenyl)ethan-1-one to obtain 12.3 g of the title compound as a pale yellow powder. (Yield: 93%)
Rf value: 0.18 (ethyl acetate:hexane=1:1).
Mass spectrum (CI, m/z): 402 (M$^+$+1).
$^1$H-NMR spectrum (CDCl$_3$, δ ppm): 1.52 (s, 9H), 2.84 (brs, 6H), 6.72 (dd, J$_1$=5.2 Hz, J$_2$=1.6 Hz, 1H), 7.23-7.41 (m, 5H), 7.75 (s, 1H), 7.98 (s, 1H), 8.09 (dd, J$_1$=5.2 Hz, J$_2$=0.7 Hz, 1H).

23-2) 4-(2-t-Butoxycarbonylaminopyridin-4-yl)-3-(4-chlorophenyl)-1H-pyrazole

The reaction was carried out in the same manner as in Example 2-2) except for using 10.1 g (25.0 mmol) of 2-(2-t-butoxycarbonylaminopyridin-4-yl)-1-(4-chlorophenyl)-3-dimethylamino-2-propen-1-one obtained in Example 23-1) in place of 2-(2-t-butoxycarbonylaminopyridin-4-yl)-3-dimethylamino-1-(4-fluorophenyl)-2-propen-1-one to obtain 9.01 g of the title compound as a pale yellowish white powder. (Yield: 97%)
Rf value: 0.39 (ethyl acetate:hexane=1:1).
Mass spectrum (CI, m/z): 371 (M$^+$+1).
$^1$H-NMR spectrum (DMSO-d$_6$, δ ppm): 1.42 (s, 9H), 6.86 (dd, J$_1$=5.1 Hz, J$_2$=1.5 Hz, 1H), 7.41-7.48 (m, 4H), 7.73 (dd, J$_1$=1.5 Hz, J$_2$=0.7 Hz, 1H), 8.07 (s, 1H), 8.12 (dd, J$_1$=5.1 Hz, J$_2$=0.7 Hz, 1H), 9.66 (s, 1H), 13.39 (brs, 1H).

23-3) 4-(2-t-Butoxycarbonylaminopyridin-4-yl)-3-(4-chlorophenyl)-1-(6-chloropyridazin-3-yl)-1H-pyrazole The reaction was carried out in the same manner as in Example 1-3) except for using 4.50 g (12.1 mmol) of 4-(2-t-butoxycarbonylaminopyridin-4-yl)-3-(4-chlorophenyl)-1H-pyrazole obtained in Example 23-2) in place of 3-(4-fluorophenyl)-4-(pyridin-4-yl)-1H-pyrazole, and using 1.07 g (26.7 mmol) of sodium hydride (60% dispersed material in mineral oil) to obtain 4.08 g of the title compound as a beige powder. (Yield: 70%)
Rf value: 0.45 (ethyl acetate:hexane=1:2).
Mass spectrum (CI, m/z): 483 (M$^+$+1).
$^1$H-NMR spectrum (DMSO-d$_6$, δ ppm): 1.43 (s, 9H), 7.03 (dd, J$_1$=5.1 Hz, J$_2$=1.6 Hz, 1H), 7.06-7.60 (m, 4H), 7.82 (dd, J$_1$=1.6 Hz, J$_2$=0.7 Hz, 1H), 8.15 (d, J=9.3 Hz, 1H), 8.22 (dd, J$_1$=5.1 Hz, J$_2$=0.7 Hz, 1H), 8.39 (d, J=9.3 Hz, 1H), 9.20 (s, 1H), 9.77 (s, 1H).

23-4) 4-(2-Aminopyridin-4-yl)-3-(4-chlorophenyl)-1-(1,6-dihydro-6-oxopyridazin-3-yl)-1H-pyrazole The reaction was carried out in the same manner as in Example 1-4) except for using 3.50 g (7.24 mmol) of 4-(2-t-butoxycarbonylaminopyridin-4-yl)-3-(4-chlorophenyl)-1-(6-chloropyridazin-3-yl)-1H-pyrazole obtained in Example 23-3) in place of 1-(6-chloropyridazin-3-yl)-3-(4-fluorophenyl)-4-(pyridin-4-yl)-1H-pyrazole to obtain 1.73 g of the title compound as a white powder. (Yield: 65%)
Rf value: 0.43 (chloroform:methanol=9:1).
Mass spectrum (CI, m/z): 365 (M$^+$+1).
$^1$H-NMR spectrum (DMSO-d$_6$, δ ppm): 5.92 (s, 2H), 6.39 (d, J=0.7 Hz, 1H), 6.43 (dd, J$_1$=5.2 Hz, J$_2$=1.6 Hz, 1H), 7.11 (d, J=10.0 Hz, 1H), 7.48-7.56 (m, 4H), 7.87-7.89 (m, 1H), 8.11 (d, J=10.0 Hz, 1H), 8.57 (s, 1H), 13.06 (brs, 1H).

Example 24

4-(2-Aminopyridin-4-yl)-3-(3,4-difluorophenyl)-1-(1,6-dihydro-6-oxopyridazin-3-yl)-1H-pyrazole (Exemplary Compound No. 1-401)

24-1) 2-(2-t-Butoxycarbonylaminopyridin-4-yl)-1-(3,4-difluorophenyl)ethan-1-one

To 200 ml of a tetrahydrofuran solution containing 15.1 g (72.3 mmol) of 2-[N-(t-butoxycarbonyl)amino]-4-methylpyridine (see WO 9714417 publication) was added dropwise 100 ml of n-butyl lithium (1.6M hexane solution) under argon atmosphere at −45° C. over 30 minutes. After completion of the drowise addition, a temperature of the mixture was gradually raised, and the mixture was stirred at 0° C. for 30 minutes. Further, at the same temperature, 50 ml of a tetrahydrofuran solution containing 16.0 g (79.5 mmol) of 3,4-difluoro-N-methoxy-N-methylbenzamide (see WO 9705877 publication) was added dropwise to the mixture over 1 hour. After completion of the drowise addition with a whole amount, a temperature of the mixture was gradually raised to room temperature, and the mixture was stirred for further 2 hours.

After completion of the reaction, the reaction mixture was poured into 300 ml of an aqueous saturated ammonium chloride solution, and the solutions were separated. The aqueous layer was extracted with ethyl acetate, and the combined organic layers were washed with an aqueous saturated sodium chloride solution, dried over anhydrous magnesium sulfate, and then, concentrated under reduced pressure. To the obtained residue was added 100 ml of diisopropyl ether, precipitated crystals were collected by filtration, and then, washed with 100 ml of a mixed solvent (diisopropyl ether:hexane=1:1 (V/V)) to obtain 11.7 g of the title compound as a pale yellow powder. (Yield: 47%)
Rf value: 0.49 (ethyl acetate:hexane=1:2).
Mass spectrum (CI, m/z): 349 (M$^+$+1).

¹H-NMR spectrum (CDCl₃, δ ppm): 1.53 (s, 9H), 4.23 (s, 2H), 6.84 (dd, J₁=5.1 Hz, J₂=1.5 Hz, 1H), 7.23-7.31 (m, 1H), 7.74-7.86 (m, 3H), 7.90 (d, J=0.7 Hz, 1H), 8.20 (dd, J₁=5.1 Hz, J₂=0.7 Hz, 1H).

24-2) 2-(2-t-Butoxycarbonylaminopyridin-4-yl)-1-(3,4-difluorophenyl)-3-dimethylamino-2-propen-1-one The reaction was carried out in the same manner as in Example 2-1) except for using 10.5 g (30.0 mmol) of 2-(2-t-butoxycarbonylaminopyridin-4-yl)-1-(3,4-difluorophenyl)-ethan-1-one obtained in Example 24-1) in place of 2-(2-t-butoxycarbonylaminopyridin-4-yl)-1-(4-fluorophenyl)ethan-1-one to obtain 11.0 g of the title compound as a pale ocher powder. (Yield: 91%)

Rf value: 0.18 (ethyl acetate:hexane=1:2).

Mass spectrum (CI, m/z): 404 (M⁺+1).

¹H-NMR spectrum (CDCl₃, δ ppm): 1.52 (s, 9H), 2.86 (brs, 6H), 6.70 (dd, J₁=5.2 Hz, J₂=1.5 Hz, 1H), 7.01-7.17 (m, 1H), 7.18-7.20 (m, 1H), 7.27-7.34 (m, 1H), 7.37 (s, 1H), 7.74 (s, 1H), 7.90 (s, 1H), 8.10 (dd, J₁=5.2 Hz, J₂=0.6 Hz, 1H).

24-3) 4-(2-t-Butoxycarbonylaminopyridin-4-yl)-3-(3,4-difluorophenyl)-1H-pyrazole The reaction was carried out in the same manner as in Example 2-2) except for using 9.28 g (23.0 mmol) of 2-(2-t-butoxycarbonylaminopyridin-4-yl)-1-(3,4-difluorophenyl)-3-dimethylamino-2-propen-1-one obtained in Example 24-2) in place of 2-(2-t-butoxycarbonylaminopyridin-4-yl)-3-dimethylamino-1-(4-fluorophenyl)-2-propen-1-one to obtain 7.41 g of the title compound as a white powder. (Yield: 87%)

Rf value: 0.51 (ethyl acetate:hexane=1:2).

Mass spectrum (CI, m/z): 373 (M⁺+1).

¹H-NMR spectrum (DMSO-d₆, δ ppm): 1.42 (s, 9H), 6.92 (dd, J₁=5.2 Hz, J₂=1.6 Hz, 1H), 7.21-7.25 (m, 1H), 7.42-7.51 (m, 2H), 7.71 (dd, J₁=1.6 Hz, J₂=0.7 Hz, 1H), 8.12 (s, 1H), 8.14 (dd, J₁=5.2 Hz, J₂=0.7 Hz, 1H), 9.65 (s, 1H), 13.46 (brs, 1H).

24-4) 4-(2-t-Butoxycarbonylaminopyridin-4-yl)-1-(6-chloropyridazin-3-yl)-3-(3,4-difluorophenyl)-1H-pyrazole The reaction was carried out in the same manner as in Example 1-3) except for using 4.00 g (10.7 mmol) of 4-(2-t-butoxycarbonylaminopyridin-4-yl)-3-(3,4-difluorophenyl)-1H-pyrazole obtained in Example 24-3) in place of 3-(4-fluorophenyl)-4-(pyridin-4-yl)-1H-pyrazole, and using 945 mg (23.6 mmol) of sodium hydride (60% dispersed material in mineral oil) to obtain 4.33 g of the title compound as a white powder. (Yield: 83%)

Rf value: 0.36 (ethyl acetate:hexane=1:2).

Mass spectrum (CI, m/z): 485 (M⁺+1).

¹H-NMR spectrum (DMSO-d₆, δ ppm): 1.43 (s, 9H), 7.12 (dd, J₁=5.1 Hz, J₂=1.7 Hz, 1H), 7.34-7.65 (m, 3H), 7.79 (s, 1H), 8.16 (d, J=9.3 Hz, 1H), 8.24 (d, J=5.1 Hz, 1H), 8.41 (d, J=9.3 Hz, 1H), 9.25 (s, 1H), 9.77 (s, 1H).

24-5) 4-(2-Aminopyridin-4-yl)-3-(3,4-difluorophenyl)-1-(1,6-dihydro-6-oxopyridazin-3-yl)-1H-pyrazole The reaction was carried out in the same manner as in Example 1-4) except for using 3.50 g (7.22 mmol) of 4-(2-t-butoxycarbonylaminopyridin-4-yl)-1-(6-chloropyridazin-3-yl)-3-(3,4-difluorophenyl)-1H-pyrazole obtained in Example 24-4) in place of 1-(6-chloropyridazin-3-yl)-3-(4-fluorophenyl)-4-(pyridin-4-yl)-1H-pyrazole to obtain 1.49 g of the title compound as a white powder. (Yield: 56%)

Rf value: 0.31 (chloroform:methanol=9:1).

Mass spectrum (CI, m/z): 367 (M⁺+1).

¹H-NMR spectrum (DMSO-d₆, δ ppm): 5.93 (s, 2H), 6.38 (s, 1H), 6.46 (dd, J₁=5.3 Hz, J₂=1.6 Hz, 1H), 7.14 (d, J=10.0 Hz, 1H), 7.30-7.35 (m, 1H), 7.46-7.60 (m, 2H), 7.89 (dd, J₁=5.3 Hz, J₂=0.6 Hz, 1H), 8.14 (d, J=10.0 Hz, 1H), 8.58 (s, 1H), 13.10 (brs, 1H).

Example 25

4-(2-Aminopyridin-4-yl)-1-(1,6-dihydro-6-oxopyridazin-3-yl)-3-(3-trifluoromethylphenyl)-1H-pyrazole (Exemplary Compound No. 1-618)

25-1) 2-(2-t-Butoxycarbonylaminopyridin-4-yl)-3-dimethyl-amino-1-(3-trifluoromethylphenyl)-2-propen-1-one The reaction was carried out in the same manner as in Example 2-1) except for using 8.40 g (22.1 mmol) of 2-(2-t-butoxycarbonylaminopyridin-4-yl)-1-(3-trifluoromethylphenyl)ethan-1-one (see WO 0174811 publication) in place of 2-(2-t-butoxycarbonylaminopyridin-4-yl)-1-(4-fluorophenyl)-ethan-1-one, and adding 0.13 ml (2.21 mmol) of acetic acid to obtain 8.90 g of the title compound as a white powder. (Yield: 93%)

Rf value: 0.12 (ethyl acetate:hexane=1:2).

Mass spectrum (CI, m/z): 436 (M⁺+1).

¹H-NMR spectrum (DMSO-d₆, δ ppm): 1.45 (s, 9H), 2.79 (brs, 6H), 6.78 (d, J=4.8 Hz, 1H), 7.30 (s, 1H), 7.55-7.78 (m, 5H), 8.10 (d, J=4.8 Hz, 1H), 9.62 (s, 1H).

25-2) 4-(2-t-Butoxycarbonylaminopyridin-4-yl)-3-(3-trifluoromethylphenyl)-1H-pyrazole The reaction was carried out in the same manner as in Example 2-2) except for using 8.71 g (20.0 mmol) of 2-(2-t-butoxycarbonylaminopyridin-4-yl)-3-dimethylamino-1-(3-trifluoromethylphenyl)-2-propen-1-one obtained in Example 25-1) in place of 2-(2-t-butoxycarbonylaminopyridin-4-yl)-3-dimethylamino-1-(4-fluorophenyl)-2-propen-1-one to obtain 7.76 g of the title compound as a white powder. (Yield: 96%)

Rf value: 0.37 (ethyl acetate:hexane=1:1).

Mass spectrum (CI, m/z): 405 (M⁺+1).

¹H-NMR spectrum (DMSO-d₆, δ ppm): 1.40 (s, 9H), 6.90 (dd, J₁=5.1 Hz, J₂=1.7 Hz, 1H), 7.61-7.78 (m, 5H), 8.13-8.15 (m, 2H), 9.64 (s, 1H), 13.59 (brs, 1H).

25-3) 4-(2-t-Butoxycarbonylaminopyridin-4-yl)-1-(6-chloropyridazin-3-yl)-3-(3-trifluoromethylphenyl)-1H-pyrazole The reaction was carried out in the same manner as in Example 1-3) except for using 5.66 g (14.0 mmol) of 4-(2-t-butoxycarbonylaminopyridin-4-yl)-3-(3-trifluoromethylphenyl)-1H-pyrazole obtained in Example 25-2) in place of 3-(4-fluorophenyl)-4-(pyridin-4-yl)-1H-pyrazole, and using 1.23 g (30.8 mmol) of sodium hydride (60% dispersed material in mineral oil) to obtain 2.74 g of the title compound as a pale beige powder. (Yield: 38%)

Rf value: 0.24 (chloroform:methanol=9:1).
Mass spectrum (CI, m/z): 517 (M$^+$+1).
$^1$H-NMR spectrum (DMSO-d$_6$, δ ppm): 1.41 (s, 9H), 7.08 (dd, J$_1$=5.2 Hz, J$_2$=1.6 Hz, 1H), 7.70 (t, J=7.7 Hz, 1H), 7.80-7.87 (m, 4H), 8.16 (d, J=9.3 Hz, 1H), 8.23 (dd, J$_1$=5.2 Hz, J$_2$=0.7 Hz, 1H), 8.45 (d, J=9.3 Hz, 1H), 9.25 (s, 1H), 9.77 (brs, 1H).

25-4) 4-(2-Aminopyridin-4-yl)-1-(1,6-dihydro-6-oxopyridazin-3-yl)-3-(3-trifluoromethylphenyl)-1H-pyrazole The reaction was carried out in the same manner as in Example 1-4) except for using 2.58 g (5.00 mmol) of 4-(2-t-butoxycarbonylaminopyridin-4-yl)-1-(6-chloropyridazin-3-yl)-3-(3-trifluoromethylphenyl)-1H-pyrazole obtained in Example 25-3) in place of 1-(6-chloropyridazin-3-yl)-3-(4-fluorophenyl)-4-(pyridin-4-yl)-1H-pyrazole to obtain 1.21 g of the title compound as a white powder. (Yield: 61%)
Rf value: 0.45 (chloroform:methanol=9:1).
Mass spectrum (CI, m/z): 399 (M$^+$+1).
$^1$H-NMR spectrum (DMSO-d$_6$, δ ppm): 5.94 (brs, 2H), 6.40-6.44 (m, 2H), 7.14 (d, J=10.0 Hz, 1H), 7.67 (t, J=7.8 Hz, 1H), 7.77-7.81 (m, 2H), 7.87 (s, 1H), 7.89 (dd, J$_1$=5.1 Hz, J$_2$=0.7 Hz, 1H), 8.18 (d, J=10.0 Hz, 1H), 8.61 (s, 1H), 13.09 (brs, 1H).

Example 26

4-(2-Aminopyridin-4-yl)-3-(2-fluorophenyl)1-(1,6-dihydro-6-oxopyridazin-3-yl)-1H-pyrazole (Exemplary Compound No. 1-677)

26-1) 2-(2-t-Butoxycarbonylaminopyridin-4-yl)-1-(2-fluorophenyl)ethan-1-one

The reaction was carried out in the same manner as in Example 24-1) except for using 20.8 g (100 mmol) of 2-fluoro-N-methoxy-N-methylbenzamide (see WO 9740027 publication) in-place of 3,4-difluoro-N-methoxy-N-methylbenzamide to obtain 26.3 g of the title compound as a white powder. (Yield: 80%)
Rf value: 0.38 (ethyl acetate:hexane=1:2).
Mass spectrum (CI, m/z): 331 (M$^+$+1).
$^1$H-NMR spectrum (CDCl$_3$, δ ppm): 1.53 (s, 9H), 4.30 (d, J=2.7 Hz, 2H), 6.86 (dd, J$_1$=5.2 Hz, J$_2$=1.6 Hz, 1H), 7.13-7.27 (m, 2H), 7.51-7.58 (m, 1H), 7.85-7.90 (m, 2H), 8.24 (dd, J$_1$=5.2 Hz, J$_2$=0.7 Hz, 1H), 8.55 (brs, 1H).

26-2) 2-(2-t-Butoxycarbonylaminopyridin-4-yl)-3-dimethylamino-1-(2-fluorophenyl)-2-propen-1-one The reaction was carried out in the same manner as in Example 2-1) except for using 6.15 g (18.6 mmol) of 2-(2-t-butoxycarbonylaminopyridin-4-yl)-1-(2-fluorophenyl)ethan-1-one obtained in Example 26-1) in place of 2-(2-t-butoxycarbonylaminopyridin-4-yl)-1-(4-fluorophenyl)ethan-1-one to obtain 7.10 g of the title compound as a pale yellow powder. (Yield: 99%)
Rf value: 0.35 (ethyl acetate:hexane=1:5).
Mass spectrum (CI, m/z): 386 (M$^+$+1).
$^1$H-NMR spectrum (CDCl$_3$, δ ppm): 1.59 (s, 9H), 2.82 (brs, 6H), 6.87 (dd, J$_1$=5.1 Hz, J$_2$=1.5 Hz, 1H), 6.97-7.03 (m, 1H), 7.09-7.14 (m, 1H), 7.23-7.36 (m, 3H), 7.63 (brs, 1H), 7.75 (s, 1H), 8.11 (dd, J$_1$=5.1 Hz, J$_2$=0.7 Hz, 1H).

26-3) 4-(2-t-Butoxycarbonylaminopyridin-4-yl)-3-(2-fluorophenyl)-1H-pyrazole

The reaction was carried out in the same manner as in Example 2-2) except for using 14.6 g (37.8 mmol) of 2-(2-t-butoxycarbonylaminopyridin-4-yl)-3-dimethylamino-1-(2-fluorophenyl)-2-propen-1-one obtained by the same reaction as in Example 26-2) in place of 2-(2-t-butoxycarbonylaminopyridin-4-yl)-3-dimethylamino-1-(4-fluorophenyl)-2-propen-1-one to obtain 11.7 g of the title compound as a pale yellow powder. (Yield: 87%)
Rf value: 0.41 (chloroform:methanol=9:1).
Mass spectrum (CI, m/z): 355 (M$^+$+1).
$^1$H-NMR spectrum (DMSO-d$_6$, δ ppm): 1.42 (s, 9H), 6.78 (dd, J$_1$=5.2 Hz, J$_2$=1.6 Hz, 1H), 7.23-7.32 (m, 2H), 7.44-7.52 (m, 2H), 7.69 (d, J=0.7 Hz, 1H), 8.06 (dd, J$_1$=5.2 Hz, J$_2$=0.7 Hz, 1H), 8.17 (brs, 1H), 9.56 (s, 1H), 13.41 (brs, 1H).

26-4) 4-(2-t-Butoxycarbonylaminopyridin-4-yl)-1-(6-chloropyridazin-3-yl)-3-(2-fluorophenyl)-1H-pyrazole The reaction was carried out in the same manner as in Example 1-3) except for using 6.00 g (16.9 mmol) of 4-(2-t-butoxycarbonylaminopyridin-4-yl)-3-(2-fluorophenyl)-1H-pyrazole obtained in Example 26-3) in place of 3-(4-fluorophenyl)-4-(pyridin-4-yl)-1H-pyrazole, and using 1.49 g (37.2 mmol) of sodium hydride (60% dispersed material in mineral oil) to obtain 3.40 g of the title compound as a white powder. (Yield: 43%)
Rf value: 0.46 (ethyl acetate:hexane=1:3).
Mass spectrum (CI, m/z): 467 (M$^+$+1).
$^1$H-NMR spectrum (DMSO-d$_6$, δ ppm): 1.42 (s, 9H), 6.98 (dd, J$_1$=5.1 Hz, J$_2$=1.7 Hz, 1H), 7.27-7.39 (m, 2H), 7.52-7.65 (m, 2H), 7.78 (s, 1H), 8.14 (d, J=9.3 Hz, 1H), 8.16 (d, J=5.1 Hz, 1H), 8.36 (d, J=9.3 Hz, 1H), 9.33 (s, 1H), 9.69 (s, 1H).

26-5) 4-(2-Aminopyridin-4-yl)-3-(2-fluorophenyl)-1-(1,6-dihydro-6-oxopyridazin-3-yl)-1H-pyrazole The reaction was carried out in the same manner as in Example 1-4) except for using 3.20 g (6.85 mmol) of 4-(2-t-butoxycarbonylaminopyridin-4-yl)-1-(6-chloropyridazin-3-yl)-3-(2-fluorophenyl)-1H-pyrazole obtained in Example 26-4) in place of 1-(6-chloropyridazin-3-yl)-3-(4-fluorophenyl)-4-(pyridin-4-yl)-1H-pyrazole to obtain 2.29 g of the title compound as a white powder. (Yield: 96%)
Rf value: 0.41 (chloroform:methanol=9:1).
Mass spectrum (CI, m/z): 349 (M$_+$+1).
$^1$H-NMR spectrum (DMSO-d$_6$, δ ppm): 5.82 (brs, 2H), 6.33-6.34 (m, 2H), 7.13 (d, J=10.1 Hz, 1H), 7.26-7.36 (m, 2H), 7.50-7.58 (m, 2H), 7.79-7.81 (m, 1H), 8.08 (d, J=10.1 Hz, 1H), 8.68 (s, 1H), 13.12 (brs, 1H).

Example 27

4-(2-Ethylaminopyridin-4-yl)-3-(4-fluorophenyl)-1-(1,6-dihydro-6-oxopyridazin-3-yl)-1H-pyrazole (Exemplary Compound No. 1-76)

27-1) 4-{2-[(t-Butoxycarbonyl)ethylamino]pyridin-4-yl}-1-(6-chloropyridazin-3-yl)-3-(4-fluorophenyl)-1H-pyrazole The reaction was carried out in the same manner as in Example 3-1) except for using 3.74 g (8.00 mmol) of 4-(2-t-butoxycarbonylaminopyridin-4-yl)-1-(6-chloropyridazin-3-yl)-3-(4-fluorophenyl)-1H-pyrazole obtained by the same reaction as in Example 2-3), and using 6.24 g (40.0 mmol) of ethyl iodide in place of methyl iodide to obtain 1.66 g of the title compound as a white powder. (Yield: 42%)

Rf value: 0.29 (ethyl acetate:hexane=1:5).
Mass spectrum (CI, m/z): 495 (M$^+$+1).
$^1$H-NMR spectrum (CDCl$_3$, δ ppm): 1.24 (t, J=7.0 Hz, 3H), 1.50 (s, 9H), 3.99 (q, J=7.0 Hz, 2H), 6.89 (dd, J$_1$=5.1 Hz, J$_2$=1.6 Hz, 1H), 7.06-7.13 (m, 2H), 7.51-7.63 (m, 2H), 7.66 (d, J=9.3 Hz, 1H), 7.72 (dd, J$_1$=1.6 Hz, J$_2$=0.7 Hz, 1H), 8.29 (d, J=9.3 Hz, 1H), 8.31 (dd, J$_1$=5.1 Hz, J$_2$=0.7 Hz, 1H), 8.94 (s, 1H).

27-2) 4-(2-Ethylaminopyridin-4-yl)-3-(4-fluorophenyl)-1-(1,6-dihydro-6-oxopyridazin-3-yl)-1H-pyrazole The reaction was carried out in the same manner as in Example 1-4) except for using 1.50 g (3.03 mmol) of 4-{2-[(t-butoxycarbonyl)ethylamino]pyridin-4-yl}-1-(6-chloropyridazin-3-yl)-3-(4-fluorophenyl)-1H-pyrazole obtained in Example 27-1) in place of 1-(6-chloropyridazin-3-yl)-3-(4-fluorophenyl)-4-(pyridin-4-yl)-1H-pyrazole to obtain 180 mg of the title compound as a white powder. (Yield: 16%)

Rf value: 0.21 (chloroform:methanol=9:1).
Mass spectrum (CI, m/z): 377 (M$^+$+1).
$^1$H-NMR spectrum (DMSO-d$_6$, δ ppm): 1.09 (t, J=7.2 Hz, 3H), 3.18-3.22 (m, 2H), 6.41 (s, 1H), 6.45 (d, J=5.3 Hz, 1H), 6.66 (brs, 1H), 7.14 (d, J=10.0 Hz, 1H), 7.24-7.32 (m, 2H), 7.52-7.59 (m, 2H), 7.92 (d, J=5.3 Hz, 1H), 8.13 (d, J=10.0 Hz, 1H), 8.63 (s, 1H), 13.10 (s, 1H).

Example 28

3-(4-fluorophenyl)-1-(1,6-dihydro-6-oxopyridazin-3-yl)-4-[2-(2,2,2-trifluoroethyl)aminopyridin-4-yl]-1H-pyrazole (Exemplary Compound No. 1-78)

28-1) 4-{2-[(t-Butoxycarbonyl)(2,2,2-trifluoroethyl)amino]-pyridin-4-yl}-1-(6-chloropyridazin-3-yl)-3-(4-fluorophenyl)-1H-pyrazole The reaction was carried out in the same manner as in Example 3-1) except for using 5.60 g (12.0 mmol) of 4-(2-t-butoxycarbonylaminopyridin-4-yl)-1-(6-chloropyridazin-3-yl)-3-(4-fluorophenyl)-1H-pyrazole obtained by the same reaction as in Example 2-3), and using 4.18 g (18.0 mmol) of 2,2,2-trifluoroethyl triflate in place of methyl iodide to obtain 3.45 g of the title compound as a pale grayish white powder. (Yield: 52%)

Rf value: 0.24 (ethyl acetate:hexane=1:5).
Mass spectrum (CI, m/z): 549 (M$^+$+1).
$^1$H-NMR spectrum (DMSO-d$_6$, δ ppm): 1.40 (s, 9H), 4.72-4.81 (m, 2H), 7.26-7.34 (m, 3H), 7.53-7.60 (m, 3H), 8.15 (d, J=9.2 Hz, 1H), 8.39 (d, J=9.2 Hz, 1H), 8.39 (dd, J$_1$=5.4 Hz, J$_2$=0.7 Hz, 1H), 9.35 (s, 1H).

28-2) 3-(4-Fluorophenyl)-1-(1,6-dihydro-6-oxopyridazin-3-yl)-4-[2-(2,2,2-trifluoroethyl)aminopyridin-4-yl]-1H-pyrazole The reaction was carried out in the same manner as in Example 1-4) except for using 3.00 g (5.47 mmol) of 4-{2-[(t-butoxycarbonyl)(2,2,2-trifluoroethyl)amino]pyridin-4-yl}-1-(6-chloropyridazin-3-yl)-3-(4-fluorophenyl)-1H-pyrazole obtained in Example 28-1) in place of 1-(6-chloropyridazin-3-yl)-3-(4-fluorophenyl)-4-(pyridin-4-yl)-1H-pyrazole to obtain 1.95 g of the title compound as a white powder. (Yield: 83%)

Rf value: 0.19 (chloroform:methanol=9:1).
Mass spectrum (CI, m/z): 431 (M$^+$+1).
$^1$H-NMR spectrum (DMSO-d$_6$, δ ppm): 4.08-4.20 (m, 2H), 6.54-6.62 (m, 2H), 7.08-7.19 (m, 2H), 7.24-7.35 (m, 2H), 7.51-7.58 (m, 2H), 7.99 (dd, J$_1$=4.9 Hz, J$_2$=1.2 Hz, 1H), 8.12 (d, J=10.3 Hz, 1H), 8.64 (s, 1H), 13.10 (brs, 1H).

Example 29

4-(2-Acetylaminopyridin-4-yl)-3-(4-fluorophenyl)-1-(1,6-dihydro-6-oxopyridazin-3-yl)-1H-pyrazole (Exemplary Compound No. 1-81)

The reaction was carried out in the same manner as in Example 9 except for using 522 mg (1.36 mmol) of 4-(2-aminopyridin-4-yl)-3-(4-fluorophenyl)-1-(1,6-dihydro-6-oxopyridazin-3-yl)-1H-pyrazole obtained by the same reaction as in Example 2-4) in place of 4-(2-aminopyridin-4-yl)-3-(4-fluorophenyl)-1-([1,2,4]triazolo[4,3-b]pyridazin-6-yl)-1H-pyrazole to obtain 396 mg of the title compound as a white powder. (Yield: 75%)

Rf value: 0.53 (chloroform:methanol=9:1).
Mass spectrum (CI, m/z): 391 (M$^+$+1).
$^1$H-NMR spectrum (DMSO-d$_6$, δ ppm): 2.07 (s, 3H), 7.08 (dd, J$_1$=5.3 Hz, J$_2$=1.6 Hz, 1H), 7.15 (d, J=10.0 Hz, 1H), 7.24-7.31 (m, 2H), 7.50-7.56 (m, 2H), 8.01 (s, 1H), 8.13 (d, J=10.0 Hz, 1H), 8.27 (d, J=5.3 Hz, 1H), 8.72 (s, 1H), 10.61 (brs, 1H), 13.13 (brs, 1H).

Example 30

3-(4-Fluorophenyl)-1-(1,6-dihydro-6-oxopyridazin-3-yl)-4-(2-methoxycarbonylaminopyridin-4-yl)-1H-pyrazole (Exemplary Compound No. 1-84)

The reaction was carried out in the same manner as in Example 9 except for using 500 mg (1.30 mmol) of 4-(2-aminopyridin-4-yl)-3-(4-fluorophenyl)-1-(1,6-dihydro-6-oxopyridazin-3-yl)-1H-pyrazole obtained by the same reaction as in Example 2-4) in place of 4-(2-aminopyridin-4-yl)-3-(4-fluorophenyl)-1-([1,2,4]triazolo[4,3-b]pyridazin-6-yl)-1H-pyrazole, and using 1.23 g (13.0 mmol) of methyl chloroformate in place of acetic anhydride to obtain 44.8 mg of the title compound as a white powder. (Yield: 8%)

Rf value: 0.35 (chloroform:methanol=19:1).
Mass spectrum (CI, m/z): 407 (M$^+$+1).
$^1$H-NMR spectrum (DMSO-d$_6$, δ ppm): 3.62 (s, 3H), 7.00 (dd, J$_1$=5.2 Hz, J$_2$=1.6 Hz, 1H), 7.09 (d, J=10.0 Hz, 1H), 7.24-7.30 (m, 2H), 7.51-7.56 (m, 2H), 7.81 (s, 1H), 8.10 (d, J=10.0 Hz, 1H), 8.22 (dd, J$_1$=5.2 Hz, J$_2$=0.7 Hz, 1H), 8.70 (s, 1H), 10.17 (s, 1H), 13.11 (brs, 1H).

Example 31

4-(2-Aminopyridin-4-yl)-3-(4-fluorophenyl)-1-(1,6-dihydro-4-methyl-6-oxopyridazin-3-yl)-1H-pyrazole (Exemplary Compound No. 1-94)

31-1) 4-(2-t-Butoxycarbonylaminopyridin-4-yl)-1-(6-chloro-4-methylpyridazin-3-yl)-3-(4-fluorophenyl)-1H-pyrazole The reaction was carried out in the same manner as in Example 1-3) except for using 6.02 g (17.0 mmol) of 4-(2-t-butoxycarbonylaminopyridin-4-yl)-3-(4-fluorophenyl)-1H-pyrazole obtained by the same reaction as in Example 2-2) in place of 3-(4-fluorophenyl)-4-(pyridin-4-yl)-1H-pyrazole, 3.05 g (18.7 mmol) of 3,6-dichloro-4-methylpyridazine in place of 3,6-dichloropyridazine, and using 1.50 g (37.4 mmol) of sodium hydride (60% dispersed material in mineral oil) to obtain 800 mg of the title compound as a white powder. (Yield: 10%)

Rf value: 0.44 (ethyl acetate:hexane=3:7).

Mass spectrum (CI, m/z): 481 (M$^+$+1).

$^1$H-NMR spectrum (CDCl$_3$, δ ppm): 1.51 (s, 9H), 2.79 (d, J=1.0 Hz, 3H), 6.83 (dd, J$_1$=5.3 Hz, J$_2$=1.6 Hz, 1H), 7.03-7.11 (m, 2H), 7.49-7.56 (m, 4H), 8.06 (s, 1H), 8.16 (dd, J$_1$=5.3 Hz, J$_2$=0.7 Hz, 1H), 8.74 (s, 1H).

31-2) 4-(2-Aminopyridin-4-yl)-3-(4-fluorophenyl)-1-(1,6-dihydro-4-methyl-6-oxopyridazin-3-yl)-1H-pyrazole The reaction was carried out in the same manner as in Example 1-4) except for using 765 mg (1.59 mmol) of 4-(2-t-butoxycarbonylaminopyridin-4-yl)-1-(6-chloro-4-methylpyridazin-3-yl)-3-(4-fluorophenyl)-1H-pyrazole obtained in Example 31-1) in place of 1-(6-chloropyridazin-3-yl)-3-(4-fluorophenyl)-4-(pyridin-4-yl)-1H-pyrazole to obtain 442 mg of the title compound as a white powder. (Yield: 77%)

Rf value: 0.17 (chloroform:methanol=19:1).

Mass spectrum (CI, m/z): 363 (M$^+$+1).

$^1$H-NMR spectrum (DMSO-d$_6$, δ ppm): 2.28 (d, J=1.2 Hz, 3H), 5.90 (brs, 2H), 6.37-6.40 (m, 2H), 7.01 (d, J=1.2 Hz, 1H), 7.22-7.29 (m, 2H), 7.49-7.55 (m, 2H), 7.86 (dd, J$_1$=5.2 Hz, J$_2$=0.6 Hz, 1H), 8.39 (s, 1H), 13.13 (brs, 1H).

Example 32

4-(2-Aminopyridin-4-yl)-3-(4-fluorophenyl)-1-(1,6-dihydro-5-methyl-6-oxopyridazin-3-yl)-1H-pyrazole (Exemplary Compound No. 1-95)

32-1) 4-(2-t-Butoxycarbonylaminopyridin-4-yl)-1-(6-chloro-5-methylpyridazin-3-yl)-3-(4-fluorophenyl)-1H-pyrazole The reaction was carried out in the same manner as in Example 1-3) except for using 6.02 g (17.0 mmol) of 4-(2-t-butoxycarbonylaminopyridin-4-yl)-3-(4-fluorophenyl)-1H-pyrazole obtained by the same reaction as in Example 2-2) in place of 3-(4-fluorophenyl)-4-(pyridin-4-yl)-1H-pyrazole, 3.05 g (18.7 mmol) of 3,6-dichloro-4-methylpyridazine in place of 3,6-dichloropyridazine, and using 1.50 g (37.4 mmol) of sodium hydride (60% dispersed material in mineral oil) to obtain 1.07 g of the title compound as a white powder. (Yield: 13%)

Rf value: 0.51 (ethyl acetate:hexane=3:7).

Mass spectrum (CI, m/z): 481 (M$^+$+1).

$^1$H-NMR spectrum (CDCl$_3$, δ ppm): 1.52 (s, 9H), 2.53 (d, J=1.0 Hz, 3H), 6.80 (dd, J$_1$=5.2 Hz, J$_2$=1.5 Hz, 1H), 7.06-7.12 (m, 2H), 7.46 (brs, 1H), 7.52-7.57 (m, 2H), 8.05-8.06 (m, 1H), 8.15 (dd, J$_1$=5.2 Hz, J$_2$=0.9 Hz, 1H), 8.18 (d, J=1.0 Hz, 1H), 8.97 (s, 1H).

32-2) 4-(2-Aminopyridin-4-yl)-3-(4-fluorophenyl)-1-(1,6-dihydro-5-methyl-6-oxopyridazin-3-yl)-1H-pyrazole The reaction was carried out in the same manner as in Example 1-4) except for using 979 mg (2.04 mmol) of 4-(2-t-butoxycarbonylaminopyridin-4-yl)-1-(6-chloro-5-methylpyridazin-3-yl)-3-(4-fluorophenyl)-1H-pyrazole obtained in Example 32-1) in place of 1-(6-chloropyridazin-3-yl)-3-(4-fluorophenyl)-4-(pyridin-4-yl)-1H-pyrazole to obtain 558 mg of the title compound as a white powder. (Yield: 76%)

Rf value: 0.24 (chloroform:methanol=19:1).

Mass spectrum (CI, m/z): 363 (M$^+$+1).

$^1$H-NMR spectrum (DMSO-d$_6$, δ ppm): 2.19 (d, J=1.5 Hz, 3H), 5.97 (brs, 2H), 6.39 (dd, J$_1$=1.5 Hz, J$_2$=0.7 Hz, 1H), 6.44 (dd, J$_1$=5.3 Hz, J$_2$=1.5 Hz, 1H), 7.23-7.31 (m, 2H), 7.52-7.59 (m, 2H), 7.87 (dd, J$_1$=5.3 Hz, J$_2$=0.7 Hz, 1H), 8.07 (d, J=1.5 Hz, 1H), 8.56 (s, 1H), 12.98 (brs, 1H).

Example 33

4-(2-Aminopyridin-4-yl)-3-(4-fluorophenyl)-1-(1,6-dihydro-1-methyl-6-oxopyridazin-3-yl)-1H-pyrazole (Exemplary Compound No. 1-104)

To 1 ml of a tetrahydrofuran solution containing 100 mg (0.29 mmol) of 4-(2-aminopyridin-4-yl)-3-(4-fluorophenyl)-1(1,6-dihydro-6-oxopyridazin-3-yl)-1H-pyrazole obtained by the same reaction as in Example 2-4) was added 13.8 mg (0.34 mmol) of sodium hydride (60% dispersed material in mineral oil) under stirring at room temperature and under argon atmosphere, and the mixture was stirred for 30 minutes. Then, under ice-cooling, 0.5 ml of a tetrahydrofuran solution containing 48.9 mg (0.34 mmol) of methyl iodide was added to the mixture, and after stirring the mixture for 10 minutes, the cooling bath was removed, and a temperature of the mixture was gradually raised to room temperature. The mixture was stirred at room temperature for 1 hour, and at 50° C. for 9 hours. Provided that after 3 hours and 6.5 hours from starting stirring under heating, 0.5 ml of a tetrahydrofuran solution containing 48.9 mg (0.34 mmol) of methyl iodide was each added.

After completion of the reaction, 20 ml of water was added to the reaction mixture, and the resulting mixture was extracted with 60 ml of ethyl acetate. The organic layer was washed with an aqueous saturated sodium chloride solution, dried over anhydrous magnesium sulfate, and then, concentrated under reduced pressure. The obtained residue was applied to silica gel column chromatography (eluent; chloroform:methanol=19:1 (V/V)), and the separated fractions containing the objective compound were concentrated under reduced pressure. The obtained crude crystals were washed with 5 ml of diisopropyl ether to obtain 17.4 mg of the title compound as a white powder. (Yield: 17%)

Rf value: 0.50 (chloroform:methanol=9:1).

Mass spectrum (CI, m/z): 363 (M$^+$+1).

$^1$H-NMR spectrum (DMSO-d$_6$, δ ppm): 3.71 (s, 3H), 5.92 (s, 2H), 6.39-6.43 (m, 2H), 7.20 (d, J=9.8 Hz, 1H), 7.25-7.31 (m, 2H), 7.53-7.58 (m, 2H), 7.88 (d, J=5.1 Hz, 1H), 8.14 (d, J=9.8 Hz, 1H), 8.61 (s, 1H).

Example 34

3-(2-Fluorophenyl)-1-(1,6-dihydro-6-oxopyridazin-3-yl)-4-[2-(2,2,2-trifluoroethyl)aminopyridin-4-yl]-1H-pyrazole (Exemplary Compound No. 1-682)

34-1) 4-{2-[(t-Butoxycarbonyl)(2,2,2-trifluoroethyl)amino]-pyridin-4-yl}-1-(6-chloropyridazin-3-yl)-3-(2-fluorophenyl)-1H-pyrazole The reaction was carried out in the same manner as in Example 3-1) except for using 700 mg (1.50 mmol) of 4-(2-t-butoxycarbonylaminopyridin-4-yl)-1-(6-chloropyridazin-3-yl)-3-(2-fluorophenyl)-1H-pyrazole obtained by the same reaction as in Example 26-4) in place of 4-(2-t-butoxycarbonylaminopyridin-4-yl)-1-(6-chloropyridazin-3-yl)-3-(4-fluorophenyl)-1H-pyrazole, and using 522 mg (2.25 mmol) of 2,2,2-trifluoroethyl triflate in place of methyl iodide to obtain 715 mg of the title compound as a white powder. (Yield: 87%)

Rf value: 0.59 (chloroform:ethyl acetate=30:1).

Mass spectrum (CI, m/z): 549 ($M^+$+1).

$^1$H-NMR spectrum (DMSO-$d_6$, δ ppm): 1.37 (s, 9H), 4.72 (q, J=9.0 Hz, 2H), 7.27-7.33 (m, 2H), 7.35-7.41 (m, 1H), 7.48 (s, 1H), 7.55-7.67 (m, 2H), 8.15 (d, J=9.3 Hz, 1H), 8.35 (dd, $J_1$=5.1 Hz, $J_2$=0.7 Hz, 1H), 8.37 (d, J=9.3 Hz, 1H), 9.51 (s, 1H).

34-2) 3-(2-Fluorophenyl)-1-(1,6-dihydro-6-oxopyridazin-3-yl)-4-[2-(2,2,2-trifluoroethyl)aminopyridin-4-yl]-1H-pyrazole The reaction was carried out in the same manner as in Example 1-4) except for using 700 mg (1.28 mmol) of 4-{2-[(t-butoxycarbonyl)(2,2,2-trifluoroethyl)amino]pyridin-4-yl}-1-(6-chloropyridazin-3-yl)-3-(2-fluorophenyl)-1H-pyrazole obtained in Example 34-1) in place of 1-(6-chloropyridazin-3-yl)-3-(4-fluorophenyl)-4-(pyridin-4-yl)-1H-pyrazole to obtain 370 mg of the title compound as a beige powder. (Yield: 67%)

Rf value: 0.14 (chloroform:methanol=30:1).

Mass spectrum (CI, m/z): 431 ($M^+$+1).

$^1$H-NMR spectrum (DMSO-$d_6$, δ ppm): 4.03-4.15 (m, 2H), 6.49 (dd, $J_1$=5.4 Hz, $J_2$=1.5 Hz, 1H), 6.53 (s, 1H), 7.04 (t, J=6.7 Hz, 1H), 7.12 (d, J=10.0 Hz, 1H), 7.27-7.37 (m, 2H), 7.51-7.60 (m, 2H), 7.92 (d, J=5.4 Hz, 1H), 8.08 (d, J=10.0 Hz, 1H), 8.76 (s, 1H), 13.12 (brs, 1H).

Example 35

4-(2-Acetylaminopyridin-4-yl)-3-(2-fluorophenyl)-1-(1,6-dihydro-6-oxopyridazin-3-yl)-1H-pyrazole (Exemplary Compound No. 1-684)

The reaction was carried out in the same manner as in Example 9 except for using 49.2 mg (0.14 mmol) of 4-(2-aminopyridin-4-yl)-3-(2-fluorophenyl)-1-(1,6-dihydro-6-oxopyridazin-3-yl)-1H-pyrazole obtained in Example 26-5) in place of 4-(2-aminopyridin-4-yl)-3-(4-fluorophenyl)-1-([1,2,4]triazolo[4,3-b]pyridazin-6-yl)-1H-pyrazole to obtain 32.8 mg of the title compound as a white powder. (Yield: 60%)

Rf value: 0.28 (chloroform:methanol=19:1).

Mass spectrum (CI, m/z): 391 ($M^+$+1).

$^1$H-NMR spectrum (DMSO-$d_6$, δ ppm): 2.02 (s, 3H), 7.00 (dd, $J_1$=5.2 Hz, $J_2$=1.6 Hz, 1H), 7.13 (d, J=10.0 Hz, 1H), 7.24-7.36 (m, 2H), 7.50-7.60 (m, 2H), 8.02 (s, 1H), 8.09 (d, J=10.0 Hz, 1H), 8.20 (dd, $J_1$=5.2 Hz, $J_2$=0.7 Hz, 1H), 8.82 (s, 1H), 10.40 (brs, 1H), 13.15 (brs, 1H).

Example 36

4-(2-Cyclopropylcarbonylaminopyridin-4-yl)-3-(2-fluorophenyl)-1-(1,6-dihydro-6-oxopyridazin-3-yl)-1H-pyrazole (Exemplary Compound No. 1-823)

The reaction was carried out in the same manner as in Example 9 except for using 50.0 mg (0.14 mmol) of 4-(2-aminopyridin-4-yl)-3-(2-fluorophenyl)-1-(1,6-dihydro-6-oxopyridazin-3-yl)-1H-pyrazole obtained in Example 26-5) in place of 4-(2-aminopyridin-4-yl)-3-(4-fluorophenyl)-1-([1,2,4]triazolo[4,3-b]pyridazin-6-yl)-1H-pyrazole, and using 31.5 mg (0.30 mmol) of cyclopropylcarbonyl chloride in place of acetic anhydride to obtain 18.5 mg of the title compound as a white powder. (Yield: 31%)

Rf value: 0.31 (chloroform:ethyl acetate:methanol=15:4:1).

Mass spectrum (CI, m/z): 417 ($M^+$+1).

$^1$H-NMR spectrum (DMSO-$d_6$, δ ppm): 0.75-0.78 (m, 4H), 1.92-1.99 (m, 1H), 6.91 (dd, $J_1$=5.2 Hz, $J_2$=1.6 Hz, 1H), 7.13 (d, J=10.0 Hz, 1H), 7.24-7.36 (m, 2H), 7.49-7.60 (m, 2H), 8.07 (d, J=0.7 Hz, 1H), 8.09 (d, J=10.0 Hz, 1H), 8.19 (dd, $J_1$=5.2 Hz, $J_2$=0.7 Hz, 1H), 8.80 (s, 1H), 10.80 (s, 1H), 13.12 (brs, 1H).

Example 37

4-(2-Aminopyridin-4-yl)-3-phenyl-1-([1,2,4]triazolo-[4,3-b]pyridazin-6-yl)-1H-pyrazole (Exemplary Compound No. 2-5)

37-1) 4-(2-t-Butoxycarbonylaminopyridin-4-yl)-3-phenyl-1-([1,2,4]triazolo[4,3-b]pyridazin-6-yl)-1H-pyrazole The reaction was carried out in the same manner as in Example 5 except for using 5.00 g (14.9 mmol) of 4-(2-t-butoxycarbonylaminopyridin-4-yl)-3-phenyl-1H-pyrazole obtained in Example 20-2) in place of 3-(4-fluorophenyl)-4-(pyridin-4-yl)-1H-pyrazole, and using 1.49 g (37.2 mmol) of sodium hydride (60% dispersed material in mineral oil) to obtain 6.28 g of the title compound as a pale beige powder. (Yield: 93%)

Rf value: 0.42 (chloroform:ethyl acetate:methanol=15:4:1).

Mass spectrum (CI, m/z): 455 ($M^+$+1).

$^1$H-NMR spectrum (DMSO-$d_6$, δ ppm): 1.44 (s, 9H), 6.91 (dd, $J_1$=5.2 Hz, $J_2$=1.5 Hz, 1H), 7.44-7.48 (m, 3H), 7.53-7.57 (m, 2H), 7.89 (dd, $J_1$=1.5 Hz, $J_2$=0.7 Hz, 1H), 8.14 (d, J=9.9 Hz, 1H), 8.20 (dd, $J_1$=5.2 Hz, $J_2$=0.7 Hz, 1H), 8.60 (dd, $J_1$=9.9 Hz, $J_2$=0.7 Hz, 1H), 8.98 (s, 1H), 9.71 (d, J=0.7 Hz, 1H), 9.82 (s, 1H).

37-2) 4-(2-Aminopyridin-4-yl)-3-phenyl-1-([1,2,4]triazolo-[4,3-b]pyridazin-6-yl)-1H-pyrazole To 50 ml of a n-butanol solution containing 4.00 g (8.80 mmol) of 4-(2-t-butoxycarbonylaminopyridin-4-yl)-3-phenyl-1-([1,2,4]triazolo[4,3-b]pyridazin-6-yl)-1H-pyrazole obtained in Example 37-1) was added 1.76 ml (33.0 mmol) of conc. sulfuric acid at 50° C. After the addition, the mixture was stirred at 80° C. for 3 hours.

After completion of the reaction, the reaction mixture was poured into 200 ml of water, and neutralized with 28% aqueous ammonia. Precipitated crude crystals were collected by filtration and the obtained filtered products were washed with 100 ml of a mixed solvent (diisopropyl ether:methanol=9:1 (V/V)) to obtain 2.58 g of the title compound as a pale beige powder. (Yield: 83%)

Rf value: 0.32 (chloroform:methanol=9:1).

Mass spectrum (CI, m/z): 355 ($M^+$+1).

$^1$H-NMR spectrum (DMSO-$d_6$, δ ppm): 5.95 (brs, 2H), 6.40-6.49 (m, 2H), 7.43-7.48 (m, 3H), 7.50-7.59 (m, 2H), 7.89 (dd, $J_1$=4.4 Hz, $J_2$=1.7 Hz, 1H), 8.12 (d, J=10.0 Hz, 1H), 8.59 (dd, $J_1$=10.0 Hz, $J_2$=0.7 Hz, 1H), 8.83 (s, 1H), 9.68 (d, J=0.7 Hz, 1H).

Example 38

4-(2-Aminopyridin-4-yl)-3-(3-fluorophenyl)-1-([1,2,4]triazolo[4,3-b]pyridazin-6-yl)-1H-pyrazole (Exemplary Compound No. 2-196)

38-1) 4-(2-t-Butoxycarbonylaminopyridin-4-yl)-3-(3-fluorophenyl)-1-([1,2,4]triazolo[4,3-b]pyridazin-6-yl)-1H-pyrazole The reaction was carried out in the same manner as in Example 5 except for using 5.00 g (14.1 mmol) of 4-(2-t-butoxycarbonylaminopyridin-4-yl)-3-(3-fluorophenyl)-1H-pyrazole obtained in Example 22-2) in place of 3-(4-fluorophenyl)-4-(pyridin-4-yl)-1H-pyrazole, and using 1.41 g (35.3 mmol) of sodium hydride (60% dispersed material in mineral oil) to obtain 6.13 g of the title compound as a white powder. (Yield: 92%)

Rf value: 0.48 (chloroform:ethyl acetate:methanol=15:4:1).

Mass spectrum (FAB, m/z): 473 ($M^+$+1).

$^1$H-NMR spectrum (DMSO-$d_6$, δ ppm): 1.44 (s, 9H), 6.99 (dd, $J_1$=5.2 Hz, $J_2$=1.5 Hz, 1H), 7.27-7.42 (m, 3H), 7.47-7.55 (m, 1H), 7.88 (dd, $J_1$=1.5 Hz, $J_2$=0.7 Hz, 1H), 8.16 (d, J=9.9 Hz, 1H), 8.23 (dd, $J_1$=5.2 Hz, $J_2$=0.7 Hz, 1H), 8.61 (dd, $J_1$=9.9 Hz, $J_2$=0.8 Hz, 1H), 9.02 (s, 1H), 9.72 (d, J=0.8 Hz, 1H), 9.84 (s, 1H).

38-2) 4-(2-Aminopyridin-4-yl)-3-(3-fluorophenyl)-1-([1,2,4]triazolo[4,3-b]pyridazin-6-yl)-1H-pyrazole The reaction was carried out in the same manner as in Example 37-2) except for using 4.00 g (8.47 mmol) of 4-(2-t-butoxycarbonylaminopyridin-4-yl)-3-(3-fluorophenyl)-1-([1,2,4]triazolo[4,3-b]pyridazin-6-yl)-1H-pyrazole obtained in Example 38-1) in place of 4-(2-t-butoxycarbonylaminopyridin-4-yl)-3-phenyl-1-([1,2,4]triazolo[4,3-b]pyridazin-6-yl)-1H-pyrazole to obtain 2.44 g of the title compound as a white powder. (Yield: 78%)

Rf value: 0.40 (chloroform:methanol=9:1).

Mass spectrum (CI, m/z): 373 ($M^+$+1).

$^1$H-NMR spectrum (DMSO-$d_6$, δ ppm): 5.99 (brs, 2H), 6.44-6.48 (m, 2H), 7.27-7.34 (m, 1H), 7.37-7.42 (m, 2H), 7.47-7.55 (m, 1H), 7.92 (d, J=5.1 Hz, 1H), 8.14 (d, J=10.0 Hz, 1H), 8.60 (d, J=10.0 Hz, 1H), 8.86 (s, 1H), 9.69 (s, 1H).

Example 39

4-(2-Aminopyridin-4-yl)-3-(4-chlorophenyl)-1-([1,2,4]triazolo[4,3-b]pyridazin-6-yl)-1H-pyrazole (Exemplary Compound No. 2-287)

39-1) 4-(2-t-Butoxycarbonylaminopyridin-4-yl)-3-(4-chlorophenyl)-1-([1,2,4]triazolo[4,3-b]pyridazin-6-yl)-1H-pyrazole The reaction was carried out in the same manner as in Example 5 except for using 3.00 g (8.09 mmol) of 4-(2-t-butoxycarbonylaminopyridin-4-yl)-3-(4-chlorophenyl)-1H-pyrazole obtained in Example 23-2) in place of 3-(4-fluorophenyl)-4-(pyridin-4-yl)-1H-pyrazole, and using 809 mg (20.2 mmol) of sodium hydride (60% dispersed material in mineral oil) to obtain 3.67 g of the title compound as a white powder. (Yield: 93%)

Rf value: 0.33 (chloroform:ethyl acetate:methanol=15:4:1).

Mass spectrum (FAB, m/z): 489 ($M^+$+1).

$^1$H-NMR spectrum (DMSO-$d_6$, δ ppm): 1.44 (s, 9H), 6.98 (dd, $J_1$=5.1 Hz, $J_2$=1.5 Hz, 1H), 7.51-7.58 (m, 4H), 7.85 (d, J=0.7 Hz, 1H), 8.13 (d, J=9.9 Hz, 1H), 8.22-8.23 (m, 1H), 8.60 (dd, $J_1$=9.9 Hz, $J_2$=0.8 Hz, 1H), 9.01 (s, 1H), 9.70 (d, J=0.8 Hz, 1H), 9.80 (s, 1H).

39-2) 4-(2-Aminopyridin-4-yl)-3-(4-chlorophenyl)-1-([1,2,4]triazolo[4,3-b]pyridazin-6-yl)-1H-pyrazole The reaction was carried out in the same manner as in Example 37-2) except for using 3.00 g (6.14 mmol) of 4-(2-t-butoxycarbonylaminopyridin-4-yl)-3-(4-chlorophenyl)-1-([1,2,4]triazolo[4,3-b]pyridazin-6-yl)-1H-pyrazole obtained in Example 39-1) in place of 4-(2-t-butoxycarbonylaminopyridin-4-yl)-3-phenyl-1-([1,2,4]triazolo[4,3-b]pyridazin-6-yl)-1H-pyrazole to obtain 1.83 g of the title compound as a white powder. (Yield: 77%)

Rf value: 0.44 (chloroform:methanol=9:1).

Mass spectrum (CI, m/z): 389 ($M^+$+1).

$^1$H-NMR spectrum (DMSO-$d_6$, δ ppm): 6.00 (brs, 2H), 6.41 (d, J=0.7 Hz, 1H), 6.46 (dd, $J_1$=5.1 Hz, $J_2$=1.5 Hz, 1H), 7.51-7.62 (m, 4H), 7.91-7.92 (m, 1H), 8.12 (d, J=10.0 Hz, 1H), 8.60 (dd, $J_1$=10.0 Hz, $J_2$=0.7 Hz, 1H), 8.85 (s, 1H), 9.69 (d, J=0.7 Hz, 1H).

Example 40

4-(2-Aminopyridin-4-yl)-3-(3,4-difluorophenyl)-1-([1,2,4]triazolo[4,3-b]pyridazin-6-yl)-1H-pyrazole (Exemplary Compound No. 2-476)

40-1) 4-(2-t-Butoxycarbonylaminopyridin-4-yl)-3-(3,4-difluorophenyl)-1-([1,2,4]triazolo[4,3-b]pyridazin-6-yl)-1H-pyrazole The reaction was carried out in the same manner as in Example 5 except for using 3.00 g (8.06 mmol) of 4-(2-t-butoxycarbonylaminopyridin-4-yl)-3-(3,4-difluorophenyl)-1H-pyrazole obtained in Example 24-3) in place of 3-(4-fluorophenyl)-4-(pyridin-4-yl)-1H-pyrazole, and using 806 mg (20.1 mmol) of sodium hydride (60% dispersed material in mineral oil) to obtain 3.33 g of the title compound as a pale beige powder. (Yield: 84%)

Rf value: 0.33 (chloroform:ethyl acetate:methanol=15:4:1).

Mass spectrum (FAB, m/z): 491 ($M^+$+1).

$^1$H-NMR spectrum (DMSO-$d_6$, δ ppm): 1.44 (s, 9H), 7.07 (dd, $J_1$=5.1 Hz, $J_2$=1.6 Hz, 1H), 7.33-7.37 (m, 1H), 7.49-7.67 (m, 2H), 7.82 (dd, $J_1$=1.6 Hz, $J_2$=0.7 Hz, 1H), 8.14 (d, J=10.0 Hz, 1H), 8.24 (dd, $J_1$=5.1 Hz, $J_2$=0.7 Hz, 1H), 8.61 (dd, $J_1$=10.0 Hz, $J_2$=0.7 Hz, 1H), 9.06 (s, 1H), 9.71 (d, J=0.7 Hz, 1H), 9.82 (s, 1H).

40-2) 4-(2-Aminopyridin-4-yl)-3-(3,4-difluorophenyl)-1-([1,2,4]triazolo[4,3-b]pyridazin-6-yl)-1H-pyrazole The reaction was carried out in the same manner as in Example 37-2) except for using 3.00 g (6.12 mmol) of 4-(2-t-butoxycarbonylaminopyridin-4-yl)-3-(3,4-difluorophenyl)-1-([1,2,4]triazolo[4,3-b]pyridazin-6-yl)-1H-pyrazole obtained in Example 40-1) in place of 4-(2-t-butoxycarbonylaminopyridin-4-yl)-3-phenyl-1-([1,2,4]triazolo[4,3-b]-pyridazin-6-yl)-1H-pyrazole to obtain 2.09 g of the title compound as a white powder. (Yield: 88%)

Rf value: 0.40 (chloroform:methanol=9:1).

Mass spectrum (CI, m/z): 391 ($M^+$+1).

¹H-NMR spectrum (DMSO-d₆, δ ppm): 5.99 (brs, 2H), 6.41 (s, 1H), 6.49 (dd, J₁=5.3 Hz, J₂=1.5 Hz, 1H), 7.36-7.39 (m, 1H), 7.50-7.67 (m, 2H), 7.93 (d, J=5.3 Hz, 1H), 8.14 (d, J=10.0 Hz, 1H), 8.60 (dd, J₁=10.0 Hz, J₂=0.7 Hz, 1H), 8.87 (s, 1H), 9.68 (d, J=0.7 Hz, 1H).

Example 41

4-(2-Aminopyridin-4-yl)-1-([1,2,4]triazolo[4,3-b]-pyridazin-6-yl)-3-(3-trifluoromethylphenyl)-1H-pyrazole (Exemplary Compound No. 2-764)

41-1) 4-(2-t-Butoxycarbonylaminopyridin-4-yl)-1-([1,2,4]-triazolo[4,3-b]pyridazin-6-yl)-3-(3-trifluoromethylphenyl)-1H-pyrazole The reaction was carried out in the same manner as in Example 5 except for using 2.00 g (4.95 mmol) of 4-(2-t-butoxycarbonylaminopyridin-4-yl)-3-(3-trifluoromethylphenyl)-1H-pyrazole obtained in Example 25-2) in place of 3-(4-fluorophenyl)-4-(pyridin-4-yl)-1H-pyrazole, and using 495 mg (12.4 mmol) of sodium hydride (60% dispersed material in mineral oil) to obtain 2.37 g of the title compound as a white powder. (Yield: 92%)
Rf value: 0.80 (chloroform:methanol=9:1).
Mass spectrum (CI, m/z): 523 (M⁺+1).
¹H-NMR spectrum (DMSO-d₆, δ ppm): 1.42 (s, 9H), 7.04 (dd, J₁=5.1 Hz, J₂=1.5 Hz, 1H), 7.71 (t, J=7.7 Hz, 1H), 7.82-7.88 (m, 4H), 8.18 (d, J=10.0 Hz, 1H), 8.24 (dd, J₁=5.1 Hz, J₂=0.7 Hz, 1H), 8.61 (dd, J₁=10.0 Hz, J₂=0.7 Hz, 1H), 9.06 (s, 1H), 9.71 (d, J=0.7 Hz, 1H), 9.81 (brs, 1H).

41-2) 4-(2-Aminopyridin-4-yl)-1-([1,2,4]triazolo[4,3-b]-pyridazin-6-yl)-3-(3-trifluoromethylphenyl)-1H-pyrazole The reaction was carried out in the same manner as in Example 37-2) except for using 2.35 g (4.50 mmol) of 4-(2-t-butoxycarbonylaminopyridin-4-yl)-1-([1,2,4]triazolo[4,3-b]pyridazin-6-yl)-3-(3-trifluoromethylphenyl)-1H-pyrazole obtained in Example 41-1) in place of 4-(2-t-butoxycarbonylaminopyridin-4-yl)-3-phenyl-1-([1,2,4]triazolo[4,3-b]-pyridazin-6-yl)-1H-pyrazole to obtain 1.25 g of the title compound as a white powder. (Yield: 66%)
Rf value: 0.50 (chloroform:methanol=9:1).
Mass spectrum (CI, m/z): 423 (M⁺+1).
¹H-NMR spectrum (DMSO-d₆, δ ppm): 5.99 (brs, 2H), 6.44 (m, 1H), 6.46 (dd, J₁=5.1 Hz, J₂=1.5 Hz, 1H), 7.70 (t, J=7.8 Hz, 1H), 7.81-7.86 (m, 2H), 7.91-7.93 (m, 2H), 8.17 (d, J=10.0 Hz, 1H), 8.60 (dd, J₁=10.0 Hz, J₂=0.7 Hz, 1H), 8.89 (s, 1H), 9.69 (d, J=0.7 Hz, 1H).

Example 42

4-(2-Aminopyridin-4-yl)-3-(2-fluorophenyl)-1-([1,2,4]triazolo[4,3-b]pyridazin-6-yl)-1H-pyrazole (Exemplary Compound No. 2-838)

42-1) 4-(2-t-Butoxycarbonylaminopyridin-4-yl)-3-(2-fluorophenyl)-1-([1,2,4]triazolo[4,3-b]pyridazin-6-yl)-1H-pyrazole The reaction was carried out in the same manner as in Example 5 except for using 5.00 g (14.1 mmol) of 4-(2-t-butoxycarbonylaminopyridin-4-yl)-3-(2-fluorophenyl)-1H-pyrazole obtained in Example 26-3) in place of 3-(4-fluorophenyl)-4-(pyridin-4-yl)-1H-pyrazole, and using 1.41 g (35.3 mmol) of sodium hydride (60% dispersed material in mineral oil) to obtain 6.35 g of the title compound as a pale beige powder. (Yield: 95%)
Rf value: 0.70 (chloroform:methanol=9:1).
Mass spectrum (CI, m/z): 473 (M⁺+1).
¹H-NMR spectrum (DMSO-d₆, δ ppm): 1.44 (s, 9H), 6.92 (dd, J₁=5.3 Hz, J₂=1.5 Hz, 1H), 7.28-7.40 (m, 2H), 7.54-7.66 (m, 2H), 7.82 (s, 1H), 8.09 (d, J=10.0 Hz, 1H), 8.16 (d, J=5.3 Hz, 1H), 8.60 (d, J=10.0 Hz, 1H), 9.13 (s, 1H), 9.73 (s, 1H), 9.75 (s, 1H).

42-2) 4-(2-Aminopyridin-4-yl)-3-(3-fluorophenyl)-1-([1,2,4]triazolo[4,3-b]pyridazin-6-yl)-1H-pyrazole The reaction was carried out in the same manner as in Example 37-2) except for using 4.00 g (8.47 mmol) of 4-(2-t-butoxycarbonylaminopyridin-4-yl)-3-(2-fluorophenyl)-1-([1,2,4]triazolo[4,3-b]pyridazin-6-yl)-1H-pyrazole obtained in Example 42-1) in place of 4-(2-t-butoxycarbonylaminopyridin-4-yl)-3-phenyl-1-([1,2,4]triazolo[4,3-b]pyridazin-6-yl)-1H-pyrazole to obtain 2.71 g of the title compound as a pale beige powder. (Yield: 86%)
Rf value: 0.36 (chloroform:methanol=9:1).
Mass spectrum (CI, m/z): 373 (M⁺+1).
¹H-NMR spectrum (DMSO-d₆, δ ppm): 5.88 (brs, 2H), 6.34-6.43 (m, 2H), 7.30-7.39 (m, 2H), 7.54-7.64 (m, 2H), 7.83 (dd, J₁=5.0 Hz, J₂=0.9 Hz, 1H), 8.07 (d, J=10.0 Hz, 1H), 8.58 (dd, J₁=10.0 Hz, J₂=0.7 Hz, 1H), 8.97 (s, 1H), 9.70 (s, 1H).

Example 43

4-(2-Cyclopropylcarbonylaminopyridin-4-yl)-3-(4-fluorophenyl)-1-([1,2,4]triazolo[4,3-b]pyridazin-6-yl)-1H-pyrazole (Exemplary Compound No. 2-970)

The reaction was carried out in the same manner as in Example 9 except for using 200 mg (0.54 mmol) of 4-(2-aminopyridin-4-yl)-3-(4-fluorophenyl)-1-([1,2,4]triazolo-[4,3-b]pyridazin-6-yl)-1H-pyrazole obtained by the same reaction as in Example 8-2), and using 59.0 mg (0.56 mmol) of cyclopropylcarbonyl chloride in place of acetic anhydride to obtain 88.6 mg of the title compound as a white powder. (Yield: 37%)
Rf value: 0.36 (chloroform:ethyl acetate:methanol=15:4:1).
Mass spectrum (CI, m/z): 441 (M⁺+1).
¹H-NMR spectrum (DMSO-d₆, δ ppm): 0.78-0.81 (m, 4H), 1.97-2.05 (m, 1H), 6.97 (dd, J₁=5.3 Hz, J₂=1.6 Hz, 1H), 7.26-7.34 (m, 2H), 7.55-7.61 (m, 2H), 8.12 (d, J=9.8 Hz, 1H), 8.17-8.18 (m, 1H), 8.28-8.31 (m, 1H), 8.60 (dd, J₁=9.8 Hz, J₂=0.8 Hz, 1H), 8.95 (s, 1H), 9.70 (d, J=0.8 Hz, 1H), 10.86 (s, 1H).

Example 44

4-{2-[(Cyclopropylcarbonyl)methylamino]pyridin-4-yl}-3-(4-fluorophenyl)-1-([1,2,4]triazolo[4,3-b]pyridazin-6-yl)-1H-pyrazole (Exemplary Compound No. 2-971)

The reaction was carried out in the same manner as in Example 9 except for using 100 mg (0.26 mmol) of 3-(4-fluorophenyl)-4-(2-methylaminopyridin-4-yl)-1-([1,2,4]triazolo[4,3-b]pyridazin-6-yl)-1H-pyrazole obtained in Example 13-2) in place of 4-(2-aminopyridin-4-yl)-3-(4-fluorophenyl)-1-([1,2,4]triazolo[4,3-b]pyridazin-6-yl)-1H- pyrazole, and using 81.2 mg (0.78 mmol) of cyclopropylcarbonyl chloride in place of acetic anhydride to obtain 93.8 mg of the title compound as a pale yellow-powder. (Yield: 80%)

Rf value: 0.33 (chloroform:ethyl acetate:methanol=15:4:1).

Mass spectrum (CI, m/z): 455 ($M^+$+1).

$^1$H-NMR spectrum (DMSO-$d_6$, δ ppm): 0.54-0.60 (m, 2H), 0.76-0.81 (m, 2H), 1.58-1.66 (m, 1H), 3.27 (s, 3H), 7.28-7.36 (m, 3H), 7.44 (d, J=0.7 Hz, 1H), 7.56-7.62 (m, 2H), 8.13 (d, J=9.8 Hz, 1H), 8.51 (d, J=6.1 Hz, 1H), 8.61 (dd, $J_1$=9.8 Hz, $J_2$=0.7 Hz, 1H), 9.15 (s, 1H), 9.69 (d, J=0.7 Hz, 1H).

Example 45

4-(2-Cyclopentylcarbonylaminopyridin-4-yl)-3-(4-fluorophenyl)-1-([1,2,4]triazolo[4,3-b]pyridazin-6-yl)-1H-pyrazole (Exemplary Compound No. 2-974)

The reaction was carried out in the same manner as in Example 9 except for using 2.00 g (5.37 mmol) of 4-(2-aminopyridin-4-yl)-3-(4-fluorophenyl)-1-([1,2,4]triazolo[4,3-b]pyridazin-6-yl)-1H-pyrazole obtained by the same reaction as in Example 8-2), and using 1.07 g (8.06 mmol) of cyclopentylcarbonyl chloride in place of acetic anhydride to obtain 219 mg of the title compound as a white powder. (Yield: 9%)

Rf value: 0.46 (chloroform:ethyl acetate:methanol=15:4:1).

Mass spectrum (CI, m/z): 469 ($M^+$+1).

$^1$H-NMR spectrum (DMSO-$d_6$, δ ppm): 1.51-1.87 (m, 8H), 2.91-2.96 (m, 1H), 6.97 (dd, $J_1$=5.2 Hz, $J_2$=1.7 Hz, 1H), 7.27-7.34 (m, 2H), 7.56-7.62 (m, 2H), 8.13 (d, J=10.0 Hz, 1H), 8.21-8.22 (m, 1H), 8.27 (dd, $J_1$=5.2 Hz, $J_2$=0.7 Hz, 1H), 8.60 (dd, $J_1$=10.0 Hz, $J_2$=0.8 Hz, 1H), 8.97 (s, 1H), 9.71 (d, $J_1$=0.8 Hz, 1H), 10.50 (s, 1H).

Example 46

4-(2-Aminopyridin-4-yl)-3-(4-fluorophenyl)-1-(3-methyl-[1,2,4]triazolo[4,3-b]pyridazin-6-yl)-1H-pyrazole (Exemplary Compound No. 2-129)

46-1) 4-(2-t-Butoxycarbonylaminopyridin-4-yl)-3-(4-fluorophenyl)-1-(3-methyl-[1,2,4]triazolo[4,3-b]pyridazin-6-yl)-1H-pyrazole The reaction was carried out in the same manner as in Example 5 except for using 325 mg (0.92 mmol) of 4-(2-t-butoxycarbonylaminopyridin-4-yl)-3-(4-fluorophenyl)-1H-pyrazole obtained by the same method as in Example 2-2) in place of 3-(4-fluorophenyl)-4-(pyridin-4-yl)-1H-pyrazole, 170 mg (1.01 mmol) of 6-chloro-3-methyl-[1,2,4]triazolo-[4,3-b]pyridazine (see S. Baloniak et al., Pol. J. Chem. 68(4), 683(1994)) in place of 6-chloro-[1,2,4]triazolo[4,3-b]pyridazine, and using 91.8 mg (2.30 mmol) of sodium hydride (60% dispersed material in mineral oil) to obtain 335 mg of the title compound as a pale yellow powder. (Yield: 75%)

Rf value: 0.49 (chloroform:methanol=9:1).

Mass spectrum (EI, m/z): 486 ($M^+$).

$^1$H-NMR spectrum (DMSO-$d_6$, δ ppm): 1.44 (s, 9H), 2.78 (s, 3H), 6.99 (dd, $J_1$=5.1 Hz, $J_2$=1.5 Hz, 1H), 7.26-7.32 (m, 2H), 7.55-7.60 (m, 2H), 7.84 (s, 1H), 8.07 (d, J=10.0 Hz, 1H), 8.23 (dd, $J_1$=5.1 Hz, $J_2$=0.7 Hz, 1H), 8.52 (d, J=10.0 Hz, 1H), 9.11 (s, 1H), 9.80 (s, 1H).

46-2) 4-(2-Aminopyridin-4-yl)-3-(4-fluorophenyl)-1-(3-methyl-[1,2,4]triazolo[4,3-b]pyridazin-6-yl)-1H-pyrazole To 300 mg (0.62 mmol) of 4-(2-t-butoxycarbonylaminopyridin-4-yl)-3-(4-fluorophenyl)-1-(3-methyl-[1,2,4]triazolo[4,3-b]pyridazin-6-yl)-1H-pyrazole obtained in Example 46-1) was added 3 ml of acetic acid, and the mixture was stirred at 80° C. for 5 hours.

After completion of the reaction, the reaction mixture was concentrated under reduced pressure, poured into 50 ml of water, and neutralized with 28% aqueous ammonia. The formed precipitates were collected by filtration, the obtained residue was applied to silica gel column chromatography (eluent; chloroform:methanol=14:1 (V/V)), and the separated fractions containing the objective compound were concentrated under reduced pressure. The obtained crude crystals were washed with 20 ml of diisopropyl ether to obtain 85.9 mg of the title compound as a pale yellow powder. (Yield: 36%)

Rf value: 0.30 (chloroform:methanol=9:1).

Mass spectrum (CI, m/z): 387 ($M^+$+1).

$^1$H-NMR spectrum (DMSO-$d_6$, δ ppm): 2.50 (s, 3H), 5.97 (brs, 2H), 6.44-6.47 (m, 2H), 7.27-7.35 (m, 2H), 7.58-7.65 (m, 2H), 7.91 (dd, $J_1$=5.1 Hz, $J_2$=1.0 Hz, 1H), 8.05 (d, J=10.0 Hz, 1H), 8.51 (d, J=10.0 Hz, 1H), 8.96 (s, 1H).

Example 47

4-(2-Aminopyridin-4-yl)-3-(4-fluorophenyl)-1-(3-trifluoromethyl-[1,2,4]triazolo[4,3-b]pyridazin-6-yl)-1H-pyrazole (Exemplary Compound No. 2-130)

47-1) 4-(2-t-Butoxycarbonylaminopyridin-4-yl)-3-(4-fluorophenyl)-1-(3-trifluoromethyl-[1,2,4]triazolo[4,3-b]-pyridazin-6-yl)-1H-pyrazole The reaction was carried out in the same manner as in Example 5 except for using 290 mg (0.82 mmol) of 4-(2-t-butoxycarbonylaminopyridin-4-yl)-3-(4-fluorophenyl)-1H-pyrazole obtained by the same reaction as in Example 2-2) in place of 3-(4-fluorophenyl)-4-(pyridin-4-yl)-1H-pyrazole, 200 mg (0.90 mmol) of 6-chloro-3-trifluoromethyl-(1,2,4]triazolo[4,3-b]pyridazine (see A. Pollak et al., Monatsh. Chem. 103, 1591(1972)) in place of 6-chloro-[1,2,4]triazolo[4,3-b]pyridazine, and using 81.7 mg (2.04 mmol) of sodium hydride (60% dispersed material in mineral oil) to obtain 235 mg of the title compound as a pale brown powder. (Yield: 53%)

Rf value: 0.68 (chloroform:methanol=9:1).

Mass spectrum (CI, m/z): 541 ($M^+$+1).

$^1$H-NMR spectrum (DMSO-$d_6$, δ ppm): 1.43 (s, 9H), 7.02 (dd, $J_1$=5.3 Hz, $J_2$=1.5 Hz, 1H), 7.28-7.34 (m, 2H), 7.56-7.61 (m, 2H), 7.81-7.82 (m, 1H), 8.24 (dd, $J_1$=5.3 Hz, $J_2$=0.7 Hz, 1H), 8.35 (d, J=10.0 Hz, 1H), 8.79 (d, J=10.0 Hz, 1H), 8.96 (s, 1H), 9.79 (s, 1H).

47-2) 4-(2-Aminopyridin-4-yl)-3-(4-fluorophenyl)-1-(3-trifluoromethyl-[1,2,4]triazolo[4,3-b]pyridazin-6-yl)-1H-pyrazole The reaction was carried out in the same manner as in Example 37-2) except for using 200 mg (0.37 mmol) of 4-(2-t-butoxycarbonylaminopyridin-4-yl)-3-(4-fluorophenyl)-1-(3-trifluoromethyl-[1,2,4]triazolo[4,3-b]pyridazin-6-yl)-1H-pyrazole obtained in Example 47-1) in place of 4-(2-t-butoxycarbonylaminopyridin-4-yl)-3-phenyl-1-([1,2, 4]triazolo[4,3-b]pyridazin-6-yl)-1H-pyrazole to obtain 115 mg of the title compound as a beige powder. (Yield: 71%)

Rf value: 0.32 (chloroform:methanol=9:1).

Mass spectrum (CI, m/z): 441 (M$^+$+1).

$^1$H-NMR spectrum (DMSO-d$_6$, δ ppm): 5.99 (brs, 2H), 6.43-6.46 (m, 2H), 7.29-7.35 (m, 2H), 7.60-7.65 (m, 2H), 7.91 (d, J=4.9 Hz, 1H), 8.33 (d, J=10.0 Hz, 1H), 8.76-8.79 (m, 2H).

Example 48

4-(2-Aminopyridin-4-yl)-1-(3-amino-[1,2,4]triazolo-[4,3-b]pyridazin-6-yl)-3-(4-fluorophenyl)-1H-pyrazole (Exemplary Compound No. 2-132)

48-1) 1-(3-Amino-[1,2,4]triazolo[4,3-b]pyridazin-6-yl)-4-(2-t-butoxycarbonylaminopyridin-4-yl)-3-(4-fluorophenyl)-1H-pyrazole The reaction was carried out in the same manner as in Example 5 except for using 210 mg (0.59 mmol) of 4-(2-t-butoxycarbonylaminopyridin-4-yl)-3-(4-fluorophenyl)-1H-pyrazole obtained by the same reaction as in Example 2-2) in place of 3-(4-fluorophenyl)-4-(pyridin-4-yl)-1H-pyrazole, 110 mg (0.65 mmol) of 3-amino-6-chloro-[1,2,4]-triazolo[4,3-b]pyridazine (see N. K. Baus et al., J. Chem. Soc. 5660(1963)) in place of 6-chloro-[1,2,4]triazolo[4,3-b]pyridazine, and using 49.7 mg (1.24 mmol) of sodium hydride (60% dispersed material in mineral oil) to obtain 115 mg of the title compound as a yellow powder. (Yield: 40%)

Rf value: 0.38 (chloroform:methanol=9:1).

Mass spectrum (FAB, m/z): 488 (M$^+$+1).

$^1$H-NMR spectrum (DMSO-d$_6$, δ ppm): 1.44 (s, 9H), 6.73 (brs, 2H), 6.90 (dd, J$_1$=5.1 Hz, J$_2$=1.5 Hz, 1H), 7.26-7.32 (m, 2H), 7.54-7.60 (m, 2H), 7.77 (d, J=10.0 Hz, 1H), 7.88 (dd, J$_1$=1.5 Hz, J$_2$=0.7 Hz, 1H), 8.23 (dd, J$_1$=5.1 Hz, J$_2$=0.7 Hz, 1H), 8.24 (d, J=10.0 Hz, 1H), 9.07 (s, 1H), 9.84 (s, 1H).

48-2) 4-(2-Aminopyridin-4-yl)-1-(3-amino-[1,2,4]triazolo-[4,3-b]pyridazin-6-yl)-3-(4-fluorophenyl)-1H-pyrazole The reaction was carried out in the same manner as in Example 37-2) except for using 40.0 mg (0.082 mmol) of 1-(3-amino-[1,2,4]triazolo[4,3-b]pyridazin-6-yl)-4-(2-t-butoxycarbonylaminopyridin-4-yl)-3-(4-fluorophenyl)-1H-pyrazole obtained in Example 48-1) in place of 4-(2-t-butoxycarbonylaminopyridin-4-yl)-3-phenyl-1-([1,2,4]triazolo[4,3-b]pyridazin-6-yl)-1H-pyrazole to obtain 18.0 mg of the title compound as a yellow powder. (Yield: 57%)

Rf value: 0.22 (chloroform:methanol=9:1).

Mass spectrum (CI, m/z): 388 (M$^+$+1).

$^1$H-NMR spectrum (DMSO-d$_6$, δ ppm): 5.99 (brs, 2H), 6.41-6.43 (m, 2H), 6.70 (brs, 2H), 7.27-7.34 (m, 2H), 7.58-7.63 (m, 2H), 7.76 (d, J=10.0 Hz, 1H), 7.92 (dd, J$_1$=5.1 Hz, J$_2$=0.7 Hz, 1H), 8.23 (d, J=10.0 Hz, 1H), 8.96 (s, 1H).

Example 49

4-(2-Aminopyridin-4-yl)-1-(1,4,5,6-tetrahydro-6-oxopyridazin-3-yl)-3-phenyl-1H-pyrazole (Exemplary Compound No. 3-2)

To 17 ml of an acetic acid solution containing 1.80 g (5.45 mmol) of 4-(2-aminopyridin-4-yl)-1-(1,6-dihydro-6-oxopyridazin-3-yl)-3-phenyl-1H-pyrazole obtained in Example 20-4) was added 792 mg (10.9 mmol) of zinc (90%) at room temperature under argon atmosphere. After the addition, the mixture was stirred at 60° C. for 1 hour.

After completion of the reaction, to the reaction solution was added 47 ml of a mixed solvent (chloroform:methanol=9:1 (V/V)), and after the formed insoluble material was filtered off, the filtrate was concentrated under reduced pressure. The obtained residue was applied to silica gel column chromatography (eluent; chloroform:methanol=9:1 (V/V)), and the separated fractions containing the objective compound were concentrated under reduced pressure. The obtained crude crystals were washed with 20 ml of a mixed solvent (diisopropyl ether:methanol=20:1 (V/V)) to obtain 1.03 g of the title compound as a white powder. (Yield: 57%)

Rf value: 0.41 (chloroform:methanol=9:1).

Mass spectrum (CI, m/z): 333 (M$^+$+1).

$^1$H-NMR spectrum (CDCl$_3$, δ ppm): 2.73 (t, J=8.3 Hz, 2H), 3.46 (t, J=8.3 Hz, 2H), 4.39 (brs, 2H), 6.42 (dd, J$_1$=1.5 Hz, J$_2$=0.7 Hz, 1H), 6.57 (dd, J$_1$=5.4 Hz, J$_2$=1.5 Hz, 1H), 7.36-7.40 (m, 3H), 7.51-7.54 (m, 2H), 8.01 (dd, J$_1$=5.4 Hz, J$_2$=0.7 Hz, 1H), 8.13 (brs, 1H), 8.31 (s, 1H).

Example 50

4-(2-Aminopyridin-4-yl)-3-(4-fluorophenyl)-1-(1,4,5,6-tetrahydro-6-oxopyridazin-3-yl)-1H-pyrazole (Exemplary Compound No. 3-69)

The reaction was carried out in the same manner as in Example 49 except for using 7.18 g (20.6 mmol) of 4-(2-aminopyridin-4-yl)-3-(4-fluorophenyl)-1-(1,6-dihydro-6-oxopyridazin-3-yl)-1H-pyrazole obtained by the same reaction as in Example 2-4) in place of 4-(2-aminopyridin-4-yl)-1-(1,6-dihydro-6-oxopyridazin-3-yl)-3-phenyl-1H-pyrazole to obtain 4.48 g of the title compound as a white powder. (Yield: 62%)

Rf value: 0.41 (chloroform:methanol=9:1).

Mass spectrum (CI, m/z): 351 (M$^+$+1).

$^1$H-NMR spectrum (CDCl$_3$, δ ppm): 2.73 (t, J=8.4 Hz, 2H), 3.45 (t, J=8.4 Hz, 2H), 4.51 (brs, 2H), 6.40 (dd, J$_1$=1.5 Hz, J$_2$=0.7 Hz, 1H), 6.55 (dd, J$_1$=5.4 Hz, J$_2$=1.5 Hz, 1H), 7.03-7.11 (m, 2H), 7.47-7.54 (m, 2H), 8.01 (dd, J$_1$=5.4 Hz, J$_2$=0.7 Hz, 1H), 8.17 (brs, 1H), 8.30 (s, 1H).

Example 51

4-(2-Aminopyridin-4-yl)-3-(3-fluorophenyl)-1-(1,4,5,6-tetrahydro-6-oxopyridazin-3-yl)-1H-pyrazole (Exemplary Compound No. 3-149)

The reaction was carried out in the same manner as in Example 49 except for using 300 mg (0.86 mmol) of 4-(2-aminopyridin-4-yl)-3-(3-fluorophenyl)-1-(1,6-dihydro-6-oxopyridazin-3-yl)-1H-pyrazole obtained in Example 22-4) in place of 4-(2-aminopyridin-4-yl)-1-(1,6-dihydro-6-oxopyridazin-3-yl)-3-phenyl-1H-pyrazole to obtain 207 mg of the title compound as a white powder. (Yield: 69%)

Rf value: 0.23 (chloroform:methanol=19:1).

Mass spectrum (CI, m/z): 351 (M$^+$+1).

$^1$H-NMR spectrum (CDCl$_3$+DMSO-d$_6$, δ ppm): 2.68 (t, J=8.4 Hz, 2H), 3.41 (t, J=8.4 Hz, 2H), 5.01 (brs, 2H), 6.46-6.49 (m, 2H), 7.02-7.09 (m, 1H), 7.26-7.37 (m, 3H), 7.97 (dd, J$_1$=5.1 Hz, J$_2$=0.7 Hz, 1H), 8.34 (s, 1H), 10.37 (brs, 1H)

Example 52

4-(2-Aminopyridin-4-yl)-3-(4-chlorophenyl)-1-(1,4,5,6-tetrahydro-6-oxopyridazin-3-yl)-1H-pyrazole (Exemplary Compound No. 3-212)

The reaction was carried out in the same manner as in Example 49 except for using 300 mg (0.82 mmol) of 4-(2-aminopyridin-4-yl)-3-(4-chlorophenyl)-1-(1,6-dihydro-6-oxopyridazin-3-yl)-1H-pyrazole obtained in Example 23-4) in place of 4-(2-aminopyridin-4-yl)-1-(1,6-dihydro-6-oxopyridazin-3-yl)-3-phenyl-1H-pyrazole to obtain 147 mg of the title compound as a white powder. (Yield: 49%).

Rf value: 0.26 (chloroform:methanol=19:1).

Mass spectrum (CI, m/z): 367 ($M^+$+1).

$^1$H-NMR spectrum (CDCl$_3$, δ ppm): 2.73 (t, J=8.3 Hz, 2H), 3.45 (t, J=8.3 Hz, 2H), 4.43 (brs, 2H), 6.40 (dd, $J_1$=1.5 Hz, $J_2$=0.7 Hz, 1H), 6.55 (dd, $J_1$=5.1 Hz, $J_2$=1.5 Hz, 1H), 7.32-7.37 (m, 2H), 7.45-7.49 (m, 2H), 8.03 (dd, $J_1$=5.1 Hz, $J_2$=0.7 Hz, 1H), 8.16 (brs, 1H), 8.30 (s, 1H).

Example 53

4-(2-Aminopyridin-4-yl)-3-(3,4-difluorophenyl)-1-(1,4,5,6-tetrahydro-6-oxopyridazin-3-yl)-1H-pyrazole (Exemplary Compound No. 3-343)

The reaction was carried out in the same manner as in Example 49 except for using 300 mg (0.82 mmol) of 4-(2-aminopyridin-4-yl)-3-(3,4-difluorophenyl)-1-(1,6-dihydro-6-oxopyridazin-3-yl)-1H-pyrazole obtained in Example 24-5) in place of 4-(2-aminopyridin-4-yl)-1-(1,6-dihydro-6-oxopyridazin-3-yl)-3-phenyl-1H-pyrazole to obtain 198 mg of the title compound as a white powder. (Yield: 66%)

Rf value: 0.26 (chloroform:methanol=19:1).

Mass spectrum (CI, m/z): 369 ($M^+$+1).

$^1$H-NMR spectrum (CDCl$_3$, δ ppm): 2.74 (t, J=8.4 Hz, 2H), 3.44 (t, J=8.4 Hz, 2H), 4.49 (brs, 2H), 6.41 (dd, $J_1$=1.4 Hz, $J_2$=0.7 Hz, 1H), 6.54 (dd, $J_1$=5.4 Hz, $J_2$=1.4 Hz, 1H), 7.10-7.26 (m, 2H), 7.41 (ddd, $J_1$=11.2 Hz, $J_2$=7.7 Hz, $J_3$=2.1 Hz, 1H), 8.04 (dd, $J_1$=5.4 Hz, $J_2$=0.7 Hz, 1H), 8.16 (brs, 1H), 8.29 (s, 1H)

Example 54

4-(2-Aminopyridin-4-yl)-1-(1,4,5,6-tetrahydro-6-oxopyridazin-3-yl)-3-(3-trifluoromethylphenyl)-1H-pyrazole (Exemplary Compound No. 3-538)

The reaction was carried out in the same manner as in Example 49 except for using 797 mg (2.00 mmol) of 4-(2-aminopyridin-4-yl)-1-(1,6-dihydro-6-oxopyridazin-3-yl)-3-(3-trifluoromethylphenyl)-1H-pyrazole obtained in Example 25-4) in place of 4-(2-aminopyridin-4-yl)-1-(1,6-dihydro-6-oxopyridazin-3-yl)-3-phenyl-1H-pyrazole to obtain 387 mg of the title compound as a white powder. (Yield: 48%)

Rf value: 0.50 (chloroform:methanol=9:1).

Mass spectrum (CI, m/z): 401 ($M^+$+1).

$^1$H-NMR spectrum (CDCl$_3$+DMSO-d$_6$, δ ppm): 2.70 (t, J=8.4 Hz, 2H), 3.43 (t, J=8.4 Hz, 2H), 5.34 (brs, 2H), 6.48-6.50 (m, 2H), 7.47-7.52 (m, 1H), 7.62-7.68 (m, 2H), 7.89 (s, 1H), 7.98 (dd, $J_1$=5.4 Hz, $J_2$=1.0 Hz, 1H), 8.39 (s, 1H), 10.10 (brs, 1H).

Example 55

4-(2-Aminopyridin-4-yl)-3-(2-fluorophenyl)-1-(1,4,5,6-tetrahydro-6-oxopyridazin-3-yl)-1H-pyrazole (Exemplary Compound No. 3-597)

The reaction was carried out in the same manner as in Example 49 except for using 1.40 g (4.02 mmol) of 4-(2-aminopyridin-4-yl)-3-(2-fluorophenyl)-1-(1,6-dihydro-6-oxopyridazin-3-yl)-1H-pyrazole obtained in Example 26-5) in place of 4-(2-aminopyridin-4-yl)-1-(1,6-dihydro-6-oxopyridazin-3-yl)-3-phenyl-1H-pyrazole to obtain 540 mg of the title compound as a white powder. (Yield: 38%)

Rf value: 0.50 (chloroform:methanol=9:1).

Mass spectrum (CI, m/z): 351 ($M^+$+1).

$^1$H-NMR spectrum (DMSO-d$_6$, δ ppm): 2.60 (t, J=8.3 Hz, 2H), 3.29 (t, J=8.3 Hz, 2H), 5.80 (brs, 2H), 6.30-6.32 (m, 2H), 7.24-7.34 (m, 2H), 7.48-7.56 (m, 2H), 7.78 (dd, $J_1$=5.0 Hz, $J_2$=1.1 Hz, 1H), 8.58 (s, 1H), 10.79 (brs, 1H)

Example 56

3-(4-Fluorophenyl)-1(1,4,5,6-tetrahydro-6-oxopyridazin-3-yl)-4-[2-(2,2,2-trifluoroethyl)aminopyridin-4-yl]-1H-pyrazole (Exemplary Compound No. 3-74)

The reaction was carried out in the same manner as in Example 49 except for using 200 mg (0.47 mmol) of 3-(4-fluorophenyl)-1-(1,6-dihydro-6-oxopyridazin-3-yl)-4-[2-(2,2,2-trifluoroethyl)aminopyridin-4-yl]-1H-pyrazole obtained in Example 28-2) in place of 4-(2-aminopyridin-4-yl)-1(1,6-dihydro-6-oxopyridazin-3-yl)-3-phenyl-1H-pyrazole to obtain 130 mg of the title compound as a white powder. (Yield: 65%)

Rf value: 0.43 (chloroform:methanol=19:1).

Mass spectrum (CI, m/z): 433 ($M^+$+1).

$^1$H-NMR spectrum (CDCl$_3$, δ ppm): 2.74 (t, J=8.3 Hz, 2H), 3.45 (t, J=8.3 Hz, 2H), 4.07 (qd, $J_1$=9.1 Hz, $J_2$=6.9 Hz, 2H), 4.61 (t, J=6.9 Hz, 1H), 6.39 (dd, $J_1$=1.5 Hz, $J_2$=0.7 Hz, 1H), 6.59 (dd, $J_1$=5.4 Hz, $J_2$=1.5 Hz, 1H), 7.03-7.11 (m, 2H), 7.46-7.52 (m, 2H), 8.08 (dd, $J_1$=5.4 Hz, $J_2$=0.7 Hz, 1H), 8.15 (s, 1H), 8.31 (s, 1H).

Example 57

4-(2-Acetylaminopyridin-4-yl)-3-(4-fluorophenyl)-1-(1,4,5,6-tetrahydro-6-oxopyridazin-3-yl)-1H-pyrazole (Exemplary Compound No. 3-77)

The reaction was carried out in the same manner as in Example 9 except for using 150 mg (0.43 mmol) of 4-(2-aminopyridin-4-yl)-3-(4-fluorophenyl)-1(1,4,5,6-tetrahydro-6-oxopyridazin-3-yl)-1H-pyrazole obtained in Example 50 in place of 4-(2-aminopyridin-4-yl)-3-(4-fluorophenyl)-1-([1,2,4]triazolo[4,3-b]pyridazin-6-yl)-1H-pyrazole to obtain 119 mg of the title compound as a white powder. (Yield: 71%)

Rf value: 0.30 (chloroform:methanol=19:1).

Mass spectrum (CI, m/z): 393 ($M^+$+1).

$^1$H-NMR spectrum (CDCl$_3$+DMSO-d$_6$, δ ppm): 2.15 (s, 3H), 2.66 (t, J=8.4 Hz, 2H), 3.39 (t, J=8.4 Hz, 2H), 6.83 (dd, $J_1$=5.4 Hz, $J_2$=1.5 Hz, 1H), 7.04-7.10 (m, 2H), 7.47-7.52 (m, 2H), 8.17-8.18 (m, 2H), 8.42 (s, 1H), 10.16 (s, 1H), 10.60 (s, 1H).

Example 58

4-(2-Aminopyridin-4-yl)-3-(4-fluorophenyl)-1-(1,4,5,6-tetrahydro-4-methyl-6-oxopyridazin-3-yl)-1H-pyrazole (Exemplary Compound No. 3-90)

The reaction was carried out in the same manner as in Example 49 except for using 100 mg (0.28 mmol) of 4-(2-aminopyridin-4-yl)-3-(4-fluorophenyl)-1-(1,6-dihydro-4-methyl-6-oxopyridazin-3-yl)-1H-pyrazole obtained in Example 31-2) in place of 4-(2-aminopyridin-4-yl)-1-(1,6-dihydro-6-oxopyridazin-3-yl)-3-phenyl-1H-pyrazole to obtain 48.0 mg of the title compound as a white powder. (Yield: 48%)

Rf value: 0.24 (chloroform:methanol=19:1).

Mass spectrum (CI, m/z): 365 ($M^+$+1).

$^1$H-NMR spectrum (CDCl$_3$, δ ppm): 1.39 (d, J=7.3 Hz, 3H), 2.55 (d, J=17.0 Hz, 1H), 2.86 (dd, $J_1$=17.0 Hz, $J_2$=7.4 Hz, 1H), 3.99-4.09 (m, 1H), 4.43 (brs, 2H), 6.40 (dd, $J_1$=1.5 Hz, $J_2$=0.8 Hz, 1H), 6.55 (dd, $J_1$=5.2 Hz, $J_2$=1.5 Hz, 1H), 7.03-7.11 (m, 2H), 7.48-7.54 (m, 2H), 8.03 (dd, $J_1$=5.2 Hz, $J_2$=0.8 Hz, 1H), 8.23 (brs, 1H), 8.27 (s, 1H).

Example 59

4-(2-Aminopyridin-4-yl)-3-(4-fluorophenyl)-1-(1,4,5,6-tetrahydro-5-methyl-6-oxopyridazin-3-yl)-1H-pyrazole (Exemplary Compound No. 3-91)

The reaction was carried out in the same manner as in Example 49 except for using 100 mg (0.28 mmol) of 4-(2-aminopyridin-4-yl)-3-(4-fluorophenyl)-1-(1,6-dihydro-5-methyl-6-oxopyridazin-3-yl)-1H-pyrazole obtained in Example 32-2) in place of 4-(2-aminopyridin-4-yl)-1-(1,6-dihydro-6-oxopyridazin-3-yl)-3-phenyl-1H-pyrazole to obtain 51.9 mg of the title compound as a white powder. (Yield: 51%)

Rf value: 0.29 (chloroform:methanol=19:1).

Mass spectrum (CI, m/z): 365 ($M^+$+1).

$^1$H-NMR spectrum (DMSO-d$_6$, δ ppm): 1.19 (d, J=6.8 Hz, 3H), 2.66-2.75 (m, 1H), 2.93 (dd, $J_1$=17.2 Hz, $J_2$=12.2 Hz, 1H), 3.56 (dd, $J_1$=17.2 Hz, $J_2$=7.0 Hz, 1H), 5.89 (brs, 2H), 6.36 (s, 1H), 6.40 (d, J=5.2 Hz, 1H), 7.23-7.29 (m, 2H), 7.49-7.53 (m, 2H), 7.86 (d, J=5.2 Hz, 1H), 8.46 (s, 1H), 10.77 (brs, 1H).

Example 60

4-(2-Aminopyridin-4-yl)-3-(4-fluorophenyl)-1-(1,4,5,6-tetrahydro-1-methyl-6-oxopyridazin-3-yl)-1H-pyrazole (Exemplary Compound No. 3-100)

The reaction was carried out in the same manner as in Example 33 except for using 100 mg (0.29 mmol) of 4-(2-aminopyridin-4-yl)-3-(4-fluorophenyl)-1-(1,4,5,6-tetrahydro-6-oxopyridazin-3-yl)-1H-pyrazole obtained in Example 50 in place of 4-(2-aminopyridin-4-yl)-3-(4-fluorophenyl)-1-(1,6-dihydro-6-oxopyridazin-3-yl)-1H-pyrazole, and using 3 ml of N,N-dimethylformamide as a solvent in place of tetrahydrofuran to obtain 39.5 mg of the title compound as a white powder. (Yield: 38%)

Rf value: 0.27 (chloroform:ethyl acetate:methanol=10:10:1).

Mass spectrum (CI, m/z): 365 ($M^+$+1).

$^1$H-NMR spectrum (CDCl$_3$, δ ppm): 2.71 (t, J=8.4 Hz, 2H), 3.38-3.44 (m, 5H), 4.43 (brs, 2H), 6.42 (dd, $J_1$=1.5 Hz, $J_2$=0.7 Hz, 1H), 6.57 (dd, $J_1$=5.4 Hz, $J_2$=1.5 Hz, 1H), 7.03-7.10 (m, 2H), 7.47-7.54 (m, 2H), 8.02 (dd, $J_1$=5.4 Hz, $J_2$=0.7 Hz, 1H), 8.36 (s, 1H).

Example 61

3-(2-Fluorophenyl)-1-(1,4,5,6-tetrahydro-6-oxopyridazin-3-yl)-4-[2-(2,2,2-trifluoroethyl)aminopyridin-4-yl]-1H-pyrazole (Exemplary Compound No. 3-602)

The reaction was carried out in the same manner as in Example 49 except for using 243 mg (0.57 mmol) of 3-(2-fluorophenyl)-1-(1,6-dihydro-6-oxopyridazin-3-yl)-4-[2-(2,2,2-trifluoroethyl)aminopyridin-4-yl]-1H-pyrazole obtained in Example 34-2) in place of 4-(2-aminopyridin-4-yl)-1-(1,6-dihydro-6-oxopyridazin-3-yl)-3-phenyl-1H-pyrazole to obtain 155 mg of the title compound as a beige powder. (Yield: 64%)

Rf value: 0.49 (chloroform:methanol=9:1).

Mass spectrum (CI, m/z): 433 ($M^+$+1).

$^1$H-NMR spectrum (DMSO-d$_6$, δ ppm): 2.60 (t, J=8.4 Hz, 2H), 3.29 (t, J=8.4 Hz, 2H), 4.02-4.14 (m, 2H), 6.46 (dd, $J_1$=5.4 Hz, $J_2$=1.5 Hz, 1H), 6.51 (s, 1H), 7.03 (t, J=6.6 Hz, 1H), 7.25-7.35 (m, 2H), 7.50-7.57 (m, 2H), 7.90 (d, J=5.4 Hz, 1H), 8.66 (s, 1H), 10.81 (s, 1H).

Example 62

4-(2-Acetylaminopyridin-4-yl)-3-(2-fluorophenyl)-1-(1,4,5,6-tetrahydro-6-oxopyridazin-3-yl)-1H-pyrazole (Exemplary Compound No. 3-605)

The reaction was carried out in the same manner as in Example 9 except for using 46.7 mg (0.13 mmol) of 4-(2-aminopyridin-4-yl)-3-(2-fluorophenyl)-1-(1,4,5,6-tetra-hydro-6-oxopyridazin-3-yl)-1H-pyrazole obtained in Example 55 in place of 4-(2-aminopyridin-4-yl)-3-(4-fluorophenyl)-1-([1,2,4]triazolo[4,3-b]pyridazin-6-yl)-1H-pyrazole to obtain 9.2 mg of the title compound as a white powder. (Yield: 18%)

Rf value: 0.41 (chloroform:methanol=19:1).

Mass spectrum (CI, m/z): 393 ($M^+$+1).

$^1$H-NMR spectrum (DMSO-d$_6$, δ ppm): 2.02 (s, 3H), 2.61 (t, J=8.4 Hz, 2H), 3.30 (t, J=8.4 Hz, 2H), 6.97 (dd, $J_1$=5.2 Hz, $J_2$=1.6 Hz, 1H), 7.22-7.35 (m, 2H), 7.49-7.56 (m, 2H), 8.00 (s, 1H), 8.18 (dd, $J_1$=5.2 Hz, $J_2$=0.7 Hz, 1H), 8.71 (s, 1H), 10.39 (brs, 1H), 10.82 (brs, 1H).

Example 63

4-(2-Cyclopropylcarbonylaminopyridin-4-yl)-1-(1,4,5,6-tetrahydro-6-oxopyridazin-3-yl)-3-phenyl-1H-pyrazole (Exemplary Compound No. 3-690)

The reaction was carried out in the same manner as in Example 9 except for using 56.0 mg (0.17 mmol) of 4-(2-aminopyridin-4-yl)-1-(1,4,5,6-tetrahydro-6-oxopyridazin-3-yl)-3-phenyl-1H-pyrazole obtained in Example 49 in place of 4-(2-aminopyridin-4-yl)-3-(4-fluorophenyl)-1-([1,2,4]triazolo[4,3-b]pyridazin-6-yl)-1H-pyrazole, and using 19.3 mg (0.19 mmol) of cyclopropylcarbonyl chloride in place of acetic anhydride to obtain 55.0 mg of the title compound as a white powder. (Yield: 82%)

Rf value: 0.55 (chloroform:methanol=9:1).

Mass spectrum (CI, m/z): 401 ($M^+$+1).

$^1$H-NMR spectrum (CDCl$_3$+DMSO-d$_6$, δ ppm): 0.82-0.88 (m, 2H), 1.00-1.05 (m, 2H), 1.81-1.86 (m, 1H), 2.68 (t, J=8.4 Hz, 2H), 3.42 (t, J=8.4 Hz, 2H), 6.77 (dd, $J_1$=5.2 Hz, J$_2$=1.6 Hz, 1H), 7.33-7.38 (m, 3H), 7.48-7.51 (m, 2H), 8.12 (dd, J$_1$=5.2 Hz, J$_2$=0.9 Hz, 1H), 8.29 (s, 1H), 8.43 (s, 1H), 9.64 (brs, 1H), 9.88 (s, 1H).

Example 64

4-(2-Cyclopropylcarbonylaminopyridin-4-yl)-3-(4-fluorophenyl)-1-(1,4,5,6-tetrahydro-6-oxopyridazin-3-yl)-1H-pyrazole (Exemplary Compound No. 3-694)

The reaction was carried out in the same manner as in Example 9 except for using 27.0 mg (0.077 mmol) of 4-(2-aminopyridin-4-yl)-3-(4-fluorophenyl)-1-(1,4,5,6-tetrahydro-6-oxopyridazin-3-yl)-1H-pyrazole obtained in Example 50 in place of 4-(2-aminopyridin-4-yl)-3-(4-fluorophenyl)-1-([1,2,4]triazolo[4,3-b]pyridazin-6-yl)-1H-pyrazole, and using 8.9 mg (0.085 mmol) of cyclopropylcarbonyl chloride in place of acetic anhydride to obtain 14.6 mg of the title compound as a white powder. (Yield: 45%)
Rf value: 0.49 (chloroform:methanol=9:1).
Mass spectrum (CI, m/z): 419 (M$^+$+1).
$^1$H-NMR spectrum (CDCl$_3$+DMSO-d$_6$, δ ppm): 0.79-0.82 (m, 2H), 0.91-0.94 (m, 2H), 1.95-2.01 (m, 1H), 2.65 (t, J=8.4 Hz, 2H), 3.38 (t, J=8.4 Hz, 2H), 6.79 (dd, J$_1$=5.4 Hz, J$_2$=1.5 Hz, 1H), 7.04-7.10 (m, 2H), 7.47-7.52 (m, 2H), 8.16 (d, J=5.4 Hz, 1H), 8.22 (s, 1H), 8.41 (s, 1H), 10.48 (brs, 1H), 10.62 (brs, 1H).

Example 65

4-(2-Cyclopropylcarbonylaminopyridin-4-yl)-3-(2-fluorophenyl)-1-(1,4,5,6-tetrahydro-6-oxopyridazin-3-yl)-1H-pyrazole (Exemplary Compound No. 3-731)

The reaction was carried out in the same manner as in Example 9 except for using 50.0 mg (0.14 mmol) of 4-(2-aminopyridin-4-yl)-3-(2-fluorophenyl)-1-(1,4,5,6-tetrahydro-6-oxopyridazin-3-yl)-1H-pyrazole obtained in Example 55 in place of 4-(2-aminopyridin-4-yl)-3-(4-fluorophenyl)-1-([1,2,4]triazolo[4,3-b]pyridazin-6-yl)-1H-pyrazole, and using 15.7 mg (0.15 mmol) of cyclopropylcarbonyl chloride in place of acetic anhydride to obtain 41.9 mg of the title compound as a white powder. (Yield: 70%)
Rf value: 0.34 (chloroform:ethyl acetate:methanol=15:4:1).
Mass spectrum (CI, m/z): 419 (M$^+$+1).
$^1$H-NMR spectrum (CDCl$_3$+DMSO-d$_6$, δ ppm): 0.75-0.82 (m, 2H), 0.88-0.93 (m, 2H), 1.93-2.00 (m, 1H), 2.65 (t, J=8.4 Hz, 2H), 3.36 (t, J=8.4 Hz, 2H), 6.69 (dd, J$_1$=5.2 Hz, J$_2$=1.6 Hz, 1H), 7.09-7.15 (m, 1H), 7.24-7.29 (m, 2H), 7.42-7.54 (m, 2H), 8.09 (dd, J$_1$=5.2 Hz, J$_2$=0.6 Hz, 1H), 8.18-8.20 (m, 1H), 8.54 (s, 1H), 10.47 (s, 1H), 10.69 (s, 1H).

Example 66

3-(4-Fluorophenyl)-4-(2-methylthiopyrimidin-4-yl)-1-([1,2,4]triazolo[4,3-b]pyridazin-6-yl)-1H-pyrazole (Exemplary Compound No. 2-1033)

66-1) 3-Dimethylamino-1-(4-fluorophenyl)-2-(2-methylthiopyrimidin-4-yl)-2-propen-1-one The reaction was carried out in the same manner as in Example 2-1) except for using 3.41 g (13.0 mmol) of 1-(4-fluorophenyl)-2-(methylthiopyrimidin-4-yl)ethane-1-one (see WO 9856788 publication) in place of 2-(2-t-butoxycarbonylaminopyridin-4-yl)-1-(4-fluorophenyl)ethane-1-one to obtain 4.13 g of the title compound as a yellow oil. (Yield: quantitative)
Rf value: 0.21 (ethyl acetate:hexane=1:1).
Mass spectrum (CI, m/z): 318 (M$^+$+1).
$^1$H-NMR spectrum (DMSO-d$_6$, δ ppm): 2.22 (s, 3H), 2.90 (brs, 6H), 6.80 (d, J=5.6 Hz, 1H), 7.16-7.28 (m, 2H), 7.61-7.63 (m, 2H), 7.73 (s, 1H), 8.17 (d, J=5.6 Hz, 1H).

66-2) 3-(4-Fluorophenyl)-4-(2-methylthiopyrimidin-4-yl)-1H-pyrazole

The reaction was carried out in the same manner as in Example 2-2) except for using 4.13 g (13.0 mmol) of 3-dimethylamino-1-(4-fluorophenyl)-2-(2-methylthiopyrimidin-4-yl)-2-propen-1-one obtained in Example 66-1) in place of 2-(2-t-butoxycarbonylaminopyridin-4-yl)-3-dimethylamino-1-(4-fluorophenyl)-2-propen-1-one to obtain 3.44 g of the title compound as a white powder. (Yield: 93%)
Rf value: 0.34 (ethyl acetate:hexane=1:1).
Mass spectrum (CI, m/z): 287 (M$^+$+1).
$^1$H-NMR spectrum (DMSO-d$_6$, δ ppm): 2.23 (s, 3H), 7.14 (d, J=5.4 Hz, 1H), 7.25-7.32 (m, 2H), 7.52-7.59 (m, 2H), 8.36 (s, 1H), 8.44 (d, J=5.4 Hz, 1H), 13.53 (brs, 1H).

66-3) 3-(4-Fluorophenyl)-4-(2-methylthiopyrimidin-4-yl)-1-([1,2,4]triazolo[4,3-b]pyridazin-6-yl)-1H-pyrazole The reaction was carried out in the same manner as in Example 1-3) except for using 1.00 g (3.50 mmol) of 3-(4-fluorophenyl)-4-(2-methylthiopyrimidin-4-yl)-1H-pyrazole obtained in Example 66-2) in place of 3-(4-fluorophenyl)-4-(pyridin-4-yl)-1H-pyrazole to obtain 1.11 g of the title compound as a white powder. (Yield: 78%)
Rf value: 0.36 (chloroform:ethyl acetate:methanol=15:4:1).
Mass spectrum (CI, m/z): 405 (M$^+$+1).
$^1$H-NMR spectrum (DMSO-d$_6$, δ ppm): 2.24 (s, 3H), 7.29-7.41 (m, 3H), 7.64-7.71 (m, 2H), 8.12 (d, J=9.8 Hz, 1H), 8.59-8.64 (m, 2H), 9.34 (s, 1H), 9.72 (d, J=0.7 Hz, 1H).

Example 67

3-(4-Fluorophenyl)-4-(2-methylsulfinylpyrimidin-4-yl)-1-([1,2,4]triazolo[4,3-b]pyridazin-6-yl)-1H-pyrazole (Exemplary Compound No. 2-1034) and 3-(4-fluorophenyl)-4-(2-methylsulfonylpyrimidin-4-yl)-1-([1,2,4]triazolo[4,3-b]pyridazin-6-yl)-1H-pyrazole (Exemplary Compound No. 2-1035)

In 110 ml of a mixed solvent (chloroform:methanol:water=7:7:1 (V/V/V)) was dissolved 1.00 g (2.47 mmol) of 3-(4-fluorophenyl)-4-(2-methylthiopyrimidin-4-yl)-1-([1,2,4]-triazolo[4,3-b]pyridazin-6-yl)-1H-pyrazole obtained in Example 66-3), and 1.52 g (2.47 mmol) of OXONE was added to the mixture at room temperature. After completion of the addition, the mixture was stirred at the same temperature for 2 hours.

After completion of the reaction, 400 ml of chloroform was added to the reaction mixture and the mixture was filtered, and the obtained filtrate was successively washed with 300 ml of water, and then, 300 ml of an aqueous saturated sodium chloride solution. The organic layer was dried over anhydrous magnesium sulfate, concentrated under reduced pressure and the obtained crude crystals were applied to silica gel column chromatography (eluent; chloroform:ethyl acetate:methanol=15:4:1 (V/V/V)). Fractions containing firstly eluted 3-(4-fluorophenyl)-4-(2-methylsulfonylpyrimidin-4-yl)-1-([1,2,4]triazolo[4,3-b]pyridazin-6-yl)-1H-pyrazole were concentrated under reduced pressure to obtain 84.3 mg of Exemplary compound 2-1035 as a white powder (Yield: 8%). Moreover, fractions containing latter eluted 3-(4-fluorophenyl)-4-(2-methylsulfonylpyrimidin-4-yl)-1-([1,2,4]triazolo[4,3-b]pyridazin-6-yl)-1H-pyrazole were concentrated under reduced pressure to obtain 740 mg of Exemplary compound 2-1034 as a white powder (Yield: 71%).

3-(4-Fluorophenyl)-4-(2-methylsulfonylpyrimidin-4-yl)-1-([1,2,4]triazolo[4,3-b]pyridazin-6-yl)-1H-pyrazole Rf value: 0.17 (chloroform:ethyl acetate:methanol=15:4:1).

Mass spectrum (CI, m/z): 421 ($M^++1$)

$^1$H-NMR spectrum (DMSO-$d_6$, δ ppm): 2.75 (s, 3H), 7.29-7.37 (m, 2H), 7.73-7.80 (m, 3H), 8.13 (d, J=9.9 Hz, 1H), 8.63 (dd, $J_1$=9.9 Hz, $J_2$=0.7 Hz, 1H), 8.96 (d, J=5.4 Hz, 1H), 9.45 (s, 1H), 9.74 (d, J=0.7 Hz, 1H).

3-(4-Fluorophenyl)-4-(2-methylsulfonylpyrimidin-4-yl)-1-([1,2,4]triazolo[4,3-b]pyridazin-6-yl)-1H-pyrazole Rf value: 0.33 (chloroform:ethyl acetate:methanol=15:4:1).

Mass spectrum (CI, m/z): 437 ($M^++1$)

$^1$H-NMR spectrum (DMSO-$d_6$, δ ppm): 3.15 (s, 3H), 7.29-7.36 (m, 2H), 7.73-7.78 (m, 2H), 8.03 (d, J=5.2 Hz, 1H), 8.13 (d, J=9.9 Hz, 1H), 8.64 (dd, $J_1$=9.9 Hz, $J_2$=0.7 Hz, 1H), 9.04 (d, J=5.2 Hz, 1H), 9.55 (s, 1H), 9.74 (d, J=0.7 Hz, 1H).

Example 68

3-(4-Fluorophenyl)-4-[2-(4-methoxybenzylamino)pyrimidin-4-yl]-1-([1,2,4]triazolo[4,3-b]pyridazin-6-yl)-1H-pyrazole (Exemplary Compound No. 2-1036)

To 757 mg (1.80 mmol) of 3-(4-fluorophenyl)-4-(2-methylsulfonylpyrimidin-4-yl)-1-([1,2,4]triazolo[4,3-b]-pyridazin-6-yl)-1H-pyrazole obtained by the same reaction as in Example 67 was added 4.94 g (36.0 mmol) of 4-methoxybenzylamine, and the mixture was stirred at 70° C. for 20 minutes.

After completion of the reaction, 50 ml of diisopropyl ether was added to the reaction solution, and the precipitated crude crystals were collected by filtration and the obtained filtered products were washed with 50 ml of diisopropyl ether to obtain 864 mg of the title compound as a white powder. (Yield: 97%)

Rf value: 0.38 (chloroform:ethyl acetate:methanol=15:4:1).

Mass spectrum (CI, m/z): 494 ($M^++1$)

$^1$H-NMR spectrum (DMSO-$d_6$, δ ppm): 3.71 (s, 3H), 4.24 (brs, 2H), 6.73-6.86 (m, 3H), 7.13-7.26 (m, 4H), 7.60-7.71 (m, 3H), 8.10 (d, J=9.9 Hz, 1H), 8.25 (d, J=5.1 Hz, 1H), 8.59 (dd, $J_1$=9.9 Hz, $J_2$=0.9 Hz, 1H), 9.11 (brs, 1H), 9.71 (d, J=0.9 Hz, 1H).

Example 69

4-(2-Aminopyrimidin-4-yl)-3-(4-fluorophenyl)-1-([1,2,4]triazolo[4,3-b]pyridazin-6-yl)-1H-pyrazole (Exemplary Compound No. 2-151)

To 800 mg (1.62 mmol) of 3-(4-fluorophenyl)-4-[2-(4-methoxybenzylamino)pyrimidin-4-yl]-1-([1,2,4]triazolo[4,3-b]pyridazin-6-yl)-1H-pyrazole obtained in Example 68 was added 5.00 ml (64.8 mmol) of trifluoroacetic acid, and the mixture was stirred at 65° C. for 7 hours.

After completion of the reaction, the reaction mixture was poured into 50 ml of water, and neutralized with 28% aqueous ammonia solution. The precipitated crude crystals were collected by filtration and the obtained filtered products were successively washed with 30 ml of water, and then, with 100 ml of a mixed solvent (ethanol:diisopropyl ether=1:1 (V/V) to obtain 605 mg of the title compound as a white powder. (Yield: quantitative)

Rf value: 0.31 (chloroform:methanol=9:1).

Mass spectrum (CI, m/z): 374 ($M^++1$)

$^1$H-NMR spectrum (DMSO-$d_6$, δ ppm): 6.53 (d, J=5.0 Hz, 1H), 6.66 (s, 2H), 7.30-7.36 (m, 2H), 7.72-7.78 (m, 2H), 8.11 (d, J=10.0 Hz, 1H), 8.21 (d, J=5.0 Hz, 1H), 8.59 (dd, $J_1$=10.0 Hz, $J_2$=0.7 Hz, 1H), 9.03 (s, 1H), 9.72 (d, J=0.7 Hz, 1H).

Example 70

4-(2-Aminopyridin-4-yl)-3-(4-fluorophenyl)-1-(7,8-dihydro-[1,2,4]triazolo[4,3-b]pyridazin-6-yl)-1H-pyrazole (Exemplary Compound No. 4-70)

The reaction was carried out in the same manner as in Example 49 except for using 300 mg (0.81 mmol) of 4-(2-aminopyridin-4-yl)-3-(4-fluorophenyl)-1-([1,2,4]triazolo-[4,3-b]pyridazin-6-yl)-1H-pyrazole obtained by the same reaction as in Example 8-2) in place of 4-(2-aminopyridin-4-yl)-1-(1,6-dihydro-6-oxopyridazin-3-yl)-3-phenyl-1H-pyrazole to obtain 60.6 mg of the title compound as a white powder. (Yield: 20%)

Rf value: 0.30 (chloroform:methanol=19:1).

Mass spectrum (CI, m/z): 375 ($M^++1$).

$^1$H-NMR spectrum (CDCl$_3$, δ ppm): 3.35-3.41 (m, 2H), 3.60-3.65 (m, 2H), 4.46 (brs, 2H), 6.42 (dd, $J_1$=1.5 Hz, $J_2$=0.8 Hz, 1H), 6.57 (dd, $J_1$=5.3 Hz, $J_2$=1.5 Hz, 1H), 7.05-7.13 (m, 2H), 7.50-7.56 (m, 2H), 8.06 (dd, $J_1$=5.3 Hz, $J_2$=0.8 Hz, 1H), 8.42 (s, 1H), 8.49 (s, 1H).

Example 71

3-(4-Fluorophenyl)-1-(1,6-dihydro-6-oxopyridazin-3-yl)-4-(2-methylthiopyrimidin-4-yl)-1H-pyrazole (Exemplary Compound No. 1-837)

71-1) 1-(6-Chloropyridazin-3-yl)-3-(4-fluorophenyl)-4-(2-methylthiopyrimidin-4-yl)-1H-pyrazole The reaction was carried out in the same manner as in Example 1-3) except for using 2.41 g (8.40 mmol) of 3-(4-fluorophenyl)-4-(2-methylthiopyrimidin-4-yl)-1H-pyrazole obtained in Example 66-2) in place of 3-(4-fluorophenyl)-4-(pyridin-4-yl)-1H-pyrazole to obtain 1.08 g of the title compound as a white powder. (Yield: 32%)

Rf value: 0.26 (chloroform).

Mass spectrum (CI, m/z): 399 (M$^+$+1)

$^1$H-NMR spectrum (DMSO-d$_6$, δ ppm): 2.20 (s, 3H), 7.27-7.33 (m, 2H), 7.44 (d, J=5.2 Hz, 1H), 7.61-7.67 (m, 2H), 8.14 (d, J=9.3 Hz, 1H), 8.37 (d, J=9.3 Hz, 1H), 8.57 (d, J=5.2 Hz, 1H), 9.52 (s, 1H).

71-2) 3-(4-Fluorophenyl)-1-(1,6-dihydro-6-oxopyridazin-3-yl)-4-(2-methylthiopyrimidin-4-yl)-1H-pyrazole The reaction was carried out in the same manner as in Example 1-4) except for using 1.04 g (2.60 mmol) of 1-(6-chloropyridazin-3-yl)-3-(4-fluorophenyl)-4-(2-methylthio-pyrimidin-4-yl)-1H-pyrazole obtained in Example 71-1) in place of 1-(6-chloropyridazin-3-yl)-3-(4-fluorophenyl)-4-(pyridin-4-yl)-1H-pyrazole to obtain 973 mg of the title compound as a white powder. (Yield: 98%)

Rf value: 0.46 (chloroform:ethyl acetate:methanol=15:4:1).

Mass spectrum (CI, m/z): 381 (M$^+$+1)

$^1$H-NMR spectrum (DMSO-d$_6$, δ ppm): 2.22 (s, 3H), 7.14 (d, J=10.0 Hz, 1H), 7.25-7.35 (m, 3H), 7.59-7.64 (m, 2H), 8.11 (d, J=10.0 Hz, 1H), 8.54 (d, J=5.1 Hz, 1H), 9.05 (s, 1H), 13.16 (brs, 1H).

Example 72

3-(4-Fluorophenyl)-1-(1,6-dihydro-6-oxopyridazin-3-yl)-4-(2-methylsulfonylpyrimidin-4-yl)-1H-pyrazole (Exemplary Compound No. 1-838) and 3-(4-fluorophenyl)-1-(1,6-dihydro-6-oxopyridazin-3-yl)-4-(2-methylsulfonyl-pyrimidin-4-yl)-1H-pyrazole (Exemplary Compound No. 1-839)

The reaction was carried out in the same manner as in Example 67 except for using 837 mg (2.20 mmol) of 3-(4-fluorophenyl)-1-(1,6-dihydro-6-oxopyridazin-3-yl)-4-(2-methylthiopyrimidin-4-yl)-1H-pyrazole obtained in Example 71-2) in place of 3-(4-fluorophenyl)-4-(2-methylthiopyrimidin-4-yl)-1-([1,2,4]triazolo[4,3-b]pyridazin-6-yl)-1H-pyrazole, and fractions containing firstly eluted 3-(4-fluorophenyl)-1-(1,6-dihydro-6-oxopyridazin-3-yl)-4-(2-methylsulfonylpyrimidin-4-yl)-1H-pyrazole were concentrated under reduced pressure to obtain 67.2 mg of Exemplary compound 1-839 as a white powder (Yield: 7%). Moreover, fractions containing latter eluted 3-(4-fluorophenyl)-1-(1,6-dihydro-6-oxopyridazin-3-yl)-4-(2-methylsulfonylpyrimidin-4-yl)-1H-pyrazole were concentrated under reduced pressure to obtain 456 mg of Exemplary compound 1-838 as a white powder (Yield: 52%).

3-(4-Fluorophenyl)-1-(1,6-dihydro-6-oxopyridazin-3-yl)-4-(2-methylsulfonylpyrimidin-4-yl)-1H-pyrazole Rf value: 0.17 (chloroform:ethyl acetate:methanol=15:4:1).

Mass spectrum (FAB, m/z): 397 (M$^+$+1)

$^1$H-NMR spectrum (DMSO-d$_6$, δ ppm): 2.72 (s, 3H), 7.15 (d, J=10.0 Hz, 1H), 7.26-7.32 (m, 2H), 7.68-7.73 (m, 2H), 7.78 (d, J=5.2 Hz, 1H), 8.13 (d, J=10.0 Hz, 1H), 8.92 (d, J=5.2 Hz, 1H), 9.17 (s, 1H), 13.21 (brs, 1H).

3-(4-Fluorophenyl)-1-(1,6-dihydro-6-oxopyridazin-3-yl)-4-(2-methylsulfonylpyrimidin-4-yl)-1H-pyrazole Rf value: 0.25 (chloroform:ethyl acetate:methanol=15:4:1).

Mass spectrum (CI, m/z): 413 (M$^+$+1)

$^1$H-NMR spectrum (DMSO-d$_6$, δ ppm): 3.11 (s, 3H), 7.15 (d, J=10.1 Hz, 1H), 7.25-7.33 (m, 2H), 7.64-7.74 (m, 2H), 8.00 (d, J=5.4 Hz, 1H), 8.13 (d, J=10.1 Hz, 1H), 8.99 (d, J=5.4 Hz, 1H), 9.27 (s, 1H), 13.22 (brs, 1H).

Example 73

3-(4-Fluorophenyl)-1-(1,6-dihydro-6-oxopyridazin-3-yl)-4-[2-(4-methoxybenzylamino)pyrimidin-4-yl]-1H-pyrazole (Exemplary Compound No. 1-840)

The reaction was carried out in the same manner as in Example 68 except for using 436 mg (1.10 mmol) of 3-(4-fluorophenyl)-1-(1,6-dihydro-6-oxopyridazin-3-yl)-4-(2-methylsulfonylpyrimidin-4-yl)-1H-pyrazole obtained in Example 72 in place of 3-(4-fluorophenyl)-4-(2-methylsulfonylpyrimidin-4-yl)-1-([1,2,4]triazolo[4,3-b]pyridazin-6-yl)-1H-pyrazole to obtain 432 mg of the title compound as a white powder. (Yield: 84%)

Rf value: 0.57 (chloroform:ethyl acetate:methanol=15:4:1).

Mass spectrum (CI, m/z): 470 (M$^+$+1)

$^1$H-NMR spectrum (DMSO-d$_6$, δ ppm): 3.70 (s, 3H), 4.24 (brs, 2H), 6.64 (brs, 1H), 6.83 (d, J=8.5 Hz, 2H), 7.08-7.25 (m, 5H), 7.55 (t, J=6.6 Hz, 1H), 7.64-7.68 (m, 2H), 8.09 (d, J=10.0 Hz, 1H), 8.20 (d, J=5.1 Hz, 1H), 8.83 (s, 1H), 13.14 (brs, 1H).

Example 74

4-(2-Aminopyrimidin-4-yl)-3-(4-fluorophenyl)-1-(1,6-dihydro-6-oxopyridazin-3-yl)-1H-pyrazole (Exemplary Compound No. 1-119)

The reaction was carried out in the same manner as in Example 69 except for using 423 mg (0.90 mmol) of 3-(4-fluorophenyl)-1-(1,6-dihydro-6-oxopyridazin-3-yl)-4-[2-(4-methoxybenzylamino)pyrimidin-4-yl]-1H-pyrazole obtained in Example 73 in place of 3-(4-fluorophenyl)-4-[2-(4-methoxybenzylamino)pyrimidin-4-yl]-1-([1,2,4]triazolo[4,3-b]-pyridazin-6-yl)-1H-pyrazole to obtain 289 mg of the title compound as a white powder. (Yield: 92%)

Rf value: 0.26 (chloroform:ethyl acetate:methanol=15:4:1).

Mass spectrum (CI, m/z): 350 (M$^+$+1)

$^1$H-NMR spectrum (DMSO-d$_6$, δ ppm): 6.50 (d, J=5.0 Hz, 1H), 6.59 (brs, 2H), 7.12 (d, J=10.0 Hz, 1H), 7.25-7.33 (m, 2H), 7.67-7.74 (m, 2H), 8.11 (d, J=10.0 Hz, 1H), 8.16 (d, J=5.0 Hz, 1H), 8.76 (s, 1H), 13.12 (brs, 1H).

Example 75

4-(2-Aminopyrimidin-4-yl)-3-(4-fluorophenyl)-1-(1,4,5,6-tetrahydro-6-oxopyridazin-3-yl)-1H-pyrazole (Exemplary Compound No. 3-115)

To 25 ml of a tetrahydrofuran solution containing 34.9 mg (0.10 mmol) of 4-(2-aminopyrimidin-4-yl)-3-(4-fluorophenyl)-1-(1,6-dihydro-6-oxopyridazin-3-yl)-1H-pyrazole obtained in Example 74 were added 15.2 mg (0.40 mmol) of lithium aluminum hydride and 32.0 mg (0.24 mmol) of aluminum chloride at room temperature. After the addition, the mixture was stirred for 4.5 hours.

After completion of the reaction, the reaction mixture was poured into 100 ml of a saturated aqueous ammonium chloride solution, extracted with 100 ml of a mixed solvent (chloroform:methanol=9:1 (V/V)), and the organic layer was concentrated under reduced pressure. The resulting residue was applied to silica gel column chromatography (eluent; chloroform: ethyl acetate:methanol=15:4:1 (V/V/V)), and the separated fractions containing the objective compound were concentrated under reduced pressure to obtain 1.1 mg of the title compound as a white powder. (yield: 3%)

Rf value: 0.31 (chloroform:ethyl acetate:methanol=15:4:1).

Mass spectrum (CI, m/z): 352 (M$^+$+1).

$^1$H-NMR spectrum (CDCl$_3$, δ ppm): 2.73 (t, J=8.4 Hz, 2H), 3.44 (t, J=8.4 Hz, 2H), 5.21 (brs, 2H), 6.45 (d, J=5.2 Hz, 1H), 7.08-7.17 (m, 2H), 7.51-7.62 (m, 2H), 8.16 (d, J=5.2 Hz, 1H), 8.71 (s, 1H), 11.59 (brs, 1H).

Example 76

1-(3-Acetylamino-[1,2,4]triazolo[4,3-b]pyridazin-6-yl)-4-(2-aminopyridin-4-yl)-3-(4-fluorophenyl)-1H-pyrazole (Exemplary compound 2-135)

76-1) 1-(3-Acetylamino-[1,2,4]triazolo[4,3-b]pyridazin-6-yl)-4-(2-t-butoxycarbonylaminopyridin-4-yl)-3-(4-fluorophenyl)-1H-pyrazole To 2 ml of a pyridine solution containing 200 mg (0.41 mmol) of 1-(3-amino-[1,2,4]triazolo[4,3-b]pyridazin-6-yl)-4-(2-t-butoxycarbonylaminopyridin-4-yl)-3-(4-fluorophenyl)-1H-pyrazole obtained by the same reaction as in Example 48-1) was added 64.3 mg (0.82 mmol) of acetyl chloride, and the mixture was stirred at room temperature for 4 hours.

After completion of the reaction, the reaction mixture was poured into 100 ml of water, and the formed precipitates were collected by filtration. The obtained crude crystals were applied to silica gel column chromatography (eluent; chloroform:methanol=14:1(V/V)), and the separated fractions containing the objective compound were concentrated under reduced pressure. The obtained crude crystals were washed with 20 ml of a mixed solvent (diisopropyl ether:methanol=19:1 (V/V)) to obtain 114 mg of the title compound as a pale yellow powder. (Yield: 53%)

Rf value: 0.41 (chloroform:methanol=9:1).

Mass spectrum (FAB, m/z): 530 (M$^+$+1).

$^1$H-NMR spectrum (DMSO-d$_6$, δ ppm): 1.44 (s, 9H), 2.24 (s, 3H), 6.97 (dd, J$_1$=5.3 Hz, J$_2$=1.5 Hz, 1H), 7.27-7.33 (m, 2H), 7.56-7.60 (m, 2H), 7.83 (s, 1H), 8.10 (d, J=9.8 Hz, 1H), 8.23 (dd, J$_1$=5.3 Hz, J$_2$=0.7 Hz, 1H), 8.54 (d, J=9.8 Hz, 1H), 8.93 (s, 1H), 9.81 (s, 1H), 10.79 (brs, 1H).

76-2) 1-(3-Acetylamino-[1,2,4]triazolo[4,3-b]pyridazin-6-yl)-4-(2-aminopyridin-4-yl)-3-(4-fluorophenyl)-1H-pyrazole 1 ml of a trifluoroacetic acid solution containing 60.0 mg (0.11 mmol) of 1-(3-acetylamino-[1,2,4]triazolo-[4,3-b]pyridazin-6-yl)-4-(2-t-butoxycarbonylaminopyridin-4-yl)-3-(4-fluorophenyl)-1H-pyrazole obtained in Example 76-1) was stirred at room temperature for 1.5 hours.

After completion of the reaction, the reaction mixture was poured into 20 ml of water, and neutralized with 28% aqueous ammonia. The precipitated crude crystals were collected by filtration, and washed with 5 ml of a mixed solvent (diisopropyl ether:methanol=9:1 (V/V)) to obtain 40.0 mg of the title compound as a pale yellow powder. (Yield: 82%)

Rf value: 0.22 (chloroform:methanol=9:1).

Mass spectrum (CI, m/z): 430 (M$^+$+1).

$^1$H-NMR spectrum (DMSO-d$_6$, δ ppm): 2.24 (s, 3H), 5.98 (s, 2H), 6.43-6.45 (m, 2H), 7.28-7.33 (m, 2H), 7.58-7.63 (m, 2H), 7.90-7.92 (m, 1H), 8.09 (d, J=10.0 Hz, 1H), 8.53 (d, J=10.0 Hz, 1H), 8.79 (s, 1H), 10.79 (brs, 1H).

Example 77

4-(2-Aminopyridin-4-yl)-3-(4-fluorophenyl)-1-(1,6-dihydro-6-oxopyridazin-3-yl)-1H-pyrazole benzenesulfonate To 1.5 ml of a dimethylsulfoxide solution containing 174 mg (0.50 mmol) of 4-(2-aminopyridin-4-yl)-3-(4-fluorophenyl)-1-(1,6-dihydro-6-oxopyridazin-3-yl)-1H-pyrazole obtained by the same reaction as in Example 2-4) was added 0.3 ml of a dimethylsulfoxide solution containing 185 mg (1.05 mmol) of benzenesulfonic acid monohydrate at 45° C. over 15 minutes, and the mixture was stirred at the same temperature for 30 minutes. Then, 17 ml of ethyl acetate was added to the mixture over 10 minutes, and after gradually cooling the mixture to room temperature, the mixture was further stirred for 30 minutes. Formed crystals were collected by filtration, washed with 20 ml of ethyl acetate, and dried under reduced pressure to obtain 210 mg of the title compound as a white powder. (Yield: 83%)

$^1$H-NMR spectrum (DMSO-d$_6$, δ ppm): 6.80 (d, J=1.5 Hz, 1H), 6.90 (dd, J$_1$=6.7 Hz, J$_2$=1.5 Hz, 1H), 7.17 (d, J=10.1 Hz, 1 Hz), 7.26-7.37 (m, 5H), 7.56-7.66 (m, 4H), 7.84 (brs, 2H), 7.92 (d, J=6.7 Hz, 1H), 8.12 (d, J=10.1 Hz, 1H), 8.96 (s, 1H), 13.20 (brs, 2H).

Example 78

3-(4-Fluorophenyl)-1-(1,6-dihydro-6-oxopyridazin-3-yl)-4-[2-(2,2,2-trifluoroethyl)aminopyridin-4-yl]-1H-pyrazole sulfate To 1.5 ml of a dimethylsulfoxide solution containing 430 mg (1.00 mmol) of 3-(4-fluorophenyl)-1-(1,6-dihydro-6-oxopyridazin-3-yl)-4-[2-(2,2,2-trifluoroethyl)aminopyridin-4-yl]-1H-pyrazole obtained in Example 28-2) was added 0.2 ml of 0.041M dil. sulfuric acid at 45° C. over 5 minutes, and the mixture was stirred at the same temperature for 1 hour. Then, 3.0 ml of ethyl acetate was added to the mixture over 30 minutes, and the resulting mixture was further stirred for 5 minutes. Formed crystals were collected by filtration, washed with 100 ml of ethyl acetate, and dried under reduced pressure to obtain 464 mg of the title compound as a white powder. (Yield: 88%)

$^1$H-NMR spectrum (DMSO-d$_6$, δ ppm): 4.23-4.32 (m, 2H), 6.85 (d, J=6.1 Hz, 1H), 7.03 (s, 1H), 7.16 (d, J=10.0 Hz, 1H), 7.28-7.36 (m, 2H), 7.55-7.60 (m, 2H), 8.04 (d, J=6.1 Hz, 1H), 8.13 (d, J=10.0 Hz, 1H), 8.40 (brs, 1H), 8.94 (s, 1H), 13.20 (brs, 1H).

Example 79

4-(2-Aminopyridin-4-yl)-3-(4-fluorophenyl)-1-([1,2,4]triazolo[4,3-b]pyridazin-6-yl)-1H-pyrazole methanesulfonate

To 50 ml of a dimethylsulfoxide solution containing 5.00 g (13.4 mmol) of 4-(2-aminopyridin-4-yl)-3-(4-fluorophenyl)-1-([1,2,4]triazolo[4,3-b]pyridazin-6-yl)-1H-pyrazole obtained by the same reaction as in Example 8-2) was added 2.35 ml (36.2 mmol) of methanesulfonic acid at 50° C. over 15 minutes, and the mixture was stirred at the same temperature for 1 hour. Then, 100 ml of ethyl acetate was added to the mixture over 10 minutes, and the resulting mixture was further stirred for 1 hour. Formed crystals were collected by filtration, washed with 150 ml of ethyl acetate, and dried under reduced pressure to obtain 5.80 g of the title compound as a beige powder. (Yield: 92%)

$^1$H-NMR spectrum (DMSO-d$_6$, δ ppm): 2.33 (s, 3H), 6.84 (d, J=1.5 Hz, 1H), 6.92 (dd, J$_1$=6.7 Hz, J$_2$=1.5 Hz, 1H), 7.32-7.40 (m, 2H), 7.62-7.69 (m, 2H), 7.88 (brs, 2H), 7.94-7.97 (m, 1H), 8.12 (d, J=9.9 Hz, 1H), 8.63 (dd, J$_1$=9.9 Hz, J$_2$=0.8 Hz, 1H), 9.24 (s, 1H), 9.70 (d, J=0.8 Hz, 1H), 13.30 (brs, 1H).

Example 80

4-(2-Aminopyridin-4-yl)-3-(4-fluorophenyl)-1-(1,4,5,6-tetrahydro-6-oxopyridazin-3-yl)-1H-pyrazole methanesulfonate

To 1.5 ml of a dimethylsulfoxide solution containing 350 mg (1.00 mmol) of 4-(2-aminopyridin-4-yl)-3-(4-fluorophenyl)-1-(1,4,5,6-tetrahydro-6-oxopyridazin-3-yl)-1H-pyrazole obtained in Example 50 was added 130 μl (2.00 mmol) of methanesulfonic acid at 45° C. over 4 minutes, and the mixture was stirred at the same temperature for 30 minutes. Then, 4.5 ml of ethyl acetate was added to the mixture over 30 minutes, and the resulting mixture was further stirred for 5 minutes. Formed crystals were collected by filtration, washed with 30 ml of ethyl acetate to obtain 380 mg of the title compound as a white powder. (Yield: 85%)

$^1$H-NMR spectrum (CD$_3$OD, δ ppm): 2.70 (s, 3H), 2.73 (t, J=8.4 Hz, 2H), 3.42 (t, J=8.4 Hz, 2H), 6.81 (dd, J$_1$=6.6 Hz, J$_2$=1.7 Hz, 1H), 6.84 (dd, J$_1$=1.7 Hz, J$_2$=0.8 Hz, 1H), 7.16-7.24 (m, 2H), 7.52-7.59 (m, 2H), 7.76 (dd, J$_1$=6.6 Hz, J$_2$=0.8 Hz, 1H), 8.76 (s, 1H)

Example 81

4-(2-Acetylaminopyridin-4-yl)-3-(4-fluorophenyl)-1-(1,4,5,6-tetrahydro-6-oxopyridazin-3-yl)-1H-pyrazole hydrochloride

To 0.60 ml of a dimethylsulfoxide solution containing 58.9 mg (0.15 mmol) of 4-(2-acetylaminopyridin-4-yl)-3-(4-fluorophenyl)-1-(1,4,5,6-tetrahydro-6-oxopyridazin-3-yl)-1H-pyrazole obtained in Example 57 was added 15.5 μl (0.18 mmol) of 12N hydrochloric acid at 45° C. over 1 minute, and the mixture was stirred at the same temperature for 15 minutes. Then, 3 ml of ethyl acetate was added to the mixture over 10 minutes, and after gradually cooling the mixture to room temperature, the mixture was further stirred for 30 minutes. Formed crystals were collected by filtration, washed with 3 ml of ethyl acetate, and dried under reduced pressure to obtain 63.5 mg of the title compound as a white powder. (Yield: 99%)

$^1$H-NMR spectrum (DMSO-d$_6$, δ ppm): 2.10 (s, 3H), 2.61 (t, J=8.4 Hz, 2H), 3.32 (t, J=8.4 Hz, 2H), 7.16 (dd, J$_1$=5.6 Hz, J$_2$=1.3 Hz, 1H), 7.22-7.30 (m, 2H), 7.47-7.54 (m, 2H), 7.88 (d, J=1.3 Hz, 1H), 8.27 (dd, J$_1$=5.6 Hz, J$_2$=0.7 Hz, 1H), 8.68 (s, 1H), 10.83 (s, 1H), 10.97 (brs, 1H).

Test Example 1 Enzyme Inhibitory Test Against p38MAP Kinase (1) Preparatoin of Active Type p38MAP Kinase An active type p38MAP kinase was prepared by incubation in a reaction solution (25 mM Tris-HCl pH 7.5, 5 mM β-glycerolphosphate, 2 mM DTT, 0.1 mM Na$_3$VO$_3$, 10 mM MgCl$_2$, 1 mM ATP) containing p38MAP kinase (Stratagene, #206145) and SKK/MKK6 (Upstate, #14-225 or #14-303) at 30° C. for 1 to 3 hours. This enzyme solution was diluted 5 to 10-fold with Stock Buffer (50 mM Tris-HCl pH 7.5, 0.1 mM EGTA, 0.2 mM Orthovanadate, 0.1% 2-ME, 10% glycerol, 0.03% Brij-35, 0.5 μM Microcystin), and preserved under freezing (−80° C.).

(2) Measurement of Inhibitory Activity of p38MAP Kinase

To 34 μL of a reaction solution (25 mM HEPES, pH 7.5, 10 mM Magnesium acetate) containing the active type p38MAP kinase prepared as mentioned above and a substrate (final concentration: 250 mM EGFR; KRELVE-PLTPAGEAPNQALLR) was added 1 μL of DMSO, or a compound to be tested and dissolved in DMSO, then, the mixture was subjected to preincubation at 4° C. for 30 minutes. A reaction was started by adding 5 μL of an ATP solution (400 μM ATP, 1 μCi/μL [γ-$^{32}$P]ATP), and reacted at 30° C. for 30 minutes, and then, the reaction was stopped by adding 5 μL of 250 mM H$_3$PO$_4$. 25 μL of the reaction solution was placed on chromatography paper (Whatman, #P81), dried for about 2 minutes, and washed with 75 mM H$_3$PO$_4$. Water was removed by using 95% ethanol, it was transferred to a bial containing liquid scintillation cocktail (available from Nacalai Tesque), and radioactivity was measured. A concentration (IC$_{50}$ value) of a compound to be tested necessary for inhibiting 50% of phosphrylation ($^{32}$P) of the substrate by the enzyme was calculated as compared to that non-treated by the compound to be tested by XL-fit (available from IDBS). The test results are shown in Table 5.

TABLE 5

| Compounds to be tested Example No. | p38MAP kinase inhibition IC$_{50}$ value (nM) |
|---|---|
| Example 1 | 8.9 |
| Example 2 | 2.5 |
| Example 4 | 2.5 |
| Example 5 | 25 |
| Example 8 | 7.4 |
| Example 9 | 5.4 |
| Example 11 | 6.1 |
| Example 13 | 29 |
| Example 16 | 2.0 |
| Example 18 | 3.7 |
| Example 22 | 6.6 |
| Example 25 | 5.9 |
| Example 27 | 1.3 |
| Example 32 | 3.4 |
| Example 34 | 0.2 |
| Example 40 | 8.7 |
| Example 42 | 9.5 |
| Example 45 | 4.9 |
| Example 49 | 7.0 |

TABLE 5-continued

| Compounds to be tested Example No. | p38MAP kinase inhibition IC$_{50}$ value (nM) |
|---|---|
| Example 57 | 2.1 |
| Example 62 | 1.3 |

In the present test, the compounds of the present invention exhibited excellent p38MAP kinase inhibitory activity.

Test Example 2 Inhibition of TNF-α Production in Human PBMC (In Vitro)

Test was carried out according to the method of Welker et al. (Int. Arch. Allergy Immunol., 109, 110-115 (1996).

Heparin-added blood collected from healthy volunteer with consent was underlayed with a specific gravity-separating solution (Lymphoprep; available from Daiichi Pure Chemicals Co., Ltd.), subjected to centrifugation (800×g, 25 minutes), and a mononuclear cell layer was recovered. The obtained mononuclear cells (human PBMC) were washed twice with PBS (available from SIGMA), and resuspended in 1% FCS-containing RPMI aqueous solution (available from GIBCO) so that the cells became 5×10$^6$ cells/mL. The thus obtained cell suspension was diluted 10-fold with 1% FCS-containing RPMI medium, DMSO (or the compound to be tested) with a final concentration of 0.5% was added thereto, and cultured at 37° C. in 5% CO$_2$ for 1 hour. After that, LPS (derived from *E. Coli* 055:5B, available from SIGMA) solution prepared by PBS was added so that the final concentration thereof being 10 μg/ml, and cultivation was carried out for further 18 hours. After the cultivation, culture medium was subjected to centrifugation (800×g, 10 minutes), and a concentration of TNF-α produced in the supernatant was measured by an enzyme-linked immunosorbent assay (ELISA) kit (TNF-α ELISA Kit, available from R&D). The concentration (IC$_{50}$ value) of the test compound for inhibiting 50% of TNF-α production was calcualted by using XL-fit (available from IDBS). The test results are shown in Table 6.

TABLE 6

| Compounds to be tested Example No. | Inhibitory effect on LPS-induced TNF-α production in human PBMC IC$_{50}$ value (nM) |
|---|---|
| Example 2 | 24 |
| Example 4 | 28 |
| Example 5 | 4 |
| Example 28 | 7 |
| Example 35 | 6 |
| Example 43 | 14 |
| Example 55 | 36 |
| Example 61 | 4 |
| Example 65 | 15 |

In the present test using human PBMC, the compounds of the present invention exhibited excellent TNF-α production inhibitory activity.

Test Example 3 Inhibition of IL-6 Production in Rat (In Vivo)

A cytokine mixed solution of IL-1β and TNF-α was intravenously injected to rats to induce production of IL-6. A mixed solution of IL-1β (available from R&D) (4 μg/ml) and TNF-α (available from R&D) (2 μg/ml) dissolved in PBS was administered to tail vein of LEW series rats (female, body weight: about 140 to 170 g, available from Charles River Japan, Inc.) fasted overnight with a ratio of 1 ml/kg of the body weight. Two hours later, blood was collected from the neck vein under ether anesthesia. The collected blood was centrifuged under the conditions of 20° C. and 10,000×g to separate serum. IL-6 concentration in the serum was measured by using an enzyme-linked immunosorbent assay (ELISA) kit (IL-6 ELISA KIT, available from R&D).

The test compound or the vehicle was orally administered with a dose of 10 ml/kg of the body weight before 1 hour of the injection of the cytokine mixed solution. The control group to which the vehicle was administered and the group of the compound to be tested were each 5 rats per group. An inhibitory ratio of the group of the compound to be tested based on control group was calculated. The test results are shown in Table 7.

TABLE 7

| Compounds to be tested Example No. | Rat cytokine induced IL-6 production inhibiting ratio (%) @3 mg/Kg |
|---|---|
| Example 3 | 81 |
| Example 5 | 92 |
| Example 16 | 97 |
| Example 20 | 78 |
| Example 26 | 77 |
| Example 42 | 73 |
| Example 49 | 84 |
| Example 56 | 85 |

In the present test using rats, the compounds of the present invention exhibited excellent IL-6 production inhibitory activity.

Test Example 4 Anti-inflammatory Effect in Rat Adjuvant Arthritis Model

Heat-killed bacteria of *Mycobacterium butyricum* (available from Difco) were pulverized by agate mortar, and this was suspended in dry-heat sterilized liquid paraffin (available from Wako Pure Chemical Industries, Ltd.) so as to have 10 mg/ml, and subjected to ultrasonic wave treatment to obtain an adjuvant. 500 μg/50 μl/paw of the adjuvant was administered into right hind paw of LEW series rats (female, 7-weeks old, available from Charles River Japan, Inc.) under isoflurane (Forane, available from Abbott Japan) inhalation anesthesia to induce adjuvant arthritis. Also, liquid paraffin containing no dead bacteria was also administered in the same manner as mentioned above to prepare a non-treatment group.

The test compound was suspended in a 0.5% aqueous sodium carboxymethyl cellulose solution, or dissolved in distilled water for injection, and orally administered at a dose of 10 ml/kg once a day from the injected day of the adjuvant (0$^{th}$ day) to 27$^{th}$ day.

After 7$^{th}$, 14$^{th}$, 21$^{st}$ and 28$^{th}$ day from administration of the adjuvant, volumes of the right hind paw to which the adjuvant had been administered and of left hind paw to which no adjuvant had been administered were measured by a plethysmometer (TK-101CMP, UNICOM). An edema ratio was calculated from the following equation.

Edema ratio (%)=[(volume of hind paw at the time of measurement)/(volume of hind paw before initiation of the test)−1]×100

Moreover, edema suppressive ratio based on the control group to which the vehicle was administered was calculated from the following equation.

Edema suppressive ratio (%)=[1-{(edema ratio of test compound-administered group)−(edema ratio of non-treated group)}/{(edema ratio of control group)−(edema ratio of non-treatment group)}]×100

The test results are shown in Table 8.

TABLE 8

| Compounds to be tested Example No. | 28th day left hind paw edema suppressive ratio (%) @3 mg/Kg |
|---|---|
| 2 | 83 (28th day) |
| 8 | 79 (28th day) |
| 13 | 79 (21st day) |

In the present test, the compounds of the present invention exhibited excellent edema suppressive activity.

Preparation Example (Preparation Example 1) (Hard Capsules)

50 mg of the compound in powdered state in Example 1, 128.7 mg of lactose, 70 mg of cellulose and 1.3 mg of magnesium stearate were mixed, passed through 60 mesh sieve, and then, the powder is contained in No. 3 gelatin capsule with a weight of 250 mg to prepare a capsule.

(Preparation Example 2) (Tablets)

50 mg of the compound in Example 1, 124 mg of lactose, 25 mg of cellulose and 1 mg of magnesium stearate were mixed, and tabletted by a tabletting machine to obtain tablets containing 200 mg per tablet. The tablet may be sugar-coated thereon, if necessary.

Utilizability in Industry

The compounds represented by the formula (I) of the present invention exhibit excellent p38MAP kinase inhibitory activity and excellent activity in inhibiting the production of inflammatory cytokines (in particular, in inhibiting the production of TNF-α, IL-6) based thereon. Furthermore, they have good oral absorption property, low toxicity, and excellent stability as a medicament so that they are useful for medical purposes, particularly suitable for a prophylaxis and treatment agent for diseases to which inflammatory cytokines pertain. More specifically, the compounds of the present invention are useful as an analgesic and anti-inflammatory agent, an antiviral agent, and as a prophylaxis and treatment agent for chronic rheumatism, osteoarthritis, allergic diseases (for example, allergodermia, allergic rhinitis, etc.), asthma, chronic obstructive pulmonary disease, septicemia, psoriasis, osteoporosis, autoimmune disease (for example, systemic lupus erythematosus, ulcerative colitis, Crohn's disease, multiple sclerosis, amyotrophic lateral sclerosis, etc.), diabetes, glomerular nephritis, hepatitis, ischemic heart diseases, Alzheimer's disease, or arteriosclerosis, particularly useful as an analgesic and anti-inflammatory agent, and as a prophylaxis and treatment agent for chronic rheumatism, osteoarthritis, allergic diseases, septicemia, psoriasis, osteoporosis, ulcerative colitis, diabetes, or arteriosclerosis.

The invention claimed is:

1. A pyrazole compound represented by the formula (I):

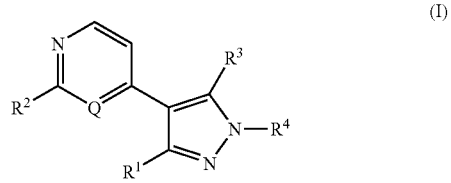

wherein $R^1$ represents a phenyl group which may be substituted by a group(s) selected from the group consisting of a halogen atom, a $C_1$-$C_6$ alkyl group, a halogeno $C_1$-$C_6$ alkyl group, a $C_1$-$C_6$ alkoxy group, a halogeno $C_1$-$C_6$ alkoxy group and a $C_1$-$C_6$ alkylthio group, $R^2$ represents a hydrogen atom, a halogen atom, a $C_1$-$C_6$ alkyl group, a $C_1$-$C_6$ alkoxy group, a $C_1$-$C_6$ alkylthio group, a $C_1$-$C_6$ alkylsulfinyl group, a $C_1$-$C_6$ alkylsulfonyl group or a group: —$NR^5R^6$ wherein $R^5$ and $R^6$ may be the same or different from each other, and each represents a hydrogen atom, a $C_1$-$C_6$ alkyl group, a halogeno $C_1$-$C_6$ alkyl group, a $C_3$-$C_7$ cycloalkyl group, a $C_1$-$C_6$ alkyl-carbonyl group, a $C_3$-$C_7$ cycloalkyl-carbonyl group, a formyl group, a $C_1$-$C_6$ alkoxy-carbonyl group or a $C_1$-$C_6$ alkylsulfonyl group, or a $C_7$-$C_{12}$ aralkyl group or a benzoyl group each of which may be substituted by a group(s) selected from the group consisting of a halogen atom, a $C_1$-$C_6$ alkyl group, a halogeno $C_1$-$C_6$ alkyl group, a $C_1$-$C_6$ alkoxy group and a halogeno $C_1$-$C_6$ alkoxy group, Q represents CH or a nitrogen atom, $R^3$ represents a hydrogen atom, a $C_1$-$C_6$ alkyl group or an amino group, $R^4$ represents the formula (II):

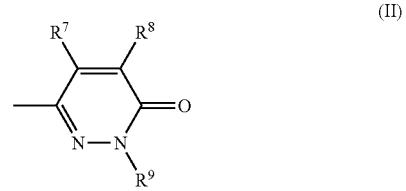

the formula (III):

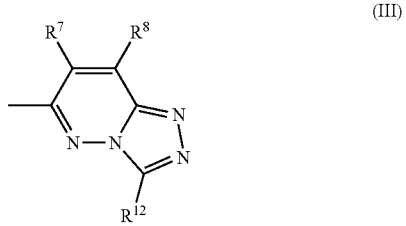

the formula (IV):

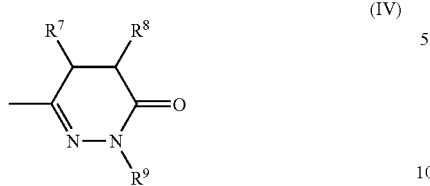

or the formula (V):

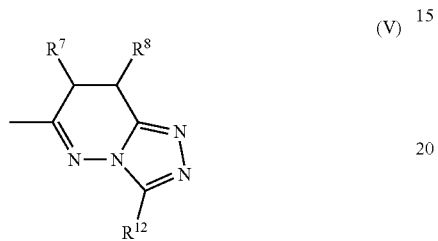

wherein $R^7$ represents a hydrogen atom or a $C_1$-$C_6$ alkyl group, $R^8$ represents a hydrogen atom, a $C_1$-$C_6$ alkyl group or a group: —$NR^{10}R^{11}$ wherein $R^{10}$ and $R^{11}$ may be the same or different from each other, and each represents a hydrogen atom, a $C_1$-$C_6$ alkyl group, a $C_1$-$C_6$ alkyl-carbonyl group, a formyl group, a $C_1$-$C_6$ alkoxy-carbonyl group or a $C_1$-$C_6$ alkylsulfonyl group, $R^9$ represents a hydrogen atom or a $C_1$-$C_6$ alkyl group, $R^{12}$ represents a hydrogen atom, a $C_1$-$C_6$ alkyl group, a halogeno $C_1$-$C_6$ alkyl group or a group: —$NR^{10}R^{11}$ wherein $R^{10}$ and $R^{11}$ may be the same or different from each other, and each represents a hydrogen atom, a $C_1$-$C_6$ alkyl group, a $C_1$-$C_6$ alkyl-carbonyl group, a formyl group, a $C_1$-$C_6$ alkoxy-carbonyl group or a $C_1$-$C_6$ alkylsulfonyl group, or a pharmaceutically acceptable salt thereof.

2. The pyrazole compound or a pharmaceutically acceptable salt thereof according to claim 1, wherein the compound is represented by the formula (I):

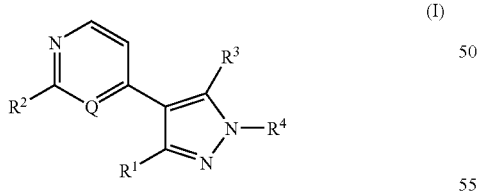

wherein $R^1$ represents a phenyl group which may be substituted by a group(s) selected from the group consisting of a halogen atom, a $C_1$-$C_6$ alkyl group, a halogeno $C_1$-$C_6$ alkyl group, a $C_1$-$C_6$ alkoxy group, a halogeno $C_1$-$C_6$ alkoxy group and a $C_1$-$C_6$ alkylthio group, $R^2$ represents a hydrogen atom, a halogen atom, a $C_1$-$C_6$ alkyl group, a $C_1$-$C_6$ alkoxy group, a $C_1$-$C_6$ alkylthio group, a $C_1$-$C_6$ alkylsulfinyl group, a $C_1$-$C_6$ alkylsulfonyl group or a group: —$NR^5R^6$ wherein $R^5$ and $R^6$ may be the same or different from each other, and each represents a hydrogen atom, a $C_1$-$C_6$ alkyl group, a halogeno $C_1$-$C_6$ alkyl group, a $C_3$-$C_7$ cycloalkyl group, a $C_1$-$C_6$ alkyl-carbonyl group, a $C_3$-$C_7$ cycloalkyl-carbonyl group, a formyl group, a $C_1$-$C_6$ alkoxy-carbonyl group or a $C_1$-$C_6$ alkylsulfonyl group, or a $C_7$-$C_{12}$ aralkyl group, or a $C_7$-$C_{12}$ aralkyl group or a benzoyl group each of which may be substituted by a group(s) selected from the group consisting of a halogen atom, a $C_1$-$C_6$ alkyl group, a halogeno $C_1$-$C_6$ alkyl group, a $C_1$-$C_6$ alkoxy group and a halogeno $C_1$-$C_6$ alkoxy group, Q represents CH or a nitrogen atom, $R^3$ represents a hydrogen atom, a $C_1$-$C_6$ alkyl group or an amino group, $R^4$ represents the formula (II):

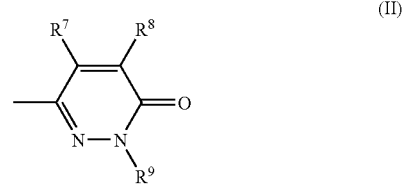

wherein $R^7$ represents a hydrogen atom or a $C_1$-$C_6$ alkyl group, $R^8$ represents a hydrogen atom, a $C_1$-$C_6$ alkyl group or a group: —$NR^{10}R^{11}$ wherein $R^{10}$ and $R^{11}$ may be the same or different from each other, and each represents a hydrogen atom, a $C_1$-$C_6$ alkyl group, a $C_1$-$C_6$ alkyl-carbonyl group, a formyl group, a $C_1$-$C_6$ alkoxy-carbonyl group or a $C_1$-$C_6$ alkylsulfonyl group, $R^9$ represents a hydrogen atom or a $C_1$-$C_6$ alkyl group.

3. The pyrazole compound or a pharmaceutically acceptable salt thereof according to claim 2, wherein $R^1$ represents a phenyl group which may be substituted by 1 to 3 group(s) selected from the group consisting of a halogen atom, a $C_1$-$C_4$ alkyl group, a halogeno $C_1$-$C_4$ alkyl group, a $C_1$-$C_4$ alkoxy group, a halogeno $C_1$-$C_4$ alkoxy group and a $C_1$-$C_4$ alkylthio group, $R^2$ represents a hydrogen atom, a halogen atom, a $C_1$-$C_4$ alkyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group or a group: —$NR^5R^6$ (wherein $R^5$ and $R^6$ may be the same or different from each other, and each represents a hydrogen atom, a $C_1$-$C_4$ alkyl group, a halogeno $C_1$-$C_4$ alkyl group, a cycloalkyl group, a $C_1$-$C_4$ alkyl-carbonyl group, a $C_3$-$C_6$ cycloalkyl-carbonyl group, a formyl group, a $C_1$-$C_4$ alkoxy-carbonyl group or a $C_1$-$C_4$ alkylsulfonyl group, or a $C_7$-$C_{12}$ aralkyl group or a benzoyl group each of which may be substituted by a group(s) selected from the group consisting of a halogen atom, a $C_1$-$C_4$ alkyl group, a halogeno $C_1$-$C_4$ alkyl group, a $C_1$-$C_4$ alkoxy group and a halogeno $C_1$-$C_4$ alkoxy group), $R^3$ represents a hydrogen atom, a $C_1$-$C_4$ alkyl group or an amino group, $R^4$ represents the formula (II)

wherein $R^7$ represents a hydrogen atom or a $C_1$-$C_4$ alkyl group, $R^8$ represents a hydrogen atom, a $C_1$-$C_4$ alkyl group, an amino group, a $C_1$-$C_4$ alkylamino group, a di($C_1$-$C_4$ alkyl)amino group, a $C_1$-$C_4$ alkyl-carbonylamino group, a formylamino group, a $C_1$-$C_4$ alkoxycarbonylamino group or a $C_1$-$C_4$ alkylsulfonylamino group, $R^9$ represents a hydrogen atom or a $C_1$-$C_4$ alkyl group.

4. The pyrazole compound or a pharmaceutically acceptable salt thereof according to claim 3, wherein $R^1$ represents a phenyl group which may be substituted by 1 to 2 group(s) selected from the group consisting of a halogen atom, a $C_1$-$C_4$ alkyl group, a fluoro $C_1$-$C_4$ alkyl group, a $C_1$-$C_4$ alkoxy group, a fluoro $C_1$-$C_4$ alkoxy group and a $C_1$-$C_4$ alkylthio group, $R^2$ represents a hydrogen atom, a halogen atom, a $C_1$-$C_4$ alkyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a di($C_1$-$C_4$ alkyl)amino group, a fluoro $C_1$-$C_4$ alkylamino group, a $C_3$-$C_6$ cycloalkylamino group, a $C_1$-$C_4$ alkylcarbonylamino group, a cycloalkyl-carbonylamino group, a N—($C_3$-$C_6$ cycloalkyl-carbonyl)-N—($C_1$-$C_4$ alkyl)amino group, a formylamino group, a $C_1$-$C_4$ alkoxy-carbonylamino group, a $C_1$-$C_4$ alkylsulfonylamino group, or a benzylamino group, a 1-phenethylamino group or a benzoylamino group the phenyl group portion thereof may be substituted by a group(s) selected from the group consisting of a halogen atom, a $C_1$-$C_4$ alkyl group, a fluoro $C_1$-$C_4$ alkyl group, a $C_1$-$C_4$ alkoxy group and a fluoro $C_1$-$C_4$ alkoxy group, $R^3$ represents a hydrogen atom, a methyl group or an amino group, $R^4$ represents the above-mentioned formula (II) wherein $R^7$ represents a hydrogen atom, a methyl group or an ethyl group, $R^8$ represents a hydrogen atom, a methyl group, an ethyl group, an amino group, a methylamino group, a dimethylamino group, an ethylamino group, a diethylamino group, an isopropylamino group, an acetylamino group, a formylamino group, a methoxycarbonylamino group, an ethoxycarbonytamino group, a methylsulfonylamino group or an ethylsulfonylamino group, $R^9$ represents a hydrogen atom, a methyl group or an ethyl group.

5. The pyrazole compound or a pharmaceutically acceptable salt thereof according to claim 4, wherein $R^1$ represents a phenyl group which may be substituted by 1 to 2 group(s) selected from the group consisting of a fluorine atom, a chlorine atom, a bromine atom, a methyl group, an ethyl group, an isopropyl group, a difluoromethyl group, a trifluoromethyl group, a 2-fluoroethyl group, a 2,2,2-trifluoroethyl group, a nitethoxy group, an ethoxy group, an isopropoxy group, a fluoromethoxy group, a difluoromethoxy group, a trifluoromethoxy group and a methylthio group, $R^2$ represents a hydrogen atom, a fluorine atom, a chlorine atom, a methyl group, a methoxy group, a methylthio group, a methylsulfinyl group, a methylsulfonyl group, an amino group, a methylamino group, a dimethylamino group, an ethylamino group, a diethylamino group, a propylamino group, an isopropylamino group, a trifluoromethylamino group, a 2,2,2-trifluoroethylamino group, a cyclopropylamino group, a cyclohexylamino group, an acetylamino group, a propionylamino group, a cyclopropylcarbonylamino group, a cyclopentylcarbonylamino group, a N-cyclopropylcarbonyl-N-methylamino group, a formylamino group, a methoxycarbonylamino group, an ethoxycarbonylamino group, a t-butoxycarbonylamino group, a methylsulfonylamino group, an ethylsulfonylamino group, or a beuzylamino group, a 1-phenethylamino group or a benzoylamino group the phenyl group portion thereof may be substituted by a group(s) selected from the group consisting of a fluorine atom, a methyl group, a trifluoromethyl group, a methoxy group and a difluoromethoxy group, $R^3$ represents a hydrogen atom, a methyl group or an amino group, $R^4$ represents the above-mentioned formula (II),
wherein $R^7$ represents a hydrogen atom or a methyl group, $R^8$ represents a hydrogen atom, a methyl group, an amino group, a methylamino group, a dimethylamino group, an acetylamino group, a formylamino group, a methoxycarbonylamino group or a methylsulfonylamino group, $R^9$ represents a hydrogen atom or a methyl group.

6. The pyrazole compound or a pharmaceutically acceptable salt thereof according to claim 5, wherein $R^1$ represents a phenyl group which may be substituted by 1 to 2 group(s) selected from the group consisting of a fluorine atom, a chlorine atom, a methyl group, a difluoromethyl group, a trifluoromethyl group, a methoxy group, a fluoromethoxy group, a difluoromethoxy group and a trifluoromethoxy group, $R^2$ represents a hydrogen atom, a fluorine atom, a methyl group, a methoxy group, a methylthio group, a methylsulfinyl group, a methylsulfonyl group, an amino group, a methylamino group, a dimethylamino group, an ethylamino group, an isopropylamino group, a 2,2,2-trifluoroethylamino group, a cyclopropylamino group, an acetylamino group, a cyclopropylcarbonylamino group, a cyclopentylcarbonylamino group, a N-cyclopropylcarbonyl-N-methylamino group, a methoxycarbonylamino group, a methylsulfonylamino group, a 4-methoxybenzylamino group, a 1-phenethylamino group or a benzoylamino group, $R^3$ represents a hydrogen atom, a methyl group or an amino group, $R^4$ represents a 1,6-dihydro-6-oxopyridazin-3-yl group, a 1,6-dihydro-4-methyl-6-oxopyridazin-3-yl group, a 1,6-dihydro-5-methyl-6-oxopyridazin-3-yl group, a 5-amino-1,6-dihydro-6-oxopyridazin-3-yl group, a 1,6-dihydro-5-methylamino-6-oxopyridazin-3-yl group, a 5-dimethylamino-1,6-dihydro-6-oxopyridazin-3-yl group, a 5-acetylamino-1,6-dihydro-6-oxopyridazin-3-yl group, a 1,6-dihydro-5-methoxycarbonylamino-6-oxopyridazin-3-yl group, a 1,6-dihydro-5-methylsulfonylamino-6-oxopyridazin-3-yl group, a 1,6-dihydro-1-methyl-6-oxopyridazin-3-yl group, a 1-ethyl-1,6-dihydro-6-oxopyridazin-3-yl group, a 1,6-dihydro-1,5-dimethyl-6-oxopyridazin-3-yl group or a 5-amino-1,6-dihydro-1-methyl-6-oxopyridazin-3-yl group.

7. The pyrazole compound or a pharmaceutically acceptable salt thereof according to claim 6, wherein $R^1$ represents a phenyl group, a 2-fluorophenyl group, a 3-fluorophenyl group, a 4-fluorophenyl group, a 3-chlorophenyl group, a 4-chlorophenyl group, a 3,4-difluorophenyl group, a 2,4-difluorophenyl group, a 3,4-dichlorophenyl group, a 3-chloro-4-fluorophenyl group, a 4-chloro-3-fluorophenyl group or a 3-trifluoromethylphenyl group, $R^2$ represents a hydrogen atom, a methoxy group, an amino group, a methylamino group, an ethylamino group, an isopropylamino group, a 2,2,2-trifluoroethylamino group, an acetylamino group, a cyclopropylcarbonylamino group, a cyclopentylcarbonylamino group, a methoxycarbonylamino group, a methylsulfonylamino group, a 4-methoxybenzylamino group, a 1-phenethylamino group or a benzoylamino group, $R^3$ represents a hydrogen atom, a methyl group or an amino group, $R^4$ represents a 1,6-dihydro-6-oxopyridazin-3-yl group, a 1,6-dihydro-4-methyl-6-oxopyridazin-3-yl group, a 1,6-dihydro-5-methyl-6-oxopyridazin-3-yl group, a 5-amino-1,6-dihydro-6-oxopyridazin-3-yl group, a 5-acetylamino-1,6-dihydro-6-oxopyridazin-3-yl group, a 1,6-dihydro-5-methoxycarbonylamino-6-oxopyridazin-3-yl group, a 1,6-dihydro-5-methylsulfonylamino-6-oxopyridazin-3-yl group, a 1,6-dihydro-1-methyl-6-oxopyridazin-3-yl group or a 5-amino-1,6-dihydro-1-methyl-6-oxopyridazin-3-yl group.

8. The pyrazole compound or a pharmaceutically acceptable salt thereof according to claim 7, wherein $R^1$ represents a phenyl group, a 2-fluorophenyl group, a 3-fluorophenyl group, a 4-fluorophenyl group, a 3-chlorophenyl group, a 4-chlorophenyl group, a 3,4-difluorophenyl group, a 2,4-difluorophenyl group, a 3,4-dichlorophenyl group, a 3-chloro-4-fluorophenyl group, a 4-chloro-3-fluorophenyl group or a 3-trifluoromethylphenyl group, $R^2$ represents a hydrogen atom, a methoxy group, an amino group, a methylamino group, an ethylamino group, an isopropylamino group, a 2,2,2-trifluoroethylamino group, an acetylamino group, a cyclopropylcarbonylamino group, a cyclopentylcarbonylamino group, a methoxycarbonylamino group, a methylsulfonylamino group, a 4-methoxybenzylamino group, a 1-phenethylamino group or a benzoyl amino group, $R^3$ represents a hydrogen atom, $R^4$ represents a 1,6-dihydro-6-oxopyridazin-3-yl group, a 1,6-dihydro-4-methyl-6-oxopyridazin-3-yl group, a 1,6-dihydro-5-methyl-6-oxopyridazin-3-yl group, a 5-amino-1,6-dihydro-6-oxopyridazin-3-yl group or a 1,6-dihydro-1-methyl-6-oxopyridazin-3-yl group.

9. The pyrazole compound or a pharmaceutically acceptable salt thereof according to claim 8, wherein the pyrazole compound is 4-(2-aminopyridin-4-yl)-1-(1,6-dihydro-6-oxopyridazin-3-yl)-3-phenyl-1H-pyrazole, 3-(4-fluorophenyl)-1-(1,6-dihydro-6-oxopyridazin-3-yl)-4-(pyridin-4-yl)-1H-pyrazole, 1-(5-amino-1,6-dihydro-6-oxopyridazin-3-yl)-3-(4-fluorophenyl)-4-(pyridin-4-yl)-1H-pyrazole, 4-(2-aminopyridin-4-yl)-3-(4-fluorophenyl)-1-(1,6-dihydro-6-oxopyridazin-3-yl)-1H-pyrazole, 3-(4-fluorophenyl)-1-(1,6-dihydro-6-oxopyridazin-3-yl)-4-(2-methylaminopyridin-4-yl)-1H-pyrazole, 4-(2-ethylaminopyridin-4-yl)-3-(4-fluorophenyl)-1-(1,6-dihydro-6-oxopyridazin-3-yl)-1H-pyrazole, 3-(4-fluorophenyl)-1-(1,6-dihydro-6-oxopyridazin-3-yl)-4-[2-(2,2,2-trifluoroethyl)aminopyridin-4-yl]-1H-pyrazole, 4-(2-acetylaminopyridin-4-yl)-3-(4-fluorophenyl)-1-(1,6-dihydro-6-oxopyridazin-3-yl)-1H-pyrazole, 3-(4-fluorophenyl)-1-(1,6-dihydro-6-oxopyridazin-3-yl)-4-(2-methoxycarbonylaminopyridin-4-yl)-1H-pyrazole, 4-(2-aminopyridin-4-yl)-3-(4-fluorophenyl)-1-(1,6-dihydro-4-methyl-6-oxopyridazin-3-yl)-1H-pyrazole, 4-(2-aminopyridin-4-yl)-3-(4-fluorophenyl)-1-(1,6-dihydro-5-methyl-6-oxopyridazin-3-yl)-1H-pyrazole, 1-(5-amino-1,6-dihydro-6-oxopyridazin-3-yl)1)-4-(2-aminopyridin-4-yl)-3-(4-fluorophenyl)-1H-pyrazole, 4-(2-aminopyridin-4-yl)-3-(4-fluorophenyl)-1-(1,6-dihydro-1-methyl-6-oxopyridazin-3-yl)-1H-pyrazole, 4-(2-aminopyrimidin-4-yl)-3-(4-fluorophenyl-1-(1,6-dihydro-6-oxopyridazin-3-yl)-1H-pyrazole, 4-(2-aminopyridin-4-yl)-3-(3-fluorophenyl)-1-(1,6-dihydro-6-oxopyridazin-3-yl)-1H-1-pyrazole, 4-(2-aminopyridin-4-yl)-3-(4-chlorophenyl)-1-(1,6-dihydro-6-oxopyridazin-3-yl)-1H-pyrazole, 4-(2-aminopyridin-4-yl)-3-(3-chlorophenyl)-1-(1,6-dihydro-6-oxopyridazin-3-yl)-1H-pyrazole, 4-(2-aminopyridin-4-yl)-3-(3,4-difluorophenyl)-1-(1,6-dihydro-6-oxopyridazin-3-yl)-1H-pyrazole, 4-(2-aminopyridin-4-yl)-3-(3,4-dichlorophenyl)-1-(1,6-dihydro-6-oxopyridazin-3-yl)-1H-pyrazole, 4-(2-aminopyridin-4-yl)-1-(1,6-dihydro-6-oxopyridazin-3-yl)-3-(3-trifluoromethylphenyl)-1H-pyrazole, 4-(2-aminopyridin-4-yl)-3-(2-fluorophenyl)-1-(1,6-dihydro-6-oxopyridazin-3-yl)-1H-pyrazole, 3-(2-fluorophenyl)-1-(1,6-dihydro-6-oxopyridazin-3-yl)-4-[2-(2,2,2-trifluoroethyl)aminopyridin-4-yl]-1H-pyrazole, 4-(2-acetylaminopyridin-4-yl)-3-(2-fluorophenyl)-1-(1,6-dihydro-6-oxopyridazin-3-yl)-1H-pyrazole, 4-(2-aminopyrimidin-4-yl)-3-(2-fluorophenyl)-1-(1,6-dihydro-6-oxopyridazin-3-yl)-1H-pyrazole, 4-(2-aminopyridin-4-yl)-3-(2,4-difluorophenyl)-1-(1,6-dihydro-6-oxopyridazin-3-yl)-1H-pyrazole, 4-(2-cyclopropylcarbonylaminopyridin-4-yl)-3-(4-fluorophenyl-1-(1,6-dihydro-6-oxopyridazin-3-yl)-1H-pyrazole, 4-(2-cyclopropylcarbonylaminopyridin-4-yl)-3-(2-fluorophenyl)-1-(1,6-dihydro-6-oxopyridazin-3-yl)-1H-pyrazole or 3-(4-fluorophenyl)-1-(1,6-dihydro-6-oxopyridazin-3-yl)-4-[2-(4-methoxybenzylamino)pyrimidin-4-yl]-1H-pyrazole.

10. The pyrazole compound or a pharmaceutically acceptable salt thereof according to claim 1, wherein the compound is represented by the formula (I):

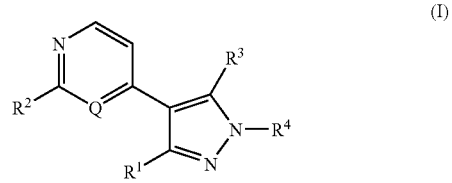

(I)

wherein $R^1$ represents a phenyl group which may be substituted by a group(s) selected from the group consisting of a halogen atom, a $C_1$-$C_6$ alkyl group, a halogeno $C_1$-$C_6$ alkyl group, a $C_1$-$C_6$ alkoxy group, a halogeno $C_1$-$C_6$ alkoxy group and a $C_1$-$C_6$ alkylthio group, $R^2$ represents a hydrogen atom, a halogen atom, a $C_1$-$C_6$ alkyl group, a $C_1$-$C_6$ alkoxy group, a $C_1$-$C_6$ alkylthio group, a $C_1$-$C_6$ alkylsulfinyl group, a $C_1$-$C_6$ alkylsulfonyl group or a group: —$NR^5R^6$ wherein $R^5$ and $R^6$ may be the same or different from each other, and each represents a hydrogen atom, a $C_1$-$C_6$ alkyl group, a halogeno $C_1$-$C_6$ alkyl group, a $C_3$-$C_7$ cycloalkyl group, a $C_1$-$C_6$ alkyl-carbonyl group, a $C_3$-$C_7$ cycloalkyl-carbonyl group, a formyl group, a $C_1$-$C_6$ alkoxy-carbonyl group or a $C_1$-$C_6$ alkylsulfonyl group, or a $C_7$-$C_{12}$ aralkyl group or a benzoyl group each of which may be substituted by a group(s) selected from the group consisting of a halogen atom, a $C_1$-$C_6$ alkyl group, a halogeno $C_1$-$C_6$ alkyl group, a $C_1$-$C_6$ alkoxy group and a halogeno $C_1$-$C_6$ alkoxy group, Q represents CH or a nitrogen atom, $R^3$ represents a hydrogen atom, a $C_1$-$C_6$ alkyl group or an amino group, $R^4$ represents the formula (III):

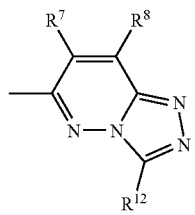

(III)

wherein $R^7$ represents a hydrogen atom or a $C_1$-$C_6$ alkyl group, $R^8$ represents a hydrogen atom, a $C_1$-$C_6$ alkyl group or a group: —$NR^{10}R^{11}$ wherein $R^{10}$ and $R^{11}$ may be the same or different from each other, and each represents a hydrogen atom, a $C_1$-$C_6$ alkyl group, a $C_1$-$C_6$ alkyl-carbonyl group, a formyl group, a $C_1$-$C_6$ alkoxy-carbonyl group or a $C_1$-$C_6$ alkylsulfonyl group, $R^{12}$ represents a hydrogen atom, a $C_1$-$C_6$ alkyl group, a halogeno $C_1$-$C_6$ alkyl group or a group: —$NR^{10}R^{11}$ wherein $R^{10}$ and $R^{11}$ may be the same or different from each other, and each represents a hydrogen atom, a $C_1$-$C_6$ alkyl group, a $C_1$-$C_6$ alkyl-carbonyl group, a formyl group, a $C_1$-$C_6$ alkoxy-carbonyl group or a $C_1$-$C_6$ alkylsulfonyl group.

11. The pyrazole compound or a pharmaceutically acceptable salt thereof according to claim 10, wherein $R^1$ represents a phenyl group which may be substituted by 1 to 3 group(s) selected from the group consisting of a halogen atom, a $C_1$-$C_4$ alkyl group, a halogeno $C_1$-$C_4$ alkyl group, a $C_1$-$C_4$ alkoxy group, a halogeno $C_1$-$C_4$ alkoxy group and a $C_1$-$C_4$ alkylthio group, $R^2$ represents a hydrogen atom, a halogen atom, a $C_1$-$C_4$ alkyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group or a group: —$NR^5R^6$ (wherein $R^5$ and $R^6$ may be the same or different from each other, and each represents a hydrogen atom, a $C_1$-$C_4$ alkyl group, a halogeno $C_1$-$C_4$ alkyl group, a cycloalkyl group, a $C_1$-$C_4$ alkyl-carbonyl group, a $C_3$-$C_6$ cycloalkyl-carbonyl group, a formyl group, a $C_1$-$C_4$ alkoxy-carbonyl group or a $C_1$-$C_4$ alkylsulfonyl group, or a $C_7$-$C_{12}$ aralkyl group or a benzoyl group each of which may be substituted by a group(s) selected from the group consisting of a halogen atom, a $C_1$-$C_4$ alkyl group, a halogeno $C_1$-$C_4$ alkyl group, a $C_1$-$C_4$ alkoxy group and a halogeno $C_1$-$C_4$ alkoxy group), $R^3$ represents a hydrogen atom, a $C_1$-$C_4$ alkyl group or an amino group, $R^4$ represents the formula (III)

wherein $R^7$ represents a hydrogen atom or a $C_1$-$C_4$ alkyl group, $R^8$ represents a hydrogen atom, a $C_1$-$C_4$ alkyl group, an amino group, a $C_1$-$C_4$ alkylamino group, a di($C_1$-$C_4$ alkyl)amino group, a $C_1$-$C_4$ alkyl-carbonylamino group, a formylamino group, a $C_1$-$C_4$ alkoxy-carbonylamino group or a $C_1$-$C_4$ alkylsulfonylamino group, $R^{12}$ represents a hydrogen atom, a $C_1$-$C_4$ alkyl group, a fluoro $C_1$-$C_4$ alkyl group, an amino group, a $C_1$-$C_4$ alkylamino group, a di($C_1$-$C_4$ alkyl)amino group, a $C_1$-$C_4$ alkyl-carbonylamino group, a formylamino group, a $C_1$-$C_4$ alkoxy-carbonylamino group or a $C_1$-$C_4$ alkylsulfonylamino group.

12. The pyrazole compound or a pharmaceutically acceptable salt thereof according to claim 11, wherein $R^1$ represents a phenyl group which may be substituted by 1 to 2 group(s) selected from the group consisting of a halogen atom, a $C_1$-$C_4$ alkyl group, a fluoro $C_1$-$C_4$ alkyl group, a $C_1$-$C_4$ alkoxy group, a fluoro $C_1$-$C_4$ alkoxy group and a $C_1$-$C_4$ alkylthio group, $R^2$ represents a hydrogen atom, a halogen atom, a $C_1$-$C_4$ alkyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a di($C_1$-$C_4$ alkyl)amino group, a fluoro $C_1$-$C_4$ alkylamino group, a $C_3$-$C_6$ cycloalkylamino group, a $C_1$-$C_4$ alkyl-carbonylamino group, a $C_3$-$C_6$ cycloalkyl-carbonylamino group, a N—($C_3$-$C_6$ cycloalkyl-carbonyl)-N—($C_1$-$C_4$ alkyl)amino group, a formylamino group, a $C_1$-$C_4$ alkoxy-carbonylamino group, a $C_1$-$C_4$ alkylsulfonylamino group, or a benzylamino group, a 1-phenethylamino group or a benzoylamino group the phenyl group portion thereof may be substituted by a group(s) selected from the group consisting of a halogen atom, a $C_1$-$C_4$ alkyl group, a fluoro $C_1$-$C_4$ alkyl group, a $C_1$-$C_4$ alkoxy group and a fluoro $C_1$-$C_4$ alkoxy group, $R^3$ represents a hydrogen atom, a methyl group or an amino group, $R^4$ represents the formula (III)

wherein $R^7$ represents a hydrogen atom, a methyl group or an ethyl group, $R^8$ represents a hydrogen atom, a methyl group, an ethyl group, an amino group, a methylamino group, a dimethylamino group, an ethylamino group, a diethylamino group, an isopropylamino group, an acetylamino group, a formylamino group, a methoxycarbonylamino group, an ethoxycarbonylamino group, a methylsulfonylamino group or an ethylsulfonylamino group, $R^{12}$ represents a hydrogen atom, a methyl group, an ethyl group, a trifluoromethyl group, a 2,2,2-trifluoroethyl group, an amino group, a methylamino group, a dimethylamino group, an ethylamino group, a diethylamino group, an isopropylamino group, an acetylamino group, a formylamino group, a methoxycarbonylamino group, an ethoxycarbonylamino group, a methylsulfonylamino group or an ethylsulfonylamino group.

13. The pyrazole compound or a pharmaceutically acceptable salt thereof according to claim 12, wherein $R^1$ represents a phenyl group which may be substituted by 1 to 2 group(s) selected from the group consisting of a fluorine atom, a chlorine atom, a bromine atom, a methyl group, an ethyl group, an isopropyl group, a difluoromethyl group, a trifluoromethyl group, a 2-fluoroethyl group, a 2,2,2-trifluoroethyl group, a methoxy group, an ethoxy group, an isopropoxy group, a fluoromethoxy group, a difluoromethoxy group, a trifluoromethoxy group and a methylthio group, $R^2$ represents a hydrogen atom, a fluorine atom, a chlorine atom, a methyl group, a methoxy group, a methylthio group, a methylsulfinyl group, a methylsulfonyl group, an amino group, a methylamino group, a dimethylamino group, an ethylamino group, a diethylamino group, a propylamino group, an isopropylamino group, a trifluoromethylamino group, a 2,2,2-trifluoroethylamino group, a cyclopropylamino group, a cyclohexylamino group, an acetylamino group, a propionylamino group, a cyclopropylcarbonylamino group, a cyclopentylcarbonylamino group, a N-cyclopropylcarbonyl-N-methylamino group, a formylamino group, a methoxycarbonylamino group, an ethoxycarbonylamino group, a t-butoxycarbonylamino group, a methylsulfonylamino group, an ethylsulfonylamino group, or a benzylamino group, a 1-phenethylamino group or a benzoylamino group the phenyl group portion thereof may be substituted by a group(s) selected from the group consisting of a fluorine atom, a methyl group, a trifluoromethyl group, a methoxy group and a difluoromethoxy group, $R^3$ represents a hydrogen atom, a methyl group or an amino group, $R^4$ represents the formula (III)

wherein $R^7$ represents a hydrogen atom or a methyl group, $R^8$ represents a hydrogen atom, a methyl group, an amino group, a methylamino group, a dimethylamino group, an acetylamino group, a formylamino group, a methoxycarbonylamino group or a methylsulfonylamino group, $R^{12}$ represents a hydrogen atom, a methyl group, a trifluoromethyl group, an amino group, a methylamino group, a dimethylamino group, an acetylamino group, a formylamino group, a methoxycarbonylamino group or a methylsulfonylamino group.

14. The pyrazole compound or a pharmaceutically acceptable salt thereof according to claim 13, wherein $R^1$ represents a phenyl group which may be substituted by 1 to 2 group(s) selected from the group consisting of a fluorine atom, a chlorine atom, a methyl group, a difluoromethyl group, a trifluoromethyl group, a methoxy group, a fluoromethoxy group, a difluoromethoxy group and a trifluoromethoxy group, $R^2$ represents a hydrogen atom, a fluorine atom, a methyl group, a methoxy group, a methylthio group, a methylsulfinyl group, a methylsulfonyl group, an amino group, a methylamino group, a dimethylamino group, an ethylamino group, an isopropylamino group, a 2,2,2-trifluoroethylamino group, a cyclopropylamino group, an acetylamino group, a cyclopropylcarbonylamino group, a cyclopentylcarbonylamino group, a N-cyclopropylcarbonyl-N-methylamino group, a methoxycarbonylamino group, a methylsulfonylamino group, a 4-methoxybenzylamino group, a 1-phenethylamino group or a benzoylamino group, $R^3$ represents a hydrogen atom, a methyl group or an amino group, $R^4$ represents a [1,2,4]triazolo[4,3-b]pyridazin-6-yl group, a 3-methyl-[1,2,4]triazolo[4,3-b]pyridazin-6-yl group, a 3-trifluoromethyl-[1,2,4]triazolo[4,3-b]pyridazin-6-yl group, a 3-(2,2,2-trifluoroethyl-[1,2,4]triazolo[4,3-b]pyridazin-6-yl group, a 3-amino-[1,2,4]triazolo[4,3-b]pyridazin-6-yl group, a 3-methylamino-[1,2,4]triazolo[4,3-b]pyridazin-6-yl group, a 3-dimethylamino-[1,2,4]triazolo[4,3-b]pyridazin-6-yl group, a 3-acetylamino-[1,2,4]triazolo[4,3-b]pyridazin-6-yl group, a 3-methoxycarbonylamino-[1,2,4]triazolo[4,3-b]pyridazin-6-yl group, a 3-methylsulfonylamino-[1,2,4]triazolo[4,3-b]pyridazin-6-yl group, a 7-methyl-[1,2,4]triazolo[4,3-b]pyridazin-6-yl group, a 8-methyl-[1,2,4]triazolo[4,3-b]pyridazin-6-yl group, a 8-amino-[1,2,4]triazolo[4,3-b]pyridazin-6-yl group, a 8-methylamino-[1,2,4]triazolo[4,3-b]pyridazin-6-yl group, a 8-dimethylamino-[1,2,4]triazolo[4,3-b]pyridazin-6-yl group, a 8-acetylamino-[1,2,4]triazolo[4,3-b]pyridazin-6-yl group, a 8-methoxycarbonylamino-[1,2,4]triazolo[4,3-b]pyridazin-6-yl group, a 8-methylsulfonylamino-[1,2,4]triazolo[4,3-b]-pyridazin-6-yl group, a 3,8-dimethyl-[1,2,4]triazolo[4,3-b]pyridazin-6-yl group, a 7,8-dimethyl-[1,2,4 ]triazolo[4,3-b]pyridazin-6-yl group, a 3-amino-8-methyl-[1,2,4]triazolo[4,3-b]pyridazin-6-yl group or a 8-amino-3-methyl-[1,2,4]triazolo[4,3-b]pyridazin-6-yl group.

15. The pyrazole compound or a pharmaceutically acceptable salt thereof according to claim 14, wherein $R^1$ represents a phenyl group, a 2-fluorophenyl group, a 3-fluorophenyl group, a 4-fluorophenyl group, a 3-chlorophenyl group, a 4-chlorophenyl group, a 3,4-difluorophenyl group, a 2,4-difluorophenyl group, a 3,4-dichlorophenyl group, a 3-chloro-4-fluorophenyl group, a 4-chloro-3-fluorophenyl group or a 3-trifluoromethylphenyl group, $R^2$ a hydrogen atom, a methoxy group, an amino group, a methylamino group, an ethylamino group, an isopropylamino group, a 2,2,2-trifluoroethylamino group, an acetylamino group, a cyclopropylcarbonylamino group, a cyclopentylcarbonylamino group, a methoxycarbonylamino group, a methylsulfonylamino group, a 4-methoxybenzylamino group, a 1-phenethylamino group or a benzoylamino group, $R^3$ represents a hydrogen atom, a methyl group or an amino group, $R^4$ represents a [1,2,4]triazolo[4,3-b]pyridazin-6-yl group, a 3-methyl-[1,2,4]triazolo[4,3-b]pyridazin-6-yl group, a 3-trifluoromethyl-[1,2,4]triazolo[4,3-b]pyridazin-6-yl group, a 3-amino-[1,2,4]triazolo[4,3-b]pyridazin-6-yl group, a 3-methylamino-[1,2,4]triazolo[4,3-b]pyridazin-6-yl group, a 3-acetylamino-[1,2,4]triazolo[4,3-b]pyridazin-6-yl group, a 3-methoxycarbonylamino-[1,2,4]triazolo[4,3-b]pyridazin-6-yl group, a 3-methylsulfonylamino-[1,2,4]triazolo[4,3-b]pyridazin-6-yl group, a 7-methyl-[1,2,4]triazolo[4,3-b]pyridazin-6-yl group, a 8-methyl-[1,2,4]triazolo[4,3-b]pyridazin-6-yl group or a 8-amino-[1,2,4]triazolo[4,3-b]pyridazin-6-yl group.

16. The pyrazole compound or a pharmaceutically acceptable salt thereof according to claim 15, wherein $R^1$ represents a phenyl group, a 2-fluorophenyl group, a 3-fluorophenyl group, a 4-fluorophenyl group, a 3-chlorophenyl group, a 4-chlorophenyl group, a 3,4-difluorophenyl group, a 2,4-difluorophenyl group, a 3,4-dichlorophenyl group, a 3-chloro-4-fluorophenyl group, a 4-chloro-3-fluorophenyl group or a 3-trifluoromethylphenyl group, $R^2$ represents a hydrogen atom, a methoxy group, an amino group, a methylamino group, an ethylamino group, an isopropylamino group, a 2,2,2-trifluoroethylamino group, an acetylamino group, a cyclopropylcarbonylamino group, a cyclopentylcarbonylamino group, a methoxycarbonylamino group, a methylsulfonylamino group, a 4-methoxybenzylamino group, a 1-phenethylamino group or a benzoylamino group, $R^3$ represents a hydrogen atom, $R^4$ represents a [1,2,4]triazolo[4,3-b]pyridazin-6-yl group, a 3-methyl-[1,2,4]triazolo[4,3-b]pyridazin-6-yl group, a 3-trifluoromethyl-[2,4]triazolo[4,3-b]pyridazin-6-yl group, a 3-amino-[1,2,4]triazolo[4,3-b]pyridazin-6-yl group or a 3-acetylamino-[1,2,4]triazolo[4,3-b]pyridazin-6-yl group.

17. The pyrazole compound or a pharmaceutically acceptable salt thereof according to claim 16, wherein the pyrazole compound is 4-(2-aminopyridin-4-yl)-3-phenyl-1-([1,2,4]triazolo[4,3-b]pyridazin-6-yl)-1H-pyrazole, 3-(4-fluorophenyl)-4-(pyridin-4-yl)-1-([1,2,4]triazolo[4,3-b]pyridazin-6-yl)-1H-pyrazole, 3-(4-fluorophenyl)-4-(2-methoxypyridin-4-yl)-1-([1,2,4]triazolo[4,3-b]pyridazin-6-yl)-1H-pyrazole, 4-(2-aminopyridin-4-yl)-3-(4-fluorophenyl)-1-([1,2,4] triazolo[4,3-b]pyridazin-6-yl)-1H-pyrazole,
3-(4-fluorophenyl)-4-(2-methylaminopyridin-4-yl)-1-([1, 2,4]triazolo[4,3-b]pyridazin-6-yl)-1H-pyrazole,
4-(2-ethylaminopyridin-4-yl)-3-(4-fluorophenyl)-1-([1,2, 4]triazolo[4,3-b]pyridazin-6-yl)-1H-pyrazole,
3-(4-fluorophenyl)-4-(2-isopropylaminopyridin-4-yl)-1-([1,2,4]triazolo[4,3-b]pyridazin-6-yl)-1H-pyrazole,
3-(4-fluorophenyl)-1-([1,2,4]triazolo[4,3-b]pyridazin-6-yl)-4-[2-(2,2,2-trifluoroethyl)aminopyridin-4-yl]-1H-pyrazole,
4-(2-acetylaminopyridin-4-yl)-3-(4-fluorophenyl)-1-([1, 2,4]triazolo[4,3-b]pyridazin-6-yl)-1H-pyrazole,
3-(4-fluorophenyl)-4-(2-methoxycarbonylaminopyridin-4-yl)-1-([1,2,4]triazolo[4,3-b]pyridazin-6-yl)-1H-pyrazole,
3-(4-fluorophenyl)-4-(2-methylsulfonylaminopyridin-4-yl)-1-([1,2,4]triazolo[4,3-b]pyridazin-6-yl)-1H-pyrazole,
3-(4-fluorophenyl)-4-[2-(1-phenethylamino)pyridin-4-yl]-1-([1,2,4]triazolo[4,3-b]pyridazin-6-yl)-1H-pyrazole,
4-benzoylaminopyridin-4-yl)-3-(4-fluorophenyl)-1-([1,2,4]triazolo[4,3-b]pyridazin-6-yl)-1H-pyrazole,
4-(2-aminopyridin-4-yl)-3-(4-fluorophenyl)-1-(3-methyl-[1,2,4]triazolo[4,3-b]pyridazin-6-yl)-1H-pyrazole,
4-(2-aminopyridin-4-yl)-3-(4-fluorophenyl)-1-(3-trifluoromethyl-[1,2,4]triazolo[4,3-b]pyridazin-6-yl)-1H-pyrazole,
4-(2-aminopyridin-4-yl)-1-(3-amino-[1,2,4]triazolo[4,3-b]pyridazin-6-yl)-3-(4-fluorophenyl)-1H-pyrazole,
1-(3-acetylamino-[1,2,4]triazolo[4,3-b]pyridazin-6-yl)-4-(2-aminopyridin-4-yl)-3-(4-fluorophenyl)-1H-pyrazole,
4-(2-aminopyrimidin-4-yl)-3-(4-fluorophenyl)-1-([1,2,4] triazolo[4,3-b]pyridazin-6-yl)-1H-pyrazole,
3-(3-fluorophenyl)-4-(pyridin-4-yl)-1-([1,2,4]triazolo[4, 3-b]pyridazin-6-yl)-1H-pyrazole,
4-(2-aminopyridin-4-yl)-3-(3-fluorophenyl)-1-([1,2,4] triazolo[4,3-b]pyridazin-6-yl)-1H-pyrazole,
4-(2-aminopyridin-4-yl)-3-(4-chlorophenyl)-1-([1,2,4] triazolo[4,3-b]pyridazin-6-yl)-1H-pyrazole,
4-(2-aminopyridin-4-yl)-3-(3-chlorophenyl)-1-([1,2,4] triazolo[4,3-b]pyridazin-6-yl)-1H-pyrazole,
3-(3,4-difluorophenyl)-4-pyridin-4-yl)-1-([1,2,4]triazolo [4,3-b]pyridazin-6-yl)-1H-pyrazole,
4-(2-aminopyridin-4-yl)-3-(3,4-difluorophenyl)-1-([1,2, 4]triazolo[4,3-b]pyridazin-6-yl)-1H-pyrazole,
4-(2-aminopyridin-4-yl)-3-(3,4-dichlorophenyl)-1-([1,2, 4]triazolo[4,3-b]pyridazin-6-yl)-1H-pyrazole,
4-(2-aminopyridin-4-yl)-3-(3-chloro-4-fluorophenyl)-1-([1,2,4]triazolo[4,3-b]pyridazin-6-yl)-1H-pyrazole,
4-(2-aminopyridin-4-yl)-3-(4-chloro-3-fluorophenyl)-1-([1,2,4]triazolo[4,3-b]pyridazin-6-yl)-1H-pyrazole,
4-(2-aminopyridin-4-yl)-1-([1,2,4]triazolo[4,3-b]pyridazin-6-yl)-3-(3-trifluoromethylphenyl)-1H-pyrazole,
4-(2-aminopyridin-4-yl)-3-(2-fluorophenyl)-1-([1,2,4] triazolo[4,3-b]pyridazin-6-yl)-1H-pyrazole,
4-(2-aminopyrimidin-4-yl)-3-(2-fluorophenyl)-1-([1,2,4] triazolo[4,3-b]pyridazin-6-yl)-1H-pyrazole,
4-(2-aminopyridin-4-yl)-3-(2,4-difluorophenyl)-1-([1,2, 4]triazolo[4,3-b]pyridazin-6-yl)-1H-pyrazole,
4-(2-cyclopropylcarbonylaminopyridin-4-yl)-3-(4-fluorophenyl)-1-([1,2,4]triazolo[4,3-b]pyridazin-6-yl)-1H-pyrazole,
4-(2-cyclopentylcarbonylaminopyridin-4-yl)-3-(4-fluorophenyl)-1-([1,2,4]triazolo[4,3-b]pyridazin-6-yl)-1H-pyrazole or
3-(4-fluorophenyl)-4-[2-(4-methoxybenzyl)aminopyrimidin-4-yl]-1-([1,2,4]triazolo[4,3-b]pyridazin-6-yl)-1H-pyrazole.

18. The pyrazole compound or a pharmaceutically acceptable salt thereof according to claim 1, wherein the compound is represented by the formula (I):

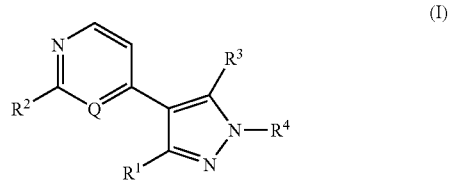

wherein $R^1$ represents a phenyl group which may be substituted by a group(s) selected from the group consisting of a halogen atom, a $C_1$-$C_6$ alkyl group, a halogeno $C_1C_6$ alkyl group, a $C_1$-$C_6$ alkoxy group, a halogeno $C_1$-$C_6$ alkoxy group and a $C_1$-$C_6$ alkylthio group, $R^2$ represents a hydrogen atom, a halogen atom, a $C_1$-$C_6$ alkyl group, a $C_1$-$C_6$ alkoxy group, a $C_1$-$C_6$ alkylthio group, a $C_1$-$C_6$ alkylsulfinyl group, a $C_1$-$C_6$ alkylsulfonyl group or a group:—$NR^5R^6$ wherein $R^5$ and $R^6$ may be the same or different from each other, and each represents a hydrogen atom, a $C_1$-$C_6$ alkyl group, a halogeno $C_1$-$C_6$ alkyl group, a $C_3$-$C_7$ cycloalkyl group, a $C_1$-$C_6$ alkyl-carbonyl group, a $C_3$-$C_7$ cycloalkyl-carbonyl group, a formyl group, a $C_1$-$C_6$ alkoxy-carbonyl group or a $C_1$-$C_6$ alkylsulfonyl group, or a $C_7$-$C_{12}$ aralkyl group or a benzoyl group each of which may be substituted by a group(s) selected from the group consisting of a halogen atom, a $C_1$-$C_6$ alkyl group, a halogeno $C_1$-$C_6$ alkyl group, a $C_1$-$C_6$ alkoxy group and a halogeno $C_1$-$C_6$ alkoxy group, Q represents CH or a nitrogen atom, $R^3$ represents a hydrogen atom, a $C_1$-$C_6$ alkyl group or an amino group, $R^4$ represents the formula (IV):

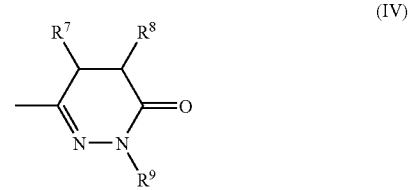

wherein $R^7$ represents a hydrogen atom or a $C_1$-$C_6$ alkyl group, $R^8$ represents a hydrogen atom, a $C_1$-$C_6$ alkyl group or a group: $NR^{10}R^{11}$ wherein $R^{10}$ and $R^{11}$ may be the same or different from each other, and each represents a hydrogen atom, a $C_1$-$C_6$ alkyl group, a $C_1$-$C_6$ alkyl-carbonyl group, a formyl group, a $C_1$-$C_6$ alkoxy-carbonyl group or a $C_1$-$C_6$ alkylsulfonyl group, $R^9$ represents a hydrogen atom or a $C_1$-$C_6$ alkyl group.

19. The pyrazole compound or a pharmaceutically acceptable salt thereof according to claim 18, wherein $R^1$ represents a phenyl group which may be substituted by 1 to 3 group(s) selected from the group consisting of a halogeno atom, a $C_1$-$C_4$ alkyl group, a halogeno $C_1$-$C_4$ alkyl group, a $C_1$-$C_4$ alkoxy group, a halogeno $C_1$-$C_4$ alkoxy group and a $C_1$-$C_4$ alkylthio group, $R^2$ represents a hydrogen atom, a halogen atom, a $C_1$-$C_4$ alkyl group, a $C_1$-$C_4$ alkoxy group, a $C_1$-$C_4$ alkylthio group, a $C_1$-$C_4$ alkylsulfonyl group, a $C_1$-$C_4$ alkylsulfonyl group or a group: —$NR^5R^6$ (wherein $R^5$ and $R^6$ may be the same or different from each other, and each represents a hydrogen atom, a $C_1$-$C_4$ alkyl group, a halogeno $C_1$-$C_4$ alkyl group, a cycloalkyl group, a $C_1$-$C_4$ alkyl-carbonyl group, a $C_3$-$C_6$ cycloalkyl-carbonyl group, a formyl group, a $C_1$-$C_4$ alkoxy-carbonyl group or a $C_1$-$C_4$ alkylsulfonyl group, or a $C_7$-$C_{12}$ aralkyl group or a benzoyl group each of which may be substituted by a group(s) selected from the group consisting of a halogeno atom, a $C_1$-$C_4$ alkyl group, a halogeno $C_1$-$C_4$ alkyl group, a $C_1$-$C_4$ alkoxy group and a halogeno $C_1$-$C_4$ alkoxy group), $R^3$ represents a hydrogen atom, a $C_1$-$C_4$ alkyl group or an amino group, $R^4$ represents the formula (IV)

wherein $R^7$ represents a hydrogen atom or a $C_1$-$C_4$ alkyl group, $R^8$ represents a hydrogen atom, a $C_1$-$C_4$ alkyl group, an amino group, a $C_1$-$C_4$ alkylamino group, a di($C_1$-$C_4$ alkyl)amino group, a $C_1$-$C_4$ alkyl-carbonylamino group, a formylamino group, a $C_1$-$C_4$ alkoxycarhonylamino group or a $C_1$-$C_4$ alkylsulfonylamino group, $R^9$ represents a hydrogen atom or a $C_1$-$C_4$ alkyl group.

20. The pyrazole compound or a pharmaceutically acceptable salt thereof according to claim 19, wherein $R^1$ represents a phenyl group which may be substituted by 1 to 2 group(s) selected from the group consisting of a halogeno atom, a $C_1$-$C_4$ alkyl group, a fluoro $C_1$-$C_4$ alkyl group, a $C_1$-$C_4$ alkoxy group, a fluoro $C_1$-$C_4$ alkoxy group and a $C_1$-$C_4$ alkylthio group, $R^2$ represents a hydrogen atom, a halogeno atom, a $C_1$-$C_4$ alkyl group, a $C_1$-$C_4$ alkoxy group, a $C_1$-$C_4$ alkylthio group, a $C_1$-$C_4$ alkylsulfonyl group, a $C_1$-$C_4$ alkylsulfonyl group, an amino group, a $C_1$-$C_4$ alkylamino group, a di($C_1$-$C_4$ alkyl)amino group, a fluoro $C_1$-$C_4$ alkylamino group, a $C_3$-$C_6$ cycloalkylamino group, a $C_1$-$C_4$ alkyl-carbonylamino group, a $C_3$-$C_6$ cycloalkyl-carbonylamino group, a N-($C_3$-$C_6$ cycloalkyl-carbonyl)-N-($C_1$-$C_4$ alkyl)amino group, a formylamino group, a $C_1$-$C_4$ alkoxy-carbonylamino group, a $C_1$-$C_4$ alkylsulfonylamino group, or a benzylamino group, a 1-phenethylamino group or a benzoylamino group the phenyl group portion thereof may be substituted by a group(s) selected from the group consisting of a halogen atom, a $C_1$-$C_4$ alkyl group, a fluoro $C_1$-$C_4$ alkyl group, a $C_1$-$C_4$ alkoxy group and a fluoro $C_1$-$C_4$ alkoxy group, $R^3$ represents a hydrogen atom, a methyl group or an amino group, $R^4$ represents the formula (IV)

wherein $R^7$ represents a hydrogen atom, a methyl group or an ethyl group, $R^8$ represents a hydrogen atom, a methyl group, an ethyl group, an amino group, a methylamino group, a dimethylamino group, an ethylamino group, a diethylamino group, an isopropylamino group, an acetylamino group, a formylamino group, a methoxycarbonylamino group, an ethoxycarbonylamino group, a methylsulfonylamino group or an ethylsulfonyl amino group, $R^9$ represents a hydrogen atom, a methyl group or an ethyl group.

21. The pyrazole compound or a pharmaceutically acceptable salt thereof according to claim 20, wherein $R^7$ represents a phenyl group which may be substituted by 1 to 2 group(s) selected from the group consisting of a fluorine atom, a chlorine atom, a bromine atom, a methyl group, an ethyl group, an isopropyl group, a difluoromethyl group, a trifluoromethyl group, a 2-fluoroethyl group, a 2,2,2-trifluoroethyl group, a methoxy group, an ethoxy group, an isopropoxy group, a fluoromethoxy group, a difluoromethoxy group, a trifluoromethoxy group and a methylthio group, $R^2$ represents a hydrogen atom, a fluorine atom, a chlorine atom, a methyl group, a methoxy group, a methylthio group, a methylsulfinyl group, a methylsulfonyl group, an amino group, a methyl amino group, a dimethylamino group, an ethylamino group, a diethyl amino group, a propylamino group, an isopropylamino group, a trifluoromethylamino group, a 2,2,2-trifluoroethylamino group, a cyclopropylamino group, a cyclohexylamino group, an acetylamino group, a propionylamino group, a cyclopropylcarbonylamino group, a cyclopentylcarbonylamino group, a N-cyclopropylcarbonyl-N-methylamino group, a formylamino group, a methoxycarbonylamino group, an ethoxycarbonylamino group, a t-butoxycarbonylamino group, a methylsulfonylamino group, an ethylsulfonylamino group, or a benzylamino group, a 1-phenethylamino group or a benzoylamino group the phenyl group portion thereof may be substituted by a group(s) selected from the group consisting of a fluorine atom, a methyl group, a trifluoromethyl group, a methoxy group and a difluoromethoxy group, $R^3$ represents a hydrogen atom, a methyl group or an amino group, $R^4$ represents the formula (IV)

wherein $R^7$ represents a hydrogen atom or a methyl group, $R^8$ represents a hydrogen atom, a methyl group, an amino group, a methylamino group, a dimethylamino group, an acetylamino group, a formylamino group, a methoxycarbonylamino group or a methylsulfonylamino group, $R^9$ represents a hydrogen atom or a methyl group.

22. The pyrazole compound or a pharmaceutically acceptable salt thereof according to claim 21, wherein $R^1$ represents a phenyl group which may be substituted by 1 or 2 group(s) selected from the group consisting of a fluorine atom, a chlorine atom, a methyl group, a difluoromethyl group, a trifluoromethyl group, a methoxy group, a fluoromethoxy group, a difluoromethoxy group and a trifluoromethoxy group, $R_2$ represents a hydrogen atom, a fluorine atom, a methyl group, a methoxy group, a methylthio group, a methylsulfinyl group, a methylsulfonyl group, an amino group, a methylamino group, a dimethylamino group, an ethylamino group, an isopropylamino group, a 2,2,2-trifluoroethylamino group, a cyclopropylamino group, an acetylamino group, a cyclopropylcarbonylamino group, a cyclopentylcarbonylamino group, a N-cyclopropylcarbonyl-N-methylamino group, a methoxycarbonylamino group, a methylsulfonylamino group, a 4-methoxybenzylamino group, a 1-phenethylamino group or a benzoylamino group, $R_3$ represents a hydrogen atom, a methyl group or an amino group, $R^4$ represents a 1,4,5,6-tetrahydro-6-oxopyridazin-3-yl group, a 1,4,5,6-tetrahydro-4-methyl-6-oxopyridazin-3-yl group, a 1,4,5,6-tetrahydro-5-methyl-6-oxopyridazin-3-yl group, a 5-amino-1,4,5,6-tetrahydro-6-oxopyridazin-3-yl group, a 1,4,5,6-tetrahydro-5-methylamino-6-oxopyridazin-3-yl group, a 5-acetylamino-1,4,5,6-tetrahydro-6-oxopyridazin-3-yl group, a 1,4,5,6-tetrahydro-5-methoxycarbonylamino-6-oxopyridazin-3-yl group, a 1,4,5,6-tetrahydro-5-methylsulfonylamino-6-oxopyridazin-3-yl group, a 1,4,5,6-tetrahydro-1-methyl-6-oxopyridazin-3-yl group, a 1,4,5,6-tetrahydro-1,4-dimethyl-6-oxopyridazin-3-yl group, a 1,4,5,6-tetrahydro-1,5-dimethyl-6-oxopyridazin-3-yl group or a 5-amino-1,4,5,6-tetrahydro-1-methyl-6-oxopyridazin-3-yl group.

23. The pyrazole compound or a pharmaceutically acceptable salt thereof according to claim 22, wherein $R_1$ represents a phenyl group, a 2-fluorophenyl group, a 3-fluorophenyl group, a 4-fluorophenyl group, a 3-chlorophenyl group, a 4-chlorophenyl group, a 3,4-difluorophenyl group, a 2,4-difluorophenyl group, a 3,4-dichlorophenyl group, a 3-chloro-4-fluorophenyl group, a 4-chloro-3-fluorophenyl group or a 3-trifluoromethyiphenyl group, $R_2$ represents a hydrogen atom, a methoxy group, an amino group, a methylamino group, an ethylamino group, an isopropylamino group, a 2,2,2-trifluoroethylamino group, an acetylamino group, a cyclopropylcarbonylamino group, a cyclopentylcarbonylamino group, a methoxycarbonylamino group, a methylsulfonylamino group, a 4-methoxybenzylamino group, a 1-phenethylamino group or a benzoylamino group, $R^3$ represents a hydrogen atom, a methyl group or an amino group, $R^4$ represents a 1,4,5,6-tetrahydro-6-oxopyridazin-3-yJ group, a 1,4,5,6-tetrahydro-4-methyl-6-oxopyridazin-3-yl group, a 1,4,5,6-tetrahydro-5-methyl-6-oxopyridazin-3-yl group, a 5-amino-1,4,5,6-tetrahydro-6-oxopyridazin-3-yl group, a 1,4,5,6-tetrahydro-1-methyl-6-oxopyridazin-3-yl group or a 1,4,5,6-tetrahydro-1,5-dimethyl-6-oxopyridazin-3-yl group.

24. The pyrazole compound or a pharmaceutically acceptable salt thereof according to claim 23, wherein $R_1$ represents a phenyl group, a 2-fluorophenyl group, a 3-fluorophenyl group, a 4-florophenyl group, a 3-chlorophenyl group, a 4-chlorophenyl group, a 3,4-difluorophenyl group, a 2,4-difluorophenyl group, a 3,4-dichlorophenyl group, a 3-chloro-4-fluorophenyl group, a 4-chloro-3-fluorophenyl group or a 3-trifluoromethylphenyl group, $R^2$ represents a hydrogen atom, a methoxy group, an amino group, a methylamino group, an ethylamino group, an isopropylamino group, a 2,2,2-trifluoroethylamino group, an acetylamino group, a cyclopropylcarbonylamino group, a cyclopentylcarbonylamino group, a methoxycarbonylamino group, a methylsulfonylamino group, a 4-methoxybenzylamino group, a 1-phenethylamino group or a benzoylamino group, $R^3$ represents a hydrogen atom, $R^4$ represents a 1,4,5,6-tetrahydro-6-oxopyridazin-3-yl group, a 1,4,5,6-tetrahydro-4-methyl-6-oxopyridazin-3-yl group, a 1,4,5,6-tetrahydro-5-methyl-6-oxopyridazin-3-yl group or a 1,4,5,6-tetrahydro-1-methyl-6-oxopyridazin-3-yl group.

25. The pyrazole compound or a pharmaceutically acceptable salt thereof according to claim 24, wherein the pyrazole compound is 4-(2-aminopyridin-4-yl)-1-(1,4,5,6-tetrahydro-6-oxopyridazin-3-yl)-13-phenyl-1H-pyrazolc 3-(4-fluorophenyl)-1-(1,4,5,6-tetrahydro-6-oxopyridazin-3-yl)-4-(pyridin-4-yl)-1H-pyrazole, 4-(2-aminopyridin-4-yl)-3-(4-fluoropheny-1-(1,4,5,6-tetrahydro-6-oxopyridazin-3-yl)-1H-pyrazole, 3-(4-fluorophenyl)-1-(1,4,5,6-tetrahydro-6-oxopyridazin-3-yl)-4-[2-(2,2,2-trifluoroethyl)aminopyridin-4-yl]-1H-pyrazole, 4-(2-acetylaminopyridin-4-yl)-3-(4-fluorophenyl)-1-(1,4,5,6-tetrahydro-6-oxopyridazin-3-yl)-1H-pyrazole, 4-(2-aminopyridin-4-yl)-3-(4-fluorophenyl)-1-(1,4,5,6-tetrahydro-4-methyl-6-oxopyridazin-3-yl)-1H-pyrazole, 4-(2-aminopyridin-4-yl)-3-(4-fluorophenyl)-1-(1,4,5,6-tetrahydro-5-methyl-6-oxopyridazin-3-yl)-1H-pyrazole, 4-(2-aminopyridin-4-yl)-3-(4-fluorophenyl)-1-(1,4,5,6-tetrahydro-1-methyl-6-oxopyridazin-3-yl)-1H-pyrazole, 4-(2-aminopyridin-4-yl)-3-(4-fluorophenyl)-1-(1,4,5,6-tetrahydro-6-oxopyridazin-3-yl)-1H-pyrazole, 4-(2-aminopyridin-4-yl)-3-(3-fluorophenyl)-1-(1,4,5,6-tetrahydro-6-oxopyridazin-3-yl)-1H-pyrazole, 4-(2-aminopyridin-4-yl)-3-(4-chlorophenyl-1-(1,4,5,6-tetrahydro-6-oxopyridazin-3-yl)-1H-pyrazole, 4-(2-aminopyridin-4-yl)-3-(3-chlorophenyl)-1-(1,4,5,6-tetrahydro-6-oxopyridazin-3-yl)1H-pyrazole, 4-(2-aminopyridin-4-yl)-3-(3,4-difluorophenyl)-1-(1,4,5,6-tetrahydro-6-oxopyridazin-3-yl)-1H-pyrazole, 4-(2-aminopyridin-4-yl)-3-(3,4-dichlorophenyl)-1-(1,4,5,6-tetrahydro-6-oxopyridazin-3yl)-1H-pyrazole, 4-(2-aminopyridin-4-yl)-3-(3-chloro-4-florophenyl)-1-(1,4,5,6-tetrahydro-6-oxopyridazin-3yl)-1H-pyrazole, 4-(2-aminopyridin-4-yl)-3-(4-chloro-3-fluorophenyl)-1-(1,4,5,6-tetrahydro-6-oxopyridazin-3-yl)-1H-pyrazole, 4-(2-aminopyridin-4-yl)-1-(1,4,5,6-tetrahydro-6-oxopyridazin-3-yl)-3-(3-trifluoromethylphenyl)-1H-pyrazole, 4-(2-aminopyridin-4-yl)-3-(2-fluorophenyl-1-(1,4,5,6-tetrahydro-6-oxopyridazin-3-yl)-1H-pyrazole, 3-(2-fluorophenyl)-1-(1,4,5,6-tetrahydro-6-oxopyridazin-3-yl)-4-[2-(2,2,2-trifluoroethyl)aminopyridin-4-yl]-1H-pyrazole, 4-(2-acetylaminopyridin-4-yl)-3-(2-fluorophenyl)-1-(1,4,5,6-tetrahydro-6-oxopyridazin-3-yl)-1H-pyrazole, 4-(2-aminopyridin-4-yl)-3-(2-fluorophenyl-1-(1,4,5,6-tetrahydro-6-oxopyridazin-3-yl)-1H-pyrazole, 4-(2-aminopyridin-4-yl)-3-(2,4-difluorophenyl)-1-(1,4,5,6-tetrahydro-6-oxopyridazin-3-yl)-1H-pyrazole, 4-(2-cyclopropylcarbonylaminopyridin-4-yl)-(1,4,5,6-tetrahydro-6-oxopyridazin-3-yl)-3-phenyl-1-1H-pyrazole, 4-(2-cyclopropylcarbonylaminopyridin-4-yl)-3-(4-fluorophenyl)-1-(1,4,5,6-tetrahydro-6-oxopyridazin-3-yl)-1H-pyrazole or 4-(2-cyclopropylcarbonylaminopyridin-4-yl)-3-(2-fluorophenyl)-1-(1,4,5,6-tetrahydro-6-oxopyridazin-3-yl)-1H-pyrazole.

26. The pyrazole compound or a pharmaceutically acceptable salt thereof according to claim 1, wherein the compound is represented by the formula (I):

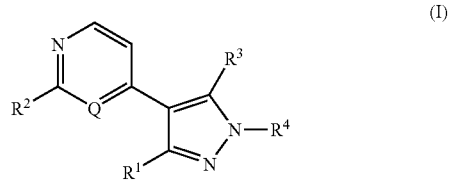

wherein $R_1$ represents a phenyl group which may be substituted by a group(s) selected from the group consisting of a halogeno atom, a $C_1$-$C_6$ alkyl group, a halogeno $C_1$-$C_6$ alkyl group, $C_1$-$C_6$ alkoxy group, a halogeno $C_1$-$C_6$ alkoxy group and a $C_1$-$C_6$ alkylthio group, $R^2$ represents a hydrogen atom, a halogeno atom, a $C_1$-$C_6$ alkyl group, a $C_1$-$C_6$ alkoxy group, a $C_1$-$C_6$ alkylthio group, a $C_1$-$C_6$ alkylsulfonyl group, a $C_1$-$C_6$ alkylsulfonyl group or a group: —$NR^5R^6$ wherein $R^5$ and $R^6$ may be the same or different from each other, and each represents a hydrogen atom, a $C_1$-$C_6$ alkyl group, a halogeno $C_1$-$C_6$ alkyl group, a $C_3$-$C_7$ cycloalkyl group, a $C_1$-$C_6$ alkyl-carbonyl group, a $C_3$-$C_7$ cycloalkyl-carbonyl group, a formyl group, a $C_1$-$C_6$ alkoxy-carbonyl group or a $C_1$-$C_6$ alkylsulfonyl group, or a $C_7$-$C_{12}$ aralkyl group or a benzoyl group each of which may be substituted by a group(s) selected from the group consisting of a halogeno atom, a $C_1$-$C_6$ alkyl group, a halogeno $C_1$-$C_6$ alkyl group, a $C_1$-$C_6$ alkoxy group and a halogeno $C_1$-$C_6$ alkoxy group, Q represents CH or a nitrogen atom, $R^3$ represents a hydrogen atom, a $C_1$-$C_6$ alkyl group or an amino group, $R^4$ represents the formula (V):

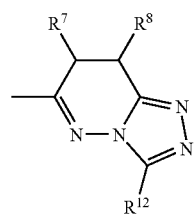

(V)

wherein $R^7$ represents a hydrogen atom or a $C_1$-$C_6$ alkyl group, $R^8$ represents a hydrogen atom, a $C_1$-$C_6$ alkyl group or a group: —$NR^{10}R^{11}$ wherein $R^{10}$ and $R^{11}$ may be the same or different from each other, and each represents a hydrogen atom, a $C_1$-$C_6$ alkyl group, a $C_1$-$C_6$ alkyl-carbonyl group, a formyl group, a $C_1$-$C_6$ alkoxy-carbonyl group or a $C_1$-$C_6$ alkylsuffonyl group, $R^{12}$ represents a hydrogen atom, a $C_1$-$C_6$ alkyl group, a halogeno $C_1$-$C_6$ alkyl group or a group: —$NR^{10}R^{11}$ wherein $R^{10}$ and $R^{11}$ maybe the same or different from each other, and each represents a hydrogen atom, a $C_1$-$C6$ alkyl group, a $C_1$-$C_6$ alkyl-carbonyl group, a formyl group, a $C_1$-$C_6$ alkoxy-carbonyl group or a $C_1$-$C_6$ alkylsulfonyl group.

27. The pyrazole compound or a pharmaceutically acceptable salt thereof according to claim 26, wherein $R^1$ represents a phenyl group which may be substituted by 1 to 3 group(s) selected from the group consisting of a halogeno atom, a $C_1$-$C_4$ alkyl group, a halogeno $C_1$-$C_4$ alkyl group, a $C_1$-$C_4$ alkoxy group, a halogeno $C_1$-$C_4$ alkoxy group and a $C_1$-$C_4$ alkyithio group, $R^2$ represents a hydrogen atom, a halogeno atom, a $C_1$-$C_4$ alkyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group or a group: —$NR^5R^6$ (wherein $R^5$ and $R^6$ may be the same or different from each other, and each represents a hydrogen atom, a $C_1$-$C_4$ alkyl group, a halogeno $C_1$-$C_4$ alkyl group, a cycloalkyl group, a $C_1$-$C_4$ alkyl-carbonyl group, a $C_3$-$C_6$ cycloalkyl-carbonyl group, a formyl group, a $C_1$-$C_4$ alkoxy-carbonyl group or a $C_1$-$C_4$ alkylsulfonyl group, or a $C_7$-$C_{12}$ aralkyl group or a benzoyl group each of which may be substituted by a group(s) selected from the group consisting of a halogeno atom, a $C_1$-$C_4$ alkyl group, a halogeno $C_1$-$C_4$ alkyl group, a $C_1$-$C_4$ alkoxy group and a halogeno $C_1$-$C_4$ alkoxy group), $R^3$ represents a hydrogen atom, a $C_1$-$C_4$ alkyl group or an amino group, $R^4$ the formula (V)

wherein $R^7$ represents a hydrogen atom or a $C_1$-$C_4$ alkyl group, $R^8$ represents a hydrogen atom, a $C_1$-$C_4$ alkyl group, an amino group, a $C_1$-$C_4$ alkylamino group, a di($C_1$-$C_4$ alkyl)amino group, a $C_1$-$C_4$ alkyl-carbonylamino group, a formylamino group, a $C_1$-$C_4$ alkoxycarbonylamino group or a $C_1$-$C_4$ alkylsulfonylamino group, $R^{12}$ represents a hydrogen atom, a $C_1$-$C_4$ alkyl group, a fluoro $C_1$-$C_4$ alkyl group, an amino group, a $C_1$-$C_4$ alkylamino group, a di($C_1$-$C_4$ alkyl)amino group, a $C_1$-$C_4$ alkyl-carbonylamino group, a formylamino group, a $C_1$-$C_4$ alkoxy-carbonylamino group or a $C_1$-C4 alkylsulfonylamino group.

28. The pyrazole compound or a pharmaceutically acceptable salt thereof according to claim 27, wherein $R^1$ represents a phenyl group which may be substituted by 1 to 2 group(s) selected from the group consisting of a halogeno atom, a $C_1$-$C_4$ alkyl group, a fluoro $C_1$-$C_4$ alkyl group, a $C_1$-$C_4$ alkoxy group, a fluoro $C_1$-$C_4$ alkoxy group and a $C_1$-$C_4$ alkylthio group, $R^2$ represents a hydrogen atom, a halogeno atom, a $C_1$-$C_4$ alkyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a di($C_1$-$C_4$ alkyl)amino group, a fluoro $C_1$-$C_4$ alkylamino group, a $C_3$-$C_6$ cycloalkylamino group, a $C_1$-$C_4$ alkyl-carbonylamino group, a $C_3C_6$ cycloalkyl-carbonylamino group, a N-($C_3$-$C_6$ cycloalkyl-carbonyl)-N—($C_1$-$C_4$ alkyl)amino group, a formylamino group, a $C_1$-$C_4$ alkoxy-carbonylamino group, a $C_1$-$C_4$ alkylsulfonylamino group, or a benzylamino group, a 1-phenethylamino group or a benzoylamino group the phenyl group portion thereof may be substituted by a group(s) selected from the group consisting of a halogen atom, a $C_1$-$C_4$ alkyl group, a fluoro $C_{1-C4}$ alkyl group, a $C_1$-$C_4$ alkoxy group and a fluoro $C_1$-$C_4$ alkoxy group, $R^3$ represents a hydrogen atom, a methyl group or an amino group, $R^4$ the formula (V)

wherein $R^7$ represents a hydrogen atom, a methyl group or an ethyl group, $R^8$ represents a hydrogen atom, a methyl group, an ethyl group, an amino group, a methylamino group, a dimethylamino group, an ethylamino group, a diethylamino group, an isopropylamino group, an acetylamino group, a formylamino group, a methoxycarbonylamino group, an ethoxycarbonylamino group, a methylsulfonylamino group or an ethylsulfonylamino group, $R^{12}$ represents a hydrogen atom, a methyl group, an ethyl group, a trifluoromethyl group, a 2,2,2-trifluoroethyl group, an amino group, a methylamino group, a dimethylamino group, an ethylamino group, a diethylamino group, an isopropylamino group, an acetylamino group, a formylamino group, a methoxycarbonylamino group, an ethoxycarbonylamino group, a methylsulfonylamino group or an ethylsulfonylamino group.

29. The pyrazole compound or a pharmaceutically acceptable salt thereof according to claim 28, wherein $R^1$ represents a phenyl group which may be substituted by 1 to 2 group(s) selected from the group consisting of a fluorine atom, a chlorine atom, a bromine atom, a methyl group, an ethyl group, an isopropyl group, a difluoromethyl group, a trifluoromethyl group, a 2-fluoroethyl group, a 2,2,2-trifluoroethyl group, a methoxy group, an ethoxy group, an isopropoxy group, a fluoromethoxy group, a difluoromethoxy group, a trifluoromethoxy group and a methylthio group, $R^2$ represents a hydrogen atom, a fluorine atom, a chlorine atom, a methyl group, a methoxy group, a methylthio group, a methylsulfonyl group, a methylsulfonyl group, an amino group, a methylamino group, a dimethylamino group, an ethylamino group, a diethylamino group, a propylamino group, an isopropylamino group, a trifluoromethylamino group, a 2,2,2-trifluoroethylamino group, a cyclopropylamino group, a cyclohexylamino group, an acetylamino group, a propionylamino group, a cyclopropylcarbonylamino group, a cyclopentylcarbonylamino group, a N-cyclopropylcarbonyl-N-methylamino group, a formylamino group, a methoxycarbonylamino group, an ethoxycarbonylamino group, a t-butoxycarbonylamino group, a methylsulfonylamino group, an ethylsulfonylamino group, or a benzylamino group, a 1-phenethylamino group or a benzoylamino group the phenyl group portion thereof may be substituted by a group(s) selected from the group consisting of a fluorine atom, a methyl group, a trifluoromethyl group, a methoxy group and a difluoromethoxy group, $R^3$ represents a hydrogen atom, a methyl group or an amino group, $R^4$ the formula (V)

wherein $R^7$ represents a hydrogen atom or a methyl group, $R^8$ represents a hydrogen atom, a methyl group, an amino group, a methylamino group, a dimethylamino group, an acetylamino group, a formylamino group, a methoxycarbonylamino group or a methylsulfonylamino group, $R^{12}$ represents a hydrogen atom, a methyl group, a trifluoromethyl group, an amino group, a methylamino group, a dimethylamino group, an acetylamino group, a formylamino group, a methoxycarbonylamino group or a methylsulfonylamino group.

30. The pyrazole compound or a pharmaceutically acceptable salt thereof according to claim 29, wherein $R^1$ represents a phenyl group which may be substituted by 1 or 2 group(s) selected from the group consisting of a fluorine atom, a chlorine atom, a methyl group, a difluoromethyl group, a trifluoromethyl group, a methoxy group, a fluoromethoxy group, a difluoromethoxy group and a trifluoromethoxy group, $R^3$ represents a hydrogen atom, a fluorine atom, a methyl group, a methoxy group, a methylthio group, a methylsulfinyl group, a methylsulfonyl group, an amino group, a methylamino group, a dimethylamino group, an ethylamino group, an isopropylamino group, a 2,2,2-trifluoroethylamino group, a cyclopropylamino group, an acetylamino group, a cyclopropylcarbonylamino group, a cyclopentylcarbonylamino group, a N-cyclopropylcarbonyl-N-methylamino group, a methoxycarbonylamino group, a methylsulfonylamino group, a 4-methoxybenzylamino group, a 1-phenethylamino group or a benzoylamino group, $R^3$ represents a hydrogen atom, a methyl group or an amino group, $R^4$ represents a 7,8-dihydro-[1,2,4]triazolo[4,3-b]pyridazin-6-yl group, a 7,8-dihydro-3-methyl-[1,2,4]triazolo[4,3-b]pyridazin-6-yl group, a 7,8-dihydro-3-trifluoromethyl-[1,2,4]triazolo[4,3-b]pyridazin-6-yl group, a 3-amino-7,8-dihydro-[1,2,4]triazolo[4,3-b]pyridazin-6-yl group, a 7,8-dihydro-3-methylamino-[1,2,4]triazolo [4,3-b]pyridazin-6-yl group, a 3-acetylamino-7,8-dihydro-[1,2,4]triazolo[4,3-b]pyridazin-6-yl group, at 7,8-dihydro-3-methoxycarbonylamino-[1,2,4]triazolo[4,3-b]pyridazin-6-yl group, a 7,8-dihydro-3-methylsulfonylamino-[1,2,4]triazolo[4,3-b]pyridazin-6-yl group, a 7,8-dihydro-7-methyl-[1,2,4]triazolo[4,3-b]pyridazin-6-yl group, a 7,8-dihydro-8-methyl-[1,2,4]triazolo[4,3-b]pyridazin-6-yl group or a 8-amino-7,8-dihydro-[1,2,4]triazolo [4,3-b]pyridazin-6-yl group.

31. The pyrazole compound or a pharmaceutically acceptable salt thereof according to claim 30, wherein $R^1$ represents a phenyl group, a 2-fluorophenyl group, a 3-fluorophenyl group, a 4-fluorophenyl group, a 3-chlorophenyl group, a 4-chlorophenyl group, a 3,4-difluorophenyl group, a 2,4-difluorophenyl group, a 3,4-dichlorophenyl group, a 3-chloro-4-fluorophenyl group, a 4-chloro-3-fluorophenyl group or a 3-trifluoromethylphenyl group, $R^2$ represents a hydrogen atom, a methoxy group, an amino group, a methylamino group, an ethylamino group, an isopropylamino group, a 2,2,2-trifluoroethylamino group, an acetylamino group, a cyclopropylcarbonylamino group, a cyclopentylcarbonylamino group, a methoxycarbonylamino group, a methylsulfonylamino group, a 4-methoxybenzylamino group, a 1-phenethylamino group or a benzoylamino group, $R^3$ represents a hydrogen atom, a methyl group or an amino group, and $R^4$ represents a 7,8-dihydro-[1,2,4]triazolo[14,3-b]pyridazin-6-yl group, a 7,8-dihydro-3-methyl-[1,2,4]triazolo[4,3-b]pyridazin-6-yl group, a 7,8-dihydro-3-trifluoromethyl-[1,2,4]triazolo [4,3-b]pyridazin-6-yl group, a 3-amino-7,8-dihydro-[1,2,4]triazolo[4,3-b]pyridazin-6-yl group, a 7,8-dihydro-7-methyl-[1,2,4]triazolo [4,3-b]pyridazin-6-yl group or a 7,8-dihydro-8-methyl-[1,2,4]triazole[4,3-b]pyridazin-6-yl group.

32. The pyrazole compound or a pharmaceutically acceptable salt thereof according to claim 31, wherein $R^1$ represents a phenyl group, a 2-fluorophenyl group, a 3-fluorophenyl group, a 4-fluorophenyl group, a 3-chlorophenyl group, a 4-chlorophenyl group, a 3,4-difluorophenyl group, a 2,4-difluorophenyl group, a 3,4-dichlorophenyl group, a 3-chloro-4-fluorophenyl group, a 4-chloro-3-fluorophenyl group or a 3-trifluoromethylphenyl group, $R^2$ represents a hydrogen atom, a methoxy group, an amino group, a methylamino group, an ethylamino group, an isopropylamino group, a 2,2,2-trifluoroethylamino group, an acetylamino group, a cyclopropylcarbonylamino group, a cyclopentylcarbonylamino group, a methoxycarbonylamino group, a methylsulfonylamino group, a 4-methoxybenzylamino group, a 1-phenethylamino group or a benzoylamino group, $R^3$ represents a hydrogen atom, and $R^4$ represents a 7,8-dihydro-[1,2,4]triazolo[4,3-b]pyridazin-6-yl group or a 7,8-dihydro-3-methyl-[1,2,4]triazolo[4,3-b]pyridazin-6-yl group.

33. The pyrazole compound or a pharmaceutically acceptable salt thereof according to claim 32, wherein the pyrazole compound is 4-(2-aminopyridin-4-yl)-1-(7,8-dihydro-[1,2,4]triazolo [4,3-b]pyridazin-6-yl)-3-phenyl-1H-pyrazole, 3-(4-fluorophenyl)-1-(7,8-dihydro-[1,2,4]triazolo [4,3-b] pyridazin-6-yl)-4-(pyridin-4yl)-1H-pyrazole, 4-(2-aminopyridin-4-yl)-3-(4-fluorophenyl)-1-(7,8-dihydro-[1,2,4]triazolo[4,3-b]pyridazin-6yl)-1H-pyrazole, 3-(4-fluorophenyl)-1-(7,8-dihydro-[1,2,4]triazolo[4,3-b]pyridazin-6-yl)-4-[2-(2,2,2-trifluoroethyl)aminopyridin-4-yl]-1H-pyrazole, 4-(2-acetylaminopyridin-4-yl)-3-(4-fluorophenyl)-1-(7,8-dihydro-[1,2,4]triazolo[4,3-b]pyridazin-6-yl)-1H-pyrazole, 4-(2-cyclopropylcarbonylaminopyridin-4-yl)-3-(4-fluorophenyl)-1-(7,8-dihydro-[1,2,4]triazolo[4,3-b]pyridazin-6-yl-1H-pyrazole, 4-(2-aminopyridin-4-yl)-3-(4-fluorophenyl)-1-(7,8-dihydro-[1,2,4]triazolo[4,3-b]pyridazin-6-yl)-1H-pyrazole, 4-(2-aminopyridin-4-yl)-3-(3-fluorophenyl)-1-(7,8-dihydro-[1,2,4]triazolo[4,3-b]pyridazin-6-yl)-1 1H-pyrazole, 4-(2-aminopyridin-4-yl)-3-(2-fluorophenyl)-1-(7,8-dihydro-[1,2,4]triazolo[4,3-b]pyridazin-6-yl)-1H-pyrazole, 3-(2-fluorophenyl)-1-(7,8-dihydro-[1,2,4]triazolo[4,3-b]pyridazin-6-yl)-4-[2-(2,2,2-trifluoroethyl)aminopyridin-4-yl]-1H-pyrazole, 4-(2-acetylaminopyridin-4-yl)-3-(2-fluorophenyl)-1-(7,8-dihydro-[1,2,4]triazolo[4,3-b]pyridazin-6-yl)-1H-pyrazole, 4-(2-cyclopropylcarbonylaminopyridin-4-yl)-3-(2-fluorophenyl)-1-(7,8-dihydro-[1,2,4]triazolo[4,3-b]pyridazin-6-yl)-1H-pyrazole, 4-(2-aminopyridin-4-yl)-3-(4-chlorophenyl)-1-(7,8-dihydro-[1,2,4]triazolo[4,3-b]pyridazin-6yl)-1H-pyrazole, 4-(2-aminopyridin-4-yl-3-(3-chlorophenyl)-1-(7,8-dihydro-[1,2,4]triazolo[4,3-b]pyridazin-6-yl)-1H-pyrazole, 4-(2-aminopyridin-4-yl)-3-(3,4-difluorophenyl)-1-(7,8-dihydro-[1,2,4]triazolo[4,3-b]pyridazin-6-yl)-1H-pyrazole, 3-(3,4-difluorophenyl)-1-(7,8-dihydro-[1,2,4]triazolo[4,3-b]pyridazin-6-yl)-4-[2-(2,2,2-trifluoroethyl)aminopyridin-4-yl]-1H-pyrazole, 4-(2-acetylaminopyridin-4-yl)-3-(3,4-difluorophenyl)-1-(7,8-dihydro-[1,2,4]triazolo[4,3-b]pyridazin-6-yl)-1H-pyrazole, 4-(2-cyclopropylcarbonylaminopyridin-4-yl)-3-(3,4-difluorophenyl)-1-(7,8-dihydro-[1,2,4]triazolo[4,3-b]pyridazin-6-yl)-1H-pyrazole, 4-(2-aminopyridin-4-yl)-3-(3,4-dichlorophenyl)-1-(7,8-dihydro-[1,2,4]triazolo[4,3-b]pyridazin-6-yl)-1H-pyrazole or 4-(2-aminopyridin-4-yl)-1-(7,8-dihydro-[1,2,4]triazolo[4,3-b]pyridazin-6-yl)-3-(3-trifluoromethylphenyl)-1H-pyrazole.

34. A pharmaceutical composition comprising a pharmaceutically effective amount of the compound according to claim 1 or a salt thereof as an effective ingredient, and a pharmaceutically acceptable carrier therefor.

35. A method of treating rheumatoid arthritis in a patient in need thereof, comprising administering to said patient the pharmaceutical composition according to claim 34.

* * * * *

UNITED STATES PATENT AND TRADEMARK OFFICE
CERTIFICATE OF CORRECTION

PATENT NO. : 7,294,625 B2  
APPLICATION NO. : 10/528994  
DATED : November 13, 2007  
INVENTOR(S) : Masahiko Hagihara et al.

It is certified that error appears in the above-identified patent and that said Letters Patent is hereby corrected as shown below:

At columns 63-97 in Table 2 compound "$R^9$" should be --$R^{12}$--.

At columns 121-143 in Table 4 compound "$R^9$" should be --$R^{12}$--.

Signed and Sealed this

Twenty-eighth Day of April, 2009

JOHN DOLL  
*Acting Director of the United States Patent and Trademark Office*